(12) United States Patent
Van Allen et al.

(10) Patent No.: US 11,377,696 B2
(45) Date of Patent: Jul. 5, 2022

(54) PBRM1 BIOMARKERS PREDICTIVE OF ANTI-IMMUNE CHECKPOINT RESPONSE

(71) Applicant: Dana-Farber Cancer Institute, Inc., Boston, MA (US)

(72) Inventors: Eliezer Van Allen, Brookline, MA (US); Diana Miao, Newton, MA (US); Toni K. Choueiri, Westwood, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 289 days.

(21) Appl. No.: 16/475,574

(22) PCT Filed: Jan. 3, 2018

(86) PCT No.: PCT/US2018/012209
§ 371 (c)(1),
(2) Date: Jul. 2, 2019

(87) PCT Pub. No.: WO2018/132287
PCT Pub. Date: Jul. 19, 2018

(65) Prior Publication Data
US 2019/0338369 A1     Nov. 7, 2019

Related U.S. Application Data

(60) Provisional application No. 62/445,094, filed on Jan. 11, 2017.

(51) Int. Cl.
*C12Q 1/6886* (2018.01)
*G01N 33/50* (2006.01)
*G01N 33/574* (2006.01)

(52) U.S. Cl.
CPC ....... *C12Q 1/6886* (2013.01); *G01N 33/5011* (2013.01); *G01N 33/574* (2013.01); *C12Q 2600/106* (2013.01); *G01N 2333/70532* (2013.01); *G01N 2800/52* (2013.01)

(58) Field of Classification Search
CPC .................................................. C12Q 1/6886
USPC ...................................................... 424/174.1
See application file for complete search history.

(56) References Cited

U.S. PATENT DOCUMENTS

2016/0115556 A1*   4/2016   Erlander ............ A61B 10/0045
                                                         435/6.11
2016/0299146 A1   10/2016   Garraway et al.

FOREIGN PATENT DOCUMENTS

WO    WO-2012/038744 A2    3/2012
WO    WO-2018/132287 A1    7/2018

OTHER PUBLICATIONS

Joseph et al (J Urol, 2016, 195(1): 180-187).*
Tockman et al (Cancer Res., 1992, 52:2711s-2718s).*
Varela et al (Nature, 2011, 469(27): 539-542).*
Pawlowski et al (Int J Cancer, 2013, 132: E11-E17).*
International Preliminary Report on Patentability for International Application No. PCT/US2018/12209 dated Jun. 20, 2018.
Braun et al., "Genomic approaches to understanding response and resistance to immunotherapy," Clin. Cancer Res., 22(23):5642-5650 (2016).
International Search Report and Written Opinion for International Applications No. PCT/US18/12209 dated Jun. 20, 2018.

\* cited by examiner

*Primary Examiner* — Sean E Aeder
(74) *Attorney, Agent, or Firm* — Foley Hoag LLP

(57) ABSTRACT

The present invention is based on the identification of novel biomarkers predictive of responsiveness to anti-immune checkpoint therapies.

12 Claims, 37 Drawing Sheets
Specification includes a Sequence Listing.

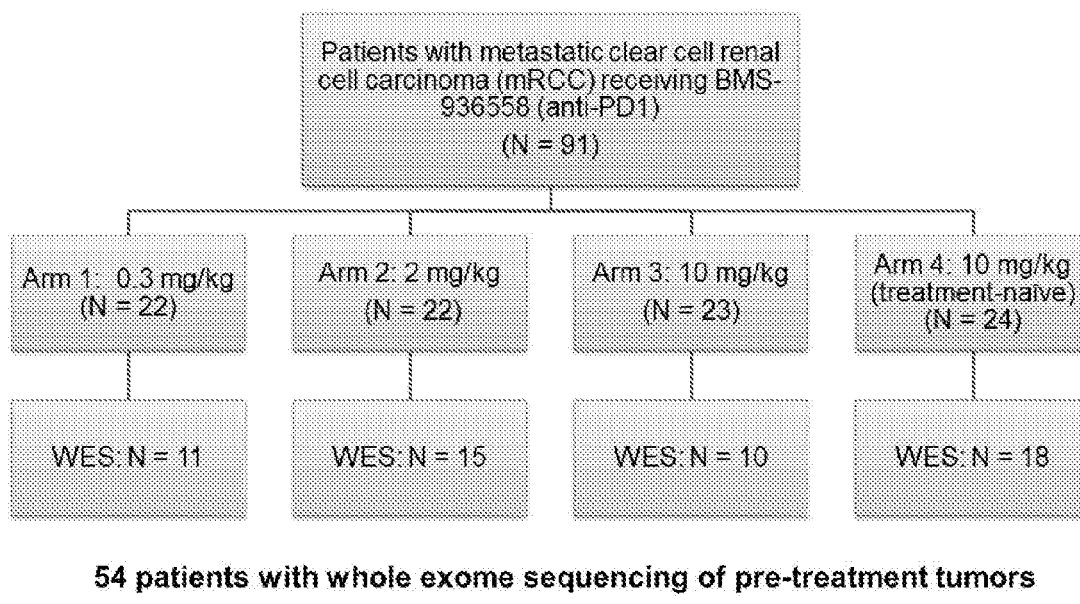

54 patients with whole exome sequencing of pre-treatment tumors

Categories of Clinical Response

- Extreme responder:
  - CR or PR by RECIST or SD by RECIST with decrease in objective tumor burden lasting >6 months (PFS > 6 months)
  - One patient with limited tumor progression followed by further tumor regression was included in extreme responders (5_50)
- Extreme progressor: PD with PFS < 3 months
- Stable disease: Patients falling "in between" extreme responders and extreme progressors
  - SD without objective decrease in tumor burden or with PFS < 6 months
  - PD with PFS > 3 months

- Not evaluable (NE): No RECIST evaluation made
- Mixed response (X): Simultaneous tumor shrinkage and growth

- 3/37 samples excluded due to early death on treatment (clinical response not evaluable) (5_2, 5_29, 6_99)

B

D

A

B

C

*N=85/91 patients with documented PD-L1 staining

D

*N=83/91 patients with documented RECIST evaluations

A

FDR q-value = 0.045

B

FDR q-value = 0.094

C

FDR q-value = 0.071

D

FDR q-value = 0.095

A

B

PBRM1 BIOMARKERS PREDICTIVE OF ANTI-IMMUNE CHECKPOINT RESPONSE

CROSS-REFERENCE TO RELATED APPLICATIONS

This application is the U.S. national phase of International Patent Application No. PCT/US2018/012209, filed on Jan. 3, 2018, which claims the benefit of priority to U.S. Provisional Application Ser. No. 62/445,094, filed on 11 Jan. 2017; the entire contents of each of said applications are incorporated herein in their entirety by this reference.

BACKGROUND OF THE INVENTION

Immune checkpoint inhibitors, including monoclonal antibodies targeting programmed cell death-1 (PD-1) and its ligand PD-L1, have yielded durable clinical benefit for patients with a range of tumor types, including metastatic melanoma, non-small cell lung cancer (NSCLC), and bladder cancer (Topalian et al. (2015) Cancer cell 27:450-461). Renal cell carcinoma (RCC) has been known to be immunotherapy-responsive for more than 20 years, with high-dose interleukin-2 yielding durable complete responses in a small minority of patient. Recently, immune checkpoint blockade has been shown to be remarkably effective in RCC, yielding superior rates of objective response compared to everolimus (Motzer et al. (2015) N. Engl. J. Med. 373:1803-1813). However, responses only occurred in about a quarter of patients, and immunohistochemistry for PD-L1 was not predictive of treatment response (Choueiri et al. (2016) Clin. Cancer Res. 22:5461-5471; Motzer et al. (2015), supra), making identification of pre-treatment predictors of patient benefit a clinical priority.

Studies featuring somatic genetic analysis of patients receiving immune checkpoint therapies for metastatic melanoma, non-small cell lung cancer, and colorectal cancer have demonstrated that pre-treatment tumor mutational load, neoantigen burden, microsatellite instability, gene expression signatures, and neoantigen clonality can influence likelihood of response (Hugo et al. (2016) Cell 165:35-44; Le et al. (2015) N. Engl. J. Med. 372:2509-2520; McGranahan et al. (2016) Science 351:1463-1469; Rizvi et al. (2015) Science 348:124-128; Snyder et al. (2014) N. Engl. J. Med. 371:2189-2199; and Van Allen et al. (2015) Science 350: 207-211). These studies support the concept that highly mutated tumors generate tumor-specific antigens (neoantigens) that mediate a strong immune response to cancer cells after the administration of immune checkpoint therapies that disrupt immunosuppression in the tumor microenvironment.

In contrast to melanoma, non-small cell lung cancer, and microsatellite-unstable colorectal cancer, which commonly harbor more than 10 to 400 mutations per megabase (Mb), clear cell renal cell carcinoma (ccRCC) has an average of 1.1 nonsynonymous mutations/Mb, without significant outliers (Cancer Genome Atlas Research (2013) Nature 499: 43-49), while ranking among the highest across multiple tumor types in cytolytic activity (Rooney et al. (2015) Cell 160:48-61), immune infiltration score, and T cell infiltration score (Şenbabaoğlu et al. (2016) Genome Biol. 17:231), suggesting that distinct molecular mechanisms other than mutational burden or neoantigen burden may underlie its T-cell enriched microenvironment and responsiveness to immune checkpoint therapy. RCC is also characterized by frequent alterations in von Hippel Lindau protein (VHL), a tumor suppressor that regulates the transcription factor hypoxia inducible factor 1a (HIF1A) central to controlling angiogenesis. Alterations in SWItch/Sucrose Non-Fermentable (SWI/SNF) chromatin remodeling complex are also common. SWI/SNF subunits commonly mutated in ccRCC include polybromo 1 (PBRM1), AT-Rich Interaction Domain 1A (ARID1A), and Transcription activator BRG1 (SMARCA4) are also common. Other commonly mutated genes included the histone deubiquitinase BRCA1 Associated Protein 1 (BAP1), and the histone methyltransferase SET domain containing 2 (SETD2). The genes encoding VHL, PBRM1, BAP1, and SETD2 are all clustered in the small arm of chromosome 3 (chr3p), and arm-level deletions of chr3p are exceedingly common in ccRCC (>90% of samples; TCGA (2013) Nature 499:43-49). While the relationship between these DNA-level alterations affecting chromatin remodeling, angiogenesis, and response to hypoxia and the enrichment in immune cell infiltration in ccRCC is still not fully understood, experimental studies aiming to characterize the functional impact of PBRM1 loss have identified upregulation of the interleukin-6-mediated signaling pathway as one effect of re-expressing PBRM1 in PBRM1-deficient RCC cell lines (Chowdhury et al. (2016) PLoS One 11:e0153718).

In clinical studies of patients receiving anti-PD-1 therapy for metastatic RCC, whole genome microarray characterization of pre-treatment tumors from 11 patients revealed that nonresponders had higher expression of genes related to cell metabolism and solute transport, while responders overexpressed immune markers (Ascierto et al. (2016) Cancer Immunol Res. 4:726-733). Germline variants in STAT3, a transcription factor associated with immune function, have also previously been linked to response to immunotherapy with high-dose interferon (Eto et al. (2013) Eur. Urol. 63:745-752). However, no study has yet examined pre-treatment tumor whole exome and whole transcriptome sequencing with matched germline whole exome sequencing in well-annotated cohorts of renal cell carcinoma patients treated with immune checkpoint inhibitor therapy (e.g., anti-PD1 therapy used to treat metastatic RCC) to discover alterations in specific genes, transcriptional profiles, and immunological features that may predict response to immune checkpoint therapy. Accordingly, there remains a great need in the art to identify biomarkers predictive of response to immune checkpoint therapy for improved clinical stratification and enhanced understanding of the mechanism of these drugs.

SUMMARY OF THE INVENTION

The present invention is based, at least in part, on the discovery that loss-of-function mutation of PBRM1 is a highly specific biomarker for prediction of clinical outcomes (e.g., improved clinical outcomes such as tumor shrinkage and prolonged survival) in renal cell carcinoma patients treated with immune checkpoint therapies, such as those comprising an anti-PD-1 therapeutic (e.g., PD-1 blocking antibody).

In one aspect, a method of identifying the likelihood of a cancer in a subject to be responsive to an immune checkpoint therapy, the method comprising a) obtaining or providing a subject sample from a patient having cancer; b) measuring the amount or activity of at least one biomarker listed in Table 1 in the subject sample; and c) comparing said amount or activity of the at least one biomarker listed in Table 1 in a control sample, wherein the absence of or a significantly decreased amount or activity of the at least one biomarker listed in Table 1 in the subject sample and/or the presence of or a significantly increased amount or activity of the at least one biomarker listed in Table 1 having a loss of function mutation in the subject sample, relative to the control sample identifies the cancer as being more likely to be responsive to the immune checkpoint therapy; and wherein the presence of or a significantly increased amount or activity of the at least one biomarker listed in Table 1 in the subject sample and/or the absence of or a decreased amount or activity of the at least one biomarker listed in Table 1 having a loss of function mutation in the subject sample, relative to the control sample identifies the cancer as being less likely to be responsive to the immune checkpoint therapy, is provided.

In another aspect, a method of identifying the likelihood of a cancer in a subject to be responsive to immune checkpoint therapy, the method comprising a) obtaining or providing a subject sample from a patient having cancer, wherein the sample comprises nucleic acid molecules from the subject; b) determining the copy number of at least one biomarker listed in Table 1 in the subject sample; and c) comparing said copy number to that of a control sample, wherein a decreased copy number of the at least one biomarker listed in Table 1 in the in the subject sample and/or an increased copy number of the at least one biomarker listed in Table 1 having a loss of function mutation in the subject sample, relative to the control sample identifies the cancer as being more likely to be responsive to the immune checkpoint therapy; and wherein a wild type or increased copy number of the biomarker in the subject sample and/or a decreased copy number of the at least one biomarker listed in Table 1 having a loss of function mutation in the sample relative to the control sample identifies the cancer as being less likely to be responsive to the immune checkpoint therapy, is provided.

Numerous embodiments are further provided that can be applied to any aspect of the present invention and/or combined with any other embodiment described herein. For example, in one embodiment, the method provided herein further comprises recommending, prescribing, or administering the immune checkpoint therapy if the cancer is determined likely to be responsive to the immune checkpoint therapy or administering an anti-cancer therapy other than the immune checkpoint therapy if the cancer is determined be less likely to be responsive to the immune checkpoint therapy. The anti-cancer therapy may be, for example, selected from the group consisting of targeted therapy, chemotherapy, radiation therapy, and/or hormonal therapy. In another embodiment, the control sample described herein is determined from a cancerous or non-cancerous sample from either the patient or a member of the same species to which the patient belongs. In still another embodiment, the control sample is a cancerous or non-cancerous sample from the patient obtained from an earlier point in time than the patient sample. In yet another embodiment, the control sample is obtained before the patient has received immune checkpoint therapy and the patient sample is obtained after the patient has received immune checkpoint therapy. In another embodiment, the control sample described herein comprises cells or does not comprise cells. In still another embodiment, the control sample comprises cancer cells known to be responsive or non-responsive to the immune checkpoint therapy.

In another aspect, a method of assessing the efficacy of an agent for treating a cancer in a subject that is unlikely to be responsive to an immune checkpoint therapy, comprising a) detecting in a first subject sample and maintained in the presence of the agent the amount or activity of at least one biomarker listed in Table 1; b) detecting the amount or activity of the at least one biomarker listed in Table 1 in a second subject sample and maintained in the absence of the test compound; and c) comparing the amount or activity of the at least one biomarker listed in Table 1 from steps a) and b), wherein the presence of or a significantly increased amount or activity of the at least one biomarker listed in Table 1 in the first subject sample and/or the absence of or a decreased amount or activity of the at least one biomarker listed in Table 1 having a loss of function mutation in the first subject sample, relative to at least one subsequent subject sample, indicates that the agent treats the cancer in the subject, is provided.

In another aspect, a method of assessing the efficacy of an agent for treating a cancer in a subject or prognosing progression of a cancer in a subject, comprising a) detecting in a subject sample at a first point in time the amount or activity of at least one biomarker listed in Table 1; b) repeating step a) during at least one subsequent point in time after administration of the agent; and c) comparing the expression and/or activity detected in steps a) and b), wherein the presence of or a significantly increased amount or activity of the at least one biomarker listed in Table 1 in the first subject sample and/or the absence of or a decreased amount or activity of the at least one biomarker listed in Table 1 having a loss of function mutation in the first subject sample, relative to at least one subsequent subject sample, indicates that the cancer is unlikely to progress or that the agent treats the cancer in the subject, is provided. In one embodiment, between the first point in time and the subsequent point in time, the subject has undergone treatment, completed treatment, and/or is in remission for the cancer. In another embodiment, the first and/or at least one subsequent sample is selected from the group consisting of ex vivo and in vivo samples. In still another embodiment, the first and/or at least one subsequent sample is obtained from an animal model of the cancer. In yet another embodiment, the first and/or at least one subsequent sample is a portion of a single sample or pooled samples obtained from the subject.

In another aspect, a cell-based assay for screening for agents that have a cytotoxic or cytostatic effect on a cancer cell that is unresponsive to an immune checkpoint therapy comprising, contacting the cancer cell with a test agent, and determining the ability of the test agent to decrease the amount or activity of at least one biomarker listed in Table 1 in the subject sample and/or increase the amount or activity of the at least one biomarker listed in Table 1 having a loss of function mutation, is provided. In one embodiment, the step of contacting occurs in vivo, ex vivo, or in vitro. In another embodiment, the subject sample and/or the control sample has not been contacted with a renal cell cancer treatment or inhibitor of an immune checkpoint. In still another embodiment, the subject has not been administered a renal cell cancer treatment or inhibitor of an immune checkpoint. In yet another embodiment, the method or the cell-based assay provided herein further comprises recommending, prescribing, or administering at least one additional anti-cancer therapeutic agent. In another embodiment, the at least one additional anti-cancer therapeutic agent is nivolumab and/or an anti-PBRM-1 therapeutic agent.

As described above, numerous embodiments are contemplated for any aspect of the present invention described herein. For example, in one embodiment, the subject sample is selected from the group consisting of serum, whole blood, plasma, urine, cells, cell lines, and biopsies. In another embodiment, the amount of the at least one biomarker listed in Table 1 is detected using a reagent which specifically binds with the protein. For example, the reagent may be selected from the group consisting of an antibody, an antibody derivative, and an antibody fragment. In still another embodiment, the at least one biomarker listed in Table 1 is assessed by detecting the presence in the sample of a transcribed polynucleotide or portion thereof. For example, the transcribed polynucleotide may be an mRNA or a cDNA. The transcribed polynucleotide can be detected by identifying a nucleic acid that anneals with the biomarker nucleic acid, or a portion thereof, under stringent hybridization conditions. In yet another embodiment, the step of detecting further comprises amplifying the transcribed polynucleotide. In another embodiment, the at least one biomarker listed in Table 1 is human PBRM-1, or a fragment thereof. In still another embodiment, the immune checkpoint therapy described herein comprises at least one antibody selected from the group consisting of anti-PD-1 antibodies, anti-CTLA-4 antibodies, anti-PD-L1 antibodies, anti-PD-L2 antibodies, and combinations thereof. For example, the immune checkpoint therapy may comprise nivolumab. In yet another embodiment, the likelihood of the cancer in the subject to be responsive to immune checkpoint therapy is the likelihood of at least one criteria selected from the group consisting of cellular proliferation, tumor burden, m-stage, metastasis, progressive disease, clinical benefit rate, survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria. In another embodiment, the cancer is a solid tumor. In still another embodiment, the cancer is a renal cell cancer. In yet another embodiment, the renal cell cancer is a clear cell renal cell cancer (ccRcc). In another embodiment, the clear cell renal cell cancer is a metastatic clear cell renal cell carcinoma (mRCC). In still another embodiment, the subject described herein is a mammal. In yet another embodiment, the mammal is an animal model of cancer. In another embodiment, the mammal is a human.

Figure 1:
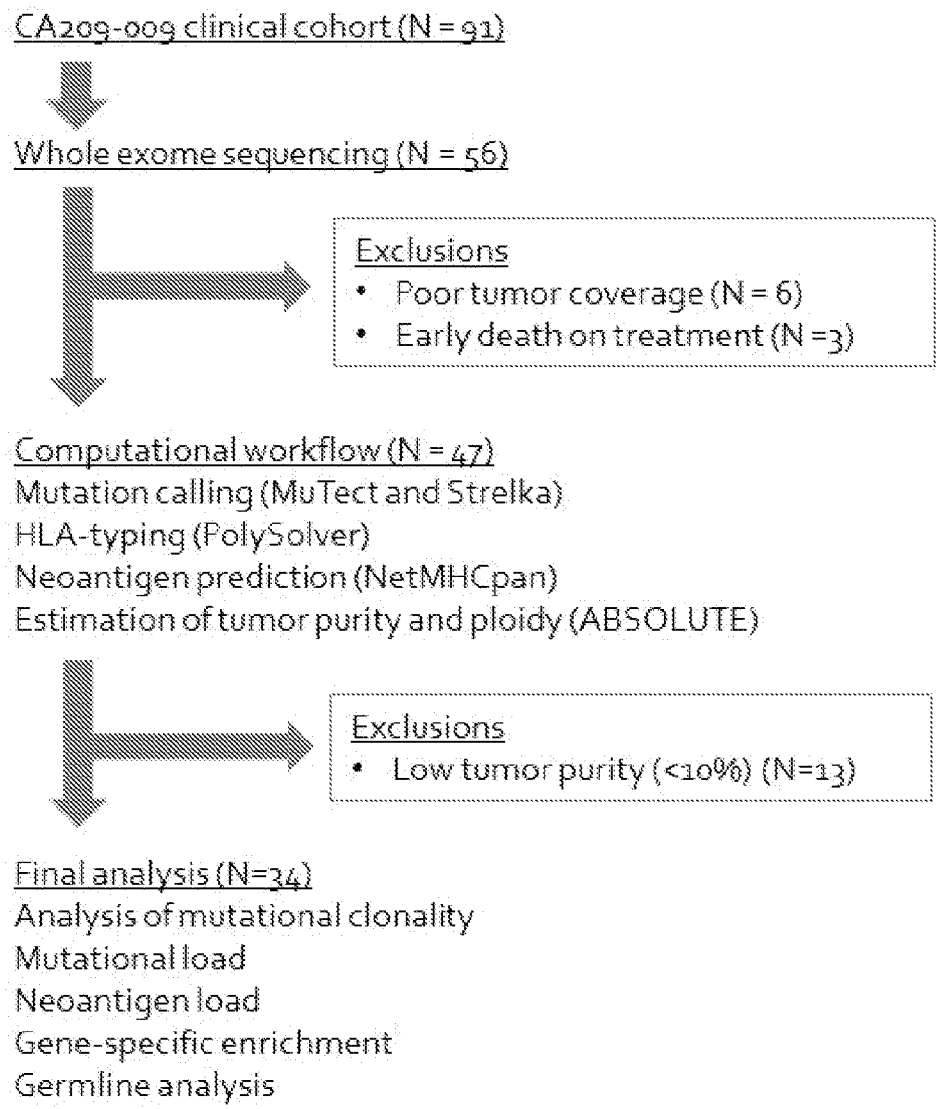
FIG. 1 includes 5 panels, identified as panels A, B, C, D, and E, which show the cohort consolidation and clinical characteristics of the training cohort. Panels A and B summarize the clinical cohort investigated unless otherwise indicated, such as at Panel D. Generally, of the 91 patients who received anti-PD1 monotherapy (nivolumab) as part of CA209-009, 56 had available pre-treatment tumor for whole exome sequencing. After quality control, 34 pre-treatment tumors were processed through standardized analytical pipelines and included in the final analysis cohort (Panel B). Sixteen samples (the leftmost column) were excluded for low sample purity (including patients who had early death on treatment) (Panel C). Patient were classified into clinical response groups based on objective tumor response RECIST classifications (complete response: CR, partial response: PR, stable disease: SD, or progressive disease: PD) (CITE: RECIST) as well as duration of progression-free survival (PFS) (time from starting immune checkpoint therapy to experiencing objective tumor growth). "Extreme responders" had CR or PR by RECIST or SD with objective tumor shrinkage lasting >6 months) while "extreme progressors" experienced PD by RECIST with PFS<3 months). A third group called "intermediate benefit" or "stable disease" had responses to therapy intermediate between the extreme responders and extreme progressors, based on a combination of objective tumor response by RECIST and duration of progression-free survival. Patients' overall survival (OS) following initiation therapy (in years) vs. PFS (in years) and PFS vs. decrease in tumor burden are shown in Panels C and D. One patient with early minor tumor growth followed by sustained tumor shrinkage was classified as an extreme-responder despite short PFS (see FIG. 2).
Figure 1:
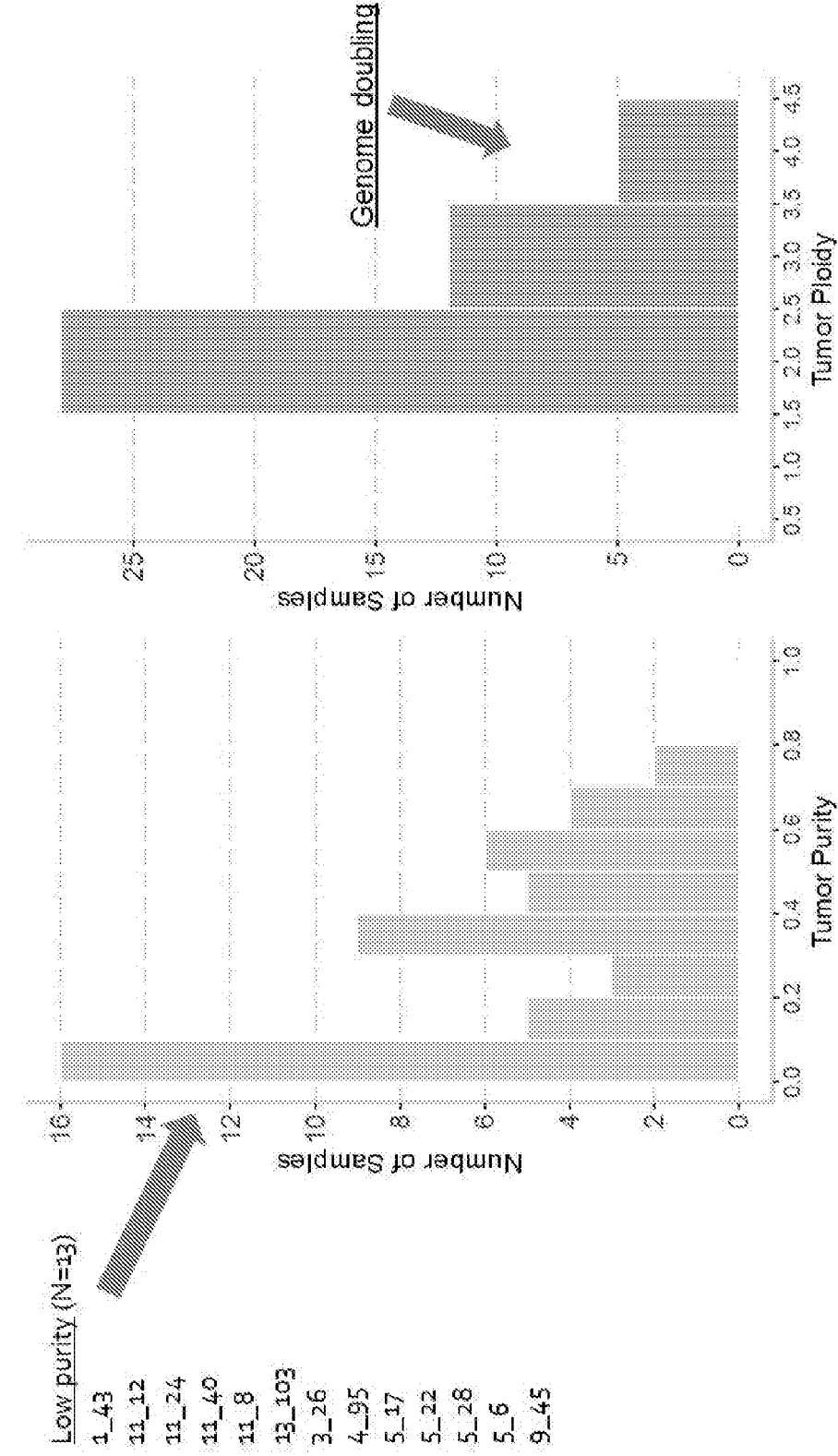
Figure 1:
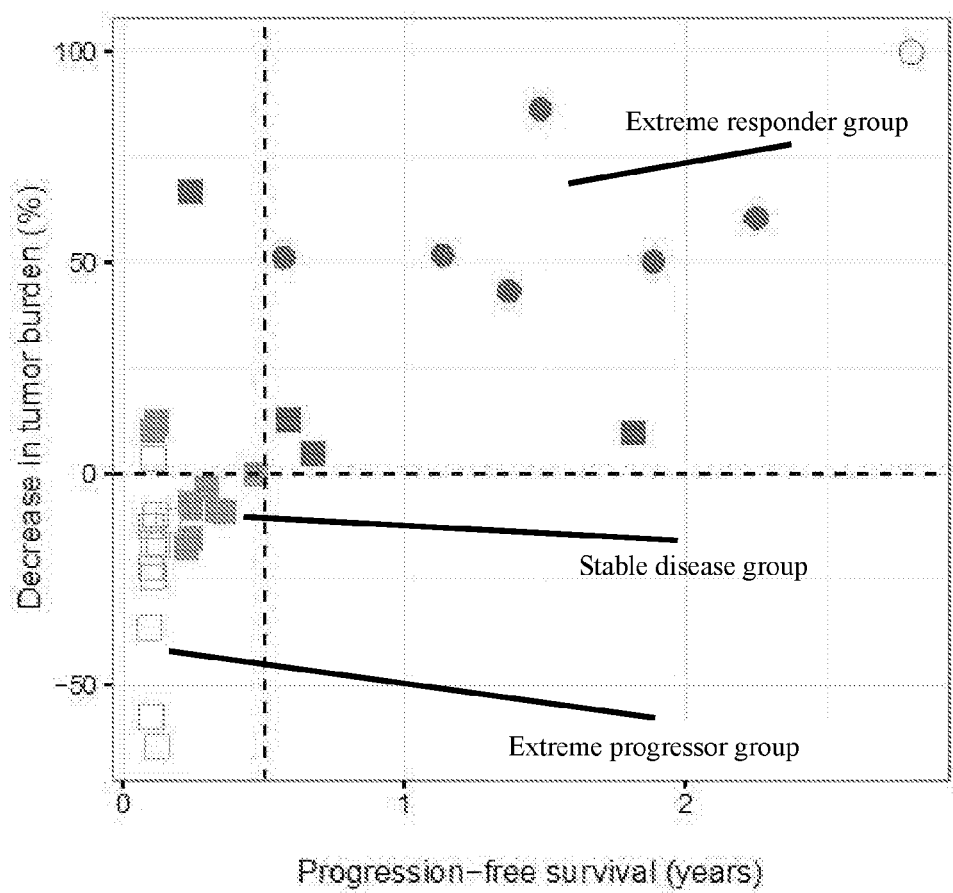
Figure 1:
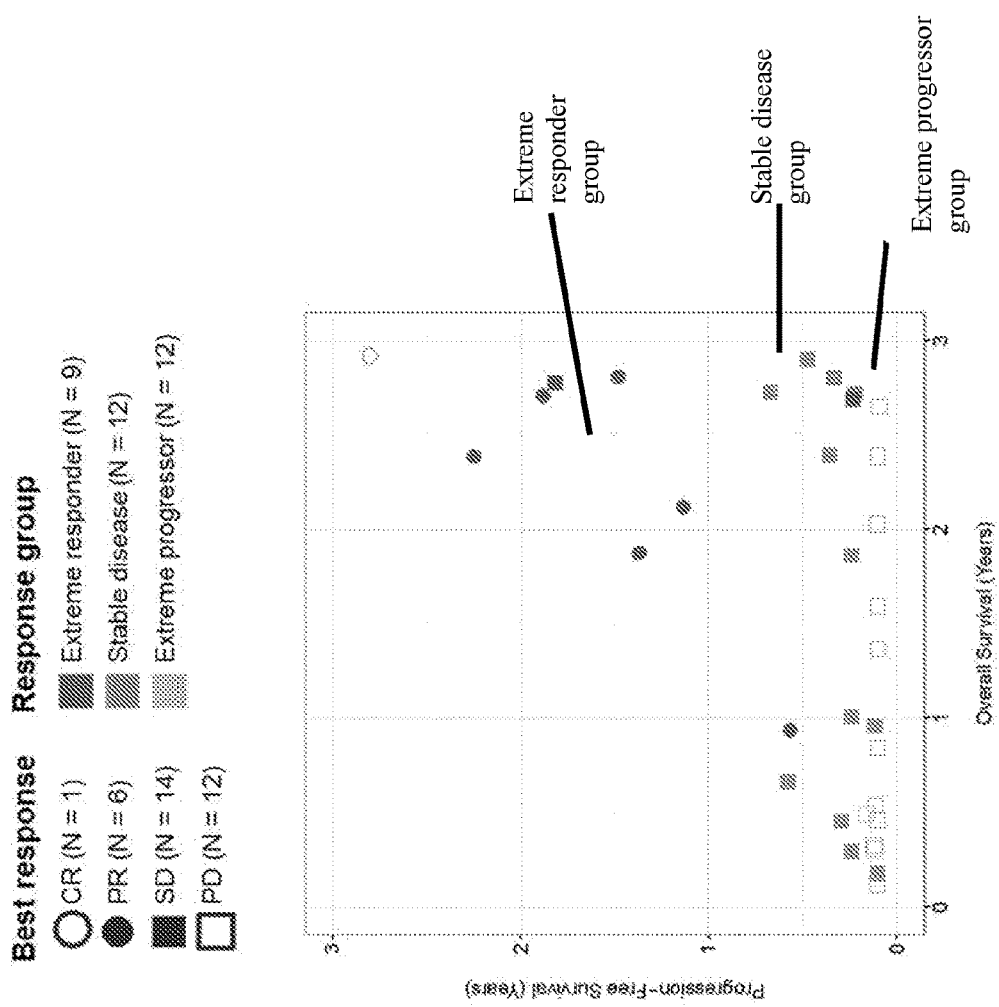

Note that for every figure containing a histogram, the bars from left to right for each discrete measurement correspond to the figure boxes from top to bottom in the figure legend as indicated.

DETAILED DESCRIPTION OF THE INVENTION

It has been determined herein that PBRM1 is a highly specific biomarker for predicted clinical outcome in cancer patients (e.g., renal cell carcinoma patients) receiving anti-immune checkpoint-based therapy (e.g., anti-PD1/PD-L1 agents alone or in combination with other anti-cancer therapeutics). Accordingly, the present invention relates, in part, to methods for stratifying patients and predicting response of a cancer in a subject to immune checkpoint therapy based upon a determination and analysis of mutations, described herein, of biomarkers, compared to a control. In addition, such analyses can be used in order to provide useful anti-immune checkpoint treatment regimens (e.g., based on predictions of clinical response, subject survival or relapse, timing of adjuvant or neoadjuvant treatment, etc.).

I. Definitions

The articles "a" and "an" are used herein to refer to one or more than one (i.e. to at least one) of the grammatical object of the article. By way of example, "an element" means one element or more than one element.

The term "altered amount" or "altered level" refers to increased or decreased copy number (e.g., germline and/or somatic) of a biomarker nucleic acid, e.g., increased or decreased expression level in a cancer sample, as compared to the expression level or copy number of the biomarker nucleic acid in a control sample. The term "altered amount" of a biomarker also includes an increased or decreased protein level of a biomarker protein in a sample, e.g., a cancer sample, as compared to the corresponding protein level in a normal, control sample. Furthermore, an altered amount of a biomarker protein may be determined by detecting posttranslational modification such as methylation status of the marker, which may affect the expression or activity of the biomarker protein.

The amount of a biomarker in a subject is "significantly" higher or lower than the normal amount of the biomarker, if the amount of the biomarker is greater or less, respectively, than the normal level by an amount greater than the standard error of the assay employed to assess amount, and preferably at least 20%, 30%, 40%, 50%, 60%, 70%, 80%, 90%, 100%, 150%, 200%, 300%, 350%, 400%, 500%, 600%, 700%, 800%, 900%, 1000% or more than that amount. Such "significance" can be assessed from any desired or known point of comparison, such as a particular post-treatment versus pre-treatment biomarker measurement ratio (e.g., 1-fold, 1.1-fold, 1.2-fold, 1.3-fold, 1.4-fold, 1.5-fold, and the like) or a particular pre-treatment serum biomarker protein measurement (e.g., 2,500 pg/ml, 2,750 pg/ml, 3,000 pg/ml, 3,175 pg/ml, 3,250 pg/ml, 3,500 pg/ml, and the like). Alternately, the amount of the biomarker in the subject can be considered "significantly" higher or lower than the normal amount if the amount is at least about two, and preferably at least about three, four, or five times, higher or lower, respectively, than the normal amount of the biomarker. Such "significance" can also be applied to any other measured parameter described herein, such as for expression, inhibition, cytotoxicity, cell growth, and the like.

The term "altered level of expression" of a biomarker refers to an expression level or copy number of the biomarker in a test sample, e.g., a sample derived from a patient suffering from cancer, that is greater or less than the standard error of the assay employed to assess expression or copy number, and is preferably at least twice, and more preferably three, four, five or ten or more times the expression level or copy number of the biomarker in a control sample (e.g., sample from a healthy subjects not having the associated disease) and preferably, the average expression level or copy number of the biomarker in several control samples. The altered level of expression is greater or less than the standard error of the assay employed to assess expression or copy number, and is preferably at least 20%, 30%, 40%, 50%, 60%, 70%, 80%, 90%, 100%, 150%, 200%, 300%, 350%, 400%, 500%, 600%, 700%, 800%, 900%, 1000% or more times the expression level or copy number of the biomarker in a control sample (e.g., sample from a healthy subjects not having the associated disease) and preferably, the average expression level or copy number of the biomarker in several control samples.

The term "altered activity" of a biomarker refers to an activity of the biomarker which is increased or decreased in a disease state, e.g., in a cancer sample, as compared to the activity of the biomarker in a normal, control sample. Altered activity of the biomarker may be the result of, for example, altered expression of the biomarker, altered protein level of the biomarker, altered structure of the biomarker, or, e.g., an altered interaction with other proteins involved in the same or different pathway as the biomarker or altered interaction with transcriptional activators or inhibitors.

The term "altered structure" of a biomarker refers to the presence of mutations or allelic variants within a biomarker nucleic acid or protein, e.g., mutations which affect expression or activity of the biomarker nucleic acid or protein, as compared to the normal or wild-type gene or protein. For example, mutations include, but are not limited to substitutions, deletions, or addition mutations. Mutations may be present in the coding or non-coding region of the biomarker nucleic acid.

The term "PBRM1" refers to protein Polybromo-1, which is a subunit of ATP-dependent chromatin-remodeling complexes. PBRM1 functions in the regulation of gene expression as a constituent of the evolutionary-conserved SWI/SNF chromatin remodeling complexes (Euskirchen et al. (2012) *J. Biol. Chem.* 287:30897-30905). Beside BRD7 and BAF200, PBRM1 is one of the unique components of the SWI/SNF-B complex, also known as polybromo/BRG1-associated factors (or PBAF), absent in the SWI/SNF-A (BAF) complex (Xue et al. (2000) *Proc Natl Acad Sci USA.* 97:13015-13020; Brownlee et al. (2012) *Biochem Soc Trans.* 40:364-369). On that account, and because it contains bromodomains known to mediate binding to acetylated histones, PBRM1 has been postulated to target the PBAF complex to specific chromatin sites, therefore providing the functional selectivity for the complex (Xue et al. (2000), supra; Lemon et al. (2001) *Nature* 414:924-928; Brownlee et al. (2012), supra). Although direct evidence for PBRM1 involvement is lacking, SWI/SNF complexes have also been shown to play a role in DNA damage response (Park et al. (2006) *EMBO J.* 25:3986-3997). In vivo studies have shown that PBRM1 deletion leads to embryonic lethality in mice, where PBRM1 is required for mammalian cardiac chamber maturation and coronary vessel formation (Wang et al. (2004) *Genes Dev.* 18:3106-3116; Huang et al. (2008) *Dev Biol.* 319:258-266). PBRM1 mutations are most predominant in renal cell carcinomas (RCCs) and have been detected in over 40% of cases, placing PBRM1 second (after VHL) on the list of most frequently mutated genes in this cancer (Varela et al. (2011) *Nature* 469:539-542; Hakimi et al. (2013) *Eur Urol.* 63:848-854; Pena-Llopis et al. (2012) *Nat Genet.* 44:751-759; Pawlowski et al. (2013) *Int J Cancer.* 132:E11-E17). PBRM1 mutations have also been found in a smaller group of breast and pancreatic cancers (Xia et al. (2008) *Cancer Res.* 68:1667-1674; Shain et al. (2012) *Proc Natl Acad Sci USA.* 109:E252-E259; Numata et al. (2013) *Int J Oncol.* 42:403-410). PBRM1 mutations are more common in patients with advanced disease stage (Hakimi et al. (2013), supra), and loss of PBRM1 protein expression has been associated with advanced tumour stage, low differentiation grade and worse patient outcome (Pawlowski et al. (2013), supra). In another study, no correlation between PBRM1 status and tumour grade was found (Pena-Llopis et al. (2012), supra). Although PBRM1-mutant tumours are associated with better prognosis than BAP1-mutant tumours, tumours mutated for both PBRM1 and BAP1 exhibit the greatest aggressiveness (Kapur et al. (2013) *Lancet Oncol.* 14:159-167). PBRM1 is ubiquitously expressed during mouse embryonic development (Wang et al. (2004), supra) and has been detected in various human tissues including pancreas, kidney, skeletal muscle, liver, lung, placenta, brain, heart, intestine, ovaries, testis, prostate, thymus and spleen (Xue et al. (2000), supra; Horikawa and Barrett (2002) *DNA Seq.* 13:211-215).

PBRM1 protein localises to the nucleus of cells (Nicolas and Goodwin (1996) *Gene* 175:233-240). As a component of the PBAF chromatin-remodelling complex, it associates with chromatin (Thompson (2009) *Biochimie*. 91:309-319), and has been reported to confer the localisation of PBAF complex to the kinetochores of mitotic chromosomes (Xue et al. (2000), supra). Human PBRM1 gene encodes a 1582 amino acid protein, also referred to as BAF180. Six bromodomains (BD1-6), known to recognize acetylated lysine residues and frequently found in chromatin-associated proteins, constitute the N-terminal half of PBRM1 (e.g., six BD domains at amino acid residue no. 44-156, 182-284, 383-484, 519-622, 658-762, and 775-882 of SEQ ID NO:2). The C-terminal half of PBRM1 contains two bromo-adjacent homology (BAH) domains (BAH1 and BAH2, e.g., at amino acid residue no. 957-1049 and 1130-1248 of SE ID NO:2), present in some proteins involved in transcription regulation. High mobility group (HMG) domain is located close to the C-terminus of PBRM1 (e.g., amino acid residue no. 1328-1377 of SEQ ID NO:2). HMG domains are found in a number of factors regulating DNA-dependent processes where HMG domains often mediate interactions with DNA.

The term "PBRM1" is intended to include fragments, variants (e.g., allelic variants), and derivatives thereof. Representative human PBRM1 cDNA and human PBRM1 protein sequences are well-known in the art and are publicly available from the National Center for Biotechnology Information (NCBI). For example, two different human PBRM1 isoforms are known. Human PBRM1 transcript variant 2 (NM_181042.4) represents the longest transcript. Human PBRM1 transcript variant 1 (NM_018313.4, having a CDS from the 115-4863 nucleotide residue of SEQ ID NO:1) differs in the 5' UTR and uses an alternate exon and splice site in the 3' coding region, thus encoding a distinct protein sequence (NP 060783.3, as SEQ ID NO:2) of the same length as the isoform (NP 851385.1) encoded by variant 2. Nucleic acid and polypeptide sequences of PBRM1 orthologs in organisms other than humans are well known and include, for example, chimpanzee PBRM1 (XM_009445611.2 and XP 009443886.1, XM_009445608.2 and XP_009443883.1, XM_009445602.2 and XP_009443877.1, XM_016941258.1 and XP_016796747.1, XM_016941256.1 and XP_016796745.1, XM_016941249.1 and XP_016796738.1, XM_016941260.1 and XP_016796749.1, XM_016941253.1 and XP_016796742.1, XM_016941250.1 and XP_016796739.1, XM_016941261.1 and XP_016796750.1, XM_009445605.2 and XP_009443880.1, XM_016941252.1 and XP_016796741.1, XM_009445603.2 and XP_009443878.1, XM_016941263.1 and XP_016796752.1, XM_016941262.1 and XP_016796751.1, XM_009445604.2 and XP_009443879.1, XM_016941251.1 and XP_016796740.1, XM_016941257.1 and XP_016796746.1, XM_016941255.1 and XP_016796744.1, XM_016941254.1 and XP_016796743.1, XM_016941265.1 and XP_016796754.1, XM_016941264.1 and XP_016796753.1, XM_016941248.1 and XP_016796737.1, XM_009445617.2 and XP_009443892.1, XM_009445616.2 and XP_009443891.1, XM_009445619.2 and XP_009443894.1 XM_009445615.2 and XP_009443890.1, XM_009445618.2 and XP_009443893.1, and XM_016941266.1 and XP_016796755.1), rhesus monkey PBRM1 (XM_015130736.1 and XP_014986222.1, XM_015130739.1 and XP_014986225.1, XM_015130737.1 and XP_014986223.1, XM_015130740.1 and XP_014986226.1, XM_015130727.1 and XP_014986213.1, XM_015130726.1 and XP_014986212.1, XM_015130728.1 and XP_014986214.1, XM_015130743.1 and XP_014986229.1, XM_015130731.1 and XP_014986217.1, XM_015130745.1 and XP_014986231.1, XM_015130741.1 and XP_014986227.1, XM_015130734.1 and XP_014986220.1, XM_015130744.1 and XP_014986230.1, XM_015130748.1 and XP_014986234.1, XM_015130746.1 and XP_014986232.1, XM_015130742.1 and XP_014986228.1, XM_015130747.1 and XP_014986233.1, XM_015130730.1 and XP_014986216.1, XM_015130732.1 and XP_014986218.1, XM_015130733.1 and XP_014986219.1, XM_015130735.1 and XP_014986221.1, XM_015130738.1 and XP_014986224.1, and XM_015130725.1 and XP_014986211.1), dog PBRM1 (XM 005632441.2 and XP_005632498.1, XM_014121868.1 and XP_013977343.1, XM_005632451.2 and XP_005632508.1, XM_014121867.1 and XP_013977342.1, XM_005632440.2 and XP_005632497.1, XM_005632446.2 and XP_005632503.1, XM_533797.5 and XP_533797.4, XM_005632442.2 and XP_005632499.1, XM_005632439.2 and XP_005632496.1, XM_014121869.1 and XP_013977344.1, XM_005632448.1 and XP_005632505.1, XM_005632449.1 and XP_005632506.1, XM_005632452.1 and XP_005632509.1, XM_005632445.1 and XP_005632502.1, XM_005632450.1 and XP_005632507.1, XM_005632453.1 and XP_005632510.1, XM_014121870.1 and XP_013977345.1, XM_005632443.1 and XP_005632500.1, XM_005632444.1 and XP_005632501.1, and XM_005632447.2 and XP_005632504.1), cow PBRM1 (XM_005222983.3 and XP_005223040.1, XM_005222979.3 and XP_005223036.1, XM_015459550.1 and XP_015315036.1, XM_015459551.1 and XP_015315037.1, XM_015459548.1 and XP_015315034.1, XM_010817826.1 and XP_010816128.1, XM_010817829.1 and XP_010816131.1, XM_010817830.1 and XP_010816132.1, XM_010817823.1 and XP_010816125.1, XM_010817824.2 and XP_010816126.1, XM_010817819.2 and XP_010816121.1, XM_010817827.2 and XP_010816129.1, XM_010817828.2 and XP_010816130.1, XM_010817817.2 and XP_010816119.1, and XM_010817818.2 and XP_010816120.1), mouse PBRM1 (NM_001081251.1 and NP 001074720.1), chicken PBRM1 (NM_205165.1 and NP 990496.1), tropical clawed frog PBRM1 (XM_018090224.1 and XP_017945713.1), zebrafish PBRM1 (XM_009305786.2 and XP_009304061.1, XM_009305785.2 and XP_009304060.1, and XM_009305787.2 and XP_009304062.1), fruit fly PBRM1 (NM_143031.2 and NP 651288.1), and worm PBRM1 (NM_001025837.3 and NP 001021008.1 and .NM_001025838.2 and NP 001021009.1).

Representative sequences of PBRM1 orthologs are presented below in Table 1. Anti-PBRM1 antibodies suitable for detecting PBRM1 protein are well-known in the art and include, for example, ABE70 (rabbit polyclonal antibody, EMD Millipore, Billerica, Mass.), TA345237 and TA345238 (rabbit polyclonal antibodies, OriGene Technologies, Rockville, Md.), NBP2-30673 (mouse monoclonal) and other polyclonal antibodes (Novus Biologicals, Littleton, Colo.), ab196022 (rabiit mAb, AbCam, Cambridge, Mass.), PAH437Hu01 and PAH437Hu02 (rabbit polyclonal antibodies, Cloud-Clone Corp., Houston, Tex.), GTX100781 (GeneTex, Irvine, Calif.), 25-498 (ProSci, Poway, Calif.), sc-367222 (Santa Cruz Biotechnology, Dallas, Tex.), etc. In addition, reagents are well-known for detecting PBRM1 expression (see, for example, PBRM1 Hu-Cy3 or Hu-Cy5 SmartFlare™ RNA Detection Probe (EMD Millipore). Moreover, mutilple siRNA, shRNA, CRISPR constructs for reducing PBRM1 expression can be found in the commercial product lists of the above-referenced companies. Ribavirin and PFI 3 are known PBRM1 inhibitors. It is to be noted that the term can further be used to refer to any combination of features described herein regarding PBRM1 molecules. For example, any combination of sequence composition, percentage identify, sequence length, domain structure, functional activity, etc. can be used to describe an PBRM1 molecule of the present invention.

The term "PBRM1 loss of function mutation" refers to any mutation in a PBRM1-related nucleic acid or protein that results in reduced or eliminated PBRM1 protein amounts and/or function. For example, nucleic acid mutations include single-base substitutions, multi-base substitutions, insertion mutations, deletion mutations, frameshift mutations, missesnse mutations, nonsense mutations, splice-site mutations, epigenetic modifications (e.g., methylation, phosphorylation, acetylation, ubiquitylation, sumoylation, histone acetylation, histone deacetylation, and the like), and combinations thereof. In some embodiments, the mutation is a "nonsynonymous mutation," meaning that the mutation alters the amino acid sequence of PBRM1. Such mutations reduce or eliminate PBRM1 protein amounts and/or function by eliminating proper coding sequences required for proper PBRM1 protein translation and/or coding for PBRM1 proteins that are non-functional or have reduced function (e.g., deletion of enzymatic and/or structural domains, reduction in protein stability, alteration of sub-cellular localization, and the like). Such mutations are well-known in the art. In addition, a representative list describing a wide variety of structural mutations correlated with the functional result of reduced or eliminated PBRM1 protein amounts and/or function is described in Table 1 and the Examples. Without being bound by theory, it is believed that nonsense, frameshift, and splice-site mutations are particularly amenable to PBRM1 loss of function because they are known to be indicative of lack of PBRM1 expression in cell lines harboring such mutations.

Unless otherwise specified here within, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., a biomarker polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, *Nature Biotechnology* 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, biomarker peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. Preferably, antibodies of the present invention bind specifically or substantially specifically to a biomarker polypeptide or fragment thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

Antibodies may also be "humanized", which is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the present invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

The term "assigned score" refers to the numerical value designated for each of the biomarkers after being measured in a patient sample. The assigned score correlates to the absence, presence or inferred amount of the biomarker in the sample. The assigned score can be generated manually (e.g., by visual inspection) or with the aid of instrumentation for image acquisition and analysis. In certain embodiments, the assigned score is determined by a qualitative assessment, for example, detection of a fluorescent readout on a graded scale, or quantitative assessment. In one embodiment, an "aggregate score," which refers to the combination of assigned scores from a plurality of measured biomarkers, is determined. In one embodiment the aggregate score is a summation of assigned scores. In another embodiment, combination of assigned scores involves performing mathematical operations on the assigned scores before combining them into an aggregate score. In certain, embodiments, the aggregate score is also referred to herein as the "predictive score."

The term "biomarker" refers to a measurable entity of the present invention that has been determined to be predictive of immune checkpoint therapy effects on a cancer. Biomarkers can include, without limitation, nucleic acids and proteins, including those shown in Table 1, the Examples, and the Figures.

A "blocking" antibody or an antibody "antagonist" is one which inhibits or reduces at least one biological activity of the antigen(s) it binds. In certain embodiments, the blocking antibodies or antagonist antibodies or fragments thereof described herein substantially or completely inhibit a given biological activity of the antigen(s).

The term "body fluid" refers to fluids that are excreted or secreted from the body as well as fluids that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

The terms "cancer" or "tumor" or "hyperproliferative" refer to the presence of cells possessing characteristics typical of cancer-causing cells, such as uncontrolled proliferation, immortality, metastatic potential, rapid growth and proliferation rate, and certain characteristic morphological features, as well as evading immune destruction (Hanahan and Weinberg (2000) 100:57-70; Hanahan and Weinberg (2011) *Cell* 144:646-674). In some embodiments, such cells exhibit such characteristics in part or in full due to the expression and activity of immune checkpoint proteins, such as PD-1, PD-L1, and/or CTLA-4. Cancer cells are often in the form of a tumor, but such cells may exist alone within an animal, or may be a non-tumorigenic cancer cell, such as a leukemia cell. As used herein, the term "cancer" includes premalignant as well as malignant cancers. Cancers include, but are not limited to, B cell cancer, e.g., multiple myeloma, Waldenstrom's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithlelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is nonsmall-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

In certain embodiments, the cancer encompasses renal cell carcinoma (RCC). The term "renal cell carcinoma" generally refers to a type of kidney cancer that starts in the lining of the proximal convoluted tubule, a part of the very small tubes in the kidney that transport waste molecules from the blood to the urine. RCC is the most common type of kidney cancer in adults, responsible for approximately 90-95% of cases. Renal cell carcinoma is the most common type of kidney cancer in adults. It occurs most often in men 50 to 70 years old. The different types of RCC are generally distinguished by the way that cancer cells appear when viewed under a microscope, such as clear cell RCC (ccRCC), papillary RCC, chromophobe RCC, oncocytoma RCC, collecting duct RCC, and other unclassified RCC. In clear cell RCC or conventional RCC, the cells have a clear or pale appearance. CCRCC classically has apical nuclei, i.e. the nucleus is adjacent to the luminal aspect (Bing and Tomaszewski (2011) *Case Rep Transplant.* 2011:387645). In most glandular structures the nuclei are usually basally located, i.e. in the cytoplasm adjacent to the basement membrane. They typically stain with CK7 and do not stain with TFE3 and AMACR (Rohan et al. (2011) *Mod Pathol.* 24:1207-1220). Around 70 to 80 percent of individuals with renal cell cancer have clear cell RCC. The growth of these cells can be either slow or fast. Metastatic renal cell carcinoma (mRCC) is the spread of the primary renal cell carcinoma from the kidney to other organs. About 25-30% of people have this metastatic spread by the time they are diagnosed with renal cell carcinoma. This high proportion is explained by the fact that clinical signs are generally mild until the disease progresses to a more severe state. The most common sites for metastasis are the lymph nodes, lung, bones, liver and brain. mRCC has a poor prognosis compared to other cancers, though average survival times have increased in the last few years due to treatment advances. Average survival time in 2008 for the metastatic form of the disease was under a year and by 2013 this improved to an average of 22 months. Despite this improvement, the 5-year survival rate for mRCC remains under 10%. About 20-25% of suffers remain unresponsive to all treatments and in these cases, the disease has a rapid progression. The known risk factors of kidney cancer include, e.g., smoking, obesity, dialysis treatment, family history of the disease, high blood pressure, horseshoe kidney, long-term use of certain medicines, such as pain pills or water pills (diuretics), polycystic kidney disease, von Hippel-Lindau disease (a hereditary disease that affects blood vessels in the brain, eyes, and other body parts), etc. Symptoms of RCC may include any of the following: abdominal pain and swelling, back pain, blood in the urine, swelling of the veins around a testicle (varicocele), flank pain, weight loss, excessive hair growth in females, pale skin, vision problems, etc. The initial symptoms of RCC often include: blood in the urine (occurring in 40% of affected persons at the time they first seek medical attention), flank pain (40%), a mass in the abdomen or flank (25%), weight loss (33%), fever (20%), high blood pressure (20%), night sweats and generally feeling unwell. When RCC metastasises, it most commonly spreads to the lymph nodes, lungs, liver, adrenal glands, brain or bones. RCC is also associated with a number of paraneoplastic syndromes (PNS) which are conditions caused by either the hormones produced by the tumour or by the body's attack on the tumour and are present in about 20% of those with RCC. These paraneoplastic syndromes most commonly affect tissues which have not been invaded by the cancer. The most common PNSs seen in people with RCC are: high blood calcium levels, polycythaemia (the opposite of anaemia, due to an overproduction of erythropoietin), thrombocytosis (too many platelets in the blood, leading to an increased tendency for blood clotting and bleeds) and secondary amyloidosis. For exam and diagnosis, a physical exam may reveal mass or swelling of the abdomen and/or a varicocele in the male scrotum. Diagnostic tests include, e.g., abdominal CT scan, blood chemistry, complete blood count (CBC), intravenous pyelogram (IVP), liver function tests, renal arteriography, ultrasound of the abdomen and kidney, and urine tests. Tests for detecting spread RCC may include abdominal CT scan, adominal MM, bone scan, chest x-ray or CT scan, and PET scan. Availabe treatment for RCC may include surgery to remove of all or part of the kidney (nephrectomy). This may include removing the bladder, surrounding tissues, or lymph nodes. Chemotherapy or radiation therapy is generally not effective for treating kidney cancer. Current immunotherapies include the immune system medicines interleukin-2 (IL-2) and nivolumab, developed after observing that in some cases there was spontaneous regression (Davar et al. (2013) "Immunotherapy for Renal Cell Carcinoma". *Renal Cell Carcinoma Clinical Management*. Humana. pp. 279-302). Other targeted therapies include anti-angiogenesis therapies (e.g., bevacizumab (Avastin®)), tyrosine kinase inhibitors (TKIs) (e.g., cabozantinib (Cabometyx™), pazopanib (Votrient®), sorafenib (Nexavar), axitinib (INLYTA®) and sunitinib (Sutent®)), mTOR inhibitors (e.g., Everolimus (Afinitor®) and temsirolimus))(Torise®), and other inhibitors to growth factors that have been shown to promote the growth and spread of tumours (e.g., lenvatinib (LENVIMA®), also see Santoni et al. (2013) *Expert Review of Anticancer Therapy*. 13:697-709; Stroup (2013) "Neoadjuvant Targeted Therapy and Consolidative Surgery" *Renal Cell Carcinoma Clinical Management*. Humana. pp. 219-230).

The term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The terms "conjoint therapy" and "combination therapy," as used herein, refer to the administration of two or more therapeutic substances, e.g., combinations of anti-immune checkpoint therapies, multiple inhibitors of an immune checkpoint of interest, combinations of immune checkpoint therapy with an inhibitor of PBRM1, and combinations thereof. The different agents comprising the combination therapy may be administered concomitant with, prior to, or following the administration of one or more therapeutic agents.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control cancer patient (can be stored sample or previous sample measurement) with a known outcome; normal tissue or cells isolated from a subject, such as a normal patient or the cancer patient, cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care cancer therapy). It will be understood by those of skill in the art that such control samples and reference standard expression product levels can be used in combination as controls in the methods of the present invention. In one embodiment, the control may comprise normal or non-cancerous cell/tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy, and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing standard of care therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods of the present invention are not limited to use of a specific cut-point in comparing the level of expression product in the test sample to the control.

The "copy number" of a biomarker nucleic acid refers to the number of DNA sequences in a cell (e.g., germline and/or somatic) encoding a particular gene product. Generally, for a given gene, a mammal has two copies of each gene. The copy number can be increased, however, by gene amplification or duplication, or reduced by deletion. For example, germline copy number changes include changes at one or more genomic loci, wherein said one or more genomic loci are not accounted for by the number of copies in the normal complement of germline copies in a control (e.g., the normal copy number in germline DNA for the same species as that from which the specific germline DNA and corresponding copy number were determined). Somatic copy number changes include changes at one or more genomic loci, wherein said one or more genomic loci are not accounted for by the number of copies in germline DNA of a control (e.g., copy number in germline DNA for the same subject as that from which the somatic DNA and corresponding copy number were determined).

The "normal" copy number (e.g., germline and/or somatic) of a biomarker nucleic acid or "normal" level of expression of a biomarker nucleic acid or protein is the activity/level of expression or copy number in a biological sample, e.g., a sample containing tissue, whole blood, serum, plasma, buccal scrape, saliva, cerebrospinal fluid, urine, stool, and bone marrow, from a subject, e.g., a human, not afflicted with cancer, or from a corresponding non-cancerous tissue in the same subject who has cancer.

As used herein, the term "costimulate" with reference to activated immune cells includes the ability of a costimulatory molecule to provide a second, non-activating receptor mediated signal (a "costimulatory signal") that induces proliferation or effector function. For example, a costimulatory signal can result in cytokine secretion, e.g., in a T cell that has received a T cell-receptor-mediated signal. Immune cells that have received a cell-receptor mediated signal, e.g., via an activating receptor are referred to herein as "activated immune cells."

The term "determining a suitable treatment regimen for the subject" is taken to mean the determination of a treatment regimen (i.e., a single therapy or a combination of different therapies that are used for the prevention and/or treatment of the cancer in the subject) for a subject that is started, modified and/or ended based or essentially based or at least partially based on the results of the analysis according to the present invention. One example is determining whether to provide targeted therapy against a cancer to provide immunotherapy that generally increases immune responses against the cancer (e.g., immune checkpoint therapy). Another example is starting an adjuvant therapy after surgery whose purpose is to decrease the risk of recurrence, another would be to modify the dosage of a particular chemotherapy. The determination can, in addition to the results of the analysis according to the present invention, be based on personal characteristics of the subject to be treated. In most cases, the actual determination of the suitable treatment regimen for the subject will be performed by the attending physician or doctor.

The term "diagnosing cancer" includes the use of the methods, systems, and code of the present invention to determine the presence or absence of a cancer or subtype thereof in an individual. The term also includes methods, systems, and code for assessing the level of disease activity in an individual.

A molecule is "fixed" or "affixed" to a substrate if it is covalently or non-covalently associated with the substrate such that the substrate can be rinsed with a fluid (e.g. standard saline citrate, pH 7.4) without a substantial fraction of the molecule dissociating from the substrate.

The term "expression signature" or "signature" refers to a group of two or more coordinately expressed biomarkers. For example, the genes, proteins, metabolites, and the like making up this signature may be expressed in a specific cell lineage, stage of differentiation, or during a particular biological response. The biomarkers can reflect biological aspects of the tumors in which they are expressed, such as the cell of origin of the cancer, the nature of the non-malignant cells in the biopsy, and the oncogenic mechanisms responsible for the cancer. Expression data and gene expression levels can be stored on computer readable media, e.g., the computer readable medium used in conjunction with a microarray or chip reading device. Such expression data can be manipulated to generate expression signatures.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-AT-TGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

The term "immune checkpoint" refers to a group of molecules on the cell surface of CD4+ and/or CD8+ T cells that fine-tune immune responses by down-modulating or inhibiting an anti-tumor immune response. Immune checkpoint proteins are well known in the art and include, without limitation, CTLA-4, PD-1, VISTA, B7-H2, B7-H3, PD-L1, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, and A2aR (see, for example, WO 2012/177624). The term further encompasses biologically active protein fragment, as well as nucleic acids encoding full-length immune checkpoint proteins and biologically active protein fragments thereof. In some embodiment, the term further encompasses any fragment according to homology descriptions provided herein.

"Immune checkpoint therapy" refers to the use of agents that inhibit immune checkpoint nucleic acids and/or proteins. Inhibition of one or more immune checkpoints can block or otherwise neutralize inhibitory signaling to thereby upregulate an immune response in order to more efficaciously treat cancer. Exemplary agents useful for inhibiting immune checkpoints include antibodies, small molecules, peptides, peptidomimetics, natural ligands, and derivatives of natural ligands, that can either bind and/or inactivate or inhibit immune checkpoint proteins, or fragments thereof; as well as RNA interference, antisense, nucleic acid aptamers, etc. that can downregulate the expression and/or activity of immune checkpoint nucleic acids, or fragments thereof. Exemplary agents for upregulating an immune response include antibodies against one or more immune checkpoint proteins block the interaction between the proteins and its natural receptor(s); a non-activating form of one or more immune checkpoint proteins (e.g., a dominant negative polypeptide); small molecules or peptides that block the interaction between one or more immune checkpoint proteins and its natural receptor(s); fusion proteins (e.g. the extracellular portion of an immune checkpoint inhibition protein fused to the Fc portion of an antibody or immunoglobulin) that bind to its natural receptor(s); nucleic acid molecules that block immune checkpoint nucleic acid transcription or translation; and the like. Such agents can directly block the interaction between the one or more immune checkpoints and its natural receptor(s) (e.g., antibodies) to prevent inhibitory signaling and upregulate an immune response. Alternatively, agents can indirectly block the interaction between one or more immune checkpoint proteins and its natural receptor(s) to prevent inhibitory signaling and upregulate an immune response. For example, a soluble version of an immune checkpoint protein ligand such as a stabilized extracellular domain can binding to its receptor to indirectly reduce the effective concentration of the receptor to bind to an appropriate ligand. In one embodiment, anti-PD-1 antibodies, anti-PD-L1 antibodies, and anti-CTLA-4 antibodies, either alone or in combination, are used to inhibit immune checkpoints.

"Ipilimumab" is a representative example of an immune checkpoint therapy. Ipilimumab (previously MDX-010; Medarex Inc., marketed by Bristol-Myers Squibb as YERVOY™) is a fully human anti-human CTLA-4 monoclonal antibody that blocks the binding of CTLA-4 to CD80 and CD86 expressed on antigen presenting cells, thereby, blocking the negative down-regulation of the immune responses elicited by the interaction of these molecules (see, for example, WO 2013/169971, U.S. Pat. Publ. 2002/0086014, and U.S. Pat. Publ. 2003/0086930.

The term "immune response" includes T cell mediated and/or B cell mediated immune responses. Immune responses can also include B- and T-cell independent and rely on macrophages and NK cells (along with other cell types) instead (innate immunity). Exemplary immune responses include T cell responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages.

The term "immunotherapeutic agent" can include any molecule, peptide, antibody or other agent which can stimulate a host immune system to generate an immune response to a tumor or cancer in the subject. Various immunotherapeutic agents are useful in the compositions and methods described herein.

The term "inhibit" includes the decrease, limitation, or blockage, of, for example a particular action, function, or interaction. In some embodiments, cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

The term "interaction", when referring to an interaction between two molecules, refers to the physical contact (e.g., binding) of the molecules with one another. Generally, such an interaction results in an activity (which produces a biological effect) of one or both of said molecules.

An "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a biomarker polypeptide or fragment thereof, in which the protein is separated from cellular components of the cells from which it is isolated or recombinantly produced. In one embodiment, the language "substantially free of cellular material" includes preparations of a biomarker protein or fragment thereof, having less than about 30% (by dry weight) of non-biomarker protein (also referred to herein as a "contaminating protein"), more preferably less than about 20% of non-biomarker protein, still more preferably less than about 10% of non-biomarker protein, and most preferably less than about 5% non-biomarker protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

A "kit" is any manufacture (e.g. a package or container) comprising at least one reagent, e.g. a probe or small molecule, for specifically detecting and/or affecting the expression of a marker of the present invention. The kit may be promoted, distributed, or sold as a unit for performing the methods of the present invention. The kit may comprise one or more reagents necessary to express a composition useful in the methods of the present invention. In certain embodiments, the kit may further comprise a reference standard, e.g., a nucleic acid encoding a protein that does not affect or regulate signaling pathways controlling cell growth, division, migration, survival or apoptosis. One skilled in the art can envision many such control proteins, including, but not limited to, common molecular tags (e.g., green fluorescent protein and beta-galactosidase), proteins not classified in any of pathway encompassing cell growth, division, migration, survival or apoptosis by GeneOntology reference, or ubiquitous housekeeping proteins. Reagents in the kit may be provided in individual containers or as mixtures of two or more reagents in a single container. In addition, instructional materials which describe the use of the compositions within the kit can be included.

The term "neoadjuvant therapy" refers to a treatment given before the primary treatment. Examples of neoadjuvant therapy can include chemotherapy, radiation therapy, and hormone therapy. For example, in treating breast cancer, neoadjuvant therapy can allows patients with large breast cancer to undergo breast-conserving surgery.

The "normal" level of expression of a biomarker is the level of expression of the biomarker in cells of a subject, e.g., a human patient, not afflicted with a cancer. An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

The term "pre-determined" biomarker amount and/or activity measurement(s) may be a biomarker amount and/or activity measurement(s) used to, by way of example only, evaluate a subject that may be selected for a particular treatment, evaluate a response to a treatment such as an anti-immune checkpoint inhibitor therapy, and/or evaluate the disease state. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements. In another embodiment, the amounts determined and/or compared in a method described herein are based on relative measurements, such as ratios (e.g., serum biomarker normalized to the expression of a housekeeping or otherwise generally constant biomarker). The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

The term "predictive" includes the use of a biomarker nucleic acid and/or protein status, e.g., over- or under-activity, emergence, expression, growth, remission, recurrence or resistance of tumors before, during or after therapy, for determining the likelihood of response of a cancer to anti-immune checkpoint treatment (e.g., therapeutic antibodies against CTLA-4, PD-1, PD-L1, and the like). Such predictive use of the biomarker may be confirmed by, e.g., (1) increased or decreased copy number (e.g., by FISH, FISH plus SKY, single-molecule sequencing, e.g., as described in the art at least at J. Biotechnol., 86:289-301, or qPCR), overexpression or underexpression of a biomarker nucleic acid (e.g., by ISH, Northern Blot, or qPCR), increased or decreased biomarker protein (e.g., by IHC), or increased or decreased activity, e.g., in more than about 5%, 6%, 7%, 8%, 9%, 10%, 11%, 12%, 13%, 14%, 15%, 20%, 25%, 30%, 40%, 50%, 60%, 70%, 80%, 90%, 95%, 100%, or more of assayed human cancers types or cancer samples; (2) its absolute or relatively modulated presence or absence in a biological sample, e.g., a sample containing tissue, whole blood, serum, plasma, buccal scrape, saliva, cerebrospinal fluid, urine, stool, or bone marrow, from a subject, e.g. a human, afflicted with cancer; (3) its absolute or relatively modulated presence or absence in clinical subset of patients with cancer (e.g., those responding to a particular immune checkpoint therapy or those developing resistance thereto).

The term "pre-malignant lesions" as described herein refers to a lesion that, while not cancerous, has potential for becoming cancerous. It also includes the term "pre-malignant disorders" or "potentially malignant disorders." In particular this refers to a benign, morphologically and/or histologically altered tissue that has a greater than normal risk of malignant transformation, and a disease or a patient's habit that does not necessarily alter the clinical appearance of local tissue but is associated with a greater than normal risk of precancerous lesion or cancer development in that tissue (leukoplakia, erythroplakia, erytroleukoplakia lichen planus (lichenoid reaction) and any lesion or an area which histological examination showed atypia of cells or dysplasia.

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

The term "probe" refers to any molecule which is capable of selectively binding to a specifically intended target molecule, for example, a nucleotide transcript or protein encoded by or corresponding to a biomarker nucleic acid. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

The term "prognosis" includes a prediction of the probable course and outcome of cancer or the likelihood of recovery from the disease. In some embodiments, the use of statistical algorithms provides a prognosis of cancer in an individual. For example, the prognosis can be surgery, development of a clinical subtype of cancer (e.g., solid tumors, such as lung cancer, melanoma, and renal cell carcinoma), development of one or more clinical factors, development of intestinal cancer, or recovery from the disease.

The term "response to immune checkpoint therapy" relates to any response of the hyperproliferative disorder (e.g., cancer) to an immune checkpoint therapy, preferably to a change in tumor mass and/or volume after initiation of neoadjuvant or adjuvant chemotherapy or as prolonged patient survival following treatment compared to patients not receiving the therapy. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Responses may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to biomarker measurements that were determined prior to administration of any cancer therapy. The outcome measurement may be pathologic response to therapy given in the neoadjuvant setting. Alternatively, outcome measures, such as overall survival and disease-free survival can be monitored over a period of time for subjects following cancer therapy for whom biomarker measurement values are known. In certain embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of a cancer therapy can be determined using well-known methods in the art, such as those described in the Examples section.

The term "resistance" refers to an acquired or natural resistance of a cancer sample or a mammal to a cancer therapy (i.e., being nonresponsive to or having reduced or limited response to the therapeutic treatment), such as having a reduced response to a therapeutic treatment (cessation of tumor shrinkage and development of tumor growth while receiving a given therapy) by 25% or more, for example, 30%, 40%, 50%, 60%, 70%, 80%, or more, to 2-fold, 3-fold, 4-fold, 5-fold, 10-fold, 15-fold, 20-fold or more. The reduction in response can be measured by comparing with the same cancer sample or mammal before the resistance is acquired, or by comparing with a different cancer sample or a mammal who is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi-drug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In some embodiments, the term "reverses resistance" means that the use of a second agent in combination with a primary cancer therapy (e.g., chemotherapeutic or radiation therapy) is able to produce a significant decrease in tumor volume at a level of statistical significance (e.g., p<0.05) when compared to tumor volume of untreated tumor in the circumstance where the primary cancer therapy (e.g., chemotherapeutic or radiation therapy) alone is unable to produce a statistically significant decrease in tumor volume compared to tumor volume of untreated tumor. This generally applies to tumor volume measurements made at a time when the untreated tumor is growing log rhythmically.

The terms "response" or "responsiveness" refers to an anti-cancer response, e.g. in the sense of reduction of tumor size or inhibiting tumor growth. The terms can also refer to an improved prognosis, for example, as reflected by an increased time to recurrence, which is the period to first recurrence censoring for second primary cancer as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive).

An "RNA interfering agent" as used herein, is defined as any agent which interferes with or inhibits expression of a target biomarker gene by RNA interference (RNAi). Such RNA interfering agents include, but are not limited to, nucleic acid molecules including RNA molecules which are homologous to the target biomarker gene of the present invention, or a fragment thereof, short interfering RNA (siRNA), and small molecules which interfere with or inhibit expression of a target biomarker nucleic acid by RNA interference (RNAi).

"RNA interference (RNAi)" is an evolutionarily conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see Coburn, G. and Cullen, B. (2002) *J. of Virology* 76(18):9225), thereby inhibiting expression of the target biomarker nucleic acid. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target biomarker nucleic acids. As used herein, "inhibition of target biomarker nucleic acid expression" or "inhibition of marker gene expression" includes any decrease in expression or protein activity or level of the target biomarker nucleic acid or protein encoded by the target biomarker nucleic acid. The decrease may be of at least 30%, 40%, 50%, 60%, 70%, 80%, 90%, 95% or 99% or more as compared to the expression of a target biomarker nucleic acid or the activity or level of the protein encoded by a target biomarker nucleic acid which has not been targeted by an RNA interfering agent.

The term "sample" used for detecting or determining the presence or level of at least one biomarker is typically whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method of the present invention further comprises obtaining the sample from the individual prior to detecting or determining the presence or level of at least one marker in the sample.

The term "sensitize" means to alter cancer cells or tumor cells in a way that allows for more effective treatment of the associated cancer with a cancer therapy (e.g., anti-immune checkpoint, chemotherapeutic, and/or radiation therapy). In some embodiments, normal cells are not affected to an extent that causes the normal cells to be unduly injured by the immune checkpoint therapy. An increased sensitivity or a reduced sensitivity to a therapeutic treatment is measured according to a known method in the art for the particular treatment and methods described herein below, including, but not limited to, cell proliferative assays (Tanigawa N, Kern D H, Kikasa Y, Morton D L, *Cancer Res* 1982; 42: 2159-2164), cell death assays (Weisenthal L M, Shoemaker R H, Marsden J A, Dill P L, Baker J A, Moran E M, Cancer Res 1984; 94: 161-173; Weisenthal L M, Lippman M E, Cancer Treat Rep 1985; 69: 615-632; Weisenthal L M, In: Kaspers G J L, Pieters R, Twentyman P R, Weisenthal L M, Veerman A J P, eds. Drug Resistance in Leukemia and Lymphoma. Langhorne, P A: Harwood Academic Publishers, 1993: 415-432; Weisenthal L M, Contrib Gynecol Obstet 1994; 19: 82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 25% or more, for example, 30%, 40%, 50%, 60%, 70%, 80%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy can be equally applied to methods for sensitizing hyperproliferative or otherwise cancerous cells (e.g., resistant cells) to the cancer therapy.

The term "synergistic effect" refers to the combined effect of two or more anti-immune checkpoint agents can be greater than the sum of the separate effects of the anticancer agents alone.

"Short interfering RNA" (siRNA), also referred to herein as "small interfering RNA" is defined as an agent which functions to inhibit expression of a target biomarker nucleic acid, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) *RNA* 9:493-501 incorporated by reference herein).

RNA interfering agents, e.g., siRNA molecules, may be administered to a patient having or at risk for having cancer, to inhibit expression of a biomarker gene which is overexpressed in cancer and thereby treat, prevent, or inhibit cancer in the subject.

The term "subject" refers to any healthy animal, mammal or human, or any animal, mammal or human afflicted with a cancer, e.g., lung, ovarian, pancreatic, liver, breast, prostate, and colon carcinomas, as well as melanoma and multiple myeloma. The term "subject" is interchangeable with "patient."

The term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods of the present invention may be administered in a sufficient amount to produce a reasonable benefit/risk ratio applicable to such treatment.

The terms "therapeutically-effective amount" and "effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. In some embodiments, the $LD_{50}$ (lethal dosage) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the agent relative to no administration of the agent. Similarly, the $ED_{50}$ (i.e., the concentration which achieves a half-maximal inhibition of symptoms) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. Also, Similarly, the $IC_{50}$ (i.e., the concentration which achieves half-maximal cytotoxic or cytostatic effect on cancer cells) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. In some embodiments, cancer cell growth in an assay can be inhibited by at least about 10%, 15%, 20%, 25%, 30%, 35%, 40%, 45%, 50%, 55%, 60%, 65%, 70%, 75%, 80%, 85%, 90%, 95%, or even 100%. In another embodiment, at least about a 10%, 15%, 20%, 25%, 30%, 35%, 40%, 45%, 50%, 55%, 60%, 65%, 70%, 75%, 80%, 85%, 90%, 95%, or even 100% decrease in a solid malignancy can be achieved.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a biomarker nucleic acid and normal post-transcriptional processing (e.g. splicing), if any, of the RNA transcript, and reverse transcription of the RNA transcript.

As used herein, the term "unresponsiveness" includes refractivity of immune cells to stimulation, e.g., stimulation via an activating receptor or a cytokine. Unresponsiveness can occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) *Science* 257:1134).

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA encoding a biomarker nucleic acid (or any portion thereof) can be used to derive the polypeptide amino acid sequence, using the genetic code to translate the DNA or RNA into an amino acid sequence. Likewise, for polypeptide amino acid sequence, corresponding nucleotide sequences that can encode the polypeptide can be deduced from the genetic code (which, because of its redundancy, will produce multiple nucleic acid sequences for any given amino acid sequence). Thus, description and/or disclosure herein of a nucleotide sequence which encodes a polypeptide should be considered to also include description and/or disclosure of the amino acid sequence encoded by the nucleotide sequence. Similarly, description and/or disclosure of a polypeptide amino acid sequence herein should be considered to also include description and/or disclosure of all possible nucleotide sequences that can encode the amino acid sequence.

Finally, nucleic acid and amino acid sequence information for the loci and biomarkers of the present invention (e.g., biomarkers listed in Table 1) are well known in the art and readily available on publicly available databases, such as the National Center for Biotechnology Information (NCBI). For example, exemplary nucleic acid and amino acid sequences derived from publicly available sequence databases are provided below.

TABLE 1

SEQ ID NO: 1 Human PBRM1 Transcript Variant 1 cDNA Sequence (NM_018313.4)

```
   1 gcggccgcgg ccggaggagc aatagcagca gccgtggcgg ccacggggcg gggcgcggcg
  61 gtcggtgacc gcggccgggg ctgcaggcgg cggagcggct ggaagttgga ttccatgggt
 121 tccaagagaa gaagagctac ctccccttcc agcagtgtca gcggggactt tgatgatggg
 181 caccattctg tgtcaacacc aggcccaagc aggaaaagga ggagactttc aatcttcca
 241 actgtagatc ctattgccgt gtgccatgaa ctctataata ccatccgaga ctataaggat
 301 gaacagggca gacttctctg tgagctcttc attagggcac aaagcgaag aaatcaacca
 361 gactattatg aagtggtttc tcagcccatt gacttgatga aaatccaaca gaaactaaaa
 421 atggaagagt atgatgatgt taatttgctg actgctgact ccagcttct ttttaacaat
 481 gcaaagtcct attataagcc agattctcct gaatataaag ccgcttgcaa actctgggat
 541 ttgtaccttc gaacaagaaa tgagtttgtt cagaaaggag aagcagatga cgaagatgat
 601 gatgaagatg ggcaagacaa tcagggcaca gtgactgaag atcttctcc agcttacttg
 661 aaggagatcc tggagcagct tcttgaagcc atagttgtag ctacaaatcc atcaggacgt
 721 ctcattagcg aactttttca gaaactgcct tctaaagtgc aatatccaga ttattatgca
 781 ataattaagg agcctataga tctcaagacc attgcccaga ggatacagaa tggaagctac
 841 aaaagtattc atgcaatggc caaagatata gatctcctcg caaaaaatgc caaaacttat
 901 aatgagcctg gctctcaagt attcaaggat gcaaattcaa ttaaaaaaat attttatatg
 961 aaaaaggctg aaattgaaca tcatgaaatg gctaagtcaa gtcttcgaat gaggactcca
1021 tccaacttgg ctgcagccag actgacaggt ccttcacaca gtaaaggcag ccttggtgaa
1081 gagagaaatc ccactagcaa gtattaccgt aataaaagag cagtacaagg aggtcgttta
1141 tcagcaatta caatggcact tcaatatggc tcagaaagtg aagaagatgc tgctttagct
1201 gctgcacgct atgaagaggg agagtcagaa gcagaaagca tcacttcctt tatggatgtt
1261 tcaaatcctt tttatcagct ttatgacaca gttaggagtt gtcggaataa ccaagggcag
1321 ctaatagctg aacctttta ccatttgcct tcaaagaaaa aatacctga ttattaccag
1381 caaattaaaa tgcccatatc actacaacag atccgaacaa aactgaagaa tcaagaatat
1441 gaaactttag atcatttgga gtgtgatctg aatttaatgt ttgaaaatgc caaacgctat
1501 aatgtgccca ttcagccat ctacaagcga gttctaaaat tgcagcaagt tatgcaggca
1561 aagaagaaag agcttgccag gagagacgat atcgaggacg agacagcat gatctcttca
1621 gccacctctg atactggtag tgccaaaaga aaaagtaaaa agaacataag aaagcagcga
1681 atgaaaatct tattcaatgt tgttcttgaa gctcgagagc aggttcagg cagaagactt
1741 tgtgacctat ttatggttaa accatccaaa aaggactatc ctgattatta taaaatcatc
1801 ttggagccaa tggacttgaa aataattgag cataacatcc gcaatgacaa atatgctggt
1861 gaagagggaa tgatagaaga catgaagctg atgttccgga tgccaggca ctataatgag
1921 gagggctccc aggtttataa tgatgcacat atcctggaga agttactcaa ggagaaaagg
1981 aaagagctgg gcccactgcc tgatgatgat gacatggctt ctcccaaact caagctgagt
2041 aggaagagtg gcatttctcc taaaaaatca aaatacatga ctccaatgca gcagaaacta
2101 aatgaggtct atgaagctgt aaagaactat actgataaga gggtcgccg cctcagtgcc
2161 atatttctga ggcttccctc tagatctgag ttgcctgact actatctgac tattaaaaag
2221 cccatggaca tggaaaaaat tcgaagtcac atgatggcca acaagtacca agatattgac
2281 tctatggttg aggactttgt catgatgttt aataatgcct gtacatacaa tgagccggag
```

TABLE 1-continued

```
2341 tctttgatct acaaagatgc tcttgttcta cacaaagtcc tgcttgaaac acgcagagac
2401 ctggagggag atgaggactc tcatgtccca aatgtgactt tgctgattca agagcttatc
2461 cacaatcttt tgtgtcagt catgagtcat caggatgatg agggaagatg ctacagcgat
2521 tctttagcag aaaattcctgc tgtggatccc aactttccta caaaccacc ccttacattt
2581 gacataatta ggaagaatgt tgaaaataat cgctaccgtc ggcttgattt atttcaagag
2641 catatgtttg aagtattgga acgagcaaga aggatgaatc ggacagattc agaaatatat
2701 gaagatgcag tagaacttca gcagttttt attaaaattc gtgatgaact ctgcaaaaat
2761 ggagagattc ttcttttcacc ggcactcagc tataccacaa acatttgca taatgatgtg
2821 gagaaagaga gaaaggaaaa attgccaaaa gaaatagagg aagataaact aaaacgagaa
2881 gaagaaaaaa gagaagctga aaagagtgaa gattcctctg tgctgcagg cctctcaggc
2941 ttacatcgca catacagcca ggactgtagc tttaaaaaca gcatgtacca tgttggagat
3001 tacgtctatg tggaacctgc agaggccaac ctacaaccac atatcgtctg tattgaaaga
3061 ctgtgggagg attcagctga aaagaagtt tttaagagtg actattacaa caaagttcca
3121 gttagtaaaa ttctaggcaa gtgtgtggtc atgtttgtca aggaatactt taagttatgc
3181 ccagaaaact tccgagatga ggatgttttt gtctgtgaat cacggtattc tgccaaaacc
3241 aaatctttta agaaaattaa actgtggacc atgcccatca gctcagtcag gtttgtccct
3301 cgggatgtgc ctctgcctgt ggttcgcgtg gcctctgtat ttgcaaatgc agataaaggt
3361 gatgatgaga gaatacaga caactcagag gacagtcgag ctgaagacaa ttttaacttg
3421 gaaaaggaaa aagaagatgt ccctgtggaa atgtccaatg gtgaaccagg ttgccactac
3481 tttgagcagc tccattacaa tgacatgtgg ctgaaggttg gcgactgtgt cttcatcaag
3541 tcccatggcc tggtgcgtcc tcgtgtgggc agaattgaaa aagtatgggt tcgagatgga
3601 gctgcatatt tttatggccc catcttcatt cacccagaag aaacagagca tgagcccaca
3661 aaaatgttct acaaaaaga agtatttctg agtaatctgg aagaaacctg ccccatgaca
3721 tgtattctcg gaaagtgtgc tgtgttgtca ttcaaggact tcctctcctg caggccaact
3781 gaaataccag aaaatgacat tctgcttttgt gagagccgct acaatgagag cgacaagcag
3841 atgaagaaat tcaaaggatt gaagaggttt tcactctctg ctaaagtggt agatgatgaa
3901 atttactact tcagaaaacc aattgttcct cagaaggagc catcacccctt gctgaaaaag
3961 aagatccagt tgctagaagc taaatttgcc gagttagaag gtggagatga tgatattgaa
4021 gagatgggag aagaagatag tgagtctacc ccaaagtctg ccaaaggcag tgcaaagaag
4081 gaaggctcca acggaaaaat caacatgagt ggctacatcc tgttcagcag tgagatgagg
4141 gctgtgatta aggcccaaca cccagactac tctttcgggg agctcagccg cctggtgggg
4201 acagaatgga gaaatcttga gacagccaag aaagcagaat atgaaggcat gatgggtggc
4261 tatccgccag gccttccacc tttgcagggc ccagttgatg gccttgttag catgggcagc
4321 atgcagccac ttcaccctgg ggggcctcca ccccaccatc ttccgccagg tgtgcctggc
4381 ctcccgggca tccaccacc gggtgtgatg aaccaaggag tggcccctat ggtagggact
4441 ccagcaccag gtggaagtcc atatggacaa caggtgggag ttttgggcc tccagggcag
4501 caggcaccac ctccatatcc cggcccacat ccagctggac cccctgtcat acagcagcca
4561 acaacacccca tgtttgtagc tcccccacca aagacccagc ggcttcttca ctcagaggcc
4621 tacctgaaat acattgaagg actcagtgcg gagtccaaca gcattagcaa gtgggatcag
4681 acactggcag ctcgaagacg cgacgtccat ttgtcgaaag aacaggagag ccgcctaccc
```

TABLE 1-continued

```
4741 tctcactggc tgaaaagcaa aggggcccac accaccatgg cagatgccct ctggcgcctt 4801 cgagatttga tgctccggga caccctcaac attcgccaag catacaacct agaaaatgtt 4861 taatcacatc attacgtttc ttttatatag aagcataaag agttgtggat cagtagccat 4921 tttagttact gggggtgggg ggaaggaaca aaggaggata attttttattg cattttactg 4981 tacatcacaa ggccattttt atatacggac acttttaata agctatttca atttgtttgt 5041 tatattaagt tgactttatc aaatacacaa agatttttt gcatatgttt ccttcgttta 5101 aaaccagttt cataattggt tgtatatgta gacttggagt tttatctttt tacttgttgc 5161 catggaactg aaaccattag aggttttgt cttggcttgg ggttttttgtt ttcttggttt 5221 tgggtttttt tatatatata tataaaagaa caaaatgaaa aaaacacac acacacaaga 5281 gtttacagat tagtttaaat tgataatgaa atgtgaagtt tgtcctagtt tacatcttag 5341 agaggggagt atacttgtgt ttgtttcatg tgcctgaata tcttaagcca ctttctgcaa 5401 aagctgtttc ttacagatga agtgctttct ttgaaaggtg gttatttagg ttttagatgt 5461 ttaatagaca cagcacattt gctctattaa ctcagaggct cactacagaa atatgtaatc 5521 agtgctgtgc atctgtctgc agctaatgta cctcctggac accaggaggg gaaaaagcac 5581 tttttcaatt gtgctgagtt agacatctgt gagttagact atggtgtcag tgattttgc 5641 agaacacgtg cacaccctg aggtatgttt aatctaggca ggtacgttta aggatatttt 5701 gatctattta taatgaattc acaatttatg cctataaatt tcagatgatt taaaatttta 5761 aacctgttac attgaaaaac attgaagttc gtcttgaaga aagcattaag gtatgcatgg 5821 aggtgattta ttttaaaca taacacctaa cctaacatgg gtaagagagt atggaactag 5881 atatgagctg tataagaagc ataattgtga acaagtagat tgattgcctt catatacaag 5941 tatgttttag tattccttat ttccttatta tcagatgtat ttttctttt aagtttcaat 6001 gttgttataa ttctcaacca gaaatttaat actttctaaa atatttttta aatttagctt 6061 gtgcttttga attacaggag aagggaatca taatttaata aaacgcttac tagaaagacc 6121 attacagatc ccaaacactt gggtttggtg accctgtctt tcttatatga ccctacaata 6181 aacatttgaa ggcagcatag gatggcagac agtaggaaca ttgtttcact tggcggcatg 6241 tttttgaaac ctgctttata gtaactgggt gattgccatt gtggtagagc ttccactgct 6301 gtttataatc tgagagagtt aatctcagag gatgcttttt tccttttaat ctgctatgaa 6361 tcagtaccca gatgtttaat tactgtactt attaaatcat gagggcaaaa gagtgtagaa 6421 tggaaaaaag tctcttgtat ctagatactt taaatatggg aggccctta acttaattgc 6481 ctttagtcaa ccactggatt tgaatttgca tcaagtattt taaataatat tgaatttaaa 6541 aaaatgtatt gcagtagtgt gtcagtacct tattgttaaa gtgagtcaga taaatcttca 6601 attcctggct atttgggcaa ttgaatcatc atggactgta taatgcaatc agattatttt 6661 gtttctagac atccttgaat tacaccaaag aacatgaaat ttagttgtgg ttaaattatt 6721 tatttatttc atgcattcat tttatttccc ttaaggtctg gatgagactt ctttggggag 6781 cctctaaaaa aattttttcac tggggggccac gtgggtcatt agaagccaga gctctcctcc 6841 aggctccttc ccagtgccta gaggtgctat aggaaacata gatccagcca ggggcttccc 6901 taaagcagtg cagcaccggc ccagggcatc actagacagg ccctaattaa gttttttta 6961 aaaagcctgt gtatttattt tagaatcatg ttttctgta tattaacttg ggggatatcg 7021 ttaatattta ggatataaga tttgaggtca gccatcttca aaaagaaaa aaaaattgac 7081 tcaagaaagt acaagtaaac tatacacctt tttttcataa gttttaggaa ctgtagtaat
```

TABLE 1-continued

```
7141 gtggcttaga aagtataatg gcctaaatgt tttcaaaatg taagttcctg tggagaagaa 7201 ttgtttatat tgcaaacggg gggactgagg ggaacctgta ggtttaaaac agtatgtttg 7261 tcagccaact gatttaaaag gcctttaact gttttggttg ttgttttttt tttaagccac 7321 tctcccttc ctatgaggaa gaattgagag gggcacctat ttctgtaaaa tccccaaatt 7381 ggtgttgatg attttgagct tgaatgtttt catacctgat taaaacttgg tttattctaa 7441 tttctgtatc atatcatctg aggtttacgt ggtaactagt cttataacat gtatgtatct 7501 ttttttttgtt gttcatctaa agcttttaa tccaataaa tacagagttt gcaaagtgat 7561 ttggattaac caggaaaaaa aaaaaaaaaa aa
```

SEQ ID NO: 2 Human PBRM1 Variant 1 Amino Acid Sequence (NP_060783.3)

```
   1 mgskrrrats psssysgdfd dghhsystpg psrkrrrlsn lptvdpiavc helyntirdy 61 kdeqgrllce lfirapkrrn qpdyyevvsq pidlmkiqqk lkmeeyddvn lltadfqllf 121 nnaksyykpd speykaackl wdlylrtrne fvqkgeadde dddedgqdnq gtvtegsspa 181 ylkeileqll eaivvatnps grliselfqk lpskvqypdy yaiikepidl ktiagriqng 241 syksihamak didllaknak tynepgsqvf kdansikkif ymkkaeiehh emakssrmr 301 tpsnlaaarl tgpshskgsl geernptsky yrnkravqgg rlsaitmalq ygseseedaa 361 laaaryeege seaesitsfm dvsnpfyqly dtvrscrnnq gqliaepfyh lpskkkypdy 421 yqqikmpisl qqirtklknq eyetldhlec dlnlmfenak rynvpnsaiy krvlklqqvm 481 qakkkelarr ddiedgdsmi ssatsdtgsa krkskknirk qrmkilfnvv learepgsgr 541 rlcdlfmvkp skkdypdyyk iilepmdlki iehnirndky ageegmiedm klmfrnarhy 601 neegsqvynd ahilekllke krkelgplpd dddmaspklk lsrksgispk kskymtpmqq 661 klnevyeavk nytdkrgrrl saiflrlpsr selpdyylti kkpmdmekir shmmankyqd 721 idsmvedfvm mfnnactyne pesliykdal vlhkvlletr rdlegdedsh vpnvtlliqe 781 lihnlfvsvm shqddegrcy sdslaeipav dpnfpnkppl tfdiirknve nnryrrldlf 841 qehmfevler arrmnrtdse iyedavelqq ffikirdelc kngeillspa lsyttkhlhn 901 dvekerkekl pkeieedklk reeekreaek sedssgaagl sglhrtysqd csfknsmyhv 961 gdyvyvepae anlqphivci erlwedsaek evfksdyynk vpvskilgkc vvmfvkeyfk 1021 lcpenfrded vfvcesryysa ktksfkkikl wtmpissvrf vprdvplpvv rvasvfanad 1081 kgddeknttdn sedsraednf nlekekedvp vemsngepgc hyfeqlhynd mwlkvgdcvf 1141 ikshglvrpr vgriekvwvr dgaayfygpi fihpeetehe ptkmfykkev flsnleetcp 1201 mtcilgkcav lsfkdflscr pteipendil lcesrynesd kqmkkfkglk rfslsakvvd 1261 deiyyfrkpi vpqkepspll ekkiqlleak faeleggddd ieemgeedse stpksakgsa 1321 kkegskrkin msgyilfsse mravikaqhp dysfgelsrl vgtewrnlet akkaeyegmm 1381 ggyppglppl qgpvdglvsm gsmqplhpgg ppphhlppgv pglpgipppg vmnqgvapmv 1441 gtpapggspy gqqvgvlgpp gqqapppypg phpagppviq qpttpmfvap ppktqrllhs 1501 eaylkyiegl saesnsiskw dqtlaarrrd vhlskeqesr lpshwlkskg ahttmadalw 1561 rlrdlmlrdt lnirqaynle nv
```

SEQ ID NO: 3 Human PBRM1 Transcript Variant 2 cDNA Sequence (NM_181042.4)

```
   1 gcggccgggg ctgcaggcgg cggagcggct ggcttgccaa cacttggtgt cacatgtgag 61 cctcccacat gtattcactc tccattccag ctctgtgatt gaactctgct cttattgact 121 agggggcagt tgggcaggca tgcctcattc ctggaattga cagtcattcc taataagttg
```

TABLE 1-continued

```
 181 gattccatgg gttccaagag aagaagagct acctcccctt ccagcagtgt cagcggggac
 241 tttgatgatg ggcaccattc tgtgtcaaca ccaggcccaa gcaggaaaag gaggagactt
 301 tccaatcttc caactgtaga tcctattgcc gtgtgccatg aactctataa taccatccga
 361 gactataagg atgaacaggg cagacttctc tgtgagctct tcattagggc accaaagcga
 421 agaaatcaac cagactatta tgaagtggtt tctcagccca ttgacttgat gaaaatccaa
 481 cagaaactaa aaatggaaga gtatgatgat gttaatttgc tgactgctga cttccagctt
 541 cttttttaaca atgcaaagtc ctattataag ccagattctc ctgaatataa agccgcttgc
 601 aaactctggg atttgtacct tcgaacaaga aatgagtttg ttcagaaagg agaagcagat
 661 gacgaagatg atgatgaaga tgggcaagac aatcagggca cagtgactga aggatcttct
 721 ccagcttact tgaaggagat cctggagcag cttcttgaag ccatagttgt agctacaaat
 781 ccatcaggac gtctcattag cgaactttt cagaaactgc cttctaaagt gcaatatcca
 841 gattattatg caataattaa ggagcctata gatctcaaga ccattgccca gaggatacag
 901 aatggaagct acaaaagtat tcatgcaatg gccaagatta tagatctcct cgcaaaaaat
 961 gccaaaactt ataatgagcc tggctctcaa gtattcaagg atgcaaattc aattaaaaaa
1021 atattttata tgaaaaaggc tgaaattgaa catcatgaaa tggctaagtc aagtcttcga
1081 atgaggactc catccaactt ggctgcagcc agactgacag gtccttcaca cagtaaaggc
1141 agccttggtg aagagagaaa tcccactagc aagtattacc gtaataaaag agcagtacaa
1201 ggaggtcgtt tatcagcaat acaatggca cttcaatatg gctcagaaag tgaagaagat
1261 gctgctttag ctgctgcacg ctatgaagag ggagagtcag aagcagaaag catcacttcc
1321 tttatggatg tttcaaatcc ttttttatcag ctttatgaca cagttaggag ttgtcggaat
1381 aaccaagggc agctaatagc tgaacctttt taccatttgc cttcaaagaa aaaatacct
1441 gattattacc agcaaattaa aatgcccata tcactacaac agatccgaac aaaactgaag
1501 aatcaagaat atgaaacttt agatcatttg gagtgtgatc tgaatttaat gtttgaaaat
1561 gccaaacgct ataatgtgcc caattcagcc atctacaagc gagttctaaa attgcagcaa
1621 gttatgcagg caaagaagaa agagcttgcc aggagagacg atatcgagga cggagacagc
1681 atgatctctt cagccacctc tgatactggt agtgccaaaa gaaaaagtaa aagaacata
1741 agaaagcagc gaatgaaaat cttattcaat gttgttcttg aagctcgaga gccaggttca
1801 ggcagaagac tttgtgacct atttatggtt aaaccatcca aaaaggacta tcctgattat
1861 tataaaatca tcttggagcc aatggacttg aaaataattg agcataacat ccgcaatgac
1921 aaatatgctg gtgaagaggg aatgatagaa gacatgaagc tgatgttccg gaatgccagg
1981 cactataatg aggagggctc ccaggtttat aatgatgcac atatcctgga gaagttactc
2041 aaggagaaaa ggaaagagct gggcccactg cctgatgatg atgacatggc ttctcccaaa
2101 ctcaagctga gtaggaagag tggcatttct cctaaaaaat caaatacat gactccaatg
2161 cagcagaaac taaatgaggt ctatgaagct gtaaagaact atactgataa gaggggtcgc
2221 cgcctcagtg ccatatttct gaggcttccc tctagatctg agttgcctga ctactatctg
2281 actattaaaa agcccatgga catggaaaaa attcgaagtc acatgatggc caacaagtac
2341 caagatattg actctatggt tgaggacttt gtcatgatgt ttaataatgc ctgtacatac
2401 aatgagccgg agtctttgat ctacaaagat gctcttgttc tacacaaagt cctgcttgaa
2461 acacgcagag acctggaggg agatgaggac tctcatgtcc caaatgtgac tttgctgatt
2521 caagagctta tccacaatct ttttgtgtca gtcatgagtc atcaggatga tgagggaaga
```

TABLE 1-continued

```
2581 tgctacagcg attctttagc agaaattcct gctgtggatc ccaactttcc taacaaacca
2641 cccttacat ttgacataat taggaagaat gttgaaaata atcgctaccg tcggcttgat
2701 ttatttcaag agcatatgtt tgaagtattg gaacgagcaa gaaggatgaa tcggacagat
2761 tcagaaatat atgaagatgc agtagaactt cagcagtttt ttattaaaat tcgtgatgaa
2821 ctctgcaaaa atggagagat tcttctttca ccggcactca gctataccac aaaacatttg
2881 cataatgatg tggagaaaga gagaaaggaa aaattgccaa agaaatagaa ggaagataaa
2941 ctaaaacgag aagaagaaaa aagagaagct gaaaagagtg aagattcctc tggtgctgca
3001 ggcctctcag gcttacatcg cacatacagc caggactgta gctttaaaaa cagcatgtac
3061 catgttggag attacgtcta tgtggaacct gcagaggcca acctacaacc acatatcgtc
3121 tgtattgaaa gactgtggga ggattcagct ggtgaaaaat ggttgtatgg ctgttggttt
3181 taccgaccaa atgaaacatt ccacctggct acacgaaaat ttctagaaaa agaagttttt
3241 aagagtgact attacaacaa agttccagtt agtaaaattc taggcaagtg tgtggtcatg
3301 tttgtcaagg aatactttaa gttatgccca gaaaacttcc gagatgagga tgtttttgtc
3361 tgtgaatcac ggtattctgc caaaaccaaa tcttttaaga aaattaaact gtggaccatg
3421 cccatcagct cagtcaggtt tgtccctcgg gatgtgcctc tgcctgtggt tcgcgtggcc
3481 tctgtatttg caaatgcaga taaggtgat gatgagaaga atacagacaa ctcagaggac
3541 agtcgagctg aagacaattt taacttggaa aaggaaaaag aagatgtccc tgtggaaatg
3601 tccaatggtg aaccaggttg ccactacttt gagcagctcc attacaatga catgtggctg
3661 aaggttggcg actgtgtctt catcaagtcc catggcctgg tgcgtcctcg tgtgggcaga
3721 attgaaaaag tatgggttcg agatggagct gcatattttt atggcccat cttcattcac
3781 ccagaagaaa cagagcatga gcccacaaaa atgttctaca aaaagaagt atttctgagt
3841 aatctggaag aaacctgccc catgacatgt attctcggaa agtgtgctgt gttgtcattc
3901 aaggacttcc tctcctgcag gccaactgaa ataccagaaa atgacattct gctttgtgag
3961 agccgctaca atgagagcga caagcagatg aagaaattca aaggattgaa gaggttttca
4021 ctctctgcta aagtggtaga tgatgaaatt tactacttca gaaaaccaat tgttcctcag
4081 aaggagccat cacctttgct ggaaaagaag atccagttgc tagaagctaa atttgccgag
4141 ttagaaggtg gagatgatga tattgaagag atgggagaag aagatagtga ggtcattgaa
4201 cctccttctc tacctcagct tcagaccccc ctggccagtg agctggacct catgccctac
4261 acaccccac agtctacccc aaagtctgcc aaaggcagtg caaagaagga aggctccaaa
4321 cggaaaatca acatgagtgg ctacatcctg ttcagcagtg agatgagggc tgtgattaag
4381 gcccaacacc cagactactc tttcggggag ctcagccgcc tggtggggac agaatggaga
4441 aatcttgaga cagccaagaa agcagaatat gaaggtgtga tgaaccaagg agtggcccct
4501 atggtaggga ctccagcacc aggtggaagt ccatatggac aacaggtggg agttttgggg
4561 cctccagggc agcaggcacc acctccatat cccggcccac atccagctgg accccctgtc
4621 atacagcagc caacaacacc catgtttgta gctcccccac caaagaccca gcggcttctt
4681 cactcagagg cctacctgaa atacattgaa ggactcagtg cggagtccaa cagcattagc
4741 aagtgggatc agacactggc agctcgaaga gcgcgacgtcc atttgtcgaa agaacaggag
4801 agccgcctac cctctcactg gctgaaaagc aaaggggccc acaccaccat ggcagatgcc
4861 ctctggcgcc ttcgagattt gatgctccgg gacacccctca acattcgcca agcatacaac
4921 ctagaaaatg tttaatcaca tcattacgtt tcttttatat agaagcataa agagttgtgg
```

TABLE 1-continued

```
4981 atcagtagcc attttagtta ctgggggtgg ggggaaggaa caaaggagga taatttttat 5041 tgcattttac tgtacatcac aaggccattt ttatatacgg acacttttaa taagctattt 5101 caatttgttt gttatattaa gttgacttta tcaaatacac aaagattttt ttgcatatgt 5161 ttccttcgtt taaaaccagt ttcataattg gttgtatatg tagacttgga gttttatctt 5221 tttacttgtt gccatggaac tgaaaccatt agaggttttt gtcttggctt ggggttttttg 5281 ttttcttggt tttgggtttt tttatatata tatataaaag aacaaaatga aaaaaaacac 5341 acacacacaa gagtttacag attagtttaa attgataatg aaatgtgaag tttgtcctag 5401 tttacatctt agagagggga gtatacttgt gtttgtttca tgtgcctgaa tatcttaagc 5461 cactttctgc aaaagctgtt tcttacagat gaagtgcttt ctttgaaagg tggttattta 5521 ggttttagat gtttaataga cacagcacat ttgctctatt aactcagagg ctcactacag 5581 aaatatgtaa tcagtgctgt gcatctgtct gcagctaatg tacctcctgg acaccaggag 5641 gggaaaaagc acttttttcaa ttgtgctgag ttagacatct gtgagttaga ctatggtgtc 5701 agtgattttt gcagaacacg tgcacaaccc tgaggtatgt ttaatctagg caggtacgtt 5761 taaggatatt ttgatctatt tataatgaat tcacaattta tgcctataaa tttcagatga 5821 tttaaaattt taaacctgtt acattgaaaa acattgaagt tcgtcttgaa gaaagcatta 5881 aggtatgcat ggaggtgatt tatttttaaa cataacacct aacctaacat gggtaagaga 5941 gtatggaact agatatgagc tgtataagaa gcataattgt gaacaagtag attgattgcc 6001 ttcatataca agtatgtttt agtattcctt atttccttat tatcagatgt atttttttctt 6061 ttaagtttca atgttgttat aattctcaac cagaaattta atactttcta aaatattttt 6121 taaatttagc ttgtgctttt gaattacagg agaagggaat cataatttaa taaaacgctt 6181 actagaaaga ccattacaga tcccaaacac ttgggtttgg tgaccctgtc tttcttatat 6241 gaccctacaa taaacatttg aaggcagcat aggatggcag acagtaggaa cattgtttca 6301 cttggcggca tgttttttgaa acctgcttta tagtaactgg gtgattgcca ttgtggtaga 6361 gcttccactg ctgtttataa tctgagagag ttaatctcag aggatgcttt tttccttttta 6421 atctgctatg aatcagtacc cagatgttta attactgtac ttattaaatc atgagggcaa 6481 aagagtgtag aatggaaaaa agtctcttgt atctagatac tttaaatatg ggaggcccttt 6541 taacttaatt gcctttagtc aaccactgga tttgaatttg catcaagtat tttaaataat 6601 attgaattta aaaaaatgta ttgcagtagt gtgtcagtac cttattgtta aagtgagtca 6661 gataaatctt caattcctgg ctatttgggc aattgaatca tcatgactg tataatgcaa 6721 tcagattatt ttgtttctag acatccttga attacaccaa agaacatgaa atttagttgt 6781 ggttaaatta tttatttatt tcatgcattc attttatttc ccttaaggtc tggatgagac 6841 ttctttgggg agcctctaaa aaaattttc actgggggcc acgtgggtca ttagaagcca 6901 gagctctcct ccaggctcct tcccagtgcc tagaggtgct ataggaaaca tagatccagc 6961 caggggcttc cctaaagcag tgcagcaccg gcccagggca tcactagaca ggccctaatt 7021 aagttttttt taaaaagcct gtgtatttat tttagaatca tgttttttctg tatattaact 7081 tgggggatat cgttaatatt taggatataa gatttgaggt cagccatctt caaaaaagaa 7141 aaaaaaattg actcaagaaa gtacaagtaa actatacacc ttttttttcat aagttttagg 7201 aactgtagta atgtggctta gaaagtataa tggcctaaat gttttcaaaa tgtaagttcc 7261 tgtggagaag aattgtttat attgcaaacg ggggactga ggggaacctg taggtttaaa 7321 acagtatgtt tgtcagccaa ctgatttaaa aggccttttaa ctgttttggt tgttgttttt
```

TABLE 1-continued

```
7381 tttttaagcc actctcccct tcctatgagg aagaattgag aggggcacct atttctgtaa 7441 aatccccaaa ttggtgttga tgattttgag cttgaatgtt ttcatacctg attaaaactt 7501 ggtttattct aatttctgta tcatatcatc tgaggtttac gtggtaacta gtcttataac 7561 atgtatgtat ctttttttg ttgttcatct aaagcttttt aatccaaat
```

SEQ ID NO: 4 Human PBRM1 Variant 2 Amino Acid Sequence (NP_851385.1)

```
   1 mgskrrrats pssssysgdfd dghhsystpg psrkrrrlsn lptvdpiavc helyntirdy 61 kdeqgrllce lfirapkrrn qpdyyevvsq pidlmkiqqk lkmeeyddvn lltadfqllf 121 nnaksyykpd speykaackl wdlylrtrne fvqkgeadde dddedgqdnq gtvtegsspa 181 ylkeileqll eaivvatnps grliselfqk lpskvqypdy yaiikepidl ktiaqrigng 241 syksihamak didllaknak tynepgsqvf kdansikkif ymkkaeiehh emaksslrmr 301 tpsnlaaarl tgpshskgsl geernptsky yrnkravqgg rlsaitmalq ygseseedaa 361 laaaryeege seaesitsfm dvsnpfyqly dtvrscrnnq gqliaepfyh lpskkkypdy 421 yqqikmpisl qqirtklknq eyetldhlec dlnlmfenak rynvpnsaiy krvlklqqvm 481 qakkkelarr ddiedgdsmi ssatsdtgsa krkskknirk qrmkilfnvv learepgsgr 541 rlcdlfmvkp skkdypdyyk iilepmdlki iehnirndky ageegmiedm klmfrnarhy 601 neegsqvynd ahilekllke krkelgplpd dddmaspklk lsrksgispk kskymtpmqq 661 klnevyeavk nytdkrgrrl saiflrlpsr selpdyylti kkpmdmekir shmmankyqd 721 idsmvedfvm mfnnactyne pesliykdal vlhkvlletr rdlegdedsh vpnvtlliqe 781 lihnlfvsvm shqddegrcy sdslaeipav dpnfpnkppl tfdiirknve nnryrrldlf 841 qehmfevler arrmnrtdse iyedavelqq ffikirdelc kngeillspa lsyttkhlhn 901 dvekerkekl pkeieedklk reeekreaek sedssgaagl sglhrtysqd csfknsmyhv 961 gdyvyvepae anlqphivci erlwedsage kwlygcwfyr pnetfhlatr kflekevfks 1021 dyynkvpvsk ilgkcvvmfv keyfklcpen frdedvfvce srysaktksf kkiklwtmpi 1081 ssvrfvprdv plpvvrvasv fanadkgdde kntdnsedsr aednfnleke kedvpvemsn 1141 gepgchyfeq lhyndmwlkv gdcvfikshg lvrprvgrie kvwvrdgaay fygpifihpe 1201 eteheptkmf ykkevflsnl eetcpmtcil gkcavlsfkd flscrpteip endillcesr 1261 ynesdkqmkk fkglkrfsls akvvddeiyy frkpivpqke pspllekkiq lleakfaele 1321 ggdddieemg eedseviepp slpqlqtpla seldlmpytp pqstpksakg sakkegskrk 1381 inmsgyilfs semravikaq hpdysfgels rlvgtewrnl etakkaeyeg vmnqgvapmv 1441 gtpapggspy gqqvgvlgpp gqqapppypg phpagppviq qpttpmfvap ppktqrllhs 1501 eaylkyiegl saesnsiskw dqtlaarrrd vhlskeqesr lpshwlkskg ahttmadalw 1561 rlrdlmlrdt lnirqaynle nv
```

SEQ ID NO: 5 Mouse PBRM1 cDNA Sequence (NM_001081251.1)

```
   1 ggatttacgg cagcactggg aggggtgagg gcggtgaggg cggcgggtgc cggagagacg 61 gccgcggcca gaggagcgct agcagccgtg gcggccacgg ggcggggctc ggcggtcggg 121 gaccgcagcc ggggctgcag gcggcggagc ggcgggcttg ccaacacttg gtgtcacatg 181 tgagcctccc acatgtgtgc actctccatt ccagctctgt gattgaactc tgctcttatt 241 gactagggg cacttgggca ggcatgcttc attcctggag ttgacagtca tttcataaga 301 agttggattc catgggttcc aagagaagaa gagccacctc tccttccagc agtgtcagtg 361 gagactttga tgacgggcac cattctgtgc ctacaccagg cccaagcagg aaaggagaa
```

TABLE 1-continued

```
 421 gactgtccaa tcttccaact gtagatccta ttgctgtgtg ccatgaactc tataacacca
 481 tccgagacta aaggatgaa cagggcagac tcctctgtga gctgttcatt agggctccaa
 541 agcggagaaa tcaaccagac tattatgaag tggtttctca gcccattgac ttgatgaaaa
 601 tccaacagaa acttaaaatg gaagagtatg atgatgttaa tctactgact gctgacttcc
 661 agctgctttt taacaatgca aaggcctact ataagccaga ttcccctgag tataaagctg
 721 cttgtaaact ctgggatttg taccttcgaa caagaaatga gtttgttcag aaaggagaag
 781 cagacgatga agatgatgac gaagatgggc aagacaatca aggcacactg gctgacggct
 841 cttctccagg ttatctgaag gagatcctgg agcagcttct tgaagccata gttgtagcca
 901 caaatccatc aggacggctc atcagtgaac ttttcagaa actgccttcc aaagtgcaat
 961 atccagacta ttatgcaata attaaggaac ctatagatct caagaccatt gctcagagga
1021 tacagaatgg aagctacaaa agtatacacg caatggccaa agatatagat cttctagcaa
1081 aaaatgccaa acatacaat gagcctgggt ctcaagtatt caaggatgcc aattcgatta
1141 aaaaaatatt ttatatgaaa aaggcagaaa ttgaacatca tgaaatgact aaatcaagtc
1201 ttcgaataag gactgcatca aatttggctg cagccaggct gacaggtcct tcgcacaata
1261 aaagcagcct tggtgaagaa agaaacccca ctagcaagta ttaccgtaat aaaagagcag
1321 tccaagggg tcgcttgtca gcaattacca tggcacttca gtatggatca gagagtgaag
1381 aggacgctgc tttagctgct gcacgctatg aagaagggga atctgaagca gagagcatca
1441 cttccttcat ggacgtttcc aaccccttc atcagcttta cgacacagtt aggagctgta
1501 ggaatcacca agggcagctc atagctgaac ctttcttcca tttgccttca aagaaaaaat
1561 acccagatta ttatcagcaa attaaaatgc ccatatcact tcaacagatc agaacaaagc
1621 taaagaacca agaatatgaa actttagatc atttggagtg tgatctgaat ttaatgtttg
1681 aaaatgccaa acgttataac gttcccaatt cagccatcta taagcgagtt ctaaaactgc
1741 agcaagtcat gcaggcaaag aagaaggagc ttgcgaggag agatgacatt gaggacggag
1801 acagcatgat ctcctcagcc acttctgaca ctggtagtgc caaaaggaaa aggaatactc
1861 atgacagtga gatgttgggt ctcaggaggc tatccagtaa aaagaacata agaaaacagc
1921 gaatgaaaat tttattcaat gttgttcttg aagctcgaga gccaggttca ggcagaagac
1981 tttgcgatct atttatggtt aagccatcca agaaggacta tcctgattat tataaaatca
2041 tcttagagcc aatggacctg aaaataattg agcataacat ccgaaatgac aaatatgcag
2101 gtgaagaagg aatgatggaa gacatgaaac tcatgttccg caatgccagg cactacaatg
2161 aggagggctc ccaggtatac aatgatgccc atatcctgga gaagttactc aaagataaaa
2221 ggaaagagct gggccctctg cctgatgatg atgcatggc ttctcccaaa cttaaattga
2281 gtaggaagag tggtgtttct cctaagaaat caaagtacat gactccaatg cagcagaaac
2341 tgaatgaagt gtatgaagct gtaaagaact atactgataa gagggtcgc cgccttagtg
2401 ctatatttct aagactcccc tctagatcag agctgcctga ctactacctg accattaaaa
2461 agcccatgga catggaaaaa attcgaagtc acatgatggc aaacaagtac caagacatag
2521 attctatggt agaggacttt gtcatgatgt ttaataatgc ctgtacctac aatgaaccag
2581 agtctttgat ctacaaagat gcccttgtac tgcataaagt cctccttgag actcggagag
2641 acctggaggg agatgaggat tctcatgtcc ctaatgtgac gttgctgatt caagagctca
2701 tccataacct ttttgtgtca gtcatgagtc atcaggatga cgaagggagg tgttacagcg
2761 actccttagc agaaattcct gctgtggatc ccaactctcc caataaacct ccccttacat
```

TABLE 1-continued

```
2821 ttgacattat caggaaaaat gttgaaagta atcggtatcg gcgacttgat ttatttcagg
2881 agcatatgtt tgaagtattg gaacgggcaa gaaggatgaa ccggacagat tccgaaatat
2941 atgaggatgc tgtagaactt cagcagtttt ttattagaat tcgtgatgaa ctctgcaaaa
3001 atggagagat ccttctttct ccagcactca gctataccac aaaacacttg cataacgatg
3061 tggaaaaaga aaaaaggaa aaattgccta agaaataga ggaagataaa ctaaaacgcg
3121 aagaagaaaa aagagaagct gaaaaaagtg aagattcctc aggtactaca ggcctctcag
3181 gcttacatcg tacatacagc caggactgca gctttaagaa cagcatgtat catgtcggag
3241 attatgtcta tgttgaacct gcggaggcca atctacaacc acatatagtg tgtattgaga
3301 gactgtggga ggattcagct ggtgaaaaat ggttgtacgg ctgttggttt tatcggccaa
3361 atgaaacatt ccatttggct acacgaaaat ttctagaaaa agaagttttt aagagtgact
3421 actacaataa agtacctgtt agtaaaattc taggcaaatg tgtagtcatg tttgtcaagg
3481 aatactttaa attatgtcca gaaactttc gcgatgagga tgttttttgtc tgtgaatcga
3541 ggtattctgc caaaaccaaa tcttttaaga aattaaact gtggaccatg cccatcagtt
3601 cagttagatt tgtccctcgg gatgtgcctt tgcctgtggt ccgagtggcc tctgtgtttg
3661 caaatgcaga taaggggat gatgagaaga atacagacaa ctcagatgac aatagagctg
3721 aagacaattt taacttggaa aaggaaaaag aagatgttcc tgtggagatg tccaatggtg
3781 agccaggttg ccactacttt gagcagcttc ggtacaatga catgtggctg aaggttggtg
3841 attgtgtctt catcaaatcc cacggcttgg tgcgccctcg tgtgggcaga attgagaaag
3901 tatgggtccg agatggagct gcatattttt atggccctat cttcattcat ccagaagaaa
3961 cagaacatga gcccacaaaa atgttctaca aaaagaagt gtttctgagt aatctggaag
4021 agacctgccc tatgagttgt attctgggga atgtgcagt gctgtcattc aaggacttcc
4081 tctcctgcag gccaactgaa ataccagaaa atgacattct gctttgtgag agccgctata
4141 atgagagtga caagcagatg aagaagttca agggtttgaa gaggttttca ctctctgcta
4201 aagttgtaga tgatgaaatc tactacttca gaaaaccaat cattcctcag aaggaaccct
4261 cacctttgtt agaaaagaag atacaattgc tagaagctaa atttgcagag ttagaaggag
4321 gagatgatga tattgaggag atgggagaag aggatagtga agtcattgaa gctccatctc
4381 tacctcaact gcagacaccc ctggccaatg agttggacct catgccctat acaccccac
4441 agtctacccc aaagtctgcc aaaggcagtg caaagaagga agttctaaa cgaaaaatca
4501 acatgagtgg ctacattttg ttcagcagtg aaatgagagc tgtgattaaa gcccagcacc
4561 cagactactc ttttgggag ctcagcagac tggtggggac agaatggaga aaccttgaaa
4621 cagccaagaa agcagaatat gaagagcggg cagctaaagt tgctgagcag caggagagag
4681 agcgagcagc acagcaacag cagccgagtg cttctccccg agcaggcacc cctgtggggg
4741 ctctcatggg ggtggtgcca ccaccaacac caatggggat gctcaatcag cagttgacac
4801 ctgttgcagg catgatgggt ggctatccgc caggccttcc accttttgcag ggcccagttg
4861 atggccttgt tagcatgggc agcatgcagc cacttcaccc tggggggcct ccacctcacc
4921 atcttccgcc aggtgtgcct ggcctcccag gcatcccacc accgggtgtg atgaatcaag
4981 gagtagcccc catggtaggg actccagcac caggtgaag tccgtatgga caacaggtag
5041 gagttttggg acctccaggg cagcaggcac cacctccata tcctggtcct catccagctg
5101 gccccctgt catacagcag ccaacaacgc ccatgtttgt ggctccccca ccaaagaccc
5161 aaaggcttct ccactcagag gcctacctga aatacattga aggactcagt gctgaatcca
```

TABLE 1-continued

```
5221 acagcattag caagtgggac caaactttgg cagctcgaag acgggatgtc catttgtcca
5281 aagaacagga gagccgccta ccttctcact ggctcaaaag taaaggggca cacaccacca
5341 tggcagatgc cctctggcgc ctacgggatt taatgcttcg agacactctc aacatccgac
5401 aggcatacaa cctagaaaat gtttaatcac atcactgttt cttctgtgga agcaaagagt
5461 tgtggagcgg tagccatttt agttactggg gtgggaggga ggaacaaagg atgataattt
5521 ttattgcatt ttattgtaca tcacacagcc attttatat aaggacactt ttaataagct
5581 atttcaaatt tggttttgtt acattaagtt gactatcaaa tacacaaaag atttttttg
5641 catatgtttc ctttgtttaa aaccagtttc ataattggtt atatatagta atagttttat
5701 ctttacttgt taaaggactt aaatcatcaa aggttttggc ttggcttagg gttttcgttt
5761 tcttttttat aaatatatat tatatatata tacacatata aaagaaaaaa tgaaaaaaaa
5821 gtttacaaat ttaagttgac aatgaaatgt gaagttggtc ctagtttaca tcttagagga
5881 atgtatatgt atgttttaca tgcctaaata tctgcaggtt ttcttacagg taaagcgaag
5941 tgctttgaaa agtttagatt atacatgtgt gacagatgcg gcatatttgc tctattaaca
6001 cagaggctta ctatagaaat ctaaagtcaa tgctgtacat ccatccagtt agtgtaactg
6061 aagggaaatg taactttgtg ctgagttaga catctgtatt gtcagtgatt cttgtagaat
6121 atgtgctcag atctgagtta tatttagttt tggaaggtaa gttgaagagt acttttgatc
6181 agtttatgat tcagtttatg attttagttt ttgccttcat gttatacatt tatgatttga
6241 aactgtacat ctgttacctt gaaaaacatt gaagaaagta ctgaagtgtg catggaggtg
6301 gtttaagcat aatacttaac ccaagaaaga gtgtaagtgg acacaagctg tgcctgcaca
6361 tagctgtgca gggtagactg cctacataca catggccggg attctttatt tccttgttat
6421 caattatagt gctttgtttg tttcagggtt ggaattctca accagaaata atactttcta
6481 aaatatttta aaattcagct tgtgctttgg attatagaag gaattatac tttaagaaaa
6541 tgttcacaaa aaaaaaaaa aaaaaaggac tattacagat cccaatactt ggatttggtg
6601 accttgtctt tctttctttt cttgagacat ggtcctacta ccaaccctgg ctggactgga
6661 gctcagtgta tagaccaggc tagtctcaaa ctctgcctct tcctcccaag tgctgggatt
6721 aagggcaggt accatagtgc tcagcaacca caaccctgtc tttccaacac ggccctagcg
6781 taagcactga ggcagtgtgc agtgctcagg cagcagcaaa catttcccgg gggtggtttt
6841 gaacctgctt gggtggttgt gtggtgctga cgctgccact gccctgttgt tcattgagaa
6901 tgattgttaa atgacactct tcctttagaa tataacggat cagtactcat gtttaattgc
6961 catgcttaat aaatcatgag aacaaaagag tatagaatgg aaagcattcc ctggtagcta
7021 ctttaaatac aggagccctg taacttaata ccagtagtca accactggat ctcagttttc
7081 atcaagtatt ttaaataaat aatcttaaat tttaaaatac gtactgcaga gtatgccagt
7141 atcttattgt taaaactgaa tcaaataaat cttcgattcc tggttatttg gaccattgac
7201 tcatcatgga ctatataatg taataagatt cttttctctt aaggtatcct tgaattacac
7261 caaagaacca gaaacttaat tttggttaaa ttatttattt atttcatgca ttaattttct
7321 ttttcttttt aaaggtttag atgaggctcc ttagggagtc tctaaaaccg cttcactatc
7381 agcaaccagg agtactagaa gccagagcac tcttcctcct ggctcctccc cagtgctcta
7441 gtgctgtagg aaccaagagc cagccccagg ttccccgagg cagtaaaaat ccagcacagg
7501 gggctgtgtc cctaaggcaa gccctgatta ccttttaaaaa aaccaaaaa aacaaacaaa
7561 aaaaaaaaac ctaattaact aaagcattta aggcactatt tattttagaa tcatgctttt
```

TABLE 1-continued

```
7621 gaagagcatc agtgattact tagggtgtaa tatgtaaaga tcagacatct ccaaaaacag 7681 aaaaagtaca agtaaacaac acactttctc atgactttta agaactgtag taatgtggct 7741 taggaaatat aatggcctaa ttgttttcaa aatgtaagtt cctgtgaaga attttgttta 7801 tattgggttg gggacctata ggtttaaaat agaatgtcag tcagctgact taaaaaacat 7861 tggtttact aagtctgcct tccccttcta aggaagaact gagtgggtaa gggacaggtg 7921 tgtaaaatct ccaaatggat gttacagctt tcagcttgaa cgtttgtttc cagacctgat 7981 taaaatttgg tttattctaa tttctgtact atatcatctg aggttttaag tggtaactgg 8041 ttctatacca tgtatgtatc atatgtttgt tcatcaaagc tttttaatcc aaataaaaac 8101 aacagtttgc aaagtga
```

SEQ ID NO: 6 Mouse PBRM1 Amino Acid Sequence (NP_001074720.1)

```
   1 mgskrrrats psssysgdfd dghhsvptpg psrkrrrlsn lptvdpiavc helyntirdy
  61 kdeqgrllce lfirapkrrn qpdyyevvsq pidlmkiqqk lkmeeyddvn lltadfqllf
 121 nnakayykpd speykaackl wdlylrtrne fvqkgeadde dddedgqdnq gtladgsspg
 181 ylkeileqll eaivvatnps grliselfqk lpskvqypdy yaiikepidl ktiaqriqng
 241 syksihamak didllaknak tynepgsqvf kdansikkif ymkkaeiehh emtksslrir
 301 tasnlaaarl tgpshnkssl geernptsky yrnkravqgg rlsaitmalq ygseseedaa
 361 laaaryeege seaesitsfm dvsnpfhqly dtvrscrnhq gqliaepffh lpskkkypdy
 421 yqqikmpisl qqirtklknq eyetldhlec dlnlmfenak rynvpnsaiy krvlklqqvm
 481 qakkkelarr ddiedgdsmi ssatsdtgsa krkrnthdse mlglrrlssk knirkqrmki
 541 lfnvvleare pgsgrrlcdl fmvkpskkdy pdyykiilep mdlkiiehni rndkyageeg
 601 mmedmklmfr narhyneegs qvyndahile kllkdkrkel gplpddddma spklklsrks
 661 gvspkkskym tpmqqklnev yeavknytdk rgrrlsaifl rlpsrselpd yyltikkpmd
 721 mekirshmma nkyqdidsmv edfvmmfnna ctynepesli ykdalvlhkv lletrrdleg
 781 dedshvpnvt lliqelihnl fvsvmshqdd egrcysdsla eipavdpnsp nkppltfdii
 841 rknvesnryr rldlfqehmf evlerarrmn rtdseiyeda velqqffiri rdelckngei
 901 llspalsytt khlhndveke kkeklpkeie edklkreeek reaeksedss gttglsglhr
 961 tysqdcsfkn smyhvgdyvy vepaeanlqp hivcierlwe dsagekwlyg cwfyrpnetf
1021 hlatrkflek evfksdyynk vpvskilgkc vvmfvkeyfk lcpenfrded vfvcesrysa
1081 ktksfkkikl wtmpissvrf vprdvplpvv rvasvfanad kgddekntdn sddnraednf
1141 nlekekedvp vemsngepgc hyfeqlrynd mwlkvgdovf ikshglvrpr vgriekvwvr
1201 dgaayfygpi fihpeetehe ptkmfykkev flsnleetcp mscilgkcav lsfkdflscr
1261 pteipendil lcesrynesd kqmkkfkglk rfslsakvvd deiyyfrkpi ipqkepspll
1321 ekkiqlleak faeleggddd ieemgeedse vieapslpql qtplaneldl mpytppqstp
1381 ksakgsakke sskrkinmsg yilfssemra vikaqhpdys fgelsrlvgt ewrnletakk
1441 aeyeeraakv aeqqerereaa qqqqpsaspr agtpvgalmg vvppptpmgm lnqqltpvag
1501 mmggyppglp plqgpvdglv smgsmqplhp ggppphhlpp gvpglpgipp pgvmnqgvap
1561 mvgtpapggs pygqqvgvlg ppgqqapppy pgphpagppv iqqpttpmfv apppktqrll
1621 hseaylkyie glsaesnsis kwdqtlaarr rdvhlskeqe srlpshwlks kgahttmada
1681 lwrlrdlmlr dtlnirqayn lenv
```

Included in Table 1 are RNA nucleic acid molecules (e.g., thymines replaced with uredines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 1, or a portion thereof. Such nucleic acid molecules can have a function of the full-length nucleic acid as described further herein.

Included in Table 1 are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 1, or a portion thereof. Such polypeptides can have a function of the full-length polypeptide as described further herein.

Included in Table 1 is PBRM1, including any PBRM1 cDNA or polypeptide.

Included in Table 1 are PBRM1 nucleic acid and/or amino acid sequences encoding or representing PBRM1 having reduced or eliminated PBRM1 function (e.g., truncating PBRM1 mutations causing encoding of incomplete PBRM1 protein). Many of these mutations were found in RCC patients which is insensitive to immune checkpoint therapies. Some exemplary mutations are listed below and are also found in Table 6 filed herewith:

1. Truncating PBRM1 alterations in patients training cohort passing whole exome quality control (N=34; genomic positions in the table can be determined from PBRM1_ENST00000337303.4_Nonsense_Mutation_p.E449*|PBRM|_ENST00000394830.3_Nonsense_Mutation_p.E449*|PBRM1 ENST00000409114.3 Nonsense_Mutation_p.E449*|PBRM|_ENST00000409767.1 Nonsense_Mutation_p.E449*| PBRM1 ENST00000410007.1 Nonsense_Mutation_p.E449*|PBRM|_ENST00000296302.7_Nonsense_Mutation_p.E449*|PBRM|_ENST00000409057.1_Nonsense_Mutation_p.E449*; NM_018165.4; or uc003der.2)

| patient_id | Hugo_Symbol | PBRM1_mean_coverage | Chromosome | Start_position | End_position | Variant_Classification | Reference Allele | Tumor_Seq_Allele1 | Tumor_Seq_Allele2 |
|---|---|---|---|---|---|---|---|---|---|
| 9_97 | PBRM1 | 119.39 | 3 | 52663008 | 52663008 | Nonsense_Mutation | C | C | A |
| 9_52 | PBRM1 | 97.9 | 3 | 52613205 | 52613205 | Frame_Shift_Del | T | T | — |
| 9_27 | PBRM1 | 248.99 | 3 | 52598081 | 52598101 | In_Frame_Del | TCA TCA TCT ACC ACT TTA GCA | TCA TCA TCT ACC ACT TTA GCA | — |
| 9_119 | PBRM1 | 28.57 | 3 | 52682459 | 52682459 | Splice_Site | C | C | G |
| 8_105 | NA | 146.47 | NA | NA | NA | NA | | | |
| 6_39 | NA | 130.38 | NA | NA | NA | NA | | | |
| 5_73 | NA | 181.65 | NA | NA | NA | NA | | | |
| 5_50 | PBRM1 | 135.79 | 3 | 52712515 | 52712515 | Splice_Site | C | C | T |
| 5_41 | NA | 123.22 | NA | NA | NA | NA | | | |
| 5_21 | PBRM1 | 125.64 | 3 | 52613210 | 52613210 | Frame_Shift_Del | T | T | — |
| 5_18 | PBRM1 | 126.07 | 3 | 52678748 | 52678748 | Nonsense_Mutation | C | C | C |
| 5_106 | PBRM1 | 155.18 | 3 | 52620610 | 52620614 | Frame_Shift_Del | ATTTT | ATTTT | — |
| 5_1 | NA | 138.81 | NA | NA | NA | NA | | | |
| 4_68 | NA | 100.73 | NA | NA | NA | NA | | | |
| 3_15 | PBRM1 | 94.84 | 3 | 52613194 | 52613194 | Nonsense_Mutation | C | C | A |
| 3_117 | PBRM1 | 146.69 | 3 | 52643375 | 52643375 | Nonsense_Mutation | G | G | A |
| 3_114 | PBRM1 | 111.22 | 3 | 52662964 | 52662964 | Frame_Shift_Del | A | A | — |
| 2_85 | NA | 47.52 | NA | NA | NA | NA | NA | NA | NA |

-continued

| | | | | | | | | | |
|---|---|---|---|---|---|---|---|---|---|
| 2_84 | PBRM1 | 130.86 | 3 | 52696272 | 52696272 | Frame_Shift_Del | T | T | — |
| 2_58 | NA | 95.31 | NA | NA | NA | NA | | | |
| 2_102 | PBRM1 | 266.4 | 3 | 52663052 | 52663052 | Splice_Site | C | C | T |
| 13_96 | PBRM1 | 164.39 | 3 | 52643489 | 52643489 | Frame_Shift_Del | A | A | — |
| 13_90 | NA | 124.87 | NA | NA | NA | NA | | | |
| 12_115 | NA | 115.51 | NA | NA | NA | NA | | | |
| 11_93 | PBRM1 | 173.78 | 3 | 52651277 | 52651277 | Splice_Site | C | C | T |
| 11_79 | PBRM1 | 67.19 | 3 | 52621487 | 52621487 | Frame_Shift_Del | T | T | — |
| 11_56 | NA | 221.56 | NA | NA | NA | NA | | | |
| 11_25 | NA | 124.35 | NA | NA | NA | NA | | | |
| 11_14 | PBRM1 | 131.63 | 3 | 52623201 | 52623201 | Frame_Shift_Del | G | G | — |
| 11_11 | NA | 62.73 | NA | NA | NA | NA | | | |
| 11_10 | PBRM1 | 89.9 | 3 | 52623120 | 52623120 | Frame_Shift_Del | G | G | — |
| 1_62 | PBRM1 | 131.16 | 3 | 52613062 | 52613068 | Splice_Site | ACACTCA | ACACTCA | — |
| 1_32 | NA | 120.85 | NA | NA | NA | NA | | | |
| 1_20 | PBRM1 | 28.98 | 3 | 52649455 | 52649456 | Frame_Shift_Ins | — | — | T |

| patient_id | Protein_Change | Variant_Type | i_tumor_f | t_alt_count | t_ref_count | clonal | Indel_Caller |
|---|---|---|---|---|---|---|---|
| 9_97 | p.E417* | SNP | 0.278481 | 22 | 57 | 1 | NA |
| 9_52 | p.D1148fs | DEL | 0.235955056 | 21 | 68 | 1 | strelka, indelocator |
| 9_27 | p.AKVVDDE1249del | DEL | 0.15 | 14 | 77 | not evaluable | indelocator |
| 9_119 | | SNP | 0.666667 | 10 | 5 | 1 | NA |
| 8_105 | NA | NA | NA | NA | NA | NA | |
| 6_39 | NA | NA | NA | NA | NA | NA | NA |
| 5_73 | NA | NA | NA | NA | NA | NA | NA |
| 5_50 | | SNP | 0.213592 | 22 | 81 | 1 | NA |
| 5_41 | NA | NA | NA | NA | NA | NA | NA |
| 5_21 | p.K1146fs | DEL | 0.441666667 | 53 | 67 | 1 | strelka, indelocator |
| 5_18 | p.E291* | SNP | 0.150943 | 8 | 45 | 1 | NA |
| 5_106 | p.KI1087fs | DEL | 0.067137809 | 19 | 264 | 0 | strelka, indelocator |
| 5_1 | NA | NA | NA | NA | NA | NA | NA |
| 4_68 | NA | NA | NA | NA | NA | NA | NA |
| 3_15 | p.E1105* | SNP | 0.53 | 53 | 47 | 1 | NA |
| 3_117 | p.Q809* | SNP | 0.288 | 36 | 89 | 1 | NA |

-continued

| | | | | | | | |
|---|---|---|---|---|---|---|---|
| 3_114 | p.N463fs | DEL | 0.108695652 | 10 | 82 | 1 | strelka, indelocator |
| 2_85 | NA | NA | NA | NA | NA | NA | NA |
| 2_84 | p.K135fs | DEL | 0.171428571 | 12 | 58 | 1 | strelka, indelocator |
| 2_58 | NA | NA | NA | NA | NA | NA | NA |
| 2_102 | | SNP | 0.235849 | 25 | 81 | 1 | NA |
| 13_96 | p.S818fs | DEL | 0.402654867 | 91 | 135 | 1 | strelka, indelocator |
| 13_90 | NA | NA | NA | NA | NA | NA | NA |
| 12_115 | NA | NA | NA | NA | NA | NA | NA |
| 11_93 | | SNP | 0.12766 | 6 | 41 | 1 | NA |
| 11_79 | p.N1017fs | DEL | 0.464285714 | 13 | 15 | 1 | strelka, indelocator |
| 11_56 | NA | NA | NA | NA | NA | NA | NA |
| 11_25 | NA | NA | NA | NA | NA | NA | NA |
| 11_14 | p.D965fs | DEL | 0.25 | 15 | 45 | 1 | strelka, indelocator |
| 11_11 | NA | NA | NA | NA | NA | NA | NA |
| 11_10 | p.I992fs | DEL | 0.55 | 55 | 45 | 1 | strelka, indelocator |
| 1_62 | | DEL | 0.17370892 | 37 | 176 | 0 | strelka |
| 1_32 | NA | NA | NA | NA | NA | NA | NA |
| 1_20 | p.H627fs | INS | 0.363636364 | 8 | 14 | 1 | strelka, indelocator |

Patient_id = CA209009_XX (XX: the id in the above table)

2. Truncating PBRM1 alterations in validation cohort (N=28)

| patient_id | Hugo_Symbol | Chromosome | Start_position | End_position | Variant_Classification | Reference_Allele | Tumor_Seq_Allele1 | Tumor_Seq_Allele2 | Protein_Change |
|---|---|---|---|---|---|---|---|---|---|
| CA8808 | PBRM1 | 3 | 52595873 | 52595873 | Frame_Shift_Del | G | G | — | p.Q1415fs |
| KA4076 | NA | NA | NA | NA | NA | | | | NA |
| KE5236 | PBRM1 | 3 | 52597356 | 52597359 | Frame_Shift_Del | AGGT | AGGT | — | p.LP1310fs |
| KE6262 | PBRM1 | 3 | 52643586 | 52643596 | Frame_Shift_Del | ATGAGAGTCCT | ATGAGAGTCCT | — | p.EDSH782fs |
| MC1838 | NA | NA | NA | NA | NA | | | | NA |
| PD_005 | PBRM1 | 3 | 52668656 | 52668656 | Nonsense_Mutation | G | G | T | p.Y389* |
| PD_007 | NA | NA | NA | NA | NA | | | | NA |
| PD_010 | PBRM1 | 3 | 52702580 | 52702580 | Nonsense_Mutation | A | A | C | p.Y106* |

-continued

| | | | | | | | | | |
|---|---|---|---|---|---|---|---|---|---|
| PD_011 | NA | NA | NA | NA | NA | | | | NA |
| PD_012 | NA | NA | NA | NA | NA | | | | NA |
| PD_013 | PBRM1 | 3 | 52597487 | 52597488 | Frame_Shift_Del | CC | CC | — | p.E1315fs |
| PD_014 | PBRM1 | 3 | 52610662 | 52610663 | Frame_Shift_Del | AG | AG | — | p.F1211fs |
| PD_015 | PBRM1 | 3 | 52637540 | 52637540 | Frame_Shift_Del | AG | AG | — | p.R941fs |
| PD_018 | NA | NA | NA | NA | NA | | | | NA |
| PD_019 | NA | NA | NA | NA | NA | | | | NA |
| PD_020 | NA | NA | NA | NA | NA | | | | NA |
| PD_021 | PBRM1 | 3 | 52713723 | 52713723 | Frame_Shift_Del | C | C | — | p.G2fs |
| PD_022 | NA | NA | NA | NA | NA | | | | NA |
| PD_023 | PBRM1 | 3 | 52663053 | 52663053 | Splice_Site | T | T | A | |
| PD_024 | NA | NA | NA | NA | NA | | | | NA |
| PD_025 | PBRM1 | 3 | 52595829 | 52595829 | Frame_Shift_Del | C | C | — | p.G1429fs |
| PD_026 | NA | NA | NA | NA | NA | | | | NA |
| RCC.PD1.DNA.1026 | NA | NA | NA | NA | NA | | | | NA |
| RCC.PD1.DNA.1101 | PBRM1 | 3 | 52595804 | 52595804 | Frame_Shift_Del | C | C | — | p.A1438fs |
| RCC.PD1.DNA.1137 | NA | NA | NA | NA | NA | | | | NA |
| RCC.PD1.DNA.944 | NA | NA | NA | NA | NA | | | | NA |
| RCC.PD1.DNA.949 | NA | NA | NA | NA | NA | | | | NA |
| VA1008 | PBRM1 | 3 | 52643943 | 52643943 | Frame_Shift_Del | T | T | — | p.K619fs |

| patient_id | Variant_Type | i_tumor_f | t_alt_count | t_ref_count | clonal_dm | |
|---|---|---|---|---|---|---|
| CA8808 | DEL | 0.259090909 | 57 | 163 | not evaluable | strelka, indelocator |
| KA4076 | NA | NA | NA | NA | NA | NA |
| KE5236 | DEL | 0.09 | 8 | 85 | not evaluable | indelocator |
| KE6262 | DEL | 0.098214286 | 11 | 101 | 1 | strelka, indelocator |
| MC1838 | NA | NA | NA | NA | NA | NA |
| PD_005 | SNP | 0.287356 | 25 | 62 | 1 | NA |
| PD_007 | NA | NA | NA | NA | NA | NA |

-continued

| | | | | | | |
|---|---|---|---|---|---|---|
| PD_010 | SNP | 0.15 | 6 | 34 | 0 | |
| PD_011 | NA | NA | NA | NA | NA | NA |
| PD_012 | NA | NA | NA | NA | NA | NA |
| PD_013 | DEL | 0.1171875 | 15 | 113 | 1 | strelka, indelocator |
| PD_014 | DEL | 0.288888889 | 26 | 64 | 1 | strelka, indelocator |
| PD_015 | DEL | 0.204545455 | 18 | 70 | 1 | strelka, indelocator |
| PD_018 | NA | NA | NA | NA | NA | NA |
| PD_019 | NA | NA | NA | NA | NA | NA |
| PD_020 | NA | NA | NA | NA | NA | NA |
| PD_021 | DEL | 0.36 | 18 | 32 | 1 | strelka, indelocator |
| PD_022 | NA | NA | NA | NA | NA | NA |
| PD_023 | SNP | 0.214286 | 9 | 33 | 1 | NA |
| PD_024 | NA | NA | NA | NA | NA | NA |
| PD_025 | DEL | 0.154411765 | 21 | 115 | 1 | strelka, indelocator |
| PD_026 | NA | NA | NA | NA | NA | NA |
| RCC.PD1.DNA.1026 | NA | NA | NA | NA | NA | NA |
| RCC.PD1.DNA.1101 | DEL | 0.133540373 | 43 | 279 | 1 | strelka, indelocator |
| RCC.PD1.DNA.1137 | NA | NA | NA | NA | NA | NA |
| RCC.PD1.DNA.944 | NA | NA | NA | NA | NA | NA |
| RCC.PD1.DNA.949 | NA | NA | NA | NA | NA | NA |
| VA1008 | DEL | 0.06 | 15 | 253 | not evaluable | indelocator |

II. Subjects

In one embodiment, the subject for whom predicted likelihood of efficacy of an immune checkpoint therapy is determined, is a mammal (e.g., mouse, rat, primate, non-human mammal, domestic animal, such as a dog, cat, cow, horse, and the like), and is preferably a human.

In another embodiment of the methods of the present invention, the subject has not undergone treatment, such as chemotherapy, radiation therapy, targeted therapy, and/or immune checkpoint therapy. In still another embodiment, the subject has undergone treatment, such as chemotherapy, radiation therapy, targeted therapy, and/or immune checkpoint therapy.

In certain embodiments, the subject has had surgery to remove cancerous or precancerous tissue. In other embodiments, the cancerous tissue has not been removed, e.g., the cancerous tissue may be located in an inoperable region of the body, such as in a tissue that is essential for life, or in a region where a surgical procedure would cause considerable risk of harm to the patient.

The methods of the present invention can be used to determine the responsiveness to anti-immune checkpoint therapies of renal cell carcinomas, particularly because kidney cancers are genomically different from many cancers according to cancer-related mutational load and composition. However, as described in herein, the methods of the present invention can, in certain embodiments, be applied to cancers other than renal cell carcinoma. In one embodiment, the cancers are solid tumors, such as lung cancer, melanoma, and/or renal cell carcinoma. In another embodiment, the cancer is an epithelial cancer such as, but not limited to, brain cancer (e.g., glioblastomas) bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In still other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, brenner, or undifferentiated. In some embodiments, the cancers are mesenchymal tumors, such as sarcoma.

III. Sample Collection, Preparation and Separation

In some embodiments, biomarker amount and/or activity measurement(s) in a sample from a subject is compared to a predetermined control (standard) sample. The sample from the subject is typically from a diseased tissue, such as cancer cells or tissues. The control sample can be from the same subject or from a different subject. The control sample is typically a normal, non-diseased sample. However, in some embodiments, such as for staging of disease or for evaluating the efficacy of treatment, the control sample can be from a diseased tissue. The control sample can be a combination of samples from several different subjects. In some embodiments, the biomarker amount and/or activity measurement(s) from a subject is compared to a pre-determined level. This pre-determined level is typically obtained from normal samples. As described herein, a "pre-determined" biomarker amount and/or activity measurement(s) may be a biomarker amount and/or activity measurement(s) used to, by way of example only, evaluate a subject that may be selected for treatment, evaluate a response to an immune checkpoint therapy, and/or evaluate a response to a combination immune checkpoint therapy. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements.

In another embodiment, the amounts determined and/or compared in a method described herein are based on relative measurements, such as ratios (e.g., biomarker copy numbers, level, and/or activity before a treatment vs. after a treatment, such biomarker measurements relative to a spiked or man-made control, such biomarker measurements relative to the expression of a housekeeping gene, and the like). For example, the relative analysis can be based on the ratio of pre-treatment biomarker measurement as compared to post-treatment biomarker measurement. Pre-treatment biomarker measurement can be made at any time prior to initiation of anti-cancer therapy. Post-treatment biomarker measurement can be made at any time after initiation of anti-cancer therapy. In some embodiments, post-treatment biomarker measurements are made 1, 2, 3, 4, 5, 6, 7, 8, 9, 10, 11, 12, 13, 14, 15, 16, 17, 18, 19, 20 weeks or more after initiation of anti-cancer therapy, and even longer toward indefinitely for continued monitoring. Treatment can comprise anti-cancer therapy, such as a therapeutic regimen comprising an anti-PD1 monoclonal antibody (e.g., nivolumab) alone or in combination with other anti-cancer agents, such as anti-PD-L1/PD-L2 antibodies, anti-VEGF agents (e.g., bevacizumab), agents described in the Examples, Figures, and Tables, or anti-PBRM1 agents.

The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

In some embodiments of the present invention the change of biomarker amount and/or activity measurement(s) from the pre-determined level is about 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 fold or greater, or any range in between, inclusive. Such cutoff values apply equally when the measurement is based on relative changes, such as based on the ratio of pre-treatment biomarker measurement as compared to post-treatment biomarker measurement.

Biological samples can be collected from a variety of sources from a patient including a body fluid sample, cell sample, or a tissue sample comprising nucleic acids and/or proteins. "Body fluids" refer to fluids that are excreted or secreted from the body as well as fluids that are normally not (e.g., amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit). In a preferred embodiment, the subject and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow. In one embodiment, the sample is serum, plasma, or urine. In another embodiment, the sample is serum.

The samples can be collected from individuals repeatedly over a longitudinal period of time (e.g., once or more on the order of days, weeks, months, annually, biannually, etc.). Obtaining numerous samples from an individual over a period of time can be used to verify results from earlier detections and/or to identify an alteration in biological pattern as a result of, for example, disease progression, drug treatment, etc. For example, subject samples can be taken and monitored every month, every two months, or combinations of one, two, or three month intervals according to the present invention. In addition, the biomarker amount and/or activity measurements of the subject obtained over time can be conveniently compared with each other, as well as with those of normal controls during the monitoring period, thereby providing the subject's own values, as an internal, or personal, control for long-term monitoring.

Sample preparation and separation can involve any of the procedures, depending on the type of sample collected and/or analysis of biomarker measurement(s). Such procedures include, by way of example only, concentration, dilution, adjustment of pH, removal of high abundance polypeptides (e.g., albumin, gamma globulin, and transferrin, etc.), addition of preservatives and calibrants, addition of protease inhibitors, addition of denaturants, desalting of samples, concentration of sample proteins, extraction and purification of lipids.

The sample preparation can also isolate molecules that are bound in non-covalent complexes to other protein (e.g., carrier proteins). This process may isolate those molecules bound to a specific carrier protein (e.g., albumin), or use a more general process, such as the release of bound molecules from all carrier proteins via protein denaturation, for example using an acid, followed by removal of the carrier proteins.

Removal of undesired proteins (e.g., high abundance, uninformative, or undetectable proteins) from a sample can be achieved using high affinity reagents, high molecular weight filters, ultracentrifugation and/or electrodialysis. High affinity reagents include antibodies or other reagents (e.g., aptamers) that selectively bind to high abundance proteins. Sample preparation could also include ion exchange chromatography, metal ion affinity chromatography, gel filtration, hydrophobic chromatography, chromatofocusing, adsorption chromatography, isoelectric focusing and related techniques. Molecular weight filters include membranes that separate molecules on the basis of size and molecular weight. Such filters may further employ reverse osmosis, nanofiltration, ultrafiltration and microfiltration.

Ultracentrifugation is a method for removing undesired polypeptides from a sample. Ultracentrifugation is the centrifugation of a sample at about 15,000-60,000 rpm while monitoring with an optical system the sedimentation (or lack thereof) of particles. Electrodialysis is a procedure which uses an electromembrane or semipermeable membrane in a process in which ions are transported through semi-permeable membranes from one solution to another under the influence of a potential gradient. Since the membranes used in electrodialysis may have the ability to selectively transport ions having positive or negative charge, reject ions of the opposite charge, or to allow species to migrate through a semipermeable membrane based on size and charge, it renders electrodialysis useful for concentration, removal, or separation of electrolytes.

Separation and purification in the present invention may include any procedure known in the art, such as capillary electrophoresis (e.g., in capillary or on-chip) or chromatography (e.g., in capillary, column or on a chip). Electrophoresis is a method which can be used to separate ionic molecules under the influence of an electric field. Electrophoresis can be conducted in a gel, capillary, or in a microchannel on a chip. Examples of gels used for electrophoresis include starch, acrylamide, polyethylene oxides, agarose, or combinations thereof. A gel can be modified by its cross-linking, addition of detergents, or denaturants, immobilization of enzymes or antibodies (affinity electrophoresis) or substrates (zymography) and incorporation of a pH gradient. Examples of capillaries used for electrophoresis include capillaries that interface with an electrospray.

Capillary electrophoresis (CE) is preferred for separating complex hydrophilic molecules and highly charged solutes. CE technology can also be implemented on microfluidic chips. Depending on the types of capillary and buffers used, CE can be further segmented into separation techniques such as capillary zone electrophoresis (CZE), capillary isoelectric focusing (CIEF), capillary isotachophoresis (cITP) and capillary electrochromatography (CEC). An embodiment to couple CE techniques to electrospray ionization involves the use of volatile solutions, for example, aqueous mixtures containing a volatile acid and/or base and an organic such as an alcohol or acetonitrile.

Capillary isotachophoresis (cITP) is a technique in which the analytes move through the capillary at a constant speed but are nevertheless separated by their respective mobilities. Capillary zone electrophoresis (CZE), also known as free-solution CE (FSCE), is based on differences in the electrophoretic mobility of the species, determined by the charge on the molecule, and the frictional resistance the molecule encounters during migration which is often directly proportional to the size of the molecule. Capillary isoelectric focusing (CLEF) allows weakly-ionizable amphoteric molecules, to be separated by electrophoresis in a pH gradient. CEC is a hybrid technique between traditional high performance liquid chromatography (HPLC) and CE.

Separation and purification techniques used in the present invention include any chromatography procedures known in the art. Chromatography can be based on the differential adsorption and elution of certain analytes or partitioning of analytes between mobile and stationary phases. Different examples of chromatography include, but not limited to, liquid chromatography (LC), gas chromatography (GC), high performance liquid chromatography (HPLC), etc.

IV. Biomarker Nucleic Acids and Polypeptides

One aspect of the present invention pertains to the use of isolated nucleic acid molecules that correspond to biomarker nucleic acids that encode a biomarker polypeptide or a portion of such a polypeptide. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

A biomarker nucleic acid molecule of the present invention can be isolated using standard molecular biology techniques and the sequence information in the database records described herein. Using all or a portion of such nucleic acid sequences, nucleic acid molecules of the present invention can be isolated using standard hybridization and cloning techniques (e.g., as described in Sambrook et al., ed., *Molecular Cloning: A Laboratory Manual, 2nd ed.*, Cold Spring Harbor Laboratory Press, Cold Spring Harbor, N.Y., 1989).

A nucleic acid molecule of the present invention can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule of the present invention can be prepared by standard synthetic techniques, e.g., using an automated DNA synthesizer.

Moreover, a nucleic acid molecule of the present invention can comprise only a portion of a nucleic acid sequence, wherein the full length nucleic acid sequence comprises a marker of the present invention or which encodes a polypeptide corresponding to a marker of the present invention. Such nucleic acid molecules can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a biomarker nucleic acid sequence. Probes based on the sequence of a biomarker nucleic acid molecule can be used to detect transcripts or genomic sequences corresponding to one or more markers of the present invention. The probe comprises a label group attached thereto, e.g., a radioisotope, a fluorescent compound, an enzyme, or an enzyme co-factor.

A biomarker nucleic acid molecules that differ, due to degeneracy of the genetic code, from the nucleotide sequence of nucleic acid molecules encoding a protein which corresponds to the biomarker, and thus encode the same protein, are also contemplated.

In addition, it will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

The term "allele," which is used interchangeably herein with "allelic variant," refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene or allele. For example, biomarker alleles can differ from each other in a single nucleotide, or several nucleotides, and can include substitutions, deletions, and insertions of nucleotides. An allele of a gene can also be a form of a gene containing one or more mutations.

The term "allelic variant of a polymorphic region of gene" or "allelic variant", used interchangeably herein, refers to an alternative form of a gene having one of several possible nucleotide sequences found in that region of the gene in the population. As used herein, allelic variant is meant to encompass functional allelic variants, non-functional allelic variants, SNPs, mutations and polymorphisms.

The term "single nucleotide polymorphism" (SNP) refers to a polymorphic site occupied by a single nucleotide, which is the site of variation between allelic sequences. The site is usually preceded by and followed by highly conserved sequences of the allele (e.g., sequences that vary in less than 1/100 or 1/1000 members of a population). A SNP usually arises due to substitution of one nucleotide for another at the polymorphic site. SNPs can also arise from a deletion of a nucleotide or an insertion of a nucleotide relative to a reference allele. Typically the polymorphic site is occupied by a base other than the reference base. For example, where the reference allele contains the base "T" (thymidine) at the polymorphic site, the altered allele can contain a "C" (cytidine), "G" (guanine), or "A" (adenine) at the polymorphic site. SNP's may occur in protein-coding nucleic acid sequences, in which case they may give rise to a defective or otherwise variant protein, or genetic disease. Such a SNP may alter the coding sequence of the gene and therefore specify another amino acid (a "missense" SNP) or a SNP may introduce a stop codon (a "nonsense" SNP). When a SNP does not alter the amino acid sequence of a protein, the SNP is called "silent." SNP's may also occur in noncoding regions of the nucleotide sequence. This may result in defective protein expression, e.g., as a result of alternative spicing, or it may have no effect on the function of the protein.

As used herein, the terms "gene" and "recombinant gene" refer to nucleic acid molecules comprising an open reading frame encoding a polypeptide corresponding to a marker of the present invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the present invention.

In another embodiment, a biomarker nucleic acid molecule is at least 7, 15, 20, 25, 30, 40, 60, 80, 100, 150, 200, 250, 300, 350, 400, 450, 550, 650, 700, 800, 900, 1000, 1100, 1200, 1300, 1400, 1500, 1600, 1700, 1800, 1900, 2000, 2200, 2400, 2600, 2800, 3000, 3500, 4000, 4500, or more nucleotides in length and hybridizes under stringent conditions to a nucleic acid molecule corresponding to a marker of the present invention or to a nucleic acid molecule encoding a protein corresponding to a marker of the present invention. As used herein, the term "hybridizes under stringent conditions" is intended to describe conditions for hybridization and washing under which nucleotide sequences at least 60% (65%, 70%, 75%, 80%, preferably 85%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

In addition to naturally-occurring allelic variants of a nucleic acid molecule of the present invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the present invention pertains to nucleic acid molecules encoding a polypeptide of the present invention that contain changes in amino acid residues that are not essential for activity. Such polypeptides differ in amino acid sequence from the naturally-occurring proteins which correspond to the markers of the present invention, yet retain biological activity. In one embodiment, a biomarker protein has an amino acid sequence that is at least about 40% identical, 50%, 60%, 70%, 75%, 80%, 83%, 85%, 87.5%, 90%, 91%, 92%, 93%, 94%, 95%, 96%, 97%, 98%, 99% or identical to the amino acid sequence of a biomarker protein described herein.

An isolated nucleic acid molecule encoding a variant protein can be created by introducing one or more nucleotide substitutions, additions or deletions into the nucleotide sequence of nucleic acids of the present invention, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In some embodiments, the present invention further contemplates the use of anti-biomarker antisense nucleic acid molecules, i.e., molecules which are complementary to a sense nucleic acid of the present invention, e.g., complementary to the coding strand of a double-stranded cDNA molecule corresponding to a marker of the present invention or complementary to an mRNA sequence corresponding to a marker of the present invention. Accordingly, an antisense nucleic acid molecule of the present invention can hydrogen bond to (i.e. anneal with) a sense nucleic acid of the present invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a polypeptide of the present invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules of the present invention are typically administered to a subject or generated in situ such that they hybridize with or bind to cellular mRNA and/or genomic DNA encoding a polypeptide corresponding to a selected marker of the present invention to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the present invention includes direct injection at a tissue site or infusion of the antisense nucleic acid into a blood- or bone marrow-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the present invention can be an α-anomeric nucleic acid molecule. An α-anomeric nucleic acid molecule forms specific double-stranded hybrids with complementary RNA in which, contrary to the usual α-units, the strands run parallel to each other (Gaultier et al. (1987) *Nucleic Acids Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

The present invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach (1988) *Nature* 334:585-591) can be used to catalytically cleave mRNA transcripts to thereby inhibit translation of the protein encoded by the mRNA. A ribozyme having specificity for a nucleic acid molecule encoding a polypeptide corresponding to a marker of the present invention can be designed based upon the nucleotide sequence of a cDNA corresponding to the marker. For example, a derivative of a Tetrahymena L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742). Alternatively, an mRNA encoding a polypeptide of the present invention can be used to select a catalytic RNA having a specific ribonuclease activity from a pool of RNA molecules (see, e.g., Bartel and Szostak (1993) *Science* 261:1411-1418).

The present invention also encompasses nucleic acid molecules which form triple helical structures. For example, expression of a biomarker protein can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des.* 6(6):569-84; Helene (1992) *Ann. N.Y. Acad. Sci.* 660:27-36; and Maher (1992) *Bioassays* 14(12):807-15.

In various embodiments, the nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acid molecules (see Hyrup et al. (1996) *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., 51 nucleases (Hyrup (1996), supra; or as probes or primers for DNA sequence and hybridization (Hyrup (1996), supra; Perry-O'Keefe et al. (1996) *Proc. Natl. Acad. Sci. USA* 93:14670-14675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996), supra). The synthesis of PNA-DNA chimeras can be performed as described in Hyrup (1996), supra, and Finn et al. (1996) *Nucleic Acids Res.* 24(17):3357-3363. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al. (1989) *Nucleic Acids Res.* 17:5973-5988). PNA monomers are then coupled in a step-wise manner to produce a chimeric molecule with a 5' PNA segment and a 3' DNA segment (Finn et al. (1996) *Nucleic Acids Res.* 24:3357-3363). Alternatively, chimeric molecules can be synthesized with a 5' DNA segment and a 3' PNA segment (Peterser et al. (1975) *Bioorganic Med. Chem. Lett.* 5:1119-11124).

In other embodiments, the oligonucleotide can include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) *Bio/Techniques* 6:958-976) or intercalating agents (see, e.g., Zon (1988) *Pharm. Res.* 5:539-549). To this end, the oligonucleotide can be conjugated to another molecule, e.g., a peptide, hybridization triggered cross-linking agent, transport agent, hybridization-triggered cleavage agent, etc.

Another aspect of the present invention pertains to the use of biomarker proteins and biologically active portions thereof. In one embodiment, the native polypeptide corresponding to a marker can be isolated from cells or tissue sources by an appropriate purification scheme using standard protein purification techniques. In another embodiment, polypeptides corresponding to a marker of the present invention are produced by recombinant DNA techniques. Alternative to recombinant expression, a polypeptide corresponding to a marker of the present invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a biomarker polypeptide include polypeptides comprising amino acid sequences sufficiently identical to or derived from a biomarker protein amino acid sequence described herein, but which includes fewer amino acids than the full length protein, and exhibit at least one activity of the corresponding full-length protein. Typically, biologically active portions comprise a domain or motif with at least one activity of the corresponding protein. A biologically active portion of a protein of the present invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the present invention.

Preferred polypeptides have an amino acid sequence of a biomarker protein encoded by a nucleic acid molecule described herein. Other useful proteins are substantially identical (e.g., at least about 40%, preferably 50%, 60%, 70%, 75%, 80%, 83%, 85%, 88%, 90%, 91%, 92%, 93%, 94%, 95%, 96%, 97%, 98%, or 99%) to one of these sequences and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J Mol. Biol.* 215:403-410. BLAST nucleotide searches can be performed with the NBLAST program, score=100, wordlength=12 to obtain nucleotide sequences homologous to a nucleic acid molecules of the present invention. BLAST protein searches can be performed with the XBLAST program, score=50, wordlength=3 to obtain amino acid sequences homologous to a protein molecules of the present invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, (1988) *Comput Appl Biosci,* 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The present invention also provides chimeric or fusion proteins corresponding to a biomarker protein. As used herein, a "chimeric protein" or "fusion protein" comprises all or part (preferably a biologically active part) of a polypeptide corresponding to a marker of the present invention operably linked to a heterologous polypeptide (i.e., a polypeptide other than the polypeptide corresponding to the marker). Within the fusion protein, the term "operably linked" is intended to indicate that the polypeptide of the present invention and the heterologous polypeptide are fused in-frame to each other. The heterologous polypeptide can be fused to the amino-terminus or the carboxyl-terminus of the polypeptide of the present invention.

One useful fusion protein is a GST fusion protein in which a polypeptide corresponding to a marker of the present invention is fused to the carboxyl terminus of GST sequences. Such fusion proteins can facilitate the purification of a recombinant polypeptide of the present invention.

In another embodiment, the fusion protein contains a heterologous signal sequence, immunoglobulin fusion protein, toxin, or other useful protein sequence. Chimeric and fusion proteins of the present invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the present invention can be cloned into such an expression vector such that the fusion moiety is linked in-frame to the polypeptide of the present invention.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the present invention pertains to the described polypeptides having a signal sequence, as well as to polypeptides from which the signal sequence has been proteolytically cleaved (i.e., the cleavage products). In one embodiment, a nucleic acid sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the biomarker polypeptides described herein. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a biomarker protein which function as either agonists (mimetics) or as antagonists can be identified by screening combinatorial libraries of mutants, e.g., truncation mutants, of the protein of the present invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the present invention from a degenerate oligonucleotide sequence. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of the coding sequence of a polypeptide corresponding to a marker of the present invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the present invention (Arkin and Yourvan (1992) *Proc. Natl. Acad. Sci. USA* 89:7811-7815; Delgrave et al. 91993) *Protein Engineering* 6(3):327-331).

The production and use of biomarker nucleic acid and/or biomarker polypeptide molecules described herein can be facilitated by using standard recombinant techniques. In some embodiments, such techniques use vectors, preferably expression vectors, containing a nucleic acid encoding a biomarker polypeptide or a portion of such a polypeptide. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the present invention is intended to include such other forms of expression vectors, such as viral vectors (e.g., replication defective retroviruses, adenoviruses and adeno-associated viruses), which serve equivalent functions.

The recombinant expression vectors of the present invention comprise a nucleic acid of the present invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, Calif. (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the present invention can be introduced into host cells to thereby produce proteins or peptides, including fusion proteins or peptides, encoded by nucleic acids as described herein.

The recombinant expression vectors for use in the present invention can be designed for expression of a polypeptide corresponding to a marker of the present invention in prokaryotic (e.g., *E. coli*) or eukaryotic cells (e.g., insect cells {using baculovirus expression vectors}, yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al. (1988) *Gene* 69:301-315) and pET 11d (Studier et al., p. 60-89, In *Gene Expression Technology: Methods in Enzymology* vol. 185, Academic Press, San Diego, Calif., 1991). Target biomarker nucleic acid expression from the pTrc vector relies on host RNA polymerase transcription from a hybrid trp-lac fusion promoter. Target biomarker nucleic acid expression from the pET 11d vector relies on transcription from a T7 gn10-lac fusion promoter mediated by a co-expressed viral RNA polymerase (T7 gn1). This viral polymerase is supplied by host strains BL21 (DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacterium with an impaired capacity to proteolytically cleave the recombinant protein (Gottesman, p. 119-128, *In Gene Expression Technology: Methods in Enzymology* vol. 185, Academic Press, San Diego, Calif., 1990. Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the present invention can be carried out by standard DNA synthesis techniques.

In another embodiment, the expression vector is a yeast expression vector. Examples of vectors for expression in yeast *S. cerevisiae* include pYepSecl (Baldari et al. (1987) *EMBO J.* 6:229-234), pMFa (Kurjan and Herskowitz (1982) *Cell* 30:933-943), pJRY88 (Schultz et al. (1987) *Gene* 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al. (1983) *Mol. Cell Biol.* 3:2156-2165) and the pVL series (Lucklow and Summers (1989) *Virology* 170:31-39).

In yet another embodiment, a nucleic acid of the present invention is expressed in mammalian cells using a mammalian expression vector. Examples of mammalian expression vectors include pCDM8 (Seed (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Camper and Tilghman (1989) *Genes Dev.* 3:537-546).

The present invention further provides a recombinant expression vector comprising a DNA molecule cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the present invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes (see Weintraub et al. (1986) *Trends in Genetics*, Vol. 1(1)).

Another aspect of the present invention pertains to host cells into which a recombinant expression vector of the present invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

V. Analyzing Biomarker Nucleic Acids and Polypeptides

Biomarker nucleic acids and/or biomarker polypeptides can be analyzed according to the methods described herein and techniques known to the skilled artisan to identify such genetic or expression alterations useful for the present invention including, but not limited to, 1) an alteration in the level of a biomarker transcript or polypeptide, 2) a deletion or addition of one or more nucleotides from a biomarker gene, 4) a substitution of one or more nucleotides of a biomarker gene, 5) aberrant modification of a biomarker gene, such as an expression regulatory region, and the like.

a. Methods for Detection of Copy Number

Methods of evaluating the copy number of a biomarker nucleic acid are well known to those of skill in the art. The presence or absence of chromosomal gain or loss can be evaluated simply by a determination of copy number of the regions or markers identified herein.

In one embodiment, a biological sample is tested for the presence of copy number changes in genomic loci containing the genomic marker. A copy number of at least 3, 4, 5, 6, 7, 8, 9, or 10 is predictive of poorer outcome of anti-immune checkpoint treatment.

Methods of evaluating the copy number of a biomarker locus include, but are not limited to, hybridization-based assays. Hybridization-based assays include, but are not limited to, traditional "direct probe" methods, such as Southern blots, in situ hybridization (e.g., FISH and FISH plus SKY) methods, and "comparative probe" methods, such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches.

In one embodiment, evaluating the biomarker gene copy number in a sample involves a Southern Blot. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal RNA (e.g., a non-amplified portion of the same or related cell, tissue, organ, etc.) provides an estimate of the relative copy number of the target nucleic acid. Alternatively, other methods well known in the art to detect RNA can be used, such that higher or lower expression relative to an appropriate control (e.g., a non-amplified portion of the same or related cell tissue, organ, etc.) provides an estimate of the relative copy number of the target nucleic acid.

An alternative means for determining genomic copy number is in situ hybridization (e.g., Angerer (1987) *Meth. Enzymol* 152: 649). Generally, in situ hybridization comprises the following steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application. In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained. The probes are typically labeled, e.g., with radioisotopes or fluorescent reporters. In one embodiment, probes are sufficiently long so as to specifically hybridize with the target nucleic acid(s) under stringent conditions. Probes generally range in length from about 200 bases to about 1000 bases. In some applications it is necessary to block the hybridization capacity of repetitive sequences. Thus, in some embodiments, tRNA, human genomic DNA, or Cot-I DNA is used to block non-specific hybridization.

An alternative means for determining genomic copy number is comparative genomic hybridization. In general, genomic DNA is isolated from normal reference cells, as well as from test cells (e.g., tumor cells) and amplified, if necessary. The two nucleic acids are differentially labeled and then hybridized in situ to metaphase chromosomes of a reference cell. The repetitive sequences in both the reference and test DNAs are either removed or their hybridization capacity is reduced by some means, for example by prehybridization with appropriate blocking nucleic acids and/or including such blocking nucleic acid sequences for said repetitive sequences during said hybridization. The bound, labeled DNA sequences are then rendered in a visualizable form, if necessary. Chromosomal regions in the test cells which are at increased or decreased copy number can be identified by detecting regions where the ratio of signal from the two DNAs is altered. For example, those regions that have decreased in copy number in the test cells will show relatively lower signal from the test DNA than the reference compared to other regions of the genome. Regions that have been increased in copy number in the test cells will show relatively higher signal from the test DNA. Where there are chromosomal deletions or multiplications, differences in the ratio of the signals from the two labels will be detected and the ratio will provide a measure of the copy number. In another embodiment of CGH, array CGH (aCGH), the immobilized chromosome element is replaced with a collection of solid support bound target nucleic acids on an array, allowing for a large or complete percentage of the genome to be represented in the collection of solid support bound targets. Target nucleic acids may comprise cDNAs, genomic DNAs, oligonucleotides (e.g., to detect single nucleotide polymorphisms) and the like. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Methods of preparing immobilized chromosomes or arrays and performing comparative genomic hybridization are well known in the art (see, e.g., U.S. Pat. Nos. 6,335,167; 6,197,501; 5,830,645; and 5,665,549 and Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology*, Vol. 33: In situ Hybridization Protocols, Choo, ed., Humana Press, Totowa, N.J. (1994), etc.) In another embodiment, the hybridization protocol of Pinkel, et al. (1998) *Nature Genetics* 20: 207-211, or of Kallioniemi (1992) *Proc. Natl Acad Sci USA* 89:5321-5325 (1992) is used.

In still another embodiment, amplification-based assays can be used to measure copy number. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g. healthy tissue, provides a measure of the copy number.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the present invention. In fluorogenic quantitative PCR, quantitation is based on amount of fluorescence signals, e.g., TaqMan and SYBR green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

Loss of heterozygosity (LOH) and major copy proportion (MCP) mapping (Wang, Z. C., et al. (2004) *Cancer Res* 64(1):64-71; Seymour, A. B., et al. (1994) *Cancer Res* 54, 2761-4; Hahn, S. A., et al. (1995) *Cancer Res* 55, 4670-5; Kimura, M., et al. (1996) *Genes Chromosomes Cancer* 17, 88-93; Li et al., (2008) *MBC Bioinform.* 9, 204-219) may also be used to identify regions of amplification or deletion.

b. Methods for Detection of Biomarker Nucleic Acid Expression

Biomarker expression may be assessed by any of a wide variety of well known methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In preferred embodiments, activity of a particular gene is characterized by a measure of gene transcript (e.g. mRNA), by a measure of the quantity of translated protein, or by a measure of gene product activity. Marker expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In another embodiment, detecting or determining expression levels of a biomarker and functionally similar homologs thereof, including a fragment or genetic alteration thereof (e.g., in regulatory or promoter regions thereof) comprises detecting or determining RNA levels for the marker of interest. In one embodiment, one or more cells from the subject to be tested are obtained and RNA is isolated from the cells. In a preferred embodiment, a sample of breast tissue cells is obtained from the subject.

In one embodiment, RNA is obtained from a single cell. For example, a cell can be isolated from a tissue sample by laser capture microdissection (LCM). Using this technique, a cell can be isolated from a tissue section, including a stained tissue section, thereby assuring that the desired cell is isolated (see, e.g., Bonner et al. (1997) *Science* 278:1481; Emmert-Buck et al. (1996) *Science* 274:998; Fend et al. (1999)*Am. J Path.* 154:61 and Murakami et al. (2000) *Kidney Int.* 58:1346). For example, Murakami et al., supra, describe isolation of a cell from a previously immunostained tissue section.

It is also possible to obtain cells from a subject and culture the cells in vitro, such as to obtain a larger population of cells from which RNA can be extracted. Methods for establishing cultures of non-transformed cells, i.e., primary cell cultures, are known in the art.

When isolating RNA from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA in the tissue and cells may quickly become degraded. Accordingly, in a preferred embodiment, the tissue or cells obtained from a subject is snap frozen as soon as possible.

RNA can be extracted from the tissue sample by a variety of methods, e.g., the guanidium thiocyanate lysis followed by CsCl centrifugation (Chirgwin et al. (1979) *Biochemistry* 18:5294-5299). RNA from single cells can be obtained as described in methods for preparing cDNA libraries from single cells, such as those described in Dulac, C. (1998) *Curr. Top. Dev. Biol.* 36:245 and Jena et al. (1996) *J Immunol. Methods* 190:199. Care to avoid RNA degradation must be taken, e.g., by inclusion of RNAsin.

The RNA sample can then be enriched in particular species. In one embodiment, poly(A)+RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the MessageMaker kit (Life Technologies, Grand Island, N.Y.).

In a preferred embodiment, the RNA population is enriched in marker sequences. Enrichment can be undertaken, e.g., by primer-specific cDNA synthesis, or multiple rounds of linear amplification based on cDNA synthesis and template-directed in vitro transcription (see, e.g., Wang et al. (1989) *PNAS* 86, 9717; Dulac et al., supra, and Jena et al., supra).

The population of RNA, enriched or not in particular species or sequences, can further be amplified. As defined herein, an "amplification process" is designed to strengthen, increase, or augment a molecule within the RNA. For example, where RNA is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

Various amplification and detection methods can be used. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., *PCR Methods and Applications* 4: 80-84 (1994). Real time PCR may also be used.

Other known amplification methods which can be utilized herein include but are not limited to the so-called "NASBA" or "3SR" technique described in *PNAS USA* 87: 1874-1878 (1990) and also described in *Nature* 350 (No. 6313): 91-92 (1991); Q-beta amplification as described in published European Patent Application (EPA) No. 4544610; strand displacement amplification (as described in G. T. Walker et al., *Clin. Chem.* 42: 9-13 (1996) and European Patent Application No. 684315; target mediated amplification, as described by PCT Publication WO9322461; PCR; ligase chain reaction (LCR) (see, e.g., Wu and Wallace, *Genomics* 4, 560 (1989), Landegren et al., *Science* 241, 1077 (1988)); self-sustained sequence replication (SSR) (see, e.g., Guatelli et al., *Proc. Nat. Acad. Sci.* USA, 87, 1874 (1990)); and transcription amplification (see, e.g., Kwoh et al., *Proc. Natl. Acad. Sci. USA* 86, 1173 (1989)).

Many techniques are known in the state of the art for determining absolute and relative levels of gene expression, commonly used techniques suitable for use in the present invention include Northern analysis, RNase protection assays (RPA), microarrays and PCR-based techniques, such as quantitative PCR and differential display PCR. For example, Northern blotting involves running a preparation of RNA on a denaturing agarose gel, and transferring it to a suitable support, such as activated cellulose, nitrocellulose or glass or nylon membranes. Radiolabeled cDNA or RNA is then hybridized to the preparation, washed and analyzed by autoradiography.

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with hematoxylin to demonstrate the histological composition of the sample, and dark field imaging with a suitable light filter shows the developed emulsion. Non-radioactive labels such as digoxigenin may also be used.

Alternatively, mRNA expression can be detected on a DNA array, chip or a microarray. Labeled nucleic acids of a test sample obtained from a subject may be hybridized to a solid surface comprising biomarker DNA. Positive hybridization signal is obtained with the sample containing biomarker transcripts. Methods of preparing DNA arrays and their use are well known in the art (see, e.g., U.S. Pat. Nos: 6,618,6796; 6,379,897; 6,664,377; 6,451,536; 548,257; U.S. 20030157485 and Schena et al. (1995) *Science* 20, 467-470; Gerhold et al. (1999) *Trends In Biochem. Sci.* 24, 168-173; and Lennon et al. (2000) *Drug Discovery Today* 5, 59-65, which are herein incorporated by reference in their entirety).

Serial Analysis of Gene Expression (SAGE) can also be performed (See for example U.S. Patent Application 20030215858).

To monitor mRNA levels, for example, mRNA is extracted from the biological sample to be tested, reverse transcribed, and fluorescently-labeled cDNA probes are generated. The microarrays capable of hybridizing to marker cDNA are then probed with the labeled cDNA probes, the slides scanned and fluorescence intensity measured. This intensity correlates with the hybridization intensity and expression levels.

Types of probes that can be used in the methods described herein include cDNA, riboprobes, synthetic oligonucleotides and genomic probes. The type of probe used will generally be dictated by the particular situation, such as riboprobes for in situ hybridization, and cDNA for Northern blotting, for example. In one embodiment, the probe is directed to nucleotide regions unique to the RNA. The probes may be as short as is required to differentially recognize marker mRNA transcripts, and may be as short as, for example, 15 bases; however, probes of at least 17, 18, 19 or 20 or more bases can be used. In one embodiment, the primers and probes hybridize specifically under stringent conditions to a DNA fragment having the nucleotide sequence corresponding to the marker. As herein used, the term "stringent conditions" means hybridization will occur only if there is at least 95% identity in nucleotide sequences. In another embodiment, hybridization under "stringent conditions" occurs when there is at least 97% identity between the sequences.

The form of labeling of the probes may be any that is appropriate, such as the use of radioisotopes, for example, $^{32}P$ and $^{35}S$. Labeling with radioisotopes may be achieved, whether the probe is synthesized chemically or biologically, by the use of suitably labeled bases.

In one embodiment, the biological sample contains polypeptide molecules from the test subject. Alternatively, the biological sample can contain mRNA molecules from the test subject or genomic DNA molecules from the test subject.

In another embodiment, the methods further involve obtaining a control biological sample from a control subject, contacting the control sample with a compound or agent capable of detecting marker polypeptide, mRNA, genomic DNA, or fragments thereof, such that the presence of the marker polypeptide, mRNA, genomic DNA, or fragments thereof, is detected in the biological sample, and comparing the presence of the marker polypeptide, mRNA, genomic DNA, or fragments thereof, in the control sample with the presence of the marker polypeptide, mRNA, genomic DNA, or fragments thereof in the test sample.

c. Methods for Detection of Biomarker Protein Expression

The activity or level of a biomarker protein can be detected and/or quantified by detecting or quantifying the expressed polypeptide. The polypeptide can be detected and quantified by any of a number of means well known to those of skill in the art. Aberrant levels of polypeptide expression of the polypeptides encoded by a biomarker nucleic acid and functionally similar homologs thereof, including a fragment or genetic alteration thereof (e.g., in regulatory or promoter regions thereof) are associated with the likelihood of response of a cancer to an immune checkpoint therapy. Any method known in the art for detecting polypeptides can be used. Such methods include, but are not limited to, immunodiffusion, immunoelectrophoresis, radioimmunoassay (MA), enzyme-linked immunosorbent assays (ELISAs), immunofluorescent assays, Western blotting, binder-ligand assays, immunohistochemical techniques, agglutination, complement assays, high performance liquid chromatography (HPLC), thin layer chromatography (TLC), hyperdiffusion chromatography, and the like (e.g., Basic and Clinical Immunology, Sites and Terr, eds., Appleton and Lange, Norwalk, Conn. pp 217-262, 1991 which is incorporated by reference). Preferred are binder-ligand immunoassay methods including reacting antibodies with an epitope or epitopes and competitively displacing a labeled polypeptide or derivative thereof.

For example, ELISA and MA procedures may be conducted such that a desired biomarker protein standard is labeled (with a radioisotope such as $^{125}I$ or $^{35}S$, or an assayable enzyme, such as horseradish peroxidase or alkaline phosphatase), and, together with the unlabelled sample, brought into contact with the corresponding antibody, whereon a second antibody is used to bind the first, and radioactivity or the immobilized enzyme assayed (competitive assay). Alternatively, the biomarker protein in the sample is allowed to react with the corresponding immobilized antibody, radioisotope- or enzyme-labeled anti-biomarker proteinantibody is allowed to react with the system, and radioactivity or the enzyme assayed (ELISA-sandwich assay). Other conventional methods may also be employed as suitable.

The above techniques may be conducted essentially as a "one-step" or "two-step" assay. A "one-step" assay involves contacting antigen with immobilized antibody and, without washing, contacting the mixture with labeled antibody. A "two-step" assay involves washing before contacting, the mixture with labeled antibody. Other conventional methods may also be employed as suitable.

In one embodiment, a method for measuring biomarker protein levels comprises the steps of: contacting a biological specimen with an antibody or variant (e.g., fragment) thereof which selectively binds the biomarker protein, and detecting whether said antibody or variant thereof is bound to said sample and thereby measuring the levels of the biomarker protein.

Enzymatic and radiolabeling of biomarker protein and/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect biomarker protein according to a practitioner's preference based upon the present disclosure. One such technique is Western blotting (Towbin et at., Proc. Nat. Acad. Sci. 76:4350 (1979)), wherein a suitably treated sample is run on an SDS-PAGE gel before being transferred to a solid support, such as a nitrocellulose filter. Anti-biomarker protein antibodies (unlabeled) are then brought into contact with the support and assayed by a secondary immunological reagent, such as labeled protein A or anti-immunoglobulin (suitable labels including $^{125}$I, horseradish peroxidase and alkaline phosphatase). Chromatographic detection may also be used.

Immunohistochemistry may be used to detect expression of biomarker protein, e.g., in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabelling. The assay is scored visually, using microscopy.

Anti-biomarker protein antibodies, such as intrabodies, may also be used for imaging purposes, for example, to detect the presence of biomarker protein in cells and tissues of a subject. Suitable labels include radioisotopes, iodine ($^{125}$I, $^{121}$I), carbon ($^{14}$C), sulphur ($^{35}$S), tritium ($^{3}$H), indium ($^{112}$In), and technetium ($^{99}$mTc), fluorescent labels, such as fluorescein and rhodamine, and biotin.

For in vivo imaging purposes, antibodies are not detectable, as such, from outside the body, and so must be labeled, or otherwise modified, to permit detection. Markers for this purpose may be any that do not substantially interfere with the antibody binding, but which allow external detection. Suitable markers may include those that may be detected by X-radiography, NMR or MM. For X-radiographic techniques, suitable markers include any radioisotope that emits detectable radiation but that is not overtly harmful to the subject, such as barium or cesium, for example. Suitable markers for NMR and MM generally include those with a detectable characteristic spin, such as deuterium, which may be incorporated into the antibody by suitable labeling of nutrients for the relevant hybridoma, for example.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99. The labeled antibody or antibody fragment will then preferentially accumulate at the location of cells which contain biomarker protein. The labeled antibody or antibody fragment can then be detected using known techniques.

Antibodies that may be used to detect biomarker protein include any antibody, whether natural or synthetic, full length or a fragment thereof, monoclonal or polyclonal, that binds sufficiently strongly and specifically to the biomarker protein to be detected. An antibody may have a $K_d$ of at most about $10^{-6}$M, $10^{-7}$M, $10^{-8}$M, $10^{-9}$M, $10^{-10}$M, $10^{-11}$M, $10^{-12}$M. The phrase "specifically binds" refers to binding of, for example, an antibody to an epitope or antigen or antigenic determinant in such a manner that binding can be displaced or competed with a second preparation of identical or similar epitope, antigen or antigenic determinant. An antibody may bind preferentially to the biomarker protein relative to other proteins, such as related proteins.

Antibodies are commercially available or may be prepared according to methods known in the art.

Antibodies and derivatives thereof that may be used encompass polyclonal or monoclonal antibodies, chimeric, human, humanized, primatized (CDR-grafted), veneered or single-chain antibodies as well as functional fragments, i.e., biomarker protein binding fragments, of antibodies. For example, antibody fragments capable of binding to a biomarker protein or portions thereof, including, but not limited to, Fv, Fab, Fab' and F(ab') 2 fragments can be used. Such fragments can be produced by enzymatic cleavage or by recombinant techniques. For example, papain or pepsin cleavage can generate Fab or F(ab') 2 fragments, respectively. Other proteases with the requisite substrate specificity can also be used to generate Fab or F(ab') 2 fragments. Antibodies can also be produced in a variety of truncated forms using antibody genes in which one or more stop codons have been introduced upstream of the natural stop site. For example, a chimeric gene encoding a F(ab') 2 heavy chain portion can be designed to include DNA sequences encoding the CH, domain and hinge region of the heavy chain.

Synthetic and engineered antibodies are described in, e.g., Cabilly et al., U.S. Pat. No. 4,816,567 Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0451216 B1; and Padlan, E. A. et al., EP 0519596 A1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single-chain antibodies. Antibodies produced from a library, e.g., phage display library, may also be used.

In some embodiments, agents that specifically bind to a biomarker protein other than antibodies are used, such as peptides. Peptides that specifically bind to a biomarker protein can be identified by any means known in the art. For example, specific peptide binders of a biomarker protein can be screened for using peptide phage display libraries.

d. Methods for Detection of Biomarker Structural Alterations

The following illustrative methods can be used to identify the presence of a structural alteration in a biomarker nucleic acid and/or biomarker polypeptide molecule in order to, for example, identify PBRM1 proteins that having mutations such as described herein.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in a biomarker nucleic acid such as a biomarker gene (see Abravaya et al. (1995) Nucleic Acids Res. 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a biomarker gene under conditions such that hybridization and amplification of the biomarker gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) *Proc. Natl. Acad. Sci. USA* 87:1874-1878), transcriptional amplification system (Kwoh, D. Y. et al. (1989) *Proc. Natl. Acad. Sci. USA* 86:1173-1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a biomarker nucleic acid from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in biomarker nucleic acid can be identified by hybridizing a sample and control nucleic acids, e.g., DNA or RNA, to high density arrays containing hundreds or thousands of oligonucleotide probes (Cronin, M. T. et al. (1996) *Hum. Mutat.* 7:244-255; Kozal, M. J. et al. (1996) *Nat. Med.* 2:753-759). For example, biomarker genetic mutations can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene. Such biomarker genetic mutations can be identified in a variety of contexts, including, for example, germline and somatic mutations.

In yet another embodiment, any of a variety of sequencing reactions known in the art can be used to directly sequence a biomarker gene and detect mutations by comparing the sequence of the sample biomarker with the corresponding wild-type (control) sequence. Examples of sequencing reactions include those based on techniques developed by Maxam and Gilbert (1977) *Proc. Natl. Acad. Sci. USA* 74:560 or Sanger (1977) *Proc. Natl. Acad Sci. USA* 74:5463. It is also contemplated that any of a variety of automated sequencing procedures can be utilized when performing the diagnostic assays (Naeve (1995) *Biotechniques* 19:448-53), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in a biomarker gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes formed by hybridizing (labeled) RNA or DNA containing the wild-type biomarker sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with SI nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl. Acad. Sci. USA* 85:4397 and Saleeba et al. (1992) *Methods Enzymol.* 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in biomarker cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a biomarker sequence, e.g., a wild-type biomarker treated with a DNA mismatch repair enzyme, and the cleavage products, if any, can be detected from electrophoresis protocols or the like (e.g., U.S. Pat. No. 5,459,039.)

In other embodiments, alterations in electrophoretic mobility can be used to identify mutations in biomarker genes. For example, single strand conformation polymorphism (SSCP) may be used to detect differences in electrophoretic mobility between mutant and wild type nucleic acids (Orita et al. (1989) *Proc Natl. Acad. Sci USA* 86:2766; see also Cotton (1993) *Mutat. Res.* 285:125-144 and Hayashi (1992) *Genet. Anal. Tech. Appl.* 9:73-79). Single-stranded DNA fragments of sample and control biomarker nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature*

313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163; Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

3. Anti-Cancer Therapies

The efficacy of immune checkpoint therapy is predicted according to biomarker amount and/or activity associated with a cancer in a subject according to the methods described herein. In one embodiment, such immune checkpoint therapy or combinations of therapies (e.g., anti-PD-1 antibodies) can be administered once a subject is indicated as being a likely responder to immune checkpoint therapy. In another embodiment, such immune checkpoint therapy can be avoided once a subject is indicated as not being a likely responder to immune checkpoint therapy and an alternative treatment regimen, such as targeted and/or untargeted anti-cancer therapies can be administered. Combination therapies are also contemplated and can comprise, for example, one or more chemotherapeutic agents and radiation, one or more chemotherapeutic agents and immunotherapy, or one or more chemotherapeutic agents, radiation and chemotherapy, each combination of which can be with immune checkpoint therapy.

The term "targeted therapy" refers to administration of agents that selectively interact with a chosen biomolecule to thereby treat cancer. For example, anti-PBRM1 agents, such as therapeutic monoclonal blocking antibodies, which are well-known in the art and described above, can be used to target tumor microenvironments and cells expressing unwanted PBRM1. Similarly, nivolumab (Opdivo®) is a human IgG4 anti-PD-1 monoclonal antibody that blocks PD-1 activity (see, for example, Wang et al. (2014) *Cancer Immunol. Res.* 2:846-856; Johnson et al. (2015) *Ther. Adv. Med. Oncol.* 7:97-106; and Sundar et al. (2015) *Ther. Adv. Med. Oncol.* 7:85-96).

Immunotherapy is one form of targeted therapy that may comprise, for example, the use of cancer vaccines and/or sensitized antigen presenting cells. For example, an oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They may also act as vectors for anticancer genes, allowing them to be specifically delivered to the tumor site. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

The term "untargeted therapy" refers to administration of agents that do not selectively interact with a chosen biomolecule yet treat cancer. Representative examples of untargeted therapies include, without limitation, chemotherapy, gene therapy, and radiation therapy.

In one embodiment, chemotherapy is used. Chemotherapy includes the administration of a chemotherapeutic agent. Such a chemotherapeutic agent may be, but is not limited to, those selected from among the following groups of compounds: platinum compounds, cytotoxic antibiotics, antimetabolities, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1, 8-naphthalimide; (Trevigen); 6(5H)-phenanthridinone (Trevigen); benzamide (U.S. Pat. Re. 36,397); and NU1025 (Bowman et al.). The mechanism of action is generally related to the ability of PARP inhibitors to bind PARP and decrease its activity. PARP catalyzes the conversion of .beta.-nicotinamide adenine dinucleotide (NAD+) into nicotinamide and poly- ADP-ribose (PAR). Both poly (ADP-ribose) and PARP have been linked to regulation of transcription, cell proliferation, genomic stability, and carcinogenesis (Bouchard V. J. et. al. Experimental Hematology, Volume 31, Number 6, June 2003, pp. 446-454(9); Herceg Z.; Wang Z.-Q. Mutation Research/Fundamental and Molecular Mechanisms of Mutagenesis, Volume 477, Number 1, 2 Jun. 2001, pp. 97-110(14)). Poly(ADP-ribose) polymerase 1 (PARP1) is a key molecule in the repair of DNA single-strand breaks (SSBs) (de Murcia J. et al. 1997. Proc Natl Acad Sci USA 94:7303-7307; Schreiber V, Dantzer F, Ame J C, de Murcia G (2006) Nat Rev Mol Cell Biol 7:517-528; Wang Z Q, et al. (1997) Genes Dev 11:2347-2358). Knockout of SSB repair by inhibition of PARP1 function induces DNA double-strand breaks (DSBs) that can trigger synthetic lethality in cancer cells with defective homology-directed DSB repair (Bryant H E, et al. (2005) Nature 434:913-917; Farmer H, et al. (2005) Nature 434:917-921). The foregoing examples of chemotherapeutic agents are illustrative, and are not intended to be limiting.

In another embodiment, radiation therapy is used. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In another embodiment, hormone therapy is used. Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In another embodiment, hyperthermia, a procedure in which body tissue is exposed to high temperatures (up to 106° F.) is used. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (e.g., radiation therapy, chemotherapy, and biological therapy) to try to increase their effectiveness. Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It can be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, can cause discomfort or even significant local pain in about half the patients treated. It can also cause blisters, which generally heal rapidly.

In still another embodiment, photodynamic therapy (also called PDT, photoradiation therapy, phototherapy, or photochemotherapy) is used for the treatment of some types of cancer. It is based on the discovery that certain chemicals known as photosensitizing agents can kill one-celled organisms when the organisms are exposed to a particular type of light. PDT destroys cancer cells through the use of a fixed-frequency laser light in combination with a photosensitizing agent. In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells. The laser light used in PDT can be directed through a fiber-optic (a very thin glass strand). The fiber-optic is placed close to the cancer to deliver the proper amount of light. The fiber-optic can be directed through a bronchoscope into the lungs for the treatment of lung cancer or through an endoscope into the esophagus for the treatment of esophageal cancer. An advantage of PDT is that it causes minimal damage to healthy tissue. However, because the laser light currently in use cannot pass through more than about 3 centimeters of tissue (a little more than one and an eighth inch), PDT is mainly used to treat tumors on or just under the skin or on the lining of internal organs. Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and can include coughing, trouble swallowing, abdominal pain, and painful breathing or shortness of breath. In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early nonsmall cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity.

In yet another embodiment, laser therapy is used to harness high-intensity light to destroy cancer cells. This technique is often used to relieve symptoms of cancer such as bleeding or obstruction, especially when the cancer cannot be cured by other treatments. It may also be used to treat cancer by shrinking or destroying tumors. The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also can be used for very precise surgical work, such as repairing a damaged retina in the eye or cutting through tissue (in place of a scalpel). Although there are several different kinds of lasers, only three kinds have gained wide use in medicine: Carbon dioxide ($CO_2$) laser—This type of laser can remove thin layers from the skin's surface without penetrating the deeper layers. This technique is particularly useful in treating tumors that have not spread deep into the skin and certain precancerous conditions. As an alternative to traditional scalpel surgery, the $CO_2$ laser is also able to cut the skin. The laser is used in this way to remove skin cancers. Neodymium:yttrium-aluminum-garnet (Nd:YAG) laser—Light from this laser can penetrate deeper into tissue than light from the other types of lasers, and it can cause blood to clot quickly. It can be carried through optical fibers to less accessible parts of the body. This type of laser is sometimes used to treat throat cancers. Argon laser—This laser can pass through only superficial layers of tissue and is therefore useful in dermatology and in eye surgery. It also is used with light-sensitive dyes to treat tumors in a procedure known as photodynamic therapy (PDT). Lasers have several advantages over standard surgical tools, including: Lasers are more precise than scalpels. Tissue near an incision is protected, since there is little contact with surrounding skin or other tissue. The heat produced by lasers sterilizes the surgery site, thus reducing the risk of infection. Less operating time may be needed because the precision of the laser allows for a smaller incision. Healing time is often shortened; since laser heat seals blood vessels, there is less bleeding, swelling, or scarring. Laser surgery may be less complicated. For example, with fiber optics, laser light can be directed to parts of the body without making a large incision. More procedures may be done on an outpatient basis. Lasers can be used in two ways to treat cancer: by shrinking or destroying a tumor with heat, or by activating a chemical—known as a photosensitizing agent—that destroys cancer cells. In PDT, a photosensitizing agent is retained in cancer cells and can be stimulated by light to cause a reaction that kills cancer cells. $CO_2$ and Nd:YAG lasers are used to shrink or destroy tumors. They may be used with endoscopes, tubes that allow physicians to see into certain areas of the body, such as the bladder. The light from some lasers can be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems can produce a cutting area as small as 200 microns in diameter—less than the width of a very fine thread. Lasers are used to treat many types of cancer. Laser surgery is a standard treatment for certain stages of glottis (vocal cord), cervical, skin, lung, vaginal, vulvar, and penile cancers. In addition to its use to destroy the cancer, laser surgery is also used to help relieve symptoms caused by cancer (palliative care). For example, lasers may be used to shrink or destroy a tumor that is blocking a patient's trachea (windpipe), making it easier to breathe. It is also sometimes used for palliation in colorectal and anal cancer. Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

The duration and/or dose of treatment with anti-immune checkpoint therapies may vary according to the particular anti-immune checkpoint agent or combination thereof. An appropriate treatment time for a particular cancer therapeutic agent will be appreciated by the skilled artisan. The present invention contemplates the continued assessment of optimal treatment schedules for each cancer therapeutic agent, where the phenotype of the cancer of the subject as determined by the methods of the present invention is a factor in determining optimal treatment doses and schedules.

Any means for the introduction of a polynucleotide into mammals, human or non-human, or cells thereof may be adapted to the practice of this invention for the delivery of the various constructs of the present invention into the intended recipient. In one embodiment of the present invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well known and any can be selected for a particular application. In one embodiment of the present invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991). A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the present invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J. Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant biomarker polypeptides, and fragments thereof, can be administered to subjects. In some embodiments, fusion proteins can be constructed and administered which have enhanced biological properties. In addition, the biomarker polypeptides, and fragment thereof, can be modified according to well-known pharmacological methods in the art (e.g., pegylation, glycosylation, oligomerization, etc.) in order to further enhance desirable biological activities, such as increased bioavailability and decreased proteolytic degradation.

4. Clincal Efficacy

Clinical efficacy can be measured by any method known in the art. For example, the response to a therapy, such as anti-immune checkpoint therapies, relates to any response of the cancer, e.g., a tumor, to the therapy, preferably to a change in tumor mass and/or volume after initiation of neoadjuvant or adjuvant chemotherapy. Tumor response may be assessed in a neoadjuvant or adjuvant situation where the size of a tumor after systemic intervention can be compared to the initial size and dimensions as measured by CT, PET, mammogram, ultrasound or palpation and the cellularity of a tumor can be estimated histologically and compared to the cellularity of a tumor biopsy taken before initiation of treatment. Response may also be assessed by caliper measurement or pathological examination of the tumor after biopsy or surgical resection. Response may be recorded in a quantitative fashion like percentage change in tumor volume or cellularity or using a semi-quantitative scoring system such as residual cancer burden (Symmans et al., *J. Clin. Oncol.* (2007) 25:4414-4422) or Miller-Payne score (Ogston et al., (2003) *Breast* (Edinburgh, Scotland) 12:320-327) in a qualitative fashion like "pathological complete response" (pCR), "clinical complete remission" (cCR), "clinical partial remission" (cPR), "clinical stable disease"

(cSD), "clinical progressive disease" (cPD) or other qualitative criteria. Assessment of tumor response may be performed early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed.

In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular anti-immune checkpoint therapeutic regimen is at least 25%, 30%, 35%, 40%, 45%, 50%, 55%, 60%, 65%, 70%, 75%, 80%, 85%, or more.

Additional criteria for evaluating the response to anti-immune checkpoint therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

For example, in order to determine appropriate threshold values, a particular anti-immune checkpoint therapeutic regimen can be administered to a population of subjects and the outcome can be correlated to biomarker measurements that were determined prior to administration of any immune checkpoint therapy. The outcome measurement may be pathologic response to therapy given in the neoadjuvant setting. Alternatively, outcome measures, such as overall survival and disease-free survival can be monitored over a period of time for subjects following immune checkpoint therapy for whom biomarker measurement values are known. In certain embodiments, the same doses of anti-immune checkpoint agents are administered to each subject. In related embodiments, the doses administered are standard doses known in the art for anti-immune checkpoint agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of an immune checkpoint therapy can be determined using methods such as those described in the Examples section.

5. Further Uses and Methods of the Present Invention

The methods described herein can be used in a variety of diagnostic, prognostic, and therapeutic applications. In any method described herein, such as a diagnostic method, prognostic method, therapeutic method, or combination thereof, all steps of the method can be performed by a single actor or, alternatively, by more than one actor. For example, diagnosis can be performed directly by the actor providing therapeutic treatment. Alternatively, a person providing a therapeutic agent can request that a diagnostic assay be performed. The diagnostician and/or the therapeutic interventionist can interpret the diagnostic assay results to determine a therapeutic strategy. Similarly, such alternative processes can apply to other assays, such as prognostic assays. The compositions described herein can also be used in a variety of diagnostic, prognostic, and therapeutic applications regarding biomarkers described herein, such as those listed in Table 1. Moreover, any method of diagnosis, prognosis, prevention, and the like described herein can be be applied to a therapy or test agent of interest, such as immune checkpoint therapies, EGFR therapies, anti-cancer therapies, and the like.

a. Screening Methods

One aspect of the present invention relates to screening assays, including non-cell based assays. In one embodiment, the assays provide a method for identifying whether a cancer is likely to respond to immune checkpoint therapy and/or whether an agent can inhibit the growth of or kill a cancer cell that is unlikely to respond to immune checkpoint therapy.

In one embodiment, the present invention relates to assays for screening test agents which bind to, or modulate the biological activity of, at least one biomarker listed in Table 1. In one embodiment, a method for identifying such an agent entails determining the ability of the agent to modulate, e.g. inhibit, the at least one biomarker listed in Table 1.

In one embodiment, an assay is a cell-free or cell-based assay, comprising contacting at least one biomarker listed in Table 1, with a test agent, and determining the ability of the test agent to modulate (e.g. inhibit) the enzymatic activity of the biomarker, such as by measuring direct binding of substrates or by measuring indirect parameters as described below.

For example, in a direct binding assay, biomarker protein (or their respective target polypeptides or molecules) can be coupled with a radioisotope or enzymatic label such that binding can be determined by detecting the labeled protein or molecule in a complex. For example, the targets can be labeled with $^{125}$I, $^{35}$S, $^{14}$C, or $^{3}$H, either directly or indirectly, and the radioisotope detected by direct counting of radioemmission or by scintillation counting. Alternatively, the targets can be enzymatically labeled with, for example, horseradish peroxidase, alkaline phosphatase, or luciferase, and the enzymatic label detected by determination of conversion of an appropriate substrate to product. Determining the interaction between biomarker and substrate can also be accomplished using standard binding or enzymatic analysis assays. In one or more embodiments of the above described assay methods, it may be desirable to immobilize polypeptides or molecules to facilitate separation of complexed from uncomplexed forms of one or both of the proteins or molecules, as well as to accommodate automation of the assay.

Binding of a test agent to a target can be accomplished in any vessel suitable for containing the reactants. Non-limiting examples of such vessels include microtiter plates, test tubes, and micro-centrifuge tubes. Immobilized forms of the antibodies of the present invention can also include antibodies bound to a solid phase like a porous, microporous (with an average pore diameter less than about one micron) or macroporous (with an average pore diameter of more than about 10 microns) material, such as a membrane, cellulose, nitrocellulose, or glass fibers; a bead, such as that made of agarose or polyacrylamide or latex; or a surface of a dish, plate, or well, such as one made of polystyrene.

In an alternative embodiment, determining the ability of the agent to modulate the interaction between the biomarker and a substrate or a biomarker and its natural binding partner can be accomplished by determining the ability of the test agent to modulate the activity of a polypeptide or other product that functions downstream or upstream of its position within the signaling pathway (e.g., feedback loops). Such feedback loops are well-known in the art (see, for example, Chen and Guillemin (2009) *Int. J. Tryptophan Res.* 2:1-19).

The present invention further pertains to novel agents identified by the above-described screening assays. Accordingly, it is within the scope of this invention to further use an agent identified as described herein in an appropriate animal model. For example, an agent identified as described herein can be used in an animal model to determine the efficacy, toxicity, or side effects of treatment with such an agent. Alternatively, an antibody identified as described herein can be used in an animal model to determine the mechanism of action of such an agent.

b. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining the amount and/or activity level of a biomarker listed in Table 1 in the context of a biological sample (e.g., blood, serum, cells, or tissue) to thereby determine whether an individual afflicted with a cancer is likely to respond to immune checkpoint therapy, whether in an original or recurrent cancer. Such assays can be used for prognostic or predictive purpose to thereby prophylactically treat an individual prior to the onset or after recurrence of a disorder characterized by or associated with biomarker polypeptide, nucleic acid expression or activity. The skilled artisan will appreciate that any method can use one or more (e.g., combinations) of biomarkers listed in Table 1.

Another aspect of the present invention pertains to monitoring the influence of agents (e.g., drugs, compounds, and small nucleic acid-based molecules) on the expression or activity of a biomarker listed in Table 1. These and other agents are described in further detail in the following sections.

The skilled artisan will also appreciated that, in certain embodiments, the methods of the present invention implement a computer program and computer system. For example, a computer program can be used to perform the algorithms described herein. A computer system can also store and manipulate data generated by the methods of the present invention which comprises a plurality of biomarker signal changes/profiles which can be used by a computer system in implementing the methods of this invention. In certain embodiments, a computer system receives biomarker expression data; (ii) stores the data; and (iii) compares the data in any number of ways described herein (e.g., analysis relative to appropriate controls) to determine the state of informative biomarkers from cancerous or pre-cancerous tissue. In other embodiments, a computer system (i) compares the determined expression biomarker level to a threshold value; and (ii) outputs an indication of whether said biomarker level is significantly modulated (e.g., above or below) the threshold value, or a phenotype based on said indication.

In certain embodiments, such computer systems are also considered part of the present invention. Numerous types of computer systems can be used to implement the analytic methods of this invention according to knowledge possessed by a skilled artisan in the bioinformatics and/or computer arts. Several software components can be loaded into memory during operation of such a computer system. The software components can comprise both software components that are standard in the art and components that are special to the present invention (e.g., dCHIP software described in Lin et al. (2004) *Bioinformatics* 20, 1233-1240; radial basis machine learning algorithms (RBM) known in the art).

The methods of the present invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

In certain embodiments, the computer comprises a database for storage of biomarker data. Such stored profiles can be accessed and used to perform comparisons of interest at a later point in time. For example, biomarker expression profiles of a sample derived from the non-cancerous tissue of a subject and/or profiles generated from population-based distributions of informative loci of interest in relevant populations of the same species can be stored and later compared to that of a sample derived from the cancerous tissue of the subject or tissue suspected of being cancerous of the subject.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

c. Diagnostic Assays

The present invention provides, in part, methods, systems, and code for accurately classifying whether a biological sample is associated with a cancer that is likely to respond to immune checkpoint therapy. In some embodiments, the present invention is useful for classifying a sample (e.g., from a subject) as associated with or at risk for responding to or not responding to immune checkpoint therapy using a statistical algorithm and/or empirical data (e.g., the amount or activity of a biomarker listed in Table 1).

An exemplary method for detecting the amount or activity of a biomarker listed in Table 1, and thus useful for classifying whether a sample is likely or unlikely to respond to immune checkpoint therapy involves obtaining a biological sample from a test subject and contacting the biological sample with an agent, such as a protein-binding agent like an antibody or antigen-binding fragment thereof, or a nucleic acid-binding agent like an oligonucleotide, capable of detecting the amount or activity of the biomarker in the biological sample. In some embodiments, at least one antibody or antigen-binding fragment thereof is used, wherein two, three, four, five, six, seven, eight, nine, ten, or more such antibodies or antibody fragments can be used in combination (e.g., in sandwich ELISAs) or in serial. In certain instances, the statistical algorithm is a single learning statistical classifier system. For example, a single learning statistical classifier system can be used to classify a sample as a based upon a prediction or probability value and the presence or level of the biomarker. The use of a single learning statistical classifier system typically classifies the sample as, for example, a likely immune checkpoint therapy responder or progressor sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the sample classification results to a clinician, e.g., an oncologist.

In another embodiment, the diagnosis of a subject is followed by administering to the individual a therapeutically effective amount of a defined treatment based upon the diagnosis.

In one embodiment, the methods further involve obtaining a control biological sample (e.g., biological sample from a subject who does not have a cancer or whose cancer is susceptible to immune checkpoint therapy), a biological sample from the subject during remission, or a biological sample from the subject during treatment for developing a cancer progressing despite immune checkpoint therapy.

d. Prognostic Assays

The diagnostic methods described herein can furthermore be utilized to identify subjects having or at risk of developing a cancer that is likely or unlikely to be responsive to immune checkpoint therapy. The assays described herein, such as the preceding diagnostic assays or the following assays, can be utilized to identify a subject having or at risk of developing a disorder associated with a misregulation of the amount or activity of at least one biomarker described in Table 1, such as in cancer. Alternatively, the prognostic assays can be utilized to identify a subject having or at risk for developing a disorder associated with a misregulation of the at least one biomarker described in Table 1, such as in cancer. Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with the aberrant biomarker expression or activity.

e. Treatment Methods

The compositions described herein (including dual binding antibodies and derivatives and conjugates thereof) can be used in a variety of in vitro and in vivo therapeutic applications using the formulations and/or combinations described herein. In one embodiment, anti-immune checkpoint agents can be used to treat cancers determined to be responsive thereto. For example, antibodies that block the interaction between PD-L1, PD-L2, and/or CTLA-4 and their receptors (e.g., PD-L1 binding to PD-1, PD-L2 binding to PD-1, and the like) can be used to treat cancer in subjects identified as likely responding thereto.

6. Pharmaceutical Compositions

In another aspect, the present invention provides pharmaceutically acceptable compositions which comprise a therapeutically-effective amount of an agent that modulates (e.g., decreases) biomarker expression and/or activity, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., inhibits) biomarker expression and/or activity, or expression and/or activity of the complex, or composition comprising an agent that modulates (e.g., inhibits) biomarker expression and/or activity, or expression and/or activity of the complex, which is effective for producing some desired therapeutic effect, e.g., cancer treatment, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., inhibits) biomarker expression and/or activity, or expression and/or activity of the complex encompassed by the present invention. These salts can be prepared in situ during the final isolation and purification of the respiration uncoupling agents, or by separately reacting a purified respiration uncoupling agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", J. Pharm. Sci. 66:1-19).

In other cases, the agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., inhibits) biomarker expression and/or activity, or expression and/or activity of the complex. These salts can likewise be prepared in situ during the final isolation and purification of the respiration uncoupling agents, or by separately reacting the purified respiration uncoupling agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., inhibits) biomarker expression and/or activity, with the carrier and, optionally, one or more accessory ingredients. In general, the formulations are prepared by uniformly and intimately bringing into association a respiration uncoupling agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a respiration uncoupling agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more respiration uncoupling agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., inhibits) biomarker expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a respiration uncoupling agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., inhibits) biomarker expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., inhibits) biomarker expression and/or activity, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a respiration uncoupling agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more respiration uncoupling agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the present invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., inhibits) biomarker expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the respiration uncoupling agents of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods of the present invention so as to obtain an amount of the active ingredient, which is effective to achieve the desired therapeutic response for a particular subject, composition, and mode of administration, without being toxic to the subject.

The nucleic acid molecules of the present invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The present invention also encompasses kits for detecting and/or modulating biomarkers described herein. A kit of the present invention may also include instructional materials disclosing or describing the use of the kit or an antibody of the disclosed invention in a method of the disclosed invention as provided herein. A kit may also include additional components to facilitate the particular application for which the kit is designed. For example, a kit may additionally contain means of detecting the label (e.g., enzyme substrates for enzymatic labels, filter sets to detect fluorescent labels, appropriate secondary labels such as a sheep anti-mouse-HRP, etc.) and reagents necessary for controls (e.g., control biological samples or standards). A kit may additionally include buffers and other reagents recognized for use in a method of the disclosed invention. Non-limiting examples include agents to reduce non-specific binding, such as a carrier protein or a detergent.

Exemplification

This invention is further illustrated by the following examples, which should not be construed as limiting.

Example 1: Materials and Methods for Example 2 a. Clinical Cohort Consolidation

The training cohort was gathered from patients enrolled in CA209-009 (NCT01358721), a study of nivolumab (BMS-936558) monotherapy in metastatic renal cell carcinoma. The validation cohort was gathered from patients at the Dana-Farber Cancer Institute and Memorial Sloan Kettering Cancer Institute who received immune checkpoint therapy as monotherapy or in combination with other immune checkpoint or targeted therapies and had banked adequate pre-treatment tumor tissue for whole exome characterization. All patients provided consent to an Institutional Review Board protocol that allows research molecular characterization of tumor and germline samples.

b. DNA and RNA Extraction and Sequencing

After fixation and mounting, 5-10 10 μm slices from formalin-fixed, paraffin-embedded (FFPE) tumor blocks were obtained, and tumor-enriched tissue was macrodissected. Paraffin was removed from FFPE sections and cores using CitriSolv™ (Fisher Scientific, Hampton, N.H.), followed by ethanol washes and tissue lysis overnight at 56° C. Samples were then incubated at 90° C. to remove DNA crosslinks, and DNA- and when possible, RNA-extraction was performed using Qiagen AllPrep DNA/RNA Mini Kit (#51306, Qiagen, Hilden, Germany). Germline DNA was obtained from adjacent PBMCs.

Whole exome and whole transcriptome sequencing of tumor and germline samples were performed as previously described (Van Allen et al. (2015) *Science* 350:207-211; Van Allen et al. (2014) *Nat. Med.* 20:682-688). All samples in the training cohort were sequenced using the Illumina exome, while a portion of the samples in the validation cohort were sequenced using the Agilent exome (Table 4A). The Illumina exome uses Illumina's in-solution DNA probe based hybrid selection method to target approximately 37.7 Mb of mainly exonic territory, using similar principles as the Broad Institute-Agilent Technologies developed in-solution RNA probe based hybrid selection method (Agilent SureSelect™ All Exon V2) (Fisher et al. (2011) *Genome Biol.* 12:R1; Gnirke et al. (2009) *Nat. Biotechnol.* 27:182-189) to generate Illumina exome sequencing libraries.

Pooled libraries were normalized to 2 nM and denatured using 0.2 N NaOH prior to sequencing. Flowcell cluster amplification and sequencing were performed according to the manufacturer's protocols using either the HiSeq 2000 v3 or HiSeq 2500. Each run was a 76 bp paired-end with a dual eight-base index barcode read. Data was analyzed using the Broad Picard Pipeline, which includes de-multiplexing and data aggregation.

Exome sequence data processing was performed using established analytical pipelines at the Broad Institute. A BAM file was produced using the Picard pipeline (at the World Wide Web address of picard.sourceforge.net), which aligns the tumor and normal sequences to the hg19 human genome build using Illumina sequencing reads. The BAM was uploaded into the Firehose pipeline (at the World Wide Web address of broadinstitute.org/cancer/cga/Firehose), which manages input and output files to be executed by GenePattern (Reich et al. (2006) *Nat. Genet.* 38:500-501). Samples with mean target coverage less than 25× in the tumor and less than 15× in matched normal were excluded.

Quality control modules within Firehose were applied to all sequencing data for comparison of the origin of tumor and normal genotypes and to assess fingerprinting concordance. Cross-contamination of samples was estimated using ContEst (Cibulskis et al. (2011) *Bioinformatics* 27:2601-2602). Samples with ContEst estimates exceeding 5% were excluded from analysis.

c. Whole Exome and Whole Transcriptome Analyses

MuTect was applied to identify somatic single-nucleotide variants (Cibulskis et al. (2013) *Nat. Biotechnol.* 31:213-219). Strelka was used to identify somatic insertions and deletions (Saunders et al. (2012) *Bioinformatics* 28:1811-1817) across the whole exome. Indelocator, which detects small insertions and deletions after local realignment of tumor and normal sequences, was additionally applied to provide further sensitivity to detect indels in PBRM1 (Cancer Genome Atlas Research (2011) *Nature* 474:609-615). The union of indels called by Strelka and Indelocator was used for final analysis. Artifacts introduced by DNA oxidation during sequencing were computationally removed using a filter-based method (Costello et al. (2013) *Nuc. Acids Res.* 41:e67). All somatic mutations detected by whole-exome sequencing were analyzed for potential false positive calls by performing a comparison to mutation calls from a panel of 2,500 germline DNA samples (Stachler et al. (2015) *Nat. Genet.* 47:1047-1055). Mutations found in germline samples were removed from analysis. Annotation of identified variants was done using Oncotator (available at the World Wide Web address of www.broadinstitute.org/cancer/cga/oncotator). All nonsynonymous alterations in PBRM1 were manually reviewed in Integrated Genomics Viewer (IGV_2.3.57) for sequencing quality (Thorvaldsdottir et al. (2013) *Brief Bioinform* 14:178-192).

Copy ratios were calculated for each captured target by dividing the tumor coverage by the median coverage obtained in a set of reference normal samples. The resulting copy ratios were segmented using the circular binary segmentation algorithm (Olshen et al. (2004) *Biostatistics* 5:557-572). Allelic copy number alterations were called while taking into account sample-specific overall chromosomal aberrations (focality) (Brastianos et al. (2015) *Cancer Discov.* 5:1164-1177). Inference of mutational clonality, tumor purity, and tumor ploidy was accomplished with ABSOLUTE (Carter et al. (2012) *Nat Biotechnol.* 30:413-421). Samples had to have estimated tumor purity greater than 10% to be included in the final analysis. As a final quality control metric to ensure adequate sequencing coverage and tumor purity to detect relevant oncogenic events, all samples had to have at least one nonsynonymous mutation in at least one high confidence or candidate cancer driver gene to be included in the final analysis (Tamborero et al. (2013) *Sci. Rep.* 3:2650).

The 4-digit HLA type for each sample was inferred using Polysolver (Shukla et al. (2015) *Nat. Biotechnol.* 33:1152-1158). Neo-epitopes were predicted for each patient by defining all novel amino acid 9mers and 10mers resulting from each single nucleotide polymorphism and indel and determining whether the predicted binding affinity to the patient's germline HLA alleles was <500 nM using NetMHCpan (v2.4) (Hoof et al. (2009) *Immunogenetics* 61:1-13; Karosiene et al. (2013) *Immunogenetics* 65:711-724; Nielsen et al. (2007) *PLoS One* 2:e796).

d. TCGA Analysis

Whole exome mutations annotation files (MAFs) and whole transcriptome gene expression data (RSEM) were downloaded from the Firebrowse KIRC TCGA data release (2016_01_28). Samples with whole transcriptome sequencing in normal tissue only, as well as samples derived from FFPE (N=3), were excluded from analysis.

e. Serum Biomarker Analyses

Serum biomarker analyses were performed as described previously in Choueiri et al. (2016) *Clin. Cancer Res.* 22:5461-5471.

f. Statistical Analyses

Comparisons of neoantigen and mutational load between response groups and of expression levels of individual genes between PBRM1-truncated and PBRM1-wildtype tumors were done with the non-parametric Wilcoxon rank-sum test. Comparisons of the proportion of patients with truncating alterations in PBRM1 by clinical response group were done with the Pearson's chi-squared test without continuity correction. Kaplan-Meier analyses were done using the R packages survival and survminer. All comparisons were two-sided with an alpha-level of 0.05. All statistical analyses were done in R version 3.2.3.

Given the low mutational burden and high tumor microenvironment immune activity characteristic of renal cell carcinoma, it is believed that specific somatic genetic features other than mutational load drive response to immune checkpoint inhibitors in ccRCC. As part of a prospective clinical trial (Choueiri et al. (2016), supra), Applicants analyzed a clinical cohort of 91 patients with metastatic clear cell renal cell carcinoma (mRCC) treated with anti-PD1 therapy (nivolumab) (FIG. 1A; Arm 1: 0.3 mg/kg (N=22); Arm 2: 2 mg/kg (N=22); Arm 3: 10 mg/kg (N=23), and Arm 4: 10 mg/kg (N=24)). Among 56 patients with attempted whole exome sequenceing of pre-treatment tumors, 34 had high-quality whole exome sequencing (WES) for discovery of genetic predictors of response to immune checkpoint therapy, and then validated the findings in an independent cohort of WES of pre-treatment tumors from 28 patients (FIG. 1B). Applicants also analyzed pre-treatment whole transcriptome sequencing (WTS) from a subset of 42 patients from both the training and validation cohorts to assess the impact of genetic changes associated with treatment response on tumor gene expression and immune infiltration.

Example 2: Loss-of-Function of PBRM1 Correlates with Response to Anti-PD1/PD-L1 Therapy in Renal Cell Carcinoma Quality-control metrics were applied to both the training and validation cohorts to ensure sensitive mutation detection (Cibulskis et al. (2011), supra) (FIG. 1B and Table 2A). Of the samples included in the final analysis, average exome-wide target coverage was 140-fold for tumor samples (range: 27-210) and 91-fold (range: 48-168) for matched germline samples. Analysis methods used herein include somatic mutation identification (single nucleotide polymorphisms and insertions and deletions) (as in Cibulskis et al. (2013), supra and Saunders et al. (2012) *Bioinformatics* 28:1811-1817), human lymphocyte antigen (HLA) typing from germline WES (as in Shukla et al. (2015) *Nat. Bio-*

*technol.* 33:1152-1158), neoantigen prediction (as in Hoof et al. (2009) *Immunogenetics* 61:1-13), and estimation of mutational clonality and tumor purity and ploidy (Carter et al. (2012) *Nat Biotechnol.* 30:413-421) using established methods (as in Example 1 and FIG. 1B). In the training cohort, of the 56 out of 91 patients for whom adequate pre-treatment tissue was available for WES, 34 passed quality control and were included in the final analysis (FIG. 1B). For example, sample VA1008 having a chromosome 3p deletion was excluded as having low tumor purity (estimated tumor purity=0.11). Among these 56 pairs matched tumor and normal samples, Sample 2_664 contains germline BAM only, while Sample 4_49 contains tumor BAM only. As quality control for sequenced tissue, 6 of 56 samples were excluded due to poor tumor coverage. They were Samples 4_54 (0.079×), 9_47 (0.30×), 8_100 (7.71×), 11_5 (8.69×), 1_72 (9.63×), and 9_66 (8.72×). Another sample, 9_119 (26.88×), was not excluded. For this sample, with estimated tumor purity of 0.49 and mean target coverage of 27×, a sensitivity of ~90% detected a heterozygous mutation in CA-209009-9_119 (see Cibulskis et al. (2013), supra). Quality control for copy number was also performed.

TABLE 2A

Sequencing Metrics and Inclusion/Exclusion Criteria for Whole Exome Sequencing in Training Cohort (N = 56)

| patient_id | tumor_mtc | normal_mtc | bait_set | absolute_inferred_purity |
|---|---|---|---|---|
| CA209009_1_20 | 34.147062 | 92.688228 | whole_exome_illumina_coding_v1 | 0.51 |
| CA209009_1_32 | 165.03915 | 80.054054 | whole_exome_illumina_coding_v1 | 0.39 |
| CA209009_1_62 | 163.21171 | 81.718582 | whole_exome_illumina_coding_v1 | 0.49 |
| CA209009_11_10 | 153.907825 | 93.664757 | whole_exome_illumina_coding_v1 | 0.76 |
| CA209009_11_11 | 81.495132 | 108.704189 | whole_exome_illumina_coding_v1 | 0.38 |
| CA209009_11_14 | 157.03659 | 99.990083 | whole_exome_illumina_coding_v1 | 0.25 |
| CA209009_11_25 | 150.766602 | 87.494869 | whole_exome_illumina_coding_v1 | 0.32 |
| CA209009_11_56 | 136.739597 | 86.544731 | whole_exome_illumina_coding_v1 | 0.56 |
| CA209009_11_79 | 112.238316 | 91.306045 | whole_exome_illumina_coding_v1 | 0.8 |
| CA209009_11_93 | 193.622831 | 94.511787 | whole_exome_illumina_coding_v1 | 0.2 |
| CA209009_12_115 | 150.50973 | 89.411498 | whole_exome_illumina_coding_v1 | 0.63 |
| CA209009_13_90 | 147.435982 | 79.577243 | whole_exome_illumina_coding_v1 | 0.3 |
| CA209009_13_96 | 189.081727 | 96.347659 | whole_exome_illumina_coding_v1 | 0.67 |
| CA209009_2_102 | 130.03582 | 97.794738 | whole_exome_illumina_coding_v1 | 0.48 |
| CA209009_2_58 | 142.586967 | 82.644492 | whole_exome_illumina_coding_v1 | 0.69 |
| CA209009_2_84 | 166.18581 | 88.436816 | whole_exome_illumina_coding_v1 | 0.45 |
| CA209009_3_114 | 135.707278 | 77.721511 | whole_exome_illumina_coding_v1 | 0.29 |
| CA209009_3_117 | 173.22159 | 68.856331 | whole_exome_illumina_coding_v1 | 0.33 |
| CA209009_3_15 | 143.012126 | 79.906338 | whole_exome_illumina_coding_v1 | 0.69 |
| CA209009_4_68 | 107.126976 | 88.452741 | whole_exome_illumina_coding_v1 | 0.17 |
| CA209009_5_1 | 157.143939 | 89.39856 | whole_exome_illumina_coding_v1 | 0.2 |
| CA209009_5_106 | 176.007671 | 81.059438 | whole_exome_illumina_coding_v1 | 0.35 |
| CA209009_5_18 | 139.328276 | 75.654059 | whole_exome_illumina_coding_v1 | 0.21 |
| CA209009_5_21 | 178.624687 | 105.356301 | whole_exome_illumina_coding_v1 | 0.51 |
| CA209009_5_41 | 138.664874 | 93.93237 | whole_exome_illumina_coding_v1 | 0.19 |
| CA209009_5_50 | 162.205322 | 85.879444 | whole_exome_illumina_coding_v1 | 0.31 |
| CA209009_5_73 | 158.127987 | 100.10628 | whole_exome_illumina_coding_v1 | 0.6 |
| CA209009_6_39 | 147.571574 | 114.169462 | whole_exome_illumina_coding_v1 | 0.13 |
| CA209009_8_105 | 152.057615 | 91.424807 | whole_exome_illumina_coding_v1 | 0.48 |
| CA209009_9_119 | 26.875509 | 90.734659 | whole_exome_illumina_coding_v1 | 0.49 |
| CA209009_9_27 | 125.149722 | 97.245404 | whole_exome_illumina_coding_v1 | 0.34 |
| CA209009_9_52 | 131.064027 | 90.415506 | whole_exome_illumina_coding_v1 | 0.54 |
| CA209009_9_97 | 210.012354 | 98.486524 | whole_exome_illumina_coding_v1 | 0.38 |
| CA209009_2_85 | 43.586957 | 168.436641 | whole_exome_illumina_coding_v1 | 0.13 |
| CA209009_5_2 | 159.912441 | 69.844188 | whole_exome_illumina_coding_v1 | 0.52 |
| CA209009_5_29 | 150.205436 | 89.123637 | whole_exome_illumina_coding_v1 | NA |
| CA209009_6_99 | 34.101887 | 117.822339 | whole_exome_illumina_coding_v1 | 0.36 |
| CA209009_1_72 | 9.627872 | 94.01896 | whole_exome_illumina_coding_v1 | NA |
| CA209009_11_5 | 8.689284 | 89.713424 | whole_exome_illumina_coding_v1 | 0.36 |
| CA209009_4_54 | 0.007939 | 84.883698 | whole_exome_illumina_coding_v1 | NA |
| CA209009_8_100 | 7.711684 | 105.962605 | whole_exome_illumina_coding_v1 | 0.34 |
| CA209009_9_47 | 0.298156 | 95.4427 | whole_exome_illumina_coding_v1 | NA |
| CA209009_9_66 | 8.71954 | 98.033649 | whole_exome_illumina_coding_v1 | 0.46 |
| CA209009_1_43 | 105.603458 | 72.354112 | whole_exome_illumina_coding_v1 | 0.06 |
| CA209009_11_12 | 162.560923 | 104.266666 | whole_exome_illumina_coding_v1 | 0.05 |
| CA209009_11_24 | 166.047506 | 75.247762 | whole_exome_illumina_coding_v1 | 0.1 |
| CA209009_11_40 | 154.736269 | 87.045058 | whole_exome_illumina_coding_v1 | 0.1 |
| CA209009_11_8 | 154.801856 | 83.048353 | whole_exome_illumina_coding_v1 | NA |
| CA209009_13_103 | 138.626523 | 96.365324 | whole_exome_illumina_coding_v1 | NA |
| CA209009_3_26 | 159.566974 | 100.887491 | whole_exome_illumina_coding_v1 | 0.07 |
| CA209009_4_95 | 143.956046 | 90.060356 | whole_exome_illumina_coding_v1 | 0.09 |
| CA209009_5_17 | 129.343681 | 81.980679 | whole_exome_illumina_coding_v1 | 0.04 |
| CA209009_5_22 | 144.076612 | 97.672268 | whole_exome_illumina_coding_v1 | 0.06 |
| CA209009_5_28 | 162.443009 | 89.968028 | whole_exome_illumina_coding_v1 | 0.08 |
| CA209009_5_6 | 145.806274 | 83.646769 | whole_exome_illumina_coding_v1 | 0.07 |
| CA209009_9_45 | 132.158193 | 79.179771 | whole_exome_illumina_coding_v1 | 0.06 |

TABLE 2A-continued

Sequencing Metrics and Inclusion/Exclusion Criteria for Whole Exome Sequencing in Training Cohort (N = 56)

| patient_id | absolute_inferred_ploidy | genome_doubling | exclusion_reason |
| --- | --- | --- | --- |
| CA209009_1_20 | 1.78 | 0 | 0 |
| CA209009_1_32 | 2.21 | 0 | 0 |
| CA209009_1_62 | 1.83 | 0 | 0 |
| CA209009_11_10 | 2 | 0 | 0 |
| CA209009_11_11 | 3.56 | 1 | 0 |
| CA209009_11_14 | 3.67 | 1 | 0 |
| CA209009_11_25 | 1.99 | 0 | 0 |
| CA209009_11_56 | 1.89 | 0 | 0 |
| CA209009_11_79 | 1.96 | 0 | 0 |
| CA209009_11_93 | 3 | 1 | 0 |
| CA209009_12_115 | 1.64 | 0 | 0 |
| CA209009_13_90 | 2.67 | 1 | 0 |
| CA209009_13_96 | 1.8 | 0 | 0 |
| CA209009_2_102 | 1.97 | 0 | 0 |
| CA209009_2_58 | 1.81 | 0 | 0 |
| CA209009_2_84 | 1.93 | 0 | 0 |
| CA209009_3_114 | 1.97 | 0 | 0 |
| CA209009_3_117 | 1.87 | 0 | 0 |
| CA209009_3_15 | 1.97 | 0 | 0 |
| CA209009_4_68 | 3.19 | 1 | 0 |
| CA209009_5_1 | 3.6 | 1 | 0 |
| CA209009_5_106 | 1.9 | 0 | 0 |
| CA209009_5_18 | 2.3 | 0 | 0 |
| CA209009_5_21 | 3.39 | 1 | 0 |
| CA209009_5_41 | 4.28 | 1 | 0 |
| CA209009_5_50 | 1.81 | 0 | 0 |
| CA209009_5_73 | 1.83 | 0 | 0 |
| CA209009_6_39 | 1.92 | 0 | 0 |
| CA209009_8_105 | 2.06 | 0 | 0 |
| CA209009_9_119 | 3.08 | 1 | 0 |
| CA209009_9_27 | 1.93 | 0 | 0 |
| CA209009_9_52 | 1.88 | 0 | 0 |
| CA209009_9_97 | 2.2 | 0 | 0 |
| CA209009_2_85 | 4.12 | 1 | 0 |
| CA209009_5_2 | 1.68 | 0 | EarlyDeath |
| CA209009_5_29 | NA | NA | EarlyDeath |
| CA209009_6_99 | 2.77 | 1 | EarlyDeath |
| CA209009_1_72 | NA | NA | LowCoverage |
| CA209009_11_5 | 1.98 | 0 | LowCoverage |
| CA209009_4_54 | NA | NA | LowCoverage |
| CA209009_8_100 | 2.01 | 0 | LowCoverage |
| CA209009_9_47 | NA | NA | LowCoverage |
| CA209009_9_66 | 2.16 | 0 | LowCoverage |
| CA209009_1_43 | 2.43 | 0 | LowPurity |
| CA209009_11_12 | 2.74 | 0 | LowPurity |
| CA209009_11_24 | 2.46 | 0 | LowPurity |
| CA209009_11_40 | 2.44 | 0 | LowPurity |
| CA209009_11_8 | NA | NA | LowPurity |
| CA209009_13_103 | NA | NA | LowPurity |
| CA209009_3_26 | 2.96 | 0 | LowPurity |
| CA209009_4_95 | 2.57 | 0 | LowPurity |
| CA209009_5_17 | 3.61 | 1 | LowPurity |
| CA209009_5_22 | 2.91 | 0 | LowPurity |
| CA209009_5_28 | 2.45 | 0 | LowPurity |
| CA209009_5_6 | 2.69 | 0 | LowPurity |
| CA209009_9_45 | 2.58 | 0 | LowPurity |

Figure 2:
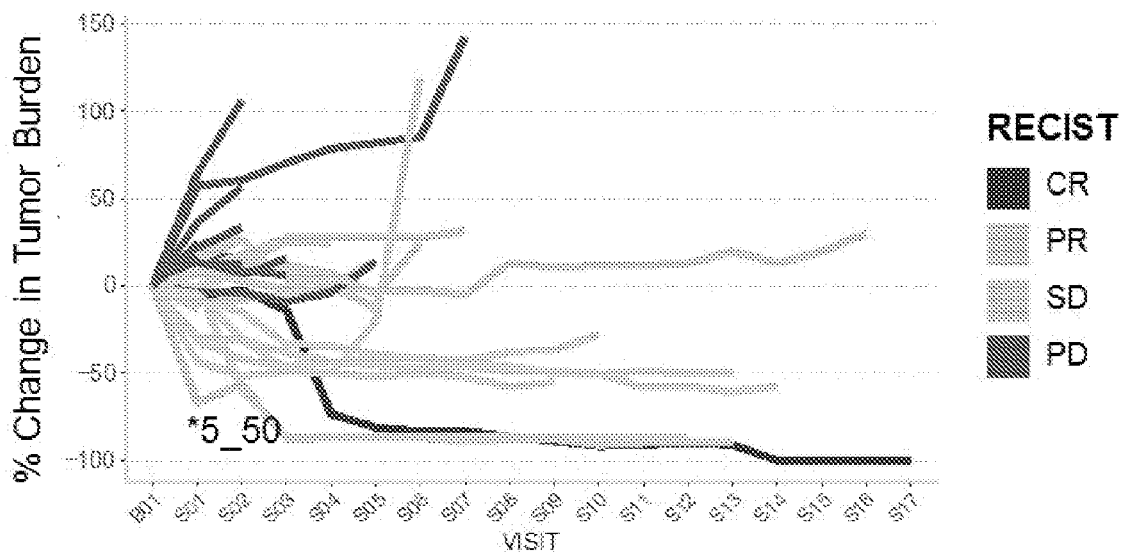
FIG. 2 includes 4 panels, identified as panels A, B, C, and D, which show the patient response classifications described in FIG. 1. One patient (5_50) had early tumor growth (likely pseudoprogression) in the setting of overall response to therapy followed by sustained tumor response and was classified as an extreme responder despite disease progression by RECIST criteria prior to 6 months. The results shown in Panels A and B versus those of Panels C and D correspond to the clinical cohort described in Panels A and D, respectively, of FIG. 1.
Figure 2:
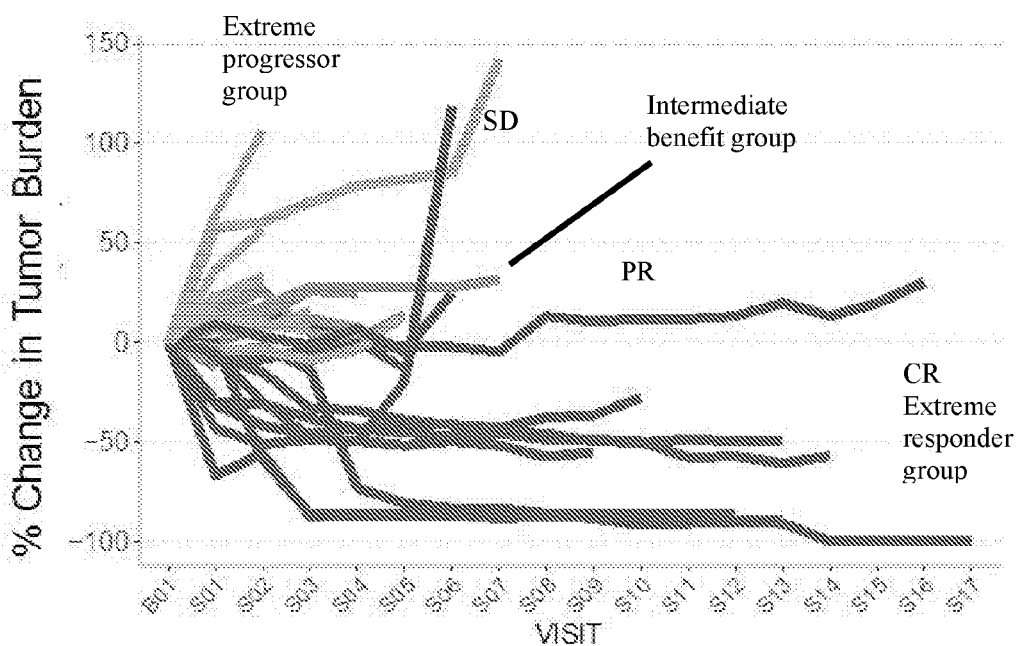
Figure 2:
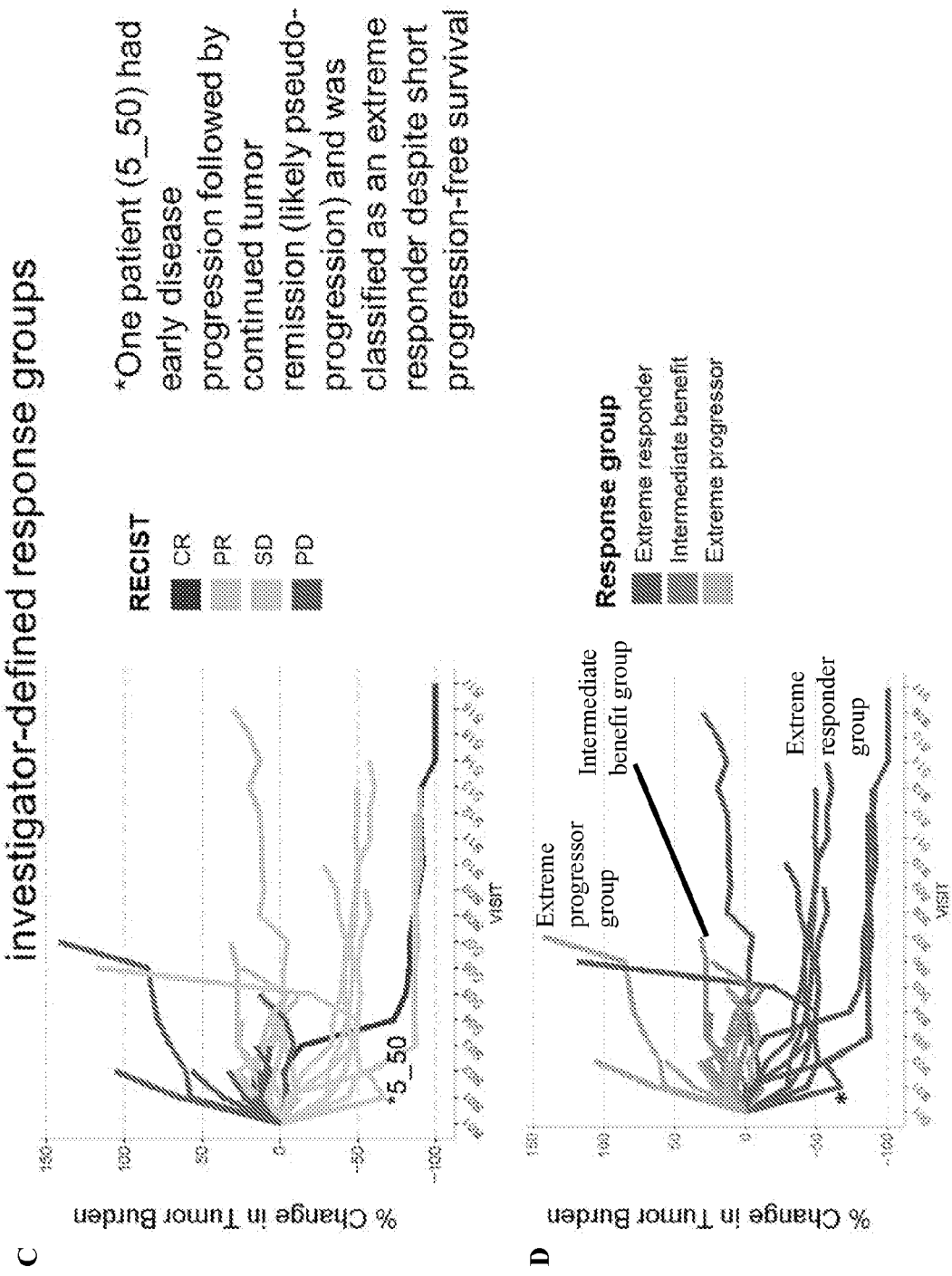
Figure 3:
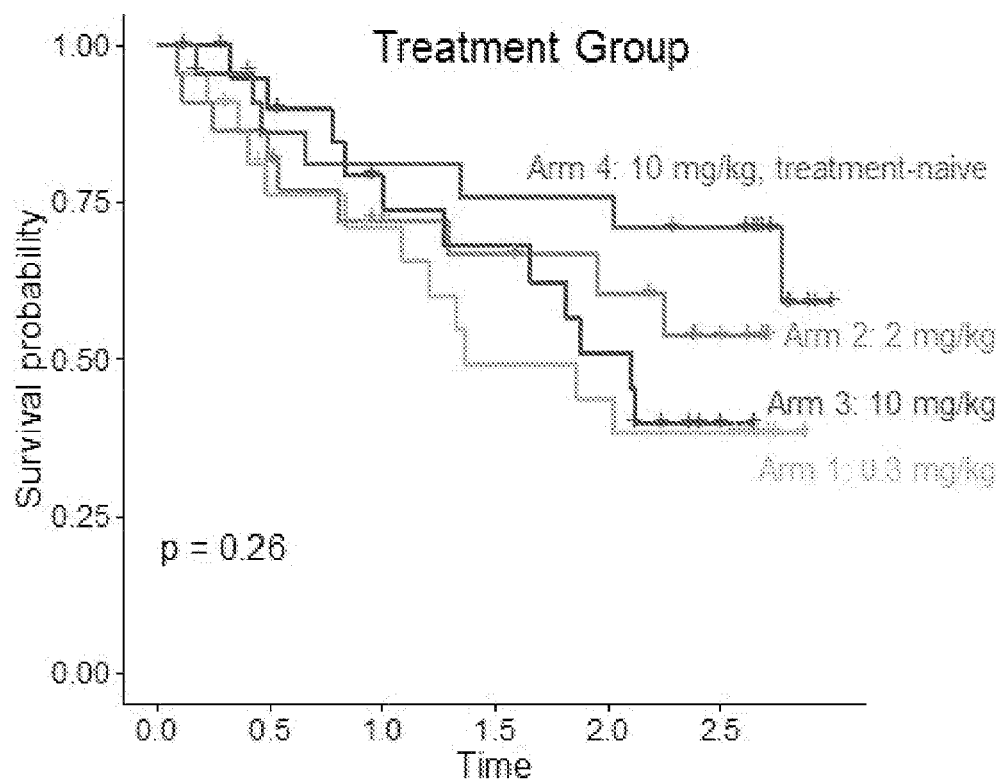
FIG. 3 includes 4 panels, identified as panels A, B, C, and D, which compare the patient survival probability vs. different clinical characteristics, including different groups receiving different dosages of treatment (Panel A), different sexes (Panel B), pre-treatment tumor immunohistochemical staining for the PD-1 ligand PD-L1(Panel C), and response by RECIST criteria (Panel D). Kaplan-Meier analyses showed that baseline clinical characteristics, including pre-treatment PD-L1 immunohistochemistry (Panel C), did not influence overall survival. Objective tumor response by RECIST criteria was strongly associated with overall survival (p=0.00027). Two patients who did not receive staging scans (RECIST not evaluable) following commencement of anti-PD1 therapy were excluded from further analyses.
Figure 3:
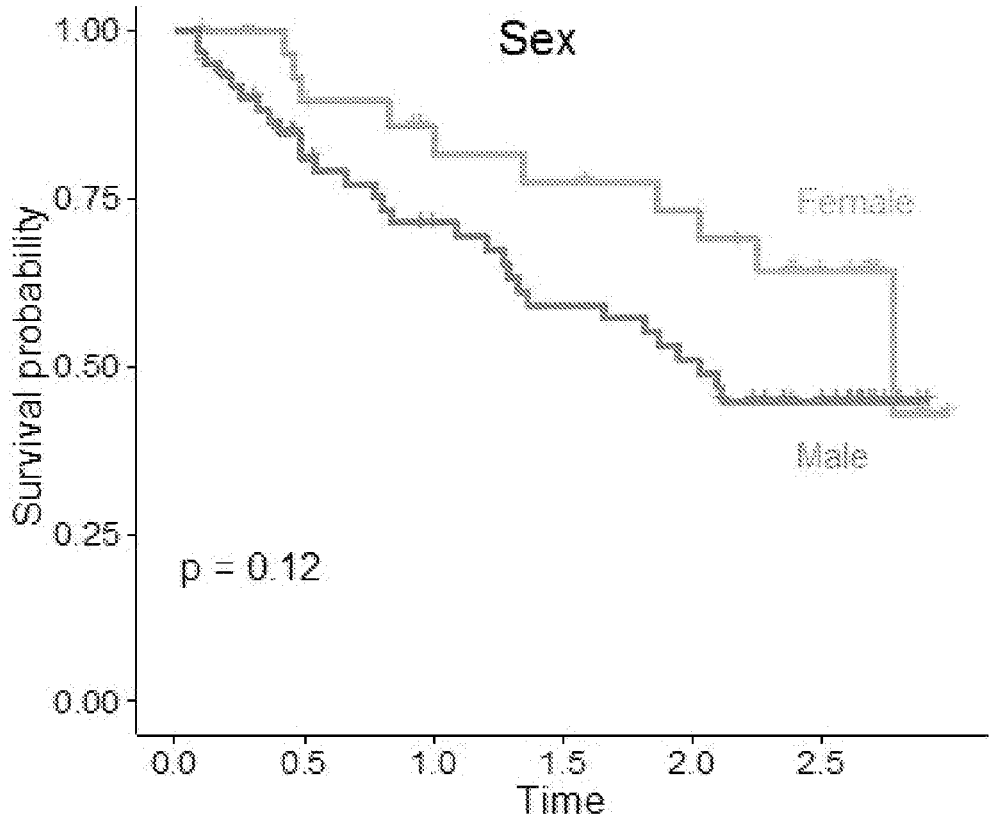
Figure 3:
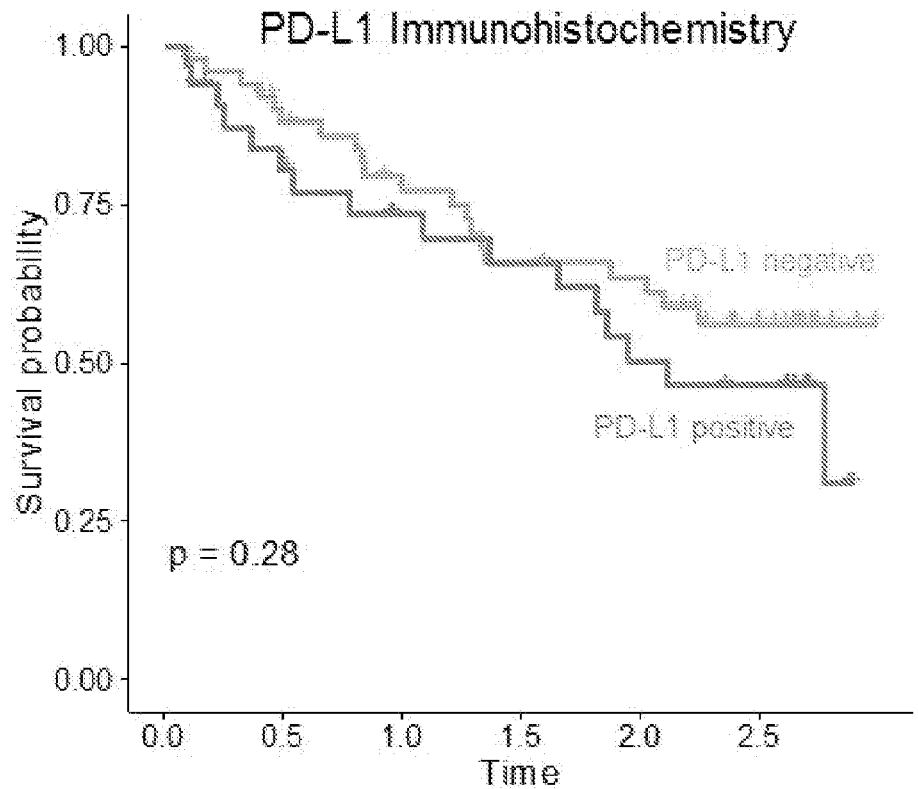
Figure 3:
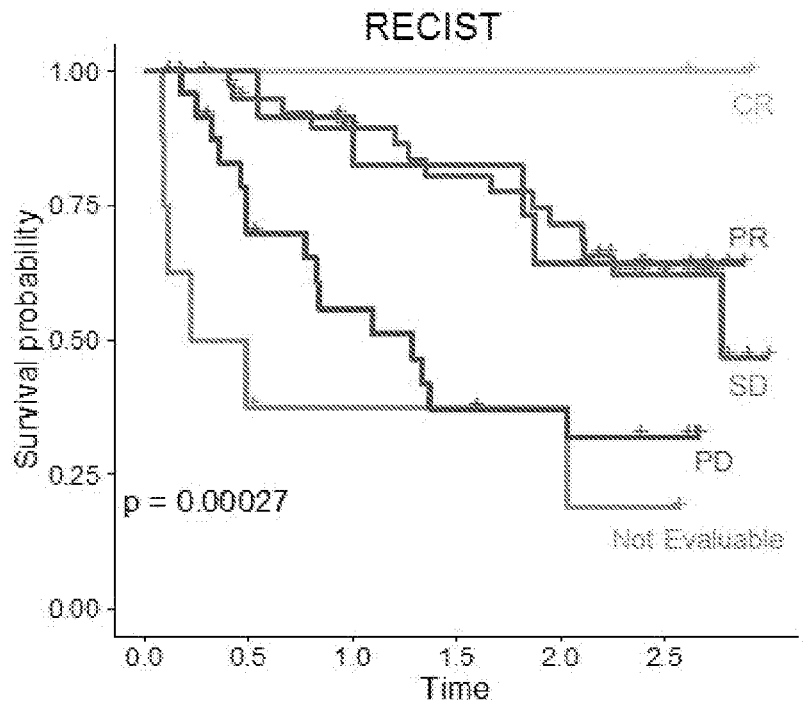

To stratify clinical cohort between patients who most clearly derived durable clinical benefit from anti-PD1 therapy and those who did not, three response categories were defined based on a composite end point incorporating RECIST criteria (Eisenhauer et al. (2009) Eur. J. Cancer 45:228-247), tumor shrinkage, and progression-free survival (PFS) (FIGS. 2-3 and Table 2B). "Extreme responders" included all patients with complete response (CR) or partial response (PR) by RECIST. Patients with stable disease (SD) as their best response by RECIST were also considered extreme responders if they had objective reduction in tumor size lasting at least 6 months, such as at least 12 months. "Extreme progressors" experienced early tumor growth: progressive disease (PD) by RECIST as best response with progression in less than 3 months. An intermediate group of patients who experienced SD or PR with objective tumor shrinkage lasting less than 6 months (or sometimes less than 12 months as indicated in certain figures) or PD with PFS longer than 3 months were called "intermediate benefit." One patient (5_50) was classified as an "extreme responder" despite experiencing a short period of early tumor progression (PFS=2.9 months), which likely represented pseudo-progression, as further follow-up showed sustained tumor remission (FIGS. 1B and 2A-2B). Three patients who experienced death on-treatment prior to the first staging scans were excluded from analysis (Table 2A). Not evaluable (NE): No RECIST evaluation made. Mixed response (X): Simultaneous tumor shrinkage and growth.

Figure 11:
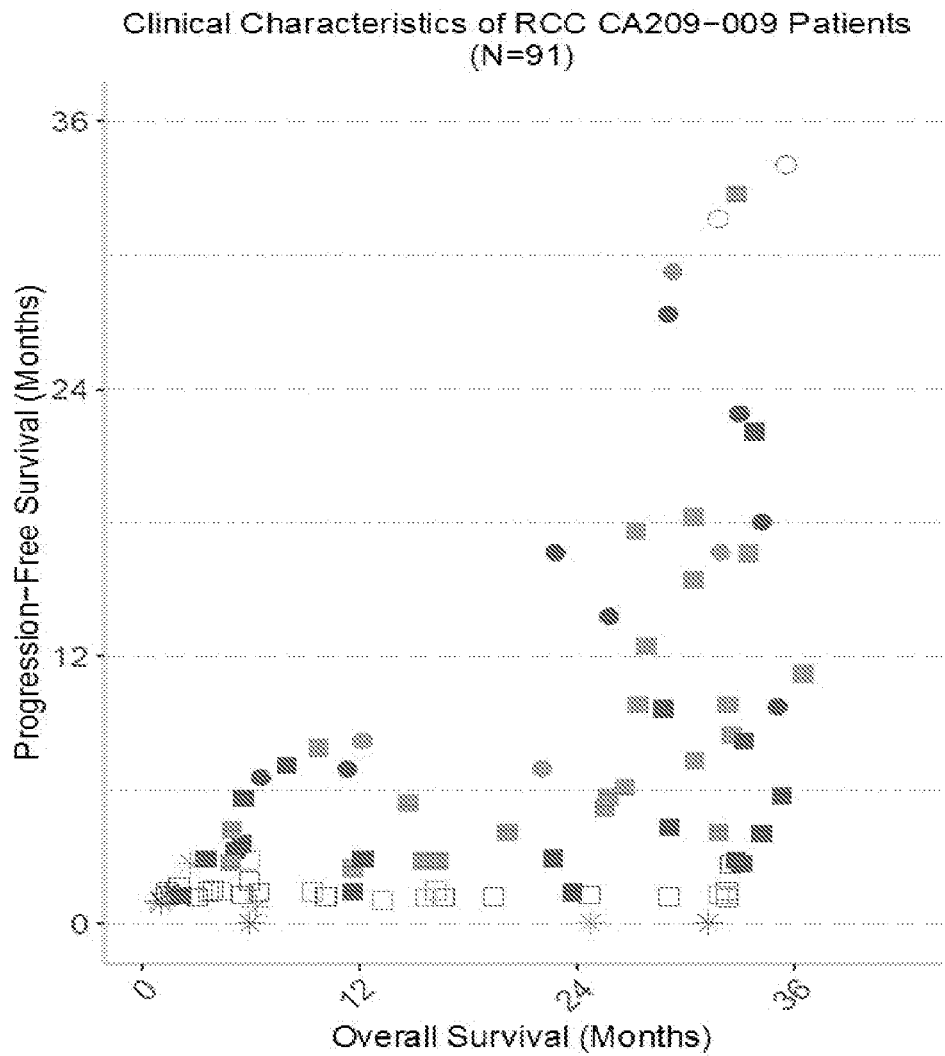
FIG. 11 summarizes the clinical characteristics of RCC CA209-009 patients (N=91).

Detailed clinical information and immunohistochemical staining was available for all 91 patients in the training cohort. Pre-treatment immunohistochemical staining for PD-L1 was positive at ≥1% for 30% of patients and at ≥5% for 16% of patients, which is generally representative of other large cohorts of clear cell RCC (Table 2B) (Motzer et al. (2015), supra). Duration of overall survival did not vary significantly by dose of therapy, patient gender, or PD-L1 immunohistochemical staining in Kaplan-Meier analyses, while objective tumor response by RECIST substantially prolonged duration of overall survival (FIG. 3A-3D). For a summary of results, see FIG. 11.

TABLE 2B

Clinical characteristics of patients receiving anti-PD1 therapy (nivolumab) in training cohort (N = 91)

| patient_id | wes | sex | age | treatment_group | best_RECIST | max_tumor_change | os_days | os_censor | pfs_days | pfs_censor |
|---|---|---|---|---|---|---|---|---|---|---|
| CA209009_1_20 | 1 | M | 76 | 10 mg/kg-N | CR | −100 | 1065 | 1 | 1022 | 1 |
| CA209009_2_48 | 0 | M | 62 | 2 mg/kg | SD | −3 | 983 | 1 | 983 | 1 |
| CA209009_9_45 | 0 | M | 60 | 10 mg/kg-N | CR | −86 | 953 | 1 | 949 | 1 |
| CA209009_9_88 | 0 | F | 63 | 10 mg/kg | PR | −77 | 878 | 1 | 878 | 1 |
| CA209009_5_106 | 1 | F | 61 | 2 mg/kg | PR | −61 | 870 | 1 | 821 | 1 |
| CA209009_2_58 | 1 | F | 55 | 2 mg/kg | PR | −50 | 988 | 1 | 687 | 1 |
| CA209009_3_15 | 1 | F | 73 | 10 mg/kg | SD | −10 | 1013 | 0 | 663 | 0 |
| CA209009_15_81 | 0 | F | 45 | 10 mg/kg | SD | −28 | 912 | 1 | 548 | 0 |
| CA209009_11_14 | 1 | M | 59 | 10 mg/kg-N | PR | −86 | 1025 | 1 | 541 | 0 |
| CA209009_14_107 | 0 | M | 82 | 10 mg/kg | SD | 2 | 817 | 1 | 529 | 0 |
| CA209009_9_34 | 0 | F | 61 | 2 mg/kg | PR | −59 | 957 | 1 | 500 | 0 |
| CA209009_11_93 | 1 | M | 64 | 10 mg/kg | PR | −43 | 684 | 0 | 500 | 0 |
| CA209009_9_47 | 0 | M | 69 | 0.3 mg/kg | SD | −44 | 1003 | 1 | 499 | 0 |
| CA209009_15_94 | 0 | F | 41 | 10 mg/kg | SD | −31 | 912 | 1 | 463 | 0 |
| CA209009_9_119 | 1 | M | 72 | 10 mg/kg | PR | −52 | 773 | 1 | 414 | 0 |
| CA209009_13_111 | 0 | M | 68 | 10 mg/kg-N | SD | −3 | 834 | 1 | 374 | 0 |
| CA209009_11_13 | 0 | F | 64 | 10 mg/kg-N | SD | 0 | 1094 | 1 | 337 | 0 |
| CA209009_15_75 | 0 | F | 70 | 2 mg/kg | SD | −10 | 821 | 0 | 295 | 1 |
| CA209009_11_57 | 0 | M | 48 | 10 mg/kg | SD | 0 | 969 | 1 | 295 | 0 |
| CA209009_11_8 | 0 | M | 60 | 0.3 mg/kg | PR | −73 | 1051 | 1 | 292 | 0 |
| CA209009_13_103 | 0 | M | 51 | 10 mg/kg | SD | 4 | 862 | 1 | 289 | 0 |
| CA209009_4_54 | 0 | F | 65 | 0.3 mg/kg | SD | 8 | 976 | 1 | 254 | 0 |
| CA209009_9_30 | 0 | F | 60 | 10 mg/kg | PR | −37 | 365 | 0 | 246 | 0 |
| CA209009_9_52 | 1 | F | 63 | 10 mg/kg-N | SD | −5 | 995 | 1 | 246 | 0 |
| CA209009_14_89 | 0 | M | 78 | 2 mg/kg | SD | −21 | 293 | 0 | 237 | 0 |
| CA209009_5_4 | 0 | M | 65 | 2 mg/kg | SD | 5 | 914 | 1 | 220 | 0 |
| CA209009_1_32 | 1 | M | 65 | 10 mg/kg-N | SD | −13 | 240 | 0 | 213 | 1 |
| CA209009_15_76 | 0 | M | 42 | 10 mg/kg | PR | −44 | 662 | 0 | 209 | 0 |
| CA209009_3_114 | 1 | F | 57 | 0.3 mg/kg | PR | −51 | 340 | 1 | 208 | 0 |
| CA209009_5_22 | 0 | M | 63 | 2 mg/kg | PR | −43 | 197 | 0 | 197 | 0 |
| CA209009_8_100 | 0 | F | 58 | 2 mg/kg | SD | 5 | 798 | 1 | 184 | 1 |
| CA209009_11_10 | 1 | F | 64 | 10 mg/kg-N | SD | 0 | 1058 | 1 | 173 | 1 |
| CA209009_10_112 | 0 | M | 54 | 10 mg/kg | SD | 17 | 772 | 0 | 171 | 0 |
| CA209009_5_17 | 0 | M | 55 | 10 mg/kg-N | SD | −4 | 169 | 1 | 169 | 0 |
| CA209009_9_74 | 0 | M | 67 | 0.3 mg/kg | SD | 4 | 440 | 0 | 163 | 0 |
| CA209009_2_64 | 0 | M | 59 | 10 mg/kg | SD | 2 | 766 | 0 | 157 | 1 |
| CA209009_11_79 | 1 | F | 61 | 2 mg/kg | SD | 9 | 873 | 1 | 130 | 0 |
| CA209009_5_23 | 0 | M | 66 | 10 mg/kg-N | SD | −2 | 149 | 1 | 127 | 1 |
| CA209009_4_49 | 0 | M | 60 | 10 mg/kg | SD | 3 | 605 | 0 | 123 | 0 |
| CA209009_11_71 | 0 | M | 57 | 0.3 mg/kg | SD | 12 | 954 | 1 | 123 | 0 |
| CA209009_11_11 | 1 | M | 50 | 10 mg/kg-N | SD | 9 | 1024 | 1 | 122 | 0 |
| CA209009_2_102 | 1 | M | 64 | 0.3 mg/kg | SD | 3 | 165 | 1 | 108 | 0 |
| CA209009_5_6 | 0 | F | 59 | 10 mg/kg-N | SD | −19 | 155 | 0 | 99 | 0 |
| CA209009_2_84 | 1 | F | 55 | 0.3 mg/kg | SD | 8 | 680 | 0 | 88 | 0 |
| CA209009_1_62 | 1 | F | 48 | 10 mg/kg | SD | 7 | 106 | 1 | 87 | 0 |
| CA209009_12_115 | 1 | M | 60 | 2 mg/kg | SD | 15 | 366 | 1 | 87 | 0 |
| CA209009_1_118 | 0 | M | 82 | 0.3 mg/kg | PD | 29 | 177 | 0 | 86 | 0 |
| CA209009_5_50 | 1 | F | 63 | 10 mg/kg-N | SD | −67 | 982 | 1 | 86 | 0 |
| CA209009_11_5 | 0 | F | 63 | 10 mg/kg-N | SD | 0 | 492 | 0 | 85 | 0 |
| CA209009_1_86 | 0 | M | 71 | 10 mg/kg | SD | 7 | 464 | 0 | 85 | 0 |
| CA209009_14_80 | 0 | M | 61 | 0.3 mg/kg | SD | 4 | 147 | 0 | 82 | 0 |
| CA209009_2_42 | 0 | M | 42 | 0.3 mg/kg | NE | . | 81 | 0 | 81 | 0 |
| CA209009_14_59 | 0 | M | 64 | 0.3 mg/kg | SD | 8 | 991 | 1 | 81 | 0 |
| CA209009_11_56 | 1 | F | 62 | 2 mg/kg | SD | 17 | 992 | 1 | 81 | 0 |
| CA209009_11_40 | 0 | M | 32 | 10 mg/kg-N | PD | 8 | 974 | 1 | 80 | 0 |
| CA209009_14_87 | 0 | F | 62 | 2 mg/kg | SD | 19 | 350 | 1 | 75 | 0 |
| CA209009_5_73 | 1 | M | 77 | 2 mg/kg | PD | 11 | 178 | 0 | 58 | 0 |
| CA209009_11_24 | 0 | M | 70 | 10 mg/kg-N | PD | 6 | 62 | 0 | 51 | 0 |
| CA209009_8_105 | 1 | M | 64 | 10 mg/kg | PD | 17 | 118 | 0 | 45 | 0 |
| CA209009_15_83 | 0 | M | 46 | 0.3 mg/kg | PD | 24 | 486 | 0 | 45 | 0 |
| CA209009_1_43 | 0 | M | 74 | 10 mg/kg-N | PD | −8 | 968 | 1 | 44 | 0 |
| CA209009_15_77 | 0 | M | 50 | 0.3 mg/kg | PD | 1 | 132 | 0 | 44 | 0 |
| CA209009_1_72 | 0 | M | 58 | 10 mg/kg | PD | 6 | 283 | 0 | 43 | 0 |
| CA209009_5_28 | 0 | M | 47 | 10 mg/kg-N | PD | 30 | 43 | 1 | 43 | 0 |
| CA209009_5_18 | 1 | M | 68 | 0.3 mg/kg | PD | 65 | 111 | 0 | 43 | 0 |
| CA209009_5_21 | 1 | M | 64 | 10 mg/kg | SD | −13 | 349 | 1 | 43 | 1 |
| CA209009_5_41 | 1 | M | 66 | 10 mg/kg | PD | 10 | 195 | 1 | 42 | 0 |

TABLE 2B-continued

Clinical characteristics of patients receiving anti-PD1 therapy (nivolumab) in training cohort (N = 91)

| | | | | | | | | | |
|---|---|---|---|---|---|---|---|---|---|
| CA209009_2_85 | 1 | M | 36 | 2 mg/kg | SD | −12 | 712 | 0 | 42 | 1 |
| CA209009_6_99 | 0 | M | 50 | 2 mg/kg | NE | . | 41 | 0 | 41 | 0 |
| CA209009_4_68 | 1 | M | 69 | 0.3 mg/kg | PD | −4 | 740 | 0 | 39 | 0 |
| CA209009_11_38 | 0 | M | 69 | 10 mg/kg-N | PD | 0 | 955 | 1 | 39 | 0 |
| CA209009_13_51 | 0 | M | 45 | 10 mg/kg-N | PD | 12 | 967 | 1 | 39 | 0 |
| CA209009_11_25 | 1 | F | 72 | 10 mg/kg-N | PD | 16 | 167 | 0 | 39 | 0 |
| CA209009_5_1 | 1 | M | 49 | 10 mg/kg | PD | 24 | 43 | 1 | 38 | 0 |
| CA209009_3_117 | 1 | M | 58 | 10 mg/kg-N | SD | −10 | 64 | 1 | 38 | 1 |
| CA209009_13_96 | 1 | F | 75 | 2 mg/kg | PD | 12 | 582 | 1 | 37 | 0 |
| CA209009_6_39 | 1 | M | 72 | 0.3 mg/kg | PD | 13 | 306 | 0 | 37 | 0 |
| CA209009_9_97 | 1 | M | 54 | 2 mg/kg | PD | 22 | 871 | 1 | 37 | 0 |
| CA209009_14_69 | 0 | F | 40 | 10 mg/kg | PD | 53 | 303 | 0 | 37 | 0 |
| CA209009_5_3 | 0 | F | 57 | 10 mg/kg | PD | 64 | 43 | 1 | 37 | 0 |
| CA209009_9_66 | 0 | M | 47 | 2 mg/kg | PD | 38 | 470 | 0 | 36 | 0 |
| CA209009_4_95 | 0 | M | 55 | 2 mg/kg | PD | 47 | 92 | 0 | 36 | 0 |
| CA209009_13_90 | 1 | M | 54 | 0.3 mg/kg | PD | 57 | 499 | 0 | 36 | 0 |
| CA209009_9_27 | 1 | M | 59 | 0.3 mg/kg | PD | 36 | 968 | 1 | 35 | 0 |
| CA209009_14_98 | 0 | M | 65 | 0.3 mg/kg | PD | −49 | 398 | 0 | 32 | 0 |
| CA209009_5_2 | 0 | M | 48 | 0.3 mg/kg | NE | . | 31 | 0 | 31 | 0 |
| CA209009_3_26 | 0 | M | 55 | 2 mg/kg | NE | . | 33 | 0 | 28 | 0 |
| CA209009_5_63 | 0 | F | 71 | 2 mg/kg | NE | . | 189 | 1 | 22 | 0 |
| CA209009_5_29 | 0 | M | 67 | 0.3 mg/kg | NE | . | 937 | 1 | 1 | 1 |
| CA209009_13_36 | 0 | F | 69 | 10 mg/kg-N | NE | . | 741 | 0 | 1 | 1 |
| CA209009_11_12 | 0 | F | 69 | 10 mg/kg | NE | . | 179 | 0 | 1 | 1 |

| patient_id | cell_membrane_pdl1_0percent | cell_membrane_pdl1_1plus_percent | cell_membrane_pdl1_2plus_percent |
|---|---|---|---|
| CA209009_1_20 | 100 | 0 | 0 |
| CA209009_2_48 | 100 | 0 | 0 |
| CA209009_9_45 | 97 | 1 | 1 |
| CA209009_9_88 | 100 | 0 | 0 |
| CA209009_5_106 | 100 | 0 | 0 |
| CA209009_2_58 | 20 | 25 | 25 |
| CA209009_3_15 | 99 | 1 | 0 |
| CA209009_15_81 | NA | NA | NA |
| CA209009_11_14 | 100 | 0 | 0 |
| CA209009_14_107 | 100 | 0 | 0 |
| CA209009_9_34 | 95 | 2 | 2 |
| CA209009_11_93 | 100 | 0 | 0 |
| CA209009_9_47 | 100 | 0 | 0 |
| CA209009_15_94 | 100 | 0 | 0 |
| CA209009_9_119 | 100 | 0 | 0 |
| CA209009_13_111 | 100 | 0 | 0 |
| CA209009_11_13 | 100 | 0 | 0 |
| CA209009_15_75 | 100 | 0 | 0 |
| CA209009_11_57 | 95 | 4 | 1 |
| CA209009_11_8 | 97 | 3 | 0 |
| CA209009_13_103 | 94 | 3 | 2 |
| CA209009_4_54 | 100 | 0 | 0 |
| CA209009_9_30 | 100 | 0 | 0 |
| CA209009_9_52 | 100 | 0 | 0 |
| CA209009_14_89 | 100 | 0 | 0 |
| CA209009_5_4 | 100 | 0 | 0 |
| CA209009_1_32 | 100 | 0 | 0 |
| CA209009_15_76 | 99 | 1 | 0 |
| CA209009_3_114 | 100 | 0 | 0 |
| CA209009_5_22 | 70 | 5 | 10 |
| CA209009_8_100 | 100 | 0 | 0 |
| CA209009_11_10 | 97 | 3 | 0 |
| CA209009_10_112 | 98 | 2 | 0 |
| CA209009_5_17 | 100 | 0 | 0 |
| CA209009_9_74 | 100 | 0 | 0 |
| CA209009_2_64 | 100 | 0 | 0 |
| CA209009_11_79 | 100 | 0 | 0 |
| CA209009_5_23 | 100 | 0 | 0 |
| CA209009_4_49 | 99 | 1 | 0 |
| CA209009_11_71 | 100 | 0 | 0 |
| CA209009_11_11 | 100 | 0 | 0 |
| CA209009_2_102 | 100 | 0 | 0 |
| CA209009_5_6 | NA | NA | NA |
| CA209009_2_84 | 95 | 5 | 0 |
| CA209009_1_62 | NA | NA | NA |
| CA209009_12_115 | 100 | 0 | 0 |
| CA209009_1_118 | 98 | 1 | 1 |
| CA209009_5_50 | 91 | 5 | 3 |
| CA209009_11_5 | 100 | 0 | 0 |
| CA209009_1_86 | 100 | 0 | 0 |

TABLE 2B-continued

Clinical characteristics of patients receiving anti-PD1 therapy (nivolumab) in training cohort (N = 91)

| patient_id | | | |
|---|---|---|---|
| CA209009_14_80 | 100 | 0 | 0 |
| CA209009_2_42 | 95 | 3 | 2 |
| CA209009_14_59 | 84 | 10 | 5 |
| CA209009_11_56 | 100 | 0 | 0 |
| CA209009_11_40 | 100 | 0 | 0 |
| CA209009_14_87 | 38 | 26 | 30 |
| CA209009_5_73 | 100 | 0 | 0 |
| CA209009_11_24 | 100 | 0 | 0 |
| CA209009_8_105 | 100 | 0 | 0 |
| CA209009_15_83 | 100 | 0 | 0 |
| CA209009_1_43 | 100 | 0 | 0 |
| CA209009_15_77 | 94 | 6 | 0 |
| CA209009_1_72 | 95 | 5 | 0 |
| CA209009_5_28 | 97 | 1 | 2 |
| CA209009_5_18 | NA | NA | NA |
| CA209009_5_21 | 96 | 4 | 0 |
| CA209009_5_41 | 100 | 0 | 0 |
| CA209009_2_85 | 95 | 2 | 2 |
| CA209009_6_99 | 97 | 3 | 0 |
| CA209009_4_68 | 100 | 0 | 0 |
| CA209009_11_38 | 95 | 5 | 0 |
| CA209009_13_51 | 100 | 0 | 0 |
| CA209009_11_25 | 100 | 0 | 0 |
| CA209009_5_1 | 100 | 0 | 0 |
| CA209009_3_117 | 98 | 2 | 0 |
| CA209009_13_96 | 100 | 0 | 0 |
| CA209009_6_39 | 100 | 0 | 0 |
| CA209009_9_97 | 100 | 0 | 0 |
| CA209009_14_69 | 100 | 0 | 0 |
| CA209009_5_3 | 97 | 2 | 1 |
| CA209009_9_66 | 100 | 0 | 0 |
| CA209009_4_95 | 85 | 10 | 4 |
| CA209009_13_90 | 25 | 35 | 20 |
| CA209009_9_27 | 68 | 30 | 2 |
| CA209009_14_98 | 97 | 1 | 1 |
| CA209009_5_2 | 100 | 0 | 0 |
| CA209009_3_26 | 91 | 5 | 3 |
| CA209009_5_63 | 95 | 3 | 1 |
| CA209009_5_29 | 100 | 0 | 0 |
| CA209009_13_36 | NA | NA | NA |
| CA209009_11_12 | NA | NA | NA |

| patient_id | cell_membrane_pdl1_3plus_percent | pdl1_positive_1percent | pdl1_positive_5percent | response_category |
|---|---|---|---|---|
| CA209009_1_20 | 0 | 0 | 0 | extreme_responder |
| CA209009_2_48 | 0 | 0 | 0 | extreme_responder |
| CA209009_9_45 | 1 | 1 | 0 | extreme_responder |
| CA209009_9_88 | 0 | 0 | 0 | extreme_responder |
| CA209009_5_106 | 0 | 0 | 0 | extreme_responder |
| CA209009_2_58 | 30 | 1 | 1 | extreme_responder |
| CA209009_3_15 | 0 | 0 | 0 | extreme_responder |
| CA209009_15_81 | NA | NA | NA | extreme_responder |
| CA209009_11_14 | 0 | 0 | 0 | extreme_responder |
| CA209009_14_107 | 0 | 0 | 0 | extreme_responder |
| CA209009_9_34 | 1 | 1 | 0 | extreme_responder |
| CA209009_11_93 | 0 | 0 | 0 | extreme_responder |
| CA209009_9_47 | 0 | 0 | 0 | extreme_responder |
| CA209009_15_94 | 0 | 0 | 0 | extreme_responder |
| CA209009_9_119 | 0 | 0 | 0 | extreme_responder |
| CA209009_13_111 | 0 | 0 | 0 | extreme_responder |
| CA209009_11_13 | 0 | 0 | 0 | extreme_responder |
| CA209009_15_75 | 0 | 0 | 0 | stable_disease |
| CA209009_11_57 | 0 | 1 | 1 | stable_disease |
| CA209009_11_8 | 0 | 1 | 0 | extreme_responder |
| CA209009_13_103 | 1 | 1 | 0 | stable_disease |
| CA209009_4_54 | 0 | 0 | 0 | stable_disease |
| CA209009_9_30 | 0 | 0 | 0 | extreme_responder |
| CA209009_9_52 | 0 | 0 | 0 | stable_disease |
| CA209009_14_89 | 0 | 0 | 0 | stable_disease |
| CA209009_5_4 | 0 | 0 | 0 | stable_disease |
| CA209009_1_32 | 0 | 0 | 0 | stable_disease |
| CA209009_15_76 | 0 | 1 | 0 | extreme_responder |
| CA209009_3_114 | 0 | 0 | 0 | extreme_responder |
| CA209009_5_22 | 15 | 1 | 1 | extreme_responder |
| CA209009_8_100 | 0 | 0 | 0 | stable_disease |
| CA209009_11_10 | 0 | 1 | 0 | stable_disease |
| CA209009_10_112 | 0 | 1 | 0 | stable_disease |

TABLE 2B-continued

Clinical characteristics of patients receiving anti-PD1 therapy (nivolumab) in training cohort (N = 91)

| | | | | |
|---|---|---|---|---|
| CA209009_5_17 | 0 | 0 | 0 | stable_disease |
| CA209009_9_74 | 0 | 0 | 0 | stable_disease |
| CA209009_2_64 | 0 | 0 | 0 | stable_disease |
| CA209009_11_79 | 0 | 0 | 0 | stable_disease |
| CA209009_5_23 | 0 | 0 | 0 | stable_disease |
| CA209009_4_49 | 0 | 0 | 0 | stable_disease |
| CA209009_11_71 | 0 | 0 | 0 | stable_disease |
| CA209009_11_11 | 0 | 0 | 0 | stable_disease |
| CA209009_2_102 | 0 | 0 | 0 | stable_disease |
| CA209009_5_6 | NA | NA | NA | stable_disease |
| CA209009_2_84 | 0 | 0 | 0 | stable_disease |
| CA209009_1_62 | NA | NA | NA | stable_disease |
| CA209009_12_115 | 0 | 0 | 0 | stable_disease |
| CA209009_1_118 | 0 | 1 | 0 | extreme_progressor |
| CA209009_5_50 | 1 | 1 | 1 | extreme_responder |
| CA209009_11_5 | 0 | 0 | 0 | stable_disease |
| CA209009_1_86 | 0 | 0 | 0 | stable_disease |
| CA209009_14_80 | 0 | 0 | 0 | stable_disease |
| CA209009_2_42 | 0 | 0 | 1 | not_evaluable |
| CA209009_14_59 | 1 | 1 | 1 | stable_disease |
| CA209009_11_56 | 0 | 0 | 0 | stable_disease |
| CA209009_11_40 | 0 | 0 | 0 | extreme_progressor |
| CA209009_14_87 | 6 | 1 | 1 | stable_disease |
| CA209009_5_73 | 0 | 0 | 0 | extreme_progressor |
| CA209009_11_24 | 0 | 0 | 0 | extreme_progressor |
| CA209009_8_105 | 0 | 0 | 0 | extreme_progressor |
| CA209009_15_83 | 0 | 0 | 0 | extreme_progressor |
| CA209009_1_43 | 0 | 0 | 0 | extreme_progressor |
| CA209009_15_77 | 0 | 1 | 0 | extreme_progressor |
| CA209009_1_72 | 0 | 1 | 1 | extreme_progressor |
| CA209009_5_28 | 0 | 1 | 0 | extreme_progressor |
| CA209009_5_18 | NA | NA | NA | extreme_progressor |
| CA209009_5_21 | 0 | 1 | 0 | stable_disease |
| CA209009_5_41 | 0 | 0 | 0 | extreme_progressor |
| CA209009_2_85 | 1 | 1 | 0 | stable_disease |
| CA209009_6_99 | 0 | 1 | 0 | not_evaluable |
| CA209009_4_68 | 0 | 0 | 0 | extreme_progressor |
| CA209009_11_38 | 0 | 1 | 1 | extreme_progressor |
| CA209009_13_51 | 0 | 0 | 0 | extreme_progressor |
| CA209009_11_25 | 0 | 0 | 0 | extreme_progressor |
| CA209009_5_1 | 0 | 0 | 0 | extreme_progressor |
| CA209009_3_117 | 0 | 0 | 0 | stable_disease |
| CA209009_13_96 | 0 | 0 | 0 | extreme_progressor |
| CA209009_6_39 | 0 | 0 | 0 | extreme_progressor |
| CA209009_9_97 | 0 | 0 | 0 | extreme_progressor |
| CA209009_14_69 | 0 | 0 | 0 | extreme_progressor |
| CA209009_5_3 | 0 | 1 | 0 | extreme_progressor |
| CA209009_9_66 | 0 | 0 | 0 | extreme_progressor |
| CA209009_4_95 | 1 | 1 | 1 | extreme_progressor |
| CA209009_13_90 | 20 | 1 | 1 | extreme_progressor |
| CA209009_9_27 | 0 | 1 | 1 | extreme_progressor |
| CA209009_14_98 | 1 | 1 | 0 | extreme_progressor |
| CA209009_5_2 | 0 | 0 | 0 | not_evaluable |
| CA209009_3_26 | 1 | 1 | 1 | not_evaluable |
| CA209009_5_63 | 1 | 1 | 1 | not_evaluable |
| CA209009_5_29 | 0 | 0 | 0 | not_evaluable |
| CA209009_13_36 | NA | NA | NA | not_evaluable |
| CA209009_11_12 | NA | NA | NA | not_evaluable |

All patients listed in Table 2B were treated with nivolumab. For sex, M represents male and F represents female.

Figure 4:
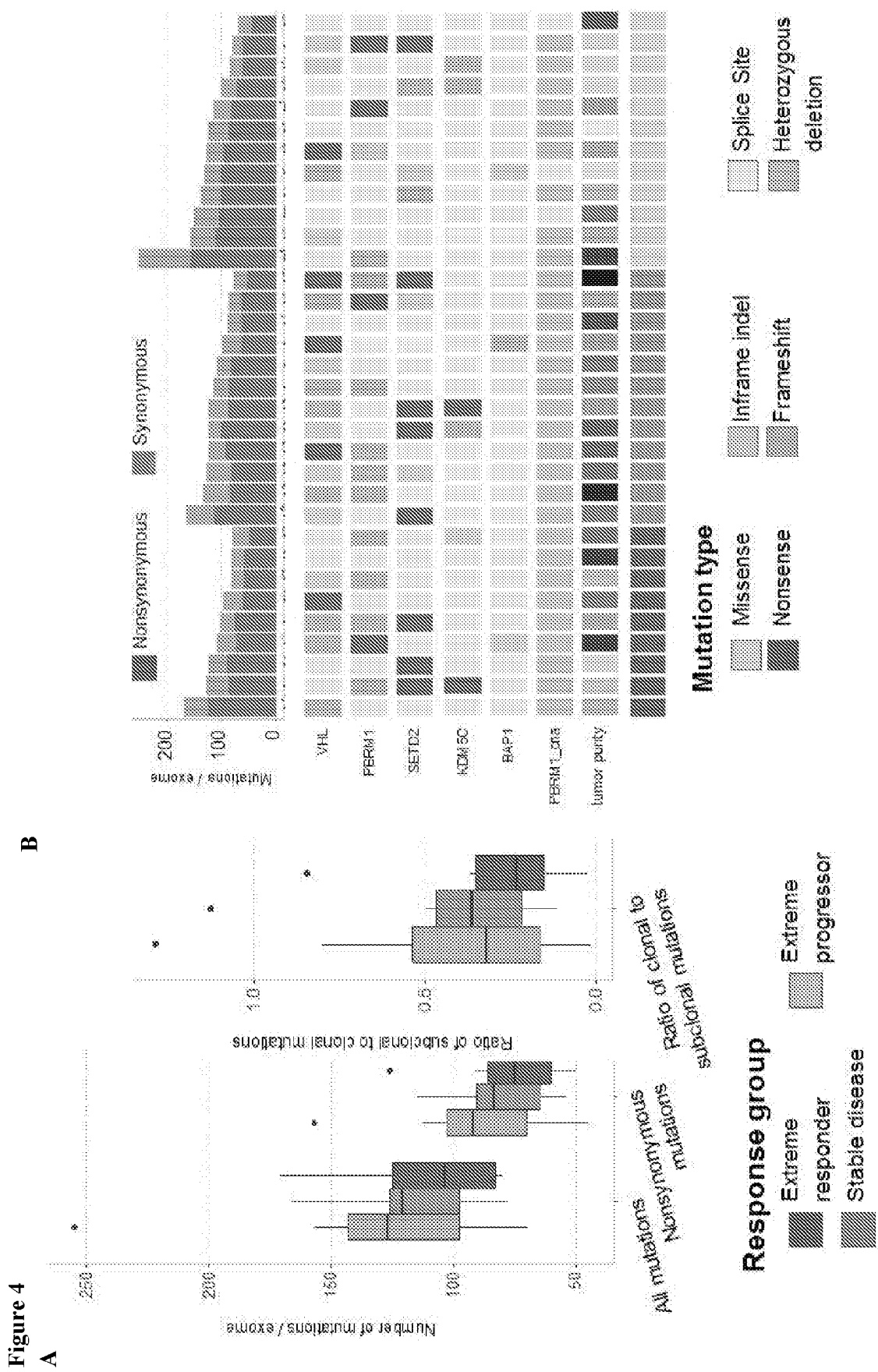
FIG. 4 includes 5 panels, identified as panels A, B, C, D, and E, which show whole exome features of the training cohort (N=41). Overall number of detected mutations per sample (all changes to the DNA sequence of a gene) and nonsynonymous mutations (mutations that change the amino acid sequence of the resulting protein encoded by a gene) per sample were similar for patients classified as extreme progressors, extreme responders, or intermediate benefit (Panel A). The ratio of clonal to subclonal mutations was not associated with clinical benefit. Nonsynonymous mutational burden, mutations in gene commonly mutated in clear-cell renal cell carcinoma, estimated tumor purity by ABSOLUTE (Carter et al. (202) *Nat. Biotechnol.* 30:413-421), and outcomes with immune checkpoint blockade are shown in a stacked CoMut plot (Panel B). The five shown genes were selected as the intersection between significantly mutated genes in TCGA clear-cell renal cell carcinoma and 7 genes significantly mutated by MutSigCV (Lawrence et al. (2013) *Nature* 499:214-218) in this cohort (see Table 2C). Truncating mutations in PBRM1 were significantly more common in extreme responders (8/9) vs. extreme progressors (3/12) (p=0.0037; q=0.026; Pearson's chi-squared, FDR over 7 genes significantly mutated by MutSigCV) (Panel C). Dashed red line indicates p<0.01. Genes in black were significantly mutated across the entire cohort by MutSigCV, while genes in grey were mutated at lower levels. Patients with truncating alterations in PBRM1 had prolonged overall survival compared to those without truncating PBRM1 mutations (p=0.042; Cox proportional hazards) (Panel D). Three patients with truncating alterations in PBRM1 who were "extreme progressors" due to early tumor growth on anti-PD1 monotherapy had longer-than-expected overall survival (9_97: PFS 1.2 months, OS 28.6+ months and 13_96: PFS 1.2 months; OS 19.1+ months), with duration of overall survival being unevaluable in a third due to censoring (5_18: PFS 1.4 months, OS 3.6+ months) (Panel E).
Figure 4:
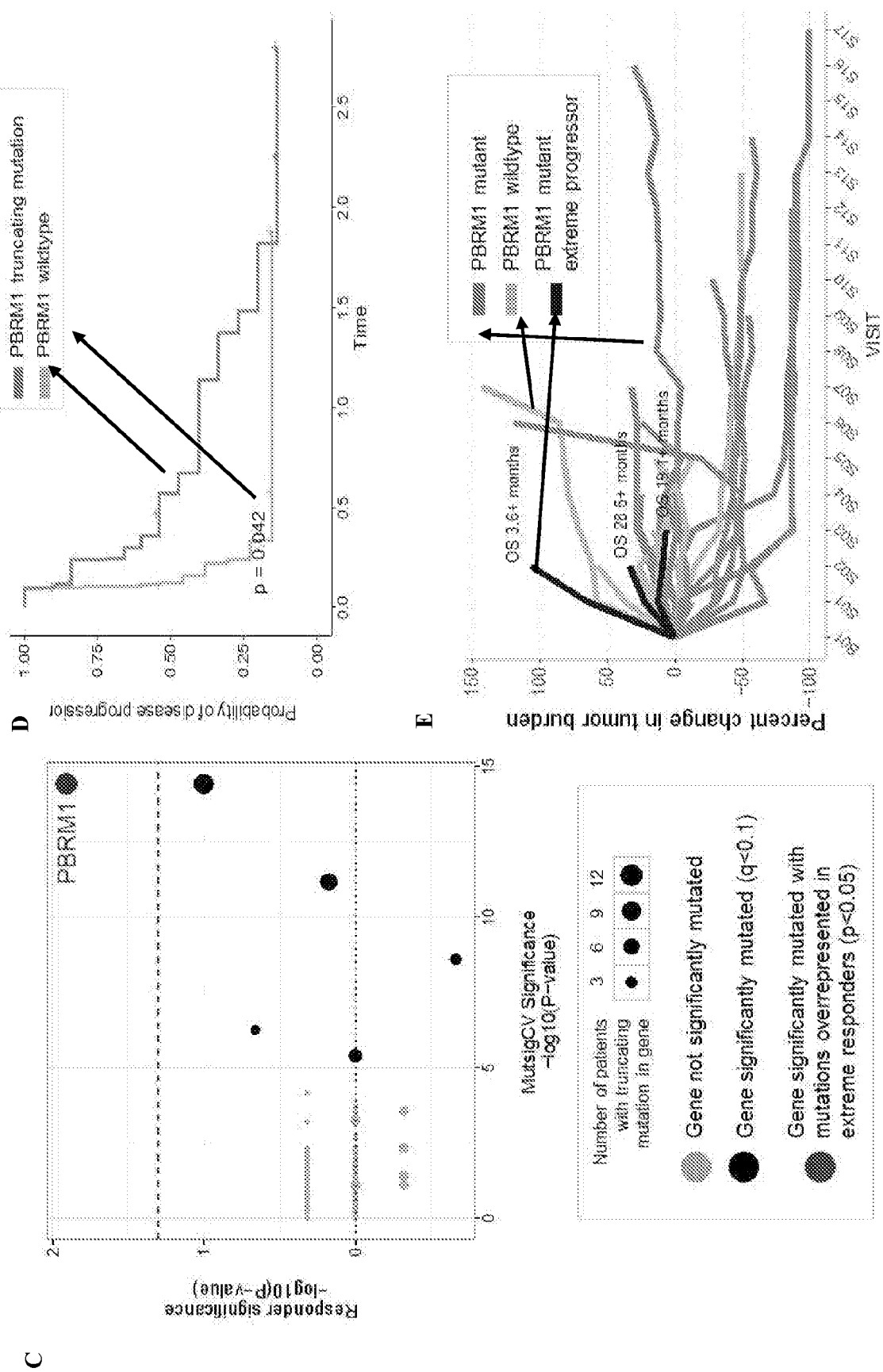
Figure 5:
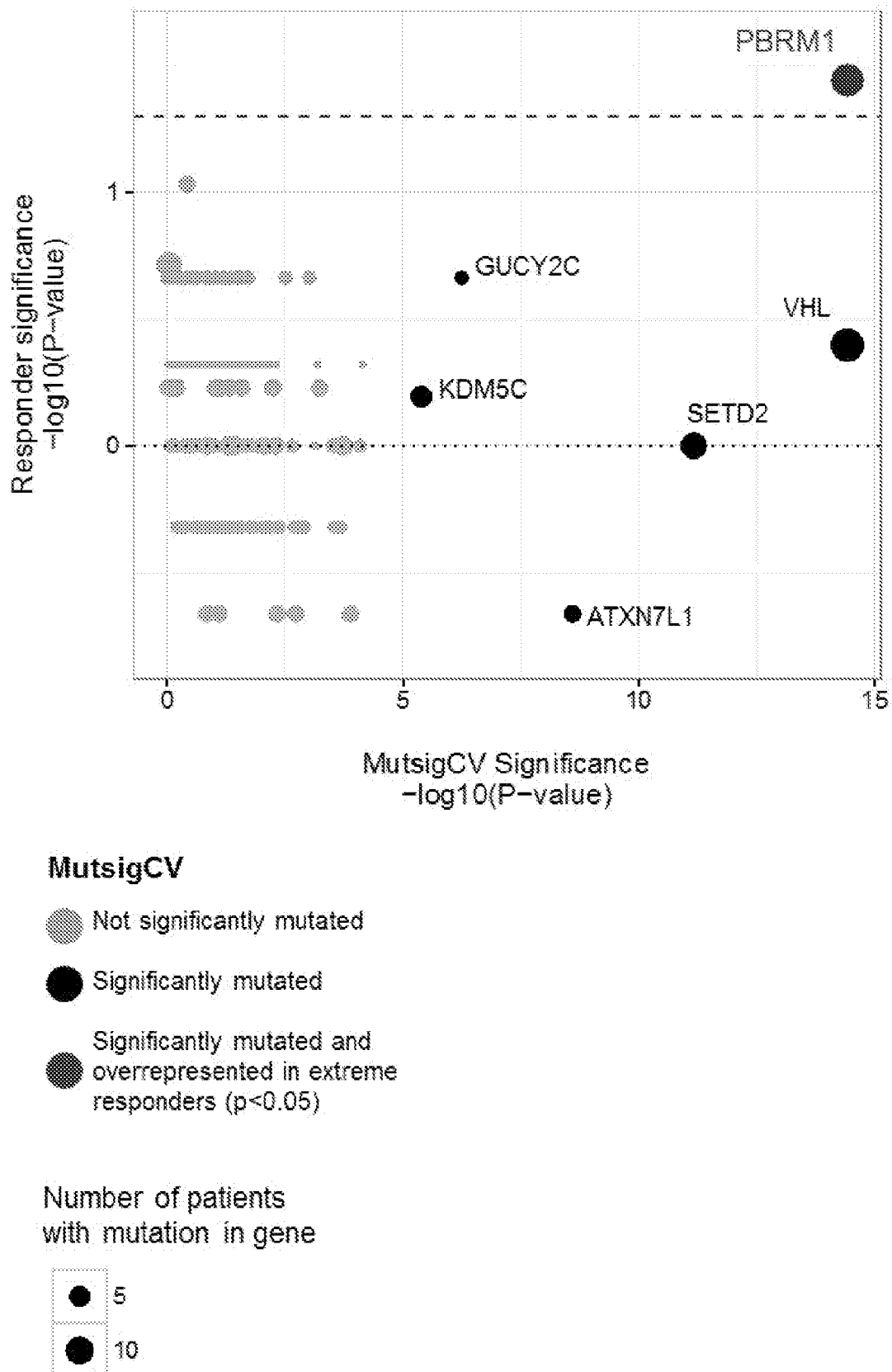
FIG. 5 show genes significantly mutated in extreme responders vs. extreme progressors. Of all 2,285 genes containing at least 1 nonsynonymous mutation in the training cohort, PBRM1 was the only gene mutated significantly more frequently in extreme responders vs. extreme progressors (8/9 extreme responders vs. 4/12 extreme progressors, p=0.011; Pearson's chi-squared) prior to correcting for multiple hypothesis testing. Genes in black were significantly mutated across the entire training cohort according to MutSigCV, while genes in grey were not. Dashed red line indicates p<0.01.
Figure 6:
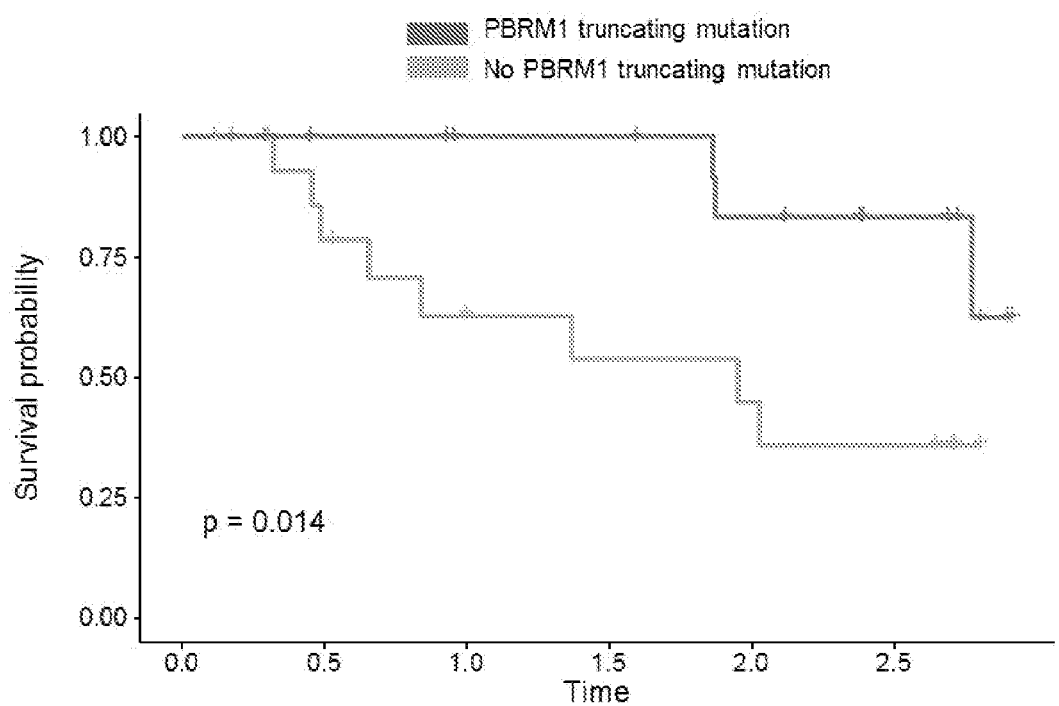
FIG. 6 shows that patients with truncating mutations in PBRM1 had objective decreases in tumor burden and prolonged overall survival on immune checkpoint monotherapy.
Figure 7:
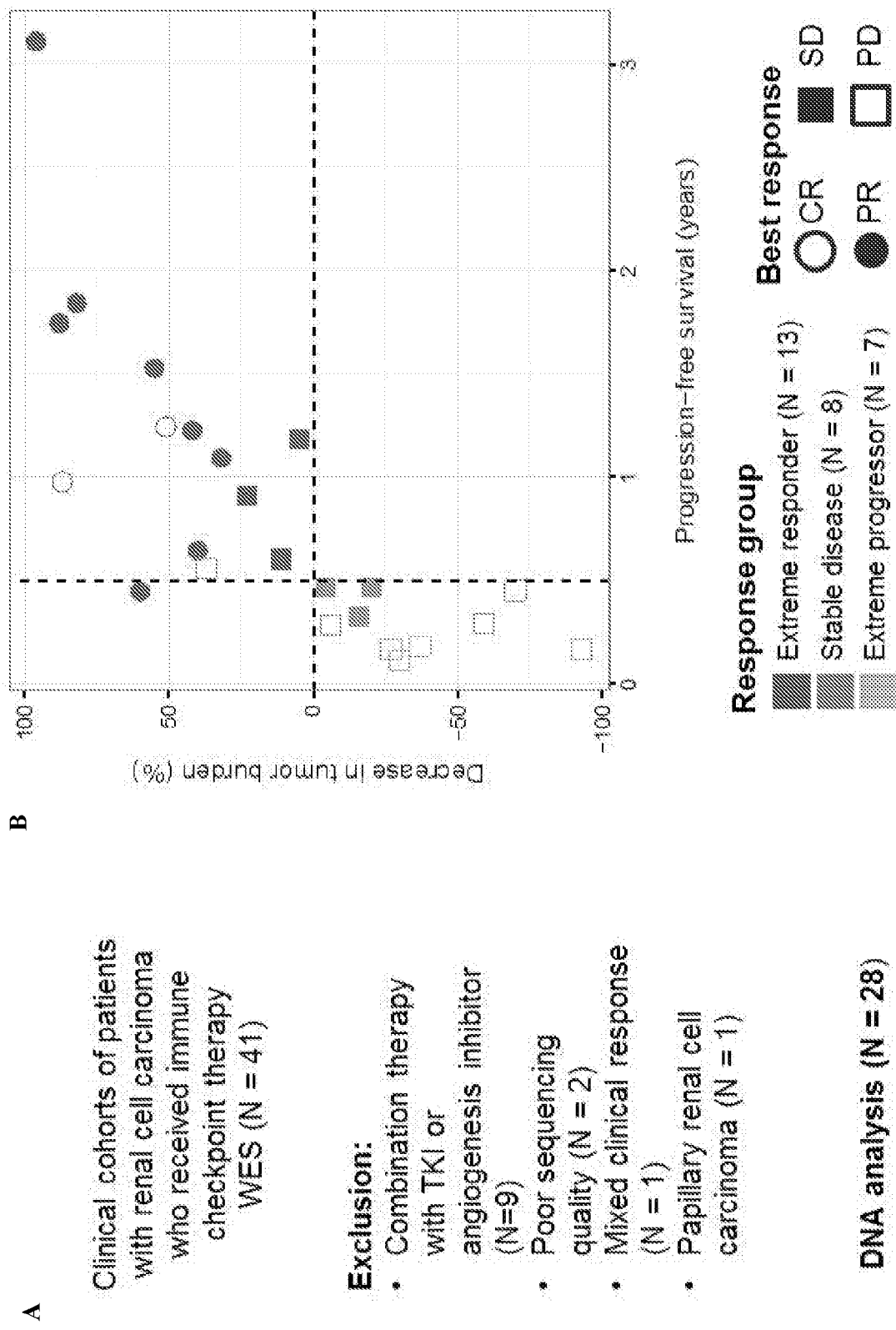
FIG. 7 includes 4 panels, identified as panels A, B, C, and D, which show the association between PBRM1 alterations and clinical benefit from immune checkpoint therapies in a validation cohort of patients with clear-cell renal cell carcinoma treated with monoclonal antibodies targeting PD-1 and PD-L1, either alone or in combination with monoclonal antibodies targeting the immune checkpoint cytotoxic T lymphocyte-associated protein 4 (CTLA-4). A clinical cohort of 41 patients treated with immune checkpoint therapy for metastatic renal cell carcinoma was narrowed to 28 patients in the final validation cohort (Panel A). Patients were stratified into extreme responder, extreme progressor, and intermediate benefit groups using the same definitions as in the training cohort (Panel B). Truncating alterations in PBRM1 were significantly more frequent in patients with extreme response to immune checkpoint monotherapy compared to those experiencing extreme progression (8/13 vs. 1/7) (p=0.043; Pearson's chi-squared) (Panel C). Truncating alterations in PBRM1 frequently occurred in the context of heterozygous deletion of chromosome 3p, though 2 patients with frameshift alterations in PBRM1 who were copy-neutral at chromosome 3p also experienced extreme response (Panel D).
Figure 7:
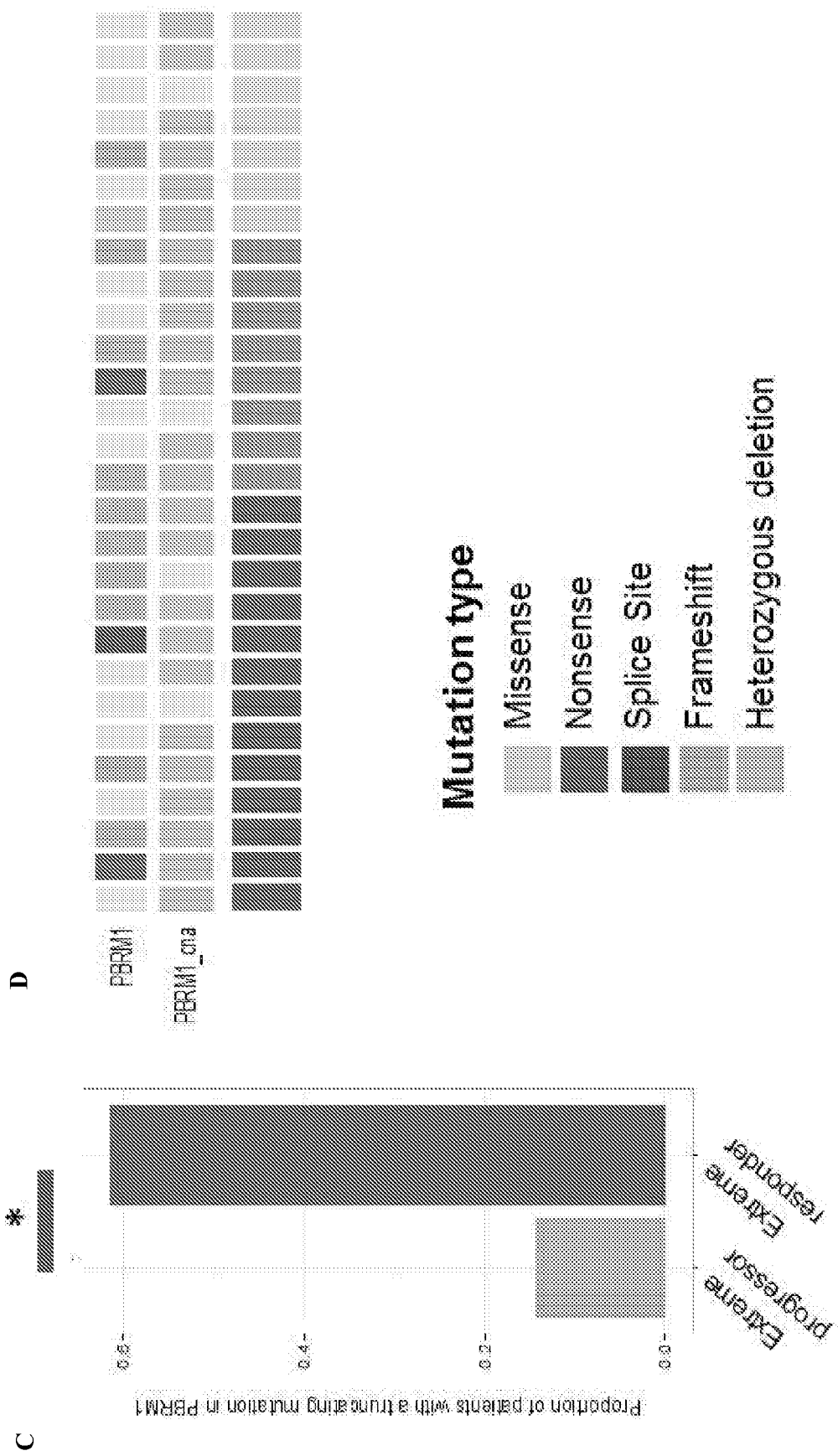

On whole exome analysis, overall mutational loads were moderate in the 34 patients with high-quality WES in the training cohort (median 116.5, range 70-255), and mutational burden did not predict response to therapy, nor did burden of clonal mutations or the ratio of subclonal to clonal mutations (p>0.05 for all; Wilcoxon rank sum) (FIG. 4A-4B, Table 2C). Thus, the role of mutations in particular genes in mediating response needs to be solved. To identify significantly mutated genes in this cohort, MutSigCV (Lawrence et al. (2013) Nature 499:214-218, available at the website of the Broad Insitute of the World Wide Web address of software.broadinstitute.orgicancer/software/genepattern/modules/docs/MutSigCV) program was implemented to identify genes mutated more frequently than expected by chance, after correcting for patient-specific mutation frequencies and spectra and gene-specific mutation rates, expression levels, and replication times. This analysis identified six significantly mutated genes (Table 2D), consistent with prior studies of ccRCC, including VHL, PBRM1, and SETD2 (Cancer Genome Atlas Research, 2013). Of these 6, mutations in PBRM1 were more common in extreme responders to anti-PD1 therapy than in extreme progressors (p=0.019; Pearson's chi-squared) (FIG. 5). It was also noted that some subjects had deletions in various chromosomes. For example, subjects CA209009_12_115 and KE6262 had arm-level monoallelic deletion of chromosome 15, including B2M; subjects PD_005, PD_007, CA209009_5_1, and CA209009_13_96 had arm-level monoallelic deletion of chromosome 6, including HLA-A, HLA-B, HLA-C, TAP1, TAP2, and TAPBP; subject VA1008 had focal monoallelic deletion of chromosome 6, including HLA-A, HLA-B, HLA-C, TAP1, TAP2, and TAPBP; subject CA209009_8_105 had focal monoallelic deletion of chromosome 6, including HLA-A, HLA-B, and HLA-C; subject CA209009_11_25 had arm-level monoallelic deletion of chromosome 6, including HLA-A, HLA-B, HLA-C, and TAPBP; subject CA209009_11_93 had a large monoallelic deletion of chromosome 6, including HLA-B, HLA-C, and TAPBP; and subject CA209009_5_503 had a large monoallelic deletion of chromosome 6, including HLA-A, HLA-B, TAP1, TAP2, and TAPBP. Furthermore, it was observed that truncating mutations (frameshift indels, nonsense, or splice-site) in PBRM1 occurred significantly more frequently in the extreme responders (p=0.0064; Pearson's chi-squared) after correcting for false discovery among the 6 genes mutated significantly in the training cohort (q=0.039; Benjamini-Hochberg) (FIG. 4C, Table 2E). All truncating PBRM1 alterations were in the context of chromosome 3p deletions (FIG. 4B), resulting in expected complete loss-of-function of PBRM1. Most of these alterations were predicted to be clonal (present in all tumor cells), with the two subclonal alterations found in one patient with stable disease and another with extreme response to anti-PD1 therapy (Table 2E). Patients with truncating mutations in PBRM1 had significantly prolonged progression-free survival compared to those without truncating alterations in PBRM1 (p=0.042) (FIG. 4D), and prolonged overall survival as well (p=0.014) (FIG. 6), with sustained reductions in tumor burden (FIG. 7B). Of note, two of the three extreme progressors with PBRM1 truncating mutations had long OS (>1.5 years), and all three were still alive at the time of censoring (FIG. 7B). Additionally, of the three patients with SD and objective tumor regression but PFS of insufficient duration to be considered an exceptional responder, 2 were PBRM1 mutants, while the third (2_85) had relatively low tumor sequencing coverage over PBRM1 (48-fold) and low tumor purity (estimated 13% tumor cells), making it possible that we were insufficiently powered to detect a PBRM1 mutation in this patient. In a focused search for PBRM1 alterations in the 6 tumors initially excluded from analysis for quality-control reasons (FIG. 1B), two additional truncating mutations were found. One was a poorly-supported splice site alteration (4/35 reads, all in reverse direction) in an extreme progressor (4_95), while the other was a well-supported nonsense alteration (22/417 reads) in an extreme responder (5_6).

TABLE 2C

Summary of Mutational Burden in Training Cohort (N = 34)

| sample | all_mutations | all_nonsynonymous | all_synonymous | clonal_mutations |
| --- | --- | --- | --- | --- |
| CA209009_1_20 | 80 | 50 | 30 | 51 |
| CA209009_1_32 | 125 | 89 | 36 | 103 |
| CA209009_1_62 | 110 | 82 | 28 | 68 |
| CA209009_11_10 | 135 | 85 | 50 | 84 |
| CA209009_11_11 | 100 | 63 | 37 | 64 |
| CA209009_11_14 | 128 | 86 | 42 | 107 |
| CA209009_11_25 | 157 | 113 | 44 | 107 |
| CA209009_11_56 | 125 | 102 | 23 | 55 |
| CA209009_11_79 | 78 | 54 | 24 | 47 |
| CA209009_11_93 | 125 | 91 | 34 | 101 |
| CA209009_12_115 | 90 | 64 | 26 | 52 |
| CA209009_13_90 | 140 | 102 | 38 | 96 |
| CA209009_13_96 | 255 | 157 | 98 | 83 |
| CA209009_2_102 | 166 | 115 | 51 | 92 |
| CA209009_2_58 | 82 | 60 | 22 | 39 |
| CA209009_2_84 | 117 | 87 | 30 | 71 |
| CA209009_2_85 | 83 | 52 | 31 | 72 |
| CA209009_3_114 | 83 | 59 | 24 | 65 |
| CA209009_3_117 | 86 | 65 | 21 | 71 |
| CA209009_3_15 | 110 | 75 | 35 | 77 |
| CA209009_4_68 | 132 | 102 | 30 | 108 |
| CA209009_5_1 | 84 | 61 | 23 | 66 |
| CA209009_5_106 | 104 | 76 | 28 | 70 |
| CA209009_5_18 | 81 | 61 | 20 | 51 |
| CA209009_5_21 | 128 | 82 | 46 | 92 |
| CA209009_5_41 | 102 | 73 | 29 | 87 |
| CA209009_5_50 | 171 | 126 | 45 | 122 |
| CA209009_5_73 | 70 | 45 | 25 | 36 |
| CA209009_6_39 | 126 | 86 | 40 | 117 |
| CA209009_8_105 | 152 | 105 | 47 | 118 |
| CA209009_9_119 | 97 | 62 | 35 | 81 |
| CA209009_9_27 | 128 | 98 | 30 | 78 |
| CA209009_9_52 | 125 | 94 | 31 | 94 |
| CA209009_9_97 | 116 | 82 | 34 | 77 |

| sample | subclonal_mutations | clonality_unknown | all_neoantigens |
| --- | --- | --- | --- |
| CA209009_1_20 | 18 | 11 | 32 |
| CA209009_1_32 | 12 | 10 | 134 |
| CA209009_1_62 | 23 | 19 | 172 |
| CA209009_11_10 | 26 | 25 | 93 |
| CA209009_11_11 | 25 | 11 | 110 |
| CA209009_11_14 | 11 | 10 | 114 |

TABLE 2C-continued

| Summary of Mutational Burden in Training Cohort (N = 34) | | | |
|---|---|---|---|
| CA209009_11_25 | 33 | 17 | 139 |
| CA209009_11_56 | 62 | 8 | 100 |
| CA209009_11_79 | 22 | 9 | 170 |
| CA209009_11_93 | 17 | 7 | 177 |
| CA209009_12_115 | 26 | 12 | 148 |
| CA209009_13_90 | 39 | 5 | 180 |
| CA209009_13_96 | 107 | 65 | 153 |
| CA209009_2_102 | 44 | 30 | 149 |
| CA209009_2_58 | 33 | 10 | 64 |
| CA209009_2_84 | 28 | 18 | 106 |
| CA209009_2_85 | 0 | 11 | 57 |
| CA209009_3_114 | 10 | 8 | 82 |
| CA209009_3_117 | 14 | 1 | 80 |
| CA209009_3_15 | 18 | 15 | 116 |
| CA209009_4_68 | 18 | 6 | 126 |
| CA209009_5_1 | 11 | 7 | 99 |
| CA209009_5_106 | 26 | 8 | 83 |
| CA209009_5_18 | 29 | 1 | 233 |
| CA209009_5_21 | 21 | 15 | 100 |
| CA209009_5_41 | 5 | 10 | 127 |
| CA209009_5_50 | 31 | 18 | 242 |
| CA209009_5_73 | 29 | 5 | 59 |
| CA209009_6_39 | 2 | 7 | 65 |
| CA209009_8_105 | 18 | 16 | 246 |
| CA209009_9_119 | 2 | 14 | 70 |
| CA209009_9_27 | 41 | 9 | 189 |
| CA209009_9_52 | 15 | 16 | 143 |
| CA209009_9_97 | 26 | 13 | 144 |

TABLE 2D

| MutSigCV results in training cohort (N = 34) | | | | | | | | | |
|---|---|---|---|---|---|---|---|---|---|
| rank | gene | longname | code len | nnei | nncd | nsil | nmis | nstp | nspl | nind |
| 1 | VHL | von Hippel-Lindau tumor suppressor | 650 | 489 | 0 | 0 | 8 | 5 | 1 | 9 |
| 2 | PBRM1 | polybromo 1 | 5417 | 111 | 0 | 1 | 0 | 4 | 4 | 12 |
| 3 | SETD2 | SET domain containing 2 | 7777 | 25 | 0 | 1 | 4 | 8 | 0 | 2 |
| 4 | ATXN7L1 | ataxin 7-like 1 | 2723 | 76 | 0 | 0 | 2 | 0 | 0 | 3 |
| 5 | GUCY2C | guanylate cyclase 2C (heat stable enterotoxin receptor) | 3326 | 16 | 0 | 0 | 0 | 1 | 0 | 2 |
| 6 | KDM5C | lysine (K)-specific demethylase 5C | 4879 | 24 | 0 | 0 | 1 | 2 | 1 | 3 |

| rank | nnon | npat | nsite | pCV | pCL | pFN | P | q |
|---|---|---|---|---|---|---|---|---|
| 1 | 23 | 23 | 22 | 1.00E−16 | 8.18E−01 | 9.67E−01 | 3.77E−15 | 3.46E−11 |
| 2 | 20 | 20 | 20 | 1.00E−16 | 1 | 7.19E−01 | 3.77E−15 | 3.46E−11 |
| 3 | 14 | 13 | 14 | 2.26E−13 | 1 | 5.37E−01 | 6.80E−12 | 4.16E−08 |
| 4 | 5 | 5 | 3 | 1.06E−07 | 8.25E−04 | 1.85E−02 | 2.54E−09 | 1.17E−05 |
| 5 | 3 | 3 | 2 | 2.00E−05 | 3.00E−03 | 4.78E−01 | 5.68E−07 | 2.08E−03 |
| 6 | 7 | 7 | 7 | 4.46E−07 | 1 | 3.50E−01 | 4.10E−06 | 1.25E−02 |

Only six identified genes, among 18,345 genes tested, are shown in Table 2D.

TABLE 2E

Truncating PBRM1 alterations in patients training cohort passing whole exome quality control (N = 34)

| patient_id | Hugo_Symbol | | PBRM1_mean_coverage | Chromo-some | Start_position | End_position | Variant_Classi-fication | Reference_Allele | Tumor_Seq_Allele1 | Tumor_Seq_Allele2 |
|---|---|---|---|---|---|---|---|---|---|---|
| CA209009_9_97 | PBRM1 | 1 | 119.39 | 3 | 52663008 | 52663008 | Nonsense_Mutation | C | C | A |
| CA209009_9_52 | PBRM1 | 1 | 97.9 | 3 | 52613205 | 52613205 | Frame_Shift_Del | T | T | - |
| CA209009_9_27 | PBRM1 | 0 | 248.99 | 3 | 52598081 | 52598101 | In_Frame_Del | TCA TCA TCT ACC ACT TTA GCA | TCA TCA TCT ACC ACT TTA GCA | - |
| CA209009_9_119 | PBRM1 | 1 | 28.57 | 3 | 52682459 | 52682459 | Splice_Site | C | C | G |
| CA209009_8_105 | NA | 0 | 146.47 | NA | NA | NA | NA | | | |
| CA209009_6_39 | NA | 0 | 130.38 | NA | NA | NA | NA | | | |
| CA209009_5_73 | NA | 0 | 181.65 | NA | NA | NA | NA | | | |
| CA209009_5_50 | PBRM1 | 1 | 135.79 | 3 | 52712515 | 52712515 | Splice_Site | C | C | T |
| CA209009_5_41 | NA | 0 | 123.22 | NA | NA | NA | NA | | | |
| CA209009_5_21 | PBRM1 | 1 | 125.64 | 3 | 52613210 | 52613210 | Frame_Shift_Del | T | T | - |
| CA209009_5_18 | PBRM1 | 1 | 126.07 | 3 | 52678748 | 52678748 | Nonsense_Mutation | C | C | A |
| CA209009_5_106 | PBRM1 | 1 | 155.18 | 3 | 52620610 | 52620614 | Frame_Shift_Del | ATTTT | ATTTT | - |
| CA209009_5_1 | NA | 0 | 138.81 | NA | NA | NA | NA | | | |
| CA209009_4_68 | NA | 0 | 100.73 | NA | NA | NA | NA | | | |
| CA209009_3_15 | PBRM1 | 1 | 94.84 | 3 | 52613194 | 52613194 | Nonsense_Mutation | C | C | A |
| CA209009_3_117 | PBRM1 | 1 | 146.69 | 3 | 52643375 | 52643375 | Nonsense_Mutation | G | G | A |
| CA209009_3_114 | PBRM1 | 1 | 111.22 | 3 | 52662964 | 52662964 | Frame_Shift_Del | A | A | - |
| CA209009_2_85 | NA | 0 | 47.52 | NA | NA | NA | NA | NA | NA | NA |
| CA209009_2_84 | PBRM1 | 1 | 130.86 | 3 | 52696272 | 52696272 | Frame_Shift_Del | T | T | - |
| CA209009_2_58 | NA | 0 | 95.31 | NA | NA | NA | NA | | | |
| CA209009_2_102 | PBRM1 | 1 | 266.4 | 3 | 52663052 | 52663052 | Splice_Site | C | C | T |

TABLE 2E-continued

Truncating PBRM1 alterations in patients training cohort passing whole exome quality control (N = 34)

| patient_id | Hugo_Symbol | | | | Start_position | End_position | Variant_Classification | Reference_Allele | Tumor_Seq_Allele1 | Tumor_Seq_Allele2 | Protein_Change | Variant_Type | i_tumor_f | t_alt_count | t_ref_count | clonal | Indel_Caller |
|---|---|---|---|---|---|---|---|---|---|---|---|---|---|---|---|---|---|
| CA209009_13_96 | PBRM1 | 1 | 164.39 | 3 | 52643489 | 52643489 | Frame_Shift_Del | A | A | - | | | | | | | |
| CA209009_13_90 | NA | 0 | 124.87 | NA | NA | NA | NA | | | | | | | | | | |
| CA209009_12_115 | NA | 0 | 115.51 | NA | NA | NA | NA | | | | | | | | | | |
| CA209009_11_93 | PBRM1 | 1 | 173.78 | 3 | 52651277 | 52651277 | Splice_Site | C | C | T | | | | | | | |
| CA209009_11_79 | PBRM1 | 1 | 67.19 | 3 | 52621487 | 52621487 | Frame_Shift_Del | T | T | - | | | | | | | |
| CA209009_11_56 | NA | 0 | 221.56 | NA | NA | NA | NA | | | | | | | | | | |
| CA209009_11_25 | NA | 0 | 124.35 | NA | NA | NA | NA | | | | | | | | | | |
| CA209009_11_14 | PBRM1 | 1 | 131.63 | 3 | 52623201 | 52623201 | Frame_Shift_Del | G | G | - | | | | | | | |
| CA209009_11_11 | NA | 0 | 62.73 | NA | NA | NA | NA | | | | | | | | | | |
| CA209009_11_10 | PBRM1 | 1 | 89.9 | 3 | 52623120 | 52623120 | Frame_Shift_Del | G | G | - | | | | | | | |
| CA209009_1_62 | PBRM1 | 1 | 131.16 | 3 | 52613062 | 52613068 | Splice_Site | ACACTCA | ACACTCA | - | | | | | | | |
| CA209009_1_32 | NA | 0 | 120.85 | NA | NA | NA | NA | | | | | | | | | | |
| CA209009_1_20 | PBRM1 | 1 | 28.98 | 3 | 52649455 | 52649456 | Frame_Shift_Ins | - | - | T | | | | | | | |
| CA209009_9_97 | | | | | | | | | | | p.E417* | SNP | 0.278481 | 22 | 57 | 1 | NA |
| CA209009_9_52 | | | | | | | | | | | p.D1148fs | DEL | 0.235955056 | 21 | 68 | 1 | strelka, indelocator |
| CA209009_9_27 | | | | | | | | | | | p.AKVVDDE1249del | DEL | 0.15 | 14 | 77 | not evaluable | indelocator |
| CA209009_9_119 | | | | | | | | | | | | SNP | 0.666667 | 10 | 5 | 1 | NA |
| CA209009_8_105 | | | | | | | | | | | NA | NA | NA | NA | NA | NA | NA |
| CA209009_6_39 | | | | | | | | | | | NA | NA | NA | NA | NA | NA | NA |
| CA209009_5_73 | | | | | | | | | | | NA | NA | NA | NA | NA | NA | NA |
| CA209009_5_50 | | | | | | | | | | | | SNP | 0.213592 | 22 | 81 | 1 | NA |
| CA209009_5_41 | | | | | | | | | | | NA | NA | NA | NA | NA | NA | NA |
| CA209009_5_21 | | | | | | | | | | | p.K1146fs | DEL | 0.441666667 | 53 | 67 | 1 | strelka, indelocator |

TABLE 2E-continued

Truncating PBRM1 alterations in patients training cohort passing whole exome quality control (N = 34)

| | | | | | | | |
|---|---|---|---|---|---|---|---|
| CA209009_5_18 | p.E291* | SNP | 0.150943 | 8 | 45 | 1 | NA |
| CA209009_5_106 | p.KI1087fs | DEL | 0.067137809 | 19 | 264 | 0 | strelka, indelocator |
| CA209009_5_1 | NA | NA | NA | NA | NA | NA | NA |
| CA209009_4_68 | NA | NA | NA | NA | NA | NA | NA |
| CA209009_3_15 | p.E1105* | SNP | 0.53 | 53 | 47 | 1 | NA |
| CA209009_3_117 | p.Q809* | SNP | 0.288 | 36 | 89 | 1 | NA |
| CA209009_3_114 | p.N463fs | DEL | 0.108695652 | 10 | 82 | 1 | strelka, indelocator |
| CA209009_2_85 | NA | NA | NA | NA | NA | NA | NA |
| CA209009_2_84 | p.K135fs | DEL | 0.171428571 | 12 | 58 | 1 | strelka, indelocator |
| CA209009_2_58 | NA | NA | NA | NA | NA | NA | NA |
| CA209009_2_102 | | SNP | 0.235849 | 25 | 81 | 1 | NA |
| CA209009_13_96 | p.S818fs | DEL | 0.402654867 | 91 | 135 | 1 | strelka, indelocator |
| CA209009_13_90 | NA | NA | NA | NA | NA | NA | NA |
| CA209009_12_115 | NA | NA | NA | NA | NA | NA | NA |
| CA209009_11_93 | | SNP | 0.12766 | 6 | 41 | 1 | NA |
| CA209009_11_79 | p.N1017fs | DEL | 0.464285714 | 13 | 15 | 1 | strelka, indelocator |
| CA209009_11_56 | NA | NA | NA | NA | NA | NA | NA |
| CA209009_11_25 | NA | NA | NA | NA | NA | NA | NA |
| CA209009_11_14 | p.D965fs | DEL | 0.25 | 15 | 45 | 1 | strelka, indelocator |
| CA209009_11_11 | NA | NA | NA | NA | NA | NA | NA |
| CA209009_11_10 | p.I992fs | DEL | 0.55 | 55 | 45 | 1 | strelka, indelocator |
| CA209009_1_62 | | | DEL | 0.17370892 | 37 | 176 | 0 | strelka |
| CA209009_1_32 | NA | NA | NA | NA | NA | NA | NA |
| CA209009_1_20 | p.H627fs | INS | 0.363636364 | 8 | 14 | 1 | strelka, indelocator |

Figure 8:
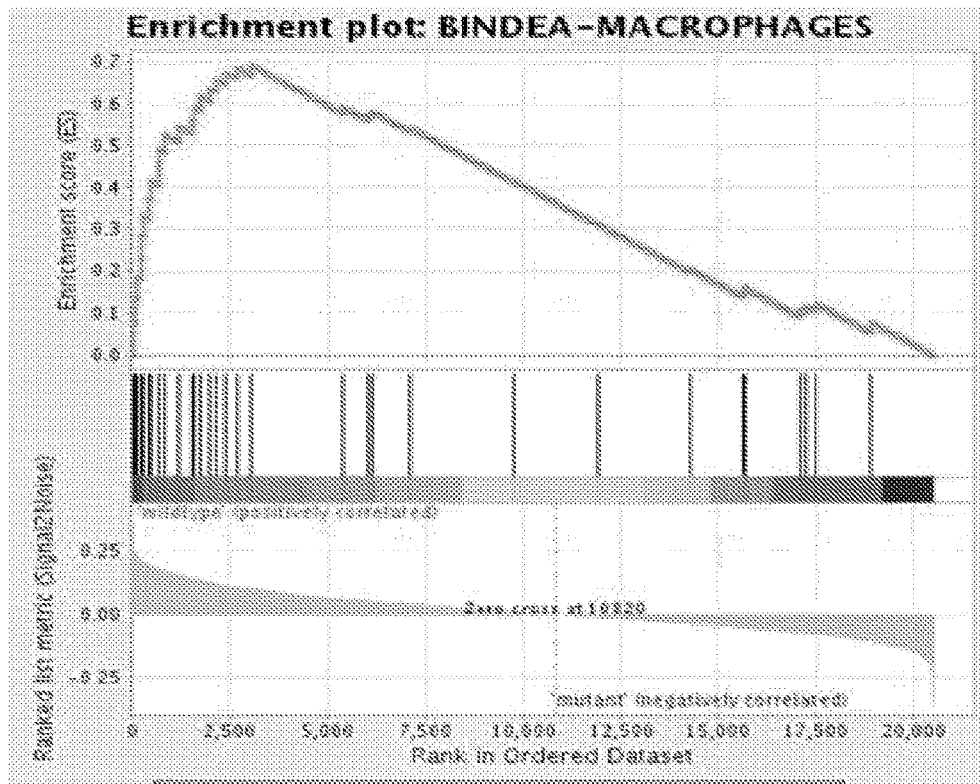
FIG. 8 includes 4 panels, identified as panels A, B, C, and D, which show the gene set enrichment analysis (GSEA) (Subramanian et al. (2005) Proc. Natl. Acad. Sci. 102: 15545-15550) of gene sets significantly enriched in untreated ccRCC tumors from the TCGA in tumors with truncating alterations in PBRM1 versus those without. GSEA showed that PBRM1-truncated tumors had significantly decreased infiltration of macrophages (Panel A), TH1 cells (Panel B), TH2 cells (Panel C), and T cells (Panel D).
Figure 8:
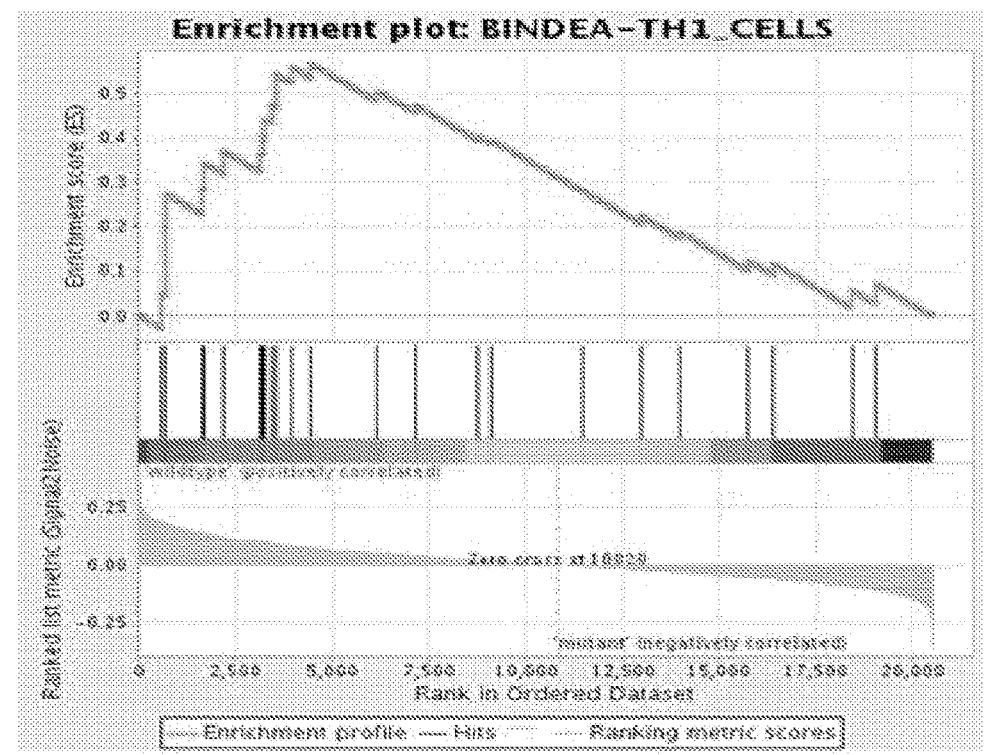
Figure 8:
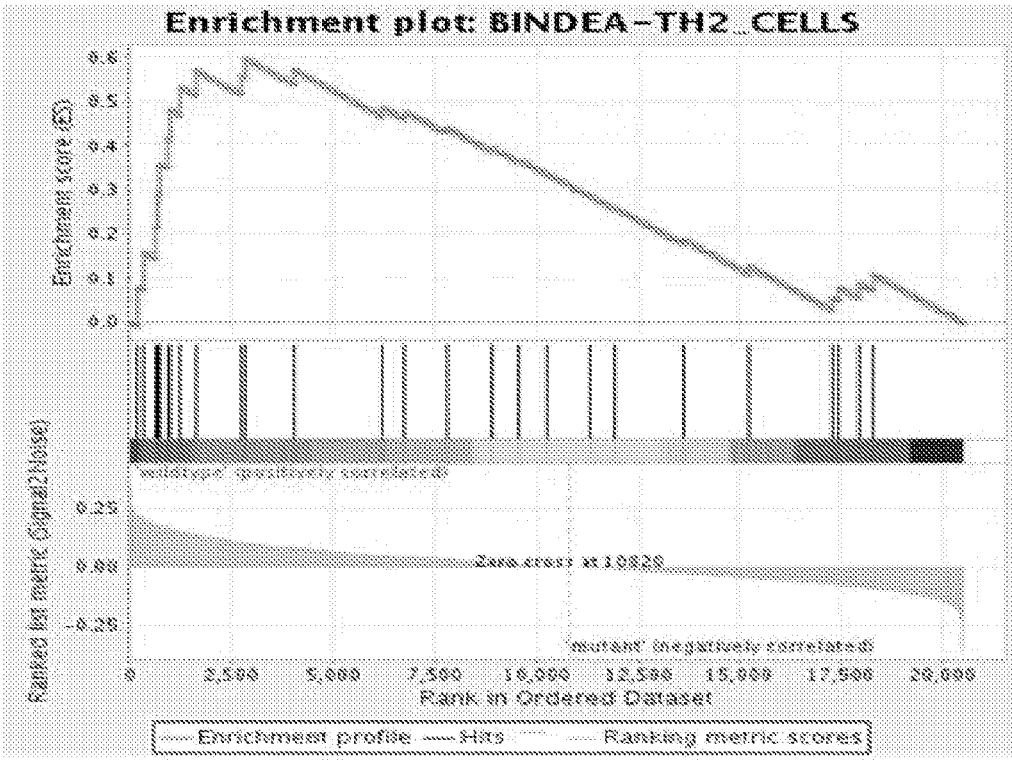
Figure 8:
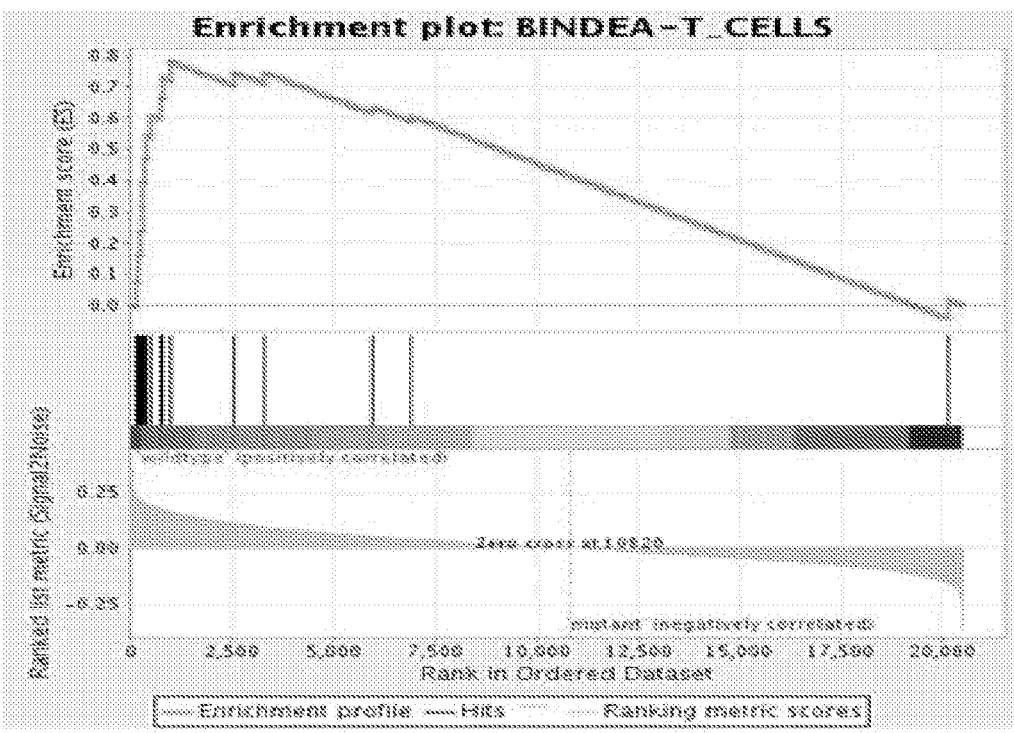

A validation cohort of 41 patients (see Table 3) treated with immune checkpoint therapy for alterations in PBRM1 was then examined to confirm the association between PBRM1 mutational status and response to immune checkpoint therapy. After limiting analyses to those treated with immune checkpoint monotherapy and applying the same quality control standards and definitions of clinical response as in the training cohort, PBRM1 status was assessed in 28 patients (FIGS. 7A-7B and Tables 4A-4C). Extreme responders to immune checkpoint therapy were significantly more likely than extreme progressors to harbor truncating alterations in PBRM1 (8/13 vs. 1/7, p=0.043; Pearson's chi-squared) (FIG. 7C-7D). Again, all but one truncating event in PBRM1 occurred in the setting of chromosome 3p deletion, though this was likely a false negative due to low tumor purity (FIG. 8). One patient (VA1008) likely had CN loss over chromose 3p, though low tumor purity made calling this deletion difficult.

In examining germline variants in WES of germline tissue across both the training and validation cohorts (N=91), including samples that failed quality control for tumor WES, 4 nonsynonymous variants (all in extreme responders), but no truncating alterations in PBRM1, were observed (Table 5A). Further analysis covers the frameshift and nonsense variants in genes thought to be associated with hereditary cancer syndromes (Hart et al. (2016) *BMJ Open* 6:e010332), as well as genes involved in JAK/STAT signaling and immune checkpoints. Almost all alterations were heterozygous and have been previously observed in a database of germline variants from more than 60 thousand ethnically diverse individuals (ExAC) (Lek et al. (2016) *Nature* 536: 285-291) (Table 5B). Two patients (CA8808: extreme responder and RCC.1101: stable disease) had a heterozygous frameshift alteration in PD-L2 (p.L10 fs), which has been observed at frequency of 0.2% in ExAC.

Figure 12:
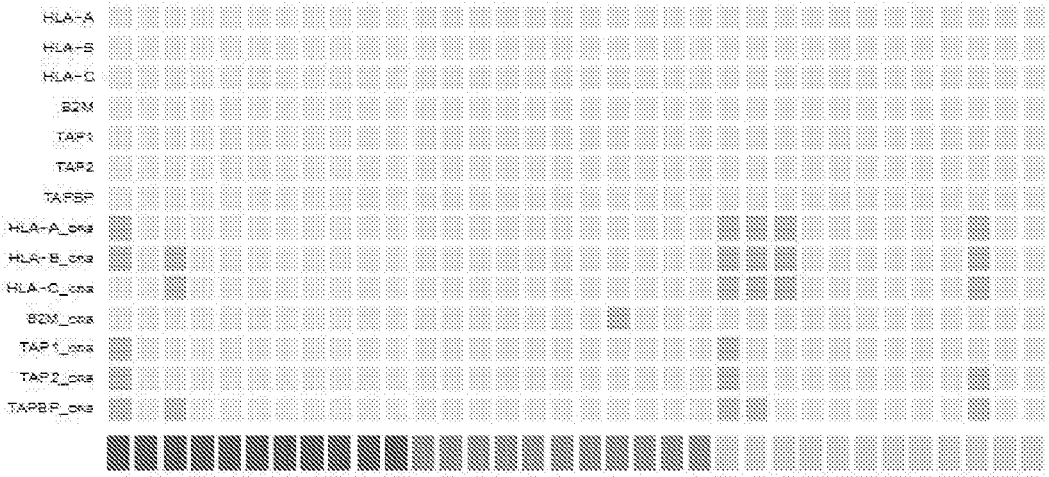
FIG. 12 compares training cohort (CA209009) with validation cohort (DFCI+MSKCC). Mutations and copy number alterations in B2M, HLA, and other antigen presentation machinery were rare and did not segregate by response status.
Figure 12:
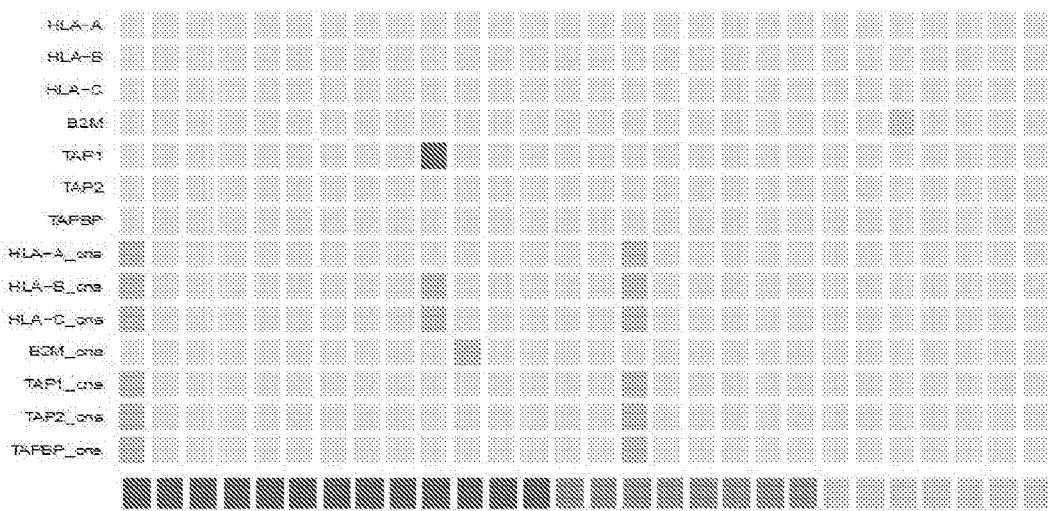

In the somatic space, alterations affecting antigen presentation machinery were rare. In the training cohort, no patients harbored nonsynonymous alterations in TAP1, TAP2, B2M, TAPBP, or any of the HLA Class I alleles. One patient with intermediate benefit (12_115) had a heterozygous deletion of B2M. Six patients (2 extreme responders, 1 intermediate benefit, 2 extreme progressors) had loss of heterozygosity (LOH) in chromosome 6p affecting the HLA and TAP loci. In the validation cohort, one patient had a nonsense mutation in TAP1 (VA1008; extreme responder), one had a missense mutation in B2M (PD_021; extreme progressor), and one had LOH of B2M (KE6262; extreme responder). Three patients had LOH over chromosome 6p (2 extreme responders, 1 intermediate benefit; see also FIG. 12).

TABLE 3

Clinical cohort consolidation

| Cohort name | Sequencing platform | Drug | Number of patients |
|---|---|---|---|
| DFCI Agilent | Agilent | nivolumab | 5 |
| DFCI Kurelt | Illumina | atezolizumab | 2 |
| | | atezolizumab + bevacizumab | 3 |
| | | axitinib + avelumab | 2 |
| | | axitinib + pembrolizumab | 4 |
| | | nivolumab | 13 |
| | | nivolumab + ipilimumab | 5 |
| MSKCC | Agilent | nivolumab | 6 |
| | | nivolumab + ipilimumab | 1 |

TABLE 4A

Sequencing Metrics and Inclusion/Exclusion Criteria for Whole Exome Sequencing in Validation Cohort (N = 41)

| patient_id | tumor_mtc | normal_mtc | bait_set | absolute_inferred_purity | absolute_inferred_ploidy | genome_doubling | exclusion_reason |
|---|---|---|---|---|---|---|---|
| RCC-PD_010 | 131.1804 | 84.152599 | whole_exome_illumina_coding_v1 | 0.55 | 1.76 | 0 | 0 |
| RCC-PD_030 | 129.113198 | 117.952235 | whole_exome_illumina_coding_v1 | 0.38 | 1.94 | 0 | MixedResponse |
| BL5166_T1 | 145.877429 | 122.453144 | whole_exome_agilent_1 | NA | NA | NA | LowPurity |
| RCC-PD_029 | NA | 89.149597 | whole_exome_illumina_coding_v1 | NA | NA | NA | FailedSequencing |
| RCC-PD_001 | 126.512191 | 83.258112 | whole_exome_illumina_coding_v1 | 0.5 | 1.91 | 0 | CombinationT KI |
| RCC-PD_003 | 126.083408 | 90.88862 | whole_exome_illumina_coding_v1 | 0.46 | 1.9 | 0 | CombinationT KI |
| RCC-PD_004 | 135.674171 | 100.347012 | whole_exome_illumina_coding_v1 | 0.4 | 3.78 | 1 | CombinationT KI |
| RCC-PD_006 | 149.115421 | 72.503658 | whole_exome_illumina_coding_v1 | 0.5 | 2.37 | 0 | CombinationT KI |
| RCC-PD_008 | 159.873929 | 91.682176 | whole_exome_illumina_coding_v1 | 0.39 | 1.95 | 0 | CombinationT KI |
| RCC-PD_027 | 180.675064 | 91.140713 | whole_exome_illumina_coding_v1 | 0.45 | 2.99 | 1 | CombinationT KI |
| RCC-PD_028 | 150.285278 | 98.786695 | whole_exome_illumina_coding_v1 | 0.25 | 1.79 | 0 | CombinationT KI |
| RCC-PD_031 | 178.994864 | 93.923124 | whole_exome_illumina_coding_v1 | 0.55 | 2.07 | 0 | CombinationT KI |
| RCC-PD_002 | 106.860416 | 72.680181 | whole_exome_illumina_coding_v1 | 0.5 | 1.89 | 0 | CombinationT KI |
| RCC-PD_005 | 125.608438 | 102.090575 | whole_exome_illumina_coding_v1 | 0.47 | 1.82 | 0 | 0 |
| RCC-PD_007 | 141.661729 | 101.362659 | whole_exome_illumina_coding_v1 | 0.57 | 1.99 | 0 | PapillaryRCC |
| RCC-PD_009 | 122.598167 | 87.563055 | whole_exome_illumina_coding_v1 | 0.41 | 2.08 | 0 | 0 |
| RCC-PD_011 | 104.135516 | 82.878525 | whole_exome_illumina_coding_v1 | 0.32 | 2.01 | 0 | 0 |
| RCC-PD_012 | 133.950619 | 87.549415 | whole_exome_illumina_coding_v1 | 0.39 | 3.44 | 1 | 0 |
| RCC-PD_013 | 145.082205 | 91.170952 | whole_exome_illumina_coding_v1 | 0.22 | 4.02 | 1 | 0 |
| RCC-PD_014 | 127.306107 | 78.539083 | whole_exome_illumina_coding_v1 | 0.25 | 2.1 | 0 | 0 |
| RCC-PD_015 | 105.708638 | 93.290512 | whole_exome_illumina_coding_v1 | 0.36 | 1.84 | 0 | 0 |
| RCC-PD_018 | 145.443729 | 95.372761 | whole_exome_illumina_coding_v1 | 0.61 | 1.97 | 0 | 0 |
| RCC-PD_019 | 148.823821 | 87.774525 | whole_exome_illumina_coding_v1 | 0.42 | 1.86 | 0 | 0 |
| RCC- | 151.788377 | 102.972091 | whole_exome_illumina_coding_v1 | 0.18 | | | |

TABLE 4A-continued

Sequencing Metrics and Inclusion/Exclusion Criteria for Whole Exome Sequencing in Validation Cohort (N = 41)

| patient_id | tumor_mtc | normal_mtc | bait_set | absolute_inferred_purity | absolute_inferred_ploidy | genome_doubling | exclusion_reason |
|---|---|---|---|---|---|---|---|
| PD_020 RCC- | 159.181781 | 95.98438 | whole_exome_illumina_coding_v1 | 0.58 | 1.9 | 0 | 0 |
| PD_021 RCC- | 148.651377 | 98.276519 | whole_exome_illumina_coding_v1 | 0.53 | 1.97 | 0 | 0 |
| PD_022 RCC- | 135.431357 | 86.807511 | whole_exome_illumina_coding_v1 | 0.19 | 2.65 | 1 | 0 |
| PD_023 RCC- | 92.006306 | 83.700183 | whole_exome_illumina_coding_v1 | 0.27 | 2.01 | 0 | 0 |
| PD_024 RCC- | 74.164294 | 48.102291 | whole_exome_illumina_coding_v1 | 0.35 | 1.99 | 0 | 0 |
| PD_025 RCC- | 166.502187 | 89.436443 | whole_exome_illumina_coding_v1 | 0.76 | 1.98 | 0 | 0 |
| PD_026 CA8808_T1 | 123.073315 | 103.475727 | whole_exome_agilent_1 | 0.43 | 1.96 | 0 | 0 |
| KA4076_T1 | 126.229037 | 120.209259 | whole_exome_agilent_1 | 0.56 | 2.03 | 0 | 0 |
| KE5236_T1 | 132.886302 | 140.196056 | whole_exome_agilent_1 | 0.33 | 2 | 0 | 0 |
| KE6262_T1 | 99.539361 | 106.858872 | whole_exome_agilent_1 | 0.11 | 4.16 | 1 | 0 |
| MC1838_T1 | 149.730846 | 118.307339 | whole_exome_agilent_1 | 0.41 | 1.99 | 0 | 0 |
| VA1008_T1 | 142.542157 | 89.429498 | whole_exome_agilent_1 | 0.14 | 1.74 | 0 | 0 |
| RCC.PD1.DNA.1101.T | 92.348009 | 81.023695 | whole_exome_agilent_1.1_refseq_plus_3_boosters | 0.3 | 1.97 | 0 | 0 |
| RCC.PD1.DNA.1137.T | 71.474257 | 96.238769 | whole_exome_agilent_1.1_refseq_plus_3_boosters | 0.31 | 3.43 | 1 | 0 |
| RCC.PD1.DNA.1026.T | 136.955167 | 87.050978 | whole_exome_agilent_1.1_refseq_plus_3_boosters | 0.26 | 2.15 | 0 | 0 |
| RCC.PD1.DNA.944.T | 126.472115 | 95.64198 | whole_exome_agilent_1.1_refseq_plus_3_boosters | 0.66 | 1.89 | 0 | 0 |
| RCC.PD1.DNA.949.T | 101.276419 | 96.351667 | whole_exome_agilent_1.1_refseq_plus_3_boosters | 0.43 | 3.91 | 1 | 0 |

TABLE 4B

Clinical Information for Immune-Checkpoint-Treated Patients in Validation Cohort (N = 41)

| patient_id | drug | best_recist | sex | age | max_tumor_change | histology | os_days | os_censor |
|---|---|---|---|---|---|---|---|---|
| VA1008 | nivolumab + ipilimumab | PR | M | 76 | −96 | clear-cell | 1135 | 1 |
| RCC.PD1.DNA.949 | nivolumab | PR | F | 60 | −40 | clear-cell | 364 | 0 |
| RCC.PD1.DNA.944 | nivolumab | PD | M | 47 | 37 | clear-cell | 134 | 1 |
| RCC.PD1.DNA.1137 | nivolumab | SD | F | 61 | 16 | clear-cell | 1584 | 1 |
| RCC.PD1.DNA.1101 | nivolumab | SD | M | 67 | 4 | clear-cell | 439 | 0 |
| RCC.PD1.DNA.1026 | nivolumab | CR | M | 60 | −87 | clear-cell | 1442 | 1 |
| RCC-PD_031 | axitinib + avelumab | PR | M | 68 | −49 | clear-cell | 165 | 1 |
| RCC-PD_030 | nivolumab | X | M | 72 | −43 | clear-cell | 395 | 0 |
| RCC-PD_029 | nivolumab | PR | M | 54 | −49 | clear-cell | 856 | 0 |
| RCC-PD_028 | atezolizumab + bevacizumab | PR | M | 77 | −43 | clear-cell | 210 | 1 |
| RCC-PD_027 | axitinib + avelumab | PR | M | 59 | −42 | clear-cell | 210 | 1 |
| RCC-PD_026 | nivolumab | SD | F | 70 | 20 | clear-cell | 377 | 1 |
| RCC-PD_025 | nivolumab | SD | M | 74 | −23 | clear-cell | 1724 | 1 |
| RCC-PD_024 | nivolumab | PD | M | 52 | 30 | clear-cell | 304 | 0 |
| RCC-PD_023 | atezolizumab | PR | M | 69 | −88 | clear-cell | 637 | 1 |
| RCC-PD_022 | nivolumab | PD | F | 66 | NA | clear-cell | 247 | 1 |
| RCC-PD_021 | nivolumab | PD | F | 63 | NA | clear-cell | 185 | 0 |
| RCC-PD_020 | nivolumab | PD | F | 64 | NA | clear-cell | 203 | 1 |
| RCC-PD_019 | nivolumab | SD | M | 60 | −11 | clear-cell | 230 | 1 |
| RCC-PD_018 | nivolumab | PR | F | 69 | −82 | clear-cell | 1189 | 0 |
| RCC-PD_015 | nivolumab | PD | M | 71 | 6 | clear-cell | 814 | 0 |
| RCC-PD_014 | nivolumab + ipilimumab | SD | F | 68 | −5 | clear-cell | 433 | 1 |
| RCC-PD_013 | nivolumab + ipilimumab | PR | M | 66 | −32 | clear-cell | 399 | 1 |
| RCC-PD_012 | atezolizumab | PD | M | 67 | −50 | clear-cell | 581 | 1 |
| RCC-PD_011 | nivolumab | PD | M | 40 | −37 | clear-cell | 327 | 0 |
| RCC-PD_010 | nivolumab + ipilimumab | CR | M | 51 | −51 | clear-cell | 454 | 1 |
| RCC-PD_009 | nivolumab + ipilimumab | PD | M | 56 | 8 | papillary | 377 | 1 |
| RCC-PD_008 | axitinib + pembrolizumab | PR | F | 69 | −69 | clear-cell | 462 | 1 |
| RCC-PD_007 | nivolumab + ipilimumab | PR | M | 60 | −42 | clear-cell | 448 | 1 |
| RCC-PD_006 | axitinib + pembrolizumab | PR | M | 68 | −52 | clear-cell | 398 | 1 |
| RCC-PD_005 | nivolumab | PD | M | 62 | NA | clear-cell | 277 | 1 |
| RCC-PD_004 | axitinib + pembrolizumab | SD | M | 54 | −16 | clear-cell | 481 | 1 |
| RCC-PD_003 | atezolizumab + bevacizumab | SD | M | 52 | −16 | clear-cell | 679 | 1 |
| RCC-PD_002 | atezolizumab + bevacizumab | SD | M | 65 | −14 | clear-cell | 534 | 1 |
| RCC-PD_001 | axitinib + pembrolizumab | PR | F | 66 | −53 | clear-cell | 572 | 1 |
| MC1838 | nivolumab | PD | M | 64 | 93 | clear-cell | 622 | 0 |
| KE6262 | nivolumab | PR | M | 68 | −60 | clear-cell | 903 | 1 |

TABLE 4B-continued

Clinical Information for Immune-Checkpoint-Treated Patients in Validation Cohort (N = 41)

| | | | | | | | | |
|---|---|---|---|---|---|---|---|---|
| KE5236 | nivolumab | PD | M | 58 | 70 | clear-cell | 997 | 1 |
| KA4076 | nivolumab | PD | F | 61 | 59 | clear-cell | 727 | 0 |
| CA8808 | nivolumab | PR | M | 62 | −55 | clear-cell | 560 | 1 |
| BL5166 | nivolumab | SD | M | 64 | −11 | clear-cell | 622 | 0 |

| patient_id | pfs_days | pfs_censor | prior_immune_checkpoint | response_category | response_toni |
|---|---|---|---|---|---|
| VA1008 | 1135 | 1 | 0 | extreme_responder | extreme_responder |
| RCC.PD1.DNA.949 | 235 | 0 | 0 | extreme_responder | extreme_responder |
| RCC.PD1.DNA.944 | 67 | 0 | 0 | extreme_progressor | extreme_progressor |
| RCC.PD1.DNA.1137 | 119 | 0 | 0 | stable_disease | stable_disease |
| RCC.PD1.DNA.1101 | 171 | 0 | 0 | stable_disease | stable_disease |
| RCC.PD1.DNA.1026 | 357 | 1 | 0 | extreme_responder | extreme_responder |
| RCC-PD_031 | 123 | 0 | 0 | extreme_responder | stable_disease |
| RCC-PD_030 | 93 | 0 | 0 | not_evaluable | stable_disease |
| RCC-PD_029 | 189 | 0 | 0 | extreme_responder | extreme_responder |
| RCC-PD_028 | 210 | 1 | 0 | extreme_responder | extreme_responder |
| RCC-PD_027 | 210 | 1 | 0 | extreme_responder | extreme_responder |
| RCC-PD_026 | 171 | 0 | 0 | stable_disease | stable_disease |
| RCC-PD_025 | 333 | 0 | 0 | stable_disease | extreme_responder |
| RCC-PD_024 | 41 | 0 | 0 | extreme_progressor | extreme_progressor |
| RCC-PD_023 | 637 | 1 | 0 | extreme_responder | extreme_responder |
| RCC-PD_022 | 80 | 0 | 0 | extreme_progressor | extreme_progressor |
| RCC-PD_021 | 68 | 0 | 0 | extreme_progressor | extreme_progressor |
| RCC-PD_020 | 47 | 0 | 0 | extreme_progressor | extreme_progressor |
| RCC-PD_019 | 220 | 0 | 0 | stable_disease | extreme_responder |
| RCC-PD_018 | 672 | 0 | 0 | extreme_responder | extreme_responder |
| RCC-PD_015 | 105 | 0 | 0 | stable_disease | stable_disease |
| RCC-PD_014 | 433 | 1 | 0 | extreme_responder | extreme_responder |
| RCC-PD_013 | 399 | 1 | 0 | extreme_responder | extreme_responder |
| RCC-PD_012 | 61 | 0 | 0 | extreme_progressor | extreme_progressor |
| RCC-PD_011 | 205 | 0 | 0 | stable_disease | extreme_responder |
| RCC-PD_010 | 454 | 1 | 0 | extreme_responder | extreme_responder |
| RCC-PD_009 | 89 | 0 | 0 | extreme_progressor | extreme_progressor |
| RCC-PD_008 | 462 | 1 | 0 | extreme_responder | extreme_responder |
| RCC-PD_007 | 448 | 1 | 0 | extreme_responder | extreme_responder |
| RCC-PD_006 | 398 | 1 | 0 | extreme_responder | extreme_responder |
| RCC-PD_005 | 168 | 0 | 0 | stable_disease | stable_disease |
| RCC-PD_004 | 481 | 1 | 0 | extreme_responder | extreme_responder |
| RCC-PD_003 | 479 | 0 | 0 | extreme_responder | extreme_responder |
| RCC-PD_002 | 255 | 0 | 1 | stable_disease | extreme_responder |
| RCC-PD_001 | 572 | 1 | 0 | extreme_responder | extreme_responder |
| MC1838 | 60 | 0 | 0 | extreme_progressor | extreme_progressor |
| KE6262 | 163 | 0 | 0 | extreme_responder | stable_disease |

TABLE 4B-continued

Clinical Information for Immune-Checkpoint-Treated Patients in Validation Cohort (N = 41)

| KE5236 | 165 | 0 | 0 | stable_disease | stable_disease |
| KA4076 | 107 | 0 | 0 | stable_disease | stable_disease |
| CA8808 | 558 | 0 | 0 | extreme_responder | extreme_responder |
| BL5166 | 156 | 0 | 0 | stable_disease | stable_disease |

For sex, M represents male and F represents female.

TABLE 4C

Truncating PBRM1 alterations in validation cohort

| patient_id | Hugo_Symbol | Chromo-some | Start position | End position | Variant_Classi-fication | Reference_Allele | Tumor_Seq_Allele1 | Tumor_Seq_Allele2 | Protein_Change |
|---|---|---|---|---|---|---|---|---|---|
| CA8808 | PBRM1 | 3 | 52595873 | 52595873 | Frame_Shift_Del | G | G | - | p.Q1415fs |
| KA4076 | NA | NA | NA | NA | NA | | | | NA |
| KE5236 | PBRM1 | 3 | 52597356 | 52597359 | Frame_Shift_Del | AGGT | AGGT | - | p.LP1310fs |
| KE6262 | PBRM1 | 3 | 52643586 | 52643596 | Frame_Shift_Del | ATGAGAGTCCT | ATGAGAGTCCT | - | p.EDSH782fs |
| MC1838 | NA | NA | NA | NA | NA | | | | NA |
| PD_005 | PBRM1 | 3 | 52668656 | 52668656 | Nonsense_Mutation | G | G | T | p.Y389* |
| PD_007 | NA | NA | NA | NA | NA | | | | NA |
| PD_010 | PBRM1 | 3 | 52702580 | 52702580 | Nonsense_Mutation | A | A | C | p.Y106* |
| PD_011 | NA | NA | NA | NA | NA | | | | NA |
| PD_012 | NA | NA | NA | NA | NA | | | | NA |
| PD_013 | PBRM1 | 3 | 52597487 | 52597488 | Frame_Shift_Del | CC | CC | - | p.E1315fs |
| PD_014 | PBRM1 | 3 | 52610662 | 52610663 | Frame_Shift_Del | AG | AG | - | p.F1211fs |
| PD_015 | PBRM1 | 3 | 52637540 | 52637540 | Frame_Shift_Del | AG | AG | - | p.R941fs |
| PD_018 | NA | NA | NA | NA | NA | | | | NA |
| PD_019 | NA | NA | NA | NA | NA | | | | NA |
| PD_020 | NA | NA | NA | NA | NA | | | | NA |
| PD_021 | PBRM1 | 3 | 52713723 | 52713723 | Frame_Shift_Del | C | C | - | p.G2fs |
| PD_022 | NA | NA | NA | NA | NA | | | | NA |
| PD_023 | PBRM1 | 3 | 52663053 | 52663053 | Splice_Site | T | T | A | |
| PD_024 | NA | NA | NA | NA | NA | | | | NA |

TABLE 4C-continued

Truncating PBRM1 alterations in validation cohort

| | | | | | | | | | |
|---|---|---|---|---|---|---|---|---|---|
| PD_025 | PBRM1 | 3 | 52595829 | 52595829 | Frame_Shift_Del | C | C | - | p.G1429fs |
| PD_026 | NA | NA | NA | NA | NA | | | | NA |
| RCC.PD1.DNA.1026 | NA | NA | NA | NA | NA | | | | NA |
| RCC.PD1.DNA.1101 | PBRM1 | 3 | 52595804 | 52595804 | Frame_Shift_Del | C | C | - | p.A1438fs |
| RCC.PD1.DNA.1137 | NA | NA | NA | NA | NA | | | | NA |
| RCC.PD1.DNA.944 | NA | NA | NA | NA | NA | | | | NA |
| RCC.PD1.DNA.949 | NA | NA | NA | NA | NA | | | | NA |
| VA1008 | PBRM1 | 3 | 52643943 | 52643943 | Frame_Shift_Del | T | T | - | p.K619fs |

| patient_id | Variant_Type | i_tumor_f | t_alt_count | t_ref_count | clonal_dm | |
|---|---|---|---|---|---|---|
| CA8808 | DEL | 0.259090909 | 57 | 163 | not evaluable | strelka, indelocator |
| KA4076 | NA | NA | NA | NA | NA | NA |
| KE5236 | DEL | 0.09 | 8 | 85 | not evaluable | indelocator |
| KE6262 | DEL | 0.098214286 | 11 | 101 | 1 | strelka, indelocator |
| MC1838 | NA | NA | NA | NA | NA | NA |
| PD_005 | SNP | 0.287356 | 25 | 62 | 1 | NA |
| PD_007 | NA | NA | NA | NA | NA | NA |
| PD_010 | SNP | 0.15 | 6 | 34 | 0 | |
| PD_011 | NA | NA | NA | NA | NA | NA |
| PD_012 | NA | NA | NA | NA | NA | NA |
| PD_013 | DEL | 0.1171875 | 15 | 113 | 1 | strelka, indelocator |
| PD_014 | DEL | 0.288888889 | 26 | 64 | 1 | strelka, indelocator |
| PD_015 | DEL | 0.204545455 | 18 | 70 | 1 | strelka, indelocator |
| PD_018 | NA | NA | NA | NA | NA | NA |
| PD_019 | NA | NA | NA | NA | NA | NA |
| PD_020 | NA | NA | NA | NA | NA | NA |
| PD_021 | DEL | 0.36 | 18 | 32 | 1 | strelka, indelocator |
| PD_022 | NA | NA | NA | NA | NA | NA |
| PD_023 | SNP | 0.214286 | 9 | 33 | 1 | NA |
| PD_024 | NA | NA | NA | NA | NA | NA |
| PD_025 | DEL | 0.154411765 | 21 | 115 | 1 | strelka, |

TABLE 4C-continued

Truncating PBRM1 alterations in validation cohort

|  |  |  |  |  |  | indelocator |
|---|---|---|---|---|---|---|
| PD_026 | NA | NA | NA | NA | NA | NA |
| RCC.PD1.DNA.1026 | NA | NA | NA | NA | NA | NA |
| RCC.PD1.DNA.1101 | DEL | 0.133540373 | 43 | 279 | 1 | strelka, indelocator |
| RCC.PD1.DNA.1137 | NA | NA | NA | NA | NA | NA |
| RCC.PD1.DNA.944 | NA | NA | NA | NA | NA | NA |
| RCC.PD1.DNA.949 | NA | NA | NA | NA | NA | NA |
| VA1008 | DEL | 0.06 | 15 | 253 | not evaluable | indelocator |

TABLE 4D

Truncating PBRM1 alterations in patients receiving immune checkpoint therapy in combination with angiogenesis inhibitor or tyrosine kinase inhibitor in validation cohort (N = 9)

| patient_id | Hugo_Symbol | Chromosome | Start_position | End_position | Variant_Classification | Reference_Allele | Tumor_Seq_Allele1 |
|---|---|---|---|---|---|---|---|
| PD_001 | NA | NA | NA | NA | NA | NA | NA |
| PD_003 | NA | NA | NA | NA | NA | NA | NA |
| PD_004 | PBRM1 | 3 | 52584647 | 52584647 | Frame_Shift_Del | C | C |
| PD_006 | PBRM1 | 3 | 52643374 | 52643374 | Missense_Mutation | T | T |
| PD_008 | PBRM1 | 3 | 52643907 | 52643907 | Frame_Shift_Del | A | A |
| PD_027 | PBRM1 | 3 | 52682460 | 52682460 | Splice_Site | T | T |
| PD_028 | NA | NA | NA | NA | NA | NA | NA |
| PD_031 | PBRM1 | 3 | 52712580 | 52712580 | Nonsense_Mutation | G | G |
| PD_002 | NA | NA | NA | NA | NA | NA | NA |

| patient_id | Tumor_Seq_Allele2 | Protein_Change | i_tumor_f | t_alt_count | t_ref_count | clonal_dm | indel_caller |
|---|---|---|---|---|---|---|---|
| PD_001 | NA | NA | NA | NA | NA | NA | NA |
| PD_003 | NA | NA | NA | NA | NA | NA | NA |
| PD_004 | — | p.V1476fs | 0.55 | 6 | 5 | 1 | indelocator |
| PD_006 | G | p.Q809P | 0.378788 | 25 | 41 | 1 | NA |
| PD_008 | — | p.N631fs | 0.25 | 13 | 40 | 1 | strelka, indelocator |
| PD_027 | G |  | 0.510638 | 24 | 23 | 1 | NA |
| PD_028 | NA | NA | NA | NA | NA | NA | NA |
| PD_031 | A | p.R58* | 0.323529 | 22 | 46 | 1 | NA |
| PD_002 | NA | NA | NA | NA | NA | NA | NA |

TABLE 5A

Germline variants in PBRM1 in training and validation cohorts (N = 91)

| sample | Start_position | End_position | Reference_Allele | Tumor_Seq_Allele1 | Tumor_Seq_Allele2 | Variant_Classification |
|---|---|---|---|---|---|---|
| CA209009_1_20 | 52584587 | 52584587 | G | G | A | Missense_Mutation |
| PD_027 | 52597433 | 52597433 | C | C | T | Missense_Mutation |
| PD_029 | 52643398 | 52643398 | C | C | T | Missense_Mutation |
| PD_031 | 52668826 | 52668826 | G | G | A | Missense_Mutation |

| sample | cDNA_Change | Codon_Change | Protein_Change | t_alt_count | t_ref_count | ExAC_AF |
|---|---|---|---|---|---|---|
| CA209009_1_20 | c.4636C > T | c. (4636-4638) Ccc > Tcc | P.P1546S | 6 | 2 | 0.0004622 |
| PD_027 | c.3997G > A | c. (3997-3999) Gag > Aag | p.E1333K | 41 | 57 | 4.12E−05 |

TABLE 5A-continued

Germline variants in PBRM1 in training and validation cohorts (N = 91)

| | | | | | | | |
|---|---|---|---|---|---|---|---|
| PD_029 | c.2543G > A | c. (2542-2544) cGc > cAc | p.R848H | 38 | 54 | 8.24E−06 |
| PD_031 | c.1093C > T | c. (1093-1095) Cgc > Tgc | P.R365C | 35 | 35 | 0.0002141 |

All samples had germline variations (SNPs) on PBRMI (Chrom. 3).

TABLE 5B

Germline variants in cancer susceptibility genes in training and validation cohorts (N = 91)

| Sample | Hugo_Symbol | Chromosome | Start_position | End_position | Reference_Allele | Tumor_Seq_Allele1 | Tumor_Seq_Allele2 | Variant_Classification | Variant_Type |
|---|---|---|---|---|---|---|---|---|---|
| PD_020 | TYK2 | 19 | 10472493 | 10472493 | G | G | A | Nonsense_Mutation | SNP |
| KE62621 | FANCF | 11 | 22646654 | 22646654 | G | G | A | Nonsense_Mutation | SNP |
| CA209009_9_47 | BRIP1 | 17 | 59937229 | 59937229 | C | C | A | Nonsense_Mutation | SNP |
| CA209009_5_50 | BUB1B | 15 | 40502334 | 40502334 | C | C | T | Nonsense_Mutation | SNP |
| CA209009_11_10 | XRCC2 | 7 | 152345927 | 152345927 | G | G | A | Nonsense_Mutation | SNP |
| CA209009_5_28 | FANCM | 14 | 45636336 | 45636336 | C | C | T | Nonsense_Mutation | SNP |
| CA209009_1_43 | FANCM | 14 | 45667921 | 45667921 | C | C | T | Nonsense_Mutation | SNP |
| RCC.PD1.DNA.1101 | PDCD1LG2 | 9 | 5522576 | 5522576 | G | G | - | Frame_Shift_Del | DEL |
| CA8808 | PDCD1LG2 | 9 | 5522576 | 5522576 | G | G | - | Frame_Shift_Del | DEL |
| CA209009_5_22 | FANCL | 2 | 58386928 | 58386929 | - | - | TAAT | Frame_Shift_Ins | INS |
| PD_011 | BRCA2 | 13 | 32972626 | 32972626 | A | A | T | Nonsense_Mutation | SNP |
| PD_003 | BRCA2 | 13 | 32972626 | 32972626 | A | A | T | Nonsense_Mutation | SNP |
| PD_013 | MSR1 | 8 | 16012594 | 16012594 | G | G | A | Nonsense_Mutation | SNP |
| CA209009_9_52 | AR | X | 66766357 | 66766374 | GGCGGCGGCGGC | GGCGGCGGCGGC | - | In_Frame_Del | DEL |
| RCC.PD1.DNA.1101 | GEN1 | 2 | 17962994 | 17962998 | AAGTT | AAGTT | - | Frame_Shift_Del | DEL |
| RCC.PD1.DNA.1082 | GEN1 | 2 | 17962994 | 17962998 | AAGTT | AAGTT | - | Frame_Shift_Del | DEL |

TABLE 5B-continued

Germline variants in cancer susceptibility genes
in training and validation cohorts (N = 91)

| Sample | Gene | Chr | Start | End | Ref | Alt | | Effect | Type |
|---|---|---|---|---|---|---|---|---|---|
| RCC.PD1.DNA.1026 | GEN1 | 2 | 17962994 | 17962998 | AAGTT | AAGTT | - | Frame_Shift_Del | DEL |
| PD_027 | GEN1 | 2 | 17962994 | 17962998 | AAGTT | AAGTT | - | Frame_Shift_Del | DEL |
| PD_026 | GEN1 | 2 | 17962994 | 17962998 | AAGTT | AAGTT | - | Frame_Shift_Del | DEL |
| PD_009 | GEN1 | 2 | 17962994 | 17962998 | AAGTT | AAGTT | - | Frame_Shift_Del | DEL |
| PD_006 | GEN1 | 2 | 17962994 | 17962998 | AAGTT | AAGTT | - | Frame_Shift_Del | DEL |
| PD_004 | GEN1 | 2 | 17962994 | 17962998 | AAGTT | AAGTT | - | Frame_Shift_Del | DEL |
| PD_002 | GEN1 | 2 | 17962994 | 17962998 | AAGTT | AAGTT | - | Frame_Shift_Del | DEL |
| KA40761 | GEN1 | 2 | 17962994 | 17962998 | AAGTT | AAGTT | - | Frame_Shift_Del | DEL |
| CA209009_9_45 | GEN1 | 2 | 17962994 | 17962998 | AAGTT | AAGTT | - | Frame_Shift_Del | DEL |
| CA209009_9_119 | GEN1 | 2 | 17962994 | 17962998 | AAGTT | AAGTT | - | Frame_Shift_Del | DEL |
| CA209009_5_17 | GEN1 | 2 | 17962994 | 17962998 | AAGTT | AAGTT | - | Frame_Shift_Del | DEL |
| CA209009_5_1 | GEN1 | 2 | 17962994 | 17962998 | AAGTT | AAGTT | - | Frame_Shift_Del | DEL |
| CA209009_3_26 | GEN1 | 2 | 17962994 | 17962998 | AAGTT | AAGTT | - | Frame_Shift_Del | DEL |
| CA209009_3_114 | GEN1 | 2 | 17962994 | 17962998 | AAGTT | AAGTT | - | Frame_Shift_Del | DEL |
| CA209009_11_79 | GEN1 | 2 | 17962994 | 17962998 | AAGTT | AAGTT | - | Frame_Shift_Del | DEL |
| CA209009_11_5 | GEN1 | 2 | 17962994 | 17962998 | AAGTT | AAGTT | - | Frame_Shift_Del | DEL |
| CA209009_11_40 | GEN1 | 2 | 17962994 | 17962998 | AAGTT | AAGTT | - | Frame_Shift_Del | DEL |
| CA209009_11_12 | GEN1 | 2 | 17962994 | 17962998 | AAGTT | AAGTT | - | Frame_Shift_Del | DEL |
| PD_005 | IL16 | 15 | 81565493 | 81565494 | - | - | A | Frame_Shift_Ins | INS |

TABLE 5B-continued

Germline variants in cancer susceptibility genes
in training and validation cohorts (N = 91)

| | | | | | | | | |
|---|---|---|---|---|---|---|---|---|
| CA209009_9_52 | AR | X | 66766358 | 66766359 | GC | GC | - | Frame_Shift_Del | DEL |

| Sample | cDNA_Change | Codon_Change | Protein_Change | dbSNP_RS | t_alt_count | t_ref_count | ExAC_AF |
|---|---|---|---|---|---|---|---|
| PD_020 | c.1912C > T | c.(1912-1914) Cga > Tga | p.R638* | | 85 | 105 | 8.24E-06 |
| KE62621 | c.703C > T | c.(703-705) Caa > Taa | p.Q235* | | 101 | 75 | 8.24E-06 |
| CA209009_9_47 | c.133G > T | c.(133-135) Gag > Tag | p.E45* | | 70 | 101 | 8.24E-06 |
| CA209009_5_50 | c.2308C > T | c.(2308-2310) Cga > Tga | p.R770* | | 54 | 74 | 1.65E-05 |
| CA209009_11_10 | c.643C > T | c.(643-645) Cga > Tga | p.R215* | | 22 | 21 | 4.12E-05 |
| CA209009_5_28 | c.1894C > T | c.(1894-1896) Cga > Tga | p.R632* | | 50 | 55 | 6.59E-05 |
| CA209009_1_43 | c.5713C > T | c.(5713-5715) Cga > Tga | p.R1905* | | 41 | 38 | 0.0008813 |
| RCC.PD1.DNA.1101 | c.30delG | c.(28-30) ctgfs | p.L10fs | | 82 | 62 | 0.001985 |
| CA8808 | c.30delG | c.(28-30) ctgfs | p.L10fs | | 110 | 107 | 0.001985 |
| CA209009_5_22 | c.1114_1115insATTA | c.(1114-1116) accfs | p.T372fs | | 38 | 53 | 0.002834 |
| PD_011 | c.9976A > T | c.(9976-9978) Aaa > Taa | p.K3326* | | 49 | 48 | 0.00701 |
| PD_003 | c.9976A > T | c.(9976-9978) Aaa > Taa | p.K3326* | | 61 | 42 | 0.00701 |
| PD_013 | c.931C > T | c.(931-933) Cga > Tga | p.R311* | | 45 | 50 | 0.007348 |
| CA209009_9_52 | | | | | 104 | 233 | 0.01489 |
| RCC.PD1.DNA.1101 | c.2515_2519delAAGTT | c.(2515-2520) aagttgfs | p.KL839fs | rs149936944 | 27 | 31 | 0.088 |
| RCC.PD1.DNA.1082 | c.2515_2519delAAGTT | c.(2515-2520) aagttgfs | p.KL839fs | rs149936944 | 22 | 34 | 0.088 |
| RCC.PD1.DNA.1026 | c.2515_2519delAAGTT | c.(2515-2520) aagttgfs | p.KL839fs | rs149936944 | 59 | 0 | 0.088 |
| PD_027 | c.2515_2519delAAGTT | c.(2515-2520) aagttgfs | p.KL839fs | rs149936944 | 32 | 32 | 0.088 |
| PD_026 | c.2515_2519delAAGTT | c.(2515-2520) aagttgfs | p.KL839fs | rs149936944 | 41 | 36 | 0.088 |
| PD_009 | c.2515_2519delAAGTT | c.(2515-2520) aagttgfs | p.KL839fs | rs149936944 | 30 | 27 | 0.088 |
| PD_006 | c.2515_2519delAAGTT | c.(2515-2520) aagttgfs | p.KL839fs | rs149936944 | 22 | 36 | 0.088 |
| PD_004 | c.2515_2519delAAGTT | c.(2515-2520) aagttgfs | p.KL839fs | rs149936944 | 38 | 35 | 0.088 |
| PD_002 | c.2515_2519delAAGTT | c.(2515-2520) aagttgfs | p.KL839fs | rs149936944 | 50 | 0 | 0.088 |

TABLE 5B-continued

Germline variants in cancer susceptibility genes
in training and validation cohorts (N = 91)

| | | | | | | | |
|---|---|---|---|---|---|---|---|
| KA40761 | c.2515_2519delAAGTT | c.(2515-2520) aagttgfs | p.KL839fs | rs149936944 | 57 | 53 | 0.088 |
| CA209009_9_45 | c.2515_2519delAAGTT | c.(2515-2520) aagttgfs | p.KL839fs | rs149936944 | 47 | 0 | 0.088 |
| CA209009_9_119 | c.2515_2519delAAGTT | c.(2515-2520) aagttgfs | p.KL839fs | rs149936944 | 25 | 27 | 0.088 |
| CA209009_5_17 | c.2515_2519delAAGTT | c.(2515-2520) aagttgfs | p.KL839fs | rs149936944 | 33 | 0 | 0.088 |
| CA209009_5_1 | c.2515_2519delAAGTT | c.(2515-2520) aagttgfs | p.KL839fs | rs149936944 | 24 | 20 | 0.088 |
| CA209009_3_26 | c.2515_2519delAAGTT | c.(2515-2520) aagttgfs | p.KL839fs | rs149936944 | 27 | 29 | 0.088 |
| CA209009_3_114 | c.2515_2519delAAGTT | c.(2515-2520) aagttgfs | p.KL839fs | rs149936944 | 26 | 25 | 0.088 |
| CA209009_11_79 | c.2515_2519delAAGTT | c.(2515-2520) aagttgfs | p.KL839fs | rs149936944 | 21 | 20 | 0.088 |
| CA209009_11_5 | c.2515_2519delAAGTT | c.(2515-2520) aagttgfs | p.KL839fs | rs149936944 | 24 | 34 | 0.088 |
| CA209009_11_40 | c.2515_2519delAAGTT | c.(2515-2520) aagttgfs | p.KL839fs | rs149936944 | 23 | 20 | 0.088 |
| CA209009_11_12 | c.2515_2519delAAGTT | c.(2515-2520) aagttgfs | p.KL839fs | rs149936944 | 32 | 38 | 0.088 |
| PD_005 | c.738_739insA | c.(739-741) aaafs | p.K247fs | | 37 | 43 | |
| CA209009_9_52 | c.1370_1371delGC | c.(1369-1371) ggcfs | p.G473fs | | 104 | 233 | 0.01489 |

Figure 9:
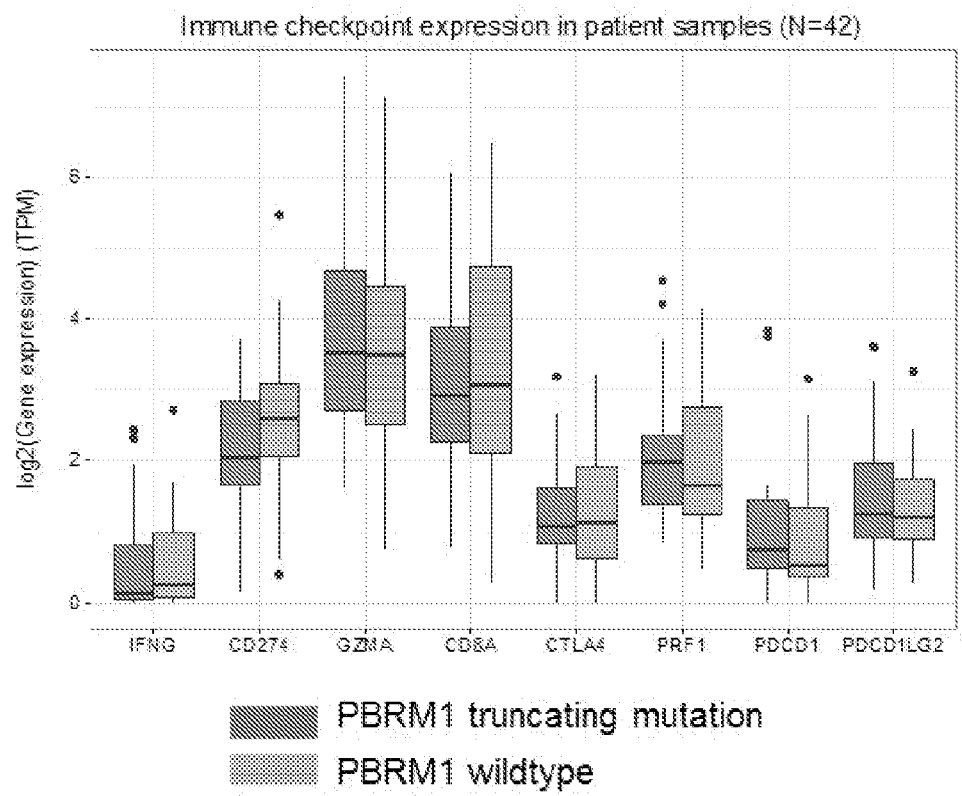
FIG. 9 includes 2 panels, identified as panels A and B, which show that expression of the immune checkpoints PD-L1 and PD-1 as well as CD8A and IFNG were significantly lower in PBRM1-mutant compared to PBRM1-wild-type ccRCC (TCGA). No significant differences were noted in levels of expression of immune checkpoints (CTLA4, PDCD1: encoding PD-1, CD274: encoding PD-L1, PDCD1LG2: encoding the PD-1 ligand PD-L2). Markers of cytolytic activity (GZMA, PRF1), interferon gamma (IFNγ), or CD8 T cells (CD8A) were noted between tumors with truncating mutations in PBRM1 (blue) versus those without (yellow) in pre-treatment patient samples (Panel A). However, analysis in a larger set of TCGA clear-cell RCC reveals significantly lower expression of CD8A (p=0.0093), IFNG (p=0.00105), PD-L2 (p=0.0173), and PD-1 (p=0.0165) in PBRM1-mutant tumors.
Figure 9:
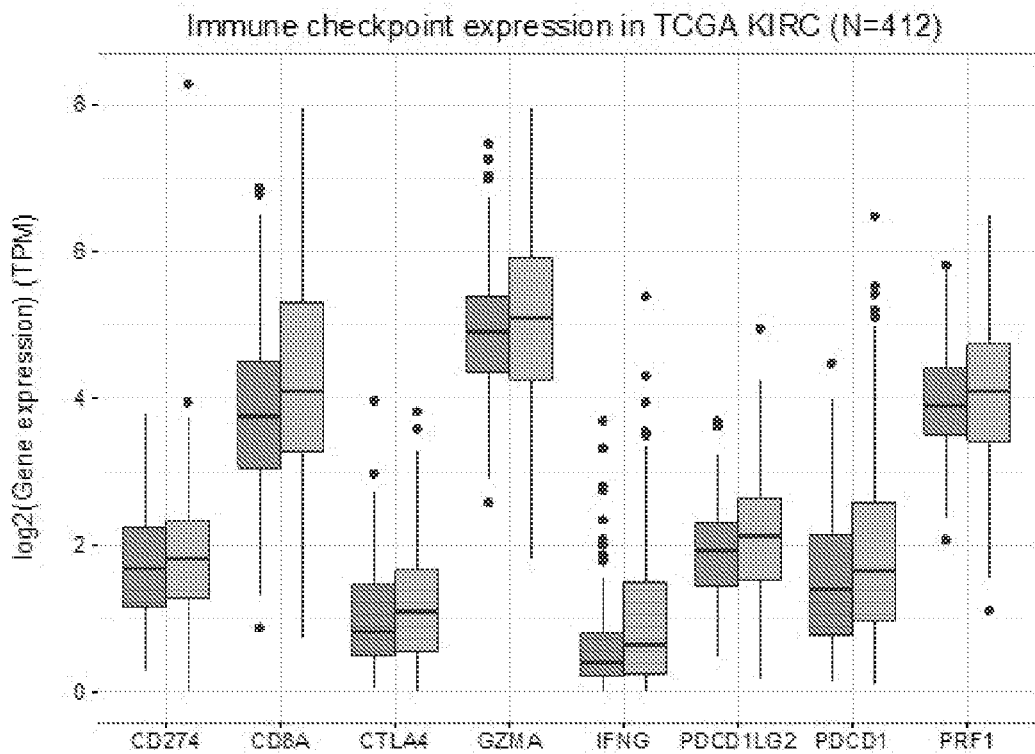

To further characterize the effect of PBRM1 truncating alterations on the tumor-immune microenvironment, publicly available genomic data from the Cancer Genome Atlas (TCGA) clear-cell RCC (KIRC) cohort with matched whole exome and whole transcriptome sequencing (Cancer Genome Atlas Research, 2013) were analyzed. A study of immune checkpoint expression in patient samples as well as in TCGA KIRC showed that the expression profiles of multiple cytokines were not significantly changed by PBRM1 truncation (FIG. 9).

TABLE 5C

| cell_type | size | enrichment_score | normalized_enrichment_score | nominal_pvalue | fdr_qvalue |
|---|---|---|---|---|---|
| MACROPHAGES | 33 | 0.70394427 | 1.9490428 | 0.0056926 | 0.006311779 |
| TH1 CELLS | 27 | 0.5918025 | 1.8246216 | 0.007067138 | 0.034245696 |
| TH2 CELLS | 26 | 0.5829762 | 1.7125602 | 0.021484375 | 0.06695327 |
| T CELLS | 16 | 0.7640042 | 1.6438433 | 0.06903353 | 0.08587655 |
| CYTOTOXIC CELLS | 16 | 0.65174156 | 1.4963382 | 0.120229006 | 0.15507422 |
| TFH CELLS | 31 | 0.43897825 | 1.4072554 | 0.08946322 | 0.2030306 |
| T HELPER CELLS | 22 | 0.4563994 | 1.2234894 | 0.26215646 | 0.38399327 |
| IDC | 31 | 0.37844718 | 1.1912937 | 0.2651515 | 0.37435225 |
| CD8 T CELLS | 36 | 0.34407476 | 1.1225885 | 0.33661416 | 0.4134009 |
| NEUTROPHILS | 27 | 0.3371452 | 0.93078756 | 0.5449331 | 0.60742164 |
| TCM CELLS | 35 | 0.28329915 | 0.8316694 | 0.65294117 | 0.68357456 |
| MAST CELLS | 28 | 0.20472227 | 0.60319847 | 0.9122203 | 0.8787396 |
| B CELLS | 28 | −0.35 | −0.93 | 0.517 | 0.989 |
| EOSINOPHILS | 30 | −0.23 | −0.78 | 0.811 | 0.686 |

| cell_type | fwer_pvalue | rank_at_max | leading_edge | enriched_set |
|---|---|---|---|---|
| MACROPHAGES | 0.006 | 2520 | tags = 58%, list = 12%, signal = 66% | wild type |

TABLE 5C-continued

| | | | | |
|---|---|---|---|---|
| TH1 CELLS | 0.049 | 4931 | tags = 59%, list = 24%, signal = 78% | wild type |
| TH2 CELLS | 0.122 | 2914 | tags = 42%, list = 14%, signal = 49% | wild type |
| T CELLS | 0.2 | 1192 | tags = 69%, list = 6%, signal = 73% | wild type |
| CYTOTOXIC CELLS | 0.385 | 3495 | tags = 63%, list = 17%, signal = 75% | wild type |
| TFH CELLS | 0.522 | 2940 | tags = 26%, list = 14%, signal = 30% | wild type |
| T HELPER CELLS | 0.756 | 3268 | tags = 27%, list = 16%, signal = 32% | wild type |
| IDC | 0.783 | 4467 | tags = 35%, list = 22%, signal = 45% | wild type |
| CD8 T CELLS | 0.845 | 1014 | tags = 17%, list = 5%, signal = 18% | wild type |
| NEUTROPHILS | 0.934 | 3421 | tags = 41%, list = 17%, signal = 49% | wild type |
| TCM CELLS | 0.964 | 2289 | tags = 17%, list = 11%, signal = 19% | wild type |
| MAST CELLS | 0.988 | 6169 | tags = 36%, list = 30%, signal = 51% | wild type |
| B CELLS | 0.928 | 4315 | tags = 43%, list = 21%, signal = 54% | mutant |
| EOSINOPHILS | 0.971 | 1013 | tags = 13%, list = 5%, singal = 14% | mutant |

Figure 10:
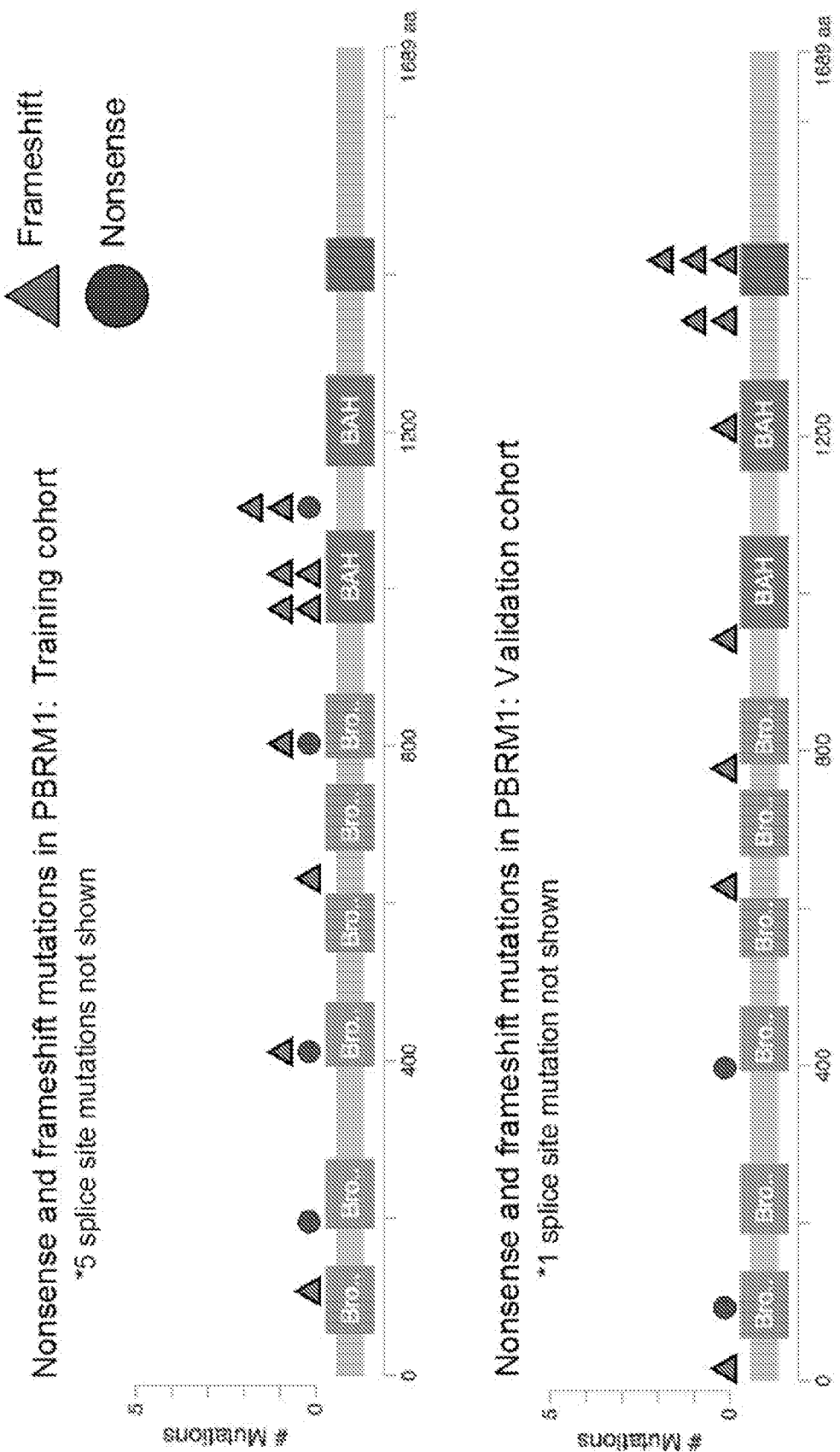
FIG. 10 shows a lollipop plot summarizing PBRM1 mutations described in the Examples.

This study found that patients with truncating alterations in PBRM1 are more likely to experience extreme response to immune checkpoint monotherapy than patients who are PBRM1-wildtype (FIG. 10). Meanwhile, nonsynonymous mutational burden, neoantigen burden, and PD-L1 staining did not distinguish clinical benefit groups, in contrast to findings in melanoma and non-small cell lung cancer (Rizvi et al. (2015) Science 348:124-128; Snyder et al. (2014) N. Engl. J. Med. 371:2189-2199; Van Allen et al. (2015) Science 350:207-211).

PBRM1 is a component of the BAF (Brg/Brahma-associated factors) or mammalian SWI/SNF complex, which is involved in ATP-dependent chromatin remodeling, and is one of the most commonly mutated genes in ccRCC. Nonsynonymous mutations in PBRM1 are seen in up to 41% of patients with ccRCC (Varela et al. (2011) Nature 469:539-542), with a majority of mutations being truncating alterations. Chromosome 3p deletions over the PBRM1 locus are also highly prevalent in ccRCC (>91% of samples), as are alterations in other components of the SWI/SNF complex, including BAP1 and SETD2, suggesting that epigenetic regulation and oncogenic metabolism are major components of ccRCC (Cancer Genome Atlas Research (2013), supra). The tumor suppressor role of PBRM1 loss in ccRCC is most often associated with metabolism, hypoxia response, and cell adhesion (Chowdhury et al. (2016), supra) but it may have interesting effects on the tumor-immune microenvironment as well.

Additionally, restoration of PBRM1 expression in PBRM1-deficient tumor cell lines leads to increased expression of genes in the interleukin-6-mediated signaling pathway (GO:0070102) (Chowdhury et al. (2016), supra, and was observed lower levels of IL-6 in the baseline serum of patients with PBRM1-truncated tumors in this study. Increased production of IL-6 mediates STAT3 activation, which has been identified as a potential orchestrator of an immunosuppressive cytokine network (Yu et al. (2009) Nat. Rev. Cancer 9:798-809), and promotes tumorigenesis in EGFR-mutant lung carcinomas (Gao et al. (2007) J Clin. Invest. 117:3846-3856). Activation of the Jak2/Stat3 pathway has been further associated with an immunosuppressive tumor microenvironment in Pten-null mice that develop prostatic neoplasia, and blockade of this pathway can restore the anti-tumor immune response (Toso et al. (2014) Cell Rep. 9:75-89). This finding is further supported by decreased macrophage and T cell infiltration in PBRM1-truncated tumors, along with decreased CRP and increased IP-10 immediately before treatment.

Taken together, these results indicate that PBRM1 status may have wide-ranging effects on tumor-immune microenvironment interactions. Clinically, alterations in PBRM1 have previously been linked with prognosis and response to other cancer therapies. A possibility cannot be fully excluded that PBRM1 has prognostic rather than predictive value. One study in 145 patients found that PBRM1-mutant tumors were associated with favorable prognosis, especially relative to BAP1-mutant tumors (Kapur et al. (2013), supra), while another study in 609 patients found no effect of PBRM1 mutations on cancer-specific survival (Hakimi et al. (2013) Clin. Cancer Res. 19:3259-3267). These studies did not distinguish between truncating and non-truncating (missense mutations, in-frame indel) variants or assess chromosome 3p.21 deletions, which could impact the ultimate presence of PBRM1 protein. Immunohistochemical staining for PBRM1 in 657 ccRCC cases found worse cancer-specific survival and progression-free survival in poorly staining samples (Nam et al. (2015) Urol. Oncol. 33:340.e9-e16), and a similar study in 204 ccRCC cases also found that loss of PBRM1 protein expression is associated with poor differentiation, late tumor stage, and shorter duration of patient overall survival (Pawlowski et al. (2013) Int. J. Cancer 132:E11-E17).

Previous studies have also investigated whether pretreatment molecular characteristics of ccRCC are correlated to response to therapy. In a cohort of 258 patients with RCC, those with PBRM1-mutant cancers were found to have longer PFS with first-line everolimus compared to those who were PBRM1-wildtype, though this finding did not hold after multiple hypothesis testing (Hsieh et al. (2016) Eur Urol. pii: S0302-2838(16)30701-1). No effect of PBRM1 status was seen with first-line sunitinib followed by everolimus in the same trial. Another study in 27 patients treated with vascular endothelial growth factor (VEGF) targeted therapies (sunitinib and pazopanib) found that PBRM1 alterations were significantly enriched in responders (Fay et al. (2016) *J. Natl. Compr. Canc. Netw.* 14:820-824), while a third study in cohort of 79 patients receiving mTOR inhibitors (everolimus and temsirolimus) found no association between PBRM1 status and response (Kwiatkowski et al. (2016) *Clin. Cancer Res.* 22:2445-2452). Another study including 117 pre-treatment tumors found no association between somatic mutations in PBRM1 and response to sunitinib (Beuselinck et al. (2015) *Clin. Cancer Res.* 21:1329-1339). Thus, the observed association between PBRM1 mutations and increased likelihood of clinical benefit from immune checkpoint therapy is a novel finding not readily explained by general decreased tumor aggressiveness or increased responsiveness to therapy in PBRM1-mutant tumors. Additionally, all extreme responders in this study were required to have objective decrease in tumor burden following immune checkpoint therapy, making it unlikely that the prognostic benefit of PBRM1 mutation alone, if real, could explain the results of this study.

This finding of increased responsiveness to immune checkpoint therapy in patients with metastatic ccRCC harboring truncating mutations in PBRM1 in independent training and validation cohorts totaling 61 patients argues for further validation in larger immunotherapy-treated RCC cohorts and for concerted effort towards characterizing the impact of SWI/SNF complex alterations on tumor-immune activity. Integration of whole exome and whole transcriptome sequencing from patient tumors identified potential downstream effects of PBRM1 alterations on immune cell infiltration. These results are believed to have important implications for exploration of PBRM1 and immune mediation, as well as guiding patient selection for immune checkpoint therapy in renal cell carcinoma, where up to 40% of patients have PBRM1-mutant disease. This finding may is also believed tobe more generally relevant in cancer immunotherapy, as more than 20% of human cancers contain a mutation in at least one subunit of the SWI/SNF or BAF complexes (Kadoch et al. (2013) *Nat. Genet.* 45:592-601; Shain and Pollack (2013) *PLoS One* 8:e55119). These results can be further applied to untreated RCC cohorts (Sato et al. (2013), supra).

Example 3: Further Confirmation of Data and Results Shown in Examples 1-2

The following provide further confirmation of the data and results provided above in Examples 1-2 by inter alia further demonstrating the data and results in additional cohorts. Generally, the following materials and methods were used to determine the further confirmation:

a. Clinical Cohort Consolidation

The discovery cohort was gathered from patients enrolled in p-009 (NCT01358721), a study of nivolumab (BMS-936558) monotherapy in metastatic renal cell carcinoma (Choueiri et al. (2016) *Clin. Cancer Res.* 22:5461-5471). Progression-free survival and overall survival were measured from Cycle 1 Day 1 (time zero) of nivolumab administration. The validation cohort was gathered from patients at the Dana-Farber Cancer Institute, Memorial Sloan Kettering Cancer Institute, and Johns Hopkins University who received anti-PD-(L)1 therapy as monotherapy or in combination with other immune checkpoint therapies and had banked adequate pre-treatment tumor tissue for molecular characterization. In addition, patients with ccRCC also treated with anti-PD-(L)1 based therapy from the Mayo Clinic with targeted panel sequencing that included the PBRM1 gene region were included in the validation cohort.

All patients were consented on an Institutional Review Board protocol that allows research molecular characterization of tumor and germline samples. Each IRB at the respective institution from the validation cohort obtained approval for 1) collection and analysis of samples, and 2) sending samples to the Dana-Farber Center for genomic analysis.

b. DNA and RNA Extraction and Sequencing

All samples from the discovery cohort and those from the Dana-Farber Cancer Institute and Memorial Sloan Kettering Cancer Institute were processed for DNA (and if possible, RNA) extraction and whole exome sequencing through standard workflows (Van Allen et al. (2014) *Nat. Med.* 20:682-688). After fixation and mounting, 5-10 10 µm slices from either Qiagen RNAlater (discovery cohort) or formalin-fixed, paraffin-embedded (FFPE, validation cohort) tumor blocks were obtained, and tumor-enriched tissue was macrodissected. Paraffin was removed from FFPE sections and cores using CitriSolv™ (Fisher Scientific), followed by ethanol washes and tissue lysis overnight at 56° C. Samples were then incubated at 90° C. to remove DNA crosslinks, and DNA- and when possible, RNA-extraction was performed using Qiagen AllPrep DNA/RNA Mini Kit (#51306). Germline DNA was obtained from adjacent PBMCs. Whole exome and whole transcriptome sequencing of tumor and germline samples were performed as previously described in Van Allen et al. (2015) *Science* 350:207-211 and Van Allen et al. (2014) *Nat. Med.* 20:682-688. All samples in the discovery cohort were sequenced using the Illumina exome, while a portion of the samples in the validation cohort were sequenced using the Agilent exome (Table 6E). The Illumina exome uses Illumina's in-solution DNA probe based hybrid selection method to target approximately 37.7 Mb of mainly exonic territory, using similar principles as the Broad Institute-Agilent Technologies developed in-solution RNA probe based hybrid selection method (Agilent SureSelect All Exon V2) (Gnirke et al. (2009) *Nat. Biotechnol.* 27:182-189; Fisher et al. (2011) *Genome Biol.* 12:R1) to generate Illumina exome sequencing libraries. Pooled libraries were normalized to 2 nM and denatured using 0.2 N NaOH prior to sequencing. Flowcell cluster amplification and sequencing were performed according to the manufacturer's protocols using either the HiSeq 2000 v3 or HiSeq 2500. Each run was a 76 bp paired-end with a dual eight-base index barcode read. Data were analyzed using the Broad Picard Pipeline, which includes de-multiplexing and data aggregation. Exome sequence data processing was performed using established analytical pipelines at the Broad Institute. A BAM file was produced using the Picard pipeline (available on the World Wide Web at picard.sourceforge.net/), which aligns the tumor and normal sequences to the hg19 human genome build using Illumina sequencing reads. The BAM was uploaded into the Firehose pipeline (available on the World Wide Web at broadinstitute.org/cancer/cga/Firehose), which manages input and output files to be executed by GenePattern (Reich et al. (2006) *Nat. Genet.* 38:500-501). Samples with mean target coverage less than 25× in the tumor and less than 15× in matched normal were excluded. Quality control modules within Firehose were applied to all sequencing data for comparison of the origin of tumor and normal genotypes and to assess fingerprinting concordance. Cross-contamination of samples was estimated using ContEst (Cibulskis et al. (2011) *Bioinform.* 27:2601-2602). Samples with ContEst estimates exceeding 5% were excluded from analysis. Clinical characteristics from samples that were excluded due to poor quality did not differ significantly from those that were included in the final analysis.

c. Whole Exome and Whole Transcriptome Analyses

MuTect was applied to identify somatic single-nucleotide variants (Cibulskis et al. (2013) *Nat. Biotechnol.* 31:213-219). Strelka was used to identify somatic insertions and deletions (Saunders et al. (2012) *Bioinform.* 28:1811-1817) across the whole exome. Indelocator, which detects small insertions and deletions after local realignment of tumor and normal sequences, was additionally applied to provide further sensitivity to detect indels in PBRM1 (Cancer Genome Atlas Research (2011) *Nature* 474:609-615). The union of indels called by Strelka and Indelocator was used for final analysis. Artifacts introduced by DNA oxidation during sequencing were computationally removed using a filter-based method (Costello et al. (2013) *Nuc. Acids Res.* 41:e67). All somatic mutations detected by whole-exome sequencing were analyzed for potential false positive calls by performing a comparison to mutation calls from a panel of 2,500 germline DNA samples (Stachler et al. (2015) *Nat. Genet.* 47:1047-1055). Mutations found in germline samples were removed from analysis. Annotation of identified variants was done using Oncotator (available on the World Wide Web at broadinstitute.org/cancer/cga/oncotator). All non-synonymous alterations in PBRM1 were manually reviewed in Integrated Genomics Viewer (IGV_2.3.57) for sequencing quality (Thorvaldsdottir et al. (2013) *Brief Bioinform.* 14:178-192). PBRM1 LOF events were defined as truncating mutations: nonsense mutations, frameshift insertions and deletions, and splice-site mutations. In-frame insertions and deletions, missense mutations, and other alterations presumed not to be truncating were considered separately. Copy ratios were calculated for each captured target by dividing the tumor coverage by the median coverage obtained in a set of reference normal samples. The resulting copy ratios were segmented using the circular binary segmentation algorithm (Olshen et al. (2004) *Biostatistics* 5:557-572). Allelic copy number alterations were called while taking into account sample-specific overall chromosomal aberrations (focality) (Brastianos et al. (2015) *Cancer Discov.* 5:1164-1177). Inference of mutational clonality, tumor purity, and tumor ploidy was accomplished with ABSOLUTE (Carter et al. (2012) *Nat. Biotechnol.* 30:413-421). Mutations were considered clonal if the expected cancer cell fraction (CCF) of the mutation as estimated by ABSOLUTE was 1, or if the probability of the mutation being clonal was greater than that of the mutation being subclonal. For the discovery cohort, samples were required to have estimated tumor purity greater than 10% to be included in the final analysis. For the validation cohort, samples included in the analysis were required to have either (a) estimated tumor purity greater than 10%, or (b) estimated tumor purity below 10% but sufficient sequencing coverage over the PBRM1 region that there would still be adequate power to detect a clonal PBRM1 alteration if it were to exist. As a final quality control metric to ensure adequate sequencing coverage and tumor purity to detect relevant oncogenic events, all samples had to have at least one nonsynonymous mutation in at least one high confidence or candidate cancer driver gene to be included in the final analysis (Tamborero et al. (2013) *Sci. Rep.* 3:2650). Mutation calls for patients from patients from Johns Hopkins University included in the validation cohort were processed through in-house standard analytic pipelines and supplied by Mark Ball, Md. (Anagnostou et al. (2017) *Cancer Disc.* 7:264-276).

d. Targeted Sequencing Analyses

Fourteen samples with targeted panel genetic sequencing were used in the validation cohort. Panel sequencing data was acquired using standard pipelines from commercial molecular profiling laboratories: FoundationOne® (Foundation Medicine, Palo Alto, Calif.) and Canis Molecular Intelligence (Canis Life Sciences, Phoenix, Ariz.) (Table 6E). A subset of these samples had PBRM1 immunohistochemical staining (IHC, Table 6G. All samples with canonical LOF mutations (frameshift insertions, frameshift deletions, splice site mutations) and available PBRM1 IHC had negative staining, indicating true PBRM1 LOF. One patient (MCA6) with missense mutation N258S, also had negative IHC staining, and was labeled a PBRM1-LOF mutant accordingly.

e. Cell Line Analysis

Whole transcriptome sequencing from PBAF-deficient and PBAF-proficient A704 cell lines was produced as previously described in Gao et al. (2017) *Proc. Natl. Acad. Sci. USA* 114:1027-1032 and is available on Gene Expression Omnibus (GEO) under Accession PRJNA371283. Differential gene expression analysis was conducted using the Bioconductor software package Empirical Analysis of Digital Gene Expression Data in R (edgeR). This package is optimized for differential expression analysis of RNA-seq data with biological replication. Raw read count data from RNA-seq analysis of two PBRM1-null cell lines, two BRG1-null cell lines, and two PBRM1- and BRG1-wild type cell lines were analyzed for differential expression between PBRM1-null (A704) and wildtype (A704BAF180 wt), and BRG1-null (A704BAF180 wt, BRG1-/-) and wild type cell lines (A704BAF180 wt). In order to assess PBAF complex functionality as a whole, the top 100 positively differentially expressed genes by quasi-likelihood F test in mutants vs. wild type from both PBRM1 and BRG1 analyses were intersected to get a final list of 48 genes significantly up-regulated in PBAF null cell lines. The same analysis was performed for the top 100 negatively differentially expressed genes, and the resulting list was 43 genes significantly up-regulated in PBAF wild type cell lines. GSEA (available on the World Wide Web at software.broadinstitute.org/gsea/index.jsp) was performed to test whether any biologically-relevant gene sets were differentially expressed between PBAF-null vs. wildtype and BRG1 null vs. wildtype cell lines. In accordance with previously proposed methods in Liberzon et al. (2015) *Cell Sys.* 1:417-425, the Hallmark gene sets (N=50) were used for an initial GSEA run, and subsequent GSEA analyses were conducted using the Founders gene sets for any Hallmark gene set significantly enriched in both PBRM1 and BRG1 null cell lines (N=5). A false discovery rate (FDR) q-value of 0.25 was used as a significance threshold for all analyses. This process resulted in a list of gene sets significantly enriched in PBAF-null vs. wildtype cell lines. GSEA analyses were repeated for RNA-Seq from untreated patient tumors from the TCGA. Gene Ontology (GO, available on the World Wide Web at geneontology.org/) term analysis was performed to identify pathways or functional associations of the core enriched genes in A704BAF180-/- versus A704BAF180 wt from the Kegg Cytokine-Cytokine Receptor Interaction gene set. Core enriched genes for A704BAF180-/- (N=53) were defined as those with a GSEA enrichment score greater than the prior gene, starting from the top of the GSEA ranked gene list (i.e., all genes until the peak of the GSEA enrichment plot). Core enriched genes for A704BAF180 wt (N=18) were those whose enrichment score was less than the prior gene, starting from the bottom of the GSEA ranked list (i.e., all genes after the trough of the GSEA enrichment plot).

f. Transcriptome Analysis

Whole transcriptome sequencing was derived from three sources: patient samples from the discovery and validation cohorts, the TCGA clear cell renal cell carcinoma (KIRC) cohort, the TCGA cutaneous melanoma (SKCM) cohort, and an independent previously published cohort of untreated clear cell renal cell carcinoma tumors (Sato) (Sato et al. (2013) Nat. Genet. 45:860-867). For the patient samples, whole transcriptome sequencing from FFPE tissues were aligned using STAR (Dobin et al. (2012) Bioinform. 29:15-21) and then quantified with RSEM (Li et al. (2011) BMC Bioinform. 12:323) to yield gene-level expression in transcripts per million (TPM). Because patient samples came from two independent cohorts, ComBat (Li et al. (2011) BMC Bioinform. 12:323) was applied prior to analyzing patient-derived RNA sequencing. Principal components analysis (PCA) was completed before and after implementing ComBat to ensure that batch effects were eliminated (Johnson et al. (2007) Biostat. 8:118-127). The final patient cohort for RNA-seq analysis included N=18 PBRM1-LOF samples and N=14 PBRM1-intact samples. For the TCGA cohort, whole exome mutation annotation files (MAFs) and whole transcriptome gene expression data were downloaded from the Firebrowse KIRC TCGA data release (2016_01_28). KIRC tumors were divided into those with truncating mutations in PBRM1 (nonsense, splice-site, frameshift) (N=102), those with intact PBRM1 function (no mutation or silent mutation) (N=288), and those with other mutations in PBRM1 (missense or inframe indel) (N=25). RNA-seq from germline samples was excluded. For the Sato cohort, whole exome mutation annotation files and gene expression data from the final analysis in the published paper were used (Sato et al. (2013) Nat. Genet. 45:860-867). The MAFs were downloaded from the online supplemental materials from the published paper and gene expression data were kindly supplied by personal communication with the authors.

g. Statistical Analyses

All comparisons of continuous variables between groups (clinical benefit vs. no clinical benefit or PBRM1-LOF vs. PBRM1-intact) were done with the non-parametric Wilcoxon rank-sum test (wilcox.test( ) R function, two-sided, from stats package) or Student's t test (t. test( ) R function, two-sided, from stats package), depending on whether distributions were expected to be approximately normal. Comparisons of the proportion of patients with truncating alterations in PBRM1 by clinical response group were done with Fisher's exact tests when comparing CB and NCB (fisher.test( ) R function, two-sided, from stats package) and Fisher-Freeman-Halton Exact tests when comparing CB, IB, and NCB fisher.test( ) R function with 2×3 contingency table, two-sided, from stats package). Kaplan-Meier analyses were done using the R packages survival and survminer. Significance testing for differences in progression-free survival or overall survival were calculated using the log-rank test. All comparisons were two-sided with an alpha level of 0.05. MutSig2CV was used to identify genes of interest among all those mutated in the discovery cohort. Subsequently, the Benjamini-Hochberg method for controlling false discovery rate (FDR) was applied to control for multiple hypothesis testing among the seven genes of interest with a threshold of q<0.1. All statistical analyses and figures were generated in R version 3.3.2.

Immune checkpoint inhibitors, such as nivolumab, extend the survival of a subset of patients with metastatic ccRCC (Motzer et al. (2015) N. Engl. J. Med. 373:1803-1813). Whether specific genomic features of ccRCC are associated with clinical benefit is unclear. In contrast to other human tumor types that respond to immunotherapy, such as non-small cell lung cancer (NSCLC), melanoma, and microsatellite-unstable colorectal adenocarcinoma, ccRCC harbors a low burden of somatic mutations (Snyder et al. (2014) N. Engl. J. Med. 371:2189-2199; Rizvi et al. (2015) Science 348:124-128; Le et al. (2015) N. Engl. J. Med. 372:2509-2520; Van Allen et al. (2015) Science 350:207-211). Melanoma and NSCLC typically harbor 10 to 400 mutations per megabase (Mb) and these genetic variants can generate tumor-specific antigens (neoantigens) that stimulate a strong anti-tumor immune response (Motzer et al. (2015) N. Engl. J. Med. 373:1803-1813; Snyder et al. (2014)N. Engl. J. Med. 371:2189-2199; Rizvi et al. (2015) Science 348:124-128; Le et al. (2015) N. Engl. J. Med. 372:2509-2520). In contrast, ccRCC harbors an average of only 1.1 mutations/Mb (Cancer Genome Atlas Research (2013) Nature 499:43-49; de Velasco et al. (2016) Cancer Immunol. Res. 4:820-822), yet it ranks highly among tumor types in terms of immune cytolytic activity (Rooney et al. (2015) Cell 160:48-618), immune infiltration score, and T cell infiltration score in the tumor microenvironment (Senbabaoglu et al. (2016) Genome Biol. 17:231).

Figure 13:
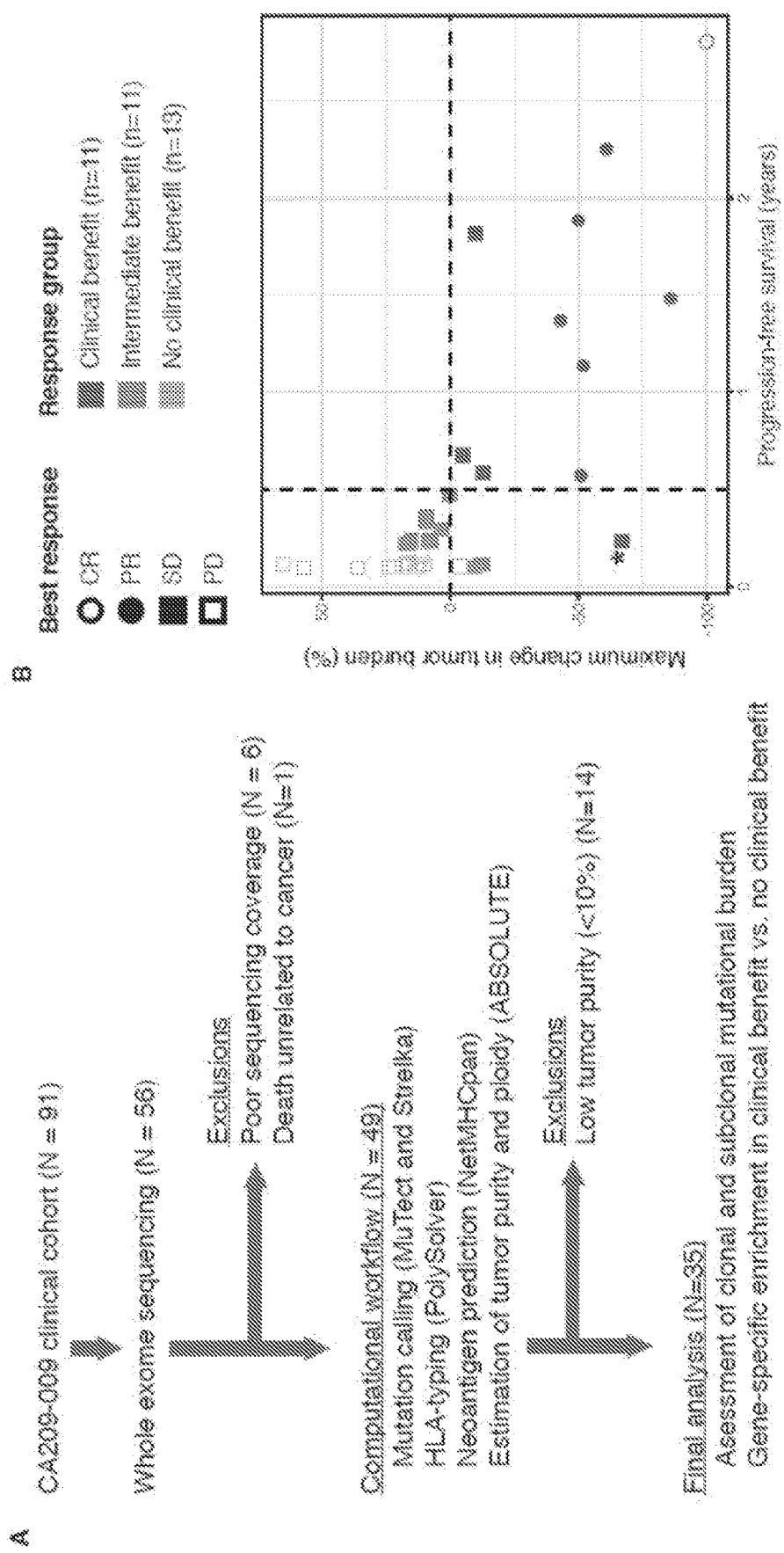
FIG. 13 includes 4 panels, identified as panels A, B, C, and D, which describe cohort consolidation and clinical characteristics of the discovery cohort. Panel A shows sample inclusion/exclusion criteria and computational workflow. Panel B shows clinical stratification by degree of objective change in tumor burden (y-axis) and duration of progression-free survival (x-axis). One patient (RCC_99) is not shown due to lack of tumor response data. *Patient RCC_50 was classified as clinical benefit despite PFS<6 months because there was continued tumor shrinkage after an initial period of minor tumor progression (see FIG. 15). Panel C shows the mutation burden in the discovery cohort by response group. Panel D shows the ratio of subclonal to clonal mutations, as estimated by ABSOLUTE, by response group. ns=not significant. Abbreviations: CR, complete response; PR, partial response; SD, stable disease; PD, progressive disease.
Figure 13:
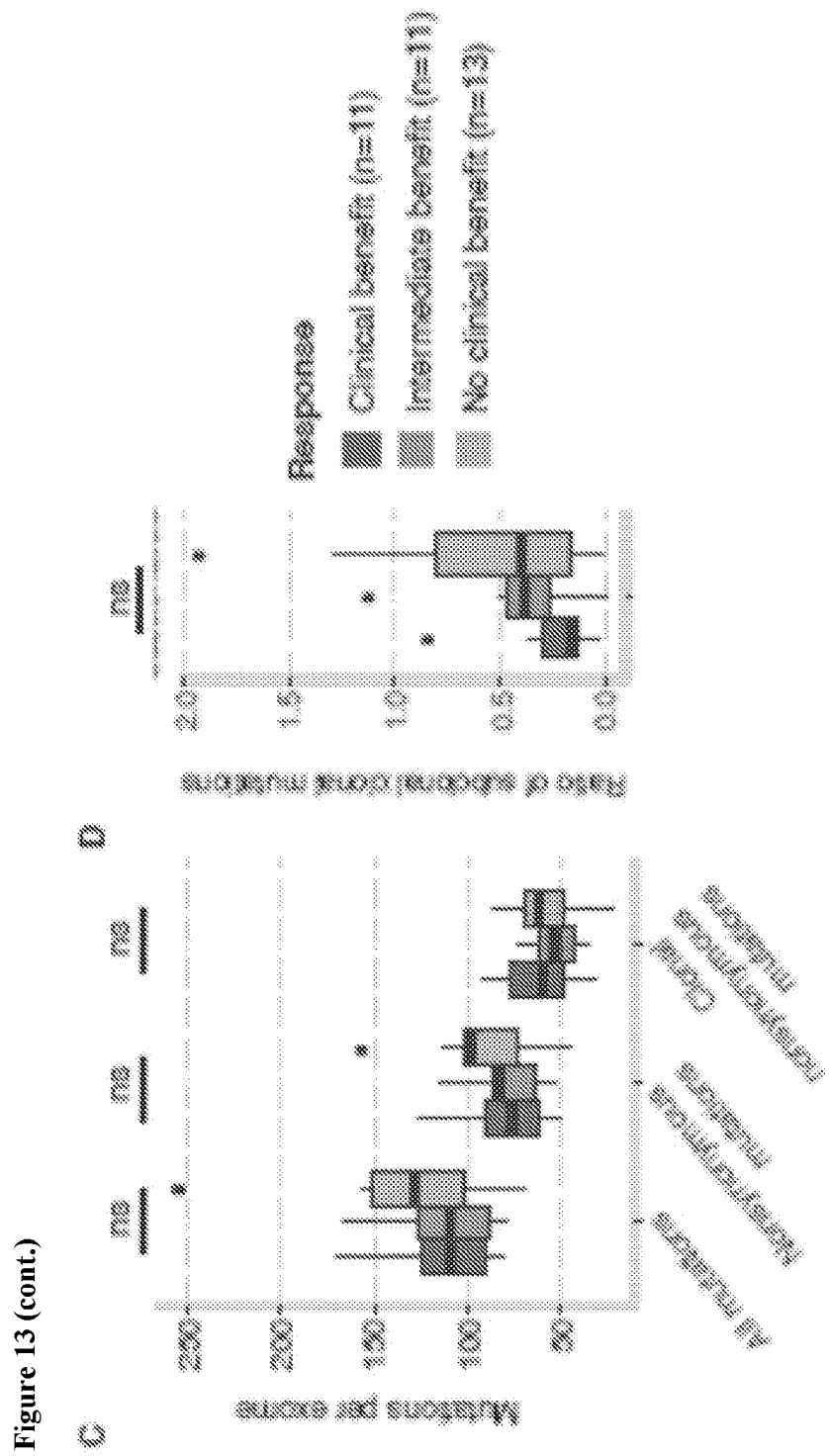

It was hypothesized that distinct molecular mechanisms underlie the immunologically active tumor microenvironment and responsiveness to immune checkpoint therapy in patients with ccRCC. As part of a prospective clinical trial (Choueiri et al. (2016) Clin. Cancer Res. 22:5461-5471), pre-treatment tumors from 35 patients with metastatic ccRCC on a clinical trial of anti-programmed cell death-1 receptor (anti-PD-1) therapy (nivolumab) were analyzed. Whole exome sequencing (WES) from paired tumor/normal tissue was performed to identify genetic correlates of clinical benefit. To validate the findings, an independent cohort of 63 patients with metastatic ccRCC treated with therapies blocking PD-1 (e.g., nivolumab) or its ligand, PD-L1 (e.g., atezolizumab), were analyzed (FIG. 13A and Table 6A).

Figure 14:
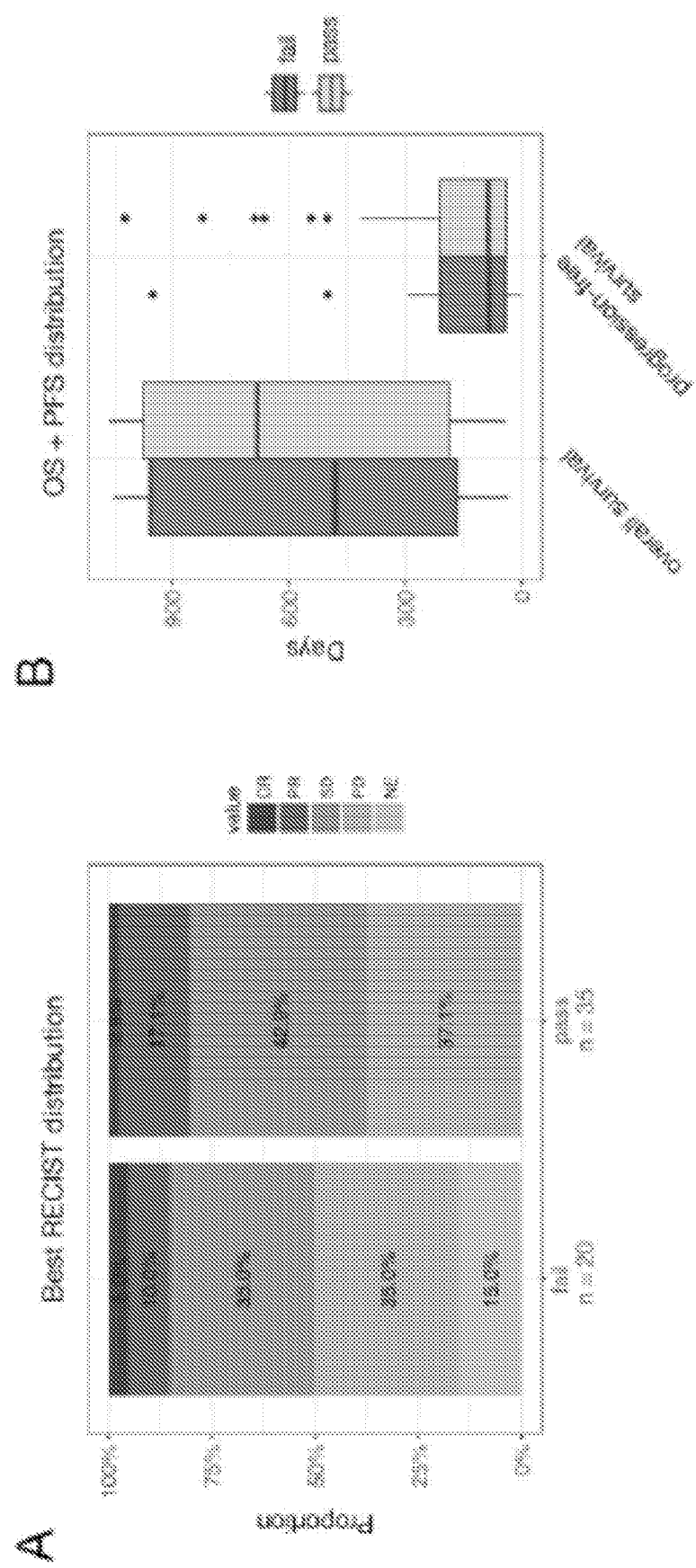
FIG. 14 includes 2 panels, identified as panels A and B, which show that clinical characteristics do not differ significantly between samples that passed and failed whole exome sequencing in the discovery cohort (N=35 pass, N=20 fail). Panel A shows a distribution of the best RECIST scores of patients whose samples passed and failed sequencing. CR=complete response; PR=partial response; SD=stable disease; PD=progressive disease; NE=not evaluable. Panel B show the overall survival (OS) and progression-free survival (PFS) distribution between patients with samples that passed sequencing and samples that failed, measured in days from anti-PD-1 treatment initiation.
Figure 15:
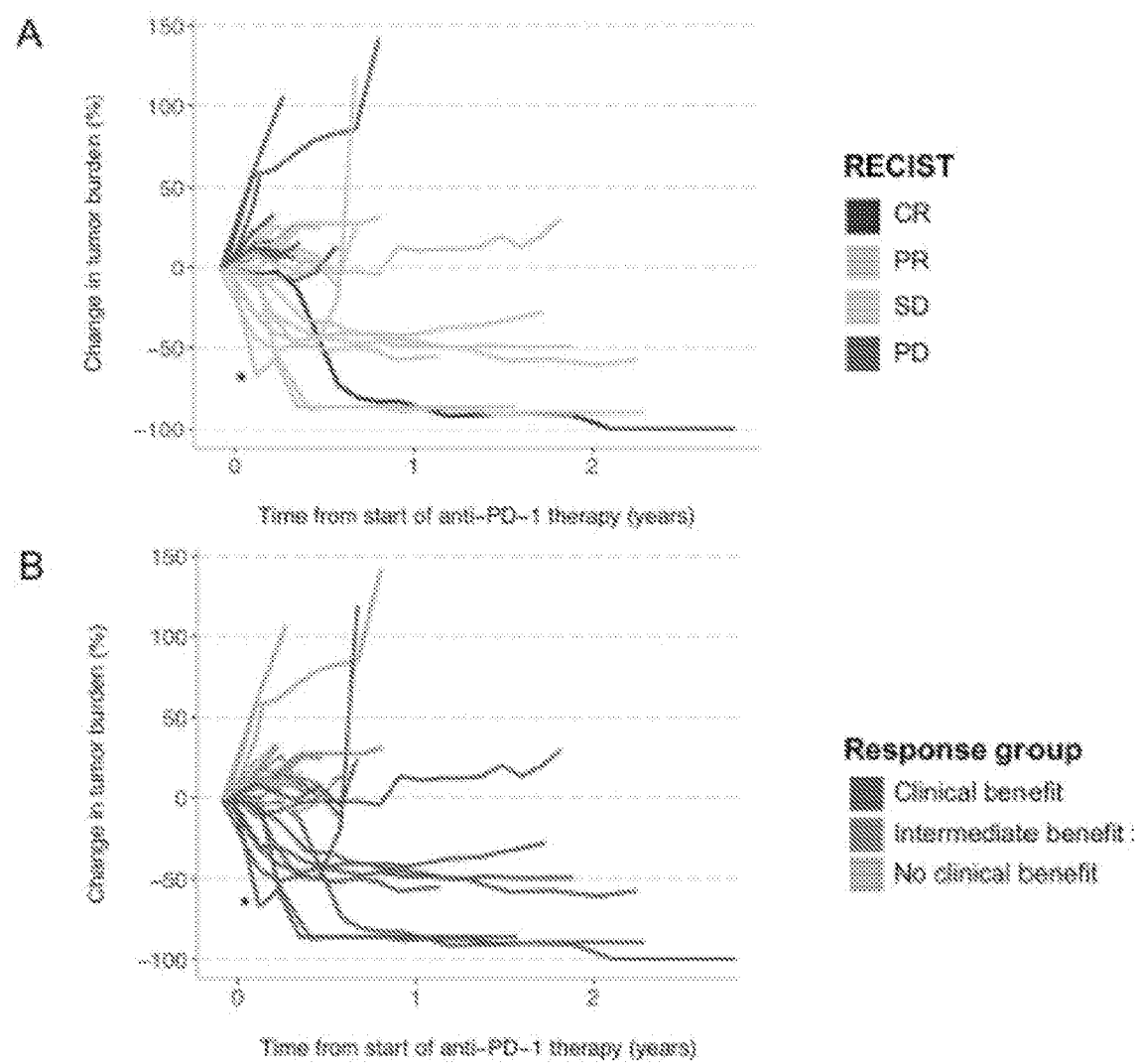
FIG. 15 includes 2 panels, identified as panels A and B, which shows spider plots of change in tumor burden for discovery cohort (N=35). Panel A shows a spider plot showing change in target tumor size in the discovery cohort over time. Shading of lines corresponds to best response by RECIST: CR=complete response (purple), PR=partial response (pink), SD=stable disease (light green), PD=progressive disease (dark green). * Patient RCC_50 was classified as clinical benefit despite early (prior to 6 months) minor increase in tumor size (likely pseudo-progression), as this was followed by sustained tumor shrinkage. Patient RCC_99 is not shown due to early clinical disease progression and lack of re-staging scans after baseline. Panel B shows a spider plot shaded by response group in this study.
Figure 16:
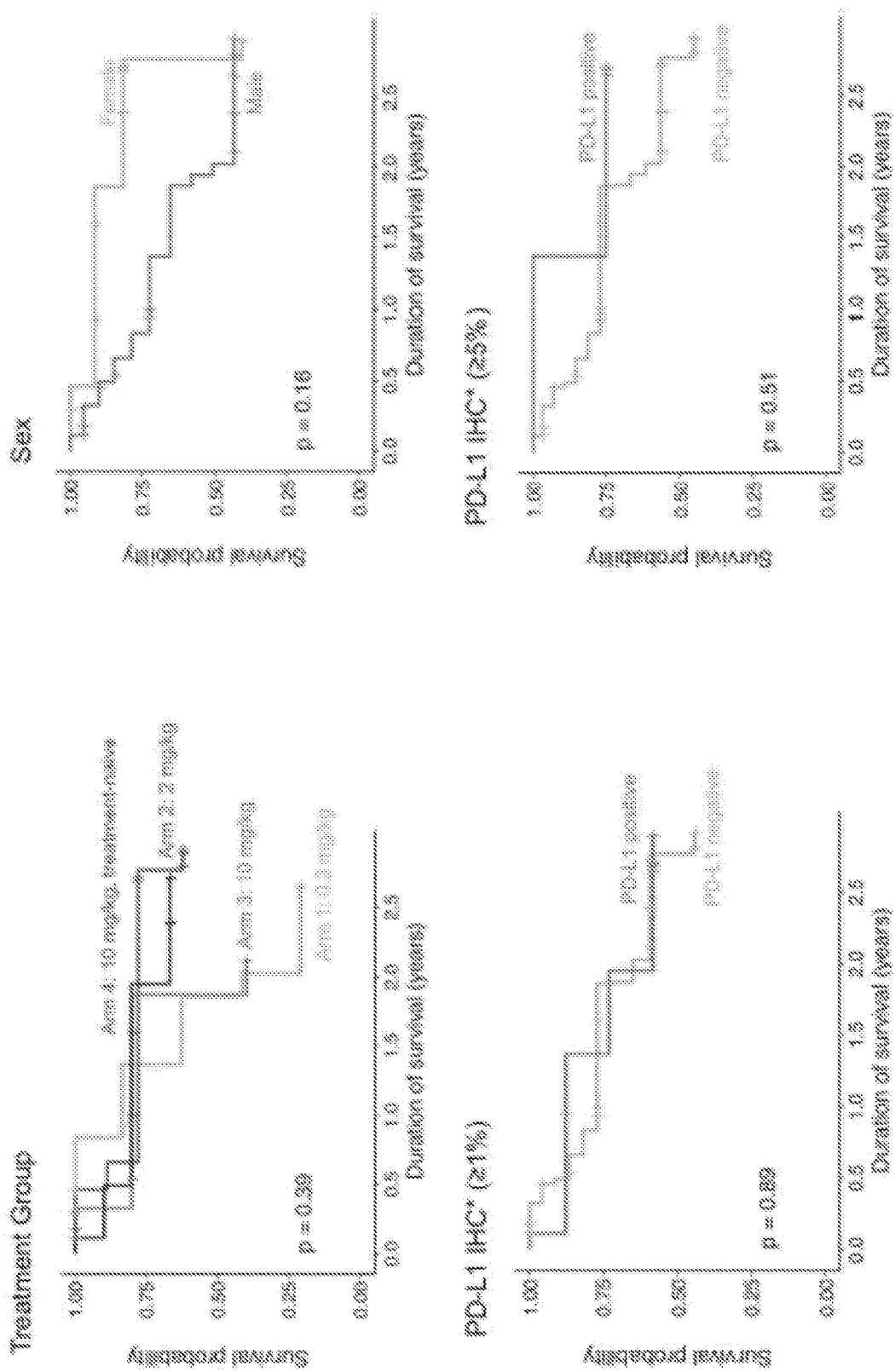
FIG. 16 shows that pre-treatment clinical covariates did not predict response to immune checkpoint therapy. Dose of immune checkpoint therapy, patient sex, and PD-L1 immunohistochemical staining did not predict patient overall survival following anti-PD-1 therapy (p>0.05, log-rank test).

Baseline clinical and demographic features in the discovery cohort have been previously described, and the subset of patients with complete pre-treatment molecular profiling did not differ substantially in clinical or demographic features from patients whose data did not pass technical quality control (FIGS. 14A-14B) or from the larger published cohort (Choueiri et al. (2016) Clin. Cancer Res. 22:5461-5471). Given previous evidence suggesting that refined clinical stratifications are necessary to assess clinical benefit from immune checkpoint blockade (Wolchok et al. (2009) Clin. Cancer Res. 15:7412-7420), a composite response endpoint incorporating RECIST (Response Evaluation Criteria In Solid Tumors) (Eisenhauer et al. (2009) Eur. J. Cancer 45:228-247), radiographic tumor shrinkage, and progression-free survival (PFS), was defined (FIG. 13B and Table 6B). Clinical benefit (CB) included patients with complete response (CR) or partial response (PR) by RECIST 1.1 (i.e., tumor shrinkage >30% from baseline) (Eisenhauer et al. (2009) Eur. J. Cancer 45:228-247) or stable disease (SD) if they had any objective reduction in tumor burden lasting at least 6 months. This modification to include some patients with SD is intended to differentiate those patients with naturally indolent disease (i.e., slow tumor growth not surpassing 20% of baseline tumor size) from those with tumor response to immune checkpoint inhibitors (Gofrit et al. (2015) Springer Plus 4:580). No clinical benefit (NCB) patients experienced progressive disease (PD) by RECIST 1.1 and were discontinued from immunotherapy within three months. All other patients were termed "intermediate benefit" (IB). One patient in the discovery cohort was classified as CB despite PFS<6 months because there was continued tumor shrinkage (~67% of baseline tumor size) after an initial period of minor tumor progression, and the patient had overall survival exceeding 32 months (FIGS. 15A-15B). Consistent with prior observations (Motzer et al. (2015) *N. Engl. J. Med.* 373:1803-1813), the dose of nivolumab, patient gender, and baseline PD-L1 immunohistochemical staining from metastatic biopsies did not predict patient overall survival (OS) following initiation of anti-PD-1 therapy (p>0.05 for all; log-rank test) (FIG. 16).

Figure 17:
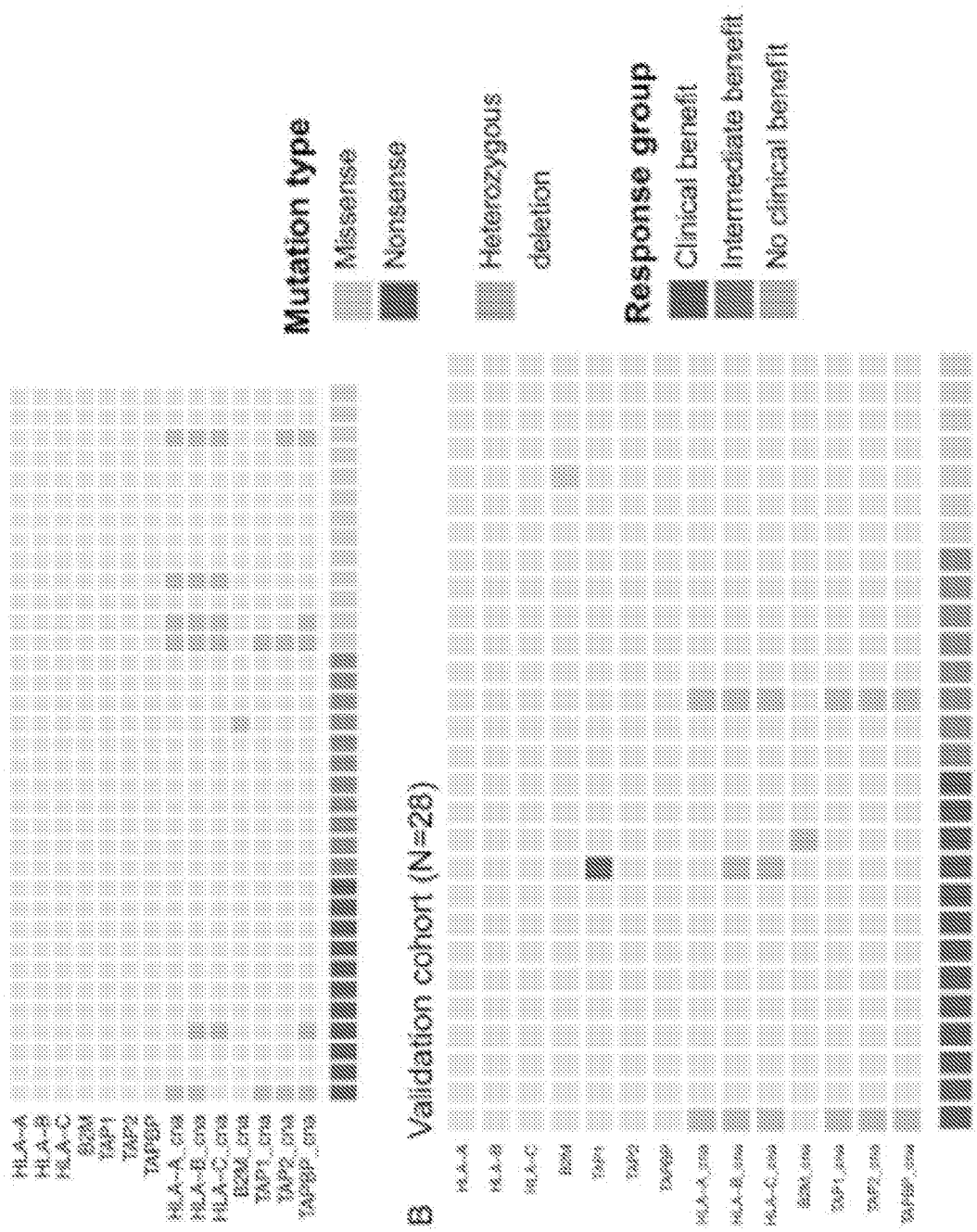
FIG. 17 includes 2 panels, identified as panels A and B, which show alterations in HLA alleles and antigen presentation machinery in the discovery and validation cohorts. Mutations and copy number alterations in discovery cohorts (panel A) (N=35) and the validation cohort (panel B) (N=41; only tumors from the MSKCC and DFCI patients in the validation cohort (41 out of 69 total validation cohort patients) had raw sequencing data available for these analyses) are shown. One clinical benefit patient in the validation cohort had a heterozygous TAP1 nonsense mutation, while two B2M mutations occurred in the no clinical benefit cohort, one missense and one nonsense.

Mean exome-wide target coverage in the discovery cohort was 128-fold for tumor sequencing and 91-fold for matched germline sequencing (Tables 6A and 6E). Overall, nonsynonymous mutation burden was moderate in the discovery cohort (median 82 per exome, range 45-157). The tumors of patients with CB and those with NCB showed similar mutation burdens and intratumoral heterogeneity (FIGS. 13C-13D and Table 6C). Mutations and copy number alterations affecting antigen presentation machinery and HLA class I alleles were uncommon and were present in tumors of both CB and NCB patients (FIGS. 17A-17B).

Figure 18:
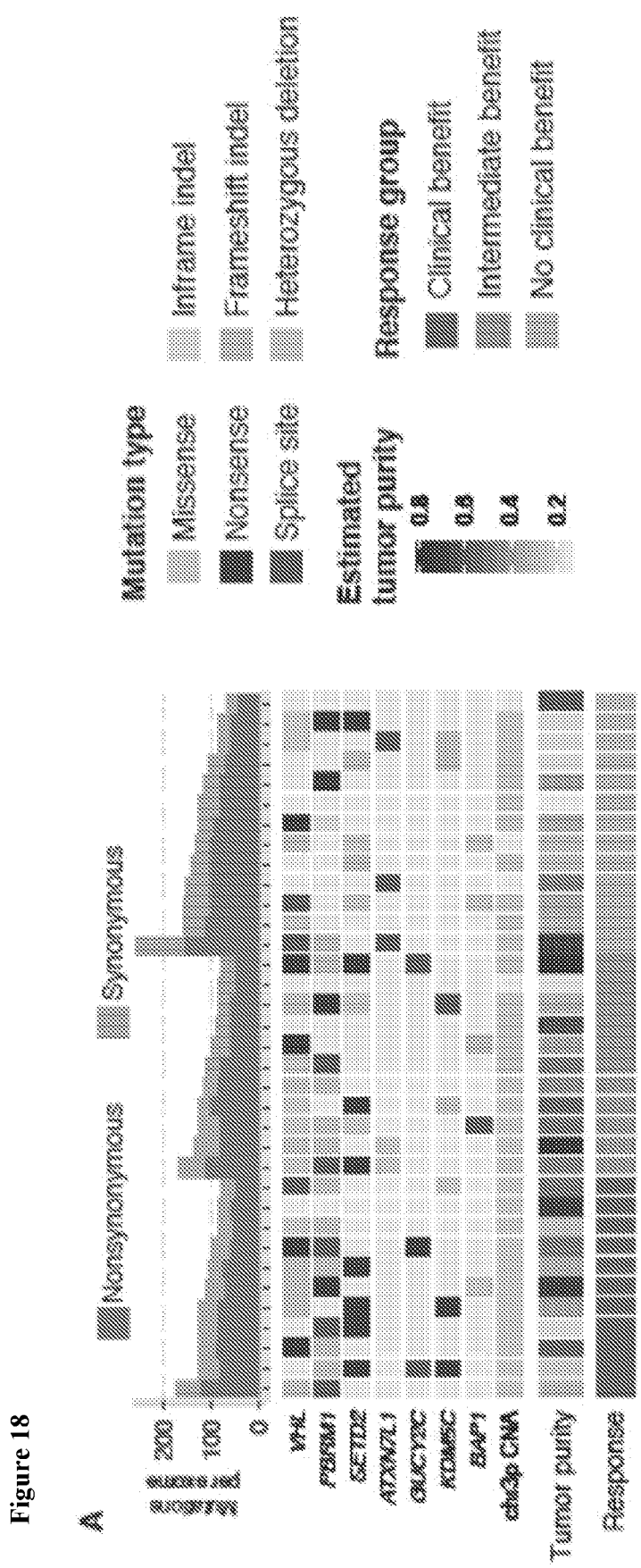
FIG. 18 includes 4 panels, identified as panels A, B, C, and D, which show that tumor genome features in the discovery cohort reveals a correlation between PBRM1 LOF mutations and clinical benefit from anti-PD-1 therapy. Panel A shows mutations in the discovery cohort. Patients are ordered by response category, with tumor mutation burden in decreasing order within each response category. Shown are the genes that were recurrently mutated at a significant frequency, as assessed by MutSig2CV analysis. CNA=copy number alteration. Panel B shows enrichment of truncating mutations in tumors from patients in the CB vs. NCB groups. The top dashed line denotes q<0.1 (Fisher's exact test). Mutations in genes above the lower black dotted line are enriched in tumors of patients with CB from anti-PD-1 therapy and mutations in genes below the line are enriched in tumors of patients with NCB. Panel C shows a Kaplan-Meier curve comparing overall survival of patients treated with anti-PD-1 therapy whose tumors did or did not harbor LOF mutations in PBRM1. See also FIG. 19 for a Kaplan-Meier curve comparing progression-free survival of these patients. Panel D shows a spider plot showing objective decrease in tumor burden in PBRM1-LOF vs. PBRM1-intact tumors. Three patients with early progression on anti-PD-1 therapy and truncating mutations in PBRM1 (darkest shading) had long and/or censored OS.
Figure 18:
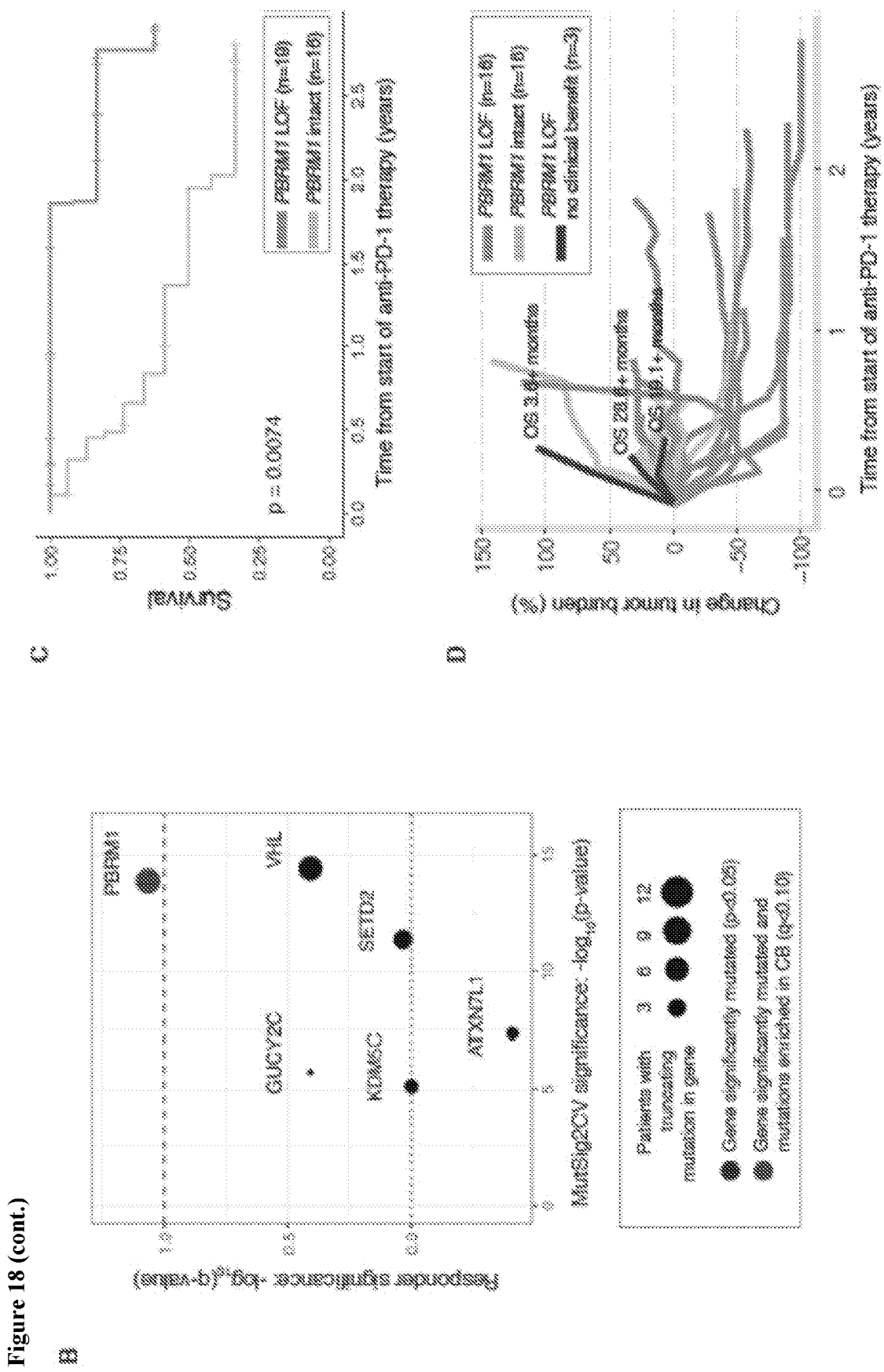
Figure 19:
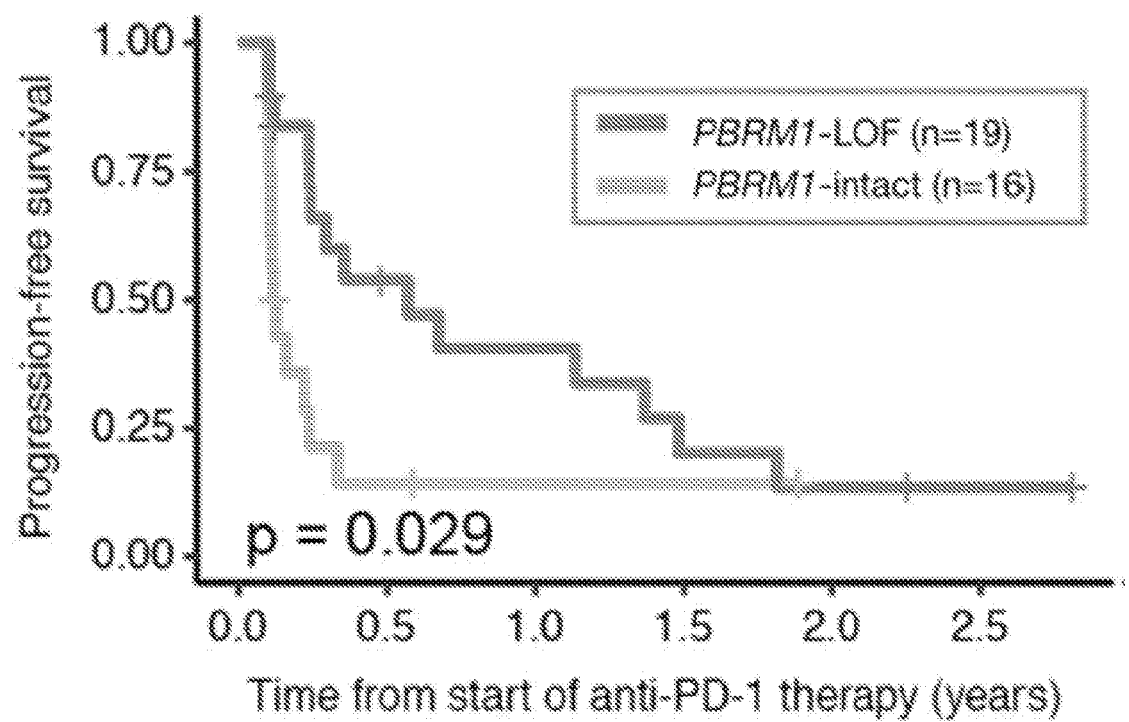
FIG. 19 shows a Kaplan-Meier curve of discovery cohort patient progression-free survival by PBRM1 mutation status. PBRM1 truncating alterations are associated with increased progression-free survival following anti-PD-1 therapy (p=0.029; log-rank test).

The analyses were next focused on the mutations most likely to be functionally important. MutSig2CV (Lawrence et al. (2013) *Nature* 499:214-218) was applied to identify genes recurrently mutated in the discovery cohort. Of these genes, the search was limited to highly deleterious variants, meaning known hotspot or putative truncating (frameshift insertion or deletion, nonsense mutation, or splice-site) mutations. Of the seven recurrently mutated genes (FIG. 18A) (Cancer Genome Atlas Research (2013) *Nature* 499: 43-49), PBRM1 was the only gene in which truncating, or loss-of-function (LOF), mutations were enriched in tumors from patients in the CB vs. NCB group (9/11 vs. 3/13; Fisher's exact p=0.012, q=0.086, odds ratio for CB=12.93, 95% C.I. 1.54-190.8) (FIG. 18B and Table 6D). In this cohort, all truncating PBRM1 alterations co-occurred with deletion of the non-mutated allele on chromosome 3p (FIG. 18A), resulting in complete LOF of PBRM1, and most of the mutations were predicted to be clonal (present in all tumor cells) (Table 6D). Prior large-scale sequencing studies have shown that PBRM1 LOF alterations occur in up to 41% of ccRCC tumors (Varela et al. (2011) *Nature* 469:539-542) and are commonly clonal events present in all or nearly all tumor cells (Gerlinger et al. (2014) *Nat. Genet.* 46:225-233). Patients whose tumors showed biallelic PBRM1 loss had significantly prolonged OS and PFS compared to patients without PBRM1 LOF (log-rank p=0.0074 and p=0.029, respectively) (FIGS. 18C and 19), and they experienced sustained reductions in tumor burden (FIG. 18D).

Figure 20:
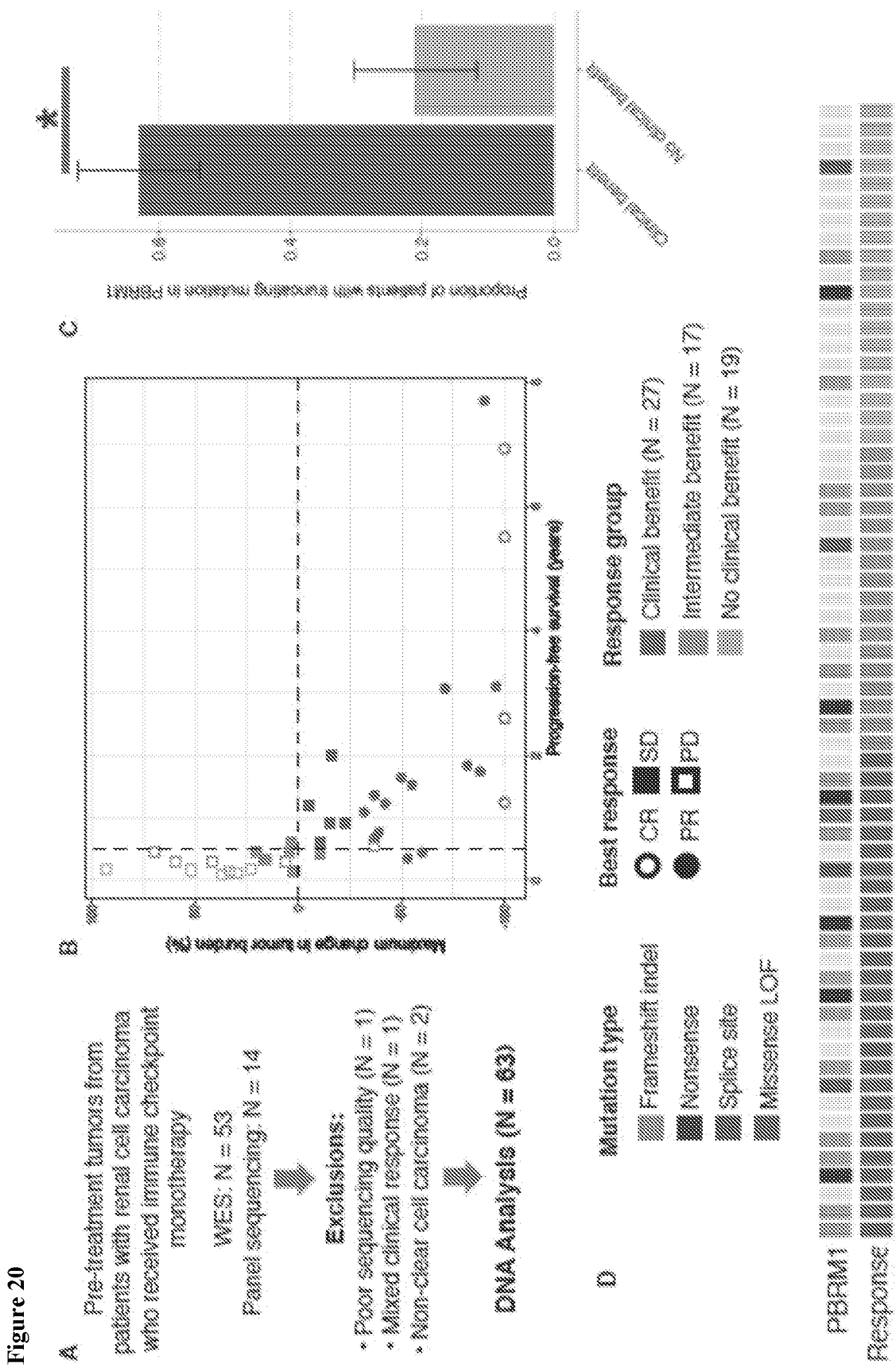
FIG. 20 includes 4 panels, identified as panels A, B, C, and D, which show that PBRM1 LOF mutations correlate with clinical benefit in a validation cohort of ccRCC patients treated with immune checkpoint inhibitors. Panel A shows selection of the validation cohort. Panel B shows clinical outcomes in the validation cohort. Ten patients without post-treatment restaging scans (eight with clinical PD, two with SD, and one with PR) as well as 14 patients with targeted panel sequencing are not shown. Panel C shows the proportion of tumors harboring PBRM1 LOF mutations in patients in the CB vs. NCB groups. Error bars are S.E. *Fisher's exact p<0.05. Panel D shows truncating alterations in PBRM1 and response to anti-PD-(L)1 therapies by sample. Shaded boxes indicate samples with truncating mutations in PBRM1, while light shading denotes samples without PBRM1 truncating mutations. Missense LOF denotes a missense mutation detected by targeted sequencing that was confirmed to be LOF by PBRM1 immunohistochemistry.

To evaluate the reproducibility of this finding, matched pre-treatment tumor and germline genomic data were examined from an additional 63 patients treated with anti-PD-(L)1 therapy, either alone or in combination with anti-CTLA-4 therapy. Of these 63 patients, PBRM1 mutation status was derived from WES in 49 patients and panel sequencing in 14 patients (FIGS. 20A-20B and Tables 6E-6F). Tumors from CB patients were more likely to harbor truncating alterations in PBRM1 (17/27 vs. 4/19, Fisher's exact p=0.0071, odds ratio for CB=6.10, 95% C.I. 1.42-32.64) (FIGS. 20C-20D and Table 6G). Although copy number alterations in all samples in the validation cohort could not be assessed, it is believed that the PBRM1 LOF mutations represented biallelic loss, as chromosome 3p deletions are nearly ubiquitous in ccRCC (Cancer Genome Atlas Research (2013) *Nature* 499:43-49). Notably, one of the four NCB patients whose tumor showed a PBRM1 LOF mutation also had an alteration in B2M, which codes for a protein important in antigen presentation. This provides a potential explanation for the patient's lack of clinical benefit from immune checkpoint blockade therapy despite having a truncating PBRM1 mutation.

Figure 21:
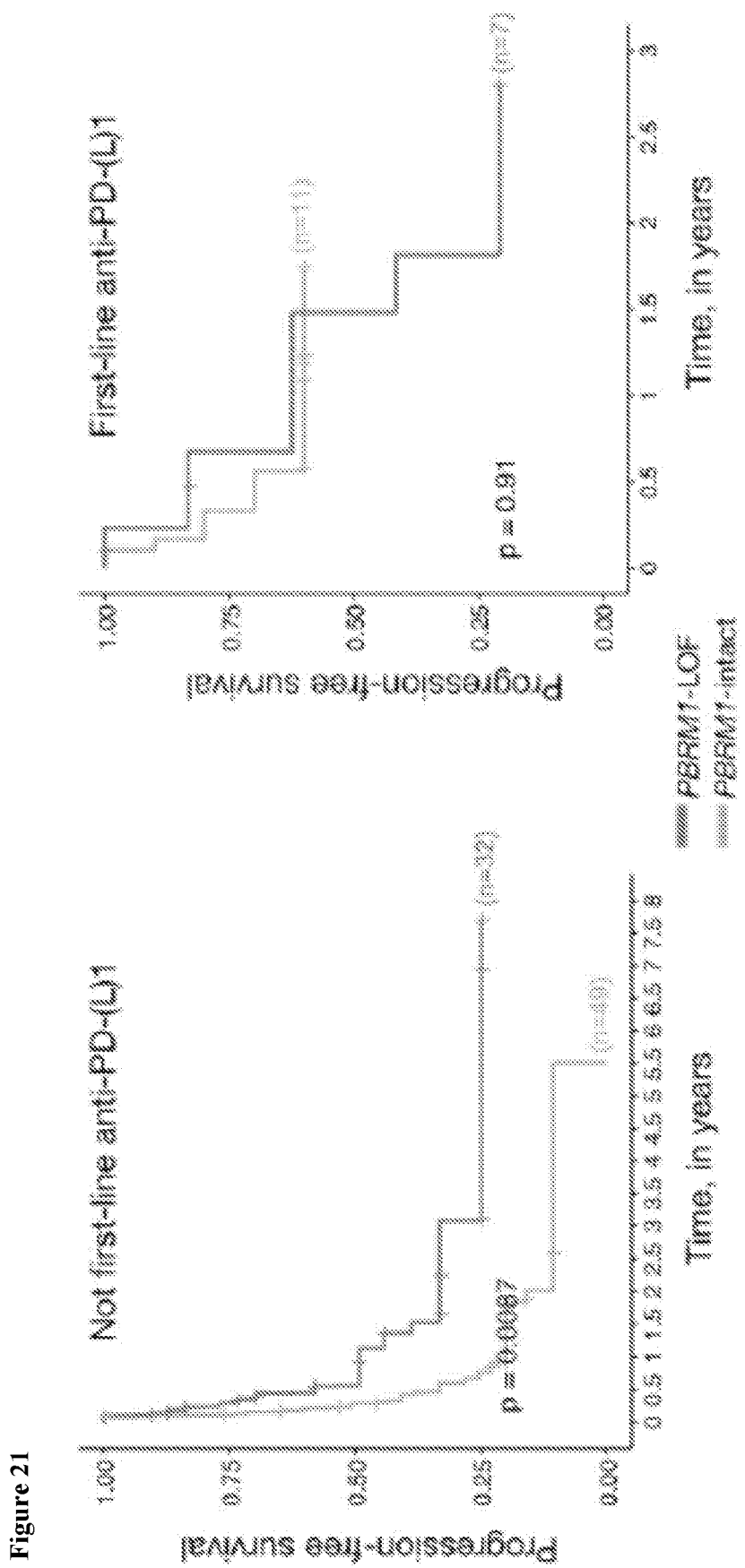
FIG. 21 shows a Kaplan-Meier curve of combined discovery and validation cohort patient progression-free survival by PBRM1 LOF mutation status, stratified by therapy line. PBRM1 truncating alterations in patients who received anti-PD-(L) 1 therapy in a setting other than first-line (N=81) were associated with increased progression-free survival (p=0.0087, log-rank test). This association was not observed in patients who received immune checkpoint blockade as first-line therapy (N=17).

While primary analyses excluded patients with intermediate benefit (IB) due to the unclear effect of immune checkpoint blockade therapy on patient outcomes in this group, the observed trend between PBRM1 mutation status and clinical benefit persisted with the inclusion of these patients as an intermediate phenotype. In both the discovery and validation cohorts, patients in the IB group had intermediate rates of PBRM1 LOF (82%, 64%, 23% for CB, IB, NCB in the discovery cohort and 63%, 41%, 21% for CB, IB, NCB in the validation cohort; Fisher-Freeman-Halton Exact p=0.017 and 0.017). Additionally, while no difference in clinical benefit was observed between treatment-naive and previously-treated patients in the discovery cohort (FIGS. 15A-15B), the progression-free survival benefit conferred by PBRM1 LOF was more prominent in tumors from previously-treated patients compared to those from patients receiving anti-PD-1 therapy as their first cancer therapy (p=0.009) (FIG. 21 and Table 6).

Figure 22:
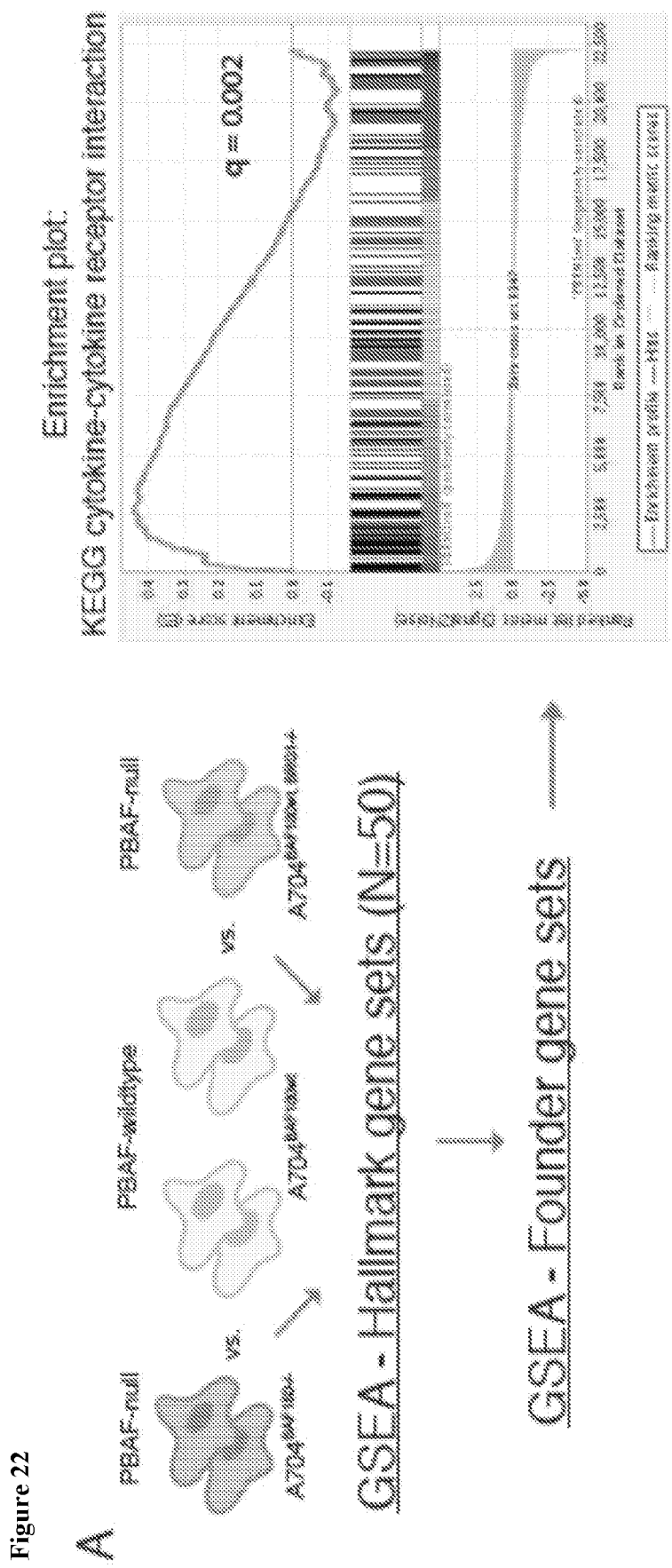
FIG. 22 includes 2 panels, identified as panels A and B, which show PBRM1 mutational status in ccRCC influences immune gene expression. Panel A shows the results of GSEA performed on PBAF-deficient (A704BAF180−/− and A704BAF180 wt, BRG1−/−) vs. PBAF-proficient (A704BAF180 wt) kidney cancer cell lines using both Hallmark and corresponding Founder gene sets. GSEA enrichment plot shown for the KEGG cytokine-cytokine receptor interaction gene set in A704BAF180−/− vs. A704BAF180 wt (PBRM1 null vs. wildtype). The enrichment plot is similar for A704BAF180 wt, BRG1−/− vs. A704BAF180 wt (BRG1 null vs. wildtype); see Table 61. Panel B shows the results of GSEA also performed on RNA-seq from pre-treatment tumors in the discovery and validation cohorts of this study (n=18 PBRM1-LOF vs. n=14 PBRM1-intact) using the Hallmark gene sets. Enrichment plots show increased expression of the hypoxia and IL6/JAK-STAT3 gene sets in the PBRM1-LOF tumors.
Figure 22:
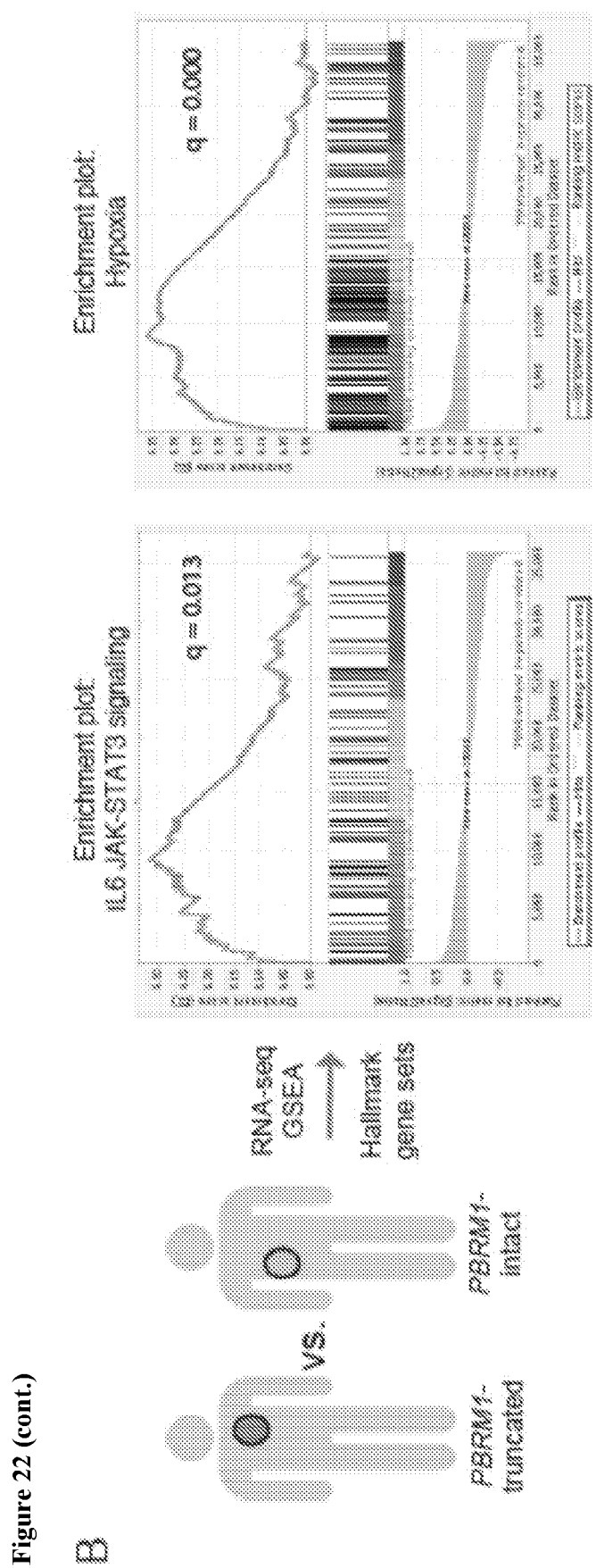
Figure 23:
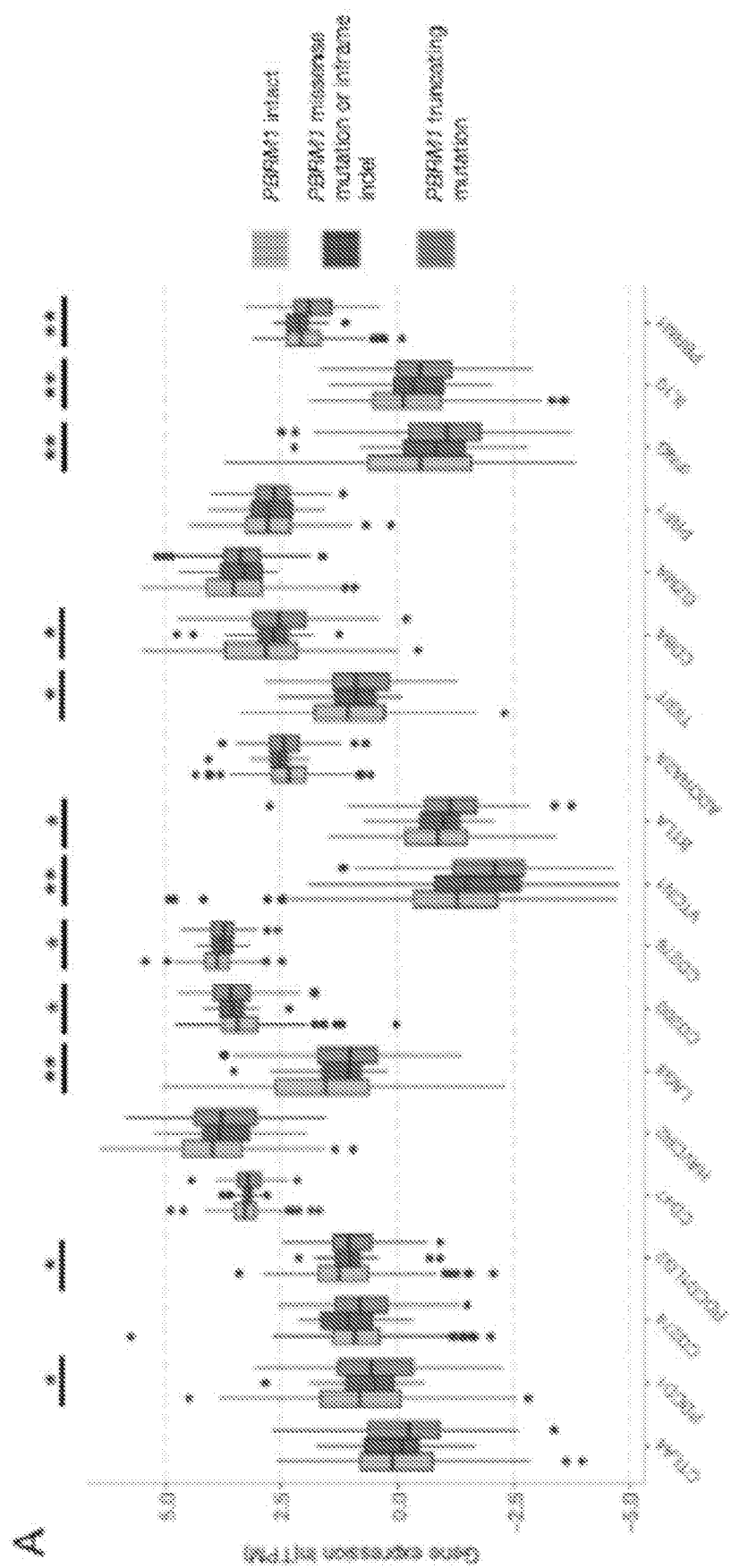
FIG. 23 includes 3 panels, identified as panels A, B, and C, which show expression of immune genes and PBRM1 in three independent ccRCC cohorts by PBRM1 mutation status. Panel A shows expression of immune checkpoints and immune cell markers in TCGA clear-cell renal cell carcinoma between PBRM1-loss-of-function (LOF) (N=104) and PBRM1-intact (N=288) tumors. Immune inhibitory ligands, including PDCD1, PDCD1LG2, LAG3, TIGIT, and VTCN1 are significantly upregulated in PBRM1-intact versus PBRM1-LOF tumors (*q<0.05, **q<0.01). Panel B shows differential immune gene expression analysis in Sato et al. (N=73 PBRM1-intact vs. N=19 PBRM-LOF) shows significant upregulation of VTCN1 in PBRM1-intact tumors (*p<0.05, **p<0.005). Panel C demonstrates that in N=32 patient tumors, no immune genes were significantly differentially expressed, although PBRM1-LOF tumors trended towards lower expression of most checkpoints (*p<0.05, **p<0.005). All three cohorts show significantly lower expression of PBRM1 in PBRM1-LOF tumors compared to PBRM1-intact tumors (p=0.0027, 0.048, and 0.022, respectively), while tumors with non-truncating mutations in PBRM1 more closely resembled the PBRM1-intact expression phenotype.
Figure 23:
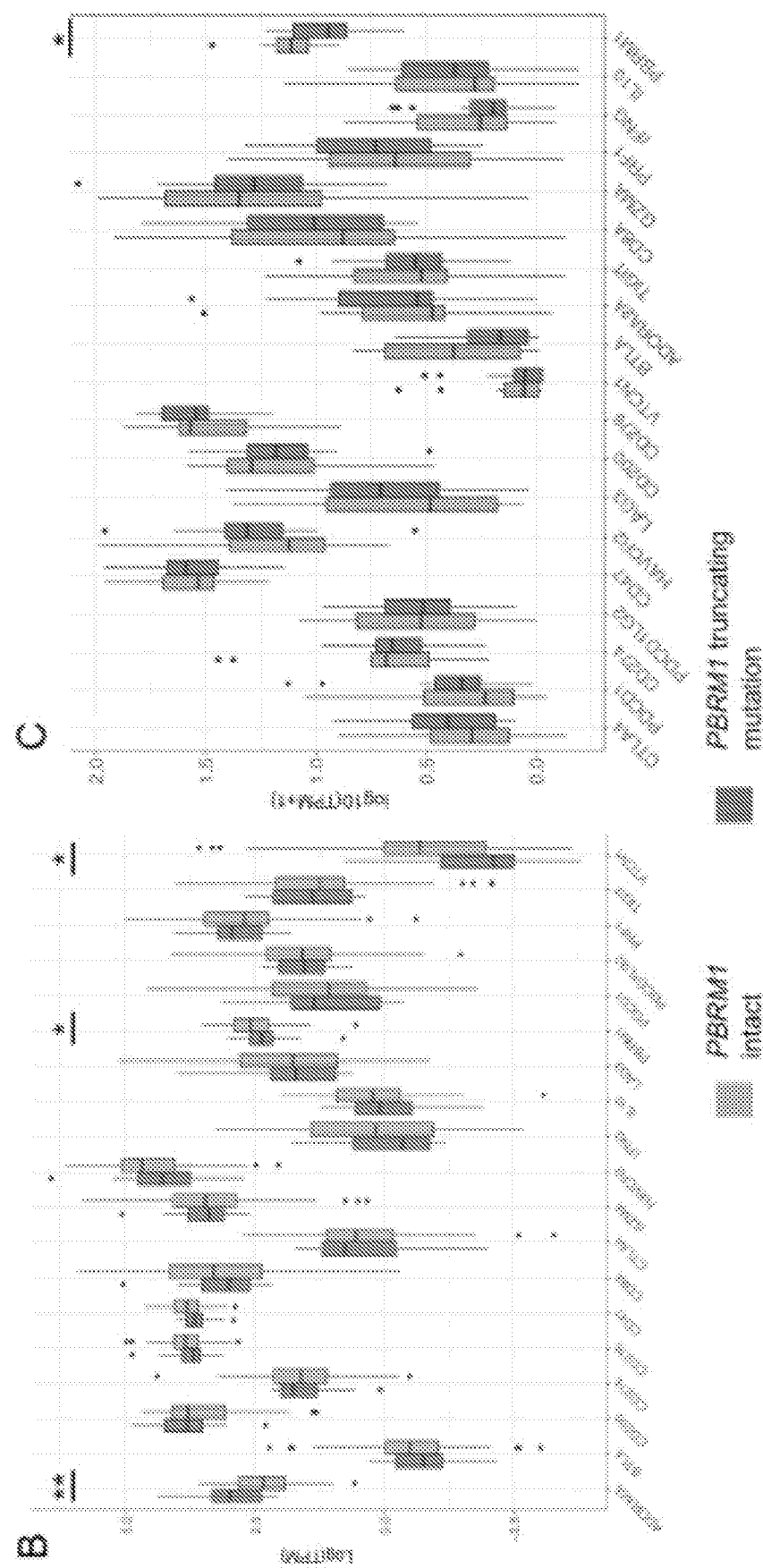
Figure 24:
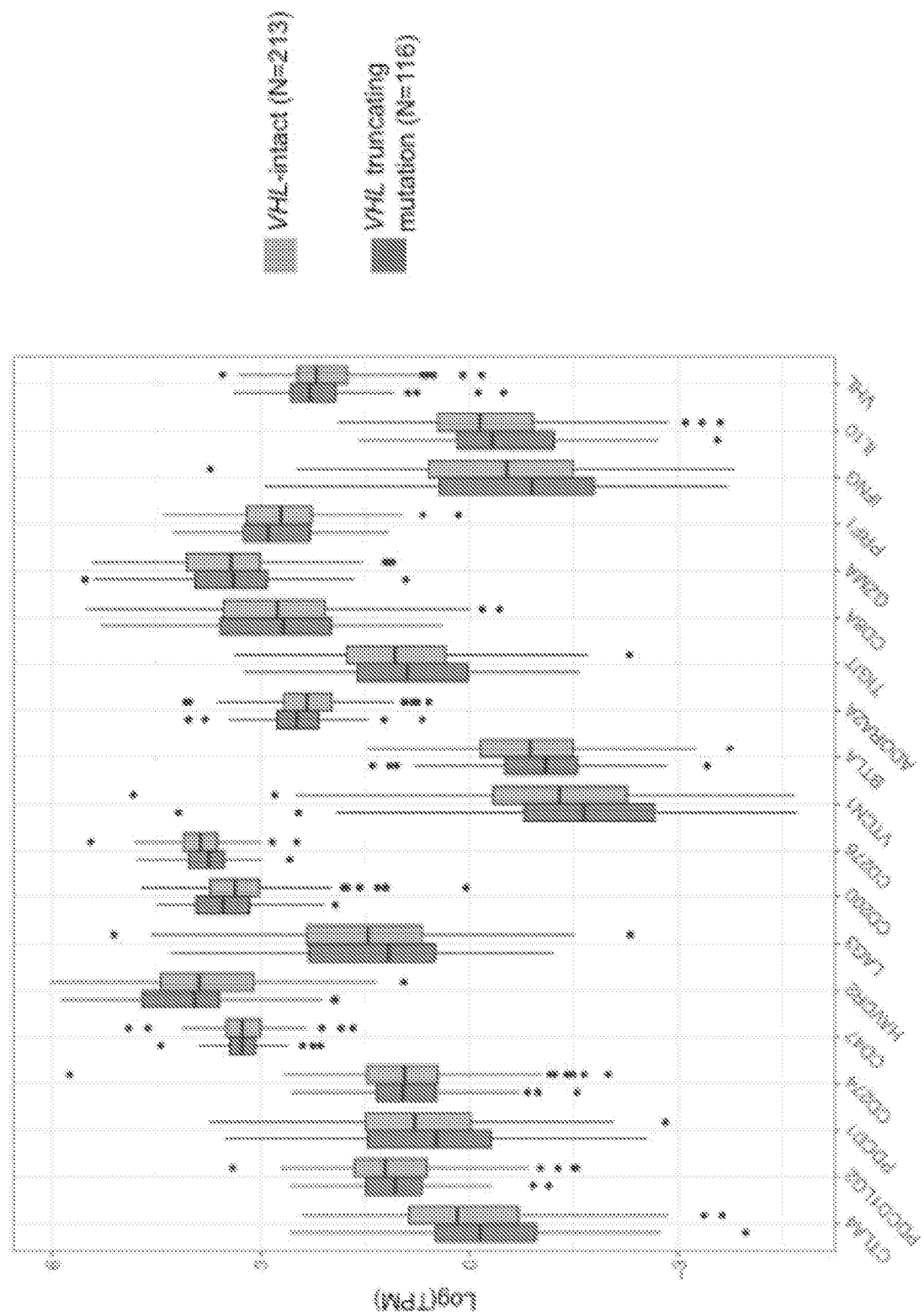
FIG. 24 show immune gene expression in TCGA KIRC by VHL mutation status. The presence or absence of truncating mutations in VHL did not correlate with expression levels of immune inhibitory ligands or other immune cell markers.

The PBRM1 gene codes for BAF180, a subunit of the PBAF subtype of the SWI/SNF chromatin remodeling complex. The PBAF complex suppresses the hypoxia transcriptional signature in VHL−/− ccRCC (Nargund et al. (2017) *Cell Reports* 18:2893-2906; Gao et al. (2017) *Proc. Natl. Acad. Sci. USA* 114:1027-1032), but its effects on tumor-immune interactions have not been thoroughly studied. To explore the potential impact of this complex on the immunophenotype of ccRCC, previously reported whole transcriptome sequencing (RNA-seq) data from A704 ccRCC cell lines with perturbations in the PBAF complex (Gao et al. (2017) *Proc. Natl. Acad. Sci. USA* 114:1027-1032/9) were analyzed. Loss of BAF180 or the related PBAF subunit BRG1, encoded by the gene SMARCA4, prevent formation of the intact PBAF complex (Gao et al. (2017) *Proc. Natl. Acad. Sci. USA* 114:1027-1032). Gene expression analyses of BAF180-null (A704BAF180−/−) cell lines vs. PBAF-wildtype (A704BAF180 wt) cell lines were performed and gene expression analyses of BRG1-null (A704BAF180 wt, BRG1−/−) cell lines vs. PBAF-wildtype (A704BAF180 wt) cell lines were also performed (FIG. 22A). Differential gene expression analysis showed substantial overlaps (~50%) between the top 100 genes differentially expressed in A704BAF180−/− vs. A704BAF180 wt and A704BAF180 wt, BRG1−/− vs. A704BAF180 wt (Table 6I). This reflects the fact that BAF180 is essential to the PBAF but not the BAF complex, while BRG1 is a required subunit of both. Thus, the BAF180-null and BRG1-null cell lines have some shared characteristics but are also biologically and phenotypically distinct. Gene set enrichment analysis (GSEA) on 50 "hallmark" gene sets representing major biological processes (Subramanian et al. (2005) *Proc. Natl. Acad. Sci. USA* 102:15545-15550) revealed five gene sets whose expression was significantly enriched in cell lines that were PBAF-deficient. These included genes linked to IL6/JAK-STAT3 signaling, TNF-α signaling via NF-κB, and IL2/STAT5 signaling (FIG. 22A and Tables 6J-6K). As expected, the hallmark hypoxia gene set was upregulated in A704BAF180−/− vs. A704BAF180 wt cell lines (family-wise error rate—FWER q=0.071) (Table 6J) (Gao et al. (2017) *Proc. Natl. Acad. Sci. USA* 114:1027-1032). Across the more refined "founder" gene sets describing these five significantly enriched hallmark gene sets, the most strongly enriched gene set in PBAF-deficient cell lines was the KEGG cytokine-cytokine receptor interaction gene set (FWER q=0.0020 for A704BAF180−/− vs. A704BAF180 wt and q=0.023 for A704BAF180 wt, BRG1−/− vs. A704BAF180 wt) (FIG. 22A and Tables 6L-6U). This gene set includes both immune-stimulatory (e.g., IL12, CCL21) and immune-inhibitory (e.g., IL10) genes, but Gene Ontology term analysis showed that the genes most strongly enriched in PBAF-deficient cell lines were immune-stimulatory (Table 6V). Previously reported GSEA analysis of untreated ccRCC from The Cancer Genome Atlas (TCGA) and a murine model of PBRM1 loss also show amplified transcriptional outputs of HIF1 and STAT3, involved in hypoxia response and JAKSTAT signaling respectively, in PBRM1-mutant vs. PBRMJ-wildtype states (Nargund et al. (2017) Cell Reports 18:2893-2906). GSEA analysis of RNA-seq from pre-treatment tumors in the discovery and validation cohorts of this study (n=18 PBRM1-LOF vs. n=14 PBRM1-intact) confirmed increased expression of the hypoxia and IL6/JAK-STAT3 gene sets in the PBRM1-LOF tumors (FIG. 22B and Tables 6W-6X). Given JAK-STAT3 pathway gene involvement in the interferon gamma (IFN-g-) signaling pathway and IFN-g-dependent cancer immunostimulation (Sharma et al. (2017) Cell 168:707-723), differential expression of these genes may impact PBRM1-LOF patients' response to anti-PD-(L)1 therapy. In addition to assessing tumor-intrinsic gene expression with GSEA, the quality of the tumor-immune microenvironment in PBRM1-LOF vs. PBRM1-intact ccRCC was further characterized in three independent cohorts: TCGA (Cancer Genome Atlas Research (2013) Nature 499:43-49), an independent cohort of untreated ccRCC tumors (Sato) (Sato et al. (2013) Nat. Genet. 45:860-867), and patient tumors. In all three cohorts, tumors harboring LOF mutations in PBRM1 showed lower expression of immune inhibitory ligands (e.g., CD276 and BTLA) (Ramsay (2013) Br. J. Haematol. 116:313-325) than those without PBRM1 mutations. This finding was unexpected as high PD-L1 staining is associated with increased responsiveness to anti-PD-1 and anti-PD-L1 agents in other cancer types (Rosenberg et al. (2016) Lancet 387:1909-1920; Topalian et al. (2012) N. Engl. J. Med. 366:2443-2454) and despite the fact that these differences were relatively small and in the context of differing degrees of tumor-stromal admixture (FIGS. 23A-23C) (Senbabaoglu et al. (2016) Genome Biol. 17:231). LOF mutations in VHL, the most commonly mutated gene in the TCGA ccRCC cohort, were also examined. VHL mutation status did not correlate with immune related gene expression (FIG. 24), indicating that observed differences in immune gene expression in the context of PBRM1 LOF is believed to be specific to the PBRM1 gene.

Based on the foregoing, it has been shown that patients with metastatic ccRCC harboring truncating mutations in PBRM1 experienced increased clinical benefit from immune checkpoint therapy. It is believed that this is due to distinct immune-related gene expression profiles in PBRM1-mutant or PBAF-deficient tumor cells compared to their PBAF-intact counterparts, as shown by RNA-seq analyses described herein. In vivo studies of mice harboring tumor clones with inactivation of PBRM1—or the related essential PBAF complex components ARID2 or BRD7—show that cells with PBAF loss are more sensitive to T-cell-mediated cytotoxicity compared to their PBAF-intact counterparts (Pan et al. (2018) Science, in press), which helps to explain the conflicting results regarding PBRM1 mutation status as a prognostic variable in ccRCC (in the absence of immunotherapy) in prior studies (Beuselinck et al. (2015) Clin. Cancer Res. 21:1329-1339; Fay et al. (2016)1 Natl. Compr. Canc. Netw. 14:820-824; Hakimi et al. (2013) Clin. Cancer Res. 19:3259-3267; Hsieh et al. (2017) Eur. Urol. 71:405-414; Kapur et al. (2013) Lancet Oncol. 14:159-167; Kwiatkowski et al. (2016) Clin. Cancer Res. 22:2445-2452; Nam et al. (2015) Urol. Oncol. 33:340.e349-316; Pawlowski et al. (2013) Int. J. Cancer 132:E11-E17; Uhlen et al. (2017) Science 357:pii eaan2507). PBRM1 also previously has been linked to longer PFS with VEGF-targeted therapies (Carlo et al. (2017) Kidney Cancer 1:49-56). Additional in vivo studies can be used to further confirm the results described herein. Given the high prevalence of PBRM1 LOF in ccRCC and of SWI/SNF alterations across all cancer types (more than 20%) (Kadoch et al. (2013) Nat. Genet. 45:592-601), these results have important implications as a molecular tool for considering immunotherapy-responsiveness in ccRCC and across cancer types.

TABLE 6A

Whole exome sequencing metrics and inclusions/exclusions for patients in the discovery cohort

| patient_id | tumor_mtc | normal_mtc | bait_set | absolute_inferred_purity |
| --- | --- | --- | --- | --- |
| RCC_20 | 34.147062 | 92.688228 | whole_exome_illumina_coding_v1 | 0.51 |
| RCC_32 | 165.03915 | 80.054054 | whole_exome_illumina_coding_v1 | 0.39 |
| RCC_62 | 163.21171 | 81.718582 | whole_exome_illumina_coding_v1 | 0.49 |
| RCC_10 | 153.907825 | 93.664757 | whole_exome_illumina_coding_v1 | 0.76 |
| RCC_11 | 81.495132 | 108.704189 | whole_exome_illumina_coding_v1 | 0.38 |
| RCC_14 | 157.03659 | 99.990083 | whole_exome_illumina_coding_v1 | 0.25 |
| RCC_25 | 150.766602 | 87.494869 | whole_exome_illumina_coding_v1 | 0.32 |
| RCC_56 | 136.739597 | 86.544731 | whole_exome_illumina_coding_v1 | 0.56 |
| RCC_79 | 112.238316 | 91.306045 | whole_exome_illumina_coding_v1 | 0.8 |
| RCC_93 | 193.622831 | 94.511787 | whole_exome_illumina_coding_v1 | 0.2 |
| RCC_115 | 150.50973 | 89.411498 | whole_exome_illumina_coding_v1 | 0.63 |
| RCC_90 | 147.435982 | 79.577243 | whole_exome_illumina_coding_v1 | 0.3 |
| RCC_96 | 189.081727 | 96.347659 | whole_exome_illumina_coding_v1 | 0.67 |
| RCC_102 | 130.03582 | 97.794738 | whole_exome_illumina_coding_v1 | 0.48 |
| RCC_58 | 142.586967 | 82.644492 | whole_exome_illumina_coding_v1 | 0.69 |
| RCC_84 | 166.18581 | 88.436816 | whole_exome_illumina_coding_v1 | 0.45 |
| RCC_85 | 43.586957 | 168.436641 | whole_exome_illumina_coding_v1 | 0.17 |
| RCC_114 | 135.707278 | 77.721511 | whole_exome_illumina_coding_v1 | 0.29 |
| RCC_117 | 173.22159 | 68.856331 | whole_exome_illumina_coding_v1 | 0.33 |
| RCC_15 | 143.012126 | 79.906338 | whole_exome_illumina_coding_v1 | 0.69 |
| RCC_68 | 107.126976 | 88.452741 | whole_exome_illumina_coding_v1 | 0.3 |
| RCC_1 | 157.143939 | 89.39856 | whole_exome_illumina_coding_v1 | 0.2 |

TABLE 6A-continued

Whole exome sequencing metrics and inclusions/exclusions for patients in the discovery cohort

| | | | | |
|---|---|---|---|---|
| RCC__106 | 176.007671 | 81.059438 | whole_exome_illumina_coding_v1 | 0.35 |
| RCC__18 | 139.328276 | 75.654059 | whole_exome_illumina_coding_v1 | 0.21 |
| RCC__21 | 178.624687 | 105.356301 | whole_exome_illumina_coding_v1 | 0.51 |
| RCC__41 | 138.664874 | 93.93237 | whole_exome_illumina_coding_v1 | 0.19 |
| RCC__50 | 162.205322 | 85.879444 | whole_exome_illumina_coding_v1 | 0.31 |
| RCC__73 | 158.127987 | 100.10628 | whole_exome_illumina_coding_v1 | 0.6 |
| RCC__39 | 147.571574 | 114.169462 | whole_exome_illumina_coding_v1 | 0.13 |
| RCC__99 | 34.101887 | 117.822339 | whole_exome_illumina_coding_v1 | 0.36 |
| RCC__105 | 152.057615 | 91.424807 | whole_exome_illumina_coding_v1 | 0.48 |
| RCC__119 | 26.875509 | 90.734659 | whole_exome_illumina_coding_v1 | 0.49 |
| RCC__27 | 125.149722 | 97.245404 | whole_exome_illumina_coding_v1 | 0.34 |
| RCC__52 | 131.064027 | 90.415506 | whole_exome_illumina_coding_v1 | 0.54 |
| RCC__97 | 210.012354 | 98.486524 | whole_exome_illumina_coding_v1 | 0.38 |
| RCC__2 | 159.912441 | 69.844188 | whole_exome_illumina_coding_v1 | 0.52 |
| RCC__72 | 9.627872 | 94.01896 | whole_exome_illumina_coding_v1 | NA |
| RCC__5 | 8.689284 | 89.713424 | whole_exome_illumina_coding_v1 | 0.36 |
| RCC__54 | 0.007939 | 84.883698 | whole_exome_illumina_coding_v1 | NA |
| RCC__100 | 7.711684 | 105.962605 | whole_exome_illumina_coding_v1 | 0.34 |
| RCC__47 | 0.298156 | 95.4427 | whole_exome_illumina_coding_v1 | NA |
| RCC__66 | 8.71954 | 98.033649 | whole_exome_illumina_coding_v1 | 0.46 |
| RCC__43 | 105.603458 | 72.354112 | whole_exome_illumina_coding_v1 | 0.06 |
| RCC__12 | 162.560923 | 104.266666 | whole_exome_illumina_coding_v1 | 0.05 |
| RCC__24 | 166.047506 | 75.247762 | whole_exome_illumina_coding_v1 | 0.1 |
| RCC__40 | 154.736269 | 87.045058 | whole_exome_illumina_coding_v1 | 0.1 |
| RCC__8 | 154.801856 | 83.048353 | whole_exome_illumina_coding_v1 | NA |
| RCC__103 | 138.626523 | 96.365324 | whole_exome_illumina_coding_v1 | |
| RCC__26 | 159.566974 | 100.887491 | whole_exome_illumina_coding_v1 | 0.07 |
| RCC__95 | 143.956046 | 90.060356 | whole_exome_illumina_coding_v1 | 0.09 |
| RCC__17 | 129.343681 | 81.980679 | whole_exome_illumina_coding_v1 | 0.04 |
| RCC__22 | 144.076612 | 97.672268 | whole_exome_illumina_coding_v1 | 0.06 |
| RCC__28 | 162.443009 | 89.968028 | whole_exome_illumina_coding_v1 | 0.08 |
| RCC__29 | 150.205436 | 89.123637 | whole_exome_illumina_coding_v1 | NA |
| RCC__6 | 145.806274 | 83.646769 | whole_exome_illumina_coding_v1 | 0.07 |
| RCC__45 | 132.158193 | 79.179771 | whole_exome_illumina_coding_v1 | 0.06 |

| patient_id | absolute_inferred_ploidy | genome_doubling | exclusion_reason |
|---|---|---|---|
| RCC__20 | 1.78 | 0 | 0 |
| RCC__32 | 2.21 | 0 | 0 |
| RCC__62 | 1.83 | 0 | 0 |
| RCC__10 | 2 | 0 | 0 |
| RCC__11 | 3.56 | 1 | 0 |
| RCC__14 | 3.67 | 1 | 0 |
| RCC__25 | 1.99 | 0 | 0 |
| RCC__56 | 1.89 | 0 | 0 |
| RCC__79 | 1.96 | 0 | 0 |
| RCC__93 | 3 | 1 | 0 |
| RCC__115 | 1.64 | 0 | 0 |
| RCC__90 | 2.67 | 1 | 0 |
| RCC__96 | 1.8 | 0 | 0 |
| RCC__102 | 1.97 | 0 | 0 |
| RCC__58 | 1.81 | 0 | 0 |
| RCC__84 | 1.93 | 0 | 0 |
| RCC__85 | 4.08 | 1 | 0 |
| RCC__114 | 1.97 | 0 | 0 |
| RCC__117 | 1.87 | 0 | 0 |
| RCC__15 | 1.97 | 0 | 0 |
| RCC__68 | 1.86 | 0 | 0 |
| RCC__1 | 3.6 | 1 | 0 |
| RCC__106 | 1.9 | 0 | 0 |
| RCC__18 | 2.3 | 0 | 0 |
| RCC__21 | 3.39 | 1 | 0 |
| RCC__41 | 4.28 | 1 | 0 |
| RCC__50 | 1.81 | 0 | 0 |
| RCC__73 | 1.83 | 0 | 0 |
| RCC__39 | 1.92 | 0 | 0 |
| RCC__99 | 2.77 | 1 | 0 |
| RCC__105 | 2.06 | 0 | 0 |
| RCC__119 | 3.08 | 1 | 0 |
| RCC__27 | 1.93 | 0 | 0 |
| RCC__52 | 1.88 | 0 | 0 |
| RCC__97 | 2.2 | 0 | 0 |
| RCC__2 | 1.68 | 0 | DeathUnrelatedCancer |
| RCC__72 | NA | NA | LowCoverage |
| RCC__5 | 1.98 | 0 | LowCoverage |
| RCC__54 | NA | NA | LowCoverage |

TABLE 6A-continued

Whole exome sequencing metrics and inclusions/exclusions for patients in the discovery cohort

| | | | |
|---|---|---|---|
| RCC_100 | 2.01 | 0 | LowCoverage |
| RCC_47 | NA | NA | LowCoverage |
| RCC_66 | 2.16 | 0 | LowCoverage |
| RCC_43 | 2.43 | 0 | LowPurity |
| RCC_12 | 2.74 | 0 | LowPurity |
| RCC_24 | 2.46 | 0 | LowPurity |
| RCC_40 | 2.44 | 0 | LowPurity |
| RCC_8 | NA | NA | LowPurity |
| RCC_103 | | | LowPurity |
| RCC_26 | 2.96 | 0 | LowPurity |
| RCC_95 | 2.57 | 0 | LowPurity |
| RCC_17 | 3.61 | 1 | LowPurity |
| RCC_22 | 2.91 | 0 | LowPurity |
| RCC_28 | 2.45 | 0 | LowPurity |
| RCC_29 | NA | NA | LowPurity |
| RCC_6 | 2.69 | 0 | LowPurity |
| RCC_45 | 2.58 | 0 | LowPurity |

TABLE 6B

Clinical characteristics of patients receiving anti-PD1 therapy (nivolumab) in discovery cohort (N = 35) (All patients at wes of 1, nivolumab as drug)

| patient_id | sex | age | treatment_group | first_line | best_RECIST | max_tumor_change | os_days | os_censor | pfs_days | pfs_censor | cell_membrane_pdl1_0percent | cell_membrane_pdl1_1plus_percent | cell_membrane_pdl1_2plus_percent | cell_membrane_pdl1_3plus_percent | pdl1_positive_1percent | pdl1_positive_5percent | response_category |
|---|---|---|---|---|---|---|---|---|---|---|---|---|---|---|---|---|---|
| RCC_97 | MALE | 54 | 2 mg/kg | 0 | PD | 22 | 871 | 1 | 37 | 0 | 100 | 0 | 0 | 0 | 0 | 0 | no clinical benefit |
| RCC_52 | FEMALE | 63 | 10 mg/kg-N | 1 | SD | −5 | 995 | 1 | 246 | 0 | 100 | 0 | 0 | 0 | 0 | 0 | clinical benefit |
| RCC_27 | MALE | 59 | 0.3 mg/kg | 0 | PD | 36 | 968 | 1 | 35 | 0 | 68 | 30 | 2 | 0 | 1 | 1 | no clinical benefit |
| RCC_119 | MALE | 72 | 10 mg/kg | 0 | PR | −52 | 773 | 1 | 414 | 0 | 100 | 0 | 0 | 0 | 0 | 0 | clinical benefit |
| RCC_105 | MALE | 64 | 10 mg/kg | 0 | PD | 17 | 118 | 0 | 45 | 0 | 100 | 0 | 0 | 0 | 0 | 0 | no clinical benefit |
| RCC_39 | MALE | 72 | 0.3 mg/kg | 0 | PD | 13 | 306 | 0 | 37 | 0 | 100 | 0 | 0 | 0 | 0 | 0 | no clinical benefit |
| RCC_73 | MALE | 77 | 2 mg/kg | 0 | PD | 11 | 178 | 0 | 58 | 0 | 100 | 0 | 0 | 0 | 0 | 0 | clinical benefit |
| RCC_50 | FEMALE | 63 | 10 mg/kg-N | 1 | SD | −67 | 982 | 1 | 86 | 0 | 91 | 5 | 3 | 1 | 1 | 1 | clinical benefit |
| RCC_41 | MALE | 66 | 10 mg/kg | 0 | PD | 10 | 195 | 1 | 42 | 0 | 100 | 0 | 0 | 0 | 0 | 0 | clinical benefit |
| RCC_18 | MALE | 68 | 0.3 mg/kg | 0 | PD | 65 | 111 | 1 | 43 | 0 | NA | NA | NA | NA | NA | NA | no clinical benefit |
| RCC_1 | MALE | 49 | 10 mg/kg | 0 | PD | 24 | 43 | 1 | 38 | 0 | 100 | 0 | 0 | 0 | 0 | 0 | clinical benefit |
| RCC_68 | MALE | 69 | 0.3 mg/kg | 0 | PD | −4 | 740 | 0 | 39 | 0 | 100 | 0 | 0 | 0 | 0 | 0 | no clinical benefit |
| RCC_15 | FEMALE | 73 | 10 mg/kg-N | 1 | SD | −10 | 1013 | 0 | 663 | 0 | 99 | 1 | 0 | 0 | 0 | 0 | clinical benefit |
| RCC_114 | FEMALE | 57 | 0.3 mg/kg | 0 | PR | −51 | 340 | 1 | 208 | 0 | 100 | 0 | 0 | 0 | 0 | 0 | clinical benefit |
| RCC_84 | FEMALE | 55 | 0.3 mg/kg | 0 | SD | 8 | 680 | 0 | 88 | 0 | 95 | 5 | 0 | 0 | 0 | 0 | intermediate benefit |
| RCC_102 | MALE | 64 | 0.3 mg/kg | 0 | SD | 3 | 165 | 1 | 108 | 0 | 100 | 0 | 0 | 0 | 0 | 0 | intermediate benefit |
| RCC_96 | FEMALE | 75 | 2 mg/kg | 0 | PD | 12 | 582 | 1 | 37 | 0 | 100 | 0 | 0 | 0 | 0 | 0 | no clinical |

TABLE 6B-continued

Clinical characteristics of patients receiving anti-PD1 therapy (nivolumab) in discovery cohort (N = 35) (All patients at wes of 1, nivolumab as drug)

| patient_id | sex | age | treatment_group | first_line | best_RECIST | max_tumor_change | os_days | os_censor | pfs_days | pfs_censor | cell_membrane_pdl1_0percent | cell_membrane_pdl1_1plus_percent | cell_membrane_pdl1_2plus_percent | cell_membrane_pdl1_3plus_percent | pdl1_positive_1percent | pdl1_positive_5percent | response_category |
|---|---|---|---|---|---|---|---|---|---|---|---|---|---|---|---|---|---|
| RCC_90 | MALE | 54 | 0.3 mg/kg | 0 | PD | 57 | 499 | 0 | 36 | 0 | 25 | 35 | 20 | 20 | 1 | 1 | benefit |
| RCC_115 | MALE | 60 | 2 mg/kg | 0 | SD | 15 | 366 | 1 | 87 | 0 | 100 | 0 | 0 | 0 | 0 | 0 | no clinical benefit |
| RCC_93 | MALE | 64 | 10 mg/kg | 0 | PR | −43 | 684 | 0 | 500 | 0 | 100 | 0 | 0 | 0 | 0 | 0 | intermediate benefit |
| RCC_79 | FEMALE | 61 | 2 mg/kg | 0 | SD | 9 | 873 | 1 | 130 | 0 | 100 | 0 | 0 | 0 | 0 | 0 | clinical benefit |
| RCC_56 | FEMALE | 62 | 2 mg/kg | 0 | SD | 17 | 992 | 1 | 81 | 0 | 100 | 0 | 0 | 0 | 0 | 0 | intermediate benefit |
| RCC_25 | FEMALE | 72 | 10 mg/kg-N | 1 | PD | 16 | 167 | 0 | 39 | 0 | 100 | 0 | 0 | 0 | 0 | 0 | no clinical benefit |
| RCC_14 | MALE | 59 | 10 mg/kg-N | 1 | PR | −86 | 1025 | 1 | 541 | 0 | 100 | 0 | 0 | 0 | 0 | 0 | clinical benefit |
| RCC_11 | MALE | 50 | 10 mg/kg-N | 1 | SD | 9 | 1024 | 1 | 122 | 0 | 100 | 0 | 0 | 0 | 0 | 0 | intermediate benefit |
| RCC_62 | FEMALE | 48 | 10 mg/kg | 0 | SD | 7 | 106 | 1 | 87 | 0 | NA | NA | NA | NA | NA | NA | intermediate benefit |
| RCC_21 | MALE | 64 | 10 mg/kg | 0 | SD | −13 | 349 | 1 | 43 | 1 | 96 | 4 | 0 | 0 | 1 | 0 | intermediate benefit |
| RCC_106 | FEMALE | 61 | 2 mg/kg | 0 | PR | −61 | 870 | 1 | 821 | 1 | 100 | 0 | 0 | 0 | 0 | 0 | clinical benefit |
| RCC_117 | MALE | 58 | 10 mg/kg-N | 1 | SD | −10 | 64 | 1 | 38 | 1 | 98 | 2 | 0 | 0 | 0 | 0 | intermediate benefit |
| RCC_85 | MALE | 36 | 2 mg/kg | 0 | SD | −12 | 712 | 0 | 42 | 1 | 95 | 2 | 2 | 1 | 0 | 0 | intermediate benefit |
| RCC_58 | FEMALE | 55 | 2 mg/kg | 0 | PR | −50 | 988 | 1 | 687 | 1 | 20 | 25 | 25 | 30 | 1 | 1 | clinical benefit |
| RCC_10 | FEMALE | 64 | 10 mg/kg-N | 1 | SD | 0 | 1058 | 0 | 173 | 1 | 97 | 3 | 0 | 0 | 1 | 0 | intermediate benefit |
| RCC_32 | MALE | 65 | 10 mg/kg-N | 1 | SD | −13 | 240 | 1 | 213 | 1 | 100 | 0 | 0 | 0 | 0 | 0 | clinical benefit |
| RCC_20 | MALE | 76 | 10 mg/kg-N | 1 | CR | −100 | 1065 | 1 | 1022 | 1 | 100 | 0 | 0 | 0 | 0 | 0 | clinical benefit |
| RCC_99 | MALE | 50 | 2 mg/kg | 0 | PD | NA | 41 | 0 | 41 | 0 | 97 | 3 | 0 | 0 | 1 | 0 | no clinical benefit |

TABLE 6C

Summary of mutational burden in the discovery cohort (N = 35)

| patient_id | all_muts | all_nonsyns | all_syns | frameshift_indels | muts_clonal | muts_subclonal | muts_uneval | nonsyns_clonal | nonsyns_subclonal | nonsyns_uneval |
|---|---|---|---|---|---|---|---|---|---|---|
| RCC_20 | 80 | 50 | 30 | 4 | 51 | 18 | 11 | 33 | 13 | 4 |
| RCC_32 | 125 | 89 | 36 | 9 | 103 | 12 | 10 | 77 | 10 | 2 |
| RCC_62 | 110 | 82 | 28 | 1 | 68 | 23 | 19 | 57 | 17 | 8 |
| RCC_10 | 135 | 85 | 50 | 7 | 84 | 26 | 25 | 65 | 17 | 3 |
| RCC_11 | 100 | 63 | 37 | 4 | 64 | 25 | 11 | 44 | 18 | 1 |
| RCC_14 | 128 | 86 | 42 | 5 | 107 | 11 | 10 | 75 | 9 | 2 |
| RCC_25 | 157 | 113 | 44 | 2 | 107 | 33 | 17 | 79 | 27 | 7 |
| RCC_56 | 125 | 102 | 23 | 8 | 55 | 62 | 8 | 43 | 54 | 5 |
| RCC_79 | 78 | 54 | 24 | 6 | 47 | 22 | 9 | 35 | 16 | 3 |
| RCC_93 | 125 | 91 | 34 | 4 | 101 | 17 | 7 | 78 | 12 | 1 |
| RCC_115 | 90 | 64 | 26 | 4 | 52 | 26 | 12 | 39 | 22 | 3 |
| RCC_90 | 140 | 102 | 38 | 5 | 96 | 39 | 5 | 70 | 30 | 2 |
| RCC_96 | 255 | 157 | 98 | 10 | 83 | 107 | 65 | 61 | 83 | 13 |
| RCC_102 | 166 | 115 | 51 | 8 | 92 | 44 | 30 | 73 | 38 | 4 |
| RCC_58 | 82 | 60 | 22 | 2 | 39 | 33 | 10 | 32 | 25 | 3 |
| RCC_84 | 117 | 87 | 30 | 9 | 71 | 28 | 18 | 59 | 22 | 6 |
| RCC_85 | 83 | 52 | 31 | 3 | 72 | 0 | 11 | 50 | 0 | 2 |
| RCC_114 | 83 | 59 | 24 | 2 | 65 | 10 | 8 | 48 | 8 | 3 |
| RCC_117 | 86 | 65 | 21 | 4 | 71 | 14 | 1 | 53 | 11 | 1 |
| RCC_15 | 110 | 75 | 35 | 5 | 77 | 18 | 15 | 58 | 10 | 7 |
| RCC_68 | 132 | 102 | 30 | 4 | 43 | 83 | 6 | 32 | 68 | 2 |
| RCC_1 | 84 | 61 | 23 | 4 | 66 | 11 | 7 | 50 | 9 | 2 |
| RCC_106 | 104 | 76 | 28 | 5 | 70 | 26 | 8 | 50 | 21 | 5 |
| RCC_18 | 81 | 61 | 20 | 2 | 51 | 29 | 1 | 40 | 21 | 0 |
| RCC_21 | 128 | 82 | 46 | 6 | 92 | 21 | 15 | 68 | 13 | 1 |
| RCC_41 | 102 | 73 | 29 | 5 | 87 | 5 | 10 | 65 | 4 | 4 |
| RCC_50 | 171 | 126 | 45 | 10 | 122 | 31 | 18 | 92 | 20 | 14 |
| RCC_73 | 70 | 45 | 25 | 0 | 36 | 29 | 5 | 22 | 23 | 0 |
| RCC_39 | 126 | 86 | 40 | 0 | 117 | 2 | 7 | 81 | 2 | 3 |
| RCC_99 | 155 | 102 | 53 | 6 | 64 | 57 | 34 | 49 | 48 | 5 |
| RCC_105 | 152 | 105 | 47 | 5 | 118 | 18 | 16 | 87 | 15 | 3 |
| RCC_119 | 97 | 62 | 35 | 4 | 81 | 2 | 14 | 60 | 2 | 0 |
| RCC_27 | 128 | 98 | 30 | 8 | 78 | 41 | 9 | 63 | 32 | 3 |
| RCC_52 | 125 | 94 | 31 | 8 | 94 | 15 | 16 | 77 | 13 | 4 |
| RCC_97 | 116 | 82 | 34 | 5 | 77 | 26 | 13 | 62 | 20 | 0 |

TABLE 6D

Truncating PBRM1 alterations in patients discovery cohort passing whole exome quality control (N = 35)

| patient_id | Hugo_Symbol | PBRM1_mean_coverage | Chromosome | Start_position | End_position | Variant_Classification | Reference_Allele | Tumor_Seq_Allele1 | Tumor_Seq_Allele2 |
|---|---|---|---|---|---|---|---|---|---|
| RCC_20 | PBRM1 | 28.98 | 3 | 52649455 | 52649456 | Frame_Shift_Ins | - | - | T |
| RCC_32 | NA | 120.85 | NA | NA | NA | NA | | | |
| RCC_62 | PBRM1 | 131.16 | 3 | 52613062 | 52613068 | Splice_Site | ACACTCA | ACACTCA | - |
| RCC_10 | PBRM1 | 89.9 | 3 | 52623120 | 52623120 | Frame_Shift_Del | G | G | - |
| RCC_11 | NA | 62.73 | NA | NA | NA | NA | | | |
| RCC_14 | PBRM1 | 131.63 | 3 | 52623201 | 52623201 | Frame_Shift_Del | G | G | - |
| RCC_25 | NA | 124.35 | NA | NA | NA | NA | | | |
| RCC_56 | NA | 221.56 | NA | NA | NA | NA | | | |
| RCC_79 | PBRM1 | 67.19 | 3 | 52621487 | 52621487 | Frame_Shift_Del | T | T | - |

TABLE 6D-continued

Truncating PBRM1 alterations in patients discovery cohort passing whole exome quality control (N = 35)

| RCC_93 | PBRM1 | 173.78 | 3 | 52651277 | 52651277 | Splice_Site | C | C | T |
|---|---|---|---|---|---|---|---|---|---|
| RCC_115 | NA | 115.51 | NA | NA | NA | NA | | | |
| RCC_90 | NA | 124.87 | NA | NA | NA | NA | | | |
| RCC_96 | PBRM1 | 164.39 | 3 | 52643489 | 52643489 | Frame_Shift_Del | A | A | - |
| RCC_102 | PBRM1 | 266.4 | 3 | 52663052 | 52663052 | Splice_Site | C | C | T |
| RCC_58 | NA | 95.31 | NA | NA | NA | NA | | | |
| RCC_84 | PBRM1 | 130.86 | 3 | 52696272 | 52696272 | Frame_Shift_Del | T | T | - |
| RCC_85 | NA | 47.52 | NA | NA | NA | NA | NA | NA | NA |
| RCC_114 | PBRM1 | 111.22 | 3 | 52662964 | 52662964 | Frame_Shift_Del | A | A | - |
| RCC_117 | PBRM1 | 146.69 | 3 | 52643375 | 52643375 | Nonsense_Mutation | G | G | A |
| RCC_15 | PBRM1 | 94.84 | 3 | 52613194 | 52613194 | Nonsense_Mutation | C | C | A |
| RCC_68 | NA | 100.73 | NA | NA | NA | NA | | | |
| RCC_1 | NA | 138.81 | NA | NA | NA | NA | | | |
| RCC_106 | PBRM1 | 155.18 | 3 | 52620610 | 52620614 | Frame_Shift_Del | ATTTT | ATTTT | - |
| RCC_18 | PBRM1 | 126.07 | 3 | 52678748 | 52678748 | Nonsense_Mutation | C | C | A |
| RCC_21 | PBRM1 | 125.64 | 3 | 52613210 | 52613210 | Frame_Shift_Del | T | T | - |
| RCC_41 | NA | 123.22 | NA | NA | NA | NA | | | |
| RCC_50 | PBRM1 | 135.79 | 3 | 52712515 | 52712515 | Splice_Site | C | C | T |
| RCC_73 | NA | 181.65 | NA | NA | NA | NA | | | |
| RCC_39 | NA | 130.38 | NA | NA | NA | NA | | | |
| RCC_99 | NA | 28.13 | NA | NA | NA | NA | | | |
| RCC_105 | NA | 146.47 | NA | NA | NA | NA | | | |
| RCC_119 | PBRM1 | 28.57 | 3 | 52682459 | 52682459 | Splice_Site | C | C | G |
| RCC_27 | PBRM1 | 248.99 | 3 | 52598081 | 52598101 | In_Frame_Del | TCATCATCTACCACTTTAGCA | TCATCATCTACCACTTTAGCA | - |
| RCC_52 | PBRM1 | 97.9 | 3 | 52613205 | 52613205 | Frame_Shift_Del | T | T | - |
| RCC_97 | PBRM1 | 119.39 | 3 | 52663008 | 52663008 | Nonsense_Mutation | C | C | A |

TABLE 6D-continued

Truncating PBRM1 alterations in patients discovery cohort passing whole exome quality control (N = 35)

| patient_id | Protein_Change | Variant_Type | i_tumor_f | t_alt_count | t_ref_count | Indel_clonal | Caller |
|---|---|---|---|---|---|---|---|
| RCC_20 | p.H627fs | INS | 0.363636364 | 8 | 14 | 1 | strelka, indelocator |
| RCC_32 | NA | NA | NA | NA | NA | NA | NA |
| RCC_62 | | DEL | 0.17370892 | 37 | 176 | 0 | strelka |
| RCC_10 | p.I992fs | DEL | 0.55 | 55 | 45 | 1 | strelka, indelocator |
| RCC_11 | NA | NA | NA | NA | NA | NA | NA |
| RCC_14 | p.D965fs | DEL | 0.25 | 15 | 45 | 1 | strelka, indelocator |
| RCC_25 | NA | NA | NA | NA | NA | NA | NA |
| RCC_56 | NA | NA | NA | NA | NA | NA | NA |
| RCC_79 | p.N1017fs | DEL | 0.464285714 | 13 | 15 | 1 | strelka, indelocator |
| RCC_93 | | SNP | 0.12766 | 6 | 41 | 1 | NA |
| RCC_115 | NA | NA | NA | NA | NA | NA | NA |
| RCC_90 | NA | NA | NA | NA | NA | NA | NA |
| RCC_96 | p.S818fs | DEL | 0.402654867 | 91 | 135 | 1 | strelka, indelocator |
| RCC_102 | | SNP | 0.235849 | 25 | 81 | 1 | NA |
| RCC_58 | NA | NA | NA | NA | NA | NA | NA |
| RCC_84 | p.K135fs | DEL | 0.171428571 | 12 | 58 | 1 | strelka, indelocator |
| RCC_85 | NA | NA | NA | NA | NA | NA | NA |
| RCC_114 | p.N463fs | DEL | 0.108695652 | 10 | 82 | 1 | strelka, indelocator |
| RCC_117 | p.Q809* | SNP | 0.288 | 36 | 89 | 1 | NA |
| RCC_15 | p.E1105* | SNP | 0.53 | 53 | 47 | 1 | NA |
| RCC_68 | NA | NA | NA | NA | NA | NA | NA |
| RCC_1 | NA | NA | NA | NA | NA | NA | NA |
| RCC_106 | p.KI1087fs | DEL | 0.067137809 | 19 | 264 | 0 | strelka, indelocator |
| RCC_18 | p.E291* | SNP | 0.150943 | 8 | 45 | 1 | NA |
| RCC_21 | p.K1146fs | DEL | 0.441666667 | 53 | 67 | 1 | strelka, indelocator |
| RCC_41 | NA | NA | NA | NA | NA | NA | NA |
| RCC_50 | | SNP | 0.213592 | 22 | 81 | 1 | NA |
| RCC_73 | NA | NA | NA | NA | NA | NA | NA |
| RCC_39 | NA | NA | NA | NA | NA | NA | NA |
| RCC_99 | NA | NA | NA | NA | NA | NA | NA |
| RCC_105 | NA | NA | NA | NA | NA | NA | NA |
| RCC_119 | | SNP | 0.666667 | 10 | 5 | 1 | NA |

TABLE 6D-continued

Truncating PBRM1 alterations in patients discovery cohort passing whole exome quality control (N = 35)

| RCC_27 | p. AKVVDDE1249del | DEL | 0.15 | 14 | 77 | 1 | indelocator |
| RCC_52 | p.D1148fs | DEL | 0.235955056 | 21 | 68 | 1 | strelka, indelocator |
| RCC_97 | p.E417* | SNP | 0.278481 | 22 | 57 | 1 | NA |

TABLE 6E

Sequencing Metrics and Inclusion/Exclusion Criteria for Whole Exome Sequencing in Validation Cohort (N = 67)

| patient_id | sequencing_type | tumor_mtc | normal_mtc | PBRM1_mean_cov | bait_set_or_panel_type | absolute_inferred_purity | absolute_inferred_ploidy | genome_doubling | exclusion_reason |
|---|---|---|---|---|---|---|---|---|---|
| CA8808_T1 | WES | 123.07315 | 103.475727 | NA | whole_exome_agilent_1 | 0.48 | 1.95 | 0 | 0 |
| KA4076_T1 | WES | 126.229037 | 120.209259 | NA | whole_exome_agilent_1 | 0.6 | 2 | 0 | 0 |
| KE5236_T1 | WES | 132.886302 | 140.196056 | NA | whole_exome_agilent_1 | 0.32 | 1.99 | 0 | 0 |
| KE6262_T1 | WES | 99.539361 | 106.858872 | NA | whole_exome_agilent_1 | 0.13 | 2.27 | 1 | 0 |
| MC1838_T1 | WES | 149.730846 | 118.307339 | NA | whole_exome_agilent_1 | 0.38 | 1.95 | 0 | 0 |
| RCC-PD_005 | WES | 125.608438 | 102.090575 | NA | whole_exome_illumina_coding_v1 | 0.47 | 1.82 | 0 | 0 |
| RCC-PD_007 | WES | 141.661729 | 101.362659 | NA | whole_exome_illumina_coding_v1 | 0.57 | 1.82 | 0 | 0 |
| RCC-PD_010 | WES | 131.1804 | 84.152599 | NA | whole_exome_illumina_coding_v1 | 0.55 | 1.76 | 0 | 0 |
| RCC-PD_011 | WES | 104.135516 | 82.878525 | NA | whole_exome_illumina_coding_v1 | 0.32 | 2.08 | 0 | 0 |
| RCC-PD_012 | WES | 150.48938 | 87.549415 | NA | whole_exome_illumina_coding_v1 | 0.39 | 2.01 | 0 | 0 |
| RCC-PD_013 | WES | 145.082205 | 91.170952 | NA | whole_exome_illumina_coding_v1 | 0.22 | 3.44 | 1 | 0 |
| RCC-PD_014 | WES | 127.306107 | 78.539083 | NA | whole_exome_illumina_coding_v1 | 0.25 | 4.02 | 1 | 0 |
| RCC-PD_015 | WES | 105.708638 | 93.290512 | NA | whole_exome_illumina_coding_v1 | 0.36 | 2.1 | 0 | 0 |
| RCC-PD_018 | WES | 145.443729 | 95.372761 | NA | whole_exome_illumina_coding_v1 | 0.61 | 1.84 | 0 | 0 |
| RCC-PD_019 | WES | 148.823821 | 87.774525 | NA | whole_exome_illumina_coding_v1 | 0.42 | 1.97 | 0 | 0 |
| RCC-PD_020 | WES | 151.788377 | 102.972091 | NA | whole_exome_illumina_coding_v1 | 0.18 | 1.86 | 0 | 0 |
| RCC-PD_021 | WES | 159.181781 | 95.98438 | NA | whole_exome_illumina_coding_v1 | 0.58 | 1.9 | 0 | 0 |
| RCC-PD_022 | WES | 148.651377 | 98.276519 | NA | whole_exome_illumina_coding_v1 | 0.53 | 1.97 | 0 | 0 |
| RCC-PD_023 | WES | 135.431357 | 86.807511 | NA | whole_exome_illumina_coding_v1 | 0.19 | 2.65 | 1 | 0 |
| RCC-PD_024 | WES | 92.006306 | 83.700183 | NA | whole_exome_illumina_coding_v1 | 0.27 | 2.01 | 0 | 0 |
| RCC-PD_025 | WES | 74.164294 | 48.102291 | NA | whole_exome_illumina_coding_v1 | 0.35 | 1.99 | 0 | 0 |
| RCC-PD_026 | WES | 166.502187 | 89.436443 | NA | whole_exome_illumina_coding_v1 | 0.76 | 1.98 | 0 | 0 |
| RCC.PD1.DNA.1026 | WES | 136.955167 | 87.050978 | NA | whole_exome_agilent_1.1_refseq_plus_3_boosters | 0.26 | 2.15 | 0 | 0 |
| RCC.PD1.DNA.1101 | WES | 92.348009 | 81.023695 | NA | whole_exome_agilent_1.1_refseq_plus_3_boosters | 0.3 | 1.97 | 0 | 0 |
| RCC.PD1.DNA.1137 | WES | 71.474257 | 96.238769 | NA | whole_exome_agilent_1.1_refseq_plus_3_boosters | 0.31 | 3.43 | 1 | 0 |
| RCC.PD1.DNA.944 | WES | 126.472115 | 95.64198 | NA | whole_exome_agilent_1.1_refseq_plus_3_boosters | 0.66 | 1.89 | 0 | 0 |
| RCC.PD1.DNA.949 | WES | 101.276419 | 96.351667 | NA | whole_exome_agilent_1.1_refseq_plus_3_boosters | 0.43 | 3.91 | 1 | 0 |
| VA1008_T1 | WES | 142.542157 | 89.429498 | NA | whole_exome_agilent_1 | 0.11 | 1.99 | 0 | 0 |
| PGDX2818T_Ex-RCC032PT1 | WES | 55.34115691 | 79.77112838 | NA | NA | NA | NA | NA | 0 |
| PGDX2817T_Ex-RCC031PT1 | WES | 103.1856033 | 69.5272945 | NA | NA | NA | NA | NA | 0 |
| PGDX2816T_Ex-RCC030PT1 | WES | 97.77199375 | 84.39103979 | NA | NA | NA | NA | NA | 0 |
| PGDX2815T_Ex-RCC029PT1 | WES | 66.32040544 | 54.48433181 | NA | NA | NA | NA | NA | 0 |
| PGDX2814T_Ex-RCC028PT1 | WES | 118.1997689 | 73.44450094 | NA | NA | NA | NA | NA | 0 |
| PGDX2813T_Ex-RCC027PT1 | WES | 33.35986673 | 65.51616024 | NA | NA | NA | NA | NA | 0 |

TABLE 6E-continued

Sequencing Metrics and Inclusion/Exclusion Criteria for Whole Exome Sequencing in Validation Cohort (N = 67)

| patient_id | sequencing_type | tumor_mtc | normal_mtc | PBRM1_mean_cov | bait_set_or_panel_type | absolute_inferred_purity | absolute_inferred_ploidy | genome_doubling | exclusion_reason |
|---|---|---|---|---|---|---|---|---|---|
| PGDX2811T_Ex-RCC025PT1 | WES | 151.2973078 | 52.69614078 | NA | NA | NA | NA | NA | 0 |
| RCC-PD_029 | WES | NA | 89.149597 | NA | whole_exome_illumina_coding_v1 | NA | NA | NA | FailedSequencing |
| BL5166_T1 | WES | 145.877429 | 122.453144 | 197.8 | whole_exome_agilent_1 | 0.07 | 1.91 | 0 | 0 |
| RCC-PD_030 | WES | 129.113198 | 117.952235 | NA | whole_exome_illumina_coding_v1 | 0.38 | 1.94 | 0 | MixedResponse |
| RCC-PD_009 | WES | 122.598167 | 87.563055 | NA | whole_exome_illumina_coding_v1 | 0.41 | 1.99 | 0 | PapillaryRCC |
| RENAL-15349_CCPM_0600855 | WES | 191.128712 | 164.148594 | NA | whole_exome_illumina_coding_v1 | 0.1 | 4.23 | 1 | 0 |
| RENAL-15349_CCPM_0600862 | WES | 126.035686 | 86.198512 | 144.04 | whole_exome_illumina_coding_v1 | 0.07 | 2 | 0 | 0 |
| RCC-IM_001 | WES | 179.289403 | 86.748087 | NA | whole_exome_illumina_coding_v1 | 0.41 | 1.51 | 0 | 0 |
| RCC-IM_002 | WES | 70.427352 | 82.150509 | NA | whole_exome_illumina_coding_v1 | 0.45 | 1.65 | 0 | 0 |
| RCC-IM_003 | WES | 160.061412 | 172.704074 | NA | whole_exome_illumina_coding_v1 | NA | NA | NA | NonClearCellRCC |
| RCC_281066 | WES | 80.371008 | 89.496933 | NA | whole_exome_illumina_coding_v1 | 0.44 | 1.89 | 0 | 0 |
| RCC_371982 | WES | 93.846727 | 91.06197 | NA | whole_exome_illumina_coding_v1 | 0.48 | 2.09 | 0 | 0 |
| RCC_390392 | WES | 78.227866 | 116.306601 | NA | whole_exome_illumina_coding_v1 | 0.46 | 1.92 | 0 | 0 |
| RCC_470874 | WES | 179.545671 | 92.161197 | NA | whole_exome_illumina_coding_v1 | 0.45 | 1.77 | 0 | 0 |
| RCC_472770 | WES | 97.99001 | 81.592339 | NA | whole_exome_illumina_coding_v1 | 0.39 | 1.86 | 0 | 0 |
| RCC_504642 | WES | 182.31248 | 116.982034 | NA | whole_exome_illumina_coding_v1 | 0.47 | 2.05 | 0 | 0 |
| RCC_509214 | WES | 129.146039 | 114.189746 | NA | whole_exome_illumina_coding_v1 | 0.57 | 1.89 | 0 | 0 |
| RCC_51974086 | WES | 159.511692 | 69.797316 | NA | whole_exome_illumina_coding_v1 | 0.78 | 1.91 | 0 | 0 |
| RCC_554652 | WES | 223.859717 | 93.016058 | NA | whole_exome_illumina_coding_v1 | 0.39 | 2.92 | 1 | 0 |
| MCA1 | targeted_panel | NA | NA | NA | Caris Molecular Intelligence + 600 gene NGS-2015 | NA | NA | NA | 0 |
| MCA2 | targeted_panel | NA | NA | NA | FoundationOne- (315 genes, 28 introns) 2014 | NA | NA | NA | 0 |
| MCA3 | targeted_panel | NA | NA | NA | Caris Molecular Intelligence + 600 gene NGS-2015 | NA | NA | NA | 0 |
| MCA4 | targeted_panel | NA | NA | NA | Caris Molecular Intelligence + 600 gene NGS-2016 | NA | NA | NA | 0 |
| MCA5 | targeted_panel | NA | NA | NA | FoundationOne- (236 genes, 47 introns) 2014 | NA | NA | NA | 0 |
| MCA6 | targeted_panel | NA | NA | NA | Caris Molecular Intelligence + 600 gene NGS-2016 | NA | NA | NA | 0 |
| MCA7 | targeted_panel | NA | NA | NA | FoundationOne- (236 genes, 47 introns) 2014 | NA | NA | NA | 0 |
| MCA8 | targeted_panel | NA | NA | NA | Caris Molecular Intelligence + 600 gene NGS-2016 | NA | NA | NA | 0 |
| MCA9 | targeted_panel | NA | NA | NA | Caris Molecular Intelligence + 600 gene NGS-2017 | NA | NA | NA | 0 |
| MCA10 | targeted_panel | NA | NA | NA | Caris Molecular | NA | NA | NA | 0 |

TABLE 6E-continued

Sequencing Metrics and Inclusion/Exclusion Criteria for Whole Exome Sequencing in Validation Cohort (N = 67)

| patient_id | sequencing type | tumor_mtc | normal_mtc | PBRM1 mean cov | bait_set_or_panel_type | absolute_inferred_purity | absolute_inferred_ploidy | genome_doubling | exclusion_reason |
|---|---|---|---|---|---|---|---|---|---|
| MCA11 | targeted_panel | NA | NA | NA | Intelligence + 600 gene NGS-2016 | NA | NA | NA | 0 |
| MCA12 | targeted_panel | NA | NA | NA | FoundationOne- (315 genes, 28 introns) 2016 | NA | NA | NA | 0 |
| MCA13 | targeted_panel | NA | NA | NA | Caris Molecular Intelligence + 600 gene NGS-2015 | NA | NA | NA | 0 |
| MCA14 | targeted_panel | NA | NA | NA | FoundationOne- (236 genes, 47 introns) 2014 | NA | NA | NA | 0 |
|  |  |  |  |  | Caris Molecular Intelligence + 600 gene NGS-2016 |  |  |  |  |

TABLE 6F

Clinical information for immune checkpoint-treated patients in validation cohort (N = 63)

| patient_id | drug | wes | best_recist | sex | age | first_line | max_tumor_change | histology | os_days | os_censor | pfs_days | pfs_censor | response_category |
|---|---|---|---|---|---|---|---|---|---|---|---|---|---|
| CA8808 | nivolumab | 1 | PR | MALE | 62 | 0 | −55 | clear-cell | 560 | 1 | 558 | 0 | clinical benefit |
| KA4076 | nivolumab | 1 | PD | FEMALE | 61 | 0 | 59 | clear-cell | 727 | 0 | 107 | 0 | intermediate benefit |
| KE5236 | nivolumab | 1 | PD | MALE | 58 | 0 | 70 | clear-cell | 997 | 1 | 165 | 0 | intermediate benefit |
| KE6262 | nivolumab | 1 | PR | MALE | 68 | 0 | −60 | clear-cell | 903 | 1 | 163 | 0 | clinical benefit |
| MC1838 | nivolumab | 1 | PD | MALE | 64 | 0 | 93 | clear-cell | 622 | 0 | 60 | 0 | no clinical benefit |
| RCC-PD_005 | nivolumab | 1 | PD | MALE | 62 | 0 | NA | clear-cell | 277 | 1 | 168 | 0 | intermediate benefit |
| RCC-PD_007 | nivolumab + ipilimumab | 1 | PR | MALE | 60 | 1 | −42 | clear-cell | 448 | 1 | 448 | 1 | clinical benefit |
| RCC-PD_010 | nivolumab + ipilimumab | 1 | CR | MALE | 51 | 1 | −100 | clear-cell | 454 | 1 | 454 | 1 | clinical benefit |
| RCC-PD_011 | nivolumab | 1 | PD | MALE | 40 | 1 | −37 | clear-cell | 327 | 0 | 205 | 0 | intermediate benefit |
| RCC-PD_012 | atezolizumab | 1 | PD | MALE | 67 | 1 | 22.7 | clear-cell | 581 | 1 | 61 | 0 | no clinical benefit |
| RCC-PD_013 | nivolumab + ipilimumab | 1 | PR | MALE | 66 | 1 | −32 | clear-cell | 399 | 1 | 399 | 1 | clinical benefit |
| RCC-PD_014 | nivolumab + ipilimumab | 1 | SD | FEMALE | 68 | 1 | −5 | clear-cell | 433 | 1 | 433 | 1 | clinical benefit |
| RCC-PD_015 | nivolumab | 1 | PD | MALE | 71 | 0 | 6 | clear-cell | 814 | 0 | 105 | 0 | intermediate benefit |
| RCC-PD_018 | nivolumab | 1 | PR | FEMALE | 69 | 0 | −82 | clear-cell | 1189 | 0 | 672 | 0 | clinical benefit |
| RCC-PD_019 | nivolumab | 1 | SD | MALE | 60 | 0 | −11 | clear-cell | 230 | 1 | 220 | 0 | clinical benefit |
| RCC-PD_020 | nivolumab | 1 | PD | FEMALE | 64 | 0 | NA | clear-cell | 203 | 1 | 47 | 0 | no clinical benefit |
| RCC-PD_021 | nivolumab | 1 | PD | FEMALE | 63 | 0 | NA | clear-cell | 185 | 0 | 68 | 0 | no clinical benefit |
| RCC-PD_022 | nivolumab | 1 | PD | FEMALE | 66 | 0 | NA | clear-cell | 247 | 1 | 80 | 0 | no clinical benefit |
| RCC-PD_023 | atezolizumab | 1 | PR | MALE | 69 | 1 | −88 | clear-cell | 637 | 1 | 637 | 1 | clinical benefit |
| RCC-PD_024 | nivolumab | 1 | PD | MALE | 52 | 0 | 30 | clear-cell | 304 | 0 | 41 | 0 | no clinical benefit |
| RCC-PD_025 | nivolumab | 1 | SD | MALE | 74 | 0 | −23 | clear-cell | 1724 | 1 | 333 | 0 | clinical benefit |
| RCC-PD_026 | nivolumab | 1 | SD | FEMALE | 70 | 0 | 20 | clear-cell | 377 | 1 | 171 | 0 | intermediate benefit |
| RCC.PD1.DNA.1026 | nivolumab | 1 | CR | MALE | 60 | 0 | −100 | clear-cell | 1442 | 1 | 949 | 1 | clinical benefit |
| RCC.PD1.DNA.1101 | nivolumab | 1 | SD | MALE | 67 | 0 | 4 | clear-cell | 440 | 0 | 163 | 0 | intermediate benefit |
| RCC.PD1.DNA.1137 | nivolumab | 1 | SD | FEMALE | 61 | 0 | 16 | clear-cell | 1584 | 1 | 119 | 0 | intermediate benefit |
| RCC.PD1.DNA.944 | nivolumab | 1 | PD | MALE | 47 | 0 | 37 | clear-cell | 470 | 0 | 36 | 0 | no clinical benefit |
| RCC.PD1.DNA.949 | nivolumab | 1 | PR | FEMALE | 60 | 0 | −37 | clear-cell | 364 | 0 | 246 | 0 | clinical benefit |
| VA1008 | nivolumab + ipilimumab | 1 | PR | MALE | 76 | 0 | −96 | clear-cell | 1135 | 1 | 1135 | 1 | clinical benefit |
| PGDX2818T_Ex-RCC032PT1 | nivolumab | 1 | CR | MALE | 51 | 0 | −100 | clear-cell | 2533 | 1 | 2533 | 1 | clinical benefit |
| PGDX2817T_Ex-RCC031PT1 | nivolumab | 1 | PD | MALE | 43 | 0 | 42 | clear-cell | 892 | 0 | 112 | 0 | intermediate benefit |
| PGDX2816T_Ex-RCC030PT1 | nivolumab | 1 | PR | MALE | 58 | 0 | −71 | clear-cell | 1755 | 1 | 1124 | 0 | clinical benefit |
| PGDX2815T_Ex-RCC029PT1 | nivolumab | 1 | PD | FEMALE | 35 | 0 | 52 | clear-cell | 501 | 0 | 59 | 0 | no clinical benefit |
| PGDX2814T_Ex-RCC028PT1 | nivolumab | 1 | PD | FEMALE | 67 | 0 | 33 | clear-cell | 148 | 0 | 51 | 0 | no clinical benefit |
| PGDX2813T_Ex-RCC027PT1 | nivolumab | 1 | CR | MALE | 68 | 0 | −100 | clear-cell | 2208 | 0 | 2012 | 0 | clinical benefit |
| PGDX2811T_Ex-RCC025PT1 | nivolumab | 1 | PR | MALE | 73 | 0 | −90 | clear-cell | 2810 | 1 | 2810 | 1 | clinical benefit |
| BL5166_T1 | nivolumab | 1 | SD | MALE | 63 | 0 | −11 | clear-cell | 622 | 0 | 156 | 0 | intermediate benefit |
| RENAL-15349_CCPM_0600855 | nivolumab | 1 | PR | MALE | 67 | 0 | −37 | clear-cell | 499 | 1 | 499 | 1 | clinical benefit |

TABLE 6F-continued

Clinical information for immune checkpoint-treated patients in validation cohort (N = 63)

| patient_id | drug | wes | best_recist | sex | age | first_line | max_tumor_change | histology | os_days | os_censor | pfs_days | pfs_censor | response_category |
|---|---|---|---|---|---|---|---|---|---|---|---|---|---|
| RENAL-15349_CCPM_0600862 | nivolumab | 1 | PD | MALE | 73 | 0 | NA | clear-cell | 293 | 1 | 66 | 0 | no clinical benefit |
| RCC-IM_001 | nivolumab | 1 | PR | NA | 40 | 0 | −39 | clear-cell | 379 | 0 | 280 | 0 | clinical benefit |
| RCC-IM_002 | nivolumab | 1 | SD | NA | 61 | 0 | −16 | clear-cell | NA | NA | 735 | 0 | clinical benefit |
| RCC_281066 | nivolumab | 1 | SD | M | 60 | 0 | NA | clear-cell | 460 | 1 | 460 | 1 | intermediate benefit |
| RCC_371982 | nivolumab | 1 | PD | M | 70 | 0 | NA | clear-cell | 448 | 0 | 71 | 0 | no clinical benefit |
| RCC_390392 | nivolumab | 1 | SD | M | 77 | 0 | 2 | clear-cell | 174 | 1 | 55 | 1 | intermediate benefit |
| RCC_470874 | nivolumab | 1 | PD | M | 59 | 0 | NA | clear-cell | 247 | 0 | 42 | 0 | no clinical benefit |
| RCC_472770 | nivolumab | 1 | PD | M | 52 | 0 | NA | clear-cell | 558 | 0 | 84 | 0 | no clinical benefit |
| RCC_504642 | nivolumab | 1 | PD | F | 55 | 0 | NA | clear-cell | 102 | 0 | 41 | 0 | no clinical benefit |
| RCC_509214 | nivolumab | 1 | PR | M | 44 | 0 | NA | clear-cell | 370 | 0 | 204 | 0 | clinical benefit |
| RCC_51974086 | nivolumab | 1 | SD | F | 81 | 0 | 3.5 | clear-cell | 456 | 0 | 220 | 0 | intermediate benefit |
| RCC_554652 | nivolumab | 1 | PR | F | 76 | 0 | NA | clear-cell | 484 | 1 | 336 | 1 | clinical benefit |
| MCA1 | atezolizumab | 0 | PD | NA | NA | 0 | NA | clear-cell | NA | NA | 85 | 0 | no clinical benefit |
| MCA2 | atezolizumab | 0 | PD | NA | NA | 0 | NA | clear-cell | NA | NA | 83 | 0 | no clinical benefit |
| MCA3 | atezolizumab | 0 | SD | NA | NA | 0 | −15 | clear-cell | NA | NA | 337 | 0 | clinical benefit |
| MCA4 | nivolumab | 0 | PD | NA | NA | 0 | NA | clear-cell | NA | NA | 145 | 0 | intermediate benefit |
| MCA5 | nivolumab | 0 | PD | NA | NA | 0 | NA | clear-cell | NA | NA | 203 | 0 | intermediate benefit |
| MCA6 | nivolumab | 0 | CR | NA | NA | 0 | NA | clear-cell | NA | NA | 196 | 0 | clinical benefit |
| MCA7 | nivolumab | 0 | PR | NA | NA | 0 | −50 | clear-cell | NA | NA | 601 | 0 | clinical benefit |
| MCA8 | nivolumab | 0 | PD | NA | NA | 0 | NA | clear-cell | NA | NA | 107 | 0 | no clinical benefit |
| MCA9 | nivolumab | 0 | PD | NA | NA | 0 | NA | clear-cell | NA | NA | 31 | 0 | no clinical benefit |
| MCA10 | nivolumab | 0 | SD | NA | NA | 0 | NA | clear-cell | NA | NA | 312 | 0 | intermediate benefit |
| MCA11 | nivolumab | 0 | SD | NA | NA | 0 | NA | clear-cell | NA | NA | NA | 0 | intermediate benefit |
| MCA12 | nivolumab | 0 | PR | NA | NA | 0 | −53 | clear-cell | NA | NA | 127 | 0 | clinical benefit |
| MCA13 | nivolumab | 0 | PR | NA | NA | 0 | −43 | clear-cell | NA | NA | NA | 0 | clinical benefit |
| MCA14 | nivolumab | 0 | PD | NA | NA | 0 | NA | clear-cell | NA | NA | 65 | 0 | no clinical benefit |

TABLE 6G

Truncating PBRM1 alterations in validation cohort (N = 63)

| patient_id | Hugo_Symbol | Chromosome | Start_position | End_position | Variant_Classification | Reference_Allele | Tumor_Seq_Allele1 | Tumor_Seq_Allele2 | Protein_Change |
|---|---|---|---|---|---|---|---|---|---|
| CA8808 | PBRM1 | 3 | 52595873 | 52595873 | Frame_Shift_Del | G | G | - | p.Q1415fs |
| KA4076 | NA | NA | NA | NA | NA | NA | NA | NA | NA |
| KE5236 | PBRM1 | 3 | 52597356 | 52597359 | Frame_Shift_Del | AG GT | AG GT | - | p.LP1310fs |

TABLE 6G-continued

Truncating PBRM1 alterations in validation cohort (N = 63)

| | | | | | | | | | |
|---|---|---|---|---|---|---|---|---|---|
| KE6262 | PBRM1 | 3 | 52643586 | 52643596 | Frame_Shift_Del | ATGAGAGTCCT | ATGAGAGTCCT | - | p.EDSH782fs |
| MC1838 | NA | NA | NA | NA | NA | NA | NA | NA | NA |
| PD_005 | PBRM1 | 3 | 52668656 | 52668656 | Nonsense_Mutation | G | G | T | p.Y389* |
| PD_007 | NA | NA | NA | NA | NA | NA | NA | NA | NA |
| PD_010 | PBRM1 | 3 | 52702580 | 52702580 | Nonsense_Mutation | A | A | C | p.Y106* |
| PD_011 | NA | NA | NA | NA | NA | NA | NA | NA | NA |
| PD_012 | PBRM1 | 3 | 52620643 | 52620643 | Missense_Mutation | C | C | G | p.R1030P |
| PD_013 | PBRM1 | 3 | 52597487 | 52597488 | Frame_Shift_Del | CC | CC | - | p.E1315fs |
| PD_014 | PBRM1 | 3 | 52610662 | 52610663 | Frame_Shift_Del | AG | AG | - | p.F1211fs |
| PD_015 | PBRM1 | 3 | 52637540 | 52637540 | Frame_Shift_Del | AG | AG | - | p.R941fs |
| PD_018 | NA | NA | NA | NA | NA | NA | NA | NA | NA |
| PD_019 | NA | NA | NA | NA | NA | NA | NA | NA | NA |
| PD_020 | NA | NA | NA | NA | NA | NA | NA | NA | NA |
| PD_021 | PBRM1 | 3 | 52713723 | 52713723 | Frame_Shift_Del | C | C | - | p.G2fs |
| PD_022 | NA | NA | NA | NA | NA | NA | NA | NA | NA |
| PD_023 | PBRM1 | 3 | 52663053 | 52663053 | Splice_Site | T | T | A | NA |
| PD_024 | NA | NA | NA | NA | NA | NA | NA | NA | NA |
| PD_025 | PBRM1 | 3 | 52595829 | 52595829 | Frame_Shift_Del | C | C | - | p.G1429fs |
| PD_026 | NA | NA | NA | NA | NA | NA | NA | NA | NA |
| RCC.PD1.DNA.1026 | NA | NA | NA | NA | NA | NA | NA | NA | NA |
| RCC.PD1.DNA.1101 | PBRM1 | 3 | 52595804 | 52595804 | Frame_Shift_Del | C | C | - | p.A1438fs |
| RCC.PD1.DNA.1137 | NA | NA | NA | NA | NA | NA | NA | NA | NA |
| RCC.PD1.DNA.944 | NA | NA | NA | NA | NA | NA | NA | NA | NA |
| RCC.PD1.DNA.949 | NA | NA | NA | NA | NA | NA | NA | NA | NA |
| VA1008 | PBRM1 | 3 | 52643943 | 52643943 | Frame_Shift_Del | T | T | - | p.K619fs |

TABLE 6G-continued

Truncating PBRM1 alterations in validation cohort (N = 63)

| | | | | | | | | | |
|---|---|---|---|---|---|---|---|---|---|
| PGDX2818T_Ex-RCC032PT1 | PBRM1 | 3 | 52652306 | 52652306 | Nonsense_Mutation | G | G | T | p.331* |
| PGDX2817T_Ex-RCC031PT1 | NA | NA | NA | NA | NA | NA | NA | NA | NA |
| PGDX2816T_Ex-RCC030PT1 | PBRM1 | 3 | 5259824 | 5259824 | Frame_Shift_Del | T | T | - | NA |
| PGDX2815T_Ex-RCC029PT1 | NA | NA | NA | NA | NA | NA | NA | NA | NA |
| PGDX2814T_Ex-RCC028PT1 | PBRM1 | 3 | 52618979 | 52618979 | Nonsense_Mutation | T | T | A | p.K621* |
| PGDX2813T_Ex-RCC027PT1 | NA | NA | NA | NA | NA | NA | NA | NA | NA |
| PGDX2811T_Ex-RCC025PT1 | PBRM1 | 3 | 52657432 | 52657432 | Frame_Shift_Del | T | T | - | NA |
| BL5166_T1 | NA | NA | NA | NA | NA | NA | NA | NA | NA |
| RENAL-15349_CCPM_0600855 | PBRM1 | 3 | 52637555 | 52637555 | Nonsense_Mutation | G | G | A | p.R889* |
| RENAL-15349_CCPM_0600862 | NA | NA | NA | NA | NA | NA | NA | NA | NA |
| RCC-IM_001 | NA | NA | NA | NA | NA | NA | NA | NA | NA |
| RCC-IM_002 | NA | NA | NA | NA | NA | NA | NA | NA | NA |
| RCC_281066 | NA | NA | NA | NA | NA | NA | NA | NA | NA |
| RCC_371982 | PBRM1 | 3 | 52682428 | 52682428 | Frame_Shift_Del | C | C | - | p.A249fs |
| RCC_390392 | PBRM1 | 3 | 52712515 | 52712515 | Splice_Site | C | C | - | NA |
| RCC_470874 | NA | NA | NA | NA | NA | NA | NA | NA | NA |
| RCC_472770 | NA | NA | NA | NA | NA | NA | NA | NA | NA |
| RCC_504642 | NA | NA | NA | NA | NA | NA | NA | NA | NA |
| RCC_509214 | PBRM1 | 3 | 52662909 | 52662909 | Splice_Site | C | C | A | NA |
| RCC_51974086 | NA | NA | NA | NA | NA | NA | NA | NA | NA |
| RCC_554652 | NA | NA | NA | NA | NA | NA | NA | NA | NA |
| MCA1 | NA | NA | NA | NA | NA | NA | NA | NA | NA |
| MCA2 | PBRM1 | NA | NA | NA | Splice_Site | NA | NA | NA | NA |
| MCA3 | PBRM1 | NA | NA | NA | Frame_Shift | NA | NA | NA | NA |
| MCA4 | PBRM1 | NA | NA | NA | Frame_Shift | NA | NA | NA | p.N609fs |

TABLE 6G-continued

Truncating PBRM1 alterations in validation cohort (N = 63)

| | | | | | | | | | |
|---|---|---|---|---|---|---|---|---|---|
| MCA5 | PBRM1 | NA | NA | NA | Frame_Shift | NA | NA | NA | p.Y608fs*34 |
| MCA6 | PBRM1 | NA | NA | NA | Missense_Mutation_LOF | NA | NA | NA | N258S |
| MCA7 | PBRM1 | NA | NA | NA | Nonsense_Mutation | NA | NA | NA | p.E1124* |
| MCA8 | NA | NA | NA | NA | NA | NA | NA | NA | NA |
| MCA9 | PBRM1 | NA | NA | NA | In_Frame_DelIns | NA | NA | NA | p.W141_L145DelInsC |
| MCA10 | NA | NA | NA | NA | NA | NA | NA | NA | NA |
| MCA11 | NA | NA | NA | NA | NA | NA | NA | NA | NA |
| MCA12 | PBRM1 | NA | NA | NA | Frame_Shift | NA | NA | NA | p.K154fs |
| MCA13 | PBRM1 | NA | NA | NA | Missense_Mutation | NA | NA | NA | p.S681R |
| MCA14 | NA | NA | NA | NA | NA | NA | NA | NA | NA |

| patient_id | Variant_Type | i_tumor_f | t_alt_count | t_ref_count | clonal_dm | indel_caller | PBRM1_IHC |
|---|---|---|---|---|---|---|---|
| CA8808 | DEL | 0.259090909 | 57 | 163 | 1 | strelka, indelocator | NA |
| KA4076 | NA | NA | NA | NA | NA | NA | NA |
| KE5236 | DEL | 0.09 | 8 | 85 | 0 | indelocator | NA |
| KE6262 | DEL | 0.098214286 | 11 | 101 | 1 | strelka, indelocator | NA |
| MC1838 | NA | NA | NA | NA | NA | NA | NA |
| PD_005 | SNP | 0.287356 | 25 | 62 | 1 | NA | NA |
| PD_007 | NA | NA | NA | NA | NA | NA | NA |
| PD_010 | SNP | 0.15 | 6 | 34 | 0 | NA | NA |
| PD_011 | NA | NA | NA | NA | NA | NA | NA |
| PD_012 | SNP | 0.358491 | 38 | 68 | 1 | NA | NA |
| PD_013 | DEL | 0.1171875 | 15 | 113 | 1 | strelka, indelocator | NA |
| PD_014 | DEL | 0.288888889 | 26 | 64 | 1 | strelka, indelocator | NA |
| PD_015 | DEL | 0.204545455 | 18 | 70 | 1 | strelka, indelocator | NA |
| PD_018 | NA | NA | NA | NA | NA | NA | NA |
| PD_019 | NA | NA | NA | NA | NA | NA | NA |
| PD_020 | NA | NA | NA | NA | NA | NA | NA |
| PD_021 | DEL | 0.36 | 18 | 32 | 1 | strelka, indelocator | NA |
| PD_022 | NA | NA | NA | NA | NA | NA | NA |
| PD_023 | SNP | 0.214286 | 9 | 33 | 1 | NA | NA |
| PD_024 | NA | NA | NA | NA | NA | NA | NA |

TABLE 6G-continued

Truncating PBRM1 alterations in validation cohort (N = 63)

| | | | | | | | |
|---|---|---|---|---|---|---|---|
| PD_025 | DEL | 0.154411765 | 21 | 115 | 1 | strelka, indelocator | NA |
| PD_026 | NA | NA | NA | NA | NA | NA | NA |
| RCC.PD1.DNA.1026 | NA | NA | NA | NA | NA | NA | NA |
| RCC.PD1.DNA.1101 | DEL | 0.133540373 | 43 | 279 | 1 | strelka, indelocator | NA |
| RCC.PD1.DNA.1137 | NA | NA | NA | NA | NA | NA | NA |
| RCC.PD1.DNA.944 | NA | NA | NA | NA | NA | NA | NA |
| RCC.PD1.DNA.949 | NA | NA | NA | NA | NA | NA | NA |
| VA1008 | DEL | 0.06 | 15 | 253 | 1 | indelocator | NA |
| PGDX2818T_Ex-RCC032PT1 | SNP | 0.483871 | 30 | 32 | NA | NA | NA |
| PGDX2817T_Ex-RCC031PT1 | NA | NA | NA | NA | NA | NA | NA |
| PGDX2816T_Ex-RCC030PT1 | DEL | 0.315789 | 18 | 39 | NA | NA | NA |
| PGDX2815T_Ex-RCC029PT1 | NA | NA | NA | NA | NA | NA | NA |
| PGDX2814T_Ex-RCC028PT1 | SNP | 0.38 | 19 | 31 | NA | NA | NA |
| PGDX2813T_Ex-RCC027PT1 | NA | NA | NA | NA | NA | NA | NA |
| PGDX2811T_Ex-RCC025PT1 | DEL | 0.327103 | 35 | 72 | NA | NA | NA |
| BL5166_T1 | NA | NA | NA | NA | NA | NA | NA |
| RENAL-15349_CCPM_0600855 | SNP | 0.026217 | 7 | 260 | 0 | NA | NA |
| RENAL-15349_CCPM_0600862 | NA | NA | NA | NA | NA | NA | NA |
| RCC-IM_001 | NA | NA | NA | NA | NA | NA | NA |
| RCC-IM_002 | NA | NA | NA | NA | NA | NA | NA |
| RCC_281066 | NA | NA | NA | NA | NA | NA | NA |
| RCC_371982 | DEL | 0.1875 | 12 | 52 | 1 | strelka, indelocator | NA |
| RCC_390392 | DEL | 0.318181818 | 21 | 45 | 1 | strelka, indelocator | NA |
| RCC_470874 | NA | NA | NA | NA | NA | NA | NA |
| RCC_472770 | NA | NA | NA | NA | NA | NA | NA |
| RCC_504642 | NA | NA | NA | NA | NA | NA | NA |
| RCC_509214 | SNP | 0.352941 | 60 | 110 | 1 | NA | NA |
| RCC_51974086 | NA | NA | NA | NA | NA | NA | NA |
| RCC_554652 | NA | NA | NA | NA | NA | NA | NA |
| MCA1 | NA | NA | NA | NA | NA | NA | positive |
| MCA2 | SNP | NA | NA | NA | NA | NA | NA |

TABLE 6G-continued

Truncating PBRM1 alterations in validation cohort (N = 63)

| | | | | | | | |
|---|---|---|---|---|---|---|---|
| MCA3 | FS | 0.33 | NA | NA | NA | NA | negative |
| MCA4 | FS | 0.09 | NA | NA | NA | NA | negative |
| MCA5 | FS | NA | NA | NA | NA | NA | negative |
| MCA6 | SNP | 0.32 | NA | NA | NA | NA | negative |
| MCA7 | SNP | NA | NA | NA | NA | NA | NA |
| MCA8 | NA | NA | NA | NA | NA | NA | positive |
| MCA9 | DELINS | 0.21 | NA | NA | NA | NA | NA |
| MCA10 | NA | NA | NA | NA | NA | NA | positive |
| MCA11 | NA | NA | NA | NA | NA | NA | NA |
| MCA12 | FS | 0.25 | NA | NA | NA | NA | negative |
| MCA13 | SNP | NA | NA | NA | NA | NA | NA |
| MCA14 | NA | NA | NA | NA | NA | NA | positive |

TABLE 6H

SWI/SNF genes

| Hugo_Symbol | Other Names | BAF | PBAF |
|---|---|---|---|
| ACTL6A | BAF53A | 1 | 1 |
| ACTL6B | BAF53B | 1 | 1 |
| ARID2 | BAF200 | 0 | 1 |
| BCL7A | | 1 | 1 |
| BCL7B | | 1 | 1 |
| BCL7C | | 1 | 1 |
| BCL11A | | 1 | 1 |
| BCL11B | | 1 | 1 |
| BRD7 | | 0 | 1 |
| BRD9 | | 1 | 0 |
| DPF1 | BAF45B | 1 | 0 |
| DPF2 | BAF45D | 1 | 0 |
| DPF3 | BAF45C | 1 | 0 |
| PBRM1 | BAF180 | 0 | 1 |
| PHF10 | BAF45A | 0 | 1 |
| SMARCA2 | BRM | 1 | 0 |
| SMARCA4 | BRG | 1 | 1 |
| SMARCB1 | BAF47, SNF1, INI1 | 1 | 1 |
| SMARCC1 | BAF155 | 1 | 1 |
| SMARCC2 | BAF170 | 1 | 1 |
| SMARCE1 | BAF57 | 1 | 1 |
| SS18 | | 1 | 0 |
| SS18L1 | CREST | 1 | 0 |
| SMARCD1 | BAF60A | 1 | 1 |
| SMARCD2 | BAF60B | 1 | 1 |
| SMARCD3 | BAF60C | 1 | 1 |
| ARID1A | BAF250A | 1 | 0 |
| ARID1B | BAF250B | 1 | 0 |

TABLE 6I

Intersection of top 100 positively differentially expressed genes in PBRM1null and BRG1null, and top 100 negatively differentially expressed genes in PBRM1 null and BRG1 null, both with respect to wild type using EdgeR

| Higher_in_mutant | Higher_in_wildtype |
|---|---|
| SEMA5B | PRRT1 |
| LOX | ARHGDIB |
| IL8 | PADI3 |
| PHGDH | MYPN |
| IGFBP3 | C19orf21 |
| SCARA3 | ITGB4 |
| COL1A1 | SUCNR1 |
| JAG1 | ERAP2 |
| NTM | ACE2 |
| SFRP4 | PADI1 |
| SDC1 | SERPINE1 |
| TFPI2 | KIAA1486 |
| NMB | B3GNT3 |
| SLC17A3 | F2R |
| CXCL1 | PKP3 |
| RASSF2 | CHSY3 |
| HMGCS1 | ACSL5 |
| SC4MOL | DOCK2 |
| ANGPTL4 | CD74 |
| UPB1 | TAGLN |
| PTPRD | FGF5 |
| MACROD2 | ADD2 |
| PEG10 | TUBA4A |
| SULF2 | HKDC1 |
| KMO | RP11-428C6.1 |
| C1QL4 | SPNS2 |
| P2RY6 | UNC13D |
| NPR3 | CAPG |
| SCD | KRTCAP3 |
| TTYH3 | SH3KBP1 |
| MAPK12 | CLTB |
| MAPK11 | MARCH4 |
| CD70 | ABCA13 |
| PDZD2 | KRT8 |
| RDH10 | WWC1 |
| ITM2B | MT2A |
| OLR1 | MYEOV |
| NPTXR | ANKRD1 |
| FAM84B | QSOX1 |
| RASSF6 | SLC1A1 |
| LGI4 | CGN |
| TNFSF10 | VCAN |

TABLE 6I-continued

Intersection of top 100 positively differentially expressed genes in PBRM1null and BRG1null, and top 100 negatively differentially expressed genes in PBRM1 null and BRG1 null, both with respect to wild type using EdgeR

| Higher_in_mutant | Higher_in_wildtype |
|---|---|
| FGF9 | SEMA6A |
| NXN | |
| CRYAB | |
| ADAMTS7 | |
| PKDCC | |
| MYO10 | |

TABLE 6J

GSEA for BAF180-null vs. BAF180-wildtype A704 cell lines on Hallmark gene sets

| NAME | SIZE | ES | NES | NOM p-val | FDR q-val | FWER p-val | RANK AT MAX | LEADING EDGE |
|---|---|---|---|---|---|---|---|---|
| HALLMARK_CHOLESTEROL_HOMEOSTASIS | 73 | 0.5499064 | 2.078206 | 0 | 0.0015 | 0.001 | 1908 | tags = 30%, list = 9%, signal = 33% |
| HALLMARK_EPITHELIAL_MESENCHYMAL_TRANSITION | 196 | 0.40123636 | 1.751494 | 0 | 0.01094041 | 0.016 | 2701 | tags = 27%, list = 12%, signal = 30% |
| HALLMARK_HYPOXIA | 196 | 0.36750925 | 1.6125246 | 0 | 0.021424314 | 0.071 | 3029 | tags = 22%, list = 14%, signal = 26% |
| HALLMARK_IL6_JAK_STAT3_SIGNALING | 75 | 0.43879578 | 1.6340721 | 0.004149378 | 0.022036757 | 0.059 | 3503 | tags = 33%, list = 16%, signal = 39% |
| HALLMARK_MTORC1_SIGNALING | 197 | 0.37888893 | 1.6442895 | 0 | 0.026279828 | 0.053 | 3178 | tags = 21%, list = 14%, signal = 25% |
| HALLMARK_E2F_TARGETS | 199 | 0.35565567 | 1.5548034 | 0.002409639 | 0.026504425 | 0.12 | 6911 | tags = 45%, list = 31%, signal = 64% |
| HALLMARK_MYOGENESIS | 185 | 0.36297417 | 1.5741123 | 0 | 0.026698643 | 0.103 | 2192 | tags = 20%, list = 10%, signal = 22% |
| HALLMARK_HEDGEHOG_SIGNALING | 34 | 0.4507803 | 1.4415807 | 0.052863438 | 0.050014596 | 0.298 | 3180 | tags = 32%, list = 14%, signal = 38% |
| HALLMARK_ANGIOGENESIS | 33 | 0.46237797 | 1.4533101 | 0.03539823 | 0.05064617 | 0.278 | 809 | tags = 15%, list = 4%, signal = 16% |
| HALLMARK_COAGULATION | 116 | 0.35500702 | 1.4640448 | 0.01843318 | 0.051064506 | 0.252 | 3903 | tags = 28%, list = 18%, signal = 33% |
| HALLMARK_TNFA_SIGNALING_VIA_NFKB | 194 | 0.31302983 | 1.3606336 | 0.017456358 | 0.095439464 | 0.524 | 2743 | tags = 23%, list = 12%, signal = 26% |
| HALLMARK_IL2_STAT5_SIGNALING | 186 | 0.30282557 | 1.3082199 | 0.03163017 | 0.13568047 | 0.704 | 4131 | tags = 27%, list = 19%, signal = 33% |
| HALLMARK_APICAL_SURFACE | 42 | 0.3483055 | 1.189489 | 0.20134228 | 0.24039724 | 0.947 | 2814 | tags = 21%, list = 13%, signal = 24% |
| HALLMARK_PANCREAS_BETA_CELLS | 27 | 0.39650375 | 1.1929086 | 0.18644068 | 0.25035873 | 0.945 | 2494 | tags = 26%, list = 11%, signal = 29% |
| HALLMARK_KRAS_SIGNALING_DN | 160 | 0.2832103 | 1.201148 | 0.091566265 | 0.2521114 | 0.935 | 1663 | tags = 14%, list = 7%, signal = 15% |
| HALLMARK_GLYCOLYSIS | 199 | 0.2657333 | 1.1636928 | 0.11809045 | 0.25848737 | 0.976 | 2702 | tags = 19%, list = 12%, signal = 21% |
| HALLMARK_KRAS_SIGNALING_UP | 174 | 0.27017388 | 1.1702893 | 0.120987654 | 0.25996405 | 0.969 | 1960 | tags = 16%, list = 9%, signal = 17% |
| HALLMARK_INFLAMMATORY_RESPONSE | 176 | 0.27770376 | 1.2042952 | 0.096618354 | 0.2642809 | 0.932 | 1973 | tags = 16%, list = 9%, signal = 17% |
| HALLMARK_NOTCH_SIGNALING | 32 | 0.3793043 | 1.2072315 | 0.19341564 | 0.27845338 | 0.93 | 1028 | tags = 19%, list = 5%, signal = 20% |
| HALLMARK_FATTY_ACID_ | 149 | 0.26660782 | 1.1278455 | 0.19148937 | 0.31431836 | 0.989 | 4502 | tags = 28%, |

TABLE 6J-continued

GSEA for BAF180-null vs. BAF180-wildtype A704 cell lines on Hallmark gene sets

| NAME | SIZE | ES | NES | NOM p-val | FDR q-val | FWER p-val | RANK AT MAX | LEADING EDGE |
|---|---|---|---|---|---|---|---|---|
| METABOLISM | | | | | | | | list = 20%, signal = 34% |
| HALLMARK_MYC_TARGETS_V2 | 58 | 0.299071 | 1.0908226 | 0.27828056 | 0.379539 | 0.998 | 4813 | tags = 24%, list = 22%, signal = 31% |
| HALLMARK_WNT_BETA_CATENIN_SIGNALING | 39 | 0.3251601 | 1.0594196 | 0.36285096 | 0.4396408 | 0.999 | 917 | tags = 13%, list = 4%, signal = 13% |
| HALLMARK_COMPLEMENT | 175 | 0.24138407 | 1.0466689 | 0.3208431 | 0.4541273 | 0.999 | 3153 | tags = 17%, list = 14%, signal = 20% |
| HALLMARK_G2M_CHECKPOINT | 198 | 0.22897714 | 1.0028436 | 0.44444445 | 0.5551898 | 1 | 6567 | tags = 35%, list = 30%, signal = 49% |
| HALLMARK_XENOBIOTIC_METABOLISM | 183 | 0.21210375 | 0.92167723 | 0.6800948 | 0.77817 | 1 | 2503 | tags = 14%, list = 11%, signal = 15% |
| HALLMARK_UV_RESPONSE_DN | 143 | 0.21846533 | 0.90516925 | 0.7117347 | 0.795592 | 1 | 3533 | tags = 19%, list = 16%, signal = 22% |
| HALLMARK_DNA_REPAIR | 147 | 0.2048023 | 0.86652255 | 0.8066826 | 0.8692663 | 1 | 4368 | tags = 20%, list = 20%, signal = 24% |
| HALLMARK_ADIPOGENESIS | 194 | 0.1918401 | 0.8391842 | 0.8989899 | 0.8999136 | 1 | 3378 | tags = 14%, list = 15%, signal = 17% |
| HALLMARK_REACTIVE_OXIGEN_SPECIES_PATHWAY | 45 | 0.23113286 | 0.79606485 | 0.78132117 | 0.9033937 | 1 | 2952 | tags = 18%, list = 13%, signal = 20% |
| HALLMARK_MYC_TARGETS_V1 | 200 | 0.184295 | 0.8095168 | 0.96217495 | 0.91855717 | 1 | 6577 | tags = 26%, list = 30%, signal = 37% |

TABLE 6K

GSEA for BAF180-wildtype, BRG1-null vs. BAF180-wildtype, BRG1-wildtype A704 cell lines on Hallmark gene sets

| NAME | SIZE | ES | NES | NOM p-val | FDR q-val | FWER p-val | RANK AT MAX | LEADING EDGE |
|---|---|---|---|---|---|---|---|---|
| HALLMARK_INFLAMMATORY_RESPONSE | 171 | 0.37973073 | 1.4245273 | 0.007470651 | 0.12658831 | 0.577 | 4252 | tags = 33%, list = 19%, signal = 41% |
| HALLMARK_TNFA_SIGNALING_VIA_NFKB | 192 | 0.37756145 | 1.4295613 | 0.003161222 | 0.1436323 | 0.553 | 4171 | tags = 34%, list = 19%, signal = 41% |
| HALLMARK_E2F_TARGETS | 199 | 0.364751 | 1.389069 | 0.009483667 | 0.15321952 | 0.702 | 7987 | tags = 43%, list = 36%, signal = 66% |
| HALLMARK_CHOLESTEROL_HOMEOSTASIS | 73 | 0.41791317 | 1.4319164 | 0.026995305 | 0.17345017 | 0.546 | 4456 | tags = 33%, list = 20%, signal = 41% |
| HALLMARK_IL6_JAK_STAT3_SIGNALING | 73 | 0.43450925 | 1.4762418 | 0.012672811 | 0.2109737 | 0.38 | 5300 | tags = 45%, list = 24%, signal = 59% |
| HALLMARK_KRAS_SIGNALING_DN | 157 | 0.36467624 | 1.346272 | 0.030139936 | 0.21358259 | 0.872 | 5009 | tags = 33%, list = 23%, signal = 42% |
| HALLMARK_IL2_STAT5_SIGNALING | 186 | 0.37655368 | 1.4375755 | 0.006430868 | 0.21618104 | 0.521 | 4601 | tags = 30%, list = 21%, signal = 37% |
| HALLMARK_APICAL_SURFACE | 42 | 0.42272592 | 1.3133029 | 0.09125 | 0.25905415 | 0.932 | 5175 | tags = 33%, list = 23%, signal = 43% |
| HALLMARK_MYOGENESIS | 187 | 0.34258145 | 1.2901036 | 0.063101605 | 0.26447582 | 0.964 | 3826 | tags = 25%, list = 17%, signal = 30% |
| HALLMARK_INTERFERON_GAMMA_RESPONSE | 179 | 0.34417737 | 1.2982914 | 0.05042017 | 0.2690372 | 0.955 | 4307 | tags = 28%, list = 19%, signal = 34% |

TABLE 6K-continued

GSEA for BAF180-wildtype, BRG1-null vs. BAF180-wildtype, BRG1-wildtype A704 cell lines on Hallmark gene sets

| NAME | SIZE | ES | NES | NOM p-val | FDR q-val | FWER p-val | RANK AT MAX | LEADING EDGE |
|---|---|---|---|---|---|---|---|---|
| HALLMARK_HEDGEHOG_SIGNALING | 34 | 0.5023723 | 1.5104364 | 0.029224904 | 0.2772426 | 0.27 | 5025 | tags = 53%, list = 23%, signal = 68% |
| HALLMARK_NOTCH_SIGNALING | 31 | 0.42534694 | 1.2741792 | 0.16558862 | 0.27971512 | 0.975 | 2449 | tags = 19%, list = 11%, signal = 22% |
| HALLMARK_COMPLEMENT | 175 | 0.32690415 | 1.2264905 | 0.10319149 | 0.35470042 | 0.994 | 1842 | tags = 14%, list = 8%, signal = 15% |
| HALLMARK_ANGIOGENESIS | 32 | 0.41938755 | 1.2168443 | 0.21501273 | 0.35581103 | 0.996 | 2204 | tags = 25%, list = 10%, signal = 28% |
| HALLMARK_HYPOXIA | 194 | 0.31979325 | 1.2073612 | 0.10867294 | 0.35997763 | 0.997 | 4118 | tags = 24%, list = 19%, signal = 29% |
| HALLMARK_EPITHELIAL_MESENCHYMAL_TRANSITION | 196 | 0.32430506 | 1.2336999 | 0.08252948 | 0.36051062 | 0.994 | 2380 | tags = 18%, list = 11%, signal = 20% |
| HALLMARK_KRAS_SIGNALING_UP | 171 | 0.3172053 | 1.1798669 | 0.14618644 | 0.39506933 | 0.998 | 5256 | tags = 36%, list = 24%, signal = 47% |
| HALLMARK_ALLOGRAFT_REJECTION | 151 | 0.31554624 | 1.1654135 | 0.17849462 | 0.41372243 | 1 | 4307 | tags = 27%, list = 19%, signal = 33% |
| HALLMARK_UV_RESPONSE_DN | 143 | 0.32053903 | 1.1812268 | 0.17083786 | 0.4144526 | 0.998 | 5057 | tags = 35%, list = 23%, signal = 45% |
| HALLMARK_WNT_BETA_CATENIN_SIGNALING | 39 | 0.36205238 | 1.1145409 | 0.32233503 | 0.52548987 | 1 | 5256 | tags = 36%, list = 24%, signal = 47% |
| HALLMARK_COAGULATION | 114 | 0.30622408 | 1.1181058 | 0.2610132 | 0.53892165 | 1 | 6237 | tags = 38%, list = 28%, signal = 52% |
| HALLMARK_ESTROGEN_RESPONSE_EARLY | 192 | 0.28934133 | 1.0933391 | 0.2798742 | 0.5427693 | 1 | 5456 | tags = 34%, list = 25%, signal = 44% |
| HALLMARK_INTERFERON_ALPHA_RESPONSE | 94 | 0.30972162 | 1.0939436 | 0.31038508 | 0.5659965 | 1 | 1566 | tags = 14%, list = 7%, signal = 15% |
| HALLMARK_BILE_ACID_METABOLISM | 105 | 0.3016164 | 1.0760891 | 0.33482143 | 0.57484317 | 1 | 2284 | tags = 15%, list = 10%, signal = 17% |
| HALLMARK_G2M_CHECKPOINT | 198 | 0.26063028 | 0.9995506 | 0.49058577 | 0.7349968 | 1 | 7925 | tags = 36%, list = 36%, signal = 55% |
| HALLMARK_APOPTOSIS | 156 | 0.25963703 | 0.9737319 | 0.53347504 | 0.7582101 | 1 | 6508 | tags = 35%, list = 29%, signal = 49% |
| HALLMARK_MTORC1_SIGNALING | 197 | 0.2644619 | 1.001003 | 0.49367088 | 0.7585766 | 1 | 5007 | tags = 22%, list = 23%, signal = 28% |
| HALLMARK_UV_RESPONSE_UP | 152 | 0.26901275 | 1.0059657 | 0.46732026 | 0.7721154 | 1 | 5325 | tags = 29%, list = 24%, signal = 38% |
| HALLMARK_PEROXISOME | 99 | 0.27292284 | 0.97732824 | 0.52553916 | 0.7735135 | 1 | 2300 | tags = 15%, list = 10%, signal = 17% |
| HALLMARK_FATTY_ACID_METABOLISM | 151 | 0.25714728 | 0.95584106 | 0.57403433 | 0.7860941 | 1 | 5981 | tags = 28%, list = 27%, signal = 38% |
| HALLMARK_ANDROGEN_RESPONSE | 95 | 0.26842615 | 0.9450292 | 0.57126826 | 0.78813064 | 1 | 5621 | tags = 31%, list = 25%, signal = 41% |
| HALLMARK_HEME_METABOLISM | 187 | 0.24242312 | 0.91873807 | 0.6635121 | 0.8300867 | 1 | 5715 | tags = 26%, list = 26%, signal = 34% |
| HALLMARK_XENOBIOTIC_METABOLISM | 183 | 0.23199143 | 0.87932944 | 0.7373949 | 0.89637834 | 1 | 5202 | tags = 24%, list = 23%, signal = 31% |
| HALLMARK_P53_PATHWAY | 193 | 0.22611341 | 0.8573577 | 0.7903564 | 0.9159724 | 1 | 4727 | tags = 23%, list = 21%, signal = 29% |

TABLE 6K-continued

GSEA for BAF180-wildtype, BRG1-null vs. BAF180-wildtype, BRG1-wildtype A704 cell lines on Hallmark gene sets

| NAME | SIZE | ES | NES | NOM p-val | FDR q-val | FWER p-val | RANK AT MAX | LEADING EDGE |
|---|---|---|---|---|---|---|---|---|
| HALLMARK_UNFOLDED_PROTEIN_RESPONSE | 112 | 0.14780428 | 0.53494364 | 1 | 0.9974952 | 1 | 4453 | tags = 14%, list = 20%, signal = 18% |
| HALLMARK_PI3K_AKT_MTOR_SIGNALING | 98 | 0.2217106 | 0.7829281 | 0.8594104 | 1 | 1 | 7204 | tags = 30%, list = 32%, signal = 44% |
| HALLMARK_ADIPOGENESIS | 193 | 0.20610817 | 0.7734336 | 0.91043204 | 1 | 1 | 5963 | tags = 23%, list = 27%, signal = 31% |
| HALLMARK_DNA_REPAIR | 147 | 0.19458589 | 0.7146128 | 0.9478827 | 1 | 1 | 9455 | tags = 36%, list = 43%, signal = 62% |
| HALLMARK_PANCREAS_BETA_CELLS | 28 | 0.24026519 | 0.6924615 | 0.8860927 | 1 | 1 | 3531 | tags = 21%, list = 16%, signal = 25% |
| HALLMARK_MITOTIC_SPINDLE | 197 | 0.17785007 | 0.67739034 | 0.97993666 | 1 | 1 | 6069 | tags = 27%, list = 27%, signal = 37% |
| HALLMARK_PROTEIN_SECRETION | 95 | 0.16087638 | 0.5635202 | 0.9966254 | 1 | 1 | 7983 | tags = 32%, list = 36%, signal = 49% |

TABLE 6L

GSEA for BAF180-null vs. BAF180-wildtype A704 cell lines on Cholesterol Homeostasis Founder gene sets

| NAME | SIZE | ES | NES | NOM p-val | FDR q-val | FWER p-val | RANK AT MAX | LEADING EDGE |
|---|---|---|---|---|---|---|---|---|
| SCHMIDT_POR_TARGETS_IN_LIMB_BUD_UPz | 24 | 0.8159034 | 2.411856 | 0 | 0 | 0 | 1862 | tags = 63%, list = 8%, signal = 68% |
| REACTOME_CHOLESTEROL_BIOSYNTHESIS | 21 | 0.81049263 | 2.3614385 | 0 | 0 | 0 | 2246 | tags = 67%, list = 10%, signal = 74% |
| HORTON_SREBF_TARGETS | 25 | 0.76518434 | 2.307628 | 0 | 0 | 0 | 1908 | tags = 52%, list = 9%, signal = 57% |
| KEGG_STEROID_BIOSYNTHESIS | 16 | 0.8001351 | 2.1263828 | 0 | 0 | 0 | 2462 | tags = 69%, list = 11%, signal = 77% |
| PODAR_RESPONSE_TO_ADAPHOSTIN_DN | 17 | 0.76344514 | 2.0490096 | 0 | 2.47E−04 | 0.001 | 1302 | tags = 53%, list = 6%, signal = 56% |
| WENG_POR_TARGETS_GLOBAL_UP | 18 | 0.6869103 | 1.9208144 | 0.004329004 | 0.001405882 | 0.004 | 1763 | tags = 39%, list = 8%, signal = 42% |
| WENG_POR_TARGETS_LIVER_UP | 37 | 0.53671414 | 1.7553303 | 0.002164502 | 0.010265792 | 0.04 | 1763 | tags = 30%, list = 8%, signal = 32% |
| LE_EGR2_TARGETS_DN | 101 | 0.4053505 | 1.6263677 | 0.004694836 | 0.02575889 | 0.109 | 1862 | tags = 18%, list = 8%, signal = 19% |
| JI_RESPONSE_TO_FSH_UP | 70 | 0.43719202 | 1.6248909 | 0.004385965 | 0.02356887 | 0.111 | 2601 | tags = 33%, list = 12%, signal = 37% |
| HOXA9_DN.V1_DN | 184 | 0.37380037 | 1.6219271 | 0 | 0.022287892 | 0.116 | 2709 | tags = 23%, list = 12%, signal = 26% |
| BURTON_ADIPOGENESIS_10 | 28 | 0.5129609 | 1.5734106 | 0.027777778 | 0.027410874 | 0.158 | 2601 | tags = 36%, list = 12%, signal = 40% |
| CSR_LATE_UP.V1_DN | 156 | 0.3417356 | 1.4487041 | 0.007211539 | 0.062628604 | 0.332 | 3441 | tags = 29%, list = 15%, signal = 35% |
| GERY_CEBP_TARGETS | 113 | 0.35047704 | 1.4065694 | 0.027210884 | 0.0758233 | 0.418 | 943 | tags = 12%, list = 4%, signal = 13% |

TABLE 6L-continued

GSEA for BAF180-null vs. BAF180-wildtype A704 cell lines on Cholesterol Homeostasis Founder gene sets

| NAME | SIZE | ES | NES | NOM p-val | FDR q-val | FWER p-val | RANK AT MAX | LEADING EDGE |
|---|---|---|---|---|---|---|---|---|
| COULOUARN_TEMPORAL_TGFB1_SIGNATURE_DN | 127 | 0.31372902 | 1.2847894 | 0.051764704 | 0.14626734 | 0.679 | 2090 | tags = 16%, list = 9%, signal = 17% |
| MTOR_UP.V1_UP | 152 | 0.29891714 | 1.2796576 | 0.04822335 | 0.14189139 | 0.69 | 3119 | tags = 24%, list = 14%, signal = 27% |
| ZHANG_GATA6_TARGETS_DN | 62 | 0.323232 | 1.1692238 | 0.21462265 | 0.25430223 | 0.893 | 2796 | tags = 24%, list = 13%, signal = 28% |
| UEDA_PERIFERAL_CLOCK | 164 | 0.26870546 | 1.14285 | 0.18717949 | 0.27674678 | 0.924 | 2961 | tags = 17%, list = 13%, signal = 20% |
| CHANG_CORE_SERUM_RESPONSE_DN | 198 | 0.25709897 | 1.1284494 | 0.15012106 | 0.28189048 | 0.941 | 2863 | tags = 18%, list = 13%, signal = 20% |
| GUO_TARGETS_OF_IRS1_AND_IRS2 | 91 | 0.28360868 | 1.0960777 | 0.27539504 | 0.31335095 | 0.964 | 1862 | tags = 18%, list = 8%, signal = 19% |
| AK.T_UP.V1_UP | 155 | 0.24117097 | 1.0295677 | 0.3721519 | 0.4158599 | 0.989 | 3180 | tags = 22%, list = 14%, signal = 25% |
| WENG_POR_DOSAGE | 19 | 0.31340367 | 0.8814183 | 0.62068963 | 0.70459986 | 0.999 | 537 | tags = 11%, list = 2%, signal = 11% |

TABLE 6M

GSEA for BAF180-wildtype, BRG1-null vs. BAF180-wildtype, BRG1-wildtype A704 cell lines on Cholesterol homeostasis founder gene sets

| NAME | SIZE | ES | NES | NOM p-val | FDR q-val | FWER p-val | RANK AT MAX | LEADING EDGE |
|---|---|---|---|---|---|---|---|---|
| SCHMIDT_POR_TARGETS_IN_LIMB_BUD_UP | 24 | 0.6280739 | 1.7496891 | 0.002766252 | 0.021879772 | 0.019 | 6248 | tags = 75%, list = 28%, signal = 104% |
| HOXA9_DN.V1_DN | 183 | 0.4092302 | 1.537419 | 0.001053741 | 0.036110204 | 0.221 | 6421 | tags = 42%, list = 29%, signal = 59% |
| KEGG_STEROID_BIOSYNTHESIS | 16 | 0.61110497 | 1.5432961 | 0.02328767 | 0.038056426 | 0.206 | 7054 | tags = 75%, list = 32%, signal = 110% |
| REACTOME_CHOLESTEROL_BIOSYNTHESIS | 21 | 0.6144767 | 1.6537449 | 0.018469658 | 0.03882323 | 0.066 | 6248 | tags = 71%, list = 28%, signal = 99% |
| HORTON_SREBF_TARGETS | 25 | 0.56918824 | 1.5941461 | 0.011952192 | 0.03994539 | 0.132 | 6248 | tags = 68%, list = 28%, signal = 95% |
| WENG_POR_TARGETS_LIVER_UP | 36 | 0.51314527 | 1.5510265 | 0.01660281 | 0.040972658 | 0.194 | 3212 | tags = 36%, list = 14%, signal = 42% |
| MTOR_UP.V1_UP | 151 | 0.41329026 | 1.5625536 | 0.003229279 | 0.043739304 | 0.175 | 4345 | tags = 34%, list = 20%, signal = 42% |
| BURTON_ADIPOGENESIS_10 | 28 | 0.5168679 | 1.5018733 | 0.024547804 | 0.0463574 | 0.311 | 5741 | tags = 57%, list = 26%, signal = 77% |
| PODAR_RESPONSE_TO_ADAPHOSTIN_DN | 17 | 0.6210147 | 1.6014676 | 0.010899182 | 0.04923035 | 0.122 | 2284 | tags = 35%, list = 10%, signal = 39% |
| COULOUARN_TEMPORAL_TGFB1_SIGNATURE_DN | 127 | 0.39380088 | 1.4252076 | 0.020697167 | 0.06673416 | 0.509 | 4514 | tags = 33%, list = 20%, signal = 41% |
| JI_RESPONSE_TO_FSH_UP | 70 | 0.42071614 | 1.4315375 | 0.024618993 | 0.06925182 | 0.493 | 3117 | tags = 31%, list = 14%, signal = 36% |
| CSR_LATE_UP.V1_DN | 156 | 0.37567928 | 1.4021397 | 0.013903744 | 0.07460156 | 0.577 | 5293 | tags = 39%, list = 24%, signal = 51% |

TABLE 6M-continued

GSEA for BAF180-wildtype, BRG1-null vs. BAF180-wildtype, BRG1-wildtype A704 cell lines on Cholesterol homeostasis founder gene sets

| NAME | SIZE | ES | NES | NOM p-val | FDR q-val | FWER p-val | RANK AT MAX | LEADING EDGE |
|---|---|---|---|---|---|---|---|---|
| CHANG_CORE_SERUM_RESPONSE_DN | 198 | 0.37701818 | 1.431742 | 0.005208334 | 0.076068304 | 0.492 | 6114 | tags = 44%, list = 28%, signal = 60% |
| WENG_POR_TARGETS_GLOBAL_UP | 18 | 0.4988817 | 1.3003886 | 0.1488178 | 0.16067472 | 0.871 | 8455 | tags = 67%, list = 38%, signal = 108% |
| GERY_CEBP_TARGETS | 112 | 0.340268 | 1.2337925 | 0.12637363 | 0.23521984 | 0.971 | 2102 | tags = 14%, list = 9%, signal = 16% |
| ACEVEDO_FGFR1_TARGETS_IN_PROSTATE_CANCER_MODEL_UP | 260 | 0.29719558 | 1.1568955 | 0.16099072 | 0.35511822 | 0.996 | 4730 | tags = 28%, list = 21%, signal = 35% |
| ZHANG_GATA6_TARGETS_DN | 61 | 0.33623016 | 1.1039963 | 0.31348723 | 0.4427688 | 1 | 2678 | tags = 21%, list = 12%, signal = 24% |
| UEDA_PERIFERAL_CLOCK | 163 | 0.28692022 | 1.0742894 | 0.32627118 | 0.48380232 | 1 | 7055 | tags = 33%, list = 32%, signal = 48% |
| LE_EGR2_TARGETS_DN | 100 | 0.28486618 | 1.0112084 | 0.48049054 | 0.5490551 | 1 | 6104 | tags = 37%, list = 27%, signal = 51% |
| AKT_UP_MTOR_DN.V1_UP | 165 | 0.26690233 | 0.98991686 | 0.51160336 | 0.56489664 | 1 | 2910 | tags = 16%, list = 13%, signal = 19% |
| AKT_UP.V1_UP | 156 | 0.27506077 | 1.0140308 | 0.4493063 | 0.5691042 | 1 | 4288 | tags = 25%, list = 19%, signal = 31% |
| GUO_TARGETS_OF_IRS1_AND_IRS2 | 89 | 0.2898395 | 1.0152373 | 0.4472477 | 0.5953482 | 1 | 5192 | tags = 30%, list = 23%, signal = 39% |
| GOTZMANN_EPITHELIAL_TO_MESENCHYMAL_TRANSITION_DN | 190 | 0.24749233 | 0.92717135 | 0.636936 | 0.66669047 | 1 | 3588 | tags = 16%, list = 16%, signal = 19% |
| UEDA_CENTRAL_CLOCK | 81 | 0.22968177 | 0.80096096 | 0.8062284 | 0.85129535 | 1 | 5742 | tags = 26%, list = 26%, signal = 35% |
| WENG_POR_DOSAGE | 19 | 0.2510292 | 0.6606327 | 0.9015048 | 0.9546578 | 1 | 2705 | tags = 16%, list = 12%, signal = 18% |

TABLE 6N

GSEA for BAF180-null vs. BAF180-wildtype A704 cell lines on IL6_JAK_STAT Founder gene sets

| NAME | GS<br> follow link to MSigDB | GS DETAILS | SIZE | ES | NES |
|---|---|---|---|---|---|
| KEGG_CYTOKINE_CYTOKINE_RECEPTOR_INTERACTION | KEGG_CYTOKINE_CYTOKINE_RECEPTOR_INTERACTION | Details . . . | 181 | 0.4415354 | 1.9151524 |
| TENEDINI_MEGAKARYOCYTE_MARKERS | TENEDINI_MEGAKARYOCYTE_MARKERS | Details . . . | 61 | 0.395845 | 1.4293368 |
| BIOCARTA_IL10_PATHWAY | BIOCARTA_IL10_PATHWAY | Details . . . | 16 | 0.5389521 | 1.4307966 |
| KEGG_JAK_STAT_SIGNALING_PATHWAY | KEGG_JAK_STAT_SIGNALING_PATHWAY | Details . . . | 109 | 0.27087787 | 1.0860411 |

| NAME | NOM p-val | FDR q-val | FWER p-val | RANK AT MAX | LEADING EDGE |
|---|---|---|---|---|---|
| KEGG_CYTOKINE_CYTOKINE_RECEPTOR_INTERACTION | 0 | 0.002002002 | 0.0577 | | tags = 29%, list = 12%, signal = 33% |
| TENEDINI_MEGAKARYOCYTE_MARKERS | 0.03794643 | 0.07527799 | 0.2693 | | tags = 26%, list = 16%, signal = 31% |
| BIOCARTA_IL10_PATHWAY | 0.08045977 | 0.11208283 | 0.2679 | | tags = 38%, list = 21%, signal = 47% |

TABLE 6N-continued

GSEA for BAF180-null vs. BAF180-wildtype A704 cell lines on IL6_JAK_STAT Founder gene sets

| KEGG_JAK_STAT_SIGNALING_PATHWAY | 0.28293738 | 0.32948533 | 0.861 | 2364 | tags = 18%, list = 11%, signal = 20% |

TABLE 6O

GSEA for BAF180-wildtype, BRG1-null vs. BAF180-wildtype, BRG1-wildtype A704 cell lines on IL6_JAK_STAT founder gene sets

| NAME | SIZE | ES | NES | NOM p-val | FDR q-val | FWER p-val | RANK AT MAX | LEADING EDGE |
|---|---|---|---|---|---|---|---|---|
| KEGG_CYTOKINE_CYTOKINE_RECEPTOR_INTERACTION | 174 | 0.45381105 | 1.7164165 | 0 | 0.023537878 | 0.023 | 3351 | tags = 30%, list = 15%, signal = 36% |
| BIOCARTA_IL10_PATHWAY | 16 | 0.61396885 | 1.5512801 | 0.03076923 | 0.05661688 | 0.149 | 5694 | tags = 63%, list = 26%, signal = 84% |
| TENEDINI_MEGAKARYOCYTE_MARKERS | 58 | 0.47523633 | 1.5752333 | 0.009779952 | 0.067951284 | 0.12 | 5049 | tags = 41%, list = 23%, signal = 53% |
| KEGG_JAK_STAT_SIGNALING_PATHWAY | 109 | 0.40122634 | 1.449788 | 0.023230089 | 0.10020399 | 0.319 | 6854 | tags = 50%, list = 31%, signal = 73% |
| MODULE_73 | 17 | 0.4175205 | 1.0875453 | 0.38537273 | 0.7025281 | 0.986 | 2810 | tags = 41%, list = 13%, signal = 47% |
| CYTOKINE_BINDING | 37 | 0.26826125 | 0.82358396 | 0.74140126 | 0.8336488 | 1 | 3257 | tags = 30%, list = 15%, signal = 35% |
| MODULE_265 | 23 | 0.3571073 | 0.9895663 | 0.5 | 0.83561146 | 1 | 2825 | tags = 39%, list = 13%, signal = 45% |
| HEMATOPOIETIN_INTERFERON_CLASSD200_DOMAIN_CYTOKINE_RECEPTOR_ACTIVITY | 25 | 0.3321352 | 0.9321065 | 0.55599475 | 0.838992 | 1 | 4703 | tags = 48%, list = 21%, signal = 61% |
| GROWTH_FACTOR_BINDING | 24 | 0.3090261 | 0.86560124 | 0.67493474 | 0.86384636 | 1 | 3257 | tags = 29%, list = 15%, signal = 34% |
| INTERLEUKIN_BINDING | 17 | 0.2834838 | 0.7304276 | 0.8388889 | 0.8643178 | 1 | 4459 | tags = 41%, list = 20%, signal = 51% |

TABLE 6P

GSEA for BAF180-null vs. BAF180-wildtype A704 cell lines on E2F Founder gene sets

| NAME | SIZE | ES | NES | NOM p-val | FDR q-val | FWER p-val | RANK AT MAX | LEADING EDGE |
|---|---|---|---|---|---|---|---|---|
| GNF2_RFC4 | 60 | 0.5323848 | 1.9698843 | 0 | 0.04113063 | 0.021 | 6900 | tags = 58%, list = 31%, signal = 84% |
| ZHOU_CELL_CYCLE_GENES_IN_IR_RESPONSE_6HR | 85 | 0.4946525 | 1.9064773 | 0 | 0.069671065 | 0.069 | 4682 | tags = 42%, list = 21%, signal = 53% |
| GRAHAM_NORMAL_QUIESCENT_VS_NORMAL_DIVIDING_DN | 82 | 0.48101547 | 1.8290602 | 0 | 0.11817522 | 0.168 | 5081 | tags = 41%, list = 23%, signal = 54% |
| MODULE_125 | 44 | 0.48651716 | 1.6430085 | 0.002150538 | 0.12799942 | 0.671 | 6383 | tags = 55%, list = 29%, signal = 76% |
| WHITEFORD_PEDIATRIC_CANCER_MARKERS | 115 | 0.40530172 | 1.6555282 | 0.002304148 | 0.1288557 | 0.629 | 6978 | tags = 49%, list = 31%, signal = 71% |
| MARKEY_RB1_CHRONIC_LOF_UP | 108 | 0.40898755 | 1.6469048 | 0 | 0.13123506 | 0.66 | 3518 | tags = 31%, list = 16%, signal = 36% |
| PUJANA_BREAST_CANCER_WITH_BRCA1_MUTATED_UP | 56 | 0.46575648 | 1.6565605 | 0.004395605 | 0.13707851 | 0.625 | 7606 | tags = 64%, list = 34%, signal = 97% |
| KAMMINGA_EZH2_TARGETS | 41 | 0.52069986 | 1.7285632 | 0.002358491 | 0.13727812 | 0.394 | 5684 | tags = 39%, list = 26%, signal = 52% |
| MISSIAGLIA_REGULATED_BY_METHYLATION_DN | 117 | 0.41643286 | 1.7019293 | 0 | 0.1373712 | 0.476 | 4926 | tags = 38%, list = 22%, signal = 48% |
| LY_AGING_PREMATURE_DN | 29 | 0.549658 | 1.7113805 | 0.010799136 | 0.14511141 | 0.455 | 3282 | tags = 28%, list = 15%, signal = 32% |
| KOBAYASHI_EGFR_SIGNALING_24HR_DN | 249 | 0.3704692 | 1.6659153 | 0 | 0.14565974 | 0.592 | 5139 | tags = 35%, list = 23%, signal = 44% |
| GNF2_SMC4L1 | 84 | 0.42501023 | 1.6584858 | 0 | 0.1458408 | 0.619 | 6814 | tags = 48%, list = 31%, signal = 68% |
| EXONUCLEASE_ACTIVITY | 19 | 0.5912168 | 1.6705523 | 0.019354839 | 0.15194333 | 0.576 | 1943 | tags = 32%, list = 9%, signal = 35% |
| MODULE_158 | 43 | 0.51076496 | 1.7321154 | 0 | 0.15483478 | 0.384 | 6515 | tags = 58%, list = 29%, signal = 82% |
| STEIN_ESRRA_TARGETS_RESPONSIVE_TO_ESTROGEN_DN | 39 | 0.48558497 | 1.6146711 | 0.013793103 | 0.15576415 | 0.751 | 4815 | tags = 44%, list = 22%, signal = 56% |

TABLE 6P-continued

GSEA for BAF180-null vs. BAF180-wildtype A704 cell lines on E2F Founder gene sets

| NAME | SIZE | ES | NES | NOM p-val | FDR q-val | FWER p-val | RANK AT MAX | LEADING EDGE |
|---|---|---|---|---|---|---|---|---|
| ZHOU_CELL_CYCLE_GENES_IN_IR_RESPONSE_24HR | 124 | 0.3967225 | 1.6749351 | 0 | 0.15974982 | 0.562 | 4658 | tags = 31%, list = 21%, signal = 39% |
| RB_DN.V1_UP | 133 | 0.38019583 | 1.5704007 | 0.002380953 | 0.16487299 | 0.853 | 3288 | tags = 23%, list = 15%, signal = 27% |
| DUTERTRE_ESTRADIOL_RESPONSE_24HR_UP | 318 | 0.37789592 | 1.7427595 | 0 | 0.16575663 | 0.354 | 6577 | tags = 48%, list = 30%, signal = 67% |
| REACTOME_DNA_STRAND_ELONGATION | 30 | 0.5053188 | 1.579908 | 0.030303031 | 0.16585435 | 0.833 | 3979 | tags = 40%, list = 18%, signal = 49% |
| GNF2_PCNA | 67 | 0.43130568 | 1.5916202 | 0.006772009 | 0.16721149 | 0.803 | 7863 | tags = 58%, list = 35%, signal = 90% |
| YU_BAP1_TARGETS | 28 | 0.5155804 | 1.5830177 | 0.022222223 | 0.16959678 | 0.823 | 5137 | tags = 46%, list = 23%, signal = 60% |
| ROSTY_CERVICAL_CANCER_PROLIFERATION_CLUSTER | 139 | 0.38421938 | 1.5708452 | 0.002347418 | 0.17128387 | 0.852 | 5728 | tags = 37%, list = 26%, signal = 50% |
| GNF2_FEN1 | 56 | 0.4400318 | 1.5927137 | 0.017391304 | 0.17471416 | 0.802 | 6577 | tags = 48%, list = 30%, signal = 68% |
| RIZ_ERYTHROID_DIFFERENTIATION | 75 | 0.3998866 | 1.5336596 | 0.015037594 | 0.20419818 | 0.92 | 3607 | tags = 27%, list = 16%, signal = 32% |
| GNF2_MCM4 | 53 | 0.4871741 | 1.7432508 | 0.004464286 | 0.20625171 | 0.353 | 7686 | tags = 60%, list = 35%, signal = 92% |
| LINDGREN_BLADDER_CANCER_CLUSTER_3_UP | 317 | 0.32804054 | 1.5342647 | 0 | 0.21121016 | 0.92 | 4914 | tags = 29%, list = 22%, signal = 37% |
| REACTOME_ACTIVATION_OF_ATR_IN_RESPONSE_TO_REPLICATION_STRESS | 35 | 0.46436146 | 1.5067408 | 0.033259425 | 0.2163146 | 0.964 | 7686 | tags = 71%, list = 35%, signal = 109% |
| REACTOME_G0_AND_EARLY_G1 | 21 | 0.51683676 | 1.5070508 | 0.046255507 | 0.22344367 | 0.964 | 4974 | tags = 48%, list = 22%, signal = 61% |
| RIZ_ERYTHROID_DIFFERENTIATION_CCNE1 | 39 | 0.458755 | 1.5162858 | 0.015184382 | 0.22479783 | 0.952 | 3485 | tags = 28%, list = 16%, signal = 33% |
| MATZUK_MEIOTIC_AND_DNA_REPAIR | 36 | 0.45465472 | 1.4960755 | 0.029612755 | 0.22674586 | 0.972 | 3835 | tags = 31%, list = 17%, signal = 37% |
| REACTOME_RESOLUTION_OF_AP_SITES_VIA_THE_MULTIPLE_NUCLEOTIDE_ | 17 | 0.56890005 | 1.5084324 | 0.046511628 | 0.22864738 | 0.962 | 4761 | tags = 53%, list = 21%, |

TABLE 6P-continued

GSEA for BAF180-null vs. BAF180-wildtype A704 cell lines on E2F Founder gene sets

| NAME | SIZE | ES | NES | NOM p-val | FDR q-val | FWER p-val | RANK AT MAX | LEADING EDGE |
|---|---|---|---|---|---|---|---|---|
| PATCH_REPLACEMENT_PATHWAY GNF2_TTK | 39 | 0.44800937 | 1.4839368 | 0.033936653 | 0.23896985 | 0.979 | 7559 | signal = 67%, tags = 59%, list = 34%, |
| FRASOR_RESPONSE_TO_SERM_OR_FULVESTRANT_DN | 50 | 0.39338014 | 1.3936495 | 0.06004619 | 0.2458462 | 1 | 6900 | signal = 89%, tags = 46%, list = 31%, |
| ZHANG_TLX_TARGETS_60HR_DN | 270 | 0.30793357 | 1.3944957 | 0.012048192 | 0.24878854 | 1 | 6615 | signal = 67%, tags = 41%, list = 30%, |
| GNF2_RRM1 | 87 | 0.36759192 | 1.3954328 | 0.04245283 | 0.2512664 | 1 | 6814 | signal = 57%, tags = 43%, list = 31%, |
| PUJANA_BRCA_CENTERED_NETWORK | 117 | 0.3418764 | 1.3995072 | 0.031100478 | 0.25297934 | 0.999 | 6911 | signal = 61%, tags = 45%, list = 31%, |
| MORI_LARGE_PRE_BII_LYMPHOCYTE_UP | 84 | 0.36455083 | 1.407738 | 0.029978586 | 0.25346023 | 0.999 | 7393 | signal = 65%, tags = 50%, list = 33%, |
| BLUM_RESPONSE_TO_SALIRASIB_DN | 332 | 0.31202888 | 1.4640918 | 0 | 0.2538471 | 0.987 | 3979 | signal = 75%, tags = 23%, list = 18%, |
| REN_BOUND_BY_E2F | 60 | 0.38417438 | 1.3956681 | 0.05373832 | 0.25533997 | 1 | 5744 | signal = 28%, tags = 42%, list = 26%, |
| MORI_PRE_BI_LYMPHOCYTE_UP | 76 | 0.36963466 | 1.3998244 | 0.037914693 | 0.25731882 | 0.999 | 6377 | signal = 56%, tags = 42%, list = 29%, |
| KAUFFMANN_MELANOMA_RELAPSE_UP | 60 | 0.39023167 | 1.4082451 | 0.058315333 | 0.2576113 | 0.999 | 6608 | signal = 59%, tags = 48%, list = 30%, |
| MODULE_54 | 251 | 0.32418767 | 1.465012 | 0.004938272 | 0.25948274 | 0.987 | 4682 | signal = 69%, tags = 29%, list = 21%, |
| PUJANA_XPRSS_INT_NETWORK | 165 | 0.32696632 | 1.3835881 | 0.021028038 | 0.2596924 | 1 | 6911 | signal = 36%, tags = 44%, list = 31%, |
| REGULATION_OF_DNA_REPLICATION | 19 | 0.52254275 | 1.4568967 | 0.047191013 | 0.25986636 | 0.989 | 5881 | signal = 63%, tags = 58%, list = 26%, |
| BIOCARTA_G1_PATHWAY | 27 | 0.46366057 | 1.409431 | 0.08553971 | 0.2604318 | 0.998 | 2997 | signal = 79%, tags = 26%, list = 13%, |
| MATZUK_SPERMATOCYTE | 68 | 0.39636797 | 1.467985 | 0.023640662 | 0.26103795 | 0.984 | 3691 | signal = 30%, tags = 24%, list = 17%, |
| SHEPARD_BMYB_MORPHOLINO_DN | 180 | 0.3260228 | 1.3998913 | 0.01686747 | 0.2620695 | 0.999 | 3851 | signal = 28%, tags = 28%, |

TABLE 6P-continued

GSEA for BAF180-null vs. BAF180-wildtype A704 cell lines on E2F Founder gene sets

| NAME | SIZE | ES | NES | NOM p-val | FDR q-val | FWER p-val | RANK AT MAX | LEADING EDGE |
|---|---|---|---|---|---|---|---|---|
| BIOCARTA_MCM_PATHWAY | 18 | 0.523641 | 1.4506925 | 0.06263982 | 0.2628194 | 0.991 | 7686 | tags = 72%, list = 17%, signal = 34% |
| ISHIDA_E2F_TARGETS | 51 | 0.40538192 | 1.4102687 | 0.046908315 | 0.2641048 | 0.998 | 6960 | tags = 59%, list = 35%, signal = 110% |
| VANTVEER_BREAST_CANCER_METASTASIS_UP | 55 | 0.391082 | 1.4123961 | 0.05 | 0.26544183 | 0.996 | 2904 | tags = 29%, list = 13%, signal = 85% |
| ZHANG_TLX_TARGETS_DN | 88 | 0.36839908 | 1.4143125 | 0.023255814 | 0.26721817 | 0.996 | 5921 | tags = 43%, list = 27%, signal = 33% |
| KEGG_BASE_EXCISION_REPAIR | 34 | 0.4475151 | 1.4440593 | 0.041484717 | 0.26807487 | 0.993 | 3979 | tags = 35%, list = 18%, signal = 59% |
| KANG_DOXORUBICIN_RESISTANCE_UP | 54 | 0.38853663 | 1.3756194 | 0.047727272 | 0.2681853 | 1 | 6814 | tags = 46%, list = 31%, signal = 43% |
| GNF2_RFC3 | 41 | 0.41752118 | 1.4149994 | 0.05689278 | 0.27123934 | 0.996 | 6900 | tags = 51%, list = 31%, signal = 67% |
| REACTOME_G2_M_CHECKPOINTS | 41 | 0.4167203 | 1.4163488 | 0.06345733 | 0.27500415 | 0.996 | 6732 | tags = 56%, list = 30%, signal = 74% |
| SOTIRIOU_BREAST_CANCER_GRADE_1_VS_3_UP | 149 | 0.3214344 | 1.3571204 | 0.02078522 | 0.27659324 | 1 | 7618 | tags = 47%, list = 34%, signal = 80% |
| ODONNELL_TARGETS_OF_MYC_AND_TFRC_DN | 44 | 0.41889706 | 1.418553 | 0.04494382 | 0.27691594 | 0.996 | 5684 | tags = 48%, list = 26%, signal = 71% |
| MARKEY_RB1_ACUTE_LOF_UP | 228 | 0.303452 | 1.35813 | 0.014319809 | 0.27882314 | 1 | 5168 | tags = 31%, list = 23%, signal = 64% |
| JOHANSSON_GLIOMAGENESIS_BY_PDGFB_UP | 55 | 0.38219306 | 1.350983 | 0.07488987 | 0.2789827 | 1 | 2725 | tags = 18%, list = 12%, signal = 40% |
| GNF2_BUB1B | 49 | 0.39280915 | 1.3487504 | 0.09512761 | 0.2793027 | 1 | 6911 | tags = 43%, list = 31%, signal = 21% |
| SIMBULAN_PARP1_TARGETS_DN | 17 | 0.5216608 | 1.420628 | 0.074235804 | 0.27934334 | 0.996 | 4341 | tags = 47%, list = 20%, signal = 62% |
| GRAHAM_CML_QUIESCENT_VS_NORMAL_QUIESCENT_UP | 77 | 0.38616616 | 1.4342515 | 0.027586207 | 0.279565 | 0.994 | 4926 | tags = 27%, list = 22%, signal = 58%, signal = 35% |

TABLE 6P-continued

GSEA for BAF180-null vs. BAF180-wildtype A704 cell lines on E2F Founder gene sets

| NAME | SIZE | ES | NES | NOM p-val | FDR q-val | FWER p-val | RANK AT MAX | LEADING EDGE |
|---|---|---|---|---|---|---|---|---|
| LI_WILMS_TUMOR | 26 | 0.46200952 | 1.423792 | 0.06772009 | 0.28035206 | 0.995 | 3332 | tags = 27%, list = 15%, signal = 32% |
| RIBONUCLEASE_ACTIVITY | 21 | 0.47635773 | 1.3620135 | 0.10927835 | 0.28049374 | 1 | 1098 | tags = 14%, list = 5%, signal = 15% |
| REACTOME_BASE_EXCISION_REPAIR | 19 | 0.48855054 | 1.3638277 | 0.12688172 | 0.2818866 | 1 | 4761 | tags = 47%, list = 21%, signal = 60% |
| STEIN_ESR1_TARGETS | 80 | 0.35570252 | 1.358726 | 0.065022424 | 0.28189817 | 1 | 4066 | tags = 30%, list = 18%, signal = 37% |
| GNF2_CCNA2 | 67 | 0.36114088 | 1.3516709 | 0.05676856 | 0.28191626 | 1 | 7686 | tags = 55%, list = 35%, signal = 84% |
| ZHAN_MULTIPLE_MYELOMA_PR_UP | 45 | 0.40132207 | 1.3656914 | 0.08056872 | 0.28249145 | 1 | 6377 | tags = 49%, list = 29%, signal = 68% |
| SONG_TARGETS_OF_IE86_CMV_PROTEIN | 60 | 0.39431137 | 1.4279 | 0.040865384 | 0.28549019 | 0.995 | 6608 | tags = 52%, list = 30%, signal = 73% |
| BURTON_ADIPOGENESIS_PEAK_AT_16HR | 39 | 0.40892777 | 1.3431141 | 0.08017817 | 0.28585017 | 1 | 3108 | tags = 23%, list = 14%, signal = 27% |
| GNF2_SMC2L1 | 32 | 0.4475485 | 1.4239812 | 0.05263158 | 0.2868688 | 0.995 | 6911 | tags = 50%, list = 31%, signal = 72% |
| MODULE_403 | 45 | 0.39438623 | 1.3375821 | 0.08017817 | 0.2914272 | 1 | 4748 | tags = 36%, list = 21%, signal = 45% |
| PYEON_HPV_POSITIVE_TUMORS_UP | 88 | 0.34147477 | 1.334982 | 0.047058824 | 0.29256615 | 1 | 3297 | tags = 27%, list = 15%, signal = 32% |
| WILCOX_RESPONSE_TO_PROGESTERONE_UP | 139 | 0.31779614 | 1.3307937 | 0.034653466 | 0.29698354 | 1 | 2958 | tags = 27%, list = 13%, signal = 31% |
| MANALO_HYPOXIA_DN | 284 | 0.29136848 | 1.3262402 | 0.020887729 | 0.3012804 | 1 | 6851 | tags = 35%, list = 31%, signal = 50% |
| BENPORATH_PROLIFERATION | 144 | 0.31483632 | 1.319144 | 0.030379746 | 0.30310413 | 1 | 4658 | tags = 27%, list = 21%, signal = 34% |
| SGCGSSAAA_V$E2F1DP2_01 | 162 | 0.30976716 | 1.3192339 | 0.023419203 | 0.30682164 | 1 | 6280 | tags = 39%, list = 28%, signal = 54% |
| NEGATIVE_REGULATION_OF_CELL_CYCLE | 75 | 0.35150585 | 1.3213702 | 0.0548926 | 0.30749267 | 1 | 3835 | tags = 24%, list = 17%, |

TABLE 6P-continued

GSEA for BAF180-null vs. BAF180-wildtype A704 cell lines on E2F Founder gene sets

| NAME | SIZE | ES | NES | NOM p-val | FDR q-val | FWER p-val | RANK AT MAX | LEADING EDGE |
|---|---|---|---|---|---|---|---|---|
| BOYAULT_LIVER_CANCER_SUBCLASS_G123_UP | 44 | 0.3800448 | 1.2972541 | 0.10294118 | 0.31085995 | 1 | 1804 | signal = 29%, tags = 16%, list = 8% |
| RB_P130_DN.V1_UP | 121 | 0.3168952 | 1.2936934 | 0.061032865 | 0.3142914 | 1 | 2543 | signal = 17%, tags = 16%, list = 11% |
| CHANG_CYCLING_GENES | 143 | 0.31158745 | 1.2972972 | 0.06904762 | 0.31442836 | 1 | 6070 | signal = 18%, tags = 41%, list = 27% |
| BAKER_HEMATOPOIESIS_STAT3_TARGETS | 16 | 0.49883923 | 1.3045712 | 0.14346895 | 0.31492957 | 1 | 5606 | signal = 56%, tags = 56%, list = 25% |
| LY_AGING_OLD_DN | 54 | 0.37244374 | 1.3087479 | 0.084415585 | 0.3151152 | 1 | 3282 | signal = 75%, tags = 22%, list = 15% |
| DNA_METABOLIC_PROCESS | 243 | 0.28880495 | 1.3062418 | 0.018735362 | 0.315527 | 1 | 4292 | signal = 26%, tags = 25%, list = 19% |
| OLSSON_E2F3_TARGETS_DN | 44 | 0.39295375 | 1.310525 | 0.108843535 | 0.31565085 | 1 | 2185 | signal = 31%, tags = 16%, list = 10% |
| DNA_REPLICATION | 98 | 0.32644168 | 1.2999647 | 0.067567565 | 0.31694692 | 1 | 6608 | signal = 18%, tags = 45%, list = 30% |
| MODULE_485 | 49 | 0.3743328 | 1.297536 | 0.108597286 | 0.31762144 | 1 | 5816 | signal = 64%, tags = 39%, list = 26% |
| GNF2_CKS1B | 37 | 0.39218175 | 1.301194 | 0.11304348 | 0.31887347 | 1 | 6911 | signal = 52%, tags = 51%, list = 31% |
| GARGALOVIC_RESPONSE_TO_OXIDIZED_PHOSPHOLIPIDS_TURQUOISE_DN | 51 | 0.36616385 | 1.2830538 | 0.12471132 | 0.33100462 | 1 | 4223 | signal = 74%, tags = 27%, list = 19% |
| CROONQUIST_IL6_DEPRIVATION_DN | 97 | 0.31885555 | 1.276713 | 0.071078435 | 0.33237627 | 1 | 6762 | signal = 34%, tags = 43%, list = 30% |
| VSE2F1_Q6_01 | 229 | 0.2868161 | 1.2773455 | 0.037037037 | 0.33474997 | 1 | 4825 | signal = 62%, tags = 28%, list = 22% |
| AFFAR_YY1_TARGETS_DN | 210 | 0.29184106 | 1.2774206 | 0.045 | 0.3383408 | 1 | 3979 | signal = 35%, tags = 25%, list = 18% |
| MODULE_397 | 111 | 0.31945032 | 1.2702408 | 0.056872036 | 0.34133938 | 1 | 3317 | signal = 30%, tags = 22%, list = 15% |
| NUCLEASE_ACTIVITY | 51 | 0.35982916 | 1.263786 | 0.1388889 | 0.35147074 | 1 | 3059 | signal = 25%, tags = 20%, list = 25% |

TABLE 6P-continued

GSEA for BAF180-null vs. BAF180-wildtype A704 cell lines on E2F Founder gene sets

| NAME | SIZE | ES | NES | NOM p-val | FDR q-val | FWER p-val | RANK AT MAX | LEADING EDGE |
|---|---|---|---|---|---|---|---|---|
| REACTOME_ACTIVATION_OF_THE_PRE_REPLICATIVE_COMPLEX | 30 | 0.40104312 | 1.2593498 | 0.17391305 | 0.3576477 | 1 | 6577 | tags = 57%, list = 14%, signal = 23% |
| GNF2_RRM2 | 40 | 0.37629777 | 1.253236 | 0.12993039 | 0.36292648 | 1 | 7909 | tags = 58%, list = 30%, signal = 80% |
| KORKOLA_TERATOMA | 37 | 0.3854039 | 1.2543806 | 0.1388889 | 0.3644212 | 1 | 872 | tags = 11%, list = 36%, signal = 89% |
| VANTVEER_BREAST_CANCER_POOR_PROGNOSIS | 51 | 0.35950112 | 1.2507282 | 0.12895928 | 0.36502436 | 1 | 5452 | tags = 43%, list = 4%, signal = 11% |
| CROONQUIST_NRAS_SIGNALING_DN | 72 | 0.33805963 | 1.2426128 | 0.12249443 | 0.36864632 | 1 | 7393 | tags = 54%, list = 25%, signal = 57% |
| RB_P107_DN.V1_UP | 134 | 0.29814488 | 1.2440923 | 0.0875 | 0.36879972 | 1 | 3979 | tags = 28%, list = 33%, signal = 81% |
| REACTOME_EXTENSION_OF_TELOMERES | 27 | 0.4090032 | 1.2443675 | 0.17699115 | 0.37191126 | 1 | 3979 | tags = 33%, list = 18%, signal = 34% |
| GROSS_HYPOXIA_VIA_ELK3_ONLY_DN | 44 | 0.36082354 | 1.2449167 | 0.15034169 | 0.3743939 | 1 | 3865 | tags = 27%, list = 18%, signal = 41% |
| ZHENG_GLIOBLASTOMA_PLASTICITY_UP | 236 | 0.274462164 | 1.2288359 | 0.050938338 | 0.37714297 | 1 | 4748 | tags = 28%, list = 17%, signal = 33% |
| VERNELL_RETINOBLASTOMA_PATHWAY_UP | 70 | 0.32801443 | 1.2373369 | 0.12230216 | 0.3772047 | 1 | 6799 | tags = 44%, list = 21%, signal = 35% |
| WONG_EMBRYONIC_STEM_CELL_CORE | 327 | 0.2648832 | 1.2355665 | 0.038356163 | 0.37993726 | 1 | 6597 | tags = 33%, list = 31%, signal = 64% |
| CELL_CYCLE_CHECKPOINT_GO_0000075 | 46 | 0.3617034 | 1.2292565 | 0.14096916 | 0.377507 | 1 | 3946 | tags = 35%, list = 30%, signal = 47% |
| BHAT1_G2M_ARREST_BY_2METHOXYESTRADIOL_UP | 107 | 0.30608615 | 1.2319682 | 0.10538641 | 0.38154486 | 1 | 3735 | tags = 23%, list = 18%, signal = 42% |
| AMUNDSON_GENOTOXIC_SIGNATURE | 100 | 0.30824658 | 1.230115 | 0.1091314 | 0.38194412 | 1 | 2516 | tags = 16%, list = 17%, signal = 28% |
| RUIZ_TNC_TARGETS_DN | 139 | 0.29295608 | 1.2226777 | 0.07259953 | 0.383599 | 1 | 5197 | tags = 35%, list = 11%, signal = 18% |
|  |  |  |  |  |  |  |  | list = 23%, signal = 45% |

TABLE 6P-continued

GSEA for BAF180-null vs. BAF180-wildtype A704 cell lines on E2F Founder gene sets

| NAME | SIZE | ES | NES | NOM p-val | FDR q-val | FWER p-val | RANK AT MAX | LEADING EDGE |
|---|---|---|---|---|---|---|---|---|
| PETROVA_PROX1_TARGETS_UP | 28 | 0.4008765 | 1.2238188 | 0.19130434 | 0.38432854 | 1 | 1909 | tags = 25%, list = 9%, signal = 27% |
| MORI_IMMATURE_B_LYMPHOCYTE_DN | 88 | 0.31508708 | 1.2159486 | 0.13013698 | 0.38895854 | 1 | 4682 | tags = 28%, list = 21%, signal = 36% |
| PID_RB_1PATHWAY | 61 | 0.33674502 | 1.2167755 | 0.1477516 | 0.39085585 | 1 | 2997 | tags = 20%, list = 13%, signal = 23% |
| KAUFFMANN_DNA_REPLICATION_GENES | 136 | 0.29238856 | 1.2172049 | 0.109947644 | 0.39348933 | 1 | 4257 | tags = 21%, list = 19%, signal = 26% |
| VECCHI_GASTRIC_CANCER_EARLY_UP | 403 | 0.25194356 | 1.2026228 | 0.036745407 | 0.41713816 | 1 | 2649 | tags = 13%, list = 12%, signal = 15% |
| BIOCARTA_P53_PATHWAY | 16 | 0.4452219 | 1.1898873 | 0.25738397 | 0.41901195 | 1 | 9112 | tags = 69%, list = 41%, signal = 116% |
| NEGATIVE_REGULATION_OF_DNA_METABOLIC_PROCESS | 17 | 0.452444 | 1.195021 | 0.23178808 | 0.42093435 | 1 | 2026 | tags = 24%, list = 9%, signal = 26% |
| V$E2F_01 | 63 | 0.32025853 | 1.1914719 | 0.17687075 | 0.42199737 | 1 | 5589 | tags = 33%, list = 25%, signal = 44% |
| OXFORD_RALA_OR_RALB_TARGETS_UP | 48 | 0.35289615 | 1.1960196 | 0.19527897 | 0.4221113 | 1 | 6184 | tags = 44%, list = 28%, signal = 60% |
| MODULE_325 | 51 | 0.33527386 | 1.1928161 | 0.19376393 | 0.4223233 | 1 | 4349 | tags = 27%, list = 20%, signal = 34% |
| YAO_TEMPORAL_RESPONSE_TO_PROGESTERONE_CLUSTER_15 | 30 | 0.37951565 | 1.1899841 | 0.19502075 | 0.4223635 | 1 | 1896 | tags = 13%, list = 9%, signal = 15% |
| BENPORATH_ES_CORE_NINE_CORRELATED | 94 | 0.30356047 | 1.1962134 | 0.13990825 | 0.4252052 | 1 | 4666 | tags = 29%, list = 21%, signal = 36% |
| V$E2F1_Q4 | 235 | 0.27007312 | 1.1974943 | 0.06388206 | 0.42586854 | 1 | 3607 | tags = 18%, list = 16%, signal = 22% |
| MODULE_252 | 235 | 0.26360464 | 1.183151 | 0.08232445 | 0.43119183 | 1 | 6802 | tags = 39%, list = 31%, signal = 56% |
| GNF2_ESPL1 | 35 | 0.355111458 | 1.1791232 | 0.21149425 | 0.43350247 | 1 | 6911 | tags = 51%, list = 31%, signal = 75% |
| MODULE_57 | 54 | 0.3385203 | 1.1802068 | 0.19222462 | 0.4345493 | 1 | 4926 | tags = 26%, list = 22% |

TABLE 6P-continued

GSEA for BAF180-null vs. BAF180-wildtype A704 cell lines on E2F Founder gene sets

| NAME | SIZE | ES | NES | NOM p-val | FDR q-val | FWER p-val | RANK AT MAX | LEADING EDGE |
|---|---|---|---|---|---|---|---|---|
| CELL_CYCLE_ARREST_GO_0007050 | 53 | 0.32590607 | 1.1636739 | 0.21198156 | 0.44674337 | 1 | 3835 | signal = 33% tags = 19%, list = 17%, |
| WINNEPENNINCKX_MELANOMA_METASTASIS_UP | 160 | 0.27584052 | 1.1643463 | 0.12787724 | 0.4485678 | 1 | 7430 | signal = 23% tags = 44%, list = 33%, |
| GCNP_SHH_UP_LATE.V1_UP | 173 | 0.26963314 | 1.165314 | 0.14563107 | 0.44976816 | 1 | 4748 | signal = 65% tags = 28%, list = 21%, |
| V$E2F1_Q4_01 | 219 | 0.26317212 | 1.170919 | 0.109725684 | 0.44992062 | 1 | 5320 | signal = 35% tags = 30%, list = 24%, |
| WHITFIELD_CELL_CYCLE_G1_S | 134 | 0.28168482 | 1.167068 | 0.16627635 | 0.45256835 | 1 | 3471 | signal = 39% tags = 22%, list = 16%, |
| REGULATION_OF_MITOTIC_CELL_CYCLE | 23 | 0.39925188 | 1.1654276 | 0.23284823 | 0.45296666 | 1 | 4815 | signal = 25% tags = 39%, list = 22%, |
| WANG_RESPONSE_TO_GSK3_INHIBITOR_SB216763_DN | 345 | 0.25190452 | 1.1674849 | 0.10106383 | 0.45485333 | 1 | 5102 | signal = 50% tags = 30%, list = 23%, |
| V$E2F_Q3 | 212 | 0.2621424 | 1.1582417 | 0.1421801 | 0.45713925 | 1 | 5144 | signal = 38% tags = 28%, list = 23%, |
| V$E2F_Q6_01 | 227 | 0.2575921 | 1.1522388 | 0.12200957 | 0.46274084 | 1 | 3595 | signal = 36% tags = 21%, list = 16%, |
| SARRIO_EPITHELIAL_MESENCHYMAL_TRANSITION_UP | 169 | 0.26500237 | 1.1530817 | 0.15384616 | 0.4639936 | 1 | 4703 | signal = 24% tags = 31%, list = 21%, |
| DNA_POLYMERASE_ACTIVITY | 17 | 0.4226581 | 1.1534702 | 0.27668846 | 0.4665431 | 1 | 722 | signal = 39% tags = 12%, list = 3%, |
| GRAHAM_CML_DIVIDING_VS_NORMAL_QUIESCENT_UP | 164 | 0.2677485 | 1.1492176 | 0.18734793 | 0.46672526 | 1 | 7422 | signal = 12% tags = 45%, list = 33%, |
| PID_BARD1_PATHWAY | 29 | 0.37072238 | 1.1467375 | 0.26406926 | 0.469454 | 1 | 3835 | signal = 67% tags = 24%, list = 17%, |
| CHIANG_LIVER_CANCER_SUBCLASS_PROLIFERATION_UP | 168 | 0.26683438 | 1.1446294 | 0.16945107 | 0.47134057 | 1 | 5315 | signal = 29% tags = 28%, list = 24%, |
| PID_FOXM1_PATHWAY | 39 | 0.3442356 | 1.1374557 | 0.25225225 | 0.47667563 | 1 | 4586 | signal = 36% tags = 28%, list = 21%, |
| LI_WILMS_TUMOR_VS_FETAL_KIDNEY_1_DN | 161 | 0.26908138 | 1.1377878 | 0.18451025 | 0.4792994 | 1 | 3282 | signal = 35% tags = 14%, |

TABLE 6P-continued

GSEA for BAF180-null vs. BAF180-wildtype A704 cell lines on E2F Founder gene sets

| NAME | SIZE | ES | NES | NOM p-val | FDR q-val | FWER p-val | RANK AT MAX | LEADING EDGE |
|---|---|---|---|---|---|---|---|---|
| WHITFIELD_CELL_CYCLE_G2 | 173 | 0.2631934 | 1.1348187 | 0.15801887 | 0.48018038 | 1 | 7199 | tags = 38%, list = 15%, signal = 16% |
| GARCIA_TARGETS_OF_FLI1_AND_DAX1_DN | 164 | 0.26511642 | 1.1380086 | 0.18266979 | 0.48210818 | 1 | 6630 | tags = 38%, list = 32%, signal = 55% |
| REGULATION_OF_DNA_METABOLIC_PROCESS | 43 | 0.34278795 | 1.1321517 | 0.25348836 | 0.48324963 | 1 | 4815 | tags = 37%, list = 30%, signal = 54% |
| GNF2_CENPF | 61 | 0.31386176 | 1.1273521 | 0.24222222 | 0.4852111 | 1 | 6515 | tags = 39%, list = 22%, signal = 47% |
| HORIUCHI_WTAP_TARGETS_DN | 301 | 0.24579187 | 1.1299635 | 0.14095744 | 0.48537546 | 1 | 5345 | tags = 27%, list = 29%, signal = 56% |
| KEGG_CELL_CYCLE | 121 | 0.2787656 | 1.1380361 | 0.18075117 | 0.48547247 | 1 | 3986 | tags = 21%, list = 24%, signal = 35% |
| VSE2F_Q3_01 | 225 | 0.25561398 | 1.1277008 | 0.18251929 | 0.4875135 | 1 | 5320 | tags = 30%, list = 18%, signal = 25% |
| LINDGREN_BLADDER_CANCER_CLUSTER_1_DN | 363 | 0.23868431 | 1.1248868 | 0.13672923 | 0.48838213 | 1 | 4821 | tags = 26%, list = 24%, signal = 39% |
| MODULE_198 | 297 | 0.24295494 | 1.1195234 | 0.1462766 | 0.49213037 | 1 | 6960 | tags = 38%, list = 22%, signal = 33% |
| VSE2F_Q6 | 226 | 0.25357646 | 1.1207881 | 0.1678487 | 0.4924103 | 1 | 3544 | tags = 21%, list = 31%, signal = 55% |
| GNF2_CKS2 | 50 | 0.3202122 | 1.1210793 | 0.2689655 | 0.49494117 | 1 | 6799 | tags = 40%, list = 16%, signal = 24% |
| SMID_BREAST_CANCER_LUMINAL_A_DN | 17 | 0.40507963 | 1.114525 | 0.30620986 | 0.5023531 | 1 | 6814 | tags = 47%, list = 31%, signal = 58% |
| SHEDDEN_LUNG_CANCER_POOR_SURVIVAL_A6 | 441 | 0.2315493 | 1.1123492 | 0.12224939 | 0.5043695 | 1 | 4682 | tags = 22%, list = 31%, signal = 68% |
| GNF2_CENPE | 40 | 0.33155906 | 1.11093 | 0.27876106 | 0.50479126 | 1 | 6911 | tags = 43%, list = 21%, signal = 27% |
| PEART_HDAC_PROLIFERATION_CLUSTER_DN | 72 | 0.29432467 | 1.1030699 | 0.25783134 | 0.522134 | 1 | 872 | tags = 7%, list = 4%, signal = 7% |

TABLE 6P-continued

GSEA for BAF180-null vs. BAF180-wildtype A704 cell lines on E2F Founder gene sets

| NAME | SIZE | ES | NES | NOM p-val | FDR q-val | FWER p-val | RANK AT MAX | LEADING EDGE |
|---|---|---|---|---|---|---|---|---|
| WHITFIELD_CELL_CYCLE_S | 153 | 0.25930515 | 1.1011199 | 0.19806764 | 0.52399784 | 1 | 3661 | tags = 22%, list = 16%, signal = 26% |
| G1_S_TRANSITION_OF_MITOTIC_CELL_CYCLE | 27 | 0.35630274 | 1.0979434 | 0.3205945 | 0.5293809 | 1 | 6767 | tags = 37%, list = 30%, signal = 53% |
| V$E2F1_Q3 | 230 | 0.2446122 | 1.0888127 | 0.22250639 | 0.55160815 | 1 | 4895 | tags = 27%, list = 22%, signal = 35% |
| V$E2F1DP1RB_01 | 219 | 0.24441566 | 1.084171 | 0.24449877 | 0.5609876 | 1 | 4815 | tags = 26%, list = 22%, signal = 32% |
| DAMAGED_DNA_BINDING | 21 | 0.37748018 | 1.0742105 | 0.36645964 | 0.5652575 | 1 | 3592 | tags = 29%, list = 16%, signal = 34% |
| WANG_CISPLATIN_RESPONSE_AND_XPC_UP | 184 | 0.24496014 | 1.0703033 | 0.284689 | 0.5663396 | 1 | 3979 | tags = 23%, list = 18%, signal = 28% |
| V$E2F4DP2_01 | 226 | 0.24129184 | 1.0745329 | 0.27930173 | 0.56783473 | 1 | 3544 | tags = 20%, list = 16%, signal = 24% |
| REGULATION_OF_CELL_CYCLE | 176 | 0.24882938 | 1.0718728 | 0.27951807 | 0.5686671 | 1 | 2958 | tags = 16%, list = 13%, signal = 18% |
| V$E2F1DP2_01 | 226 | 0.24129184 | 1.0705135 | 0.27380952 | 0.5690597 | 1 | 3544 | tags = 20%, list = 16%, signal = 24% |
| WHITFIELD_CELL_CYCLE_LITERATURE | 44 | 0.32180226 | 1.0750089 | 0.34419551 | 0.56976515 | 1 | 4815 | tags = 30%, list = 22%, signal = 38% |
| DNA_DEPENDENT_DNA_REPLICATION | 54 | 0.30361858 | 1.0761642 | 0.3170163 | 0.5699367 | 1 | 6608 | tags = 48%, list = 30%, signal = 68% |
| BURTON_ADIPOGENESIS_3 | 101 | 0.26952776 | 1.0771737 | 0.29439253 | 0.57049567 | 1 | 6960 | tags = 48%, list = 31%, signal = 69% |
| FUJII_YBX1_TARGETS_DN | 199 | 0.2463158 | 1.0787462 | 0.2647059 | 0.57270294 | 1 | 5923 | tags = 35%, list = 27%, signal = 48% |
| V$E2F1DP1_01 | 226 | 0.24129184 | 1.077429 | 0.26477543 | 0.573177 | 1 | 3544 | tags = 20%, list = 16%, signal = 24% |
| MODULE_451 | 32 | 0.3326359 | 1.0617337 | 0.36886993 | 0.58774364 | 1 | 2031 | tags = 19%, list = 9%, signal = 21% |
| REACTOME_G1_PHASE | 34 | 0.32495195 | 1.0558343 | 0.3773585 | 0.60097677 | 1 | 3518 | tags = 29%, list = 16%, signal = 16% |

TABLE 6P-continued

GSEA for BAF180-null vs. BAF180-wildtype A704 cell lines on E2F Founder gene sets

| NAME | SIZE | ES | NES | NOM p-val | FDR q-val | FWER p-val | RANK AT MAX | LEADING EDGE |
|---|---|---|---|---|---|---|---|---|
| KEGG_DNA_REPLICATION | 36 | 0.31393066 | 1.046971 | 0.33936653 | 0.6200095 | 1 | 3979 | signal = 35%, tags = 28%, list = 18%, |
| MEIOTIC_CELL_CYCLE | 28 | 0.34077063 | 1.0479791 | 0.3842795 | 0.6204566 | 1 | 3568 | signal = 34%, tags = 29%, list = 16%, |
| V$E2F_03 | 234 | 0.23456398 | 1.042715 | 0.344473 | 0.6288928 | 1 | 6280 | signal = 34%, tags = 35%, list = 28%, |
| CELL_CYCLE_GO_0007049 | 299 | 0.22635782 | 1.0385077 | 0.3508772 | 0.63457865 | 1 | 3835 | signal = 48%, tags = 18%, list = 17%, |
| GROSS_HYPOXIA_VIA_ELK3_AND_HIF1A_DN | 100 | 0.26218835 | 1.0370255 | 0.37214613 | 0.63548464 | 1 | 3112 | signal = 21%, tags = 19%, list = 14%, |
| PUJANA_BRCA2_PCC_NETWORK | 405 | 0.21916327 | 1.0386813 | 0.32258064 | 0.6376872 | 1 | 6591 | signal = 22%, tags = 35%, list = 30%, |
| GNF2_BUB1 | 26 | 0.33931977 | 1.029488 | 0.4051724 | 0.65430546 | 1 | 7321 | signal = 48%, tags = 50%, list = 33%, |
| MEIOSIS_I | 16 | 0.38233972 | 1.0197504 | 0.4232456 | 0.67703986 | 1 | 3123 | signal = 74%, tags = 25%, list = 14%, |
| FOURNIER_ACINAR_DEVELOPMENT_LATE_2 | 273 | 0.22042942 | 1.0125483 | 0.40149626 | 0.6774985 | 1 | 7446 | signal = 29%, tags = 39%, list = 34%, |
| V$E2F_Q4 | 228 | 0.23197255 | 1.0203344 | 0.39847717 | 0.6787881 | 1 | 3544 | signal = 58%, tags = 20%, list = 16%, |
| V$E2F_02 | 226 | 0.2312068 | 1.0166516 | 0.4108527 | 0.679432 | 1 | 3544 | signal = 23%, tags = 20%, list = 16%, |
| GNF2_HMMR | 47 | 0.29403916 | 1.0129237 | 0.42388758 | 0.6797991 | 1 | 7559 | signal = 23%, tags = 47%, list = 34%, |
| KEGG_MISMATCH_REPAIR | 23 | 0.3423624 | 1.0173788 | 0.43572986 | 0.6807465 | 1 | 3979 | signal = 71%, tags = 35%, list = 18%, |
| V$E2F4DP1_01 | 228 | 0.22700226 | 1.0131376 | 0.41191068 | 0.6828414 | 1 | 3544 | signal = 42%, tags = 20%, list = 16%, |
| REACTOME_PROCESSIVE_SYNTHESIS_ON_THE_LAGGING_STRAND | 15 | 0.3860097 | 1.0136039 | 0.44124168 | 0.6850931 | 1 | 3979 | signal = 23%, tags = 40%, list = 18%, |
| MODULE_197 | 167 | 0.23311728 | 1.0055324 | 0.432243 | 0.6876353 | 1 | 5144 | signal = 49%, tags = 26%, |

TABLE 6P-continued

GSEA for BAF180-null vs. BAF180-wildtype A704 cell lines on E2F Founder gene sets

| NAME | SIZE | ES | NES | NOM p-val | FDR q-val | FWER p-val | RANK AT MAX | LEADING EDGE |
|---|---|---|---|---|---|---|---|---|
| CONCANNON_APOPTOSIS_BY_EPOXOMICIN_DN | 155 | 0.2371657 | 1.0074743 | 0.4538835 | 0.6891798 | 1 | 3596 | tags = 23%, list = 34%, signal = 22%, 16% |
| REACTOME_G1_S_SPECIFIC_TRANSCRIPTION | 16 | 0.35699904 | 1.0061347 | 0.44469026 | 0.689669 | 1 | 4815 | tags = 38%, list = 26%, signal = 22%, 48% |
| WU_APOPTOSIS_BY_CDKN1A_VIA_TP53 | 52 | 0.2869195 | 0.99947405 | 0.45333335 | 0.6954689 | 1 | 6762 | tags = 48%, list = 30%, signal = 69% |
| BASE_EXCISION_REPAIR | 16 | 0.37499917 | 0.9998841 | 0.4362416 | 0.6977798 | 1 | 3694 | tags = 38%, list = 17%, signal = 45% |
| REACTOME_LAGGING_STRAND_SYNTHESIS | 19 | 0.3588135 | 1.0008832 | 0.46420825 | 0.6983574 | 1 | 3979 | tags = 37%, list = 18%, signal = 45% |
| POSITIVE_REGULATION_OF_CELL_CYCLE | 15 | 0.3664347 | 0.9937743 | 0.45436105 | 0.7091833 | 1 | 5074 | tags = 40%, list = 23%, signal = 52% |
| MUELLER_PLURINET | 287 | 0.21411699 | 0.9904966 | 0.4526316 | 0.7120756 | 1 | 6383 | tags = 32%, list = 29%, signal = 45% |
| YU_MYC_TARGETS_UP | 42 | 0.29533926 | 0.9892236 | 0.46389496 | 0.7123799 | 1 | 5602 | tags = 31%, list = 25%, signal = 41% |
| RAY_TUMORIGENESIS_BY_ERBB2_CDC25A_UP | 96 | 0.25138888 | 0.99086094 | 0.45933014 | 0.7145532 | 1 | 2402 | tags = 19%, list = 11%, signal = 21% |
| LEE_EARLY_T_LYMPHOCYTE_UP | 97 | 0.25011945 | 0.9865701 | 0.4725537 | 0.71696126 | 1 | 5139 | tags = 32%, list = 23%, signal = 41% |
| KAUFFMANN_DNA_REPAIR_GENES | 219 | 0.222108 | 0.9846902 | 0.5225653 | 0.71836126 | 1 | 3979 | tags = 20%, list = 18%, signal = 24% |
| SHEPARD_CRUSH_AND_BURN_MUTANT_DN | 164 | 0.22918515 | 0.9804757 | 0.5090909 | 0.72380483 | 1 | 4748 | tags = 27%, list = 21%, signal = 34% |
| V$E2F_Q4_01 | 227 | 0.22024323 | 0.9815795 | 0.50117093 | 0.72419137 | 1 | 5320 | tags = 30%, list = 24%, signal = 38% |
| REACTOME_FANCONI_ANEMIA_PATHWAY | 21 | 0.33812094 | 0.97732526 | 0.49082568 | 0.7300886 | 1 | 8209 | tags = 52%, list = 37%, signal = 83% |
| HOFFMANN_LARGE_TO_SMALL_PRE_BII_LYMPHOCYTE_UP | 155 | 0.2293058 | 0.966305 | 0.523918 | 0.7489484 | 1 | 6690 | tags = 39%, list = 30%, signal = 55% |

TABLE 6P-continued

GSEA for BAF180-null vs. BAF180-wildtype A704 cell lines on E2F Founder gene sets

| NAME | SIZE | ES | NES | NOM p-val | FDR q-val | FWER p-val | RANK AT MAX | LEADING EDGE |
|---|---|---|---|---|---|---|---|---|
| PID_FANCONI_PATHWAY | 47 | 0.28501362 | 0.96698177 | 0.5075269 | 0.750541 | 1 | 6732 | tags = 47%, list = 30%, signal = 67% |
| PIONTEK_PKD1_TARGETS_DN | 16 | 0.36119446 | 0.9631549 | 0.506383 | 0.7512874 | 1 | 3510 | tags = 38%, list = 16%, signal = 45% |
| CHROMATIN | 33 | 0.30065694 | 0.9636298 | 0.5053996 | 0.75342274 | 1 | 2919 | tags = 18%, list = 13%, signal = 21% |
| FERREIRA_EWINGS_SARCOMA_UNSTABLE_VS_STABLE_UP | 159 | 0.22596973 | 0.9670589 | 0.5452323 | 0.75396377 | 1 | 6650 | tags = 36%, list = 30%, signal = 51% |
| GROSS_HYPOXIA_VIA_ELK3_UP | 204 | 0.21958606 | 0.96824384 | 0.558753 | 0.7543387 | 1 | 3787 | tags = 19%, list = 17%, signal = 23% |
| SCIBETTA_KDM5B_TARGETS_DN | 77 | 0.25283283 | 0.9583655 | 0.55133927 | 0.76184374 | 1 | 5602 | tags = 32%, list = 25%, signal = 43% |
| EGUCHI_CELL_CYCLE_RB1_TARGETS | 23 | 0.32270378 | 0.9485936 | 0.52764976 | 0.77358365 | 1 | 7686 | tags = 57%, list = 35%, signal = 86% |
| WHITFIELD_CELL_CYCLE_G2_M | 211 | 0.2133046 | 0.94932085 | 0.6278481 | 0.7749125 | 1 | 3989 | tags = 20%, list = 18%, signal = 24% |
| RPS14_DN.V1_DN | 178 | 0.21893507 | 0.95011306 | 0.5891648 | 0.77629346 | 1 | 4815 | tags = 28%, list = 22%, signal = 35% |
| MOLENAAR_TARGETS_OF_CCND1_AND_CDK4_DN | 57 | 0.2673039 | 0.9522256 | 0.5271493 | 0.77740884 | 1 | 7382 | tags = 49%, list = 33%, signal = 73% |
| V$E2F1_Q6 | 225 | 0.21288314 | 0.95038515 | 0.59653467 | 0.7790583 | 1 | 3544 | tags = 19%, list = 16%, signal = 23% |
| BOYAULT_LIVER_CANCER_SUBCLASS_G3_UP | 187 | 0.21531379 | 0.93996984 | 0.6296296 | 0.7951581 | 1 | 6309 | tags = 31%, list = 28%, signal = 43% |
| RHODES_UNDIFFERENTIATED_CANCER | 68 | 0.24986419 | 0.9363587 | 0.5892473 | 0.8019492 | 1 | 7422 | tags = 43%, list = 33%, signal = 64% |
| VANTVEER_BREAST_CANCER_METASTASIS_DN | 116 | 0.22871712 | 0.9335559 | 0.6086956 | 0.80667114 | 1 | 4748 | tags = 25%, list = 21%, signal = 32% |
| GNF2_CDC2 | 61 | 0.25424793 | 0.9315171 | 0.5619048 | 0.8087767 | 1 | 7559 | tags = 44%, list = 34%, signal = 67% |
| ODONNELL_TFRC_TARGETS_DN | 117 | 0.22895187 | 0.9288347 | 0.62954545 | 0.80948067 | 1 | 1958 | tags = 12%, list = 9%, signal = |

TABLE 6P-continued

GSEA for BAF180-null vs. BAF180-wildtype A704 cell lines on E2F Founder gene sets

| NAME | SIZE | ES | NES | NOM p-val | FDR q-val | FWER p-val | RANK AT MAX | LEADING EDGE |
|---|---|---|---|---|---|---|---|---|
| GNF2_CCNB2 | 56 | 0.26242125 | 0.9296985 | 0.60393876 | 0.8103493 | 1 | 7559 | tags = 45%, list = 34%, signal = 13% |
| MODULE_123 | 225 | 0.2072971 | 0.9263362 | 0.68550366 | 0.81329805 | 1 | 3622 | tags = 19%, list = 16%, signal = 67% |
| MITSIADES_RESPONSE_TO_APLIDIN_DN | 244 | 0.20661007 | 0.9159852 | 0.7218045 | 0.8253738 | 1 | 3967 | tags = 18%, list = 18%, signal = 23% |
| BIOCARTA_CELLCYCLE_PATHWAY | 22 | 0.3144141 | 0.91380036 | 0.58474576 | 0.82761246 | 1 | 3518 | tags = 36%, list = 16%, signal = 21% |
| PETROVA_ENDOTHELIUM_LYMPHATIC_VS_BLOOD_UP | 125 | 0.22451954 | 0.9163942 | 0.6810551 | 0.8278902 | 1 | 4748 | tags = 30%, list = 21%, signal = 43% |
| BIOCARTA_G2_PATHWAY | 24 | 0.30806628 | 0.9189605 | 0.55581397 | 0.8284411 | 1 | 4926 | tags = 25%, list = 22%, signal = 37% |
| CHANG_CORE_SERUM_RESPONSE_UP | 205 | 0.20796135 | 0.9118108 | 0.7139423 | 0.82964015 | 1 | 3331 | tags = 16%, list = 15%, signal = 32% |
| WEST_ADRENOCORTICAL_TUMOR_UP | 288 | 0.19953583 | 0.90975195 | 0.7622739 | 0.83113348 | 1 | 3011 | tags = 11%, list = 14%, signal = 19% |
| KONG_E2F3_TARGETS | 93 | 0.2333433 | 0.91645014 | 0.62918663 | 0.8315079 | 1 | 7618 | tags = 53%, list = 34%, signal = 13% |
| CONDENSED_NUCLEAR_CHROMOSOME | 18 | 0.3236068 | 0.90837693 | 0.5973742 | 0.83160794 | 1 | 541 | tags = 11%, list = 2%, signal = 80% |
| REACTOME_E2F_MEDIATED_REGULATION_OF_DNA_REPLICATION | 31 | 0.28685817 | 0.91914606 | 0.5822222 | 0.8316486 | 1 | 3225 | tags = 23%, list = 15%, signal = 11% |
| NAKAMURA_CANCER_MICROENVIRONMENT_DN | 45 | 0.26146442 | 0.90145844 | 0.625 | 0.8355533 | 1 | 4815 | tags = 24%, list = 22%, signal = 26% |
| DNA_INTEGRITY_CHECKPOINT | 22 | 0.31207764 | 0.9021031 | 0.6038136 | 0.8374959 | 1 | 2295 | tags = 23%, list = 10%, signal = 31% |
| LE_EGR2_TARGETS_UP | 107 | 0.22567828 | 0.9034158 | 0.6838565 | 0.83800644 | 1 | 7145 | tags = 39%, list = 32%, signal = 25% |
| GOLDRATH_ANTIGEN_RESPONSE | 315 | 0.19614215 | 0.9041977 | 0.7881356 | 0.8396098 | 1 | 2823 | tags = 14%, list = 13%, signal = 58% |
| CELL_CYCLE_PROCESS | 181 | 0.20733057 | 0.89436126 | 0.740099 | 0.8508811 | 1 | 3835 | tags = 18%, list = 16%, |

TABLE 6P-continued

GSEA for BAF180-null vs. BAF180-wildtype A704 cell lines on E2F Founder gene sets

| NAME | SIZE | ES | NES | NOM p-val | FDR q-val | FWER p-val | RANK AT MAX | LEADING EDGE |
|---|---|---|---|---|---|---|---|---|
| GEORGES_CELL_CYCLE_MIR192_TARGETS | 61 | 0.24397157 | 0.88450396 | 0.6785714 | 0.8553726 | 1 | 5137 | tags = 34%, list = 17%, signal = 21% |
| MODULE_337 | 59 | 0.24638712 | 0.8907535 | 0.67748916 | 0.8568585 | 1 | 4553 | tags = 25%, list = 23%, signal = 45% |
| CHROMOSOME | 119 | 0.21626177 | 0.8845944 | 0.72616136 | 0.8587043 | 1 | 3952 | tags = 19%, list = 20%, signal = 32% |
| CSR_LATE_UP.V1_UP | 162 | 0.20884226 | 0.88793343 | 0.7597254 | 0.8604634 | 1 | 6013 | tags = 35%, list = 18%, signal = 23% |
| DNA_REPAIR | 121 | 0.21765089 | 0.88643444 | 0.7619048 | 0.86091167 | 1 | 4292 | tags = 21%, list = 27%, signal = 47% |
| NUCLEAR_CHROMOSOME | 52 | 0.24982874 | 0.8849984 | 0.6564417 | 0.8612027 | 1 | 3753 | tags = 23%, list = 19%, signal = 26% |
| NADERI_BREAST_CANCER_PROGNOSIS_UP | 45 | 0.251694 | 0.87826246 | 0.6903226 | 0.867421 | 1 | 3941 | tags = 24%, list = 17%, signal = 28% |
| WEST_ADRENOCORTICAL_TUMOR_MARKERS_UP | 20 | 0.31013876 | 0.8726998 | 0.6442953 | 0.8773783 | 1 | 4586 | tags = 35%, list = 18%, signal = 30% |
| DNA_RECOMBINATION | 41 | 0.26143017 | 0.8645332 | 0.6969697 | 0.88253117 | 1 | 3979 | tags = 24%, list = 21%, signal = 44% |
| MODULE_98 | 383 | 0.18384965 | 0.8645767 | 0.9104859 | 0.8859621 | 1 | 6383 | tags = 30%, list = 18%, signal = 30% |
| RESPONSE_TO_DNA_DAMAGE_STIMULUS | 155 | 0.20516442 | 0.86677235 | 0.7888349 | 0.88827926 | 1 | 4292 | tags = 21%, list = 29%, signal = 41% |
| PID_AURORA_B_PATHWAY | 38 | 0.25923198 | 0.86506176 | 0.6898148 | 0.8884687 | 1 | 7282 | tags = 39%, list = 19%, signal = 25% |
| INTERPHASE | 67 | 0.23223965 | 0.856466 | 0.754023 | 0.89718485 | 1 | 6186 | tags = 28%, list = 33%, signal = 59% |
| SASAKI_ADULT_T_CELL_LEUKEMIA | 168 | 0.19772334 | 0.85330105 | 0.84155846 | 0.9005819 | 1 | 3112 | tags = 17%, list = 28%, signal = 39% |
| ENDONUCLEASE_ACTIVITY | 24 | 0.2890893 | 0.8475868 | 0.6753247 | 0.90952533 | 1 | 3694 | tags = 21%, list = 14%, signal = 19% |

TABLE 6P-continued

GSEA for BAF180-null vs. BAF180-wildtype A704 cell lines on E2F Founder gene sets

| NAME | SIZE | ES | NES | NOM p-val | FDR q-val | FWER p-val | RANK AT MAX | LEADING EDGE |
|---|---|---|---|---|---|---|---|---|
| SHEPARD_BMYB_TARGETS | 67 | 0.22698352 | 0.83501667 | 0.7537155 | 0.931361 | 1 | 6512 | tags = 40%, list = 29%, signal = 57% |
| XU_HGF_SIGNALING_NOT_VIA_AKT1_48HR_DN | 20 | 0.29689857 | 0.8304175 | 0.6914153 | 0.93660086 | 1 | 2398 | tags = 20%, list = 11%, signal = 22% |
| BIOCARTA_ATM_PATHWAY | 20 | 0.28158852 | 0.81876826 | 0.73150104 | 0.95485157 | 1 | 7576 | tags = 50%, list = 34%, signal = 76% |
| RESPONSE_TO_ENDOGENOUS_STIMULUS | 188 | 0.1866301 | 0.81233823 | 0.9328537 | 0.9625193 | 1 | 4417 | tags = 21%, list = 20%, signal = 26% |
| WANG_METASTASIS_OF_BREAST_CANCER_ESR1_UP | 21 | 0.2829569 | 0.80946195 | 0.7505721 | 0.96375966 | 1 | 4066 | tags = 24%, list = 18%, signal = 29% |
| KTGGYRSGAA_UNKNOWN | 73 | 0.21137054 | 0.7913279 | 0.87061405 | 0.98078364 | 1 | 3979 | tags = 23%, list = 18%, signal = 28% |
| INTERPHASE_OF_MITOTIC_CELL_CYCLE | 61 | 0.21559632 | 0.78868103 | 0.8537736 | 0.980797 | 1 | 6186 | tags = 28%, list = 28%, signal = 39% |
| GNF2_CDC20 | 55 | 0.2195407 | 0.7934546 | 0.80227274 | 0.9814875 | 1 | 7559 | tags = 42%, list = 34%, signal = 63% |
| GNF2_MKI67 | 27 | 0.25541335 | 0.77952003 | 0.7891566 | 0.9831143 | 1 | 7863 | tags = 52%, list = 35%, signal = 80% |
| DELPUECH_FOXO3_TARGETS_DN | 39 | 0.23067386 | 0.7819254 | 0.81038374 | 0.98327434 | 1 | 713 | tags = 8%, list = 3%, signal = 8% |
| DOUBLE_STRANDED_DNA_BINDING | 32 | 0.24721268 | 0.7843362 | 0.78571427 | 0.983627 | 1 | 8006 | tags = 56%, list = 36%, signal = 88% |
| ZHANG_TLX_TARGETS_36HR_DN | 183 | 0.18505661 | 0.79438126 | 0.9626168 | 0.9840848 | 1 | 5791 | tags = 28%, list = 26%, signal = 37% |
| AMUNDSON_GAMMA_RADIATION_RESPONSE | 39 | 0.23116218 | 0.7757849 | 0.8237885 | 0.9845052 | 1 | 4586 | tags = 23%, list = 21%, signal = 29% |
| CELL_CYCLE_PHASE | 159 | 0.18245688 | 0.77151066 | 0.96889955 | 0.9863564 | 1 | 3835 | tags = 17%, list = 17%, signal = 20% |
| GNF2_H2AFX | 31 | 0.245504 | 0.7668124 | 0.82905984 | 0.9885595 | 1 | 7863 | tags = 42%, list = 35%, signal = 65% |
| BIOCARTA_ATRBRCA_PATHWAY | 21 | 0.2679855 | 0.75611866 | 0.79956424 | 0.9900323 | 1 | 7576 | tags = 52%, list = 34%, signal = 65% |

TABLE 6P-continued

GSEA for BAF180-null vs. BAF180-wildtype A704 cell lines on E2F Founder gene sets

| NAME | SIZE | ES | NES | NOM p-val | FDR q-val | FWER p-val | RANK AT MAX | LEADING EDGE |
|---|---|---|---|---|---|---|---|---|
| E2F1_UP.V1_UP | 181 | 0.17771947 | 0.76245344 | 0.9832134 | 0.99025416 | 1 | 3366 | tags = 15%, list = 15%, signal = 18% |
| CHROMOSOMAL_PART | 94 | 0.19201228 | 0.75130504 | 0.9491525 | 0.99154246 | 1 | 3952 | tags = 19%, list = 18%, signal = 23% |
| NUCLEOTIDYLTRANSFERASE_ACTIVITY | 46 | 0.22064428 | 0.7574412 | 0.8724832 | 0.9923186 | 1 | 2397 | tags = 11%, list = 11%, signal = 12% |
| PID_ATM_PATHWAY | 34 | 0.23613212 | 0.74652845 | 0.85209715 | 0.99284047 | 1 | 3835 | tags = 21%, list = 17%, signal = 25% |
| MMS_MOUSE_LYMPH_HIGH_4HRS_UP | 34 | 0.19298783 | 0.6210885 | 0.97863245 | 0.9972357 | 1 | 4821 | tags = 26%, list = 22%, signal = 34% |
| REACTOME_HOMOLOGOUS_RECOMBINATION_REPAIR_OF_REPLICATION_IN_DEPENDENT_DOUBLE_STRAND_BREAKS | 16 | 0.21169989 | 0.5575222 | 0.95424837 | 0.9975556 | 1 | 3979 | tags = 31%, list = 18%, signal = 38% |
| PID_ATR_PATHWAY | 38 | 0.1762004 | 0.57545614 | 0.9859719 | 0.99792004 | 1 | 7393 | tags = 42%, list = 33%, signal = 63% |
| XU_HGF_TARGETS_INDUCED_BY_AKT1_48HR_DN | 23 | 0.20875 | 0.6040176 | 0.96196866 | 0.9987243 | 1 | 6431 | tags = 26%, list = 29%, signal = 37% |
| PUJANA_BREAST_CANCER_LIT_INT_NETWORK | 100 | 0.14568026 | 0.5861298 | 1 | 0.999418 | 1 | 4926 | tags = 20%, list = 22%, signal = 26% |
| PID_AURORA_A_PATHWAY | 31 | 0.13039789 | 0.40519395 | 1 | 0.9996472 | 1 | 7863 | tags = 35%, list = 35%, signal = 55% |
| REACTOME_DOUBLE_STRAND_BREAK_REPAIR | 22 | 0.21720654 | 0.63386077 | 0.9259259 | 0.9999909 | 1 | 3979 | tags = 27%, list = 18%, signal = 33% |
| BOYAULT_LIVER_CANCER_SUBCLASS_G23_UP | 52 | 0.21013078 | 0.7321246 | 0.90531176 | 1 | 1 | 5137 | tags = 35%, list = 23%, signal = 45% |
| WAKASUGI_HAVE_ZNF143_BINDING_SITES | 57 | 0.2007666 | 0.72421956 | 0.9321267 | 1 | 1 | 2548 | tags = 11%, list = 11%, signal = 12% |
| STRUCTURE_SPECIFIC_DNA_BINDING | 55 | 0.20189369 | 0.7193361 | 0.9126214 | 1 | 1 | 4340 | tags = 24%, list = 20%, signal = 29% |
| RNA_CATABOLIC_PROCESS | 21 | 0.24913102 | 0.7153406 | 0.8574514 | 1 | 1 | 1091 | tags = 10%, list = 5%, signal = 10% |

TABLE 6P-continued

GSEA for BAF180-null vs. BAF180-wildtype A704 cell lines on E2F Founder gene sets

| NAME | SIZE | ES | NES | NOM p-val | FDR q-val | FWER p-val | RANK AT MAX | LEADING EDGE |
|---|---|---|---|---|---|---|---|---|
| JUBAN_TARGETS_OF_SPI1_AND_FLI1_DN | 85 | 0.185801 | 0.70965517 | 0.95194507 | 1 | 1 | 3630 | tags = 18%, list = 16%, signal = 21% |
| M_PHASE | 104 | 0.17733969 | 0.6991719 | 0.9678161 | 1 | 1 | 3835 | tags = 18%, list = 17%, signal = 22% |
| SLEBOS_HEAD_AND_NECK_CANCER_WITH_HPV_UP | 79 | 0.18106677 | 0.6978613 | 0.9678161 | 1 | 1 | 6611 | tags = 37%, list = 30%, signal = 52% |
| LE_NEURONAL_DIFFERENTIATION_DN | 19 | 0.24310753 | 0.6830966 | 0.87350833 | 1 | 1 | 2707 | tags = 16%, list = 12%, signal = 18% |
| MODULE_244 | 183 | 0.15612298 | 0.6769737 | 1 | 1 | 1 | 4989 | tags = 18%, list = 22%, signal = 23% |
| KEGG_HOMOLOGOUS_RECOMBINATION | 26 | 0.21819423 | 0.6692233 | 0.92050207 | 1 | 1 | 3835 | tags = 27%, list = 17%, signal = 33% |
| DEOXYRIBONUCLEASE_ACTIVITY | 22 | 0.2264191 | 0.6632232 | 0.9311111 | 1 | 1 | 3059 | tags = 18%, list = 14%, signal = 21% |
| MITOTIC_CELL_CYCLE | 149 | 0.15570225 | 0.6591574 | 0.9977477 | 1 | 1 | 4815 | tags = 19%, list = 22%, signal = 24% |
| CONDENSED_CHROMOSOME | 33 | 0.20675065 | 0.6579867 | 0.9380734 | 1 | 1 | 541 | tags = 6%, list = 2%, signal = 6% |
| LY_AGING_MIDDLE_DN | 16 | 0.24691017 | 0.64970356 | 0.88235295 | 1 | 1 | 5139 | tags = 31%, list = 23%, signal = 41% |
| CHROMATIN_BINDING | 30 | 0.20629004 | 0.64783484 | 0.9472477 | 1 | 1 | 6704 | tags = 40%, list = 30%, signal = 57% |
| FINETTI_BREAST_CANCER_KINOME_RED | 16 | 0.23619422 | 0.64430344 | 0.8930818 | 1 | 1 | 8991 | tags = 63%, list = 40%, signal = 105% |
| NEMETH_INFLAMMATORY_RESPONSE_LPS_DN | 30 | 0.20279045 | 0.6362227 | 0.96444446 | 1 | 1 | 1267 | tags = 7%, list = 6%, signal = 7% |
| MODULE_372 | 23 | 0.21186408 | 0.62316877 | 0.95353985 | 1 | 1 | 2603 | tags = 17%, list = 12%, signal = 20% |
| LL_WILMS_TUMOR_ANAPLASTIC_UP | 18 | 0.1786921 | 0.4808827 | 0.98940676 | 1 | 1 | 4586 | tags = 22%, list = 21%, signal = 28% |

TABLE 6Q

GSEA for BAF180-wildtype, BRG1-null vs. BAF180-wildtype, BRG1-wildtype A704 cell lines on E2F founder gene sets

| NAME | SIZE | ES | NES | NOM p-val | FDR q-val | FWER p-val | RANK AT MAX | LEADING EDGE |
|---|---|---|---|---|---|---|---|---|
| PYEON_HPV_POSITIVE_TUMORS_UP | 86 | 0.5272385 | 1.839632 | 0 | 0.06262126 | 0.055 | 5713 | tags = 51%, list = 26%, signal = 69% |
| RIZ_ERYTHROID_DIFFERENTIATION_CCNE1 | 38 | 0.5936944 | 1.7935095 | 0 | 0.06979053 | 0.12 | 4971 | tags = 42%, list = 22%, signal = 54% |
| BIOCARTA_P53_PATHWAY | 16 | 0.68817526 | 1.7357148 | 0.001416431 | 0.12532707 | 0.298 | 4769 | tags = 63%, list = 21%, signal = 80% |
| MODULE_372 | 23 | 0.57266676 | 1.5990293 | 0.013477089 | 0.15318382 | 0.826 | 5778 | tags = 57%, list = 26%, signal = 76% |
| PYEON_CANCER_HEAD_AND_NECK_VS_CERVICAL_UP | 180 | 0.4247083 | 1.6037453 | 0 | 0.15759799 | 0.812 | 5440 | tags = 43%, list = 24%, signal = 57% |
| MEIOSIS_I | 16 | 0.63435125 | 1.6273228 | 0.027894003 | 0.16242792 | 0.727 | 6862 | tags = 75%, list = 31%, signal = 108% |
| WHITFIELD_CELL_CYCLE_S | 154 | 0.44637805 | 1.6483345 | 0.001090513 | 0.16337588 | 0.637 | 7229 | tags = 55%, list = 33%, signal = 80% |
| BIOCARTA_G1_PATHWAY | 28 | 0.57023114 | 1.660712 | 0.005215124 | 0.16788994 | 0.586 | 5440 | tags = 57%, list = 24%, signal = 76% |
| MATZUK_MEIOTIC_AND_DNA_REPAIR | 34 | 0.5383647 | 1.6045825 | 0.010282776 | 0.17092769 | 0.808 | 5334 | tags = 50%, list = 24%, signal = 66% |
| MEIOTIC_CELL_CYCLE | 30 | 0.5437648 | 1.6319793 | 0.015625 | 0.1718576 | 0.707 | 6862 | tags = 60%, list = 31%, signal = 87% |
| BIOCARTA_ATRBRCA_PATHWAY | 21 | 0.58391106 | 1.6125102 | 0.009459459 | 0.17274452 | 0.779 | 6550 | tags = 67%, list = 29%, signal = 94% |
| RIZ_ERYTHROID_DIFFERENTIATION | 75 | 0.45804963 | 1.5684189 | 0.005675369 | 0.18671939 | 0.923 | 7037 | tags = 41%, list = 32%, signal = 60% |
| VERNELL_RETINOBLASTOMA_PATHWAY_UP | 70 | 0.4634217 | 1.5710841 | 0.009501188 | 0.19235954 | 0.917 | 7709 | tags = 54%, list = 35%, signal = 83% |
| PID_BARD1_PATHWAY | 29 | 0.5659379 | 1.6823814 | 0.002635046 | 0.19266273 | 0.498 | 7414 | tags = 66%, list = 33%, signal = 98% |
| PETROVA_PROX1_TARGETS_UP | 28 | 0.57863456 | 1.6649306 | 0.00511509 | 0.19333066 | 0.573 | 797 | tags = 21%, list = 4%, |

TABLE 6Q-continued

GSEA for BAF180-wildtype, BRG1-null vs. BAF180-wildtype, BRG1-wildtype A704 cell lines on E2F founder gene sets

| NAME | SIZE | ES | NES | NOM p-val | FDR q-val | FWER p-val | RANK AT MAX | LEADING EDGE |
|---|---|---|---|---|---|---|---|---|
| WHITFIELD_CELL_CYCLE_G1_S | 134 | 0.42525694 | 1.5520701 | 0.001089325 | 0.20529872 | 0.946 | 4372 | tags = 32%, list = 20%, signal = 22% |
| MATZUK_SPERMATOCYTE | 66 | 0.44045216 | 1.4767342 | 0.01891253 | 0.34925577 | 0.996 | 5798 | tags = 36%, list = 26%, signal = 40% |
| DNA_DEPENDENT_DNA_REPLICATION | 54 | 0.4520749 | 1.4790777 | 0.024539877 | 0.35907367 | 0.996 | 6939 | tags = 54%, list = 31%, signal = 49% |
| REGULATION_OF_DNA_REPLICATION | 19 | 0.5626945 | 1.4895319 | 0.043235704 | 0.36154857 | 0.995 | 6147 | tags = 63%, list = 28%, signal = 78% |
| ZHANG_TLX_TARGETS_36HR_DN | 183 | 0.39179507 | 1.4808265 | 0.004223865 | 0.37310576 | 0.996 | 8089 | tags = 52%, list = 36%, signal = 87% |
| KAUFFMANN_DNA_REPLICATION_GENES | 137 | 0.40041688 | 1.4609982 | 0.013100437 | 0.3859268 | 0.998 | 4039 | tags = 23%, list = 18%, signal = 81% |
| ZHANG_TLX_TARGETS_DN | 88 | 0.4166838 | 1.4548726 | 0.018348623 | 0.389864 | 0.998 | 7790 | tags = 53%, list = 35%, signal = 27% |
| DNA_REPLICATION | 98 | 0.40929762 | 1.4456508 | 0.019406393 | 0.4057281 | 0.999 | 6351 | tags = 42%, list = 29%, signal = 82% |
| PUJANA_XPRSS_INT_NETWORK | 164 | 0.3874114 | 1.4399135 | 0.010695187 | 0.40881744 | 1 | 7811 | tags = 48%, list = 35%, signal = 58% |
| VSE2F_Q6 | 226 | 0.3599759 | 1.3910922 | 0.01027 7492 | 0.41001374 | 1 | 4531 | tags = 30%, list = 20%, signal = 73% |
| GROSS_HYPOXIA_VIA_ELK3_ONLY_DN | 44 | 0.40443248 | 1.2704886 | 0.14123581 | 0.41584083 | 1 | 4537 | tags = 30%, list = 20%, signal = 37% |
| YU_BAP1_TARGETS | 28 | 0.4463093 | 1.27 16041 | 0.15045395 | 0.4173932 | 1 | 4471 | tags = 36%, list = 20%, signal = 37% |
| REACTOME_G0_AND_EARLY_G1 | 22 | 0.5040033 | 1.3914684 | 0.08412483 | 0.42002696 | 1 | 7061 | tags = 55%, list = 32%, signal = 45% |
| XU_HGF_TARGETS_INDUCED_BY_AKT1_48HR_DN | 23 | 0.45905653 | 1.2723931 | 0.16021362 | 0.4201529 | 1 | 4818 | tags = 48%, list = 22%, signal = 80% |
| DUTERTRE_ESTRADIOL_RESPONSE_24HR_UP | 319 | 0.34870973 | 1.3779316 | 0.00509165 | 0.42113948 | 1 | 6500 | tags = 39%, list = 29%, signal = 61%, signal = 54% |

TABLE 6Q-continued

GSEA for BAF180-wildtype, BRG1-null vs. BAF180-wildtype, BRG1-wildtype A704 cell lines on E2F founder gene sets

| NAME | SIZE | ES | NES | NOM p-val | FDR q-val | FWER p-val | RANK AT MAX | LEADING EDGE |
|---|---|---|---|---|---|---|---|---|
| DNA_METABOLIC_PROCESS | 243 | 0.36547664 | 1.3939599 | 0.008247423 | 0.42341417 | 1 | 6939 | tags = 41%, list = 31%, signal = 59% |
| V$E2F1DP2_01 | 227 | 0.3330221 | 1.2727325 | 0.050209206 | 0.4239942 | 1 | 4539 | tags = 27%, list = 20%, signal = 33% |
| V$E2F_Q4 | 228 | 0.3573901 | 1.3796762 | 0.010341262 | 0.42525893 | 1 | 4531 | tags = 29%, list = 20%, signal = 37% |
| V$E2F4DP2_01 | 227 | 0.3330221 | 1.2736936 | 0.048654243 | 0.42588946 | 1 | 4539 | tags = 27%, list = 20%, signal = 33% |
| V$E2F4DP1_01 | 229 | 0.33116725 | 1.2788012 | 0.04033092 | 0.42612317 | 1 | 5002 | tags = 29%, list = 23%, signal = 37% |
| GRAHAM_NORMAL_QUIESCENT_VS_NORMAL_DIVIDING_DN | 82 | 0.3643046 | 1.2614889 | 0.12041284 | 0.42706442 | 1 | 10124 | tags = 59%, list = 46%, signal = 107% |
| RB_P130_DN.V1_UP | 119 | 0.35087037 | 1.2746123 | 0.09638554 | 0.42837283 | 1 | 6445 | tags = 35%, list = 29%, signal = 49% |
| KEGG_CELL_CYCLE | 121 | 0.34851927 | 1.2761647 | 0.09010989 | 0.42903692 | 1 | 7118 | tags = 41%, list = 32%, signal = 60% |
| PUJANA_BRCA_CENTERED_NETWORK | 117 | 0.38084027 | 1.3818555 | 0.02753304 | 0.42950952 | 1 | 8801 | tags = 56%, list = 40%, signal = 92% |
| PID_RB_1PATHWAY | 60 | 0.41720495 | 1.3957446 | 0.056354918 | 0.4299672 | 1 | 5440 | tags = 43%, list = 24%, signal = 57% |
| GNF2_RFC4 | 60 | 0.378941 | 1.2620343 | 0.13739546 | 0.43020865 | 1 | 10232 | tags = 53%, list = 46%, signal = 99% |
| V$E2F1_Q4_01 | 220 | 0.32797867 | 1.2637687 | 0.046632126 | 0.4302939 | 1 | 5052 | tags = 30%, list = 23%, signal = 38% |
| KAUFFMANN_DNA_REPAIR_GENES | 219 | 0.3374719 | 1.2791452 | 0.0516333 | 0.43037856 | 1 | 8304 | tags = 45%, list = 37%, signal = 71% |
| MODULE_485 | 49 | 0.39738664 | 1.2800944 | 0.13349815 | 0.43325686 | 1 | 4222 | tags = 24%, list = 19%, signal = 30% |
| V$E2F_Q3 | 212 | 0.36750948 | 1.4023234 | 0.00729927 | 0.43391433 | 1 | 7061 | tags = 43%, list = 32%, signal = 62% |
| BIOCARTA_ATM_PATHWAY | 20 | 0.532553 | 1.4095083 | 0.05 | 0.43623218 | 1 | 6351 | tags = 60%, |

TABLE 6Q-continued

GSEA for BAF180-wildtype, BRG1-null vs. BAF180-wildtype, BRG1-wildtype A704 cell lines on E2F founder gene sets

| NAME | SIZE | ES | NES | NOM p-val | FDR q-val | FWER p-val | RANK AT MAX | LEADING EDGE |
|---|---|---|---|---|---|---|---|---|
| BHATI_G2M_ARREST_BY_2METHOXYES_TRADIOL_UP | 107 | 0.38311595 | 1.3700684 | 0.03508772 | 0.43860245 | 1 | 6356 | tags = 42%, list = 29%, signal = 84% |
| VANTVEER_BREAST_CANCER_METASTASIS_UP | 56 | 0.38941473 | 1.2801098 | 0.13189448 | 0.43881142 | 1 | 4211 | tags = 29%, list = 19%, signal = 59% |
| VANTVEER_BREAST_CANCER_POOR_PROGNOSIS | 51 | 0.42154846 | 1.3641762 | 0.063275434 | 0.4390399 | 1 | 3547 | tags = 27%, list = 16%, signal = 35% |
| DNA_INTEGRITY_CHECKPOINT | 23 | 0.46380734 | 1.2850869 | 0.14717478 | 0.44053853 | 1 | 6550 | tags = 57%, list = 29%, signal = 33% |
| STEIN_ESRRA_TARGETS_RESPONSIVE_TO_ESTROGEN_DN | 40 | 0.44711083 | 1.3608043 | 0.08734177 | 0.4405746 | 1 | 6467 | tags = 52%, list = 29%, signal = 80% |
| ZHANG_TLX_TARGETS_60HR_DN | 270 | 0.32390845 | 1.2554305 | 0.055158325 | 0.44097477 | 1 | 7716 | tags = 41%, list = 35%, signal = 74% |
| KAUFFMANN_MELANOMA_RELAPSE_UP | 60 | 0.38860944 | 1.2830427 | 0.10676157 | 0.44121704 | 1 | 8499 | tags = 50%, list = 38%, signal = 63% |
| KORKOLA_TERATOMA | 37 | 0.45559233 | 1.3961036 | 0.068268016 | 0.4418932 | 1 | 4644 | tags = 35%, list = 21%, signal = 81% |
| ENDONUCLEASE_ACTIVITY | 24 | 0.43833843 | 1.2333641 | 0.20439845 | 0.4423011 | 1 | 6760 | tags = 46%, list = 30%, signal = 44% |
| MODULE_123 | 219 | 0.33024868 | 1.2533337 | 0.056074765 | 0.4423153 | 1 | 4298 | tags = 25%, list = 19%, signal = 66% |
| REGULATION_OF_CELL_CYCLE | 176 | 0.34136325 | 1.2807763 | 0.057142857 | 0.44240785 | 1 | 6270 | tags = 35%, list = 28%, signal = 31% |
| BIOCARTA_CELLCYCLE_PATHWAY | 23 | 0.45238993 | 1.2348099 | 0.20188425 | 0.4426122 | 1 | 5440 | tags = 48%, list = 24%, signal = 49% |
| BIDUS_METASTASIS_UP | 210 | 0.32272854 | 1.2317253 | 0.08727655 | 0.44313508 | 1 | 7607 | tags = 37%, list = 34%, signal = 63% |
| BIOCARTA_G2_PATHWAY | 24 | 0.43736917 | 1.23886 | 0.19839142 | 0.44345433 | 1 | 7169 | tags = 63%, list = 32%, signal = 56% |
| WAKASUGI_HAVE_ZNF143_BINDING_SITES | 57 | 0.409766 | 1.3569037 | 0.06455542 | 0.44383404 | 1 | 9053 | tags = 54%, list = 41%, signal = 92% |

TABLE 6Q-continued

GSEA for BAF180-wildtype, BRG1-null vs. BAF180-wildtype, BRG1-wildtype
A704 cell lines on E2F founder gene sets

| NAME | SIZE | ES | NES | NOM p-val | FDR q-val | FWER p-val | RANK AT MAX | LEADING EDGE |
|---|---|---|---|---|---|---|---|---|
| BAKER_HEMATOPOIESIS_STAT3_TARGETS | 16 | 0.5255945 | 1.3536161 | 0.12208505 | 0.44457713 | 1 | 4769 | signal = 92% tags = 31%, list = 21% |
| REN_BOUND_BY_E2F | 60 | 0.371754 | 1.2354999 | 0.1558753 | 0.44478825 | 1 | 9054 | signal = 40% tags = 52%, list = 41% |
| PUJANA_BREAST_CANCER_WITH_BRCA1_MUTATED_UP | 55 | 0.42610663 | 1.4033492 | 0.046116505 | 0.44482577 | 1 | 8637 | signal = 87% tags = 58%, list = 39% |
| NEGATIVE_REGULATION_OF_CELL_CYCLE | 74 | 0.406012 | 1.411202 | 0.034319527 | 0.44537887 | 1 | 6053 | signal = 95% tags = 41%, list = 27% |
| SHEPARD_BMYB_MORPHOLINO_DN | 181 | 0.33807123 | 1.285355 | 0.05844846 | 0.44549948 | 1 | 4903 | signal = 56% tags = 29%, list = 22% |
| VSE2F_02 | 227 | 0.32596663 | 1.2411405 | 0.072916664 | 0.44575807 | 1 | 4539 | signal = 37% tags = 26%, list = 20% |
| PEART_HDAC_PROLIFERATION_CLUSTER_DN | 71 | 0.36209452 | 1.2365865 | 0.14153132 | 0.44584346 | 1 | 4802 | signal = 33% tags = 28%, list = 22% |
| VANTVEER_BREAST_CANCER_METASTASIS_DN | 116 | 0.34457853 | 1.2395557 | 0.120746434 | 0.4458923 | 1 | 4607 | signal = 36% tags = 28%, list = 21% |
| REACTOME_DNA_STRAND_ELONGATION | 30 | 0.46618944 | 1.3650514 | 0.09174312 | 0.44635457 | 1 | 2108 | signal = 36% tags = 20%, list = 9% |
| VSE2F_Q3_01 | 226 | 0.32628265 | 1.2423823 | 0.07017544 | 0.44670755 | 1 | 5052 | signal = 22% tags = 30%, list = 23% |
| CELL_CYCLE_CHECKPOINT_GO_0000075 | 47 | 0.44452986 | 1.419703 | 0.04101327 | 0.44720095 | 1 | 6550 | signal = 38% tags = 47%, list = 29% |
| CELL_CYCLE_GO_0007049 | 300 | 0.33291504 | 1.3010465 | 0.022357723 | 0.4476244 | 1 | 6550 | signal = 66% tags = 35%, list = 29% |
| REACTOME_HOMOLOGOUS_RECOMBINATION_REPAIR_OF_REPLICATION_INDEPENDENT_DOUBLE_STRAND_BREAKS | 16 | 0.48624235 | 1.2428929 | 0.18620689 | 0.4497434 | 1 | 6871 | signal = 49% tags = 56%, list = 31% |
| MODULE_403 | 46 | 0.41504624 | 1.3022362 | 0.11691542 | 0.4509891 | 1 | 7716 | signal = 81% tags = 54%, list = 35% |
| ODONNELL_TARGETS_OF_MYC_AND_TFRC_DN | 44 | 0.414673 | 1.2855059 | 0.11757576 | 0.4510636 | 1 | 8499 | signal = 83% tags = 59%, list = 38% signal = 96% |

TABLE 6Q-continued

GSEA for BAF180-wildtype, BRG1-null vs. BAF180-wildtype, BRG1-wildtype A704 cell lines on E2F founder gene sets

| NAME | SIZE | ES | NES | NOM p-val | FDR q-val | FWER p-val | RANK AT MAX | LEADING EDGE |
|---|---|---|---|---|---|---|---|---|
| WHITFIELD_CELL_CYCLE_G2 | 173 | 0.32773593 | 1.2274308 | 0.08870116 | 0.451402 | 1 | 4668 | tags = 24%, list = 21%, signal = 30% |
| DNA_DAMAGE_CHECKPOINT | 19 | 0.47475117 | 1.2434118 | 0.20430107 | 0.4525769 | 1 | 6550 | tags = 58%, list = 29%, signal = 82% |
| CHIANG_LIVER_CANCER_SUBCLASS_PROLIFERATION_UP | 168 | 0.33162174 | 1.244898 | 0.082714744 | 0.45288795 | 1 | 4651 | tags = 24%, list = 21%, signal = 30% |
| MARKEY_RB1_CHRONIC_LOF_UP | 107 | 0.3516871 | 1.2457684 | 0.123903506 | 0.455226 | 1 | 4537 | tags = 30%, list = 20%, signal = 37% |
| REACTOME_G2_M_CHECKPOINTS | 41 | 0.4280654 | 1.3096297 | 0.12531969 | 0.45602632 | 1 | 9054 | tags = 66%, list = 41%, signal = 111% |
| PID_FANCONI_PATHWAY | 47 | 0.44685096 | 1.4223179 | 0.050183598 | 0.45605284 | 1 | 8291 | tags = 64%, list = 37%, signal = 102% |
| GNF2_SMC4L1 | 84 | 0.3596912 | 1.2468225 | 0.11907514 | 0.45696002 | 1 | 8761 | tags = 46%, list = 39%, signal = 76% |
| V$E2F1_Q3 | 231 | 0.336029 | 1.2855971 | 0.041322313 | 0.4570545 | 1 | 6428 | tags = 35%, list = 29%, signal = 49% |
| V$E2F1DP1RB_01 | 220 | 0.3411136 | 1.3024278 | 0.026943006 | 0.45745027 | 1 | 5052 | tags = 30%, list = 23%, signal = 38% |
| RESPONSE_TO_DNA_DAMAGE_STIMULUS | 156 | 0.35050243 | 1.3042861 | 0.046587214 | 0.45874286 | 1 | 8304 | tags = 50%, list = 37%, signal = 79% |
| V$E2F1_Q6_01 | 230 | 0.37063718 | 1.4119506 | 0.010405827 | 0.45911348 | 1 | 7781 | tags = 46%, list = 35%, signal = 70% |
| BLUM_RESPONSE_TO_SALIRASIB_DN | 333 | 0.3331813 | 1.3109615 | 0.013224822 | 0.45926988 | 1 | 4415 | tags = 25%, list = 20%, signal = 30% |
| CHROMATIN | 33 | 0.42863253 | 1.2906651 | 0.15817694 | 0.46022883 | 1 | 4588 | tags = 39%, list = 21%, signal = 50% |
| V$E2F1_Q4 | 232 | 0.337286 | 1.2925217 | 0.034020618 | 0.46110448 | 1 | 4570 | tags = 25%, list = 21%, signal = 32% |
| V$E2F1DP1_01 | 227 | 0.3330221 | 1.2862234 | 0.03516029 | 0.46150312 | 1 | 4539 | tags = 27%, list = 20%, signal = 33% |
| DNA_POLYMERASE_ACTIVITY | 17 | 0.51129895 | 1.3051121 | 0.15912208 | 0.46312702 | 1 | 3049 | tags = 29%, |

TABLE 6Q-continued

GSEA for BAF180-wildtype, BRG1-null vs. BAF180-wildtype, BRG1-wildtype A704 cell lines on E2F founder gene sets

| NAME | SIZE | ES | NES | NOM p-val | FDR q-val | FWER p-val | RANK AT MAX | LEADING EDGE |
|---|---|---|---|---|---|---|---|---|
| REACTOME_ACTIVATION_OF_THE_PRE_REPLICATIVE_COMPLEX | 30 | 0.42164528 | 1.2219079 | 0.19325551 | 0.46342462 | 1 | 9054 | list = 14%, tags = 60%, signal = 34% |
| NEMETH_INFLAMMATORY_RESPONSE_LPS_DN | 30 | 0.44607013 | 1.3114657 | 0.112125166 | 0.46563882 | 1 | 6411 | list = 41%, tags = 43%, signal = 101% |
| KAMMINGA_EZH2_TARGETS | 41 | 0.4117876 | 1.2868892 | 0.1476846 | 0.46586663 | 1 | 9741 | list = 29%, tags = 51%, signal = 61% |
| BOYAULT_LIVER_CANCER_SUBCLASS_G23_UP | 52 | 0.37493795 | 1.2195616 | 0.17090909 | 0.4663689 | 1 | 9521 | list = 44%, tags = 60%, signal = 91% |
| BOYAULT_LIVER_CANCER_SUBCLASS_G123_UP | 44 | 0.40885055 | 1.2927094 | 0.13449565 | 0.46733078 | 1 | 3534 | list = 43%, tags = 25%, signal = 104% |
| NEGATIVE_REGULATION_OF_DNA_METABOLIC_PROCESS | 17 | 0.50903845 | 1.3207972 | 0.13458756 | 0.46742555 | 1 | 6295 | list = 16%, tags = 53%, signal = 30% |
| MODULE_125 | 44 | 0.4174832 | 1.3118248 | 0.10869565 | 0.47248983 | 1 | 8449 | list = 28%, tags = 52%, signal = 74% |
| REACTOME_FANCONI_ANEMIA_PATHWAY | 21 | 0.4878057 | 1.3140798 | 0.12264151 | 0.47280735 | 1 | 9441 | list = 38%, tags = 71%, signal = 84% |
| ZHOU_CELL_CYCLE_GENES_IN_IR_RESPONSE_6HR | 85 | 0.35011268 | 1.2140554 | 0.16743119 | 0.47437987 | 1 | 9054 | list = 42%, tags = 53%, signal = 124% |
| V$E2F_Q4_01 | 227 | 0.34803805 | 1.342341 | 0.017598344 | 0.47562048 | 1 | 5128 | list = 41%, tags = 31%, signal = 89% |
| CELL_CYCLE_PROCESS | 184 | 0.32014745 | 1.214998 | 0.10492505 | 0.47582355 | 1 | 6500 | list = 23%, tags = 35%, signal = 40% |
| V$E2F_Q6_01 | 226 | 0.34184265 | 1.3208154 | 0.018518519 | 0.47608158 | 1 | 6747 | list = 29%, tags = 39%, signal = 49% |
| LINDGREN_BLADDER_CANCER_CLUSTER_3_UP | 317 | 0.33547068 | 1.315464 | 0.024464833 | 0.47640255 | 1 | 6342 | list = 30%, tags = 32%, signal = 55% |
| FUJII_YBX1_TARGETS_DN | 198 | 0.32220778 | 1.2118708 | 0.09375 | 0.47682393 | 1 | 6261 | list = 29%, tags = 35%, signal = 44% |
| BIOCARTA_MCM_PATHWAY | 18 | 0.4536684 | 1.2096198 | 0.2091768 | 0.4797364 | 1 | 9054 | list = 28%, tags = 61%, signal = 48%, list = 41% |

TABLE 6Q-continued

GSEA for BAF180-wildtype, BRG1-null vs. BAF180-wildtype, BRG1-wildtype
A704 cell lines on E2F founder gene sets

| NAME | SIZE | ES | NES | NOM p-val | FDR q-val | FWER p-val | RANK AT MAX | LEADING EDGE |
|---|---|---|---|---|---|---|---|---|
| REACTOME_ACTIVATION_OF_ATR_IN_RESPONSE_TO_REPLICATION_STRESS | 35 | 0.44588655 | 1.3214197 | 0.09756097 | 0.4829918 | 1 | 9054 | tags = 66%, list = 41%, signal = 103% |
| MODULE_158 | 43 | 0.42425537 | 1.3374326 | 0.0882353 | 0.4830363 | 1 | 7607 | tags = 47%, list = 34%, signal = 111% |
| WILCOX_RESPONSE_TO_PROGESTERONE_UP | 139 | 0.32814986 | 1.2047398 | 0.14254859 | 0.48662063 | 1 | 6069 | tags = 38%, list = 27%, signal = 71% |
| CHIARETTI_T_ALL_RELAPSE_PROGNOSIS | 18 | 0.50308824 | 1.3280432 | 0.13597734 | 0.48701903 | 1 | 7153 | tags = 56%, list = 32%, signal = 52% |
| SCIBETTA_KDM5B_TARGETS_DN | 77 | 0.3519979 | 1.2055135 | 0.19257541 | 0.48827815 | 1 | 6568 | tags = 38%, list = 30%, signal = 82% |
| DNA_REPAIR | 121 | 0.36780778 | 1.3223782 | 0.047513813 | 0.48875025 | 1 | 8304 | tags = 50%, list = 37%, signal = 53% |
| RB_DN.V1_UP | 133 | 0.36299983 | 1.3249965 | 0.0492806 | 0.4890961 | 1 | 4765 | tags = 32%, list = 21%, signal = 79% |
| REACTOME_G1_PHASE | 34 | 0.44088387 | 1.3327861 | 0.103492886 | 0.4891206 | 1 | 4802 | tags = 38%, list = 22%, signal = 40% |
| SGCGSSAAA_V$E2F1DP2_01 | 163 | 0.35208312 | 1.3299948 | 0.03711559 | 0.48966816 | 1 | 5002 | tags = 29%, list = 23%, signal = 49% |
| PETROVA_ENDOTHELIUM_LYMPHATIC_VS_BLOOD_UP | 124 | 0.3330752 | 1.2003479 | 0.1480663 | 0.49648187 | 1 | 4601 | tags = 27%, list = 21%, signal = 37% |
| PUJANA_BRCA2_PCC_NETWORK | 404 | 0.3018975 | 1.1938198 | 0.06458123 | 0.49655923 | 1 | 8801 | tags = 46%, list = 40%, signal = 34% |
| OLSSON_E2F3_TARGETS_DN | 44 | 0.37923804 | 1.1987423 | 0.1992528 | 0.49757302 | 1 | 2312 | tags = 20%, list = 10%, signal = 75% |
| REACTOME_RESOLUTION_OF_AP_SITES_VIA_THE_MULTIPLE_NUCLEOTIDE_PATCH_REPLACEMENT_PATHWAY | 17 | 0.46676862 | 1.1972795 | 0.24386922 | 0.49794504 | 1 | 5930 | tags = 47%, list = 27%, signal = 23% |
| EXONUCLEASE_ACTIVITY | 19 | 0.45039612 | 1.1954068 | 0.25414366 | 0.49976397 | 1 | 7039 | tags = 58%, list = 32%, signal = 64% |
| DNA_DAMAGE_RESPONSESIGNAL_TRANSDUCTION | 33 | 0.40284628 | 1.1940353 | 0.22809279 | 0.49990293 | 1 | 6550 | tags = 58%, list = 29%, signal = 85%, signal = 82% |

TABLE 6Q-continued

GSEA for BAF180-wildtype, BRG1-null vs. BAF180-wildtype, BRG1-wildtype A704 cell lines on E2F founder gene sets

| NAME | SIZE | ES | NES | NOM p-val | FDR q-val | FWER p-val | RANK AT MAX | LEADING EDGE |
|---|---|---|---|---|---|---|---|---|
| FERREIRA_EWINGS_SARCOMA_UNSTABLE_VS_STABLE_UP | 160 | 0.32071027 | 1.1905507 | 0.14209402 | 0.50172865 | 1 | 8499 | tags = 45%, list = 38%, signal = 72% |
| NUCLEASE_ACTIVITY | 52 | 0.36660424 | 1.1719922 | 0.22738387 | 0.5480522 | 1 | 7039 | tags = 42%, list = 32%, signal = 62% |
| MODULE_57 | 55 | 0.36214647 | 1.1732196 | 0.24759616 | 0.5482668 | 1 | 7061 | tags = 44%, list = 32%, signal = 64% |
| YAO_TEMPORAL_RESPONSE_TO_PROGESTERONE_CLUSTER_15 | 32 | 0.39920834 | 1.1738428 | 0.23169108 | 0.5506029 | 1 | 3636 | tags = 22%, list = 16%, signal = 26% |
| V$E2F1_Q6 | 226 | 0.30330324 | 1.165586 | 0.16891192 | 0.5642348 | 1 | 8286 | tags = 45%, list = 37%, signal = 71% |
| KEGG_HOMOLOGOUS_RECOMBINATION | 26 | 0.40115663 | 1.1583151 | 0.27236843 | 0.5742607 | 1 | 6871 | tags = 46%, list = 31%, signal = 67% |
| BASE_EXCISION_REPAIR | 16 | 0.4500021 | 1.161106 | 0.28125 | 0.57437444 | 1 | 7716 | tags = 56%, list = 35%, signal = 86% |
| GARGALOVIC_RESPONSE_TO_OXIDIZED_PHOSPHOLIPIDS_TURQUOISE_DN | 51 | 0.3541276 | 1.1587772 | 0.25531915 | 0.5773484 | 1 | 4500 | tags = 24%, list = 20%, signal = 29% |
| REACTOME_BASE_EXCISION_REPAIR | 19 | 0.43393558 | 1.1473954 | 0.2892562 | 0.579132 | 1 | 5930 | tags = 42%, list = 27%, signal = 57% |
| MMS_MOUSE_LYMPH_HIGH_4HRS_UP | 33 | 0.38256466 | 1.148576 | 0.2784314 | 0.5796485 | 1 | 4393 | tags = 33%, list = 20%, signal = 41% |
| PID_ATM_PATHWAY | 34 | 0.38246185 | 1.1525896 | 0.28025478 | 0.57977974 | 1 | 6351 | tags = 41%, list = 29%, signal = 58% |
| GNF2_MCM4 | 53 | 0.3524173 | 1.1454428 | 0.25826192 | 0.5810529 | 1 | 10124 | tags = 51%, list = 46%, signal = 93% |
| MODULE_451 | 31 | 0.39108822 | 1.153259 | 0.28047183 | 0.5817704 | 1 | 2108 | tags = 16%, list = 9%, signal = 18% |
| GRAHAM_CML_QUIESCENT_VS_NORMAL_QUIESCENT_UP | 78 | 0.33614486 | 1.1502516 | 0.22916667 | 0.5830748 | 1 | 4740 | tags = 21%, list = 21%, signal = 26% |
| CELL_CYCLE_PHASE | 162 | 0.30566037 | 1.1487713 | 0.20895523 | 0.5833879 | 1 | 6351 | tags = 33%, list = 29%, signal = 46% |
| V$E2F_03 | 234 | 0.29410437 | 1.1418293 | 0.19378239 | 0.5845467 | 1 | 5052 | tags = 28%, list = 21%, signal = 35% |

TABLE 6Q-continued

GSEA for BAF180-wildtype, BRG1-null vs. BAF180-wildtype, BRG1-wildtype A704 cell lines on E2F founder gene sets

| NAME | SIZE | ES | NES | NOM p-val | FDR q-val | FWER p-val | RANK AT MAX | LEADING EDGE |
|---|---|---|---|---|---|---|---|---|
| CELL_CYCLE_ARREST_GO_0007050 | 52 | 0.3528182 | 1.1535076 | 0.23947051 | 0.5854035 | 1 | 6038 | tags = 35%, list = 23%, signal = 36% |
| POSITIVE_REGULATION_OF_CELL_CYCLE | 15 | 0.45966756 | 1.1423001 | 0.30624092 | 0.5871997 | 1 | 4769 | tags = 27%, list = 27%, signal = 47% |
| MODULE_337 | 59 | 0.3437068 | 1.139586 | 0.25894988 | 0.5875483 | 1 | 3988 | tags = 27%, list = 21%, signal = 51% |
| LINDGREN_BLADDER_CANCER_CLUSTER_1_DN | 359 | 0.2904739 | 1.1380037 | 0.15237135 | 0.5886735 | 1 | 5957 | tags = 30%, list = 18%, signal = 33% |
| V$E2F_01 | 65 | 0.33490327 | 1.1119276 | 0.2972973 | 0.5961439 | 1 | 6939 | tags = 38%, list = 27%, signal = 41% |
| GEORGES_CELL_CYCLE_MIR192_TARGETS | 61 | 0.33884498 | 1.1122179 | 0.3084223 | 0.5989164 | 1 | 8144 | tags = 52%, list = 31%, signal = 56% |
| GCNP_SHH_UP_LATE.V1_UP | 171 | 0.30077168 | 1.1332275 | 0.23961662 | 0.5998562 | 1 | 6242 | tags = 33%, list = 37%, signal = 83% |
| PID_FOXM1_PATHWAY | 39 | 0.36850864 | 1.1252751 | 0.30729166 | 0.6009434 | 1 | 5440 | tags = 36%, list = 28%, signal = 45% |
| M_PHASE | 107 | 0.31203735 | 1.1140449 | 0.28863636 | 0.601072 | 1 | 6500 | tags = 31%, list = 24%, signal = 47% |
| KTGGYRSGAA_UNKNOWN | 73 | 0.32634726 | 1.1122824 | 0.295612 | 0.60253054 | 1 | 7550 | tags = 45%, list = 29%, signal = 43% |
| LY_AGING_PREMATURE_DN | 29 | 0.3882155 | 1.1272681 | 0.32266325 | 0.60279167 | 1 | 2915 | tags = 17%, list = 34%, signal = 68% |
| CHANG_CYCLING_GENES | 143 | 0.30817467 | 1.1310683 | 0.2454252 | 0.6029239 | 1 | 4768 | tags = 24%, list = 13%, signal = 20% |
| RIBONUCLEASE_ACTIVITY | 22 | 0.40811253 | 1.1258738 | 0.31636864 | 0.6031186 | 1 | 6343 | tags = 32%, list = 21%, signal = 31% |
| REGULATION_OF_DNA_METABOLIC_PROCESS | 43 | 0.35744908 | 1.1145996 | 0.30614805 | 0.60318565 | 1 | 6705 | tags = 44%, list = 29%, signal = 44% |
| MORI_PRE_BI_LYMPHOCYTE_UP | 76 | 0.3274124 | 1.1296207 | 0.2862069 | 0.60356325 | 1 | 4570 | tags = 22%, list = 30%, signal = 63% |

TABLE 6Q-continued

GSEA for BAF180-wildtype, BRG1-null vs. BAF180-wildtype, BRG1-wildtype A704 cell lines on E2F founder gene sets

| NAME | SIZE | ES | NES | NOM p-val | FDR q-val | FWER p-val | RANK AT MAX | LEADING EDGE |
|---|---|---|---|---|---|---|---|---|
| DNA_RECOMBINATION | 41 | 0.36278692 | 1.1154684 | 0.296343 | 0.6041192 | 1 | 7474 | tags = 56%, list = 34%, signal = 28% |
| WANG_CISPLATIN_RESPONSE_AND_XPC_UP | 184 | 0.29796305 | 1.1273884 | 0.23301986 | 0.60650617 | 1 | 5313 | tags = 29%, list = 24%, signal = 84% |
| GNF2_PCNA | 67 | 0.32937458 | 1.115769 | 0.30154946 | 0.60693085 | 1 | 9683 | tags = 49%, list = 44%, signal = 38% |
| STEIN_ESR1_TARGETS | 81 | 0.31779978 | 1.106642 | 0.31294116 | 0.6078658 | 1 | 6467 | tags = 40%, list = 29%, signal = 87% |
| REACTOME_DOUBLE_STRAND_BREAK_REPAIR | 22 | 0.40390694 | 1.1041609 | 0.33781964 | 0.6080242 | 1 | 8192 | tags = 59%, list = 37%, signal = 56% |
| RB_P107_DN.V1_UP | 133 | 0.30179462 | 1.1029329 | 0.28990227 | 0.6082117 | 1 | 4879 | tags = 29%, list = 22%, signal = 94% |
| FINETTI_BREAST_CANCER_KINOME_RED | 16 | 0.4440954 | 1.1211063 | 0.3478261 | 0.60990953 | 1 | 7061 | tags = 50%, list = 32%, signal = 37% |
| MITSIADES_RESPONSE_TO_APLIDIN_DN | 243 | 0.29167166 | 1.118732 | 0.2371134 | 0.6099311 | 1 | 7790 | tags = 37%, list = 35%, signal = 73% |
| ROSTY_CERVICAL_CANCER_PROLIFERATION_CLUSTER | 139 | 0.30078912 | 1.1160735 | 0.25414366 | 0.60994726 | 1 | 6224 | tags = 29%, list = 28%, signal = 56% |
| JOHANSSON_GLIOMAGENESIS_BY_PDGFB_UP | 55 | 0.34037852 | 1.1043452 | 0.31604344 | 0.6111753 | 1 | 7070 | tags = 42%, list = 32%, signal = 41% |
| RESPONSE_TO_ENDOGENOUS_STIMULUS | 190 | 0.29485098 | 1.1168075 | 0.22770199 | 0.61168456 | 1 | 6871 | tags = 38%, list = 31%, signal = 61% |
| GNF2_FEN1 | 56 | 0.34303924 | 1.1190727 | 0.30899204 | 0.61273277 | 1 | 7790 | tags = 36%, list = 35%, signal = 54% |
| MITOTIC_CELL_CYCLE_CHECKPOINT | 21 | 0.4117884 | 1.0959709 | 0.3785235 | 0.6262292 | 1 | 6500 | tags = 43%, list = 29%, signal = 55% |
| LE_EGR2_TARGETS_UP | 106 | 0.3048985 | 1.0916537 | 0.31520534 | 0.63583624 | 1 | 4769 | tags = 25%, list = 21%, signal = 61% |
| MODULE_303 | 28 | 0.38074943 | 1.0893929 | 0.3493976 | 0.63876075 | 1 | 7061 | tags = 36%, list = 32%, signal = 31% signal = 52% |

TABLE 6Q-continued

GSEA for BAF180-wildtype, BRG1-null vs. BAF180-wildtype, BRG1-wildtype A704 cell lines on E2F founder gene sets

| NAME | SIZE | ES | NES | NOM p-val | FDR q-val | FWER p-val | RANK AT MAX | LEADING EDGE |
|---|---|---|---|---|---|---|---|---|
| V$E2F1_Q3_01 | 235 | 0.28381938 | 1.0852671 | 0.31519508 | 0.6404517 | 1 | 5550 | tags = 29%, list = 25%, signal = 39% |
| ZHAN_MULTIPLE_MYELOMA_PR_UP | 45 | 0.34538898 | 1.0859619 | 0.35732323 | 0.6420379 | 1 | 10124 | tags = 58%, list = 46%, signal = 106% |
| AMUNDSON_GENOTOXIC_SIGNATURE | 100 | 0.30098325 | 1.0834075 | 0.33333334 | 0.64254403 | 1 | 3583 | tags = 19%, list = 16%, signal = 23% |
| ZHOU_CELL_CYCLE_GENES_IN_IR_RESPONSE_24HR | 124 | 0.3019528 | 1.086621 | 0.3264418 | 0.64368314 | 1 | 6378 | tags = 32%, list = 29%, signal = 45% |
| PUJANA_BREAST_CANCER_LIT_INT_NETWORK | 100 | 0.3024451 | 1.0792933 | 0.33707866 | 0.65143365 | 1 | 7632 | tags = 43%, list = 34%, signal = 65% |
| WHITFIELD_CELL_CYCLE_M_G1 | 140 | 0.29741225 | 1.0778337 | 0.3391494 | 0.65224826 | 1 | 7925 | tags = 41%, list = 36%, signal = 63% |
| WANG_RESPONSE_TO_GSK3_INHIBITOR_SB216763_DN | 345 | 0.26970476 | 1.0671172 | 0.31319234 | 0.6817713 | 1 | 4624 | tags = 23%, list = 21%, signal = 29% |
| MODULE_325 | 51 | 0.33049893 | 1.0603688 | 0.37578028 | 0.68339276 | 1 | 3076 | tags = 22%, list = 14%, signal = 25% |
| GARCIA_TARGETS_OF_FLI1_AND_DAX1_DN | 165 | 0.28245273 | 1.0614592 | 0.3601695 | 0.68396115 | 1 | 9176 | tags = 45%, list = 41%, signal = 77% |
| GRAHAM_CML_DIVIDING_VS_NORMAL_QUIESCENT_UP | 165 | 0.2841179 | 1.0636351 | 0.34946236 | 0.6850291 | 1 | 6508 | tags = 32%, list = 29%, signal = 44% |
| WINNEPENNINCKX_MELANOMA_METASTASIS_UP | 160 | 0.2851033 | 1.061746 | 0.35927504 | 0.68684745 | 1 | 10124 | tags = 52%, list = 46%, signal = 95% |
| BOYAULT_LIVER_CANCER_SUBCLASS_G3_UP | 187 | 0.2815569 | 1.0636468 | 0.35859126 | 0.6889028 | 1 | 8780 | tags = 44%, list = 40%, signal = 72% |
| INTERPHASE | 67 | 0.30789024 | 1.0435838 | 0.4054697 | 0.68922824 | 1 | 8527 | tags = 52%, list = 38%, signal = 85% |
| REGULATION_OF_MITOTIC_CELL_CYCLE | 23 | 0.37835997 | 1.0497313 | 0.42348284 | 0.6894748 | 1 | 7427 | tags = 48%, list = 33%, signal = 72% |
| INTERPHASE_OF_MITOTIC_CELL_CYCLE | 61 | 0.3159809 | 1.0483093 | 0.39717978 | 0.6900084 | 1 | 8527 | tags = 51%, list = 38%, signal = 82% |
| SONG_TARGETS_OF_IE86_CMV_PROTEIN | 60 | 0.3179287 | 1.0515535 | 0.39787486 | 0.69109964 | 1 | 7716 | tags = 45%, |

TABLE 6Q-continued

GSEA for BAF180-wildtype, BRG1-null vs. BAF180-wildtype, BRG1-wildtype A704 cell lines on E2F founder gene sets

| NAME | SIZE | ES | NES | NOM p-val | FDR q-val | FWER p-val | RANK AT MAX | LEADING EDGE |
|---|---|---|---|---|---|---|---|---|
| WHITEFORD_PEDIATRIC_CANCER_MARKERS | 115 | 0.2941285 | 1.0538615 | 0.39053905 | 0.69164646 | 1 | 8291 | tags = 35%, list = 38%, signal = 69% |
| ZHENG_GLIOBLASTOMA_PLASTICITY_UP | 234 | 0.27269864 | 1.0499946 | 0.37460977 | 0.69240123 | 1 | 5680 | tags = 29%, list = 26%, signal = 61% |
| RAY_TUMORIGENESIS_BY_ERBB2_CDC25A_UP | 96 | 0.29605302 | 1.0436827 | 0.39338654 | 0.69257224 | 1 | 4346 | tags = 26%, list = 20%, signal = 39% |
| ODONNELL_TFRC_TARGETS_DN | 122 | 0.29402384 | 1.0546696 | 0.39606127 | 0.6930552 | 1 | 10025 | tags = 56%, list = 45%, signal = 32% |
| KOBAYASHI_EGFR_SIGNALING_24HR_DN | 250 | 0.27339545 | 1.0520165 | 0.3783784 | 0.69338197 | 1 | 7790 | tags = 41%, list = 35%, signal = 101% |
| LE_NEURONAL_DIFFERENTIATION_DN | 19 | 0.39102486 | 1.0556614 | 0.40577716 | 0.69378126 | 1 | 1053 | tags = 11%, list = 5%, signal = 62% |
| GCNP_SHH_UP_EARLY.V1_UP | 160 | 0.281336 | 1.0440953 | 0.3853606 | 0.6950538 | 1 | 8446 | tags = 46%, list = 38%, signal = 11% |
| MODULE_198 | 297 | 0.27156198 | 1.0451778 | 0.37206933 | 0.69549567 | 1 | 8291 | tags = 39%, list = 37%, signal = 73% |
| NUNODA_RESPONSE_TO_DASATINIB_IMATINIB_UP | 29 | 0.35125908 | 1.0276042 | 0.448 | 0.71113324 | 1 | 5281 | tags = 31%, list = 24%, signal = 62% |
| GNF2_SMC2L1 | 32 | 0.34641853 | 1.025546 | 0.44287547 | 0.7134221 | 1 | 10025 | tags = 59%, list = 45%, signal = 41% |
| BURTON_ADIPOGENESIS_PEAK_AT_16HR | 39 | 0.33349323 | 1.0278322 | 0.44237918 | 0.71399 | 1 | 2676 | tags = 15%, list = 12%, signal = 108% |
| MODULE_124 | 95 | 0.29049054 | 1.0280728 | 0.4409722 | 0.7169952 | 1 | 4601 | tags = 21%, list = 21%, signal = 17% |
| SLEBOS_HEAD_AND_NECK_CANCER_WITH_HPV_UP | 78 | 0.30232805 | 1.0287576 | 0.427907 | 0.7185713 | 1 | 9319 | tags = 54%, list = 42%, signal = 26% |
| SHEDDEN_LUNG_CANCER_POOR_SURVIVAL_A6 | 442 | 0.2601959 | 1.0292497 | 0.40722167 | 0.7208165 | 1 | 5463 | tags = 25%, list = 25%, signal = 92% |
| BENPORATH_PROLIFERATION | 144 | 0.2783527 | 1.0215985 | 0.44017562 | 0.7211337 | 1 | 10199 | tags = 49%, list = 46%, signal = 32% |

TABLE 6Q-continued

GSEA for BAF180-wildtype, BRG1-null vs. BAF180-wildtype, BRG1-wildtype A704 cell lines on E2F founder gene sets

| NAME | SIZE | ES | NES | NOM p-val | FDR q-val | FWER p-val | RANK AT MAX | LEADING EDGE |
|---|---|---|---|---|---|---|---|---|
| GNF2_TTK | 39 | 0.34152663 | 1.0301598 | 0.43167305 | 0.7218084 | 1 | 9683 | tags = 51%, list = 44%, signal = 91% |
| CROONQUIST_IL6_DEPRIVATION_DN | 97 | 0.2925624 | 1.0313257 | 0.41359448 | 0.72205865 | 1 | 8801 | tags = 41%, list = 40%, signal = 68% |
| MODULE_197 | 167 | 0.27391145 | 1.0152683 | 0.46244636 | 0.7287274 | 1 | 5462 | tags = 26%, list = 25%, signal = 35% |
| MODULE_252 | 234 | 0.2656011 | 1.0163232 | 0.44282743 | 0.7291807 | 1 | 7928 | tags = 36%, list = 36%, signal = 55% |
| DAMAGED_DNA_BINDING | 21 | 0.37659937 | 1.0164671 | 0.44993323 | 0.7324266 | 1 | 8304 | tags = 48%, list = 37%, signal = 76% |
| DEOXYRIBONUCLEASE_ACTIVITY | 22 | 0.36742947 | 1.0122482 | 0.45019406 | 0.7337531 | 1 | 6760 | tags = 45%, list = 30%, signal = 65% |
| PID_ATR_PATHWAY | 38 | 0.32669598 | 1.0086408 | 0.45660377 | 0.73724896 | 1 | 7607 | tags = 45%, list = 34%, signal = 68% |
| KEGG_BASE_EXCISION_REPAIR | 34 | 0.33574635 | 1.0093353 | 0.44513714 | 0.7387695 | 1 | 9037 | tags = 47%, list = 41%, signal = 79% |
| MITOTIC_CELL_CYCLE | 150 | 0.27175382 | 1.0066271 | 0.46824542 | 0.73938453 | 1 | 6270 | tags = 29%, list = 28%, signal = 41% |
| HORIUCHI_WTAP_TARGETS_DN | 301 | 0.2576669 | 1.0031742 | 0.4760936 | 0.7423474 | 1 | 9073 | tags = 42%, list = 41%, signal = 70% |
| VECCHI_GASTRIC_CANCER_EARLY_UP | 405 | 0.2534836 | 1.0040272 | 0.48944724 | 0.74324733 | 1 | 5182 | tags = 25%, list = 23%, signal = 32% |
| AFFAR_YY1_TARGETS_DN | 212 | 0.2632148 | 0.99917674 | 0.5031447 | 0.75014687 | 1 | 4600 | tags = 23%, list = 21%, signal = 28% |
| MOLENAAR_TARGETS_OF_CCND1_AND_CDK4_DN | 57 | 0.3013021 | 0.9901799 | 0.48459715 | 0.7720615 | 1 | 7628 | tags = 39%, list = 34%, signal = 59% |
| CROONQUIST_NRAS_SIGNALING_DN | 72 | 0.28571492 | 0.9843489 | 0.48963133 | 0.78501475 | 1 | 7061 | tags = 33%, list = 32%, signal = 49% |
| MARKEY_RB1_ACUTE_LOF_UP | 228 | 0.25501198 | 0.9808197 | 0.5400624 | 0.7914312 | 1 | 4802 | tags = 24%, list = 22%, signal = 30% |

TABLE 6Q-continued

GSEA for BAF180-wildtype, BRG1-null vs. BAF180-wildtype, BRG1-wildtype A704 cell lines on E2F founder gene sets

| NAME | SIZE | ES | NES | NOM p-val | FDR q-val | FWER p-val | RANK AT MAX | LEADING EDGE |
|---|---|---|---|---|---|---|---|---|
| PID_AURORA_A_PATHWAY | 31 | 0.3326504 | 0.97149783 | 0.5072084 | 0.80590636 | 1 | 5748 | tags = 32%, list = 26%, signal = 43% |
| SHEPARD_CRUSH_AND_BURN_MUTANT_DN | 163 | 0.25931618 | 0.97226787 | 0.54291844 | 0.8076891 | 1 | 5778 | tags = 28%, list = 26%, signal = 37% |
| MUELLER_PLURINET | 285 | 0.2508906 | 0.97336334 | 0.5498458 | 0.8083684 | 1 | 7488 | tags = 32%, list = 34%, signal = 48% |
| DOUBLE_STRANDED_DNA_BINDING | 32 | 0.32993537 | 0.9667149 | 0.5226064 | 0.815262 | 1 | 7595 | tags = 41%, list = 34%, signal = 62% |
| BURTON_ADIPOGENESIS_3 | 101 | 0.26917318 | 0.96023273 | 0.55937845 | 0.82939523 | 1 | 4802 | tags = 22%, list = 22%, signal = 28% |
| MODULE_244 | 183 | 0.25261924 | 0.95404893 | 0.5822785 | 0.8420635 | 1 | 7686 | tags = 32%, list = 35%, signal = 48% |
| NUCLEOTIDYLTRANSFERASE_ACTIVITY | 46 | 0.29995102 | 0.9524774 | 0.5477941 | 0.8424268 | 1 | 5100 | tags = 22%, list = 23%, signal = 28% |
| ISHIDA_E2F_TARGETS | 51 | 0.29740694 | 0.9489488 | 0.55487806 | 0.84420574 | 1 | 9937 | tags = 53%, list = 45%, signal = 96% |
| MODULE_98 | 383 | 0.24173515 | 0.9493505 | 0.653144 | 0.8468522 | 1 | 8192 | tags = 37%, list = 37%, signal = 57% |
| STRUCTURE_SPECIFIC_DNA_BINDING | 55 | 0.2926584 | 0.9435076 | 0.55741626 | 0.8508466 | 1 | 7595 | tags = 36%, list = 34%, signal = 55% |
| BENPORATH_ES_CORE_NINE_CORRELATED | 95 | 0.26689902 | 0.94446295 | 0.57652473 | 0.85213023 | 1 | 9303 | tags = 49%, list = 42%, signal = 85% |
| RPS14_DN.V1_DN | 177 | 0.24837753 | 0.9374446 | 0.6248694 | 0.8631052 | 1 | 4613 | tags = 24%, list = 21%, signal = 30% |
| MANALO_HYPOXIA_DN | 283 | 0.24170218 | 0.9352551 | 0.663926 | 0.8649086 | 1 | 4570 | tags = 19%, list = 21%, signal = 24% |
| GAVIN_FOXP3_TARGETS_CLUSTER_P6 | 87 | 0.26028508 | 0.9114183 | 0.61290324 | 0.8867134 | 1 | 7134 | tags = 33%, list = 32%, signal = 49% |
| GROSS_HYPOXIA_VIA_ELK3_AND_HIF1A_DN | 100 | 0.25491416 | 0.9097471 | 0.6453423 | 0.88704175 | 1 | 4370 | tags = 24%, list = 20%, signal = 30% |
| LI_WILMS_TUMOR_ANAPLASTIC_UP | 19 | 0.34389392 | 0.91258436 | 0.59001315 | 0.8875584 | 1 | 10520 | tags = 63%, |

TABLE 6Q-continued

GSEA for BAF180-wildtype, BRG1-null vs. BAF180-wildtype, BRG1-wildtype A704 cell lines on E2F founder gene sets

| NAME | SIZE | ES | NES | NOM p-val | FDR q-val | FWER p-val | RANK AT MAX | LEADING EDGE |
|---|---|---|---|---|---|---|---|---|
| SHEPARD_BMYB_TARGETS | 68 | 0.26642838 | 0.9071732 | 0.6092486 | 0.8893206 | 1 | 1460 | tags = 10%, list = 47%, signal = 120% |
| G1_S_TRANSITION_OF_MITOTIC_CELL_CYCLE | 27 | 0.32290238 | 0.9162803 | 0.5882353 | 0.88970286 | 1 | 8527 | tags = 56%, list = 7%, signal = 11% |
| PID_AURORA_B_PATHWAY | 38 | 0.29612312 | 0.91309714 | 0.6307885 | 0.8900131 | 1 | 4370 | tags = 21%, list = 38%, signal = 90% |
| GOLDRATH_ANTIGEN_RESPONSE | 318 | 0.23252904 | 0.91377914 | 0.7244898 | 0.8921047 | 1 | 4811 | tags = 22%, list = 20%, signal = 26% |
| LI_WILMS_TUMOR_VS_FETAL_KIDNEY_1_DN | 160 | 0.24605219 | 0.91683835 | 0.65356004 | 0.89213026 | 1 | 7790 | tags = 34%, list = 22%, signal = 27% |
| REACTOME_EXTENSION_OF_TELOMERES | 27 | 0.31878284 | 0.9169291 | 0.6108949 | 0.89582115 | 1 | 4765 | tags = 22%, list = 35%, signal = 52% |
| REACTOME_E2F_MEDIATED_REGULATION_OF_DNA_REPLICATION | 32 | 0.3055041 | 0.92101496 | 0.59180975 | 0.89749575 | 1 | 4802 | tags = 28%, list = 21%, signal = 28% |
| MISSIAGLIA_REGULATED_BY_METHYLATION_DN | 117 | 0.25388703 | 0.91750246 | 0.6426193 | 0.8984007 | 1 | 8599 | tags = 40%, list = 22%, signal = 36% |
| PID_E2F_PATHWAY | 72 | 0.26511717 | 0.8924725 | 0.6639248 | 0.9008714 | 1 | 7061 | tags = 36%, list = 39%, signal = 65% |
| GNF2_RRM1 | 87 | 0.26205435 | 0.917829 | 0.6188341 | 0.9013951 | 1 | 10124 | tags = 47%, list = 32%, signal = 53% |
| DORMOY_ELAVL1_TARGETS | 16 | 0.35215455 | 0.89995354 | 0.6144244 | 0.9022171 | 1 | 4377 | tags = 31%, list = 46%, signal = 86% |
| CHROMOSOME | 119 | 0.24726327 | 0.8942441 | 0.6868132 | 0.9040682 | 1 | 7750 | tags = 37%, list = 20%, signal = 39% |
| E2F1_UP.V1_UP | 182 | 0.23610032 | 0.8925108 | 0.72210526 | 0.9044738 | 1 | 8039 | tags = 34%, list = 35%, signal = 56% |
| REACTOME_PROCESSIVE_SYNTHESIS_ON_THE_LAGGING_STRAND | 15 | 0.35453758 | 0.89730215 | 0.62622035 | 0.9046432 | 1 | 4765 | tags = 27%, list = 36%, signal = 52% |
| RNA_CATABOLIC_PROCESS | 21 | 0.32824758 | 0.8955597 | 0.6258503 | 0.9048708 | 1 | 6343 | tags = 38%, list = 21%, signal = 34% |

TABLE 6Q-continued

GSEA for BAF180-wildtype, BRG1-null vs. BAF180-wildtype, BRG1-wildtype A704 cell lines on E2F founder gene sets

| NAME | SIZE | ES | NES | NOM p-val | FDR q-val | FWER p-val | RANK AT MAX | LEADING EDGE |
|---|---|---|---|---|---|---|---|---|
| KEGG_MISMATCH_REPAIR | 23 | 0.31686857 | 0.8839419 | 0.63289475 | 0.90528065 | 1 | 2063 | tags = 13%, list = 9%, signal = 53% |
| SASAKI_ADULT_T_CELL_LEUKEMIA | 168 | 0.23828736 | 0.8881789 | 0.7296137 | 0.90717053 | 1 | 6939 | tags = 32%, list = 31%, signal = 14% |
| GNF2_BUB1B | 49 | 0.2752565 | 0.88618875 | 0.68345326 | 0.90762746 | 1 | 7790 | tags = 33%, list = 35%, signal = 46% |
| NUCLEAR_CHROMOSOME | 52 | 0.27598214 | 0.88433754 | 0.65824306 | 0.9079744 | 1 | 7686 | tags = 40%, list = 35%, signal = 50% |
| YU_MYC_TARGETS_UP | 42 | 0.28265965 | 0.88031185 | 0.6594663 | 0.90950704 | 1 | 7442 | tags = 38%, list = 33%, signal = 62% |
| NAKAMURA_CANCER_MICROENVIRONMENT_DN | 45 | 0.27968585 | 0.87747896 | 0.66625917 | 0.91193676 | 1 | 4904 | tags = 18%, list = 22%, signal = 57% |
| MITOSIS | 80 | 0.2530464 | 0.87246853 | 0.7086705 | 0.9189224 | 1 | 3765 | tags = 16%, list = 17%, signal = 23% |
| PAL_PRMT5_TARGETS_UP | 200 | 0.22849624 | 0.8638039 | 0.7713987 | 0.9189507 | 1 | 7104 | tags = 31%, list = 32%, signal = 19% |
| LY_AGING_OLD_DN | 55 | 0.26493242 | 0.8615848 | 0.71306473 | 0.92015535 | 1 | 6195 | tags = 25%, list = 28%, signal = 45% |
| DNA_REPLICATION_INITIATION | 16 | 0.33962247 | 0.8697947 | 0.6421499 | 0.92063504 | 1 | 9220 | tags = 69%, list = 42%, signal = 35% |
| LL_WILMS_TUMOR_VS_FETAL_KIDNEY_2_UP | 29 | 0.29539564 | 0.8639146 | 0.67785233 | 0.9223553 | 1 | 4765 | tags = 24%, list = 21%, signal = 117% |
| MODULE_54 | 250 | 0.22454439 | 0.8654779 | 0.79170984 | 0.9227561 | 1 | 4765 | tags = 20%, list = 21%, signal = 31% |
| KANG_DOXORUBICIN_RESISTANCE_UP | 54 | 0.26724526 | 0.86711955 | 0.68907565 | 0.9228687 | 1 | 8499 | tags = 37%, list = 38%, signal = 25% |
| M_PHASE_OF_MITOTIC_CELL_CYCLE | 83 | 0.24474296 | 0.8540637 | 0.72445464 | 0.925178 | 1 | 3765 | tags = 16%, list = 17%, signal = 60% |
| FARMER_BREAST_CANCER_CLUSTER_2 | 33 | 0.28644726 | 0.8502835 | 0.6847682 | 0.92544687 | 1 | 6747 | tags = 30%, list = 30%, signal = 19% |
| | | | | | | | | signal = 43% |

TABLE 6Q-continued

GSEA for BAF180-wildtype, BRG1-null vs. BAF180-wildtype, BRG1-wildtype A704 cell lines on E2F founder gene sets

| NAME | SIZE | ES | NES | NOM p-val | FDR q-val | FWER p-val | RANK AT MAX | LEADING EDGE |
|---|---|---|---|---|---|---|---|---|
| CONCANNON_APOPTOSIS_BY_EPOXOMICIN_DN | 155 | 0.2304101 | 0.85201883 | 0.780065 | 0.9256471 | 1 | 3636 | tags = 19%, list = 16%, signal = 22% |
| HOFFMANN_LARGE_TO_SMALL_PRE_BII_LYMPHOCYTE_UP | 155 | 0.23037744 | 0.856891 | 0.7775378 | 0.92635566 | 1 | 4570 | tags = 21%, list = 21%, signal = 27% |
| RUIZ_TNC_TARGETS_DN | 139 | 0.23044297 | 0.85473335 | 0.7619565 | 0.9272852 | 1 | 4570 | tags = 23%, list = 21%, signal = 29% |
| HONRADO_BREAST_CANCER_BRCA1_VS_BRCA2 | 16 | 0.33600307 | 0.8473566 | 0.68105847 | 0.9275191 | 1 | 6069 | tags = 50%, list = 27%, signal = 69% |
| LEE_EARLY_T_LYMPHOCYTE_UP | 95 | 0.23925753 | 0.8433739 | 0.7483146 | 0.9317367 | 1 | 8958 | tags = 46%, list = 40%, signal = 77% |
| GNF2_RFC3 | 41 | 0.26695165 | 0.82920223 | 0.7265823 | 0.9473219 | 1 | 11198 | tags = 56%, list = 50%, signal = 113% |
| REGULATION_OF_MITOSIS | 40 | 0.27735117 | 0.832746 | 0.73173803 | 0.94810116 | 1 | 2697 | tags = 15%, list = 12%, signal = 17% |
| SOTIRIOU_BREAST_CANCER_GRADE_1_VS_3_UP | 149 | 0.22273426 | 0.8294785 | 0.80931747 | 0.9504284 | 1 | 6500 | tags = 25%, list = 29%, signal = 35% |
| SARRIO_EPITHELIAL_MESENCHYMAL_TRANSITION_UP | 168 | 0.21678355 | 0.8153494 | 0.8496802 | 0.96451414 | 1 | 4111 | tags = 22%, list = 19%, signal = 27% |
| REACTOME_LAGGING_STRAND_SYNTHESIS | 19 | 0.306489 | 0.8167572 | 0.7380952 | 0.9656359 | 1 | 8291 | tags = 42%, list = 37%, signal = 67% |
| GNF2_CCNA2 | 67 | 0.23950595 | 0.8076859 | 0.77870816 | 0.9740733 | 1 | 10124 | tags = 46%, list = 46%, signal = 85% |
| INDUCTION_OF_APOPTOSIS_BY_INTRACELLULAR_SIGNALS | 22 | 0.29047993 | 0.7988762 | 0.7735602 | 0.98105544 | 1 | 7884 | tags = 55%, list = 35%, signal = 84% |
| WONG_EMBRYONIC_STEM_CELL_CORE | 327 | 0.2027311 | 0.79904824 | 0.9016227 | 0.98434985 | 1 | 6302 | tags = 23%, list = 28%, signal = 32% |
| WANG_METASTASIS_OF_BREAST_CANCER_ESR1_UP | 21 | 0.2875412 | 0.77814585 | 0.7785515 | 0.99479026 | 1 | 9675 | tags = 57%, list = 44%, signal = 101% |
| CONDENSED_NUCLEAR_CHROMOSOME | 18 | 0.30309433 | 0.78282785 | 0.76183844 | 0.99502367 | 1 | 667 | tags = 11%, list = 3%, signal = 11% |
| DOUBLE_STRAND_BREAK_REPAIR | 23 | 0.28554407 | 0.7842453 | 0.7798913 | 0.9965019 | 1 | 6862 | tags = 39%, |

TABLE 6Q-continued

GSEA for BAF180-wildtype, BRG1-null vs. BAF180-wildtype, BRG1-wildtype
A704 cell lines on E2F founder gene sets

| NAME | SIZE | ES | NES | NOM p-val | FDR q-val | FWER p-val | RANK AT MAX | LEADING EDGE |
|---|---|---|---|---|---|---|---|---|
| SIMBULAN_PARP1_TARGETS_DN | 17 | 0.30563325 | 0.7864138 | 0.7654321 | 0.9967682 | 1 | 6892 | tags = 41%, list = 31%, signal = 57% |
| WHITFIELD_CELL_CYCLE_G2_M | 210 | 0.20307907 | 0.77888125 | 0.9089969 | 0.99722195 | 1 | 9195 | tags = 43%, list = 31%, signal = 60% |
| GNF2_BUB1 | 26 | 0.15265957 | 0.43421733 | 0.9986559 | 0.9989812 | 1 | 4570 | tags = 15%, list = 41%, signal = 72% |
| RRCCGTTA_UNKNOWN | 83 | 0.22011705 | 0.77013916 | 0.8719101 | 1 | 1 | 5913 | tags = 28%, list = 21%, signal = 19% |
| CHROMOSOMAL_PART | 94 | 0.21652947 | 0.7682454 | 0.8681818 | 1 | 1 | 7750 | tags = 35%, list = 27%, signal = 38% |
| CHANG_CORE_SERUM_RESPONSE_UP | 205 | 0.20020889 | 0.76363 | 0.9241307 | 1 | 1 | 6196 | tags = 26%, list = 35%, signal = 54% |
| HU_GENOTOXIC_DAMAGE_4HR | 35 | 0.24896917 | 0.7556239 | 0.8151042 | 1 | 1 | 4168 | tags = 14%, list = 28%, signal = 36% |
| SINGLE_STRANDED_DNA_BINDING | 34 | 0.25254515 | 0.7534236 | 0.8260309 | 1 | 1 | 7294 | tags = 29%, list = 19%, signal = 18% |
| GROSS_HYPOXIA_VIA_ELK3_UP | 204 | 0.19297273 | 0.7402942 | 0.9466527 | 1 | 1 | 5253 | tags = 20%, list = 33%, signal = 44% |
| CHROMATIN_BINDING | 30 | 0.2501886 | 0.7395669 | 0.8548813 | 1 | 1 | 10357 | tags = 57%, list = 24%, signal = 25% |
| KONG_E2F3_TARGETS | 93 | 0.20983557 | 0.7376095 | 0.89395666 | 1 | 1 | 6500 | tags = 31%, list = 47%, signal = 106% |
| GNF2_HMMR | 47 | 0.22674319 | 0.72354347 | 0.86419755 | 1 | 1 | 9937 | tags = 43%, list = 29%, signal = 44% |
| WU_APOPTOSIS_BY_CDKN1A_VIA_TP53 | 52 | 0.22379729 | 0.7229609 | 0.87529975 | 1 | 1 | 9176 | tags = 48%, list = 45%, signal = 77% |
| WEST_ADRENOCORTICAL_TUMOR_UP | 288 | 0.18519591 | 0.721704 | 0.977459 | 1 | 1 | 6500 | tags = 24%, list = 41%, signal = 82% |
| NAKAYAMA_SOFT_TISSUE_TUMORS_PCA2_UP | 83 | 0.2060155 | 0.71584517 | 0.9195923 | 1 | 1 | 2647 | tags = 11%, list = 29%, signal = 33% |

TABLE 6Q-continued

GSEA for BAF180-wildtype, BRG1-null vs. BAF180-wildtype, BRG1-wildtype A704 cell lines on E2F founder gene sets

| NAME | SIZE | ES | NES | NOM p-val | FDR q-val | FWER p-val | RANK AT MAX | LEADING EDGE |
|---|---|---|---|---|---|---|---|---|
| FOURNIER_ACINAR_DEVELOPMENT_LATE_DN | 21 | 0.25898314 | 0.70711416 | 0.8376023 | 1 | 1 | 7925 | tags = 43%, list = 36%, signal = 12% |
| GNF2_RRM2 | 40 | 0.2229693 | 0.6947614 | 0.9031056 | 1 | 1 | 9937 | tags = 43%, list = 45%, signal = 67% |
| REACTOME_G1_S_SPECIFIC_TRANSCRIPTION | 17 | 0.2678545 | 0.6924501 | 0.88551724 | 1 | 1 | 10494 | tags = 65%, list = 47%, signal = 77% |
| KEGG_DNA_REPLICATION | 36 | 0.22526753 | 0.69209665 | 0.9036458 | 1 | 1 | 7607 | tags = 31%, list = 34%, signal = 123% |
| LL_WILMS_TUMOR | 26 | 0.2432416 | 0.68723917 | 0.8931909 | 1 | 1 | 2434 | tags = 15%, list = 11%, signal = 46% |
| FOURNIER_ACINAR_DEVELOPMENT_LATE_2 | 273 | 0.17572291 | 0.68083227 | 0.9938713 | 1 | 1 | 4990 | tags = 19%, list = 22%, signal = 17% |
| CHROMOSOMEPERICENTRIC_REGION | 31 | 0.23368138 | 0.67999655 | 0.89072424 | 1 | 1 | 9646 | tags = 45%, list = 43%, signal = 24% |
| MODULE_308 | 69 | 0.19920248 | 0.67150915 | 0.9576471 | 1 | 1 | 6261 | tags = 29%, list = 28%, signal = 80% |
| MORI_IMMATURE_B_LYMPHOCYTE_DN | 88 | 0.19325547 | 0.6693833 | 0.95779604 | 1 | 1 | 7686 | tags = 34%, list = 35%, signal = 40% |
| PID_PLK1_PATHWAY | 44 | 0.21271893 | 0.6673868 | 0.9159456 | 1 | 1 | 7738 | tags = 39%, list = 35%, signal = 52% |
| MODULE_397 | 111 | 0.18808032 | 0.6619494 | 0.9746696 | 1 | 1 | 9235 | tags = 48%, list = 42%, signal = 59% |
| JUBAN_TARGETS_OF_SPI1_AND_FLI1_DN | 86 | 0.19185586 | 0.66191936 | 0.962069 | 1 | 1 | 4020 | tags = 17%, list = 18%, signal = 81% |
| DELPUECH_FOXO3_TARGETS_DN | 39 | 0.20977807 | 0.6522092 | 0.9369483 | 1 | 1 | 2062 | tags = 10%, list = 9%, signal = 21% |
| GNF2_CKS2 | 50 | 0.1999377 | 0.6472531 | 0.94795537 | 1 | 1 | 9683 | tags = 40%, list = 44%, signal = 11% |
| GNF2_CENPF | 61 | 0.19403538 | 0.641711 | 0.962963 | 1 | 1 | 9937 | tags = 38%, list = 45%, signal = 71% |

TABLE 6Q-continued

GSEA for BAF180-wildtype, BRG1-null vs. BAF180-wildtype, BRG1-wildtype A704 cell lines on E2F founder gene sets

| NAME | SIZE | ES | NES | NOM p-val | FDR q-val | FWER p-val | RANK AT MAX | LEADING EDGE |
|---|---|---|---|---|---|---|---|---|
| WHITFIELD_CELL_CYCLE_LITERATURE | 44 | 0.20166118 | 0.64135575 | 0.93658537 | 1 | 1 | 10124 | tags = 52%, list = 46%, signal = 96% |
| JEON_SMAD6_TARGETS_DN | 18 | 0.2458375 | 0.6391381 | 0.9187675 | 1 | 1 | 2304 | tags = 17%, list = 10%, signal = 19% |
| NUCLEAR_CHROMOSOME_PART | 33 | 0.20444147 | 0.6214067 | 0.95696205 | 1 | 1 | 7294 | tags = 36%, list = 33%, signal = 54% |
| XU_HGF_SIGNALING_NOT_VIA_AKT1_48HR_DN | 20 | 0.2287609 | 0.6189885 | 0.9233871 | 1 | 1 | 4372 | tags = 20%, list = 20%, signal = 25% |
| MODULE_320 | 20 | 0.22742188 | 0.61654776 | 0.9306667 | 1 | 1 | 10526 | tags = 65%, list = 47%, signal = 123% |
| GNF2_CDC2 | 61 | 0.17950688 | 0.5932809 | 0.9847775 | 1 | 1 | 9937 | tags = 39%, list = 45%, signal = 71% |
| WEST_ADRENOCORTICAL_TUMOR_MARKERS_UP | 20 | 0.21488012 | 0.5768052 | 0.96594006 | 1 | 1 | 7442 | tags = 40%, list = 33%, signal = 60% |
| REPLICATION_FORK | 18 | 0.21701467 | 0.57130104 | 0.9441417 | 1 | 1 | 8291 | tags = 44%, list = 37%, signal = 71% |
| EGUCHI_CELL_CYCLE_RB1_TARGETS | 23 | 0.20478497 | 0.56402063 | 0.9628647 | 1 | 1 | 7686 | tags = 30%, list = 35%, signal = 46% |
| MORI_LARGE_PRE_BII_LYMPHOCYTE_UP | 84 | 0.16080098 | 0.55553854 | 1 | 1 | 1 | 9054 | tags = 38%, list = 41%, signal = 64% |
| GNF2_ESPL1 | 35 | 0.18580903 | 0.553832 | 0.9898089 | 1 | 1 | 11198 | tags = 51%, list = 50%, signal = 104% |
| GREENBAUM_E2A_TARGETS_UP | 33 | 0.18239568 | 0.5511335 | 0.98278147 | 1 | 1 | 6069 | tags = 24%, list = 27%, signal = 33% |
| CONDENSED_CHROMOSOME | 33 | 0.18464331 | 0.5481924 | 0.9789082 | 1 | 1 | 667 | tags = 6%, list = 3%, signal = 6% |
| GNF2_CENPE | 40 | 0.17867468 | 0.5457817 | 0.981203 | 1 | 1 | 10025 | tags = 40%, list = 45%, signal = 73% |
| SMID_BREAST_CANCER_LUMINAL_A_DN | 16 | 0.21171118 | 0.54503566 | 0.9726402 | 1 | 1 | 6195 | tags = 19%, list = 28%, signal = 26% |
| GNF2_CKS1B | 37 | 0.17536254 | 0.53901255 | 0.98983485 | 1 | 1 | 8422 | tags = 30%, list = 30%, signal = — |

TABLE 6Q-continued

GSEA for BAF180-wildtype, BRG1-null vs. BAF180-wildtype, BRG1-wildtype A704 cell lines on E2F founder gene sets

| NAME | SIZE | ES | NES | NOM p-val | FDR q-val | FWER p-val | RANK AT MAX | LEADING EDGE |
|---|---|---|---|---|---|---|---|---|
| PENG_GLUCOSE_DEPRIVATION_DN | 160 | 0.13850647 | 0.5201427 | 1 | 1 | 1 | 8176 | tags = 38%, list = 29%, signal = 48% |
| GNF2_MKI67 | 27 | 0.18082324 | 0.51792157 | 0.9797023 | 1 | 1 | 9937 | tags = 37%, list = 44%, signal = 46% |
| CHROMOSOME_SEGREGATION | 32 | 0.17246047 | 0.51544017 | 0.98840207 | 1 | 1 | 9683 | tags = 45%, list = 44%, signal = 80% |
| FRASOR_RESPONSE_TO_SERM_OR_FULVESTRANT_DN | 50 | 0.15912758 | 0.51243126 | 0.99511003 | 1 | 1 | 8003 | tags = 44%, list = 26%, signal = 77% |
| GNF2_H2AFX | 31 | 0.16294482 | 0.4806161 | 0.9974716 | 1 | 1 | 3247 | tags = 36%, list = 10%, signal = 41% |
| GNF2_CCNB2 | 56 | 0.13789071 | 0.45175722 | 0.9998053 | 1 | 1 | 7776 | tags = 15%, list = 25%, signal = 11% |

TABLE 6R

GSEA for BAF180-null vs. BAF180-wildtype A704cell lines on TNFA Founder gene sets

| NAME | SIZE | ES | NES | NOM p-val | FDR q-val | FWER p-val | RANK AT MAX | LEADING EDGE |
|---|---|---|---|---|---|---|---|---|
| HINATA_NFKB_IMMU_INF | 17 | 0.7121733 | 1.9735836 | 0 | 0.01811983 | 0.012 | 1356 | tags = 47%, list = 6%, signal = 50% |
| PHONG_TNF_TARGETS_UP | 62 | 0.46539056 | 1.7218692 | 0 | 0.14616543 | 0.179 | 2611 | tags = 27%, list = 12%, signal = 31% |
| SCHOEN_NFKB_SIGNALING | 33 | 0.4909595 | 1.5692564 | 0.019955654 | 0.16486683 | 0.536 | 2415 | tags = 36%, list = 11%, signal = 41% |
| AMIT_SERUM_RESPONSE_60_MCF10A | 56 | 0.4424991 | 1.579713 | 0.004608295 | 0.17320979 | 0.494 | 2639 | tags = 27%, list = 12%, signal = 30% |
| MAHAJAN_RESPONSE_TO_IL1A_UP | 72 | 0.40984586 | 1.5468862 | 0.012875536 | 0.17401138 | 0.599 | 2709 | tags = 28%, list = 12%, signal = 32% |
| LINDSTEDT_DENDRITIC_CELL_MATURATION_A | 58 | 0.41769278 | 1.5015503 | 0.015873017 | 0.18031417 | 0.732 | 1356 | tags = 21%, list = 6%, signal = 22% |
| MEL18_DN.V1_UP | 135 | 0.34027582 | 1.4254444 | 0.012106538 | 0.1834423 | 0.885 | 4045 | tags = 35%, list = 18%, signal = 42% |
| ALTEMEIER_RESPONSE_TO_LPS_WITH_MECHANICAL_VENTILATION | 107 | 0.38396505 | 1.5130521 | 0.004878049 | 0.184769 | 0.706 | 2743 | tags = 25%, list = 12%, signal = 29% |
| FERRARI_RESPONSE_TO_FENRETINIDE_UP | 20 | 0.57468355 | 1.617784 | 0.026373627 | 0.1919037 | 0.406 | 1793 | tags = 30%, list = 8%, signal = 33% |
| BROWNE_HCMV_INFECTION_2HR_UP | 37 | 0.42980638 | 1.4351648 | 0.047493402 | 0.19261208 | 0.874 | 2561 | tags = 19%, list = 12%, signal = 21% |
| BMI1_DN_MEL18_DN.V1_UP | 139 | 0.34355652 | 1.4264567 | 0.007317073 | 0.19325998 | 0.884 | 2687 | tags = 24%, list = 12%, signal = 28% |
| HINATA_NFKB_TARGETS_KERATINOCYTE_UP | 85 | 0.36469486 | 1.4419237 | 0.02628206 | 0.19637743 | 0.863 | 1759 | tags = 19%, list = 8%, signal = 20% |
| AMIT_EGF_RESPONSE_60_MCF10A | 38 | 0.46031594 | 1.5187185 | 0.026431719 | 0.1965755 | 0.69 | 1793 | tags = 21%, list = 8%, signal = 23% |
| ZUCCHI_METASTASIS_DN | 41 | 0.49101514 | 1.6454661 | 0.002237137 | 0.19958329 | 0.33 | 1960 | tags = 20%, list = 9%, signal = 21% |
| GRAHAM_CML_QUIESCENT_VS_CML_DIVIDING_UP | 21 | 0.49748752 | 1.4050604 | 0.09896907 | 0.2010188 | 0.915 | 1356 | tags = 29%, list = 6%, signal = 30% |
| KRIEG_HYPOXIA_VIA_KDM3A | 51 | 0.4483681 | 1.5830749 | 0.017167382 | 0.2041567 | 0.488 | 2542 | tags = 27%, |

TABLE 6R-continued

GSEA for BAF180-null vs. BAF180-wildtype A704cell lines on TNFA Founder gene sets

| NAME | SIZE | ES | NES | NOM p-val | FDR q-val | FWER p-val | RANK AT MAX | LEADING EDGE |
|---|---|---|---|---|---|---|---|---|
| SEKI_INFLAMMATORY_RESPONSE_LPS_UP | 73 | 0.3867515 | 1.4443095 | 0.0247191 | 0.20557162 | 0.859 | 1356 | tags = 31%, list = 11%, signal = 21% |
| TIAN_TNF_SIGNALING_VIA_NFKB | 28 | 0.46444523 | 1.4525323 | 0.056947608 | 0.20914835 | 0.847 | 1356 | tags = 25%, list = 6%, signal = 22% |
| MATTIOLI_MGUS_VS_MULTIPLE_MYELOMA | 16 | 0.53781915 | 1.4550939 | 0.06081081 | 0.2228664 | 0.84 | 3175 | tags = 25%, list = 25%, signal = 27% |
| DAZARD_UV_RESPONSE_CLUSTER_G28 | 19 | 0.48236227 | 1.3739526 | 0.120430104 | 0.2244189 | 0.948 | 1356 | tags = 21%, list = 14%, signal = 29% |
| BURTON_ADIPOGENESIS_1 | 33 | 0.4289922 | 1.3806711 | 0.060538117 | 0.22504185 | 0.944 | 2940 | tags = 33%, list = 6%, signal = 22% |
| UZONYI_RESPONSE_TO_LEUKOTRIENE_AND_THROMBIN | 36 | 0.4034385 | 1.3405854 | 0.09071274 | 0.2534478 | 0.974 | 1852 | tags = 17%, list = 13%, signal = 38% |
| MODULE_178 | 15 | 0.5160862 | 1.3325039 | 0.14516129 | 0.25675952 | 0.981 | 2015 | tags = 33%, list = 8%, signal = 18% |
| HINATA_NFKB_TARGETS_FIBROBLAST_UP | 80 | 0.33661574 | 1.2855136 | 0.0900474 | 0.26094657 | 0.996 | 1759 | tags = 15%, list = 9%, signal = 37% |
| MCDOWELL_ACUTE_LUNG_INJURY_UP | 39 | 0.41243193 | 1.3430283 | 0.08163265 | 0.26111743 | 0.974 | 1447 | tags = 18%, list = 8%, signal = 16% |
| BILD_HRAS_ONCOGENIC_SIGNATURE | 240 | 0.2894971 | 1.2900707 | 0.03 | 0.2636602 | 0.994 | 2639 | tags = 17%, list = 7%, signal = 19% |
| ALK_DN.V1_UP | 113 | 0.316156773 | 1.2932228 | 0.039911307 | 0.2682712 | 0.994 | 2807 | tags = 24%, list = 12%, signal = 19% |
| KOBAYASHI_EGFR_SIGNALING_6HR_DN | 17 | 0.46688193 | 1.2732317 | 0.1633987 | 0.27098557 | 0.996 | 4237 | tags = 35%, list = 13%, signal = 27% |
| ZHOU_INFLAMMATORY_RESPONSE_FIMA_UP | 442 | 0.27361786 | 1.2944902 | 0.014285714 | 0.27551138 | 0.994 | 2640 | tags = 15%, list = 19%, signal = 44% |
| MODULE_362 | 19 | 0.4612412 | 1.3005892 | 0.13983051 | 0.27594692 | 0.993 | 2015 | tags = 32%, list = 12%, signal = 17% |
| WIEDERSCHAIN_TARGETS_OF_BMI1_AND_PCGF2 | 56 | 0.3694282 | 1.310024 | 0.090322584 | 0.28232476 | 0.99 | 2687 | tags = 23%, list = 9%, signal = 35% |
| GARGALOVIC_RESPONSE_TO_OXIDIZED_PHOSPHOLIPIDS_BLACK_UP | 33 | 0.40448025 | 1.3025057 | 0.11088296 | 0.28378433 | 0.992 | 2730 | tags = 21%, list = 12%, signal = 26% |

TABLE 6R-continued

GSEA for BAF180-null vs. BAF180-wildtype A704cell lines on TNFA Founder gene sets

| NAME | SIZE | ES | NES | NOM p-val | FDR q-val | FWER p-val | RANK AT MAX | LEADING EDGE |
|---|---|---|---|---|---|---|---|---|
| RASHI_NFKB1_TARGETS | 18 | 0.45575842 | 1.2493724 | 0.19027483 | 0.29257196 | 1 | 1356 | tags = 24%, list = 12%, signal = 17% |
| PLASARI_TGFB1_TARGETS_10HR_UP | 188 | 0.2913739 | 1.2534598 | 0.05822785 | 0.2928974 | 1 | 2815 | tags = 21%, list = 18%, signal = 6% |
| P53_DN.V2_UP | 117 | 0.2990527 | 1.2159227 | 0.11374407 | 0.29627326 | 1 | 2730 | tags = 22%, list = 13%, signal = 24% |
| BROCKE_APOPTOSIS_REVERSED_BY_IL6 | 137 | 0.29682255 | 1.24017 | 0.08395062 | 0.29763865 | 1 | 2709 | tags = 19%, list = 12%, signal = 25% |
| BURTON_ADIPOGENESIS_PEAK_AT_2HR | 50 | 0.34952435 | 1.2159503 | 0.17050691 | 0.30387002 | 1 | 2511 | tags = 22%, list = 11%, signal = 21% |
| SESTO_RESPONSE_TO_UV_C3 | 20 | 0.43132424 | 1.2187178 | 0.238229 | 0.30712342 | 1 | 543 | tags = 15%, list = 2%, signal = 25% |
| SUZUKI_RESPONSE_TO_TSA_AND_DECITABINE_1A | 19 | 0.41903538 | 1.1937535 | 0.22345133 | 0.31074792 | 1 | 3262 | tags = 32%, list = 15%, signal = 15% |
| THEILGAARD_NEUTROPHIL_AT_SKIN_WOUND_UP | 73 | 0.31508383 | 1.1962698 | 0.15311004 | 0.31408814 | 1 | 1407 | tags = 11%, list = 6%, signal = 37% |
| DAZARD_UV_RESPONSE_CLUSTER_G2 | 29 | 0.39094698 | 1.2193848 | 0.1912088 | 0.3144602 | 1 | 1856 | tags = 21%, list = 8%, signal = 12% |
| PHONG_TNF_RESPONSE_NOT_VIA_P38 | 330 | 0.259432 | 1.1995231 | 0.05851064 | 0.3162518 | 1 | 3366 | tags = 21%, list = 15%, signal = 23% |
| HAHTOLA_MYCOSIS_FUNGOIDES_CD4_UP | 58 | 0.33794093 | 1.2210118 | 0.16916488 | 0.32014048 | 1 | 2059 | tags = 19%, list = 9%, signal = 24% |
| BMI1_DN.V1_UP | 139 | 0.28091383 | 1.1807067 | 0.13711584 | 0.32538497 | 1 | 1705 | tags = 17%, list = 8%, signal = 21% |
| ZWANG_CLASS_3_TRANSIENTLY_INDUCED_BY_EGF | 206 | 0.26507318 | 1.1533595 | 0.13625866 | 0.34272358 | 1 | 2516 | tags = 16%, list = 11%, signal = 19% |
| GRAHAM_CML_QUIESCENT_VS_NORMAL_DIVIDING_UP | 50 | 0.32428753 | 1.1659062 | 0.21428572 | 0.34277838 | 1 | 4211 | tags = 32%, list = 19%, signal = 18% |
| WANG_TNF_TARGETS | 20 | 0.41113865 | 1.1544497 | 0.2805139 | 0.34758896 | 1 | 1896 | tags = 20%, list = 9%, signal = 39% |
| GALINDO_IMMUNE_RESPONSE_TO_ENTEROTOXIN | 79 | 0.30575588 | 1.1547593 | 0.20238096 | 0.35437652 | 1 | 2059 | tags = 16%, signal = 22% |

TABLE 6R-continued

GSEA for BAF180-null vs. BAF180-wildtype A704cell lines on TNFA Founder gene sets

| NAME | SIZE | ES | NES | NOM p-val | FDR q-val | FWER p-val | RANK AT MAX | LEADING EDGE |
|---|---|---|---|---|---|---|---|---|
| ZHOU_INFLAMMATORY_RESPONSE_LIVE_UP | 407 | 0.24007683 | 1.136981 | 0.11653116 | 0.35855886 | 1 | 2636 | tags = 15%, list = 9%, signal = 18% |
| KIM_WT1_TARGETS_UP | 208 | 0.25509515 | 1.1377084 | 0.1707617 | 0.36462373 | 1 | 2919 | tags = 17%, list = 12%, signal = 17% |
| MODULE_516 | 16 | 0.4157351 | 1.127287 | 0.31428573 | 0.36917233 | 1 | 2015 | tags = 25%, list = 13%, signal = 19% |
| ZHOU_INFLAMMATORY_RESPONSE_LPS_UP | 342 | 0.23887469 | 1.1214055 | 0.13611111 | 0.37299615 | 1 | 3023 | tags = 19%, list = 9%, signal = 27% |
| AMIT_EGF_RESPONSE_40_HELA | 40 | 0.33659357 | 1.1054982 | 0.28854626 | 0.3822015 | 1 | 1597 | tags = 15%, list = 14%, signal = 22% |
| BERENJENO_TRANSFORMED_BY_RHOA_FOREVER_DN | 28 | 0.35863847 | 1.1066042 | 0.30997878 | 0.38779154 | 1 | 871 | tags = 11%, list = 7%, signal = 16% |
| ABE_VEGFA_TARGETS_30MIN | 24 | 0.36268952 | 1.1101285 | 0.30232558 | 0.3884633 | 1 | 2516 | tags = 21%, list = 4%, signal = 11% |
| WINZEN_DEGRADED_VIA_KHSRP | 97 | 0.27290994 | 1.087263 | 0.2886836 | 0.4096403 | 1 | 1356 | tags = 13%, list = 11%, signal = 23% |
| AMIT_EGF_RESPONSE_120_HELA | 69 | 0.2867648 | 1.0679713 | 0.3255814 | 0.41886824 | 1 | 1356 | tags = 12%, list = 6%, signal = 14% |
| RELA_DN.V1_UP | 131 | 0.25483254 | 1.0682064 | 0.28078818 | 0.42561394 | 1 | 2292 | tags = 13%, list = 6%, signal = 12% |
| FOSTER_TOLERANT_MACROPHAGE_DN | 390 | 0.22484367 | 1.0693825 | 0.22762148 | 0.43101433 | 1 | 3518 | tags = 17%, list = 10%, signal = 14% |
| KIM_WT1_TARGETS_12HR_UP | 155 | 0.2512566 | 1.0699376 | 0.2912844 | 0.43737483 | 1 | 1861 | tags = 14%, list = 16%, signal = 20% |
| DORN_ADENOVIRUS_INFECTION_12HR_DN | 33 | 0.3322664 | 1.0522577 | 0.37938598 | 0.4438031 | 1 | 2299 | tags = 15%, list = 8%, signal = 15% |
| AMIT_SERUM_RESPONSE_40_MCF10A | 30 | 0.33023232 | 1.0180423 | 0.42152467 | 0.4886379 | 1 | 1356 | tags = 13%, list = 10%, signal = 17% |
| DIRMEIER_LMP1_RESPONSE_EARLY | 62 | 0.28488106 | 1.0283298 | 0.38863635 | 0.48976937 | 1 | 973 | tags = 10%, list = 6%, signal = 14% |
| TSAI_RESPONSE_TO_IONIZING_RADIATION | 142 | 0.24693018 | 1.0185373 | 0.40714285 | 0.4951767 | 1 | 3391 | tags = 20%, list = 4%, signal = 10% |

TABLE 6R-continued

GSEA for BAF180-null vs. BAF180-wildtype A704cell lines on TNFA Founder gene sets

| NAME | SIZE | ES | NES | NOM p-val | FDR q-val | FWER p-val | RANK AT MAX | LEADING EDGE |
|---|---|---|---|---|---|---|---|---|
| SARTIPY_BLUNTED_BY_INSULIN_RESISTANCE_UP | 19 | 0.3673268 | 1.021166 | 0.43064183 | 0.49723047 | 1 | 5197 | list = 15%, signal = 24%, tags = 53%, list = 23%, signal = 69% |
| AMIT_DELAYED_EARLY_GENES | 18 | 0.36878896 | 1.007622 | 0.4365256 | 0.505l059 | 1 | 4689 | tags = 44%, list = 21%, signal = 56% |
| MODULE_444 | 17 | 0.36739218 | 0.99056363 | 0.47111112 | 0.5356595 | 1 | 2015 | tags = 24%, list = 9%, signal = 26% |
| KIM_WT1_TARGETS_8HR_UP | 160 | 0.22465761 | 0.95971507 | 0.5491991 | 0.59616786 | 1 | 1977 | tags = 13%, list = 9%, signal = 14% |
| OSWALD_HEMATOPOIETIC_STEM_CELL_IN_COLLAGEN_GEL_UP | 217 | 0.20762564 | 0.9188322 | 0.69873416 | 0.6804433 | 1 | 2593 | tags = 12%, list = 12%, signal = 14% |
| ZHOU_TNF_SIGNALING_4HR | 54 | 0.25867853 | 0.90186983 | 0.6475584 | 0.7084501 | 1 | 2950 | tags = 13%, list = 13%, signal = 15% |
| YAO_TEMPORAL_RESPONSE_TO_PROGESTERONE_CLUSTER_5 | 26 | 0.29847574 | 0.8895064 | 0.62826085 | 0.7239441 | 1 | 6098 | tags = 50%, list = 27%, signal = 69% |
| CASORELLI_ACUTE_PROMYELOCYTIC_LEUKEMIA_UP | 160 | 0.20001574 | 0.85706544 | 0.82422805 | 0.7685506 | 1 | 2726 | tags = 15%, list = 12%, signal = 17% |
| NEMETH_INFLAMMATORY_RESPONSE_LPS_UP | 83 | 0.22265787 | 0.8598357 | 0.7648352 | 0.7736369 | 1 | 2701 | tags = 17%, list = 12%, signal = 19% |
| DORN_ADENOVIRUS_INFECTION_48HR_DN | 39 | 0.24452195 | 0.8070011 | 0.79223746 | 0.8429193 | 1 | 2299 | tags = 13%, list = 10%, signal = 14% |
| GESERICK_TERT_TARGETS_DN | 20 | 0.25546053 | 0.73272026 | 0.829932 | 0.9210089 | 1 | 2726 | tags = 15%, list = 12%, signal = 17% |
| ZHOU_TNF_SIGNALING_30MIN | 52 | 0.2028513 | 0.7123619 | 0.9402299 | 0.9262648 | 1 | 2321 | tags = 10%, list = 10%, signal = 11% |

TABLE 6S

GSEA for BAF180-wildtype, BRG1-null vs. BAF180-wildtype, BRG1-wildtype A704 cell lines on TNFA founder gene sets

| NAME | SIZE | ES | NES | NOM p-val |
|---|---|---|---|---|
| HINATA_NFKB_IMMU_INF | 16 | 0.7956981 | 2.0275013 | 0 |
| GRAHAM_CML_QUIESCENT_VS_CML_DIVIDING_UP | 19 | 0.7392491 | 1.9318271 | 0 |
| TIAN_TNF_SIGNALING_VIA_NFKB | 28 | 0.60884565 | 1.7448359 | 0.001347709 |
| LINDSTEDT_DENDRITIC_CELL_MATURATION_A | 60 | 0.532906 | 1.751974 | 0 |
| MAHAJAN_RESPONSE_TO_IL1A_UP | 71 | 0.5248131 | 1.7701857 | 0 |
| ALTEMEIER_RESPONSE_TO_LPS_WITH_MECHANICAL_VENTILATION | 107 | 0.48787904 | 1.7344346 | 0 |
| ZHANG_RESPONSE_TO_IKK_INHIBITOR_AND_TNF_UP | 210 | 0.4503261 | 1.7148049 | 0 |
| SEKI_INFLAMMATORY_RESPONSE_LPS_UP | 73 | 0.48960188 | 1.6954869 | 0 |
| SCHOEN_NFKB_SIGNALING | 33 | 0.59241396 | 1.7797453 | 0.001270648 |
| AMIT_EGF_RESPONSE_40_HELA | 41 | 0.5300786 | 1.6392726 | 0.003880983 |
| PHONG_TNF_TARGETS_UP | 61 | 0.49051544 | 1.6150428 | 0.001175088 |
| RASHI_NFKB1_TARGETS | 18 | 0.6302222 | 1.619761 | 0.005449591 |
| FERRARI_RESPONSE_TO_FENRETINIDE_UP | 20 | 0.60883987 | 1.6258345 | 0.009370817 |
| ZHOU_INFLAMMATORY_RESPONSE_LPS_UP | 342 | 0.41023487 | 1.6067731 | 0 |
| GRAHAM_CML_QUIESCENT_VS_NORMAL_DIVIDING_UP | 50 | 0.5050564 | 1.5985647 | 0.01183432 |
| ZHOU_INFLAMMATORY_RESPONSE_FIMA_UP | 441 | 0.39674795 | 1.570265 | 0 |
| DAZARD_UV_RESPONSE_CLUSTER_G28 | 18 | 0.5986828 | 1.5612339 | 0.014986376 |
| ZWANG_CLASS_3_TRANSIENTLY_INDUCED_BY_EGF | 208 | 0.4030676 | 1.5428655 | 0.002109705 |
| ZHOU_INFLAMMATORY_RESPONSE_LIVE_UP | 407 | 0.3903081 | 1.5362784 | 0 |
| MODULE_178 | 15 | 0.5890012 | 1.4863334 | 0.04403409 |
| HINATA_NFKB_TARGETS_KERATINOCYTE_UP | 83 | 0.4311268 | 1.4915149 | 0.011534025 |
| SUZUKI_RESPONSE_TO_TSA_AND_DECITABINE_1A | 21 | 0.5281676 | 1.4615421 | 0.057534248 |
| GARGALOVIC_RESPONSE_TO_OXIDIZED_PHOSPHOLIPIDS_TURQUOISE_UP | 76 | 0.42781955 | 1.4670728 | 0.019813519 |
| HINATA_NFKB_TARGETS_FIBROBLAST_UP | 80 | 0.42352152 | 1.462203 | 0.022016222 |
| BROWNE_HCMV_INFECTION_2HR_UP | 37 | 0.46076813 | 1.453608 | 0.043533932 |
| DAZARD_UV_RESPONSE_CLUSTER_G2 | 29 | 0.49761274 | 1.4343255 | 0.057544757 |
| BILD_HRAS_ONCOGENIC_SIGNATURE | 243 | 0.36789003 | 1.4173068 | 0.007216495 |
| AMIT_EGF_RESPONSE_60_MCF10A | 39 | 0.46236536 | 1.4214058 | 0.061868686 |
| BURTON_ADIPOGENESIS_1 | 33 | 0.45634245 | 1.3591001 | 0.11485643 |
| PHONG_TNF_RESPONSE_NOT_VIA_P38 | 331 | 0.34545162 | 1.3622378 | 0.005081301 |
| MODULE_362 | 19 | 0.51584405 | 1.368848 | 0.11307902 |
| BERENJENO_TRANSFORMED_BY_RHOA_FOREVER_DN | 30 | 0.46400875 | 1.3645186 | 0.10263158 |
| THEILGAARD_NEUTROPHIL_AT_SKIN_WOUND_UP | 74 | 0.40106997 | 1.3705429 | 0.051008303 |
| WINZEN_DEGRADED_VIA_KHSRP | 97 | 0.38334823 | 1.3715631 | 0.043829296 |
| ZUCCHI_METASTASIS_DN | 40 | 0.44579694 | 1.3737904 | 0.07151665 |
| TSAI_RESPONSE_TO_IONIZING_RADIATION | 141 | 0.36060056 | 1.3297915 | 0.04972973 |
| PHONG_TNF_RESPONSE_VIA_P38_PARTIAL | 156 | 0.35237262 | 1.3252659 | 0.036324788 |
| YAO_TEMPORAL_RESPONSE_TO_PROGESTERONE_CLUSTER_5 | 26 | 0.46070793 | 1.312177 | 0.13009198 |
| RASHI_RESPONSE_TO_IONIZING_RADIATION_2 | 120 | 0.3642182 | 1.3125203 | 0.057585824 |
| BROCKE_APOPTOSIS_REVERSED_BY_IL6 | 137 | 0.35121885 | 1.3012718 | 0.050438598 |
| FOSTER_TOLERANT_MACROPHAGE_DN | 387 | 0.32867518 | 1.2934465 | 0.01510574 |
| MATTIOLI_MGUS_VS_MULTIPLE_MYELOMA | 16 | 0.50519097 | 1.2941579 | 0.1520548 |
| WANG_TNF_TARGETS | 21 | 0.46284714 | 1.278999 | 0.16331995 |
| GHANDHI_DIRECT_IRRADIATION_UP | 95 | 0.36340415 | 1.2851771 | 0.107102595 |
| GARGALOVIC_RESPONSE_TO_OXIDIZED_PHOSPHOLIPIDS_BLACK_UP | 33 | 0.4297364 | 1.2800468 | 0.14431673 |
| OSWALD_HEMATOPOIETIC_STEM_CELL_IN_COLLAGEN_GEL_UP | 218 | 0.32804545 | 1.2585387 | 0.045501553 |
| NEWMAN_ERCC6_TARGETS_UP | 25 | 0.44994745 | 1.2648051 | 0.17866324 |
| AMIT_SERUM_RESPONSE_40_MCF10A | 31 | 0.42799193 | 1.2603892 | 0.1658031 |
| DORN_ADENOVIRUS_INFECTION_12HR_DN | 33 | 0.42553425 | 1.2495928 | 0.17994858 |
| MODULE_516 | 16 | 0.49408945 | 1.2413995 | 0.20144928 |
| AMIT_SERUM_RESPONSE_60_MCF10A | 56 | 0.38155204 | 1.2370442 | 0.16791044 |
| CASORELLI_ACUTE_PROMYELOCYTIC_LEUKEMIA_UP | 162 | 0.33160824 | 1.2416271 | 0.092750534 |
| VILIMAS_NOTCH1_TARGETS_UP | 41 | 0.3928831 | 1.2243944 | 0.19524406 |
| GHANDHI_BYSTANDER_IRRADIATION_UP | 72 | 0.3568436 | 1.2254226 | 0.14437869 |
| KRIEG_HYPOXIA_VIA_KDM3A | 51 | 0.38546434 | 1.2154907 | 0.19682151 |
| DIRMEIER_LMP1_RESPONSE_EARLY | 62 | 0.36244237 | 1.2077259 | 0.17562725 |
| UZONYI_RESPONSE_TO_LEUKOTRIENE_AND_THROMBIN | 36 | 0.39616778 | 1.1982558 | 0.21474774 |
| BASSO_CD40_SIGNALING_UP | 91 | 0.3448728 | 1.1989366 | 0.16912599 |
| KIM_WT1_TARGETS_UP | 208 | 0.31086197 | 1.1902792 | 0.12473795 |
| DAUER_STAT3_TARGETS_UP | 45 | 0.37520424 | 1.1873477 | 0.23241206 |
| NEMETH_INFLAMMATORY_RESPONSE_LPS_UP | 84 | 0.33773565 | 1.1683817 | 0.21658987 |
| AMIT_EGF_RESPONSE_60_HELA | 45 | 0.3688694 | 1.1710303 | 0.24368687 |
| MCDOWELL_ACUTE_LUNG_INJURY_UP | 39 | 0.37832016 | 1.1626438 | 0.24808185 |
| GALINDO_IMMUNE_RESPONSE_TO_ENTEROTOXIN | 80 | 0.3368297 | 1.15432 | 0.24473068 |
| P53_DN.V2_UP | 116 | 0.32193154 | 1.1497167 | 0.23281597 |
| SESTO_RESPONSE_TO_UV_C3 | 20 | 0.42613018 | 1.1459695 | 0.31564626 |
| HAHTOLA_MYCOSIS_FUNGOIDES_CD4_UP | 59 | 0.33914083 | 1.1251909 | 0.2789599 |
| LINDSTEDT_DENDRITIC_CELL_MATURATION_B | 49 | 0.34704745 | 1.1105912 | 0.3131936 |
| MODULE_444 | 17 | 0.4365697 | 1.1043755 | 0.33240998 |
| TGFB_UP.V1_UP | 169 | 0.2944326 | 1.0965124 | 0.2796158 |
| PLASARI_TGFB1_TARGETS_10HR_UP | 185 | 0.2863604 | 1.084853 | 0.29202586 |
| AMIT_EGF_RESPONSE_120_HELA | 68 | 0.3227459 | 1.0780765 | 0.35196194 |
| JECHLINGER_EPITHELIAL_TO_MESENCHYMAL_TRANSITION_DN | 64 | 0.3119976 | 1.0370693 | 0.41183433 |
| ALK_DN.V1_UP | 112 | 0.2847367 | 1.0313901 | 0.4108527 |
| KIM_WT1_TARGETS_12HR_UP | 155 | 0.27995437 | 1.0381294 | 0.39804772 |
| RELA_DN.V1_UP | 131 | 0.2814069 | 1.0236616 | 0.41202185 |

TABLE 6S-continued

GSEA for BAF180-wildtype, BRG1-null vs. BAF180-wildtype, BRG1-wildtype A704 cell lines on TNFA founder gene sets

| | | | |
|---|---|---|---|
| WATTEL_AUTONOMOUS_THYROID_ADENOMA_DN | 47 | 0.31701338 | 1.0098777 | 0.46683046 |
| DORN_ADENOVIRUS_INFECTION_24HR_DN | 43 | 0.3237261 | 1.0126069 | 0.4390244 |
| SCIAN_INVERSED_TARGETS_OF_TP53_AND_TP73_DN | 29 | 0.35221815 | 1.0133808 | 0.46535948 |
| AMIT_DELAYED_EARLY_GENES | 18 | 0.37205786 | 0.98065007 | 0.5014045 |
| GARGALOVIC_RESPONSE_TO_OXIDIZED_PHOSPHOLIPIDS_MAGENTA_UP | 27 | 0.33355108 | 0.96410793 | 0.53754944 |
| SARTIPY_BLUNTED_BY_INSULIN_RESISTANCE_UP | 19 | 0.3614058 | 0.95636606 | 0.55617195 |
| DORN_ADENOVIRUS_INFECTION_48HR_DN | 39 | 0.30416617 | 0.94512963 | 0.56375 |
| NAGASHIMA_NRG1_SIGNALING_UP | 170 | 0.24747676 | 0.9379042 | 0.62955034 |
| ADDYA_ERYTHROID_DIFFERENTIATON_BY_HEMIN | 67 | 0.27544057 | 0.92320794 | 0.6049238 |
| PICCALUGA_ANGIOIMMUNOBLASTIC_LYMPHOMA_DN | 129 | 0.24788302 | 0.9115519 | 0.65832424 |
| DORN_ADENOVIRUS_INFECTION_12HR_UP | 28 | 0.29113752 | 0.8355935 | 0.7047619 |
| ZHOU_TNF_SIGNALING_30MIN | 51 | 0.24958822 | 0.80074 | 0.7856273 |
| ZHOU_TNF_SIGNALING_4HR | 54 | 0.24637176 | 0.7917333 | 0.78297365 |
| ABE_VEGFA_TARGETS_30MIN | 25 | 0.24672422 | 0.7019547 | 0.8776316 |
| ABE_VEGFA_TARGETS | 16 | 0.24924366 | 0.636744 | 0.9274756 |
| RASHI_RESPONSE_TO_IONIZING_RADIATION_1 | 41 | 0.18592338 | 0.5865687 | 0.9736842 |

| NAME | FDR q-val | FWER p-val | RANK AT MAX | LEADING EDGE |
|---|---|---|---|---|
| HINATA_NFKB_IMMU_INF | 9.48E-04 | 0.001 | 396 | tags = 50%, list = 2%, signal = 51% |
| GRAHAM_CML_QUIESCENT_VS_CML_DIVIDING_UP | 0.003449188 | 0.007 | 1742 | tags = 47%, list = 8%, signal = 51% |
| TIAN_TNF_SIGNALING_VIA_NFKB | 0.01672752 | 0.1 | 2312 | tags = 43%, list = 10%, signal = 48% |
| LINDSTEDT_DENDRITIC_CELL_MATURATION_A | 0.017720906 | 0.089 | 3084 | tags = 35%, list = 14%, signal = 41% |
| MAHAJAN_RESPONSE_TO_IL1A_UP | 0.017990522 | 0.074 | 4196 | tags = 38%, list = 19%, signal = 47% |
| ALTEMEIER_RESPONSE_TO_LPS_WITH_MECHANICAL_VENTILATION | 0.018068742 | 0.123 | 4346 | tags = 42%, list = 20%, signal = 52% |
| ZHANG_RESPONSE_TO_IKK_INHIBITOR_AND_TNF_UP | 0.018946424 | 0.148 | 4335 | tags = 34%, list = 20%, signal = 42% |
| SEKI_INFLAMMATORY_RESPONSE_LPS_UP | 0.020372774 | 0.177 | 1933 | tags = 29%, list = 9%, signal = 31% |
| SCHOEN_NFKB_SIGNALING | 0.020783762 | 0.064 | 2376 | tags = 36%, list = 11%, signal = 41% |
| AMIT_EGF_RESPONSE_40_HELA | 0.036635086 | 0.324 | 4095 | tags = 41%, list = 18%, signal = 51% |
| PHONG_TNF_TARGETS_UP | 0.03720449 | 0.401 | 4095 | tags = 39%, list = 18%, signal = 48% |
| RASHI_NFKB1_TARGETS | 0.037906855 | 0.383 | 4623 | tags = 67%, list = 21%, signal = 84% |
| FERRARI_RESPONSE_TO_FENRETINIDE_UP | 0.03825266 | 0.363 | 1332 | tags = 25%, list = 6%, signal = 27% |
| ZHOU_INFLAMMATORY_RESPONSE_LPS_UP | 0.039013453 | 0.442 | 3916 | tags = 30%, list = 18%, signal = 35% |
| GRAHAM_CML_QUIESCENT_VS_NORMAL_DIVIDING_UP | 0.039890602 | 0.474 | 4220 | tags = 38%, list = 19%, signal = 47% |
| ZHOU_INFLAMMATORY_RESPONSE_FIMA_UP | 0.050020583 | 0.571 | 4761 | tags = 33%, list = 21%, signal = 42% |
| DAZARD_UV_RESPONSE_CLUSTER_G28 | 0.052049164 | 0.604 | 244 | tags = 22%, list = 1%, signal = 22% |
| ZWANG_CLASS_3_TRANSIENTLY_INDUCED_BY_EGF | 0.061013937 | 0.685 | 4404 | tags = 32%, list = 20%, signal = 39% |
| ZHOU_INFLAMMATORY_RESPONSE_LIVE_UP | 0.061709113 | 0.711 | 5270 | tags = 34%, list = 24%, signal = 44% |

TABLE 6S-continued

GSEA for BAF180-wildtype, BRG1-null vs. BAF180-wildtype, BRG1-wildtype A704 cell lines on TNFA founder gene sets

| Gene Set | Value | Value | Value | Stats |
|---|---|---|---|---|
| MODULE_178 | 0.09094207 | 0.875 | 2349 | tags = 33%, list = 11%, signal = 37% |
| HINATA_NFKB_TARGETS_KERATINOCYTE_UP | 0.09156335 | 0.859 | 3619 | tags = 31%, list = 16%, signal = 37% |
| SUZUKI_RESPONSE_TO_TSA_AND_DECITABINE_1A | 0.10243626 | 0.932 | 5765 | tags = 48%, list = 26%, signal = 64% |
| GARGALOVIC_RESPONSE_TO_OXIDIZED_PHOSPHOLIPIDS_TURQUOISE_UP | 0.105884045 | 0.917 | 6481 | tags = 54%, list = 29%, signal = 76% |
| HINATA_NFKB_TARGETS_FIBROBLAST_UP | 0.10618031 | 0.932 | 3497 | tags = 25%, list = 16%, signal = 30% |
| BROWNE_HCMV_INFECTION_2HR_UP | 0.10621111 | 0.943 | 2312 | tags = 24%, list = 10%, signal = 27% |
| DAZARD_UV_RESPONSE_CLUSTER_G2 | 0.12164423 | 0.968 | 430 | tags = 17%, list = 2%, signal = 18% |
| BILD_HRAS_ONCOGENIC_SIGNATURE | 0.13088778 | 0.98 | 3413 | tags = 22%, list = 15%, signal = 26% |
| AMIT_EGF_RESPONSE_60_MCF10A | 0.13170351 | 0.978 | 2243 | tags = 26%, list = 10%, signal = 28% |
| BURTON_ADIPOGENESIS_1 | 0.1669525 | 0.999 | 6703 | tags = 55%, list = 30%, signal = 78% |
| PHONG_TNF_RESPONSE_NOT_VIA_P38 | 0.16772734 | 0.999 | 3368 | tags = 21%, list = 15%, signal = 25% |
| MODULE_362 | 0.16896467 | 0.998 | 2349 | tags = 32%, list = 11%, signal = 35% |
| BERENJENO_TRANSFORMED_BY_RHOA_FOREVER_DN | 0.1695761 | 0.999 | 3424 | tags = 30%, list = 15%, signal = 35% |
| THEILGAARD_NEUTROPHIL_AT_SKIN_WOUND_UP | 0.17244785 | 0.998 | 5202 | tags = 32%, list = 23%, signal = 42% |
| WINZEN_DEGRADED_VIA_KHSRP | 0.17665227 | 0.998 | 3916 | tags = 32%, list = 18%, signal = 39% |
| ZUCCHI_METASTASIS_DN | 0.17920427 | 0.998 | 3432 | tags = 30%, list = 15%, signal = 35% |
| TSAI_RESPONSE_TO_IONIZING_RADIATION | 0.20238431 | 1 | 5213 | tags = 34%, list = 23%, signal = 44% |
| PHONG_TNF_RESPONSE_VIA_P38_PARTIAL | 0.20380807 | 1 | 5078 | tags = 33%, list = 23%, signal = 43% |
| YAO_TEMPORAL_RESPONSE_TO_PROGESTERONE_CLUSTER_5 | 0.21185845 | 1 | 5068 | tags = 38%, list = 23%, signal = 50% |
| RASHI_RESPONSE_TO_IONIZING_RADIATION_2 | 0.21702695 | 1 | 5049 | tags = 33%, list = 23%, signal = 43% |
| BROCKE_APOPTOSIS_REVERSED_BY_IL6 | 0.22373448 | 1 | 5272 | tags = 34%, list = 24%, signal = 45% |
| FOSTER_TOLERANT_MACROPHAGE_DN | 0.22482397 | 1 | 6068 | tags = 33%, list = 27%, signal = 45% |
| MATTIOLI_MGUS_VS_MULTIPLE_MYELOMA | 0.22912467 | 1 | 2035 | tags = 19%, list = 9%, signal = 21% |
| WANG_TNF_TARGETS | 0.2309146 | 1 | 2928 | tags = 29%, list = 13%, signal = 33% |
| GHANDHI_DIRECT_IRRADIATION_UP | 0.23219457 | 1 | 3382 | tags = 25%, list = 15%, signal = 30% |
| GARGALOVIC_RESPONSE_TO_OXIDIZED_PHOSPHOLIPIDS_BLACK_UP | 0.234369 | 1 | 4877 | tags = 39%, list = 22%, signal = 50% |

TABLE 6S-continued

GSEA for BAF180-wildtype, BRG1-null vs. BAF180-wildtype, BRG1-wildtype A704 cell lines on TNFA founder gene sets

| | | | | |
|---|---|---|---|---|
| OSWALD_HEMATOPOIETIC_STEM_CELL_IN_COLLAGEN_GEL_UP | 0.24825019 | 1 | 4491 | tags = 28%, list = 20%, signal = 35% |
| NEWMAN_ERCC6_TARGETS_UP | 0.2489162 | 1 | 1827 | tags = 24%, list = 8%, signal = 26% |
| AMIT_SERUM_RESPONSE_40_MCF10A | 0.25068888 | 1 | 4118 | tags = 32%, list = 19%, signal = 40% |
| DORN_ADENOVIRUS_INFECTION_12HR_DN | 0.25761074 | 1 | 4877 | tags = 30%, list = 22%, signal = 39% |
| MODULE_516 | 0.26132855 | 1 | 5680 | tags = 56%, list = 26%, signal = 76% |
| AMIT_SERUM_RESPONSE_60_MCF10A | 0.2633078 | 1 | 2151 | tags = 21%, list = 10%, signal = 24% |
| CASORELLI_ACUTE_PROMYELOCYTIC_LEUKEMIA_UP | 0.2660269 | 1 | 5835 | tags = 35%, list = 26%, signal = 47% |
| VILIMAS_NOTCH1_TARGETS_UP | 0.27467248 | 1 | 4323 | tags = 37%, list = 19%, signal = 45% |
| GHANDHI_BYSTANDER_IRRADIATION_UP | 0.27798596 | 1 | 2083 | tags = 21%, list = 9%, signal = 23% |
| KRIEG_HYPOXIA_VIA_KDM3A | 0.2853903 | 1 | 1078 | tags = 14%, list = 5%, signal = 14% |
| DIRMEIER_LMP1_RESPONSE_EARLY | 0.29365915 | 1 | 4323 | tags = 32%, list = 19%, signal = 40% |
| UZONYI_RESPONSE_TO_LEUKOTRIENE_AND_THROMBIN | 0.2995725 | 1 | 4213 | tags = 33%, list = 19%, signal = 41% |
| BASSO_CD40_SIGNALING_UP | 0.30355766 | 1 | 4491 | tags = 35%, list = 20%, signal = 44% |
| KIM_WT1_TARGETS_UP | 0.30792785 | 1 | 5077 | tags = 33%, list = 23%, signal = 42% |
| DAUER_STAT3_TARGETS_UP | 0.30873922 | 1 | 4095 | tags = 33%, list = 18%, signal = 41% |
| NEMETH_INFLAMMATORY_RESPONSE_LPS_UP | 0.3318771 | 1 | 4718 | tags = 32%, list = 21%, signal = 41% |
| AMIT_EGF_RESPONSE_60_HELA | 0.3323425 | 1 | 6174 | tags = 49%, list = 28%, signal = 68% |
| MCDOWELL_ACUTE_LUNG_INJURY_UP | 0.337064 | 1 | 4061 | tags = 28%, list = 18%, signal = 34% |
| GALINDO_IMMUNE_RESPONSE_TO_ENTEROTOXIN | 0.34732458 | 1 | 4491 | tags = 31%, list = 20%, signal = 39% |
| P53_DN.V2_UP | 0.3502771 | 1 | 2996 | tags = 19%, list = 13%, signal = 22% |
| SESTO_RESPONSE_TO_UV_C3 | 0.35206577 | 1 | 920 | tags = 15%, list = 4%, signal = 16% |
| HAHTOLA_MYCOSIS_FUNGOIDES_CD4_UP | 0.38515478 | 1 | 1420 | tags = 14%, list = 6%, signal = 14% |
| LINDSTEDT_DENDRITIC_CELL_MATURATION_B | 0.40690055 | 1 | 4323 | tags = 33%, list = 19%, signal = 40% |
| MODULE_444 | 0.41287807 | 1 | 2349 | tags = 29%, list = 11%, signal = 33% |
| TGFB_UP.V1_UP | 0.42247924 | 1 | 4831 | tags = 31%, list = 22%, signal = 39% |
| PLASARI_TGFB1_TARGETS_10HR_UP | 0.43959522 | 1 | 2841 | tags = 18%, list = 13%, signal = 20% |

TABLE 6S-continued

GSEA for BAF180-wildtype, BRG1-null vs. BAF180-wildtype, BRG1-wildtype A704 cell lines on TNFA founder gene sets

| Name | ES | NOM p-val | Rank | Signal |
|---|---|---|---|---|
| AMIT_EGF_RESPONSE_120_HELA | 0.44629344 | 1 | 4168 | tags = 31%, list = 19%, signal = 38% |
| JECHLINGER_EPITHELIAL_TO_MESENCHYMAL_TRANSITION_DN | 0.51697856 | 1 | 4095 | tags = 33%, list = 18%, signal = 40% |
| ALK_DN.V1_UP | 0.5219166 | 1 | 3021 | tags = 18%, list = 14%, signal = 21% |
| KIM_WT1_TARGETS_12HR_UP | 0.5219282 | 1 | 5311 | tags = 30%, list = 24%, signal = 40% |
| RELA_DN.V1_UP | 0.5316298 | 1 | 5093 | tags = 30%, list = 23%, signal = 38% |
| WATTEL_AUTONOMOUS_THYROID_ADENOMA_DN | 0.5386091 | 1 | 5245 | tags = 43%, list = 24%, signal = 56% |
| DORN_ADENOVIRUS_INFECTION_24HR_DN | 0.5396305 | 1 | 4877 | tags = 33%, list = 22%, signal = 42% |
| SCIAN_INVERSED_TARGETS_OF_TP53_AND_TP73_DN | 0.5451588 | 1 | 4323 | tags = 24%, list = 19%, signal = 30% |
| AMIT_DELAYED_EARLY_GENES | 0.58976126 | 1 | 4095 | tags = 39%, list = 18%, signal = 48% |
| GARGALOVIC_RESPONSE_TO_OXIDIZED_PHOSPHOLIPIDS_MAGENTA_UP | 0.6154671 | 1 | 5718 | tags = 33%, list = 26%, signal = 45% |
| SARTIPY_BLUNTED_BY_INSULIN_RESISTANCE_UP | 0.62259376 | 1 | 4266 | tags = 37%, list = 19%, signal = 46% |
| DORN_ADENOVIRUS_INFECTION_48HR_DN | 0.63736963 | 1 | 5203 | tags = 31%, list = 23%, signal = 40% |
| NAGASHIMA_NRG1_SIGNALING_UP | 0.6432155 | 1 | 4150 | tags = 25%, list = 19%, signal = 31% |
| ADDYA_ERYTHROID_DIFFERENTIATON_BY_HEMIN | 0.6627822 | 1 | 4729 | tags = 21%, list = 21%, signal = 26% |
| PICCALUGA_ANGIOIMMUNOBLASTIC_LYMPHOMA_DN | 0.67606705 | 1 | 7172 | tags = 36%, list = 32%, signal = 53% |
| DORN_ADENOVIRUS_INFECTION_12HR_UP | 0.7986275 | 1 | 5221 | tags = 36%, list = 24%, signal = 47% |
| ZHOU_TNF_SIGNALING_30MIN | 0.84232277 | 1 | 3128 | tags = 14%, list = 14%, signal = 16% |
| ZHOU_TNF_SIGNALING_4HR | 0.84545606 | 1 | 3277 | tags = 13%, list = 15%, signal = 15% |
| ABE_VEGFA_TARGETS_30MIN | 0.9370464 | 1 | 9755 | tags = 56%, list = 44%, signal = 100% |
| ABE_VEGFA_TARGETS | 0.97078294 | 1 | 8862 | tags = 44%, list = 40%, signal = 73% |
| RASHI_RESPONSE_TO_IONIZING_RADIATION_1 | 0.9792933 | 1 | 9321 | tags = 46%, list = 42%, signal = 80% |

TABLE 6T

GSEA for BAF180-null vs. BAF180-wildtype A704 cell lines on IL2 Founder gene sets

| NAME | SIZE | ES | NES | NOM p-val |
|---|---|---|---|---|
| WIERENGA_STAT5A_TARGETS_UP | 198 | 0.37538955 | 1.6359013 | 0 |
| WIERENGA_STAT5A_TARGETS_GROUP1 | 124 | 0.38390127 | 1.5493696 | 0.005 |
| MARZEC_IL2_SIGNALING_UP | 105 | 0.34808874 | 1.39865 | 0.039906103 |
| WIERENGA_STAT5A_TARGETS_GROUP2 | 52 | 0.40397617 | 1.404526 | 0.06026786 |
| IL21_UP.V1_UP | 153 | 0.2727604 | 1.1800731 | 0.13333334 |

TABLE 6T-continued

GSEA for BAF180-null vs. BAF180-wildtype A704 cell lines on IL2 Founder gene sets

| | | | | |
|---|---|---|---|---|
| IL2_UP.V1_UP | 167 | 0.26439285 | 1.1303729 | 0.19518073 |
| IL15_UP.V1_UP | 167 | 0.2663421 | 1.1419721 | 0.17298578 |
| ZHENG_FOXP3_TARGETS_UP | 23 | 0.40840292 | 1.1883539 | 0.23413567 |
| BOSCO_ALLERGEN_INDUCED_TH2_ASSOCIATED_MODULE | 28 | 0.24078815 | 0.99573 | 0.45454547 |

| NAME | FDR q-val | FWER p-val | RANK AT MAX | LEADING EDGE |
|---|---|---|---|---|
| WIERENGA_STAT5A_TARGETS_UP | 0.025693554 | 0.018 | 2815 | tags = 25%, list = 13%, signal = 29% |
| WIERENGA_STAT5A_TARGETS_GROUP1 | 0.026251249 | 0.034 | 2283 | tags = 22%, list = 10%, signal = 24% |
| MARZEC_IL2_SIGNALING_UP | 0.067707956 | 0.159 | 3079 | tags = 23%, list = 14%, signal = 26% |
| WIERENGA_STAT5A_TARGETS_GROUP2 | 0.08636623 | 0.152 | 3343 | tags = 35%, list = 15%, signal = 41% |
| IL21_UP.V1_UP | 0.23306713 | 0.594 | 2622 | tags = 19%, list = 12%, signal = 21% |
| IL2_UP.V1_UP | 0.23517144 | 0.699 | 2883 | tags = 21%, list = 13%, signal = 24% |
| IL15_UP.V1_UP | 0.25491062 | 0.678 | 2955 | tags = 20%, list = 13%, signal = 23% |
| ZHENG_FOXP3_TARGETS_UP | 0.2645548 | 0.573 | 4871 | tags = 43%, list = 22%, signal = 56% |
| BOSCO_ALLERGEN_INDUCED_TH2_ASSOCIATED_MODULE | 0.4475559 | 0.927 | 2516 | tags = 15%, list = 11%, signal = 17% |

TABLE 6U

GSEA for BAF180-wildtype, BRG1-null vs. BAF180-wildtype, BRG1-wildtype A704 cell lines on IL2 founder gene sets

| NAME | SIZE | ES | NES | NOM p-val |
|---|---|---|---|---|
| WIERENGA_STAT5A_TARGETS_GROUP1 | 126 | 0.49578398 | 1.8142022 | 0 |
| WIERENGA_STAT5A_TARGETS_UP | 200 | 0.4889695 | 1.8709142 | 0 |
| ZHENG_FOXP3_TARGETS_UP | 23 | 0.60290974 | 1.654486 | 0.006868132 |
| WIERENGA_STAT5A_TARGETS_GROUP2 | 52 | 0.4778286 | 1.5371454 | 0.023866348 |
| MARZEC_IL2_SIGNALING_UP | 105 | 0.3958873 | 1.4140925 | 0.030905077 |
| LU_IL4_SIGNALING | 85 | 0.3367652 | 1.17004 | 0.19861431 |
| IL2_UP.V1_UP | 162 | 0.31537378 | 1.1796162 | 0.16173361 |
| GAVIN_FOXP3_TARGETS_CLUSTER_P4 | 93 | 0.31758162 | 1.1196293 | 0.28128588 |
| BOSCO_ALLERGEN_INDUCED_TH2_ASSOCIATED_MODULE | 28 | 0.291105 | 1.0583609 | 0.3576087 |
| GAVIN_FOXP3_TARGETS_CLUSTER_P7 | 83 | 0.31101844 | 1.0731124 | 0.35606936 |
| IL15_UP.V1_UP | 164 | 0.27082396 | 1.0106155 | 0.46276596 |
| IL21_UP.V1_UP | 151 | 0.2229732 | 0.8263667 | 0.81702125 |
| GAVIN_FOXP3_TARGETS_CLUSTER_T4 | 89 | 0.24680245 | 0.85941374 | 0.73505276 |

| NAME | FDR q-val | FWER p-val | RANK AT MAX | LEADING EDGE |
|---|---|---|---|---|
| WIERENGA_STAT5A_TARGETS_GROUP1 | 5.42E-04 | 0.001 | 5171 | tags = 43%, list = 23%, signal = 56% |
| WIERENGA_STAT5A_TARGETS_UP | 0.001083333 | 0.001 | 4799 | tags = 41%, list = 22%, signal = 51% |
| ZHENG_FOXP3_TARGETS_UP | 0.0082798 | 0.021 | 1681 | tags = 30%, list = 8%, signal = 33% |
| WIERENGA_STAT5A_TARGETS_GROUP2 | 0.025304792 | 0.088 | 4799 | tags = 42%, list = 22%, signal = 54% |

TABLE 6U-continued

GSEA for BAF180-wildtype, BRG1-null vs. BAF180-wildtype,
BRG1-wildtype A704 cell lines on IL2 founder gene sets

| | | | | |
|---|---|---|---|---|
| MARZEC_IL2_SIGNALING_UP | 0.06855733 | 0.263 | 5049 | tags = 30%, list = 23%, signal = 39% |
| LU_IL4_SIGNALING | 0.3729165 | 0.926 | 4254 | tags = 27%, list = 19%, signal = 33% |
| IL2_UP.V1_UP | 0.4066424 | 0.908 | 4694 | tags = 30%, list = 21%, signal = 38% |
| GAVIN_FOXP3_TARGETS_CLUSTER_P4 | 0.4438688 | 0.971 | 2660 | tags = 16%, list = 12%, signal = 18% |
| BOSCO_ALLERGEN_INDUCED_TH2_ASSOCIATED_MODULE | 0.48443615 | 0.995 | 7046 | tags = 38%, list = 32%, signal = 55% |
| GAVIN_FOXP3_TARGETS_CLUSTER_P7 | 0.5027296 | 0.993 | 4197 | tags = 28%, list = 19%, signal = 34% |
| IL15_UP.V1_UP | 0.5466651 | 1 | 4694 | tags = 27%, list = 21%, signal = 35% |
| IL21_UP.V1_UP | 0.7926685 | 1 | 4702 | tags = 23%, list = 21%, signal = 29% |
| GAVIN_FOXP3_TARGETS_CLUSTER_T4 | 0.8019424 | 1 | 6570 | tags = 36%, list = 30%, signal = 51% |

TABLE 6V

Enriched GO terms for KEGG_CYTOKINE_CYTOKINE_RECEPTOR_INTERACTION genes in BAF180-mutant GSEA enriched vs. BAF180-mutant GSEA depleted

| Enriched genes | Depleted genes | Enriched Gene Results GO biological process complete | Homo sapiens - REFLIST (20972) | upload_1 (56) | upload_1 (expected) | upload_1 (over/under) | upload_1 (fold Enrichment) | upload_1 (P-value) |
|---|---|---|---|---|---|---|---|---|
| IL8 | CXCR6 | | | | | | | |
| CXCL1 | IL18 | cell surface receptor signaling pathway (GO:0007166) | 2211 | 50 | 5.9 | + | 8.47 | 1.94E-38 |
| PDGFRB | MET | cytokine-mediated signaling pathway (GO:0019221) | 466 | 34 | 1.24 | + | 27.32 | 6.70E-38 |
| TNFRSF13C | IL22RA1 | cellular response to cytokine stimulus (GO:0071345) | 632 | 36 | 1.69 | + | 21.33 | 6.27E-37 |
| IL11 | HGF | response to cytokine (GO:0034097) | 727 | 36 | 1.94 | + | 18.54 | 8.86E-35 |
| CCR6 | FLT4 | positive regulation of response to stimulus (GO:0048584) | 2028 | 45 | 5.42 | + | 8.31 | 9.05E-32 |
| CCL28 | KDR | cellular response to organic substance (GO:0071310) | 1915 | 44 | 5.11 | + | 8.6 | 2.74E-31 |
| TNFSF10 | ACVRL1 | cellular response to chemical stimulus (GO:0070887) | 2347 | 45 | 6.27 | + | 7.18 | 5.40E-29 |
| CX3CL1 | IL20RA | response to organic substance (GO:0010033) | 2557 | 45 | 6.83 | + | 6.59 | 2.26E-27 |
| IL6 | MPL | positive regulation of response to external stimulus (GO:0032103) | 266 | 23 | 0.71 | + | 32.38 | 4.11E-25 |
| CSF1 | LTB | signal transduction (GO:0007165) | 4867 | 52 | 13 | + | 4 | 1.10E-24 |
| CTF1 | IL6ST | chemokine-mediated signaling pathway (GO:0070098) | 73 | 17 | 0.19 | + | 87.21 | 1.14E-24 |
| CD70 | TNFRSF11B | regulation of leukocyte migration (GO:0002685) | 156 | 20 | 0.42 | + | 48.01 | 1.34E-24 |
| TNFSF14 | FIGF | single organism signaling (GO:0044700) | 5262 | 53 | 14.05 | + | 3.77 | 1.45E-24 |
| CCL5 | IL2RB | signaling (GO:0023052) | 5266 | 53 | 14.06 | + | 3.77 | 1.51E-24 |
| CCL19 | IL1B | cell communication (GO:0007154) | 5351 | 53 | 14.29 | + | 3.71 | 3.48E-24 |
| CCL2 | EDA | positive regulation of leukocyte migration (GO:0002687) | 109 | 18 | 0.29 | + | 61.84 | 1.11E-23 |

TABLE 6V-continued

Enriched GO terms for KEGG_CYTOKINE_CYTOKINE_RECEPTOR_INTERACTION
genes in BAF180-mutant GSEA enriched vs. BAF180-mutant GSEA depleted

| | | | | | | | | |
|---|---|---|---|---|---|---|---|---|
| CCL20 | IL7R | response to chemical (GO:0042221) | 3875 | 48 | 10.35 | + | 4.64 | 1.48E-23 |
| TNFRSF10D | | regulation of response to stimulus (GO:0048583) | 3696 | 47 | 9.87 | + | 4.76 | 4.17E-23 |
| TNFRSF1B | | cellular response to stimulus (GO:0051716) | 6168 | 54 | 16.47 | + | 3.28 | 1.27E-22 |
| CX3CR1 | | positive regulation of protein phosphorylation (GO:0001934) | 895 | 30 | 2.39 | + | 12.55 | 1.47E-22 |
| TNFSF9 | | regulation of response to external stimulus (GO:0032101) | 712 | 28 | 1.9 | + | 14.73 | 1.80E-22 |
| CSF2 | | regulation of cell proliferation (GO:0042127) | 1538 | 35 | 4.11 | + | 8.52 | 4.52E-22 |
| TNFRSF11A | | positive regulation of phosphorylation (GO:0042327) | 937 | 30 | 2.5 | + | 11.99 | 5.51E-22 |
| IL21R | | positive regulation of phosphorus metabolic process (GO:0010562) | 1056 | 31 | 2.82 | + | 10.99 | 7.59E-22 |
| IL17RB | | positive regulation of phosphate metabolic process (GO:0045937) | 1056 | 31 | 2.82 | + | 10.99 | 7.59E-22 |
| CXCL10 | | chemotaxis (GO:0006935) | 508 | 25 | 1.36 | + | 18.43 | 8.89E-22 |
| OSMR | | taxis (GO:0042330) | 509 | 25 | 1.36 | + | 18.39 | 9.32E-22 |
| INHBE | | immune system process (GO:0002376) | 2465 | 40 | 6.58 | + | 6.08 | 3.13E-21 |
| GDF5 | | regulation of leukocyte chemotaxis (GO:0002688) | 99 | 16 | 0.26 | + | 60.53 | 1.74E-20 |
| VEGFB | | positive regulation of signal transduction (GO:0009967) | 1433 | 33 | 3.83 | + | 8.62 | 1.87E-20 |
| CXCL3 | | immune response (GO:0006955) | 1591 | 34 | 4.25 | + | 8 | 2.72E-20 |
| CXCL2 | | cell chemotaxis (GO:0060326) | 176 | 18 | 0.47 | + | 38.3 | 5.48E-20 |
| CCR10 | | positive regulation of leukocyte chemotaxis (GO:0002690) | 81 | 15 | 0.22 | + | 69.35 | 7.30E-20 |
| IL24 | | regulation of chemotaxis (GO:0050920) | 185 | 18 | 0.49 | + | 36.44 | 1.32E-19 |
| TNFRSF19 | | positive regulation of intracellular signal transduction (GO:1902533) | 911 | 28 | 2.43 | + | 11.51 | 1.37E-19 |
| CXCL12 | | positive regulation of protein modification process (GO:0031401) | 1150 | 30 | 3.07 | + | 9.77 | 1.96E-19 |
| OSM | | positive regulation of cell communication (GO:0010647) | 1552 | 33 | 4.14 | + | 7.96 | 2.27E-19 |
| EGF | | positive regulation of signaling (GO:0023056) | 1560 | 33 | 4.17 | + | 7.92 | 2.67E-19 |
| VEGFC | | positive regulation of chemotaxis (GO:0050921) | 120 | 16 | 0.32 | + | 49.93 | 3.64E-19 |
| TGFB3 | | regulation of protein phosphorylation (GO:0001932) | 1302 | 31 | 3.48 | + | 8.92 | 3.71E-19 |
| TNFSF13 | | response to stimulus (GO:0050896) | 7800 | 55 | 20.83 | + | 2.64 | 6.92E-19 |
| KITLG | | positive regulation of biological process (GO:0048518) | 5270 | 49 | 14.07 | + | 3.48 | 1.07E-18 |
| LIFR | | positive regulation of cellular process (GO:0048522) | 4716 | 47 | 12.59 | + | 3.73 | 2.31E-18 |
| LIF | | positive regulation of protein metabolic process (GO:0051247) | 1527 | 32 | 4.08 | + | 7.85 | 2.40E-18 |
| IL20 | | regulation of locomotion (GO:0040012) | 804 | 26 | 2.15 | + | 12.11 | 2.64E-18 |
| IL13 | | regulation of phosphorylation (GO:0042325) | 1398 | 31 | 3.73 | + | 8.3 | 2.99E-18 |
| BMP7 | | inflammatory response (GO:0006954) | 462 | 22 | 1.23 | + | 17.83 | 3.00E-18 |
| IL1R1 | | regulation of intracellular signal transduction (GO:1902531) | 1725 | 33 | 4.61 | + | 7.16 | 6.09E-18 |
| AMHR2 | | positive regulation of cellular protein metabolic process (GO:0032270) | 1433 | 31 | 3.83 | + | 8.1 | 6.17E-18 |

TABLE 6V-continued

Enriched GO terms for KEGG_CYTOKINE_CYTOKINE_RECEPTOR_INTERACTION genes in BAF180-mutant GSEA enriched vs. BAF180-mutant GSEA depleted

| | | | | | | | |
|---|---|---|---|---|---|---|---|
| VEGFA | regulation of cell motility (GO:2000145) | 741 | 25 | 1.98 | + | 12.63 | 7.94E−18 |
| CXCR4 | positive regulation of cell proliferation (GO:0008284) | 847 | 26 | 2.26 | + | 11.5 | 9.61E−18 |
| INHBB | regulation of cell migration (GO:0030334) | 691 | 24 | 1.85 | + | 13.01 | 3.43E−17 |
| | regulation of cellular component movement (GO:0051270) | 806 | 25 | 2.15 | + | 11.62 | 5.90E−17 |
| | positive regulation of multicellular organismal process (GO:0051240) | 1425 | 30 | 3.81 | + | 7.88 | 8.60E−17 |
| | response to external stimulus (GO:0009605) | 1766 | 32 | 4.72 | + | 6.79 | 1.89E−16 |
| | regulation of phosphate metabolic process (GO:0019220) | 1621 | 31 | 4.33 | + | 7.16 | 2.23E−16 |
| | regulation of phosphorus metabolic process (GO:0051174) | 1634 | 31 | 4.36 | + | 7.1 | 2.81E−16 |
| | regulation of MAPK cascade (GO:0043408) | 679 | 23 | 1.81 | + | 12.69 | 5.00E−16 |
| | regulation of protein modification process (GO:0031399) | 1675 | 31 | 4.47 | + | 6.93 | 5.76E−16 |
| | regulation of signal transduction (GO:0009966) | 2752 | 37 | 7.35 | + | 5.04 | 6.05E−16 |
| | regulation of cell communication (GO:0010646) | 3051 | 38 | 8.15 | + | 4.66 | 1.71E−15 |
| | locomotion (GO:0040011) | 1188 | 27 | 3.17 | + | 8.51 | 2.58E−15 |
| | regulation of signaling (GO:0023051) | 3102 | 38 | 8.28 | + | 4.59 | 3.06E−15 |
| | positive regulation of immune system process (GO:0002684) | 954 | 25 | 2.55 | + | 9.81 | 3.21E−15 |
| | positive regulation of peptidyl-tyrosine phosphorylation (GO:0050731) | 167 | 15 | 0.45 | + | 33.64 | 3.22E−15 |
| | positive regulation of cell migration (GO:0030335) | 400 | 19 | 1.07 | + | 17.79 | 3.77E−15 |
| | positive regulation of cell motility (GO:2000147) | 414 | 19 | 1.11 | + | 17.19 | 7.08E−15 |
| | cellular response to tumor necrosis factor (GO:0071356) | 226 | 16 | 0.6 | + | 26.51 | 7.52E−15 |
| | positive regulation of cellular component movement (GO:0051272) | 425 | 19 | 1.13 | + | 16.74 | 1.14E−14 |
| | defense response (GO:0006952) | 1147 | 26 | 3.06 | + | 8.49 | 1.65E−14 |
| | positive regulation of locomotion (GO:0040017) | 442 | 19 | 1.18 | + | 16.1 | 2.34E−14 |
| | response to tumor necrosis factor (GO:0034612) | 247 | 16 | 0.66 | + | 24.26 | 3.00E−14 |
| | regulation of localization (GO:0032879) | 2485 | 34 | 6.64 | + | 5.12 | 3.83E−14 |
| | regulation of cellular process (GO:0050794) | 10399 | 56 | 27.77 | + | 2.02 | 7.14E−14 |
| | regulation of protein metabolic process (GO:0051246) | 2542 | 34 | 6.79 | + | 5.01 | 7.76E−14 |
| | regulation of cellular protein metabolic process (GO:0032268) | 2363 | 33 | 6.31 | + | 5.23 | 9.32E−14 |
| | leukocyte chemotaxis (GO:0030595) | 124 | 13 | 0.33 | + | 39.26 | 1.32E−13 |
| | positive regulation of MAPK cascade (GO:0043410) | 487 | 19 | 1.3 | + | 14.61 | 1.37E−13 |
| | regulation of immune system process (GO:0002682) | 1392 | 27 | 3.72 | + | 7.26 | 1.39E−13 |
| | regulation of peptidyl-tyrosine phosphorylation (GO:0050730) | 221 | 15 | 0.59 | + | 25.42 | 1.95E−13 |
| | response to lipopolysaccharide (GO:0032496) | 294 | 16 | 0.79 | + | 20.38 | 4.47E−13 |
| | positive regulation of developmental process (GO:0051094) | 1179 | 25 | 3.15 | + | 7.94 | 4.57E−13 |
| | response to molecule of bacterial origin (GO:0002237) | 308 | 16 | 0.82 | + | 19.45 | 9.18E−13 |

TABLE 6V-continued

Enriched GO terms for KEGG_CYTOKINE_CYTOKINE_RECEPTOR_INTERACTION
genes in BAF180-mutant GSEA enriched vs. BAF180-mutant GSEA depleted

| | | | | | | |
|---|---|---|---|---|---|---|
| regulation of biological process (GO:0050789) | 10941 | 56 | 29.21 | + | 1.92 | 1.23E−12 |
| positive regulation of macromolecule metabolic process (GO:0010604) | 2841 | 34 | 7.59 | + | 4.48 | 2.40E−12 |
| positive regulation of cellular metabolic process (GO:0031325) | 2845 | 34 | 7.6 | + | 4.48 | 2.51E−12 |
| positive regulation of tyrosine phosphorylation of STAT protein (GO:0042531) | 60 | 10 | 0.16 | + | 62.42 | 9.52E−12 |
| response to stress (GO:0006950) | 3214 | 35 | 8.58 | + | 4.08 | 1.16E−11 |
| positive regulation of metabolic process (GO:0009893) | 3033 | 34 | 8.1 | + | 4.2 | 1.77E−11 |
| cell migration (GO:0016477) | 862 | 21 | 2.3 | + | 9.12 | 2.12E−11 |
| biological regulation (GO:0065007) | 11582 | 56 | 30.93 | + | 1.81 | 2.98E−11 |
| regulation of tyrosine phosphorylation of STAT protein (GO:0042509) | 68 | 10 | 0.18 | + | 55.07 | 3.28E−11 |
| positive regulation of STAT cascade (GO:1904894) | 75 | 10 | 0.2 | + | 49.93 | 8.61E−11 |
| positive regulation of JAK-STAT cascade (GO:0046427) | 75 | 10 | 0.2 | + | 49.93 | 8.61E−11 |
| response to lipid (GO:0033993) | 817 | 20 | 2.18 | + | 9.17 | 1.07E−10 |
| localization of cell (GO:0051674) | 950 | 21 | 2.54 | + | 8.28 | 1.41E−10 |
| cell motility (GO:0048870) | 950 | 21 | 2.54 | + | 8.28 | 1.41E−10 |
| regulation of multicellular organismal process (GO:0051239) | 2656 | 31 | 7.09 | + | 4.37 | 2.64E−10 |
| regulation of apoptotic process (GO:0042981) | 1410 | 24 | 3.77 | + | 6.37 | 3.09E−10 |
| response to other organism (GO:0051707) | 753 | 19 | 2.01 | + | 9.45 | 3.41E−10 |
| response to external biotic stimulus (GO:0043207) | 754 | 19 | 2.01 | + | 9.44 | 3.50E−10 |
| regulation of programmed cell death (GO:0043067) | 1421 | 24 | 3.79 | + | 6.33 | 3.66E−10 |
| response to biotic stimulus (GO:0009607) | 786 | 19 | 2.1 | + | 9.05 | 7.28E−10 |
| myeloid leukocyte migration (GO:0097529) | 99 | 10 | 0.26 | + | 37.83 | 1.32E−09 |
| negative regulation of apoptotic process (GO:0043066) | 818 | 19 | 2.18 | + | 8.7 | 1.47E−09 |
| regulation of cell death (GO:0010941) | 1522 | 24 | 4.06 | + | 5.91 | 1.62E−09 |
| response to bacterium (GO:0009617) | 507 | 16 | 1.35 | + | 11.82 | 1.86E−09 |
| negative regulation of programmed cell death (GO:0043069) | 829 | 19 | 2.21 | + | 8.58 | 1.86E−09 |
| response to oxygen-containing compound (GO:1901700) | 1388 | 23 | 3.71 | + | 6.21 | 2.26E−09 |
| leukocyte migration (GO:0050900) | 351 | 14 | 0.94 | + | 14.94 | 3.33E−09 |
| movement of cell or subcellular component (GO:0006928) | 1442 | 23 | 3.85 | + | 5.97 | 4.99E−09 |
| negative regulation of cell death (GO:0060548) | 902 | 19 | 2.41 | + | 7.89 | 8.14E−09 |
| regulation of inflammatory response (GO:0050727) | 306 | 13 | 0.82 | + | 15.91 | 1.17E−08 |
| positive regulation of cell adhesion (GO:0045785) | 387 | 14 | 1.03 | + | 13.55 | 1.22E−08 |
| regulation of developmental process (GO:0050793) | 2263 | 27 | 6.04 | + | 4.47 | 1.97E−08 |
| positive regulation of cell differentiation (GO:0045597) | 844 | 18 | 2.25 | + | 7.99 | 3.06E−08 |
| cellular response to lipopolysaccharide (GO:0071222) | 138 | 10 | 0.37 | + | 27.14 | 3.37E−08 |

TABLE 6V-continued

Enriched GO terms for KEGG_CYTOKINE_CYTOKINE_RECEPTOR_INTERACTION
genes in BAF180-mutant GSEA enriched vs. BAF180-mutant GSEA depleted

| | | | | | | |
|---|---|---|---|---|---|---|
| cellular response to molecule of bacterial origin (GO:0071219) | 144 | 10 | 0.38 | + | 26.01 | 5.10E−08 |
| regulation of STAT cascade (GO:1904892) | 147 | 10 | 0.39 | + | 25.48 | 6.23E−08 |
| regulation of JAK-STAT cascade (GO:0046425) | 147 | 10 | 0.39 | + | 25.48 | 6.23E−08 |
| positive regulation of tyrosine phosphorylation of Stat3 protein (GO:0042517) | 37 | 7 | 0.1 | + | 70.85 | 9.39E−08 |
| regulation of lymphocyte migration (GO:2000401) | 38 | 7 | 0.1 | + | 68.99 | 1.13E−07 |
| regulation of granulocyte chemotaxis (GO:0071622) | 39 | 7 | 0.1 | + | 67.22 | 1.35E−07 |
| single-organism process (GO:0044699) | 12622 | 55 | 33.7 | + | 1.63 | 1.40E−07 |
| monocyte chemotaxis (GO:0002548) | 40 | 7 | 0.11 | + | 65.54 | 1.61E−07 |
| response to interleukin-1 (GO:0070555) | 111 | 9 | 0.3 | + | 30.36 | 1.62E−07 |
| regulation of multicellular organismal development (GO:2000026) | 1714 | 23 | 4.58 | + | 5.03 | 1.71E−07 |
| cellular response to biotic stimulus (GO:0071216) | 164 | 10 | 0.44 | + | 22.84 | 1.80E−07 |
| positive regulation of inflammatory response (GO:0050729) | 115 | 9 | 0.31 | + | 29.31 | 2.21E−07 |
| mononuclear cell migration (GO:0071674) | 42 | 7 | 0.11 | + | 62.42 | 2.26E−07 |
| regulation of tyrosine phosphorylation of Stat3 protein (GO:0042516) | 44 | 7 | 0.12 | + | 59.58 | 3.11E−07 |
| tumor necrosis factor-mediated signaling pathway (GO:0033209) | 121 | 9 | 0.32 | + | 27.86 | 3.45E−07 |
| positive regulation of ERK1 and ERK2 cascade (GO:0070374) | 178 | 10 | 0.48 | + | 21.04 | 3.97E−07 |
| regulation of ERK1 and ERK2 cascade (GO:0070372) | 248 | 11 | 0.66 | + | 16.61 | 4.73E−07 |
| cellular response to interleukin-1 (GO:0071347) | 85 | 8 | 0.23 | + | 35.25 | 7.14E−07 |
| positive regulation of neutrophil migration (GO:1902624) | 25 | 6 | 0.07 | + | 89.88 | 7.26E−07 |
| regulation of T cell migration (GO:2000404) | 25 | 6 | 0.07 | + | 89.88 | 7.26E−07 |
| regulation of cell adhesion (GO:0030155) | 643 | 15 | 1.72 | + | 8.74 | 8.04E−07 |
| enzyme linked receptor protein signaling pathway (GO:0007167) | 706 | 15 | 1.89 | + | 7.96 | 2.90E−06 |
| regulation of neutrophil migration (GO:1902622) | 32 | 6 | 0.09 | + | 70.22 | 3.15E−06 |
| induction of positive chemotaxis (GO:0050930) | 15 | 5 | 0.04 | + | >100 | 5.69E−06 |
| regulation of response to stress (GO:0080134) | 1328 | 19 | 3.55 | + | 5.36 | 6.00E−06 |
| granulocyte chemotaxis (GO:0071621) | 69 | 7 | 0.18 | + | 37.99 | 6.90E−06 |
| multicellular organism development (GO:0007275) | 4733 | 34 | 12.64 | + | 2.69 | 8.06E−06 |
| G-protein coupled receptor signaling pathway (GO:0007186) | 1192 | 18 | 3.18 | + | 5.66 | 8.20E−06 |
| anatomical structure development (GO:0048856) | 5059 | 35 | 13.51 | + | 2.59 | 9.96E−06 |
| positive regulation of transport (GO:0051050) | 915 | 16 | 2.44 | + | 6.55 | 1.11E−05 |
| granulocyte migration (GO:0097530) | 75 | 7 | 0.2 | + | 34.95 | 1.22E−05 |
| regulation of secretion (GO:0051046) | 681 | 14 | 1.82 | + | 7.7 | 1.90E−05 |
| regulation of anatomical structure morphogenesis (GO:0022603) | 960 | 16 | 2.56 | + | 6.24 | 2.19E−05 |

TABLE 6V-continued

Enriched GO terms for KEGG_CYTOKINE_CYTOKINE_RECEPTOR_INTERACTION
genes in BAF180-mutant GSEA enriched vs. BAF180-mutant GSEA depleted

| | | | | | | |
|---|---|---|---|---|---|---|
| cellular response to growth factor stimulus (GO:0071363) | 459 | 12 | 1.23 | + | 9.79 | 2.26E−05 |
| positive regulation of T cell migration (GO:2000406) | 20 | 5 | 0.05 | + | 93.62 | 2.37E−05 |
| positive regulation of leukocyte proliferation (GO:0070665) | 138 | 8 | 0.37 | + | 21.71 | 3.09E−05 |
| system development (GO:0048731) | 4138 | 31 | 11.05 | + | 2.81 | 3.27E−05 |
| positive regulation of neutrophil chemotaxis (GO:0090023) | 22 | 5 | 0.06 | + | 85.11 | 3.81E−05 |
| single-organism developmental process (GO:0044767) | 5316 | 35 | 14.19 | + | 2.47 | 4.07E−05 |
| response to growth factor (GO:0070848) | 486 | 12 | 1.3 | + | 9.25 | 4.26E−05 |
| cell activation (GO:0001775) | 1017 | 16 | 2.72 | + | 5.89 | 4.96E−05 |
| leukocyte activation (GO:0045321) | 871 | 15 | 2.33 | + | 6.45 | 4.96E−05 |
| animal organ development (GO:0048513) | 2958 | 26 | 7.9 | + | 3.29 | 5.31E−05 |
| lymphocyte migration (GO:0072676) | 52 | 6 | 0.14 | + | 43.21 | 5.57E−05 |
| developmental process (GO:0032502) | 5402 | 35 | 14.42 | + | 2.43 | 6.39E−05 |
| negative regulation of cellular process (GO:0048523) | 4252 | 31 | 11.35 | + | 2.73 | 6.46E−05 |
| regulation of cell differentiation (GO:0045595) | 1537 | 19 | 4.1 | + | 4.63 | 6.64E−05 |
| positive regulation of granulocyte chemotaxis (GO:0071624) | 25 | 5 | 0.07 | + | 74.9 | 7.17E−05 |
| positive regulation of lymphocyte migration (GO:2000403) | 25 | 5 | 0.07 | + | 74.9 | 7.17E−05 |
| positive regulation of positive chemotaxis (GO:0050927) | 25 | 5 | 0.07 | + | 74.9 | 7.17E−05 |
| regulation of positive chemotaxis (GO:0050926) | 26 | 5 | 0.07 | + | 72.02 | 8.71E−05 |
| negative regulation of biological process (GO:0048519) | 4593 | 32 | 12.26 | + | 2.61 | 9.30E−05 |
| regulation of neutrophil chemotaxis (GO:0090022) | 27 | 5 | 0.07 | + | 69.35 | 1.05E−04 |
| regulation of primary metabolic process (GO:0080090) | 5810 | 36 | 15.51 | + | 2.32 | 1.05E−04 |
| positive regulation of cell activation (GO:0050867) | 320 | 10 | 0.85 | + | 11.7 | 1.05E−04 |
| regulation of macromolecule metabolic process (GO:0060255) | 5812 | 36 | 15.52 | + | 2.32 | 1.06E−04 |
| regulation of cellular metabolic process (GO:0031323) | 5844 | 36 | 15.6 | + | 2.31 | 1.24E−04 |
| regulation of transport (GO:0051049) | 1792 | 20 | 4.79 | + | 4.18 | 1.32E−04 |
| regulation of vasculature development (GO:1901342) | 243 | 9 | 0.65 | + | 13.87 | 1.43E−04 |
| neutrophil chemotaxis (GO:0030593) | 62 | 6 | 0.17 | + | 36.24 | 1.57E−04 |
| positive regulation of nervous system development (GO:0051962) | 454 | 11 | 1.21 | + | 9.07 | 2.43E−04 |
| neutrophil migration (GO:1990266) | 67 | 6 | 0.18 | + | 33.54 | 2.47E−04 |
| regulation of defense response (GO:0031347) | 702 | 13 | 1.87 | + | 6.94 | 2.65E−04 |
| cellular response to lipid (GO:0071396) | 458 | 11 | 1.22 | + | 8.99 | 2.66E−04 |
| single-organism cellular process (GO:0044763) | 9804 | 46 | 26.18 | + | 1.76 | 4.22E−04 |
| negative regulation of cell communication (GO:0010648) | 1193 | 16 | 3.19 | + | 5.02 | 4.59E−04 |
| regulation of protein kinase activity (GO:0045859) | 737 | 13 | 1.97 | + | 6.61 | 4.67E−04 |

TABLE 6V-continued

Enriched GO terms for KEGG_CYTOKINE_CYTOKINE_RECEPTOR_INTERACTION
genes in BAF180-mutant GSEA enriched vs. BAF180-mutant GSEA depleted

| | | | | | | |
|---|---|---|---|---|---|---|
| negative regulation of signaling (GO:0023057) | 1197 | 16 | 3.2 | + | 5.01 | 4.81E−04 |
| positive chemotaxis (GO:0050918) | 37 | 5 | 0.1 | + | 50.61 | 4.97E−04 |
| single-multicellular organism process (GO:0044707) | 5509 | 34 | 14.71 | + | 2.31 | 5.03E−04 |
| positive regulation of leukocyte differentiation (GO:1902107) | 131 | 7 | 0.35 | + | 20.01 | 5.40E−04 |
| positive regulation of lymphocyte activation (GO:0051251) | 286 | 9 | 0.76 | + | 11.78 | 5.68E−04 |
| regulation of metabolic process (GO:0019222) | 6167 | 36 | 16.47 | + | 2.19 | 5.71E−04 |
| positive regulation of mononuclear cell proliferation (GO:0032946) | 133 | 7 | 0.36 | + | 19.71 | 5.98E−04 |
| regulation of cell-cell adhesion (GO:0022407) | 390 | 10 | 1.04 | + | 9.6 | 6.61E−04 |
| regulation of leukocyte proliferation (GO:0070663) | 206 | 8 | 0.55 | + | 14.54 | 6.64E−04 |
| regulation of secretion by cell (GO:1903530) | 627 | 12 | 1.67 | + | 7.17 | 6.85E−04 |
| positive regulation of neurogenesis (GO:0050769) | 392 | 10 | 1.05 | + | 9.55 | 6.93E−04 |
| response to abiotic stimulus (GO:0009628) | 1073 | 15 | 2.87 | + | 5.24 | 7.73E−04 |
| cellular process (GO:0009987) | 14854 | 55 | 39.66 | + | 1.39 | 8.07E−04 |
| positive regulation of MAP kinase activity (GO:0043406) | 218 | 8 | 0.58 | + | 13.74 | 1.02E−03 |
| regulation of angiogenesis (GO:0045765) | 219 | 8 | 0.58 | + | 13.68 | 1.05E−03 |
| positive regulation of leukocyte activation (GO:0002696) | 311 | 9 | 0.83 | + | 10.84 | 1.15E−03 |
| regulation of kinase activity (GO:0043549) | 798 | 13 | 2.13 | + | 6.1 | 1.16E−03 |
| T cell migration (GO:0072678) | 17 | 4 | 0.05 | + | 88.12 | 1.26E−03 |
| regulation of leukocyte cell-cell adhesion (GO:1903037) | 317 | 9 | 0.85 | + | 10.63 | 1.35E−03 |
| oncostatin-M-mediated signaling pathway (GO:0038165) | 4 | 3 | 0.01 | + | >100 | 1.57E−03 |
| leukemia inhibitory factor signaling pathway (GO:0048861) | 4 | 3 | 0.01 | + | >100 | 1.57E−03 |
| dendritic cell chemotaxis (GO:0002407) | 18 | 4 | 0.05 | + | 83.22 | 1.58E−03 |
| positive regulation of pathway-restricted SMAD protein phosphorylation (GO:0010862) | 48 | 5 | 0.13 | + | 39.01 | 1.79E−03 |
| regulation of MAP kinase activity (GO:0043405) | 329 | 9 | 0.88 | + | 10.24 | 1.84E−03 |
| regulation of lymphocyte chemotaxis (GO:1901623) | 19 | 4 | 0.05 | + | 78.84 | 1.95E−03 |
| regulation of calcium ion import (GO:0090279) | 99 | 6 | 0.26 | + | 22.7 | 2.41E−03 |
| positive regulation of hemopoiesis (GO:1903708) | 164 | 7 | 0.44 | + | 15.98 | 2.43E−03 |
| regulation of biological quality (GO:0065008) | 3560 | 26 | 9.51 | + | 2.74 | 2.50E−03 |
| regulation of cytokine production (GO:0001817) | 575 | 11 | 1.54 | + | 7.16 | 2.57E−03 |
| positive regulation of calcium ion import (GO:0090280) | 52 | 5 | 0.14 | + | 36.01 | 2.64E−03 |
| positive regulation of cell development (GO:0010720) | 454 | 10 | 1.21 | + | 8.25 | 2.66E−03 |
| positive regulation of cell-cell adhesion (GO:0022409) | 248 | 8 | 0.66 | + | 12.08 | 2.69E−03 |
| positive regulation of calcium ion transport (GO:0051928) | 101 | 6 | 0.27 | + | 22.25 | 2.70E−03 |
| positive regulation of secretion (GO:0051047) | 353 | 9 | 0.94 | + | 9.55 | 3.30E−03 |
| regulation of catalytic activity (GO:0050790) | 2399 | 21 | 6.41 | + | 3.28 | 3.32E−03 |

TABLE 6V-continued

Enriched GO terms for KEGG_CYTOKINE_CYTOKINE_RECEPTOR_INTERACTION
genes in BAF180-mutant GSEA enriched vs. BAF180-mutant GSEA depleted

| | | | | | | |
|---|---|---|---|---|---|---|
| negative regulation of response to stimulus (GO:0048585) | 1385 | 16 | 3.7 | + | 4.33 | 3.48E−03 |
| positive regulation of protein kinase activity (GO:0045860) | 472 | 10 | 1.26 | + | 7.93 | 3.78E−03 |
| dendritic cell migration (GO:0036336) | 23 | 4 | 0.06 | + | 65.13 | 4.16E−03 |
| positive regulation of macromolecule biosynthetic process (GO:0010557) | 1605 | 17 | 4.29 | + | 3.97 | 4.64E−03 |
| positive regulation of cytokine production (GO:0001819) | 370 | 9 | 0.99 | + | 9.11 | 4.87E−03 |
| positive regulation of mast cell chemotaxis (GO:0060754) | 6 | 3 | 0.02 | + | >100 | 5.27E−03 |
| intracellular signal transduction (GO:0035556) | 1628 | 17 | 4.35 | + | 3.91 | 5.66E−03 |
| SMAD protein signal transduction (GO:0060395) | 61 | 5 | 0.16 | + | 30.7 | 5.77E−03 |
| regulation of pathway-restricted SMAD protein phosphorylation (GO:0060393) | 61 | 5 | 0.16 | + | 30.7 | 5.77E−03 |
| developmental process involved in reproduction (GO:0003006) | 625 | 11 | 1.67 | + | 6.59 | 5.82E−03 |
| regulation of cell activation (GO:0050865) | 506 | 10 | 1.35 | + | 7.4 | 7.07E−03 |
| positive regulation of kinase activity (GO:0033674) | 509 | 10 | 1.36 | + | 7.36 | 7.46E−03 |
| positive regulation of acute inflammatory response (GO:0002675) | 27 | 4 | 0.07 | + | 55.48 | 7.85E−03 |
| positive regulation of defense response (GO:0031349) | 393 | 9 | 1.05 | + | 8.58 | 7.99E−03 |
| regulation of mast cell chemotaxis (GO:0060753) | 7 | 3 | 0.02 | + | >100 | 8.35E−03 |
| regulation of mononuclear cell proliferation (GO:0032944) | 199 | 7 | 0.53 | + | 13.17 | 8.77E−03 |
| angiogenesis (GO:0001525) | 292 | 8 | 0.78 | + | 10.26 | 9.07E−03 |
| negative regulation of hormone secretion (GO:0046888) | 67 | 5 | 0.18 | + | 27.95 | 9.11E−03 |
| positive regulation of angiogenesis (GO:0045766) | 125 | 6 | 0.33 | + | 17.98 | 9.25E−03 |
| regulation of calcium ion transport (GO:0051924) | 201 | 7 | 0.54 | + | 13.04 | 9.37E−03 |
| regulation of protein localization (GO:0032880) | 970 | 13 | 2.59 | + | 5.02 | 1.05E−02 |
| regulation of transferase activity (GO:0051338) | 974 | 13 | 2.6 | + | 5 | 1.10E−02 |
| positive regulation of protein serine/threonine kinase activity (GO:0071902) | 300 | 8 | 0.8 | + | 9.99 | 1.11E−02 |
| positive regulation of protein localization to nucleus (GO:1900182) | 129 | 6 | 0.34 | + | 17.42 | 1.11E−02 |
| reproductive structure development (GO:0048608) | 411 | 9 | 1.1 | + | 8.2 | 1.15E−02 |
| leukocyte differentiation (GO:0002521) | 302 | 8 | 0.81 | + | 9.92 | 1.16E−02 |
| regulation of lymphocyte activation (GO:0051249) | 412 | 9 | 1.1 | + | 8.18 | 1.18E−02 |
| positive regulation of T cell activation (GO:0050870) | 209 | 7 | 0.56 | + | 12.54 | 1.21E−02 |
| positive regulation of lymphocyte proliferation (GO:0050671) | 132 | 6 | 0.35 | + | 17.02 | 1.26E−02 |
| reproductive system development (GO:0061458) | 416 | 9 | 1.11 | + | 8.1 | 1.27E−02 |
| cell-cell signaling (GO:0007267) | 1158 | 14 | 3.09 | + | 4.53 | 1.28E−02 |
| signal transduction by protein phosphorylation (GO:0023014) | 421 | 9 | 1.12 | + | 8.01 | 1.40E−02 |
| cell proliferation (GO:0008283) | 687 | 11 | 1.83 | + | 6 | 1.45E−02 |

TABLE 6V-continued

Enriched GO terms for KEGG_CYTOKINE_CYTOKINE_RECEPTOR_INTERACTION genes in BAF180-mutant GSEA enriched vs. BAF180-mutant GSEA depleted

| | | | | | | |
|---|---|---|---|---|---|---|
| positive regulation of leukocyte cell-cell adhesion (GO:1903039) | 218 | 7 | 0.58 | + | 12.03 | 1.60E−02 |
| positive regulation of biosynthetic process (GO:0009891) | 1762 | 17 | 4.7 | + | 3.61 | 1.69E−02 |
| regulation of protein localization to nucleus (GO:1900180) | 220 | 7 | 0.59 | + | 11.92 | 1.70E−02 |
| response to endogenous stimulus (GO:0009719) | 1383 | 15 | 3.69 | + | 4.06 | 1.92E−02 |
| positive regulation of vasculature development (GO:1904018) | 142 | 6 | 0.38 | + | 15.82 | 1.92E−02 |
| regulation of molecular function (GO:0065009) | 2910 | 22 | 7.77 | + | 2.83 | 1.92E−02 |
| positive regulation of secretion by cell (GO:1903532) | 324 | 8 | 0.87 | + | 9.25 | 1.95E−02 |
| positive regulation of catalytic activity (GO:0043085) | 1590 | 16 | 4.25 | + | 3.77 | 2.14E−02 |
| regulation of mononuclear cell migration (GO:0071675) | 35 | 4 | 0.09 | + | 42.8 | 2.18E−02 |
| positive regulation of ion transport (GO:0043270) | 229 | 7 | 0.61 | + | 11.45 | 2.20E−02 |
| positive regulation of cell division (GO:0051781) | 81 | 5 | 0.22 | + | 23.12 | 2.29E−02 |
| regulation of leukocyte differentiation (GO:1902105) | 240 | 7 | 0.64 | + | 10.92 | 2.99E−02 |
| positive regulation of stem cell proliferation (GO:2000648) | 38 | 4 | 0.1 | + | 39.42 | 3.01E−02 |
| regulation of protein transport (GO:0051223) | 742 | 11 | 1.98 | + | 5.55 | 3.04E−02 |
| apoptotic process (GO:0006915) | 900 | 12 | 2.4 | + | 4.99 | 3.05E−02 |
| regulation of T cell chemotaxis (GO:0010819) | 11 | 3 | 0.03 | + | >100 | 3.21E−02 |
| lymphocyte chemotaxis (GO:0048247) | 39 | 4 | 0.1 | + | 38.41 | 3.34E−02 |
| response to oxygen levels (GO:0070482) | 351 | 8 | 0.94 | + | 8.54 | 3.51E−02 |
| regulation of leukocyte activation (GO:0002694) | 472 | 9 | 1.26 | + | 7.14 | 3.54E−02 |
| regulation of protein serine/threonine kinase activity (GO:0071900) | 474 | 9 | 1.27 | + | 7.11 | 3.66E−02 |
| positive regulation of peptidyl-serine phosphorylation (GO:0033138) | 90 | 5 | 0.24 | + | 20.81 | 3.80E−02 |
| positive regulation of molecular function (GO:0044093) | 1875 | 17 | 5.01 | + | 3.4 | 3.92E−02 |
| vasculature development (GO:0001944) | 480 | 9 | 1.28 | + | 7.02 | 4.05E−02 |
| negative regulation of signal transduction (GO:0009968) | 1099 | 13 | 2.93 | + | 4.43 | 4.13E−02 |
| positive regulation of epithelial cell proliferation (GO:0050679) | 164 | 6 | 0.44 | + | 13.7 | 4.36E−02 |
| cardiovascular system development (GO:0072358) | 490 | 9 | 1.31 | + | 6.88 | 4.77E−02 |
| multicellular organismal process (GO:0032501) | 6584 | 34 | 17.58 | + | 1.93 | 4.79E−02 |
| positive regulation of cell-matrix adhesion (GO:0001954) | 43 | 4 | 0.11 | + | 34.84 | 4.89E−02 |
| negative regulation of leukocyte apoptotic process (GO:2000107) | 43 | 4 | 0.11 | + | 34.84 | 4.89E−02 |
| regulation of nervous system development (GO:0051960) | 782 | 11 | 2.09 | + | 5.27 | 4.99E−02 |

| Depleted Gene Results GO biological process complete | Homo sapiens - REFLIST (20972) | upload_1 (18) | upload_1 (expected) | upload_1 (over/under) | upload_1 (fold Enrichment) | upload_1 (P-value) |
|---|---|---|---|---|---|---|
| cell surface receptor signaling pathway (GO:0007166) | 2211 | 18 | 1.9 | + | 9.49 | 2.12E−14 |

TABLE 6V-continued

Enriched GO terms for KEGG_CYTOKINE_CYTOKINE_RECEPTOR_INTERACTION genes in BAF180-mutant GSEA enriched vs. BAF180-mutant GSEA depleted

| | | | | | | |
|---|---|---|---|---|---|---|
| cytokine-mediated signaling pathway (GO:0019221) | 466 | 12 | 0.4 | + | 30 | 1.95E−12 |
| cellular response to organic substance (GO:0071310) | 1915 | 16 | 1.64 | + | 9.73 | 2.45E−11 |
| cellular response to cytokine stimulus (GO:0071345) | 632 | 12 | 0.54 | + | 22.12 | 7.21E−11 |
| response to cytokine (GO:0034097) | 727 | 12 | 0.62 | + | 19.23 | 3.77E−10 |
| response to chemical (GO:0042221) | 3875 | 18 | 3.33 | + | 5.41 | 5.17E−10 |
| cellular response to chemical stimulus (GO:0070887) | 2347 | 16 | 2.01 | + | 7.94 | 6.08E−10 |
| response to organic substance (GO:0010033) | 2557 | 16 | 2.19 | + | 7.29 | 2.35E−09 |
| signal transduction (GO:0007165) | 4867 | 18 | 4.18 | + | 4.31 | 3.13E−08 |
| single organism signaling (GO:0044700) | 5262 | 18 | 4.52 | + | 3.99 | 1.27E−07 |
| signaling (GO:0023052) | 5266 | 18 | 4.52 | + | 3.98 | 1.29E−07 |
| cell communication (GO:0007154) | 5351 | 18 | 4.59 | + | 3.92 | 1.72E−07 |
| positive regulation of multicellular organismal process (GO:0051240) | 1425 | 12 | 1.22 | + | 9.81 | 1.00E−06 |
| cellular response to stimulus (GO:0051716) | 6168 | 18 | 5.29 | + | 3.4 | 2.22E−06 |
| regulation of multicellular organismal process (GO:0051239) | 2656 | 14 | 2.28 | + | 6.14 | 4.15E−06 |
| positive regulation of response to stimulus (GO:0048584) | 2028 | 12 | 1.74 | + | 6.89 | 5.82E−05 |
| positive regulation of cell proliferation (GO:0008284) | 847 | 9 | 0.73 | + | 12.38 | 8.18E−05 |
| response to stimulus (GO:0050896) | 7800 | 18 | 6.69 | + | 2.69 | 1.52E−04 |
| positive regulation of intracellular signal transduction (GO:1902533) | 911 | 9 | 0.78 | + | 11.51 | 1.54E−04 |
| signal transduction by protein phosphorylation (GO:0023014) | 421 | 7 | 0.36 | + | 19.37 | 2.82E−04 |
| positive regulation of signal transduction (GO:0009967) | 1433 | 10 | 1.23 | + | 8.13 | 4.77E−04 |
| positive regulation of angiogenesis (GO:0045766) | 125 | 5 | 0.11 | + | 46.6 | 4.96E−04 |
| positive regulation of response to external stimulus (GO:0032103) | 266 | 6 | 0.23 | + | 26.28 | 5.56E−04 |
| positive regulation of cellular process (GO:0048522) | 4716 | 15 | 4.05 | + | 3.71 | 6.26E−04 |
| positive regulation of vasculature development (GO:1904018) | 142 | 5 | 0.12 | + | 41.03 | 9.29E−04 |
| regulation of cell proliferation (GO:0042127) | 1538 | 10 | 1.32 | + | 7.58 | 9.31E−04 |
| positive regulation of cell communication (GO:0010647) | 1552 | 10 | 1.33 | + | 7.51 | 1.01E−03 |
| positive regulation of signaling (GO:0023056) | 1560 | 10 | 1.34 | + | 7.47 | 1.06E−03 |
| positive regulation of developmental process (GO:0051094) | 1179 | 9 | 1.01 | + | 8.89 | 1.40E−03 |
| regulation of multicellular organismal development (GO:2000026) | 1714 | 10 | 1.47 | + | 6.8 | 2.58E−03 |
| positive regulation of macromolecule metabolic process (GO:0010604) | 2841 | 12 | 2.44 | + | 4.92 | 2.61E−03 |
| regulation of tissue remodeling (GO:0034103) | 68 | 4 | 0.06 | + | 68.54 | 2.68E−03 |
| positive regulation of protein phosphorylation (GO:0001934) | 895 | 8 | 0.77 | + | 10.41 | 2.69E−03 |
| regulation of intracellular signal transduction (GO:1902531) | 1725 | 10 | 1.48 | + | 6.75 | 2.74E−03 |
| positive regulation of endothelial cell proliferation (GO:0001938) | 69 | 4 | 0.06 | + | 67.54 | 2.84E−03 |
| regulation of developmental process (GO:0050793) | 2263 | 11 | 1.94 | + | 5.66 | 2.91E−03 |
| positive regulation of biological process (GO:0048518) | 5270 | 15 | 4.52 | + | 3.32 | 3.01E−03 |
| positive regulation of phosphorylation (GO:0042327) | 937 | 8 | 0.8 | + | 9.95 | 3.80E−03 |
| positive regulation of cytokine production (GO:0001819) | 370 | 6 | 0.32 | + | 18.89 | 3.83E−03 |
| regulation of response to stimulus (GO:0048583) | 3696 | 13 | 3.17 | + | 4.1 | 4.56E−03 |
| regulation of anatomical structure morphogenesis (GO:0022603) | 960 | 8 | 0.82 | + | 9.71 | 4.57E−03 |
| protein phosphorylation (GO:0006468) | 972 | 8 | 0.83 | + | 9.59 | 5.02E−03 |
| positive regulation of metabolic process (GO:0009893) | 3033 | 12 | 2.6 | + | 4.61 | 5.41E−03 |

TABLE 6V-continued

Enriched GO terms for KEGG_CYTOKINE_CYTOKINE_RECEPTOR_INTERACTION genes in BAF180-mutant GSEA enriched vs. BAF180-mutant GSEA depleted

| | | | | | | |
|---|---|---|---|---|---|---|
| regulation of programmed cell death (GO:0043067) | 1421 | 9 | 1.22 | + | 7.38 | 6.83E−03 |
| regulation of angiogenesis (GO:0045765) | 219 | 5 | 0.19 | + | 26.6 | 7.79E−03 |
| enzyme linked receptor protein signaling pathway (GO:0007167) | 706 | 7 | 0.61 | + | 11.55 | 9.21E−03 |
| positive regulation of phosphorus metabolic process (GO:0010562) | 1056 | 8 | 0.91 | + | 8.83 | 9.40E−03 |
| positive regulation of phosphate metabolic process (GO:0045937) | 1056 | 8 | 0.91 | + | 8.83 | 9.40E−03 |
| regulation of response to external stimulus (GO:0032101) | 712 | 7 | 0.61 | + | 11.45 | 9.75E−03 |
| regulation of cell death (GO:0010941) | 1522 | 9 | 1.31 | + | 6.89 | 1.22E−02 |
| positive regulation of protein metabolic process (GO:0051247) | 1527 | 9 | 1.31 | + | 6.87 | 1.25E−02 |
| regulation of endothelial cell proliferation (GO:0001936) | 101 | 4 | 0.09 | + | 46.14 | 1.28E−02 |
| regulation of vasculature development (GO:1901342) | 243 | 5 | 0.21 | + | 23.97 | 1.29E−02 |
| positive regulation of vascular endothelial growth factor production (GO:0010575) | 27 | 3 | 0.02 | + | >100 | 1.41E−02 |
| positive regulation of protein modification process (GO:0031401) | 1150 | 8 | 0.99 | + | 8.11 | 1.78E−02 |
| regulation of signal transduction (GO:0009966) | 2752 | 11 | 2.36 | + | 4.66 | 2.12E−02 |
| regulation of vascular endothelial growth factor production (GO:0010574) | 31 | 3 | 0.03 | + | >100 | 2.13E−02 |
| regulation of endothelial cell migration (GO:0010594) | 115 | 4 | 0.1 | + | 40.53 | 2.13E−02 |
| negative regulation of programmed cell death (GO:0043069) | 829 | 7 | 0.71 | + | 9.84 | 2.68E−02 |
| regulation of cellular process (GO:0050794) | 10399 | 18 | 8.93 | + | 2.02 | 2.69E−02 |
| positive regulation of lymphocyte activation (GO:0051251) | 286 | 5 | 0.25 | + | 20.37 | 2.86E−02 |
| positive regulation of cell differentiation (GO:0045597) | 844 | 7 | 0.72 | + | 9.66 | 3.01E−02 |
| angiogenesis (GO:0001525) | 292 | 5 | 0.25 | + | 19.95 | 3.16E−02 |
| positive chemotaxis (GO:0050918) | 37 | 3 | 0.03 | + | 94.47 | 3.60E−02 |
| positive regulation of lymphocyte proliferation (GO:0050671) | 132 | 4 | 0.11 | + | 35.31 | 3.67E−02 |
| positive regulation of mononuclear cell proliferation (GO:0032946) | 133 | 4 | 0.11 | + | 35.04 | 3.78E−02 |
| phosphorylation (GO:0016310) | 1290 | 8 | 1.11 | + | 7.23 | 4.20E−02 |
| positive regulation of leukocyte activation (GO:0002696) | 311 | 5 | 0.27 | + | 18.73 | 4.29E−02 |
| positive regulation of leukocyte proliferation (GO:0070665) | 138 | 4 | 0.12 | + | 33.77 | 4.37E−02 |
| regulation of protein phosphorylation (GO:0001932) | 1302 | 8 | 1.12 | + | 7.16 | 4.50E−02 |
| negative regulation of cell death (GO:0060548) | 902 | 7 | 0.77 | + | 9.04 | 4.67E−02 |
| regulation of cytokine production (GO:0001817) | 575 | 6 | 0.49 | + | 12.16 | 4.87E−02 |
| positive regulation of cell activation (GO:0050867) | 320 | 5 | 0.27 | + | 18.2 | 4.92E−02 |

Enriched genes = GSEA core enrichment (i.e. top ranked genes until running enrichment score hits peak)
Depleted genes = GSEA most negatively ranked genes (i.e. bottom ranked genes until running enrichment score hits trough)

TABLE 6W

GSEA results for gene sets enriched in pre-treatment patient tumors with truncating mutations in PBRM1

| NAME | SIZE | ES | NES | NOM p-val |
|---|---|---|---|---|
| HALLMARK_COAGULATION | 135 | 0.4634537 | 2.5861373 | 0 |
| HALLMARK_EPITHELIAL_MESENCHYMAL_TRANSITION | 198 | 0.3778765 | 2.2784488 | 0 |
| HALLMARK_TNFA_SIGNALING_VIA_NFKB | 199 | 0.36042312 | 2.161199 | 0 |
| HALLMARK_HYPOXIA | 198 | 0.36123425 | 2.1341348 | 0 |
| HALLMARK_INTERFERON_ALPHA_RESPONSE | 93 | 0.38837415 | 2.0058413 | 0 |
| HALLMARK_BILE_ACID_METABOLISM | 112 | 0.367774 | 1.9837768 | 0 |
| HALLMARK_XENOBIOTIC_METABOLISM | 199 | 0.30432338 | 1.8260752 | 0 |
| HALLMARK_ANGIOGENESIS | 36 | 0.43100646 | 1.7682568 | 0.005780347 |
| HALLMARK_INTERFERON_GAMMA_RESPONSE | 191 | 0.2959238 | 1.7434925 | 0 |
| HALLMARK_INFLAMMATORY_RESPONSE | 199 | 0.28598273 | 1.6895322 | 0 |

TABLE 6W-continued

GSEA results for gene sets enriched in pre-treatment patient tumors with truncating mutations in PBRM1

| | | | | |
|---|---|---|---|---|
| HALLMARK_GLYCOLYSIS | 199 | 0.27468395 | 1.6470891 | 0 |
| HALLMARK_IL6_JAK_STAT3_SIGNALING | 87 | 0.3154689 | 1.6223565 | 0 |
| HALLMARK_NOTCH_SIGNALING | 32 | 0.37784022 | 1.5690641 | 0.026548672 |
| HALLMARK_P53_PATHWAY | 200 | 0.26244697 | 1.5487176 | 0 |
| HALLMARK_APOPTOSIS | 160 | 0.26717153 | 1.5470705 | 0.004237288 |
| HALLMARK_IL2_STAT5_SIGNALING | 199 | 0.2597181 | 1.5294203 | 0.005555556 |
| HALLMARK_APICAL_JUNCTION | 198 | 0.25475252 | 1.5265775 | 0 |
| HALLMARK_MYOGENESIS | 200 | 0.25268936 | 1.5108361 | 0 |
| HALLMARK_UV_RESPONSE_DN | 144 | 0.25802347 | 1.4569446 | 0 |
| HALLMARK_ESTROGEN_RESPONSE_EARLY | 200 | 0.23530972 | 1.4246706 | 0 |
| HALLMARK_WNT_BETA_CATENIN_SIGNALING | 42 | 0.32717755 | 1.4034909 | 0.05732484 |
| HALLMARK_HEDGEHOG_SIGNALING | 35 | 0.32948953 | 1.3634391 | 0.0882353 |
| HALLMARK_ADIPOGENESIS | 196 | 0.22999962 | 1.3584664 | 0.005376344 |
| HALLMARK_CHOLESTEROL_HOMEOSTASIS | 73 | 0.26637354 | 1.3271515 | 0.068100356 |
| HALLMARK_REACTIVE_OXIGEN_SPECIES_PATHWAY | 47 | 0.29103118 | 1.3039039 | 0.08430233 |
| HALLMARK_APICAL_SURFACE | 44 | 0.29906154 | 1.3030225 | 0.10119048 |
| HALLMARK_TGF_BETA_SIGNALING | 54 | 0.25017482 | 1.1652176 | 0.221875 |
| HALLMARK_HEME_METABOLISM | 196 | 0.19430974 | 1.1569836 | 0.12953368 |
| HALLMARK_PANCREAS_BETA_CELLS | 38 | 0.26110435 | 1.1266103 | 0.2633229 |
| HALLMARK_FATTY_ACID_METABOLISM | 158 | 0.18055953 | 1.0471649 | 0.3488372 |
| HALLMARK_COMPLEMENT | 196 | 0.16831398 | 1.003772 | 0.46195653 |
| HALLMARK_UV_RESPONSE_UP | 154 | 0.17562571 | 0.9861503 | 0.5320197 |
| HALLMARK_KRAS_SIGNALING_DN | 193 | 0.1584056 | 0.9371324 | 0.6514286 |
| HALLMARK_ANDROGEN_RESPONSE | 99 | 0.1555059 | 0.82283705 | 0.875502 |

| NAME | FDR q-val | FWER p-val | RANK AT MAX | LEADING EDGE |
|---|---|---|---|---|
| HALLMARK_COAGULATION | 0 | 0 | 8963 | tags = 52%, list = 25%, signal = 69% |
| HALLMARK_EPITHELIAL_MESENCHYMAL_TRANSITION | 0 | 0 | 8606 | tags = 40%, list = 24%, signal = 52% |
| HALLMARK_TNFA_SIGNALING_VIA_NFKB | 0 | 0 | 9110 | tags = 40%, list = 25%, signal = 54% |
| HALLMARK_HYPOXIA | 0 | 0 | 8749 | tags = 43%, list = 24%, signal = 56% |
| HALLMARK_INTERFERON_ALPHA_RESPONSE | 0 | 0 | 9091 | tags = 39%, list = 25%, signal = 52% |
| HALLMARK_BILE_ACID_METABOLISM | 0 | 0 | 8471 | tags = 45%, list = 24%, signal = 58% |
| HALLMARK_XENOBIOTIC_METABOLISM | 0.003440355 | 0.007 | 8951 | tags = 42%, list = 25%, signal = 56% |
| HALLMARK_ANGIOGENESIS | 0.005257009 | 0.014 | 8454 | tags = 42%, list = 24%, signal = 54% |
| HALLMARK_INTERFERON_GAMMA_RESPONSE | 0.004942737 | 0.015 | 9079 | tags = 33%, list = 25%, signal = 44% |
| HALLMARK_INFLAMMATORY_RESPONSE | 0.00758099 | 0.027 | 2626 | tags = 16%, list = 7%, signal = 17% |
| HALLMARK_GLYCOLYSIS | 0.009826244 | 0.038 | 8344 | tags = 36%, list = 23%, signal = 46% |
| HALLMARK_IL6_JAK_STAT3_SIGNALING | 0.0129132 | 0.054 | 9009 | tags = 39%, list = 25%, signal = 52% |
| HALLMARK_NOTCH_SIGNALING | 0.018096626 | 0.079 | 7666 | tags = 34%, list = 21%, signal = 44% |
| HALLMARK_P53_PATHWAY | 0.01899984 | 0.09 | 8833 | tags = 32%, list = 25%, signal = 42% |
| HALLMARK_APOPTOSIS | 0.017733185 | 0.09 | 9110 | tags = 34%, list = 25%, signal = 45% |
| HALLMARK_IL2_STAT5_SIGNALING | 0.018474342 | 0.1 | 8984 | tags = 31%, list = 25%, signal = 41% |

TABLE 6W-continued

GSEA results for gene sets enriched in pre-treatment patient tumors with truncating mutations in PBRM1

| | | | | |
|---|---|---|---|---|
| HALLMARK_APICAL_JUNCTION | 0.017752696 | 0.102 | 7994 | tags = 28%, list = 22%, signal = 36% |
| HALLMARK_MYOGENESIS | 0.018697744 | 0.11 | 8694 | tags = 33%, list = 24%, signal = 43% |
| HALLMARK_UV_RESPONSE_DN | 0.026672224 | 0.166 | 8559 | tags = 35%, list = 24%, signal = 45% |
| HALLMARK_ESTROGEN_RESPONSE_EARLY | 0.032439258 | 0.206 | 7210 | tags = 28%, list = 20%, signal = 34% |
| HALLMARK_WNT_BETA_CATENIN_SIGNALING | 0.038341142 | 0.249 | 2943 | tags = 19%, list = 8%, signal = 21% |
| HALLMARK_HEDGEHOG_SIGNALING | 0.048595615 | 0.306 | 8388 | tags = 43%, list = 23%, signal = 56% |
| HALLMARK_ADIPOGENESIS | 0.048597757 | 0.316 | 3003 | tags = 16%, list = 8%, signal = 18% |
| HALLMARK_CHOLESTEROL_HOMEOSTASIS | 0.059607573 | 0.383 | 11878 | tags = 49%, list = 33%, signal = 74% |
| HALLMARK_REACTIVE_OXIGEN_SPECIES_PATHWAY | 0.06951901 | 0.444 | 6860 | tags = 28%, list = 19%, signal = 34% |
| HALLMARK_APICAL_SURFACE | 0.06738169 | 0.446 | 2182 | tags = 18%, list = 6%, signal = 19% |
| HALLMARK_TGF_BETA_SIGNALING | 0.1953661 | 0.862 | 7986 | tags = 33%, list = 22%, signal = 43% |
| HALLMARK_HEME_METABOLISM | 0.20019072 | 0.876 | 7877 | tags = 27%, list = 22%, signal = 34% |
| HALLMARK_PANCREAS_BETA_CELLS | 0.23912823 | 0.926 | 2627 | tags = 16%, list = 7%, signal = 17% |
| HALLMARK_FATTY_ACID_METABOLISM | 0.3891211 | 0.988 | 8803 | tags = 35%, list = 25%, signal = 46% |
| HALLMARK_COMPLEMENT | 0.48644838 | 0.995 | 8674 | tags = 28%, list = 24%, signal = 37% |
| HALLMARK_UV_RESPONSE_UP | 0.51797897 | 0.997 | 7933 | tags = 28%, list = 22%, signal = 36% |
| HALLMARK_KRAS_SIGNALING_DN | 0.6393933 | 1 | 3260 | tags = 13%, list = 9%, signal = 15% |
| HALLMARK_ANDROGEN_RESPONSE | 0.8739106 | 1 | 8780 | tags = 27%, list = 24%, signal = 36% |

TABLE 6X

GSEA results for gene sets enriched in pre-treatment patient tumors wildtype at PBRM1

| NAME | SIZE | ES | NES | NOM p-val |
|---|---|---|---|---|
| HALLMARK_E2F_TARGETS | 199 | −0.5751047 | −2.9363213 | 0 |
| HALLMARK_G2M_CHECKPOINT | 199 | −0.5301613 | −2.7069154 | 0 |
| HALLMARK_MYC_TARGETS_V1 | 199 | −0.45365316 | −2.341999 | 0 |
| HALLMARK_OXIDATIVE_PHOSPHORYLATION | 199 | −0.40938506 | −2.0984013 | 0 |
| HALLMARK_MYC_TARGETS_V2 | 58 | −0.46636462 | −1.9861294 | 0 |
| HALLMARK_SPERMATOGENESIS | 128 | −0.38931966 | −1.8766787 | 0 |
| HALLMARK_MITOTIC_SPINDLE | 199 | −0.29650635 | −1.5328054 | 0.003663004 |

TABLE 6X-continued

GSEA results for gene sets enriched in pre-treatment patient tumors wildtype at PBRM1

| | | | | |
|---|---|---|---|---|
| HALLMARK_DNA_REPAIR | 143 | −0.29704157 | −1.4623376 | 0.01142132 |
| HALLMARK_UNFOLDED_PROTEIN_RESPONSE | | −0.26182294 | −1.2473699 | 0.11416781 |
| HALLMARK_PROTEIN_SECRETION | 96 | −0.25048777 | −1.146313 | 0.24350205 |
| HALLMARK_MTORC1_SIGNALING | 199 | −0.20546418 | −1.0482782 | 0.35511714 |
| HALLMARK_PI3K_AKT_MTOR_SIGNALING | 105 | −0.17890021 | −0.8406621 | 0.7732096 |
| HALLMARK_ESTROGEN_RESPONSE_LATE | 199 | −0.15607864 | −0.79631424 | 0.880579 |
| HALLMARK_PEROXISOME | 103 | −0.16189572 | −0.75051486 | 0.9175978 |
| HALLMARK_KRAS_SIGNALING_UP | 198 | −0.13005705 | −0.66694486 | 0.996319 |
| HALLMARK_ALLOGRAFT_REJECTION | 190 | −0.12697595 | −0.64140904 | 0.99506783 |

| NAME | FDR q-val | FWER p-val | RANK AT MAX | LEADING EDGE |
|---|---|---|---|---|
| HALLMARK_E2F_TARGETS | 0 | 0 | 11706 | tags = 68%, list = 33%, signal = 100% |
| HALLMARK_G2M_CHECKPOINT | 0 | 0 | 8556 | tags = 51%, list = 24%, signal = 66% |
| HALLMARK_MYC_TARGETS_V1 | 0 | 0 | 10841 | tags = 54%, list = 30%, signal = 77% |
| HALLMARK_OXIDATIVE_PHOSPHORYLATION | 0 | 0 | 9234 | tags = 44%, list = 26%, signal = 59% |
| HALLMARK_MYC_TARGETS_V2 | 1.10E−04 | 0.001 | 5817 | tags = 34%, list = 16%, signal = 41% |
| HALLMARK_SPERMATOGENESIS | 3.85E−04 | 0.005 | 5701 | tags = 33%, list = 16%, signal = 39% |
| HALLMARK_MITOTIC_SPINDLE | 0.016991025 | 0.247 | 5950 | tags = 25%, list = 17%, signal = 29% |
| HALLMARK_DNA_REPAIR | 0.032129228 | 0.457 | 11381 | tags = 41%, list = 32%, signal = 59% |
| HALLMARK_UNFOLDED_PROTEIN_RESPONSE | 0.18768412 | 0.985 | 12007 | tags = 40%, list = 33%, signal = 60% |
| HALLMARK_PROTEIN_SECRETION | 0.33950403 | 1 | 10093 | tags = 30%, list = 28%, signal = 42% |
| HALLMARK_MTORC1_SIGNALING | 0.53724766 | 1 | 12410 | tags = 38%, list = 35%, signal = 57% |
| HALLMARK_PI3K_AKT_MTOR_SIGNALING | 1 | 1 | 10551 | tags = 30%, list = 29%, signal = 42% |
| HALLMARK_ESTROGEN_RESPONSE_LATE | 1 | 1 | 3036 | tags = 12%, list = 8%, signal = 13% |
| HALLMARK_PEROXISOME | 1 | 1 | 4726 | tags = 15%, list = 13%, signal = 17% |
| HALLMARK_KRAS_SIGNALING_UP | 1 | 1 | 3127 | tags = 9%, list = 9%, signal = 10% |
| HALLMARK_ALLOGRAFT_REJECTION | 0.9873257 | 1 | 10584 | tags = 28%, list = 29%, signal = 39% |

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web and/or the National Center for Biotechnology Information (NCBI) on the world wide web.

EQUIVALENTS

Those skilled in the art will recognize, or be able to ascertain using no more than routine experimentation, many equivalents to the specific embodiments of the present invention described herein. Such equivalents are intended to be encompassed by the following claims.

What is claimed is:

1. A method of treating a cancer in a subject likely to be responsive to an immune checkpoint therapy, wherein the immune checkpoint therapy comprises nivolumab, the method comprising
   i) selecting the subject, the subject having been identified according to:
   a) obtaining or providing a subject sample from a patient having cancer;
   b) measuring the amount or activity of PBRM1 in the subject sample; and
   c) comparing the amount or activity of PBRM1 in a control sample,
   wherein the absence of or a significantly decreased amount or activity of PBRM1 in the subject sample and/or the presence of or a significantly increased amount or activity of PBRM1 having a loss of function mutation in the subject sample, relative to the control sample identified the cancer as being likely to be responsive to the immune checkpoint therapy; and
   ii) administering the immune checkpoint therapy to the selected subject.

2. The method of claim 1, wherein the control sample is determined from a cancerous or non-cancerous sample from either the patient or a member of the same species to which the patient belongs, optionally wherein the control sample is a cancerous or non-cancerous sample from the patient obtained from an earlier point in time than the patient sample, optionally wherein the control sample is obtained before the patient has received immune checkpoint therapy and the patient sample is obtained after the patient has received immune checkpoint therapy.

3. The method of claim 1, wherein the control sample comprises cells or does not comprise cells.

4. The method of claim 1, wherein the control sample comprises cancer cells known to be responsive or non-responsive to the immune checkpoint therapy.

5. The method of claim 1, wherein
a) the subject sample and/or the control sample has not been contacted with a renal cell cancer treatment or inhibitor of an immune checkpoint;
b) the subject has not been administered a renal cell cancer treatment or inhibitor of an immune checkpoint; and/or
c) the subject sample is selected from the group consisting of serum, whole blood, plasma, urine, cells, cell lines, and biopsies.

6. The method of claim 1, further comprising recommending, prescribing, or administering at least one additional anti-cancer therapeutic agent, optionally wherein the at least one additional anti-cancer therapeutic agent is nivolumab and/or an anti-PBRM-1 therapeutic agent.

7. The method of claim 1, wherein the amount of PBRM1 is detected using a reagent which specifically binds with PBRM1 protein, optionally wherein the reagent is selected from the group consisting of an antibody, an antibody derivative, and an antibody fragment.

8. The method of claim 1, wherein the amount of PBRM1 is assessed by detecting the presence in the sample of a transcribed polynucleotide or portion thereof, optionally wherein
a) the transcribed polynucleotide is an mRNA or a cDNA;
b) the step of detecting further comprises amplifying the transcribed polynucleotide; and/or
c) the transcribed polynucleotide is detected by identifying a nucleic acid that anneals with PBRM1 nucleic acid, or a portion thereof, under stringent hybridization conditions.

9. The method of claim 1, wherein the likelihood of the cancer in the subject to be responsive to immune checkpoint therapy is the likelihood of at least one criteria selected from the group consisting of cellular proliferation, tumor burden, m-stage, metastasis, progressive disease, clinical benefit rate, survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria.

10. The method of claim 1, wherein the cancer is a solid tumor.

11. The method of claim 1, wherein the cancer is a renal cell cancer, optionally wherein the renal cell cancer is a clear cell renal cell cancer (ccRcc) and/or metastatic clear cell renal cell carcinoma (mRCC).

12. The method of claim 1, wherein the subject is a mammal, optionally wherein the mammal is an animal model of cancer, or a human.

* * * * *

SEQUENCE LISTING

<160> NUMBER OF SEQ ID NOS: 16

<210> SEQ ID NO 1
<211> LENGTH: 7592
<212> TYPE: DNA
<213> ORGANISM: Homo sapiens

<400> SEQUENCE: 1

| | | | | | | |
|---|---|---|---|---|---|---|
| gcggccgcgg | ccggaggagc | aatagcagca | gccgtggcgg | ccacggggcg | gggcgcggcg | 60 |
| gtcggtgacc | gcggccgggg | ctgcaggcgg | cggagcggct | ggaagttgga | ttccatgggt | 120 |
| tccaagagaa | gaagagctac | ctccccttcc | agcagtgtca | gcgggtactt | tgatgatggg | 180 |
| caccattctg | tgtcaacacc | aggcccaagc | aggaaaagga | ggagactttc | caatcttcca | 240 |
| actgtagatc | ctattgccgt | gtgccatgaa | ctctataata | ccatccgaga | ctataaggat | 300 |
| gaacagggca | gacttctctg | tgagctcttc | attgggcac | caaagcgaag | aaatcaacca | 360 |
| gactattatg | aagtggtttc | tcagcccatt | gacttgatga | aaatccaaca | gaaactaaaa | 420 |
| atggaagagt | atgatgatgt | taatttgctg | actgctgact | tccagcttct | ttttaacaat | 480 |
| gcaaagtcct | attataagcc | agattctcct | gaatataaag | ccgcttgcaa | actctgggat | 540 |
| ttgtaccttc | gaacaagaaa | tgagtttgtt | cagaaaggag | aagcagatga | cgaagatgat | 600 |
| gatgaagatg | ggcaagacaa | tcagggcaca | gtgactgaag | gatcttctcc | agcttacttg | 660 |
| aaggagatcc | tggagcagct | tcttgaagcc | atagttgtag | ctacaaatcc | atcaggacgt | 720 |
| ctcattagcg | aacttttca | gaaactgcct | tctaaagtgc | aatatccaga | ttattatgca | 780 |
| ataattaagg | agcctataga | tctcaagacc | attgcccaga | ggatacagaa | tggaagctac | 840 |
| aaaagtattc | atgcaatggc | caagatata | gatctcctcg | caaaaaatgc | caaaacttat | 900 |
| aatgagcctg | gctctcaagt | attcaaggat | gcaaattcaa | ttaaaaaaat | attttatatg | 960 |
| aaaaaggctg | aaattgaaca | tcatgaaatg | gctaagtcaa | gtcttcgaat | gaggactcca | 1020 |
| tccaacttgg | ctgcagccag | actgacaggt | ccttcacaca | gtaaaggcag | ccttggtgaa | 1080 |
| gagagaaatc | ccactagcaa | gtattaccgt | aataaaagag | cagtacaagg | aggtcgttta | 1140 |
| tcagcaatta | caatggcact | tcaatatggc | tcagaaagtg | aagaagatgc | tgctttagct | 1200 |
| gctgcacgct | atgaagaggg | agagtcgaaa | gcagaaagca | tcacttcctt | tatgatgtt | 1260 |
| tcaaatcctt | tttatcagct | ttatgacaca | gttaggagtt | gtcggaataa | ccaagggcag | 1320 |
| ctaatagctg | aaccttttta | ccatttgcct | tcaaagaaaa | aatacctga | ttattaccag | 1380 |
| caaattaaaa | tgcccatatc | actacaacag | atccgaacaa | aactgaagaa | tcaagaatat | 1440 |
| gaaactttag | atcatttgga | gtgtgatctg | aatttaatgt | ttgaaaatgc | caaacgctat | 1500 |
| aatgtgccca | attcagccat | ctacaagcga | gttctaaaat | tgcagcaagt | tatgcaggca | 1560 |
| aagaagaaag | agcttgccag | gagagacgat | atcgaggacg | gagacagcat | gatctcttca | 1620 |
| gccacctctg | atactggtag | tgccaaaaga | aaaagtaaaa | agaacataag | aaagcagcga | 1680 |
| atgaaaatct | tattcaatgt | tgttcttgaa | gctcgagagc | caggttcagg | cagaagactt | 1740 |
| tgtgacctat | ttatggttaa | accatccaaa | aaggactatc | ctgattatta | taaaatcatc | 1800 |
| ttggagccaa | tggacttgaa | aataattgag | cataacatcc | gcaatgacaa | atatgctggt | 1860 |
| gaagagggaa | tgatagaaga | catgaagctg | atgttccgga | atgccaggca | ctataatgag | 1920 |
| gagggctccc | aggtttataa | tgatgcacat | atcctggaga | agttactcaa | ggagaaaagg | 1980 |
| aaagagctgg | gccactgcc | tgatgatgat | gacatggctt | ctcccaaact | caagctgagt | 2040 |
| aggaagagtg | gcatttctcc | taaaaaatca | aaatacatga | ctccaatgca | gcagaaacta | 2100 |

```
aatgaggtct atgaagctgt aaagaactat actgataaga ggggtcgccg cctcagtgcc    2160
atatttctga ggcttccctc tagatctgag ttgcctgact actatctgac tattaaaaag    2220
cccatggaca tggaaaaaat tcgaagtcac atgatggcca acaagtacca agatattgac    2280
tctatggttg aggactttgt catgatgttt aataatgcct gtacatacaa tgagccggag    2340
tctttgatct acaaagatgc tcttgttcta cacaaagtcc tgcttgaaac acgcagagac    2400
ctggagggag atgaggactc tcatgtccca aatgtgactt tgctgattca agagcttatc    2460
cacaatcttt ttgtgtcagt catgagtcat caggatgatg agggaagatg ctacagcgat    2520
tctttagcag aaattcctgc tgtggatccc aactttccta acaaaccacc ccttacattt    2580
gacataatta ggaagaatgt tgaaaataat cgctaccgtc ggcttgattt atttcaagag    2640
catatgtttg aagtattgga acgagcaaga aggatgaatc ggacagattc agaaatatat    2700
gaagatgcag tagaacttca gcagtttttt attaaaattc gtgatgaact ctgcaaaaat    2760
ggagagattc ttcttccacc ggcactcagc tataccacaa acatttgca taatgatgtg     2820 gagaaagaga gaaggaaaa attgccaaaa gaaatagagg aagataaact aaaacgagaa     2880
gaagaaaaaa gagaagctga aaagagtgaa gattcctctg gtgctgcagg cctctcaggc    2940
ttacatcgca catacagcca ggactgtagc tttaaaaaca gcatgtacca tgttggagat    3000
tacgtctatg tggaacctgc agaggccaac ctacaaccac atatcgtctg tattgaaaga    3060
ctgtgggagg attcagctga aaaagaagtt tttaagagtg actattacaa caaagttcca    3120
gttagtaaaa ttctaggcaa gtgtgtggtc atgtttgtca aggaatactt taagttatgc    3180
ccagaaaact tccgagatga ggatgttttt gtctgtgaat cacggtattc tgccaaaacc    3240
aaatctttta agaaaattaa actgtggacc atgcccatca gctcagtcag gtttgtccct    3300
cgggatgtgc ctctgcctgt ggttcgcgtg gcctctgtat ttgcaaatgc agataaaggt    3360
gatgatgaga agaatacaga caactcagag gacagtcgag ctgaagacaa ttttaacttg    3420
gaaaaggaaa aagaagatgt ccctgtggaa atgtccaatg gtgaaccagg ttgccactac    3480
tttgagcagc tccattacaa tgacatgtgg ctgaaggttg gcgactgtgt cttcatcaag    3540
tcccatggcc tggtgcgtcc tcgtgtgggc agaattgaaa agtatgggt tcgagatgga    3600 gctgcatatt tttatggccc catcttcatt cacccagaag aaacagagca tgagcccaca    3660
aaaatgttct acaaaaaaga agtatttctg agtaatctgg aagaaacctg ccccatgaca    3720
tgtattctcg gaaagtgtgc tgtgttgtca ttcaaggact tcctctcctg caggccaact    3780
gaaataccag aaaatgacat tctgctttgt gagagccgct acaatgagag cgacaagcag    3840
atgaagaaat tcaaaggatt gaagaggttt tcactctctg ctaaagtggt agatgatgaa    3900
atttactact tcagaaaacc aattgttcct cagaaggagc catcacccttt gctggaaaag    3960 aagatccagt tgctagaagc taaatttgcc gagttagaag gtggagatga tgatattgaa    4020
gagatgggag aagaagatag tgagtctacc ccaaagtctg ccaaaggcag tgcaaagaag    4080
gaaggctcca acggaaaat caacatgagt ggctacatcc tgttcagcag tgagatgagg    4140
gctgtgatta aggcccaaca cccagactac tctttcgggg agctcagccg cctggtgggg    4200
acagaatgga gaaatcttga dacagccaag aaagcagaat atgaaggcat gatgggtggc    4260
tatccgccag gccttccacc tttgcagggc ccagttgatg gccttgttag catgggcagc    4320
atgcagccac ttcaccctgg ggggcctcca ccccaccatc ttccgccagg tgtgcctggc    4380
ctcccgggca tcccaccacc gggtgtgatg aaccaaggag tggcccctat ggtagggact    4440
```

```
ccagcaccag gtggaagtcc atatggacaa caggtgggag ttttgggggcc tccagggcag    4500 caggcaccac ctccatatcc cggcccacat ccagctggac ccctgtcat acagcagcca     4560 acaacaccca tgtttgtagc tcccccacca aagacccagc ggcttcttca ctcagaggcc    4620
tacctgaaat acattgaagg actcagtgcg gagtccaaca gcattagcaa gtgggatcag    4680
acactggcag ctcgaagacg cgacgtccat tgtcgaaag aacaggagag ccgcctaccc    4740
tctcactggc tgaaaagcaa aggggccac accaccatgg cagatgccct ctggcgcctt    4800
cgagatttga tgctccggga caccctcaac attcgccaag catacaacct agaaaatgtt    4860
taatcacatc attacgtttc ttttatatag aagcataaag agttgtggat cagtagccat    4920
tttagttact gggggtgggg ggaaggaaca aaggaggata attttttattg cattttactg    4980 tacatcacaa ggccattttt atatacggac acttttaata agctatttca atttgtttgt    5040
tatattaagt tgactttatc aaatacacaa agattttttt gcatatgttt ccttcgttta    5100
aaaccagttt cataattggt tgtatatgta gacttggagt tttatctttt tacttgttgc    5160
catggaactg aaaccattag aggttttgt cttggcttgg ggtttttgtt ttcttggttt    5220 tgggttttttt tatatatata tataaaagaa caaaatgaaa aaaaacacac acacacaaga    5280
gtttacagat tagtttaaat tgataatgaa atgtgaagtt tgtcctagtt tacatcttag    5340 agagggagt atacttgtgt ttgtttcatg tgcctgaata tcttaagcca ctttctgcaa    5400
aagctgtttc ttacagatga agtgcttct ttgaaaggtg gttatttagg ttttagatgt    5460
ttaatagaca cagcacattt gctctattaa ctcagaggct cactacagaa atatgtaatc    5520
agtgctgtgc atctgtctgc agctaatgta cctcctggac accaggaggg gaaaaagcac    5580
tttttcaatt gtgctgagtt agacatctgt gagttagact atggtgtcag tgattttttgc    5640 agaacacgtg cacaaccctg aggtatgttt aatctaggca ggtacgttta aggatatttt    5700
gatctattta taatgaattc acaatttatg cctataaatt tcagatgatt taaaatttta    5760
aacctgttac attgaaaaac attgaagttc gtccttgaaga aagcattaag gtatgcatgg    5820
aggtgattta ttttaaaca taacacctaa cctaacatgg gtaagagagt atggaactag    5880
atatgagctg tataagaagc ataattgtga acaagtagat tgattgcctt catatacaag    5940
tatgttttag tattccttat ttccttatta tcagatgtat ttttttcttt aagtttcaat    6000
gttgttataa ttctcaacca gaaatttaat acttctaaa atatttttta aatttagctt    6060
gtgcttttga attacaggag aagggaatca taatttaata aaacgcttac tagaaagacc    6120
attacagatc ccaaacactt gggtttggtg accctgtctt tcttatatga ccctacaata    6180
aacatttgaa ggcagcatag gatggcagac agtaggaaca ttgtttcact tggcggcatg    6240 ttttttgaaac ctgctttata gtaactgggt gattgccatt gtggtagagc ttccactgct    6300
gtttataatc tgagagagtt aatctcagag gatgcttttt tcctttttaat ctgctatgaa    6360 tcagtaccca gatgtttaat tactgtactt attaaatcat gagggcaaaa gagtgtagaa    6420
tggaaaaaag tctcttgtat ctagatactt taaatatggg aggcccttta acttaattgc    6480
ctttagtcaa ccactggatt tgaatttgca tcaagtattt taaataatat tgaatttaaa    6540
aaaatgtatt gcagtagtgt gtcagtacct tattgttaaa gtgagtcaga taaatcttca    6600
attcctggct atttgggcaa ttgaatcatc atggactgta taatgcaatc agattatttt    6660
gtttctagac atccttgaat tacaccaaag aacatgaaat ttagttgtgg ttaaattatt    6720
tatttatttc atgcattcat tttatttccc ttaaggtctg gatgagactt ctttggggag    6780
cctctaaaaa aatttttcac tgggggccac gtgggtcatt agaagccaga gctctcctcc    6840
```

```
aggctccttc ccagtgccta gaggtgctat aggaaacata gatccagcca ggggcttccc      6900
taaagcagtg cagcaccggc ccagggcatc actagacagg ccctaattaa gttttttta      6960 aaaagcctgt gtatttattt tagaatcatg ttttctgta tattaacttg ggggatatcg      7020
ttaatattta ggatataaga tttgaggtca gccatcttca aaaagaaaa aaaaattgac      7080 tcaagaaagt acaagtaaac tatacacctt tttttcataa gttttaggaa ctgtagtaat      7140
gtggcttaga aagtataatg gcctaaatgt tttcaaaatg taagttcctg tggagaagaa      7200
ttgtttatat tgcaaacggg gggactgagg ggaacctgta ggtttaaaac agtatgtttg      7260
tcagccaact gatttaaaag gcctttaact gttttggttg ttgttttttt tttaagccac      7320 tctcccttc ctatgaggaa gaattgagag gggcacctat ttctgtaaaa tccccaaatt      7380
ggtgttgatg atttgagct tgaatgtttt catacctgat taaaacttgg tttattctaa      7440
tttctgtatc atatcatctg aggtttacgt ggtaactagt cttataacat gtatgtatct      7500 ttttttgtt gttcatctaa agcttttaa tccaaataaa tacagagttt gcaaagtgat      7560
ttggattaac caggaaaaaa aaaaaaaaaa aa      7592

<210> SEQ ID NO 2
<211> LENGTH: 1582
<212> TYPE: PRT
<213> ORGANISM: Homo sapiens

<400> SEQUENCE: 2

Met Gly Ser Lys Arg Arg Ala Thr Ser Pro Ser Ser Ser Val Ser
1               5                   10                  15

Gly Asp Phe Asp Asp Gly His His Ser Val Ser Thr Pro Gly Pro Ser
            20                  25                  30

Arg Lys Arg Arg Arg Leu Ser Asn Leu Pro Thr Val Asp Pro Ile Ala
        35                  40                  45

Val Cys His Glu Leu Tyr Asn Thr Ile Arg Asp Tyr Lys Asp Glu Gln
    50                  55                  60

Gly Arg Leu Leu Cys Glu Leu Phe Ile Arg Ala Pro Lys Arg Arg Asn
65                  70                  75                  80

Gln Pro Asp Tyr Tyr Glu Val Val Ser Gln Pro Ile Asp Leu Met Lys
                85                  90                  95

Ile Gln Gln Lys Leu Lys Met Glu Glu Tyr Asp Asp Val Asn Leu Leu
            100                 105                 110

Thr Ala Asp Phe Gln Leu Leu Phe Asn Asn Ala Lys Ser Tyr Tyr Lys
        115                 120                 125

Pro Asp Ser Pro Glu Tyr Lys Ala Ala Cys Lys Leu Trp Asp Leu Tyr
    130                 135                 140

Leu Arg Thr Arg Asn Glu Phe Val Gln Lys Gly Glu Ala Asp Asp Glu
145                 150                 155                 160

Asp Asp Asp Glu Asp Gly Gln Asp Asn Gln Gly Thr Val Thr Glu Gly
                165                 170                 175

Ser Ser Pro Ala Tyr Leu Lys Glu Ile Leu Glu Gln Leu Leu Glu Ala
            180                 185                 190

Ile Val Val Ala Thr Asn Pro Ser Gly Arg Leu Ile Ser Glu Leu Phe
        195                 200                 205

Gln Lys Leu Pro Ser Lys Val Gln Tyr Pro Asp Tyr Tyr Ala Ile Ile
    210                 215                 220

Lys Glu Pro Ile Asp Leu Lys Thr Ile Ala Gln Arg Ile Gln Asn Gly
225                 230                 235                 240
```

```
Ser Tyr Lys Ser Ile His Ala Met Ala Lys Asp Ile Asp Leu Leu Ala
                245                 250                 255

Lys Asn Ala Lys Thr Tyr Asn Glu Pro Gly Ser Gln Val Phe Lys Asp
            260                 265                 270

Ala Asn Ser Ile Lys Lys Ile Phe Tyr Met Lys Ala Glu Ile Glu
        275                 280                 285

His His Glu Met Ala Lys Ser Ser Leu Arg Met Arg Thr Pro Ser Asn
    290                 295                 300

Leu Ala Ala Ala Arg Leu Thr Gly Pro Ser His Ser Lys Gly Ser Leu
305                 310                 315                 320

Gly Glu Glu Arg Asn Pro Thr Ser Lys Tyr Tyr Arg Asn Lys Arg Ala
                325                 330                 335

Val Gln Gly Gly Arg Leu Ser Ala Ile Thr Met Ala Leu Gln Tyr Gly
            340                 345                 350

Ser Glu Ser Glu Glu Asp Ala Ala Leu Ala Ala Ala Arg Tyr Glu Glu
        355                 360                 365

Gly Glu Ser Glu Ala Glu Ser Ile Thr Ser Phe Met Asp Val Ser Asn
    370                 375                 380

Pro Phe Tyr Gln Leu Tyr Asp Thr Val Arg Ser Cys Arg Asn Asn Gln
385                 390                 395                 400

Gly Gln Leu Ile Ala Glu Pro Phe Tyr His Leu Pro Ser Lys Lys Lys
                405                 410                 415

Tyr Pro Asp Tyr Tyr Gln Gln Ile Lys Met Pro Ile Ser Leu Gln Gln
            420                 425                 430

Ile Arg Thr Lys Leu Lys Asn Gln Glu Tyr Glu Thr Leu Asp His Leu
        435                 440                 445

Glu Cys Asp Leu Asn Leu Met Phe Glu Asn Ala Lys Arg Tyr Asn Val
    450                 455                 460

Pro Asn Ser Ala Ile Tyr Lys Arg Val Leu Lys Leu Gln Gln Val Met
465                 470                 475                 480

Gln Ala Lys Lys Lys Glu Leu Ala Arg Arg Asp Asp Ile Glu Asp Gly
                485                 490                 495

Asp Ser Met Ile Ser Ser Ala Thr Ser Asp Thr Gly Ser Ala Lys Arg
            500                 505                 510

Lys Ser Lys Lys Asn Ile Arg Lys Gln Arg Met Lys Ile Leu Phe Asn
        515                 520                 525

Val Val Leu Glu Ala Arg Glu Pro Gly Ser Gly Arg Arg Leu Cys Asp
    530                 535                 540

Leu Phe Met Val Lys Pro Ser Lys Lys Asp Tyr Pro Asp Tyr Tyr Lys
545                 550                 555                 560

Ile Ile Leu Glu Pro Met Asp Leu Lys Ile Ile Glu His Asn Ile Arg
                565                 570                 575

Asn Asp Lys Tyr Ala Gly Glu Glu Gly Met Ile Glu Asp Met Lys Leu
            580                 585                 590

Met Phe Arg Asn Ala Arg His Tyr Asn Glu Glu Gly Ser Gln Val Tyr
        595                 600                 605

Asn Asp Ala His Ile Leu Glu Lys Leu Leu Lys Glu Lys Arg Lys Glu
    610                 615                 620

Leu Gly Pro Leu Pro Asp Asp Asp Met Ala Ser Pro Lys Leu Lys
625                 630                 635                 640

Leu Ser Arg Lys Ser Gly Ile Ser Pro Lys Lys Ser Lys Tyr Met Thr
                645                 650                 655
```

```
Pro Met Gln Gln Lys Leu Asn Glu Val Tyr Glu Ala Val Lys Asn Tyr
            660                 665                 670

Thr Asp Lys Arg Gly Arg Arg Leu Ser Ala Ile Phe Leu Arg Leu Pro
            675                 680                 685

Ser Arg Ser Glu Leu Pro Asp Tyr Tyr Leu Thr Ile Lys Lys Pro Met
            690                 695                 700

Asp Met Glu Lys Ile Arg Ser His Met Met Ala Asn Lys Tyr Gln Asp
705                 710                 715                 720

Ile Asp Ser Met Val Glu Asp Phe Val Met Phe Asn Asn Ala Cys
            725                 730                 735

Thr Tyr Asn Glu Pro Glu Ser Leu Ile Tyr Lys Asp Ala Leu Val Leu
            740                 745                 750

His Lys Val Leu Leu Glu Thr Arg Arg Asp Leu Glu Gly Asp Glu Asp
            755                 760                 765

Ser His Val Pro Asn Val Thr Leu Leu Ile Gln Glu Leu Ile His Asn
            770                 775                 780

Leu Phe Val Ser Val Met Ser His Gln Asp Asp Glu Gly Arg Cys Tyr
785                 790                 795                 800

Ser Asp Ser Leu Ala Glu Ile Pro Ala Val Asp Pro Asn Phe Pro Asn
            805                 810                 815

Lys Pro Pro Leu Thr Phe Asp Ile Ile Arg Lys Asn Val Glu Asn Asn
            820                 825                 830

Arg Tyr Arg Arg Leu Asp Leu Phe Gln Glu His Met Phe Glu Val Leu
            835                 840                 845

Glu Arg Ala Arg Arg Met Asn Arg Thr Asp Ser Glu Ile Tyr Glu Asp
850                 855                 860

Ala Val Glu Leu Gln Gln Phe Phe Ile Lys Ile Arg Asp Glu Leu Cys
865                 870                 875                 880

Lys Asn Gly Glu Ile Leu Leu Ser Pro Ala Leu Ser Tyr Thr Thr Lys
            885                 890                 895

His Leu His Asn Asp Val Glu Lys Glu Arg Lys Glu Lys Leu Pro Lys
            900                 905                 910

Glu Ile Glu Glu Asp Lys Leu Lys Arg Glu Glu Lys Arg Glu Ala
            915                 920                 925

Glu Lys Ser Glu Asp Ser Ser Gly Ala Ala Gly Leu Ser Gly Leu His
            930                 935                 940

Arg Thr Tyr Ser Gln Asp Cys Ser Phe Lys Asn Ser Met Tyr His Val
945                 950                 955                 960

Gly Asp Tyr Val Tyr Val Glu Pro Ala Glu Ala Asn Leu Gln Pro His
            965                 970                 975

Ile Val Cys Ile Glu Arg Leu Trp Glu Asp Ser Ala Glu Lys Glu Val
            980                 985                 990

Phe Lys Ser Asp Tyr Tyr Asn Lys Val Pro Val Ser Lys Ile Leu Gly
            995                 1000                1005

Lys Cys Val Val Met Phe Val Lys Glu Tyr Phe Lys Leu Cys Pro
        1010                1015                1020

Glu Asn Phe Arg Asp Glu Asp Val Phe Val Cys Glu Ser Arg Tyr
        1025                1030                1035

Ser Ala Lys Thr Lys Ser Phe Lys Lys Ile Lys Leu Trp Thr Met
        1040                1045                1050

Pro Ile Ser Ser Val Arg Phe Val Pro Arg Asp Val Pro Leu Pro
        1055                1060                1065
```

-continued

```
Val Val Arg Val Ala Ser Val Phe Ala Asn Ala Asp Lys Gly Asp
    1070            1075            1080

Asp Glu Lys Asn Thr Asp Asn Ser Glu Asp Ser Arg Ala Glu Asp
    1085            1090            1095

Asn Phe Asn Leu Glu Lys Glu Lys Glu Asp Val Pro Val Glu Met
    1100            1105            1110

Ser Asn Gly Glu Pro Gly Cys His Tyr Phe Glu Gln Leu His Tyr
    1115            1120            1125

Asn Asp Met Trp Leu Lys Val Gly Asp Cys Val Phe Ile Lys Ser
    1130            1135            1140

His Gly Leu Val Arg Pro Arg Val Gly Arg Ile Glu Lys Val Trp
    1145            1150            1155

Val Arg Asp Gly Ala Ala Tyr Phe Tyr Gly Pro Ile Phe Ile His
    1160            1165            1170

Pro Glu Glu Thr Glu His Glu Pro Thr Lys Met Phe Tyr Lys Lys
    1175            1180            1185

Glu Val Phe Leu Ser Asn Leu Glu Glu Thr Cys Pro Met Thr Cys
    1190            1195            1200

Ile Leu Gly Lys Cys Ala Val Leu Ser Phe Lys Asp Phe Leu Ser
    1205            1210            1215

Cys Arg Pro Thr Glu Ile Pro Glu Asn Asp Ile Leu Leu Cys Glu
    1220            1225            1230

Ser Arg Tyr Asn Glu Ser Asp Lys Gln Met Lys Lys Phe Lys Gly
    1235            1240            1245

Leu Lys Arg Phe Ser Leu Ser Ala Lys Val Val Asp Asp Glu Ile
    1250            1255            1260

Tyr Tyr Phe Arg Lys Pro Ile Val Pro Gln Lys Glu Pro Ser Pro
    1265            1270            1275

Leu Leu Glu Lys Lys Ile Gln Leu Leu Glu Ala Lys Phe Ala Glu
    1280            1285            1290

Leu Glu Gly Gly Asp Asp Asp Ile Glu Glu Met Gly Glu Glu Asp
    1295            1300            1305

Ser Glu Ser Thr Pro Lys Ser Ala Lys Gly Ser Ala Lys Lys Glu
    1310            1315            1320

Gly Ser Lys Arg Lys Ile Asn Met Ser Gly Tyr Ile Leu Phe Ser
    1325            1330            1335

Ser Glu Met Arg Ala Val Ile Lys Ala Gln His Pro Asp Tyr Ser
    1340            1345            1350

Phe Gly Glu Leu Ser Arg Leu Val Gly Thr Glu Trp Arg Asn Leu
    1355            1360            1365

Glu Thr Ala Lys Lys Ala Glu Tyr Glu Gly Met Met Gly Gly Tyr
    1370            1375            1380

Pro Pro Gly Leu Pro Pro Leu Gln Gly Pro Val Asp Gly Leu Val
    1385            1390            1395

Ser Met Gly Ser Met Gln Pro Leu His Pro Gly Gly Pro Pro Pro
    1400            1405            1410

His His Leu Pro Pro Gly Val Pro Gly Leu Pro Gly Ile Pro Pro
    1415            1420            1425

Pro Gly Val Met Asn Gln Gly Val Ala Pro Met Val Gly Thr Pro
    1430            1435            1440

Ala Pro Gly Gly Ser Pro Tyr Gly Gln Gln Val Gly Val Leu Gly
    1445            1450            1455
```

-continued

| | | | | | | | | | | | |
|---|---|---|---|---|---|---|---|---|---|---|---|
| Pro | Pro | Gly | Gln | Gln | Ala | Pro | Pro | Tyr | Pro | Gly | Pro His Pro |
| | 1460 | | | | 1465 | | | | 1470 | | |
| Ala | Gly | Pro | Pro | Val | Ile | Gln | Gln | Pro | Thr | Thr | Pro Met Phe Val |
| 1475 | | | | | 1480 | | | | | 1485 | |
| Ala | Pro | Pro | Pro | Lys | Thr | Gln | Arg | Leu | Leu | His | Ser Glu Ala Tyr |
| 1490 | | | | | 1495 | | | | | 1500 | |
| Leu | Lys | Tyr | Ile | Glu | Gly | Leu | Ser | Ala | Glu | Ser | Asn Ser Ile Ser |
| 1505 | | | | | 1510 | | | | | 1515 | |
| Lys | Trp | Asp | Gln | Thr | Leu | Ala | Ala | Arg | Arg | Arg | Asp Val His Leu |
| 1520 | | | | | 1525 | | | | | 1530 | |
| Ser | Lys | Glu | Gln | Glu | Ser | Arg | Leu | Pro | Ser | His | Trp Leu Lys Ser |
| 1535 | | | | | 1540 | | | | | 1545 | |
| Lys | Gly | Ala | His | Thr | Thr | Met | Ala | Asp | Ala | Leu | Trp Arg Leu Arg |
| 1550 | | | | | 1555 | | | | | 1560 | |
| Asp | Leu | Met | Leu | Arg | Asp | Thr | Leu | Asn | Ile | Arg | Gln Ala Tyr Asn |
| 1565 | | | | | 1570 | | | | | 1575 | |
| Leu | Glu | Asn | Val | | | | | | | | |
| 1580 | | | | | | | | | | | |

<210> SEQ ID NO 3
<211> LENGTH: 7609
<212> TYPE: DNA
<213> ORGANISM: Homo sapiens

<400> SEQUENCE: 3

| | |
|---|---|
| gcggccgggg ctgcaggcgg cggagcggct ggcttgccaa cacttggtgt cacatgtgag | 60 |
| cctcccacat gtattcactc tccattccag ctctgtgatt gaactctgct cttattgact | 120 |
| aggggggcagt tgggcaggca tgcctcattc ctggaattga cagtcattcc taataagttg | 180 |
| gattccatgg gttccaagag aagaagagct acctcccctt ccagcagtgt cagcggggac | 240 |
| tttgatgatg gcaccattc tgtgtcaaca ccaggcccaa gcaggaaaag gaggagactt | 300 |
| tccaatcttc caactgtaga tcctattgcc gtgtgccatg aactctataa taccatccga | 360 |
| gactataagg atgaacaggg cagacttctc tgtgagctct tcattagggc accaaagcga | 420 |
| agaaatcaac cagactatta tgaagtggtt tctcagccca ttgacttgat gaaaatccaa | 480 |
| cagaaactaa aaatggaaga gtatgatgat gttaatttgc tgactgctga cttccagctt | 540 |
| ctttttaaca atgcaaagtc ctattataag ccagattctc ctgaatataa agccgcttgc | 600 |
| aaactctggg atttgtacct tcgaacaaga aatgagtttg ttcagaaagg agaagcagat | 660 |
| gacgaagatg atgatgaaga tgggcaagac aatcagggca cagtgactga aggatcttct | 720 |
| ccagcttact tgaaggagat cctggagcag cttcttgaag ccatagttgt agctacaaat | 780 |
| ccatcaggac gtctcattag cgaacttttt cagaaactgc cttctaaagt gcaatatcca | 840 |
| gattattatg caataattaa ggagcctata gatctcaaga ccattgccca gaggatacag | 900 |
| aatggaagct acaaaagtat tcatgcaatg gccaaagata tagatctcct cgcaaaaaat | 960 |
| gccaaaactt ataatgagcc tggctctcaa gtattcaagg atgcaaattc aattaaaaaa | 1020 |
| atatttttata tgaaaaaggc tgaaattgaa catcatgaaa tggctaagtc aagtcttcga | 1080 |
| atgaggactc catccaactt ggctgcagcc agactgacag gtcccttcaca cagtaaaggc | 1140 |
| agccttggtg aagagagaaa tcccactagc aagtattacc gtaataaaag agcagtacaa | 1200 |
| ggaggtcgtt tatcagcaat tacaatggca cttcaatatg gctcagaaag tgaagaagat | 1260 |
| gctgctttag ctgctgcacg ctatgaagag ggagagtcag aagcagaaag catcacttcc | 1320 |

```
tttatggatg tttcaaatcc tttttatcag ctttatgaca cagttaggag ttgtcggaat    1380
aaccaagggc agctaatagc tgaacctttt taccatttgc cttcaaagaa aaaataccct    1440
gattattacc agcaaattaa aatgcccata tcactacaac agatccgaac aaaactgaag    1500
aatcaagaat atgaaacttt agatcatttg gagtgtgatc tgaatttaat gtttgaaaat    1560
gccaaacgct ataatgtgcc caattcagcc atctacaagc gagttctaaa attgcagcaa    1620
gttatgcagg caaagaagaa agagcttgcc aggagagacg atatcgagga cggagacagc    1680
atgatctctt cagccacctc tgatactggt agtgccaaaa gaaaagtaa aaagaacata     1740 agaaagcagc gaatgaaaat cttattcaat gttgttcttg aagctcgaga gccaggttca    1800
ggcagaagac tttgtgacct atttatggtt aaaccatcca aaaggacta tcctgattat     1860 tataaaatca tcttggagcc aatggacttg aaaataattg agcataacat ccgcaatgac    1920
aaatatgctg gtgaagaggg aatgatagaa acatgaagc tgatgttccg gaatgccagg     1980
cactataatg aggagggctc ccaggtttat aatgatgcac atatcctgga gaagttactc    2040
aaggagaaaa ggaaagagct gggcccactg cctgatgatg atgacatggc ttctcccaaa    2100
ctcaagctga gtaggaagag tggcatttct cctaaaaaat caaaatacat gactccaatg    2160
cagcagaaac taaatgaggt ctatgaagct gtaaagaact atactgataa gaggggtcgc    2220
cgcctcagtg ccatatttct gaggcttccc tctagatctg agttgcctga ctactatctg    2280
actattaaaa agcccatgga catggaaaaa attcgaagtc acatgatggc caacaagtac    2340
caagatattg actctatggt tgaggacttt gtcatgatgt ttaataatgc ctgtacatac    2400
aatgagccgg agtctttgat ctacaaagat gctcttgttc tacacaaagt cctgcttgaa    2460
acacgcagag acctggaggg agatgaggac tctcatgtcc caaatgtgac tttgctgatt    2520
caagagctta tccacaatct ttttgtgtca gtcatgagtc atcaggatga tgagggaaga    2580
tgctacagcg attctttagc agaaattcct gctgtggatc ccaactttcc taacaaacca    2640 cccccttacat ttgacataat taggaagaat gttgaaaata atcgctaccg tcggcttgat    2700
ttatttcaag agcatatgtt tgaagtattg gaacgagcaa gaaggatgaa tcggacagat    2760
tcagaaatat atgaagatgc agtagaactt cagcagtttt ttattaaaat tcgtgatgaa    2820
ctctgcaaaa atggagagat tcttctttca ccggcactca gctataccac aaaacatttg    2880
cataatgatg tggagaaaga gagaaaggaa aaattgccaa agaaaataga ggaagataaa    2940
ctaaaacgag aagaagaaaa aagagaagct gaaaagagtg aagattcctc tggtgctgca    3000
ggcctctcag gcttacatcg cacatacagc caggactgta gctttaaaaa cagcatgtac    3060
catgttggag attacgtcta tgtggaacct gcagaggcca acctacaacc acatatcgtc    3120
tgtattgaaa gactgtggga ggattcagct ggtgaaaaat ggtgtatgg ctgttggttt     3180 taccgaccaa atgaaacatt ccacctggct acacgaaaat ttctagaaaa agaagttttt    3240
aagagtgact attacaacaa agttccagtt agtaaaattc taggcaagtg tgtggtcatg    3300
tttgtcaagg aatactttaa gttatgccca gaaaacttcc gagatgagga tgttttttgtc    3360 tgtgaatcac ggtattctgc caaaccaaa tcttttaaga aaattaaact gtggaccatg     3420
cccatcagct cagtcaggtt tgtccctcgg gatgtgcctc tgcctgtggt tcgcgtggcc    3480
tctgtatttg caaatgcaga taaggtgat gatgagaaga atacagacaa ctcagaggac     3540
agtcgagctg aagacaattt taacttggaa aaggaaaaag aagatgtccc tgtggaaatg    3600
tccaatggtg aaccaggttg ccactacttt gagcagctcc attacaatga catgtggctg    3660
aaggttggcg actgtgtctt catcaagtcc catggcctgg tgcgtcctcg tgtgggcaga    3720
```

```
attgaaaaag tatgggttcg agatggagct gcatattttt atggccccat cttcattcac    3780
ccagaagaaa cagagcatga gcccacaaaa atgttctaca aaaagaagt atttctgagt     3840
aatctggaag aaacctgccc catgacatgt attctcggaa agtgtgctgt gttgtcattc    3900
aaggacttcc tctcctgcag gccaactgaa ataccagaaa atgacattct gctttgtgag    3960
agccgctaca atgagagcga caagcagatg aagaaattca aaggattgaa gaggttttca    4020
ctctctgcta aagtggtaga tgatgaaatt tactacttca gaaaaccaat tgttcctcag    4080
aaggagccat cacctttgct ggaaaagaag atccagttgc tagaagctaa atttgccgag    4140
ttagaaggtg gagatgatga tattgaagag atgggagaag aagatagtga ggtcattgaa    4200
cctccttctc tacctcagct tcagaccccc ctggccagtg agctggacct catgccctac    4260
acaccccac agtctacccc aaagtctgcc aaaggcagtg caaagaagga aggctccaaa     4320
cggaaaatca acatgagtgg ctacatcctg ttcagcagtg agatgagggc tgtgattaag    4380
gcccaacacc cagactactc tttcggggag ctcagccgcc tggtggggac agaatggaga    4440
aatcttgaga cagccaagaa agcagaatat gaaggtgtga tgaaccaagg agtggcccct    4500
atggtaggga ctccagcacc aggtggaagt ccatatggac aacaggtggg agttttgggg    4560
cctccagggc agcaggcacc acctccatat cccggcccac atccagctgg accccctgtc    4620
atacagcagc caacaacacc catgtttgta gctcccccac caaagaccca gcggcttctt    4680
cactcagagg cctacctgaa atacattgaa ggactcagtg cggagtccaa cagcattagc    4740
aagtgggatc agacactggc agctcgaaga gcgcgacgtcc atttgtcgaa agaacaggag   4800
agccgcctac cctctcactg gctgaaaagc aaaggggccc acaccaccat ggcagatgcc    4860
ctctggcgcc ttcgagattt gatgctccgg gacacctca acattcgcca agcatacaac    4920
ctagaaaatg tttaatcaca tcattacgtt tcttttatat agaagcataa agagttgtgg    4980
atcagtagcc attttagtta ctgggggtgg gggaaggaa caaaggagga taatttttat     5040
tgcattttac tgtacatcac aaggccattt ttatatacgg acactttaa taagctattt     5100
caatttgttt gttatattaa gttgactttta tcaaatacac aaagatttt ttgcatatgt    5160
ttccttcgtt taaaccagt ttcataattg gttgtatatg tagacttgga gttttatctt    5220
tttacttgtt gccatggaac tgaaaccatt agaggttttt gtcttggctt ggggttttg    5280
ttttcttggt tttgggtttt tttatatata tatataaaag aacaaaatga aaaaaaacac   5340
acacacacaa gagtttacag attagtttaa attgataatg aaatgtgaag tttgtcctag    5400
tttacatctt agagagggga gtatacttgt gtttgtttca tgtgcctgaa tatcttaagc    5460
cactttctgc aaaagctgtt tcttacagat gaagtgcttt ctttgaaagg tggttattta    5520
ggttttagat gtttaataga cacagcacat ttgctctatt aactcagagg ctcactacag    5580
aaatatgtaa tcagtgctgt gcatctgtct gcagctaatg tacctcctgg acaccaggag    5640
gggaaaaagc acttttttcaa ttgtgctgag ttagacatct gtgagttaga ctatggtgtc   5700
agtgattttt gcagaacacg tgcacaaccc tgaggtatgt ttaatctagg caggtacgtt    5760
taaggatatt ttgatctatt tataatgaat tcacaattta tgcctataaa tttcagatga    5820
tttaaaattt taaacctgtt acattgaaaa acattgaagt tcgtcttgaa gaaagcatta    5880
aggtatgcat ggaggtgatt tattttttaaa cataacacct aacctaacat gggtaagaga   5940
gtatggaact agatatgagc tgtataagaa gcataattgt gaacaagtag attgattgcc    6000
ttcatataca agtatgtttt agtattccctt atttccttat tatcagatgt atttttttctt  6060
```

```
ttaagtttca atgttgttat aattctcaac cagaaattta atactttcta aaatatttt     6120 taaatttagc ttgtgctttt gaattacagg agaagggaat cataatttaa taaaacgctt     6180
actagaaaga ccattacaga tcccaaacac ttgggtttgg tgaccctgtc tttcttatat     6240
gaccctacaa taaacatttg aaggcagcat aggatggcag acagtaggaa cattgtttca     6300 cttgcggca tgtttttgaa acctgcttta tagtaactgg gtgattgcca ttgtggtaga      6360
gcttccactg ctgtttataa tctgagagag ttaatctcag aggatgcttt tttccttta     6420 atctgctatg aatcagtacc cagatgttta attactgtac ttattaaatc atgagggcaa     6480
aagagtgtag aatggaaaaa agtctcttgt atctagatac tttaaatatg ggaggccctt     6540
taacttaatt gcctttagtc aaccactgga tttgaatttg catcaagtat tttaaataat     6600
attgaattta aaaaaatgta ttgcagtagt gtgtcagtac cttattgtta aagtgagtca     6660
gataaatctt caattcctgg ctatttgggc aattgaatca tcatggactg tataatgcaa     6720
tcagattatt tgtttctag acatccttga attacaccaa agaacatgaa atttagttgt     6780
ggttaaatta tttatttatt tcatgcattc attttatttc ccttaaggtc tggatgagac     6840
ttctttgggg agcctctaaa aaattttc actggggcc acgtgggtca ttagaagcca      6900
gagctctcct ccaggctcct tcccagtgcc tagaggtgct ataggaaaca tagatccagc     6960
caggggcttc cctaaagcag tgcagcaccg cccagggca tcactagaca ggccctaatt       7020
aagttttttt taaaaagcct gtgtatttat tttagaatca tgttttttctg tatattaact     7080 tgggggatat cgttaatatt taggatataa gatttgaggt cagccatctt caaaaaagaa     7140
aaaaaaattg actcaagaaa gtacaagtaa actatacacc tttttttcat aagttttagg     7200
aactgtagta atgtggctta gaaagtataa tggcctaaat gttttcaaaa tgtaagttcc     7260
tgtggagaag aattgtttat attgcaaacg ggggactga ggggaacctg taggtttaaa      7320
acagtatgtt tgtcagccaa ctgatttaaa aggcctttaa ctgttttggt tgttgttttt     7380
tttttaagcc actctcccct tcctatgagg aagaattgag aggggcacct atttctgtaa     7440
aatccccaaa ttggtgttga tgattttgag cttgaatgtt ttcatacctg attaaaactt     7500
ggtttattct aatttctgta tcatatcatc tgaggtttac gtggtaacta gtcttataac     7560
atgtatgtat ctttttttg ttgttcatct aaagcttttt aatccaaat                   7609
```

<210> SEQ ID NO 4
<211> LENGTH: 1582
<212> TYPE: PRT
<213> ORGANISM: Homo sapiens

<400> SEQUENCE: 4

Met Gly Ser Lys Arg Arg Arg Ala Thr Ser Pro Ser Ser Ser Val Ser
1               5                   10                  15

Gly Asp Phe Asp Asp Gly His His Ser Val Ser Thr Pro Gly Pro Ser
                20                  25                  30

Arg Lys Arg Arg Arg Leu Ser Asn Leu Pro Thr Val Asp Pro Ile Ala
            35                  40                  45

Val Cys His Glu Leu Tyr Asn Thr Ile Arg Asp Tyr Lys Asp Glu Gln
        50                  55                  60

Gly Arg Leu Leu Cys Glu Leu Phe Ile Arg Ala Pro Lys Arg Arg Asn
65                  70                  75                  80

Gln Pro Asp Tyr Tyr Glu Val Val Ser Gln Pro Ile Asp Leu Met Lys
                85                  90                  95

-continued

Ile Gln Gln Lys Leu Lys Met Glu Glu Tyr Asp Asp Val Asn Leu Leu
                100                 105                 110

Thr Ala Asp Phe Gln Leu Leu Phe Asn Asn Ala Lys Ser Tyr Tyr Lys
            115                 120                 125

Pro Asp Ser Pro Glu Tyr Lys Ala Ala Cys Lys Leu Trp Asp Leu Tyr
        130                 135                 140

Leu Arg Thr Arg Asn Glu Phe Val Gln Lys Gly Ala Asp Asp Glu
145                 150                 155                 160

Asp Asp Asp Glu Asp Gly Gln Asp Asn Gln Gly Thr Val Thr Glu Gly
                165                 170                 175

Ser Ser Pro Ala Tyr Leu Lys Glu Ile Leu Gln Leu Leu Glu Ala
            180                 185                 190

Ile Val Val Ala Thr Asn Pro Ser Gly Arg Leu Ile Ser Glu Leu Phe
        195                 200                 205

Gln Lys Leu Pro Ser Lys Val Gln Tyr Pro Asp Tyr Tyr Ala Ile Ile
        210                 215                 220

Lys Glu Pro Ile Asp Leu Lys Thr Ile Ala Gln Arg Ile Gln Asn Gly
225                 230                 235                 240

Ser Tyr Lys Ser Ile His Ala Met Ala Lys Asp Ile Asp Leu Leu Ala
                245                 250                 255

Lys Asn Ala Lys Thr Tyr Asn Glu Pro Gly Ser Gln Val Phe Lys Asp
            260                 265                 270

Ala Asn Ser Ile Lys Lys Ile Phe Tyr Met Lys Lys Ala Glu Ile Glu
        275                 280                 285

His His Glu Met Ala Lys Ser Ser Leu Arg Met Arg Thr Pro Ser Asn
        290                 295                 300

Leu Ala Ala Ala Arg Leu Thr Gly Pro Ser His Ser Lys Gly Ser Leu
305                 310                 315                 320

Gly Glu Glu Arg Asn Pro Thr Ser Lys Tyr Tyr Arg Asn Lys Arg Ala
                325                 330                 335

Val Gln Gly Gly Arg Leu Ser Ala Ile Thr Met Ala Leu Gln Tyr Gly
            340                 345                 350

Ser Glu Ser Glu Glu Asp Ala Ala Leu Ala Ala Ala Arg Tyr Glu Glu
        355                 360                 365

Gly Glu Ser Glu Ala Glu Ser Ile Thr Ser Phe Met Asp Val Ser Asn
370                 375                 380

Pro Phe Tyr Gln Leu Tyr Asp Thr Val Arg Ser Cys Arg Asn Asn Gln
385                 390                 395                 400

Gly Gln Leu Ile Ala Glu Pro Phe Tyr His Leu Pro Ser Lys Lys Lys
                405                 410                 415

Tyr Pro Asp Tyr Tyr Gln Gln Ile Lys Met Pro Ile Ser Leu Gln Gln
            420                 425                 430

Ile Arg Thr Lys Leu Lys Asn Gln Glu Tyr Glu Thr Leu Asp His Leu
        435                 440                 445

Glu Cys Asp Leu Asn Leu Met Phe Glu Asn Ala Lys Arg Tyr Asn Val
        450                 455                 460

Pro Asn Ser Ala Ile Tyr Lys Arg Val Leu Lys Leu Gln Gln Val Met
465                 470                 475                 480

Gln Ala Lys Lys Lys Glu Leu Ala Arg Arg Asp Asp Ile Glu Asp Gly
                485                 490                 495

Asp Ser Met Ile Ser Ser Ala Thr Ser Asp Thr Gly Ser Ala Lys Arg
            500                 505                 510

```
Lys Ser Lys Lys Asn Ile Arg Lys Gln Arg Met Lys Ile Leu Phe Asn
            515                 520                 525

Val Val Leu Glu Ala Arg Glu Pro Gly Ser Gly Arg Arg Leu Cys Asp
        530                 535                 540

Leu Phe Met Val Lys Pro Ser Lys Lys Asp Tyr Pro Asp Tyr Tyr Lys
545                 550                 555                 560

Ile Ile Leu Glu Pro Met Asp Leu Lys Ile Ile Glu His Asn Ile Arg
                565                 570                 575

Asn Asp Lys Tyr Ala Gly Glu Glu Gly Met Ile Glu Asp Met Lys Leu
            580                 585                 590

Met Phe Arg Asn Ala Arg His Tyr Asn Glu Glu Gly Ser Gln Val Tyr
        595                 600                 605

Asn Asp Ala His Ile Leu Glu Lys Leu Leu Lys Glu Lys Arg Lys Glu
    610                 615                 620

Leu Gly Pro Leu Pro Asp Asp Asp Met Ala Ser Pro Lys Leu Lys
625                 630                 635                 640

Leu Ser Arg Lys Ser Gly Ile Ser Pro Lys Ser Lys Tyr Met Thr
                645                 650                 655

Pro Met Gln Gln Lys Leu Asn Glu Val Tyr Glu Ala Val Lys Asn Tyr
            660                 665                 670

Thr Asp Lys Arg Gly Arg Arg Leu Ser Ala Ile Phe Leu Arg Leu Pro
        675                 680                 685

Ser Arg Ser Glu Leu Pro Asp Tyr Tyr Leu Thr Ile Lys Lys Pro Met
    690                 695                 700

Asp Met Glu Lys Ile Arg Ser His Met Met Ala Asn Lys Tyr Gln Asp
705                 710                 715                 720

Ile Asp Ser Met Val Glu Asp Phe Val Met Met Phe Asn Asn Ala Cys
                725                 730                 735

Thr Tyr Asn Glu Pro Glu Ser Leu Ile Tyr Lys Asp Ala Leu Val Leu
            740                 745                 750

His Lys Val Leu Leu Glu Thr Arg Arg Asp Leu Glu Gly Asp Glu Asp
        755                 760                 765

Ser His Val Pro Asn Val Thr Leu Leu Ile Gln Glu Leu Ile His Asn
    770                 775                 780

Leu Phe Val Ser Val Met Ser His Gln Asp Asp Glu Gly Arg Cys Tyr
785                 790                 795                 800

Ser Asp Ser Leu Ala Glu Ile Pro Ala Val Asp Pro Asn Phe Pro Asn
                805                 810                 815

Lys Pro Pro Leu Thr Phe Asp Ile Ile Arg Lys Asn Val Glu Asn Asn
            820                 825                 830

Arg Tyr Arg Arg Leu Asp Leu Phe Gln Glu His Met Phe Glu Val Leu
        835                 840                 845

Glu Arg Ala Arg Arg Met Asn Arg Thr Asp Ser Glu Ile Tyr Glu Asp
    850                 855                 860

Ala Val Glu Leu Gln Gln Phe Phe Ile Lys Ile Arg Asp Glu Leu Cys
865                 870                 875                 880

Lys Asn Gly Glu Ile Leu Leu Ser Pro Ala Leu Ser Tyr Thr Thr Lys
                885                 890                 895

His Leu His Asn Asp Val Glu Lys Glu Arg Lys Glu Lys Leu Pro Lys
            900                 905                 910

Glu Ile Glu Glu Asp Lys Leu Lys Arg Glu Glu Glu Lys Arg Glu Ala
        915                 920                 925
```

-continued

Glu Lys Ser Glu Asp Ser Ser Gly Ala Ala Gly Leu Ser Gly Leu His
    930             935             940

Arg Thr Tyr Ser Gln Asp Cys Ser Phe Lys Asn Ser Met Tyr His Val
945             950             955             960

Gly Asp Tyr Val Tyr Val Glu Pro Ala Glu Ala Asn Leu Gln Pro His
            965             970             975

Ile Val Cys Ile Glu Arg Leu Trp Glu Asp Ser Ala Gly Glu Lys Trp
                980             985             990

Leu Tyr Gly Cys Trp Phe Tyr Arg Pro Asn Glu Thr Phe His Leu Ala
            995             1000            1005

Thr Arg Lys Phe Leu Glu Lys Glu Val Phe Lys Ser Asp Tyr Tyr
    1010            1015            1020

Asn Lys Val Pro Val Ser Lys Ile Leu Gly Lys Cys Val Val Met
    1025            1030            1035

Phe Val Lys Glu Tyr Phe Lys Leu Cys Pro Glu Asn Phe Arg Asp
    1040            1045            1050

Glu Asp Val Phe Val Cys Glu Ser Arg Tyr Ser Ala Lys Thr Lys
    1055            1060            1065

Ser Phe Lys Lys Ile Lys Leu Trp Thr Met Pro Ile Ser Ser Val
    1070            1075            1080

Arg Phe Val Pro Arg Asp Val Pro Leu Pro Val Val Arg Val Ala
    1085            1090            1095

Ser Val Phe Ala Asn Ala Asp Lys Gly Asp Asp Glu Lys Asn Thr
    1100            1105            1110

Asp Asn Ser Glu Asp Ser Arg Ala Glu Asp Asn Phe Asn Leu Glu
    1115            1120            1125

Lys Glu Lys Glu Asp Val Pro Val Glu Met Ser Asn Gly Glu Pro
    1130            1135            1140

Gly Cys His Tyr Phe Glu Gln Leu His Tyr Asn Asp Met Trp Leu
    1145            1150            1155

Lys Val Gly Asp Cys Val Phe Ile Lys Ser His Gly Leu Val Arg
    1160            1165            1170

Pro Arg Val Gly Arg Ile Glu Lys Val Trp Val Arg Asp Gly Ala
    1175            1180            1185

Ala Tyr Phe Tyr Gly Pro Ile Phe Ile His Pro Glu Glu Thr Glu
    1190            1195            1200

His Glu Pro Thr Lys Met Phe Tyr Lys Lys Glu Val Phe Leu Ser
    1205            1210            1215

Asn Leu Glu Glu Thr Cys Pro Met Thr Cys Ile Leu Gly Lys Cys
    1220            1225            1230

Ala Val Leu Ser Phe Lys Asp Phe Leu Ser Cys Arg Pro Thr Glu
    1235            1240            1245

Ile Pro Glu Asn Asp Ile Leu Leu Cys Glu Ser Arg Tyr Asn Glu
    1250            1255            1260

Ser Asp Lys Gln Met Lys Lys Phe Lys Gly Leu Lys Arg Phe Ser
    1265            1270            1275

Leu Ser Ala Lys Val Val Asp Asp Glu Ile Tyr Tyr Phe Arg Lys
    1280            1285            1290

Pro Ile Val Pro Gln Lys Glu Pro Ser Pro Leu Leu Glu Lys Lys
    1295            1300            1305

Ile Gln Leu Leu Glu Ala Lys Phe Ala Glu Leu Glu Gly Gly Asp
    1310            1315            1320

Asp Asp Ile Glu Glu Met Gly Glu Glu Asp Ser Glu Val Ile Glu
        1325                1330                1335

Pro Pro Ser Leu Pro Gln Leu Gln Thr Pro Leu Ala Ser Glu Leu
    1340                1345                1350

Asp Leu Met Pro Tyr Thr Pro Pro Gln Ser Thr Pro Lys Ser Ala
    1355                1360                1365

Lys Gly Ser Ala Lys Lys Glu Gly Ser Lys Arg Lys Ile Asn Met
    1370                1375                1380

Ser Gly Tyr Ile Leu Phe Ser Ser Glu Met Arg Ala Val Ile Lys
    1385                1390                1395

Ala Gln His Pro Asp Tyr Ser Phe Gly Glu Leu Ser Arg Leu Val
    1400                1405                1410

Gly Thr Glu Trp Arg Asn Leu Glu Thr Ala Lys Lys Ala Glu Tyr
    1415                1420                1425

Glu Gly Val Met Asn Gln Gly Val Ala Pro Met Val Gly Thr Pro
    1430                1435                1440

Ala Pro Gly Gly Ser Pro Tyr Gly Gln Gln Val Gly Val Leu Gly
    1445                1450                1455

Pro Pro Gly Gln Gln Ala Pro Pro Pro Tyr Pro Gly Pro His Pro
    1460                1465                1470

Ala Gly Pro Pro Val Ile Gln Gln Pro Thr Thr Pro Met Phe Val
    1475                1480                1485

Ala Pro Pro Lys Thr Gln Arg Leu Leu His Ser Glu Ala Tyr
    1490                1495                1500

Leu Lys Tyr Ile Glu Gly Leu Ser Ala Glu Ser Asn Ser Ile Ser
    1505                1510                1515

Lys Trp Asp Gln Thr Leu Ala Ala Arg Arg Asp Val His Leu
    1520                1525                1530

Ser Lys Glu Gln Glu Ser Arg Leu Pro Ser His Trp Leu Lys Ser
    1535                1540                1545

Lys Gly Ala His Thr Thr Met Ala Asp Ala Leu Trp Arg Leu Arg
    1550                1555                1560

Asp Leu Met Leu Arg Asp Thr Leu Asn Ile Arg Gln Ala Tyr Asn
    1565                1570                1575

Leu Glu Asn Val
    1580

<210> SEQ ID NO 5
<211> LENGTH: 8117
<212> TYPE: DNA
<213> ORGANISM: Mus musculus

<400> SEQUENCE: 5
ggatttacgg cagcactggg aggggtgagg gcggtgaggg cggcgggtgc cggagagacg        60
gccgcggcca gaggagcgct agcagccgtg gcggccacgg ggcggggctc ggcggtcggg       120
gaccgcagcc ggggctgcag gcggcggagc ggcgggcttg ccaacacttg gtgtcacatg       180
tgagcctccc acatgtgtgc actctccatt ccagctctgt gattgaactc tgctcttatt       240 gactagggg cacttgggca ggcatgcttc attcctggag ttgacagtca tttcataaga       300
agttggattc catgggttcc aagagaagaa gagccacctc tccttccagc agtgtcagtg       360
gagactttga tgacgggcac cattctgtgc ctacaccagg cccaagcagg aaaaggagaa       420
gactgtccaa tcttccaact gtagatccta ttgctgtgtg ccatgaactc tataacacca       480
tccgagacta aaggatgaa cagggcagac tcctctgtga gctgttcatt agggctccaa        540

```
agcggagaaa tcaaccagac tattatgaag tggtttctca gcccattgac ttgatgaaaa      600
tccaacagaa acttaaaatg gaagagtatg atgatgttaa tctactgact gctgacttcc      660
agctgctttt taacaatgca aaggcctact ataagccaga ttcccctgag tataaagctg      720
cttgtaaact ctgggatttg taccttcgaa caagaaatga gtttgttcag aaaggagaag      780
cagacgatga agatgatgac gaagatgggc aagacaatca aggcacactg gctgacggct      840
cttctccagg ttatctgaag gagatcctgg agcagcttct tgaagccata gttgtagcca      900
caaatccatc aggacggctc atcagtgaac ttttttcagaa actgccttcc aaagtgcaat      960
atccagacta ttatgcaata attaaggaac ctatagatct caagaccatt gctcagagga     1020
tacagaatgg aagctacaaa agtatacacg caatggccaa agatatagat cttctagcaa     1080
aaaatgccaa aacatacaat gagcctgggt ctcaagtatt caaggatgcc aattcgatta     1140
aaaaaatatt ttatatgaaa aaggcagaaa ttgaacatca tgaaatgact aaatcaagtc     1200
ttcgaataag gactgcatca aatttggctg cagccaggct gacaggtcct tcgcacaata     1260
aaagcagcct tggtgaagaa agaaaccccca ctagcaagta ttaccgtaat aaaagagcag     1320
tccaaggggg tcgcttgtca gcaattacca tggcacttca gtatggatca gagagtgaag     1380
aggacgctgc tttagctgct gcacgctatg aagaagggga atctgaagca gagagcatca     1440
cttccttcat ggacgtttcc aaccccttc atcagcttta cgacacagtt aggagctgta     1500
ggaatcacca agggcagctc atagctgaac ctttcttcca tttgccttca agaaaaaat     1560 acccagatta ttatcagcaa attaaaatgc ccatatcact tcaacagatc agaacaaagc     1620
taaagaacca agaatatgaa actttagatc atttggagtg tgatctgaat ttaatgtttg     1680
aaaatgccaa acgttataac gttcccaatt cagccatcta taagcgagtt ctaaaactgc     1740
agcaagtcat gcaggcaaag aagaaggagc ttgcgaggag agatgacatt gaggacggag     1800
acagcatgat ctcctcagcc acttctgaca ctggtagtgc caaaaggaaa aggaatactc     1860
atgacagtga gatgttgggt ctcaggaggc tatccagtaa aaagaacata agaaaacagc     1920
gaatgaaaat tttattcaat gttgttcttg aagctcgaga gccaggttca ggcagaagac     1980
tttgcgatct atttatggtt aagccatcca agaaggacta tcctgattat tataaaatca     2040
tcttagagcc aatggacctg aaaataattg agcataacat ccgaaatgac aaatatgcag     2100
gtgaagaagg aatgatggaa gacatgaaac tcatgttccg caatgccagg cactacaatg     2160
aggagggctc ccaggtatac aatgatgccc atatcctgga gaagttactc aaagataaaa     2220
ggaaagagct gggccctctg cctgatgatg atgacatggc ttctcccaaa cttaaattga     2280
gtaggaagag tggtgtttct cctaagaaat caaagtacat gactccaatg cagcagaaac     2340
tgaatgaagt gtatgaagct gtaaagaact atactgataa gaggggtcgc cgccttagtg     2400
ctatatttct aagactcccc tctagatcag agctgcctga ctactacctg accattaaaa     2460
agcccatgga catggaaaaa attcgaagtc acatgatggc aaacaagtac caagacatag     2520
attctatggt agaggacttt gtcatgatgt ttaataatgc ctgtacctac aatgaaccag     2580
agtctttgat ctacaaagat gcccttgtac tgcataaagt cctccttgag actcggagag     2640
acctggaggg agatgaggat tctcatgtcc ctaatgtgac gttgctgatt caagagctca     2700
tccataacct ttttgtgtca gtcatgagtc atcaggatga cgaagggagg tgttacagcg     2760 actcctagc agaaattcct gctgtggatc ccaactctcc caataaacct cccttacat     2820 ttgacattat caggaaaaat gttgaaagta atcggtatcg gcgacttgat ttatttcagg     2880
```

```
agcatatgtt tgaagtattg aacgggcaa gaaggatgaa ccggacagat tccgaaatat   2940
atgaggatgc tgtagaactt cagcagtttt ttattagaat tcgtgatgaa ctctgcaaaa   3000
atggagagat ccttctttct ccagcactca gctataccac aaaacacttg cataacgatg   3060
tggaaaaaga aaaaaggaa aaattgccta agaaataga ggaagataaa ctaaaacgcg     3120
aagaagaaaa aagagaagct gaaaaaagtg aagattcctc aggtactaca ggcctctcag   3180
gcttacatcg tacatacagc caggactgca gctttaagaa cagcatgtat catgtcggag   3240
attatgtcta tgttgaacct gcggaggcca atctacaacc acatatagtg tgtattgaga   3300
gactgtggga ggattcagct ggtgaaaaat ggttgtacgg ctgttggttt tatcggccaa   3360
atgaaacatt ccatttggct acacgaaaat ttctagaaaa agaagttttt aagagtgact   3420
actacaataa agtacctgtt agtaaaattc taggcaaatg tgtagtcatg tttgtcaagg   3480
aatactttaa attatgtcca gaaaactttc gcgatgagga tgttttttgtc tgtgaatcga   3540
ggtattctgc caaaaccaaa tcttttaaga aaattaaact gtggaccatg cccatcagtt   3600
cagttagatt tgtccctcgg gatgtgcctt tgcctgtggt ccgagtggcc tctgtgtttg   3660
caaatgcaga taaggggat gatgagaaga atacagacaa ctcagatgac aatagagctg    3720
aagacaattt taacttggaa aaggaaaaag aagatgttcc tgtggagatg tccaatggtg   3780
agccaggttg ccactacttt gagcagcttc ggtacaatga catgtggctg aaggttggtg   3840
attgtgtctt catcaaatcc cacggcttgg tgcgccctcg tgtgggcaga attgagaaag   3900
tatgggtccg agatggagct gcatattttt atggccctat cttcattcat ccagaagaaa   3960
cagaacatga gcccacaaaa atgttctaca aaaagaagt gtttctgagt aatctggaag    4020
agacctgccc tatgagttgt attctgggga atgtgcagt gctgtcattc aaggacttcc    4080
tctcctgcag gccaactgaa ataccagaaa atgacattct gctttgtgag agccgctata   4140
atgagagtga caagcagatg aagaagttca gggtttgaa gaggttttca ctctctgcta    4200
aagttgtaga tgatgaaatc tactacttca gaaaaccaat cattcctcag aaggaaccct   4260
caccttttgtt agaaaagaag atacaattgc tagaagctaa atttgcagag ttagaaggag   4320
gagatgatga tattgaggag atgggagaag aggatagtga agtcattgaa gctccatctc   4380
tacctcaact gcagacaccc ctggccaatg agttggacct catgccctat acaccccac    4440
agtctacccc aaagtctgcc aaaggcagtg caaagaagga aagttctaaa cgaaaaatca   4500
acatgagtgg ctacattttg ttcagcagtg aaatgagagc tgtgattaaa gcccagcacc   4560
cagactactc ttttggggag ctcagcagac tggtggggac agaatggaga aaccttgaaa   4620
cagccaagaa agcagaatat gaagagcggg cagctaaagt tgctgagcag caggagagag   4680
agcgagcagc acagcaacag cagccgagtg cttctccccg agcaggcacc cctgtggggg   4740
ctctcatggg ggtggtgcca ccaccaacac caatgggat gctcaatcag cagttgacac    4800
ctgttgcagg catgatgggt ggctatccgc caggccttcc acctttgcag ggcccagttg    4860
atggccttgt tagcatgggc agcatgcagc cacttcaccc tggggggcct ccacctcacc    4920
atcttccgcc aggtgtgcct ggcctcccag gcatcccacc accgggtgtg atgaatcaag    4980
gagtagcccc catggtaggg actccagcac caggtggaag tccgtatgga caacaggtag    5040
gagttttggg acctccaggg cagcaggcac cacctccata tcctggtcct catccagctg    5100
gcccccctgt catacagcag ccaacaacgc ccatgtttgt ggctcccca ccaaagaccc     5160
aaaggcttct ccactcagag gcctacctga aatacattga aggactcagt gctgaatcca   5220
acagcattag caagtgggac caaactttgg cagctcgaag acgggatgtc catttgtcca   5280
```

```
aagaacagga gagccgccta ccttctcact ggctcaaaag taaaggggca cacaccacca   5340
tggcagatgc cctctggcgc ctacgggatt taatgcttcg agacactctc aacatccgac   5400
aggcatacaa cctagaaaat gtttaatcac atcactgttt cttctgtgga agcaaagagt   5460
tgtggagcgg tagccatttt agttactggg gtgggaggga ggaacaaagg atgataattt   5520
ttattgcatt ttattgtaca tcacacagcc atttttatat aaggacactt ttaataagct   5580
atttcaaatt tggttttgtt acattaagtt gactatcaaa tacacaaaag atttttttg    5640 catatgtttc ctttgtttaa aaccagtttc ataattggtt atatatagta atagttttat   5700
ctttacttgt taaaggactt aaatcatcaa aggttttggc ttggcttagg gttttcgttt   5760
tcttttttat aaatatatat tatatatata tacacatata aagaaaaaa tgaaaaaaaa    5820 gtttacaaat ttaagttgac aatgaaatgt gaagttggtc ctagtttaca tcttagagga   5880
atgtatatgt atgttttaca tgcctaaata tctgcaggtt ttcttacagg taaagcgaag   5940
tgctttgaaa agtttagatt atacatgtgt gacagatgcg gcatatttgc tctattaaca   6000
cagaggctta ctatagaaat ctaaagtcaa tgctgtacat ccatccagtt agtgtaactg   6060
aagggaaatg taactttgtg ctgagttaga catctgtatt gtcagtgatt cttgtagaat   6120
atgtgctcag atctgagtta tatttagttt tggaaggtaa gttgaagagt acttttgatc   6180
agtttatgat tcagtttatg attttagttt ttgccttcat gttatacatt tatgatttga   6240
aactgtacat ctgttacctt gaaaaacatt gaagaaagta ctgaagtgtg catggaggtg   6300
gtttaagcat aatacttaac ccaagaagag tgtaagtgg acacaagctg tgcctgcaca    6360
tagctgtgca gggtagactg cctacataca catggccggg attctttatt tccttgttat   6420
caattatagt gctttgtttg tttcagggtt ggaattctca accagaaata atactttcta   6480
aaatatttta aaattcagct tgtgctttgg attatagaag gaaattatac tttaagaaaa   6540
tgttcacaaa aaaaaaaaa aaaaaaggac tattacagat cccaatactt ggatttggtg    6600
accttgtctt tctttctttt cttgagacat ggtcctacta ccaaccctgg ctggactgga   6660
gctcagtgta tagaccaggc tagtctcaaa ctctgcctct tcctcccaag tgctgggatt   6720
aagggcaggt accatagtgc tcagcaacca caaccctgtc tttccaacac ggccctagcg   6780
taagcactga ggcagtgtgc agtgctcagg cagcagcaaa catttcccgg gggtggtttt   6840
gaacctgctt gggtggttgt gtggtgctga cgctgccact gccctgttgt tcattgagaa   6900
tgattgttaa atgacactct tcctttagaa tataacggat cagtactcat gtttaattgc   6960
catgcttaat aaatcatgag aacaaaagag tatagaatgg aaagcattcc ctggtagcta   7020
ctttaaatac aggagccctg taacttaata ccagtagtca accactggat ctcagttttc   7080
atcaagtatt ttaaataaat aatcttaaat tttaaaatac gtactgcaga gtatgccagt   7140
atcttattgt taaaactgaa tcaaataaat cttcgattcc tggttatttg gaccattgac   7200
tcatcatgga ctatataatg taataagatt cttttctctt aaggtatcct tgaattacac   7260
caaagaacca gaaacttaat tttggttaaa ttatttattt atttcatgca ttaattttct   7320
ttttcttttt aaaggtttag atgaggctcc ttagggagtc tctaaaaccg cttcactatc   7380
agcaaccagg agtactagaa gccagagcac tcttcctcct ggctcctccc cagtgctcta   7440
gtgctgtagg aaccaagagc cagccccagg ttccccgagg cagtaaaaat ccagcacagg   7500
gggctgtgtc cctaaggcaa gccctgatta ccttttaaaaa aaccaaaaaa aacaaacaaa   7560
aaaaaaaaac ctaattaact aaagcattta aggcactatt tattttagaa tcatgctttt   7620
```

```
gaagagcatc agtgattact tagggtgtaa tatgtaaaga tcagacatct ccaaaaacag      7680
aaaaagtaca agtaaacaac acactttctc atgactttta agaactgtag taatgtggct      7740
taggaaatat aatggcctaa ttgttttcaa aatgtaagtt cctgtgaaga attttgttta      7800 tattggggttg gggacctata ggtttaaaat agaatgtcag tcagctgact taaaaaacat     7860 tggtttttact aagtctgcct tcccctttcta aggaagaact gagtgggtaa gggacaggtg    7920
tgtaaaatct ccaaatggat gttacagctt tcagcttgaa cgtttgtttc cagacctgat     7980
taaaatttgg tttattctaa tttctgtact atatcatctg aggttttaag tggtaactgg     8040
ttctatacca tgtatgtatc atatgtttgt tcatcaaagc ttttttaatcc aaataaaaac    8100 aacagtttgc aaagtga                                                   8117
```

<210> SEQ ID NO 6
<211> LENGTH: 1704
<212> TYPE: PRT
<213> ORGANISM: Mus musculus

<400> SEQUENCE: 6

```
Met Gly Ser Lys Arg Arg Ala Thr Ser Pro Ser Ser Val Ser
1               5                   10                  15

Gly Asp Phe Asp Asp Gly His His Ser Val Pro Thr Pro Gly Pro Ser
                20                  25                  30

Arg Lys Arg Arg Leu Ser Asn Leu Pro Thr Val Asp Pro Ile Ala
            35                  40                  45

Val Cys His Glu Leu Tyr Asn Thr Ile Arg Asp Tyr Lys Asp Glu Gln
        50                  55                  60

Gly Arg Leu Leu Cys Glu Leu Phe Ile Arg Ala Pro Lys Arg Arg Asn
65                  70                  75                  80

Gln Pro Asp Tyr Tyr Glu Val Val Ser Gln Pro Ile Asp Leu Met Lys
                85                  90                  95

Ile Gln Gln Lys Leu Lys Met Glu Glu Tyr Asp Asp Val Asn Leu Leu
            100                 105                 110

Thr Ala Asp Phe Gln Leu Leu Phe Asn Asn Ala Lys Ala Tyr Tyr Lys
        115                 120                 125

Pro Asp Ser Pro Glu Tyr Lys Ala Ala Cys Lys Leu Trp Asp Leu Tyr
    130                 135                 140

Leu Arg Thr Arg Asn Glu Phe Val Gln Lys Gly Glu Ala Asp Asp Glu
145                 150                 155                 160

Asp Asp Asp Glu Asp Gly Gln Asp Asn Gln Gly Thr Leu Ala Asp Gly
                165                 170                 175

Ser Ser Pro Gly Tyr Leu Lys Glu Ile Leu Glu Gln Leu Leu Glu Ala
            180                 185                 190

Ile Val Val Ala Thr Asn Pro Ser Gly Arg Leu Ile Ser Glu Leu Phe
        195                 200                 205

Gln Lys Leu Pro Ser Lys Val Gln Tyr Pro Asp Tyr Tyr Ala Ile Ile
    210                 215                 220

Lys Glu Pro Ile Asp Leu Lys Thr Ile Ala Gln Arg Ile Gln Asn Gly
225                 230                 235                 240

Ser Tyr Lys Ser Ile His Ala Met Ala Lys Asp Ile Asp Leu Leu Ala
                245                 250                 255

Lys Asn Ala Lys Thr Tyr Asn Glu Pro Gly Ser Gln Val Phe Lys Asp
            260                 265                 270

Ala Asn Ser Ile Lys Lys Ile Phe Tyr Met Lys Lys Ala Glu Ile Glu
        275                 280                 285
```

```
His His Glu Met Thr Lys Ser Ser Leu Arg Ile Arg Thr Ala Ser Asn
    290                 295                 300

Leu Ala Ala Ala Arg Leu Thr Gly Pro Ser His Asn Lys Ser Ser Leu
305                 310                 315                 320

Gly Glu Glu Arg Asn Pro Thr Ser Lys Tyr Tyr Arg Asn Lys Arg Ala
                325                 330                 335

Val Gln Gly Gly Arg Leu Ser Ala Ile Thr Met Ala Leu Gln Tyr Gly
                340                 345                 350

Ser Glu Ser Glu Glu Asp Ala Ala Leu Ala Ala Arg Tyr Glu Glu
            355                 360                 365

Gly Glu Ser Glu Ala Glu Ser Ile Thr Ser Phe Met Asp Val Ser Asn
                370                 375                 380

Pro Phe His Gln Leu Tyr Asp Thr Val Arg Ser Cys Arg Asn His Gln
385                 390                 395                 400

Gly Gln Leu Ile Ala Glu Pro Phe Phe His Leu Pro Ser Lys Lys Lys
                405                 410                 415

Tyr Pro Asp Tyr Tyr Gln Gln Ile Lys Met Pro Ile Ser Leu Gln Gln
                420                 425                 430

Ile Arg Thr Lys Leu Lys Asn Gln Glu Tyr Glu Thr Leu Asp His Leu
                435                 440                 445

Glu Cys Asp Leu Asn Leu Met Phe Glu Asn Ala Lys Arg Tyr Asn Val
450                 455                 460

Pro Asn Ser Ala Ile Tyr Lys Arg Val Leu Lys Leu Gln Gln Val Met
465                 470                 475                 480

Gln Ala Lys Lys Lys Glu Leu Ala Arg Arg Asp Ile Glu Asp Gly
                485                 490                 495

Asp Ser Met Ile Ser Ser Ala Thr Ser Asp Thr Gly Ser Ala Lys Arg
            500                 505                 510

Lys Arg Asn Thr His Asp Ser Glu Met Leu Gly Leu Arg Arg Leu Ser
                515                 520                 525

Ser Lys Lys Asn Ile Arg Lys Gln Arg Met Lys Ile Leu Phe Asn Val
            530                 535                 540

Val Leu Glu Ala Arg Glu Pro Gly Ser Gly Arg Arg Leu Cys Asp Leu
545                 550                 555                 560

Phe Met Val Lys Pro Ser Lys Lys Asp Tyr Pro Asp Tyr Tyr Lys Ile
                565                 570                 575

Ile Leu Glu Pro Met Asp Leu Lys Ile Ile Glu His Asn Ile Arg Asn
                580                 585                 590

Asp Lys Tyr Ala Gly Glu Glu Gly Met Met Glu Asp Met Lys Leu Met
            595                 600                 605

Phe Arg Asn Ala Arg His Tyr Asn Glu Glu Gly Ser Gln Val Tyr Asn
610                 615                 620

Asp Ala His Ile Leu Glu Lys Leu Leu Lys Asp Lys Arg Lys Glu Leu
625                 630                 635                 640

Gly Pro Leu Pro Asp Asp Asp Met Ala Ser Pro Lys Leu Lys Leu
                645                 650                 655

Ser Arg Lys Ser Gly Val Ser Pro Lys Lys Ser Lys Tyr Met Thr Pro
            660                 665                 670

Met Gln Gln Lys Leu Asn Glu Val Tyr Glu Ala Val Lys Asn Tyr Thr
        675                 680                 685

Asp Lys Arg Gly Arg Arg Leu Ser Ala Ile Phe Leu Arg Leu Pro Ser
            690                 695                 700
```

```
Arg Ser Glu Leu Pro Asp Tyr Tyr Leu Thr Ile Lys Lys Pro Met Asp
705                 710                 715                 720

Met Glu Lys Ile Arg Ser His Met Met Ala Asn Lys Tyr Gln Asp Ile
            725                 730                 735

Asp Ser Met Val Glu Asp Phe Val Met Met Phe Asn Asn Ala Cys Thr
        740                 745                 750

Tyr Asn Glu Pro Glu Ser Leu Ile Tyr Lys Asp Ala Leu Val Leu His
    755                 760                 765

Lys Val Leu Leu Glu Thr Arg Arg Asp Leu Gly Asp Glu Asp Ser
770                 775                 780

His Val Pro Asn Val Thr Leu Leu Ile Gln Glu Leu Ile His Asn Leu
785                 790                 795                 800

Phe Val Ser Val Met Ser His Gln Asp Asp Glu Gly Arg Cys Tyr Ser
                805                 810                 815

Asp Ser Leu Ala Glu Ile Pro Ala Val Asp Pro Asn Ser Pro Asn Lys
            820                 825                 830

Pro Pro Leu Thr Phe Asp Ile Ile Arg Lys Asn Val Glu Ser Asn Arg
        835                 840                 845

Tyr Arg Arg Leu Asp Leu Phe Gln Glu His Met Phe Glu Val Leu Glu
    850                 855                 860

Arg Ala Arg Arg Met Asn Arg Thr Asp Ser Glu Ile Tyr Glu Asp Ala
865                 870                 875                 880

Val Glu Leu Gln Gln Phe Phe Ile Arg Ile Arg Asp Glu Leu Cys Lys
                885                 890                 895

Asn Gly Glu Ile Leu Leu Ser Pro Ala Leu Ser Tyr Thr Thr Lys His
            900                 905                 910

Leu His Asn Asp Val Glu Lys Glu Lys Lys Glu Lys Leu Pro Lys Glu
            915                 920                 925

Ile Glu Glu Asp Lys Leu Lys Arg Glu Glu Lys Arg Glu Ala Glu
930                 935                 940

Lys Ser Glu Asp Ser Ser Gly Thr Thr Gly Leu Ser Gly Leu His Arg
945                 950                 955                 960

Thr Tyr Ser Gln Asp Cys Ser Phe Lys Asn Ser Met Tyr His Val Gly
                965                 970                 975

Asp Tyr Val Tyr Val Glu Pro Ala Glu Ala Asn Leu Gln Pro His Ile
        980                 985                 990

Val Cys Ile Glu Arg Leu Trp Glu Asp Ser Ala Gly Glu Lys Trp Leu
        995                 1000                1005

Tyr Gly Cys Trp Phe Tyr Arg Pro Asn Glu Thr Phe His Leu Ala
    1010                1015                1020

Thr Arg Lys Phe Leu Glu Lys Glu Val Phe Lys Ser Asp Tyr Tyr
    1025                1030                1035

Asn Lys Val Pro Val Ser Lys Ile Leu Gly Lys Cys Val Val Met
    1040                1045                1050

Phe Val Lys Glu Tyr Phe Lys Leu Cys Pro Glu Asn Phe Arg Asp
    1055                1060                1065

Glu Asp Val Phe Val Cys Glu Ser Arg Tyr Ser Ala Lys Thr Lys
    1070                1075                1080

Ser Phe Lys Lys Ile Lys Leu Trp Thr Met Pro Ile Ser Ser Val
    1085                1090                1095

Arg Phe Val Pro Arg Asp Val Pro Leu Pro Val Val Arg Val Ala
    1100                1105                1110
```

Ser Val Phe Ala Asn Ala Asp Lys Gly Asp Glu Lys Asn Thr
1115                1120               1125

Asp Asn Ser Asp Asp Asn Arg Ala Glu Asp Asn Phe Asn Leu Glu
1130                1135               1140

Lys Glu Lys Glu Asp Val Pro Val Glu Met Ser Asn Gly Glu Pro
1145                1150               1155

Gly Cys His Tyr Phe Glu Gln Leu Arg Tyr Asn Asp Met Trp Leu
1160                1165               1170

Lys Val Gly Asp Cys Val Phe Ile Lys Ser His Gly Leu Val Arg
1175                1180               1185

Pro Arg Val Gly Arg Ile Glu Lys Val Trp Val Arg Asp Gly Ala
1190                1195               1200

Ala Tyr Phe Tyr Gly Pro Ile Phe Ile His Pro Glu Glu Thr Glu
1205                1210               1215

His Glu Pro Thr Lys Met Phe Tyr Lys Lys Glu Val Phe Leu Ser
1220                1225               1230

Asn Leu Glu Glu Thr Cys Pro Met Ser Cys Ile Leu Gly Lys Cys
1235                1240               1245

Ala Val Leu Ser Phe Lys Asp Phe Leu Ser Cys Arg Pro Thr Glu
1250                1255               1260

Ile Pro Glu Asn Asp Ile Leu Leu Cys Glu Ser Arg Tyr Asn Glu
1265                1270               1275

Ser Asp Lys Gln Met Lys Lys Phe Lys Gly Leu Lys Arg Phe Ser
1280                1285               1290

Leu Ser Ala Lys Val Val Asp Asp Glu Ile Tyr Tyr Phe Arg Lys
1295                1300               1305

Pro Ile Ile Pro Gln Lys Glu Pro Ser Pro Leu Leu Glu Lys Lys
1310                1315               1320

Ile Gln Leu Leu Glu Ala Lys Phe Ala Glu Leu Glu Gly Gly Asp
1325                1330               1335

Asp Asp Ile Glu Glu Met Gly Glu Glu Asp Ser Glu Val Ile Glu
1340                1345               1350

Ala Pro Ser Leu Pro Gln Leu Gln Thr Pro Leu Ala Asn Glu Leu
1355                1360               1365

Asp Leu Met Pro Tyr Thr Pro Pro Gln Ser Thr Pro Lys Ser Ala
1370                1375               1380

Lys Gly Ser Ala Lys Lys Glu Ser Ser Lys Arg Lys Ile Asn Met
1385                1390               1395

Ser Gly Tyr Ile Leu Phe Ser Ser Glu Met Arg Ala Val Ile Lys
1400                1405               1410

Ala Gln His Pro Asp Tyr Ser Phe Gly Glu Leu Ser Arg Leu Val
1415                1420               1425

Gly Thr Glu Trp Arg Asn Leu Glu Thr Ala Lys Lys Ala Glu Tyr
1430                1435               1440

Glu Glu Arg Ala Ala Lys Val Ala Glu Gln Glu Arg Glu Arg
1445                1450               1455

Ala Ala Gln Gln Gln Gln Pro Ser Ala Ser Pro Arg Ala Gly Thr
1460                1465               1470

Pro Val Gly Ala Leu Met Gly Val Val Pro Pro Thr Pro Met
1475                1480               1485

Gly Met Leu Asn Gln Gln Leu Thr Pro Val Ala Gly Met Met Gly
1490                1495               1500

Gly Tyr Pro Pro Gly Leu Pro Pro Leu Gln Gly Pro Val Asp Gly
    1505                1510                1515

Leu Val Ser Met Gly Ser Met Gln Pro Leu His Pro Gly Gly Pro
    1520                1525                1530

Pro Pro His His Leu Pro Pro Gly Val Pro Gly Leu Pro Gly Ile
    1535                1540                1545

Pro Pro Pro Gly Val Met Asn Gln Gly Val Ala Pro Met Val Gly
    1550                1555                1560

Thr Pro Ala Pro Gly Gly Ser Pro Tyr Gly Gln Gln Val Gly Val
    1565                1570                1575

Leu Gly Pro Pro Gly Gln Gln Ala Pro Pro Tyr Pro Gly Pro
    1580                1585                1590

His Pro Ala Gly Pro Pro Val Ile Gln Gln Pro Thr Thr Pro Met
    1595                1600                1605

Phe Val Ala Pro Pro Lys Thr Gln Arg Leu Leu His Ser Glu
    1610                1615                1620

Ala Tyr Leu Lys Tyr Ile Glu Gly Leu Ser Ala Glu Ser Asn Ser
    1625                1630                1635

Ile Ser Lys Trp Asp Gln Thr Leu Ala Ala Arg Arg Arg Asp Val
    1640                1645                1650

His Leu Ser Lys Glu Gln Glu Ser Arg Leu Pro Ser His Trp Leu
    1655                1660                1665

Lys Ser Lys Gly Ala His Thr Thr Met Ala Asp Ala Leu Trp Arg
    1670                1675                1680

Leu Arg Asp Leu Met Leu Arg Asp Thr Leu Asn Ile Arg Gln Ala
    1685                1690                1695

Tyr Asn Leu Glu Asn Val
    1700

<210> SEQ ID NO 7
<211> LENGTH: 21
<212> TYPE: DNA
<213> ORGANISM: Homo sapiens

<400> SEQUENCE: 7
tcatcatcta ccactttagc a                                        21

<210> SEQ ID NO 8
<211> LENGTH: 21
<212> TYPE: DNA
<213> ORGANISM: Homo sapiens

<400> SEQUENCE: 8
tcatcatcta ccactttagc a                                        21

<210> SEQ ID NO 9
<211> LENGTH: 11
<212> TYPE: DNA
<213> ORGANISM: Homo sapiens

<400> SEQUENCE: 9
atgagagtcc t                                                   11

<210> SEQ ID NO 10
<211> LENGTH: 11
<212> TYPE: DNA
<213> ORGANISM: Homo sapiens

```
<400> SEQUENCE: 10
atgagagtcc t                                                         11

<210> SEQ ID NO 11
<211> LENGTH: 12
<212> TYPE: DNA
<213> ORGANISM: Homo sapiens

<400> SEQUENCE: 11
ggcggcggcg gc                                                        12

<210> SEQ ID NO 12
<211> LENGTH: 12
<212> TYPE: DNA
<213> ORGANISM: Homo sapiens

<400> SEQUENCE: 12
ggcggcggcg gc                                                        12

<210> SEQ ID NO 13
<211> LENGTH: 21
<212> TYPE: DNA
<213> ORGANISM: Homo sapiens

<400> SEQUENCE: 13
tcatcatcta ccactttagc a                                              21

<210> SEQ ID NO 14
<211> LENGTH: 21
<212> TYPE: DNA
<213> ORGANISM: Homo sapiens

<400> SEQUENCE: 14
tcatcatcta ccactttagc a                                              21

<210> SEQ ID NO 15
<211> LENGTH: 11
<212> TYPE: DNA
<213> ORGANISM: Homo sapiens

<400> SEQUENCE: 15
atgagagtcc t                                                         11

<210> SEQ ID NO 16
<211> LENGTH: 11
<212> TYPE: DNA
<213> ORGANISM: Homo sapiens

<400> SEQUENCE: 16
atgagagtcc t                                                         11
```